US012653914B2

(12) United States Patent
Robillard et al.

(10) Patent No.: US 12,653,914 B2
(45) Date of Patent: Jun. 16, 2026

(54) COMPOUNDS FOR FAST AND EFFICIENT CLICK RELEASE

(71) Applicant: Tagworks Pharmaceuticals B.V., Nijmegen (NL)

(72) Inventors: Marc Stefan Robillard, Nijmegen (NL); Hannes Mikula, Vienna (AT); Wolter Ten Hoeve, Nijmegen (NL); Raffaella Rossin, Nijmegen (NL)

(73) Assignee: Tagworks Pharmaceuticals B.V., Nijmegen (NL)

( * ) Notice: Subject to any disclaimer, the term of this patent is extended or adjusted under 35 U.S.C. 154(b) by 614 days.

(21) Appl. No.: 17/619,791

(22) PCT Filed: Jun. 17, 2020

(86) PCT No.: PCT/NL2020/050388
§ 371 (c)(1),
(2) Date: Dec. 16, 2021

(87) PCT Pub. No.: WO2020/256546
PCT Pub. Date: Dec. 24, 2020

(65) Prior Publication Data

US 2023/0121556 A1 Apr. 20, 2023

(30) Foreign Application Priority Data

Jun. 17, 2019 (EP) .................................... 19180683

(51) Int. Cl.

| | |
|---|---|
| ***A61K 51/10*** | (2006.01) |
| ***A61K 47/54*** | (2017.01) |
| ***A61K 47/68*** | (2017.01) |
| ***A61K 49/00*** | (2006.01) |
| ***A61P 35/00*** | (2006.01) |

(52) U.S. Cl.
CPC ........ *A61K 51/1093* (2013.01); *A61K 47/545* (2017.08); *A61K 47/6809* (2017.08); *A61K 47/6889* (2017.08); *A61K 49/0058* (2013.01); *A61P 35/00* (2018.01)

(58) Field of Classification Search
CPC ............ A61K 51/1093; A61K 47/6889; A61K 47/545; A61K 47/6809; A61K 49/0058; A61P 35/00
USPC ........................................................ 424/1.53
See application file for complete search history.

(56) References Cited

U.S. PATENT DOCUMENTS

| | | | |
|---|---|---|---|
| 4,486,414 A | 12/1984 | Pettit | |
| 4,486,444 A | 12/1984 | Shepard | |
| 4,879,278 A | 11/1989 | Pettit et al. | |
| 4,986,988 A | 1/1991 | Pettit et al. | |
| 5,138,036 A | 8/1992 | Pettit et al. | |
| 5,198,560 A | 3/1993 | Kadow et al. | |
| 5,410,024 A | 4/1995 | Pettit et al. | |
| 5,504,191 A | 4/1996 | Pettit et al. | |
| 5,521,284 A | 5/1996 | Pettit et al. | |
| 5,530,097 A | 6/1996 | Pettit et al. | |
| 5,599,902 A | 2/1997 | Pettit et al. | |
| 5,635,483 A | 6/1997 | Pettit et al. | |
| 5,663,149 A | 9/1997 | Pettit et al. | |
| 5,665,860 A | 9/1997 | Pettit et al. | |
| 5,780,588 A | 7/1998 | Pettit et al. | |
| 6,034,065 A | 3/2000 | Pettit et al. | |
| 6,239,104 B1 | 5/2001 | Pettit et al. | |
| 6,323,315 B1 | 11/2001 | Pettit et al. | |
| 7,005,132 B2 | 2/2006 | Cubicciotti | |
| 9,421,274 B2 | 8/2016 | Robillard et al. | |
| 9,427,482 B2 | 8/2016 | Rossin et al. | |
| 9,463,256 B2 | 10/2016 | Lub et al. | |
| 9,913,921 B2 | 3/2018 | Robillard et al. | |
| 9,931,408 B2 | 4/2018 | Robillard et al. | |
| 10,004,810 B2 | 6/2018 | Robillard et al. | |
| 10,376,594 B2 | 8/2019 | Robillard et al. | |
| 10,927,139 B2 | 2/2021 | Robillard et al. | |
| 10,967,069 B2 | 4/2021 | Robillard et al. | |
| 2009/0023916 A1 | 1/2009 | Fox et al. | |
| 2010/0111856 A1* | 5/2010 | Gill | C07C 323/60 424/1.49 |
| 2015/0297741 A1 | 10/2015 | Robillard | |

FOREIGN PATENT DOCUMENTS

| | | | |
|---|---|---|---|
| WO | 2010/051530 A2 | 5/2010 | |
| WO | 2010/119382 A1 | 10/2010 | |
| WO | 2010/119389 A2 | 10/2010 | |
| WO | 2012/012612 A2 | 1/2012 | |
| WO | 2012/049624 A1 | 4/2012 | |
| WO | 2012/085789 A1 | 6/2012 | |
| WO | 2012/156918 A1 | 11/2012 | |
| WO | 2012/156919 A1 | 11/2012 | |
| WO | 2014/065860 A1 | 5/2014 | |
| WO | 2014/081301 A1 | 5/2014 | |
| WO | 2014/081303 A1 | 5/2014 | |
| WO | 2016/025480 A1 | 2/2016 | |
| WO | 2018/004338 A1 | 1/2018 | |
| WO | WO-2018069375 A1 * | 4/2018 | A61K 31/4192 |

OTHER PUBLICATIONS

Miller et al. ACS Nano 2018, 12, 12814-12836. (Year: 2018).*
U.S. Appl. No. 17/169,217, filed Feb. 5, 2021, Bio-Orthogonal Drug Activation.
U.S. Appl. No. 17/023,343, filed Sep. 16, 2020, Chemically Cleavable Group.
U.S. Appl. No. 17/052,925, filed Nov. 4, 2020, Compounds Comprising a Linker for Increasing Transcyclooctene Stability.
U.S. Appl. No. 17/052,928, filed Nov. 4, 2020, Tetrazines for High Click Conjugation Yield In Vivo and High Click Release Yield.

(Continued)

*Primary Examiner* — Michael G. Hartley
*Assistant Examiner* — Sean R Donohue
(74) *Attorney, Agent, or Firm* — Foley & Lardner LLP

(57) ABSTRACT

The invention disclosed herein relates to compounds, combinations, kits, and methods using same, for use in bioorthogonal release reactions. In particular, the compounds, combinations and kits of the invention can be used to achieve fast and efficient click release. Applications of the compounds, combinations, and kits of the invention include both in vitro and in vivo applications.

30 Claims, 7 Drawing Sheets

(56) References Cited

OTHER PUBLICATIONS

U.S. Appl. No. 17/619,794, filed Dec. 16, 2021, Tetrazines for High Click Release Speed and Yield.
U.S. Appl. No. 17/619,796, filed Dec. 16, 2021, Agents for Cleaving Labels From Biomolecules In Vivo.
White et al., "Synthesis of Polyhydroxylated Pyrrolizidine Alkaloids of the Alexine Family by Tandem Ring-Closing Metathesis-Transannular Cyclization. (+)-Australine", Journal of Organic Chemistry, 2000, vol. 65, No. 26, pp. 9129-9142.
Ajay et al., "Diversity-Oriented Synthesis of cis-3,4-Dihydroxylated Piperidine and Its Higher Saturated and Unsaturated Homologues from d-Ribose and Their Glycosidase-Inhibition Study", Synlett, 2016, Vo. 27, No. 19, pp. 2721-2725.
International Search Report and Written Opinion for Corresponding International Application No. PCT/NL2020/050388 (9 Pages) (Aug. 19, 2020).
Audebert, P. et al. "Synthesis of new substituted tetrazines: electrochemical and spectroscopic properties". New Journal Chem. (2004), 28, 387-392.
Blackman, M.L. et al. "The tetrazine ligation: fast bioconjugation based on inverse-electron-demand Diels-Alder reactivity". Journal of American Chemical Society, (2008), 130(41), 13518-13519.
Blencowe, C.A. et al. "Self-immolative linkers in polymeric delivery systems". Polymer Chemistry, (2011 ), 2, 773-790.
Van Brakel, R. et al. "A doxorubicin prodrug activated by the staudinger reaction". Bioconjugate Chem. (2008), 19, 714-718.
Cere, V. et al. "Olefin Inversion. Protection of the sulfide function in the stereospecific synthesis of trans-Thiacyclooct-4-ene". Journal of Organic Chemistry, (1980), 45, 261-264.
Choe, Y.H. et al. "Anticancer drug delivery systems: multi-loaded N4-acyl poly(ethylene glycol) prodrugs of ara-C. II. Efficacy in ascites and solid tumors". Journal of Controlled Release, (2002), 79, 55-70.
Devaraj, N.K. et al. "Fast and sensitive pretargeted labeling of cancer cells via tetrazine/trans-cyclooctene cycloaddition". Angewandte Chemie International Edition, (2009), 48(38): 7013-1016.
Devaraj, N.K. et al. "Tetrazine-based cycloadditions: Application to Pretargeted live cell imaging",Bioconjugate Chem., (2008), 19(12), 2297-2299.
Geldard, J.F. et al. "The organic chemistry of a new weak field tridentate chelating agent. 3,5-Di(2-pyridyl)-1,2,4-triazole". Journal Organic Chemistry. (1965), 30, 318-319.
Grakauskas, V.A. et al. "Some 3,6-unsymmetrically disubstituted 1,2,4,5-Tetrazines". Journal American Chemical Society, (1958), 80, 3155-3159.
Greenwald, R.B. et al. "Drug delivery systems employing 1,4-or 1,6-elimination: Poly(ethylene glycol) prodrugs of amine-containing compounds". Journal Med. Chem. (1999), 42, 3657-3667.
Haba, K. et al. "Single-triggered trimeric prodrugs". Angewandte Chemie International Edition. (2005), 44, 726-730.
Haun, Jered B. et al, "Bioorthogonal Chemistry Amplifies Nanoparticle Binding and Enhances the Sensitivity of Cell Detection", Nature Nanotechnology, vol. 5, Sep. 2010, pp. 660-665.
Ingold, C.K. et al. "The Nature of the Alternating effect in carbon chains. Part XXII. An attempt further to define the probable mechanism of orientation in aromatic substitution". Journal Chem. Society. (1927), 2918-2926.
International Preliminary Report on Patentability for International Application No. PCT/IB2012/052446, Nov. 19, 2013, 10 Pages.
International Search Report and Written Opinion for International Application No. PCT/IB2012/052446, Oct. 23, 2012, 14 Pages.
Kaim, W. et al. "The new tetrafunctional (pi) acceptor ligand 3,6-Bis(2'-pyrimidyl)-1,2,4,5-tetrazine(bmtz): Diruthenium complexes of bmtz and of its 1,4-Dihydro form". Z. Naturforsch, 50b, 123-127 (1995).
Klopman, G. et al. "Computer automated log P calculations based on an extended group contribution approach". Journal Chem. Inf. Comput. Sci. (1994), 34, 752-781.
Mohsin, H. et al. "Radiolanthanide-labeled monoclonal antibody CC49 for radioimmunotherapy of cancer: biological comparison of DOTA conjugates and 149Pm, 166Ho, and 177Lu". Bioconjugate Chem. (2006), 17, 485-492.
Prevost, M. et al. "Insertions of silylenes into vinyl epoxides: Diastereoselective synthesis of functionalized, optically active trans-Dioxasilacyclooctenes". Journal of the American Chemical Society, (2009), 131, 14182-14182.
Rossin, R. et al. "In vivo chemistry for pretargeted tumor imaging in live mice". Angewandte Chemie International Edition, (2010), 49, 3375-3378.
Alley, S; Okeley N; Senter, PD; et al. "Antibody-drug conjugates: targeted drug delivery for cancer." Current Opinion in Chemical Biology, (2010), 14:529-537.
Thakur, A. et al. "Cancer therapy with bispecific antibodies: Clinical experience". Current Opinion in Molecular Therapeutics, (2010), 12(3), 340-349.
Thalhammer, F. et al. "Reaktivitat Einfacher Offenkettiger Und Cyclischer Dienophile Bei Diels-alder-reaktionen mil inversem elektronenbedarf". Tetrahedron Letters (1990), 31 (47), 6851-6854. (See English abstract.).
Tranoy-Opalinski, I. et al. "Design of self-Immolative linkers for tumour activated prodrug therapy". Anti-Cancer Agents in Medicinal Chemistry, (2008), 8, 618-637.
Viswanadhan, V.N. et al. "Atomic physicochemical parameters for three dimensional structure directed quantitative structure-activity relationships. 4. Additional parameters for hydrophobic and dispersive interactions and their application for an automated superposition of certain naturally occuring nucleoside antibiotics". Journal Chem. Inf. Comput. Sci. (1989), 29, 163-172.
Whitham, G.H. et al. "trans-Cycloalkenes. Part I. (1 RS,2RS)-Irans-Cyclo-oct-2-en-1-ol". Journal Chem. Society, (1971), 883-886.
Whitham, G.H. et al. "trans-Cycloalkenes. Part II. Application of the Dioxolan Olefin Synthesis to the Stereospecific Formation of trans-Cyclo-octene Derivatives. (1 SR,2RS)-Irans-Cyclo-oct-2-en-1-ol". Journal Chem. Society, (1971), 886-890.
Whitham, G.H. et al. "trans-Cycloalkenes. Part III. Stereochemistry and mechanism of some reactions of diastereoisomeric 3-substituted trans-cyclo-octenes". Journal Chem. Society, (1971), 891-896.
Wiessler, Manfred; et al. "Extension of the PNA world by functionalized PNA monomers eligible candidates for Inverse Diels Alder Click Chemistry", Int. Journal of Medical Science, Jun. 27, 2010, 7(4):213-223.
Wijnen, J.W. et al. "Substitute effects on an inverse electron demand hetero diels-alder reaction in aqueous solution and organic solvents: cycloaddition of substituted styrenes to Di(2-pyridyl)-1,2,4,5-tetrazine". Journal of Organic Chemistry, (1996), 61, 2001-2005.
Wolff, Manfred E. "Burgers Medicinal Chemistry", 5ed, Part 1 John Wiley & Sons, 1995, pp. 975-977.
Xia,Y. et al. "Shape-Controlled Synthesis of Metal Nanocrystals: Simple Chemistry Meets Complex Physics?", Angewandte Chemie International Edition (2009), 48, 1-5.
Atfah, M., "Diels-Alder Reactions of 3,6-Diphenyl-1,2,3,4,5-Tetrazinenad 3,6-Di(2-Pyridyl)-1,2,4,5,-tetrazine with some 1-Morpholinocycloalkenes," J. Heterocyclic Chem, 26, 717 (1989).
Banker, G.S. et al, "B. Prodrugs", Modern Pharmaceutics, 3ed, Marcel Dekker, New York, 1996, p. 451 and 596.
International Search Report and Written Opinion for Corresponding International Application No. PCT/NL2013/050850 (9 Pages) (Feb. 11, 2014).
Thomas, J., et al., "Proligands with protease-regulated binding activity identified from cell-displayed prodomain libraries," Protein Science 2009, vol. 18:2053-2059.
Thompson, S. et al. "The construction and in vitro testing of photo-activalable cancer targeting folaled anti-CD3 conjugates". Biochemical and Biophysical Research Communications, (2008), 366, 526-531.
International Search Report and Written Opinion for Corresponding International Application No. PCT/NL2019/050272 (9 Pages) (Oct. 9, 2019).
Rossin et al., "Highly Reactive trans-Cyclooctene Tags with Improved Stability for Diels-Alder Chemistry in Living Systems", Bioconjugate Chemistry, 2013, vol. 24, No. 7, pp. 1210-1217.

(56) References Cited

OTHER PUBLICATIONS

International Search Report and Written Opinion for Corresponding International Application No. PCT/NL2019/050271 (10 Pages) ( Oct. 23, 2019).
Rossin et al., "Triggered Drug Release from an Antibody—Drug Conjugate Using Fast "Click-to-Release" Chemistry in Mice", Bioconjugate Chemistry, 2016, vol. 27, No. 7, pp. 1697-1706.
International Search Report and Written Opinion for Corresponding International Application No. PCT/NL2020/050386 (17 Pages) (Nov. 5, 2020).
International Search Report and Written Opinion for Corresponding International Application No. PCT/NL2020/050387 (9 Pages) (Aug. 25, 2020).
Dawood et al., "Pd"-Oxidative Amination for Access to a 9-Azabicyclo[4.2.1]nonane Compound Library and Anatoxin-a, Eur. J. Org. Chem., 2018, 5558-5561.
Nonn et al., "Chemodiscrimination of Olefin Bonds Through Cross-Metathesis Reactions—Synthesis of Functionalized beta-Lactam and beta-Amino Acid Derivatives," Eur. J. Org. Chem., 2019, 5285-5293.

* cited by examiner

COMPOUNDS FOR FAST AND EFFICIENT CLICK RELEASE

CROSS-REFERENCE TO RELATED APPLICATIONS

This application is a 371 of PCT/NL2020/050388, filed Jun. 17, 2020, which claims the benefit of European Patent Application No. 19180683.5, filed Jun. 17, 2019.

FIELD OF THE INVENTION

The invention disclosed herein relates to compounds, combinations, kits, and methods using same, for use in bioorthogonal release reactions.

BACKGROUND

Selective chemical reactions that are orthogonal to the diverse functionality of biological systems are called bio-orthogonal reactions and occur between two abiotic groups with exclusive mutual reactivity. These can be used to selectively modify biochemical structures, such as proteins or nucleic acids, which typically proceed in water and at near-ambient temperature, and may be applied in complex chemical environments, such as those found in living organisms.

Bio-orthogonal reactions are broadly useful tools with applications that span chemical synthesis, materials science, chemical biology, diagnostics, and medicine. Especially prominent application areas for bioorthogonal reactions include drug delivery agents and prodrugs for pharmaceutical applications, as well as various reversible bioconjugates and sophisticated spectroscopic bioprobes for applications in the field of biological analysis.

One prominent bioorthogonal reaction is the inverse-electron-demand Diels Alder (IEDDA) reaction between a trans-cyclooctene (TCO) and a tetrazine (TZ). In previous studies the IEDDA reaction was used for pretargeted radioimmunoimaging, treating tumor-bearing mice with trans-cyclooctene (TCO)-tagged antibody or antibody fragments, followed one or more days later by administration and selective conjugation of a radiolabeled tetrazine probe to the TCO tag of the tumor-bound antibody [R. Rossin, M. S. Robillard, Curr. Opin. Chem. Biol. 2014, 21, 161-169].

Based on the IEDDA conjugation a release reaction has been developed, which was termed the IEDDA pyridazine elimination, a "click-to-release" approach that affords instantaneous and selective release upon conjugation [R. M. Versteegen, R. Rossin, W. ten Hoeve, H. M. Janssen, M. S. Robillard, Angew. Chem. Int. Ed. 2013, 52, 14112-14116]. IEDDA reactions between tetrazines (i.e. diene) and alkenes (i.e. dienophile) afford 4,5-dihydropyridazines, which usually tautomerize to 1,4- and 2,5-dihydropyridazines. It was demonstrated that the 1,4-dihydropyridazine product derived from a TCO containing a carbamate-linked doxorubicin (Dox) at the allylic position and tetrazine is prone to eliminate $CO_2$ and Dox via an electron cascade mechanism eventually affording aromatic pyridazine. The triggered release has been demonstrated in PBS (phosphate buffered saline), serum, cell culture and in mice and holds promise for a range of applications in medicine, chemical biology, and synthetic chemistry, including triggered drug release, biomolecule uncaging and capture&release strategies.

In general the IEDDA pyridazine elimination enables the controlled manipulation of a wide range of substrates in relatively complex environments, in the presence of a range of other chemical functional groups. This control can be temporal and, optionally, also spatial. The manipulation can be versatile, e.g. for a variety of purposes including but not limited to activating, deactivating, releasing, trapping, or otherwise altering a Construct attached to a chemically cleavable group.

The IEDDA pyridazine elimination has been applied in triggered drug release from antibody-drug conjugates (ADCs) capable of participating in an IEDDA reaction (FIG. 1). ADCs are a promising class of biopharmaceuticals that combine the target-specificity of monoclonal antibodies (mAbs) or mAb fragments with the potency of small molecule toxins. Classical ADCs are designed to bind to an internalizing cancer cell receptor leading to uptake of the ADC and subsequent intracellular release of the drug by enzymes, thiols, or lysosomal pH. Routing the toxin to the tumour, while minimizing the peripheral damage to healthy tissue, allows the use of highly potent drugs resulting in improved therapeutic outcomes. The use of the IEDDA pyridazine elimination for ADC activation allows the targeting of non-internalizing receptors, as the drug is cleaved chemically instead of biologically.

In general prodrugs, which may comprise ADCs, are an interesting application for the IEDDA pyridazine elimination reaction, in which a drug is deactivated, bound or masked by a moiety, and is reactivated, released or unmasked after an IEDDA reaction has taken place.

Background art for the aforementioned technology further includes WO2012/156919, WO2012156918A1, WO 2014/081303, and US20150297741. Herein a dienophile, the aforementioned TCO, is used as a chemically cleavable group in e.g. a protecting group in synthetic chemistry, a cleavable linker or mask in chemical biology, in vitro diagnostics, and in vivo prodrug activation. The group is attached to a Construct (e.g. molecule, protein, peptide, polymer, dye, surface) in such a way that the release of the dienophile from the Construct can be provoked by allowing the dienophile to react with a diene, the aforementioned TZ. The dienophile is an eight-membered non-aromatic cyclic alkenylene or alkenyl group, particularly a TCO group.

In some applications, the TCO is part of prodrug which is first injected in the blood stream of a subject and may be targeted to a certain part of the body, e.g. a tumor. Then, a certain percentage of the prodrug is immobilized at the targeted spot, while another percentage is cleared by the body. After several hours or days, an activator comprising a tetrazine is administered to release a drug from the prodrug, preferably only at the targeted spot. The tetrazine itself is also subject to clearance by the body at a certain clearance rate.

In general, the tetrazine reacts in an initial step with a dienophile-containing Construct (e.g. a dienophile-containing prodrug) to form a conjugate. This is referred to as the click conjugation step. Next, via one or multiple mechanisms, the Construct is preferably released from the Construct-dienophile (e.g. prodrug). It will be understood that a high yield in the click conjugation step, i.e. a high click conjugation yield, does not necessarily result in a high yield of released Construct, i.e. a high drug release yield.

From the viewpoint of bio-orthogonality the chemistry works well.

However, it is desired that better IEDDA reactions are developed.

Achieving high Construct release yields in IEDDA reactions remains a challenge both in vivo and in vitro. In particular, it is desired that the reaction between a Construct-bearing dienophile and a diene results in a high Construct release yield in vitro and/or in vivo.

Furthermore, achieving fast Construct release in IEDDA reactions remains a challenge both in vivo and in vitro. In particular, it is desired that the reaction between a Construct-bearing dienophile and a diene results in a fast Construct release in vitro and/or in vivo.

Typically, the tetrazine motifs that typically give high release are less reactive than the tetrazines that have successfully been used for click conjugations in vivo. These more reactive tetrazines give a good click conjugation yield, but result in a poor click release yield. In the abovementioned study [R. M. Versteegen, R. Rossin, W. ten Hoeve, H. M. Janssen, M. S. Robillard, Angew. Chem. Int. Ed. 2013, 52, 14112-14116], it was shown that for example 3,6-bis-(2-pyridyl)-1,2,4,5-tetrazine gives high click conjugation rate and yield, but a very poor click release yield of only 7% in PBS/MeCN (3:1) or only 12% in serum.

In addition, for tetrazines that give a high release yield, for example 3,6-bis-methyl-1,2,4,5-tetrazine, this release typically takes several hours and typically exhibits a maximum 80-90% release yield R. M. Versteegen, R. Rossin, W. ten Hoeve, H. M. Janssen, M. S. Robillard, Angew. Chem. Int. Ed. 2013, 52, 14112-14116].

For at least those reasons, it is a desire to improve the click release rate and yield of tetrazine motifs with relatively high reactivity towards dienophiles (i.e. high click conjugation yield) in vitro and/or in vivo.

Another desire is to improve the click release rate and possibly the click release yield of tetrazines with relatively good click conjugation and/or release yields in vitro and/or in vivo.

Another desire is to improve the click release rate, and preferably also the click release yield, of tetrazines with low reactivity towards dienophiles in vitro and/or in vivo.

Another desire is to achieve a combination of a high click conjugation yield with a Construct-bearing dienophile and a high Construct release yield both in vitro and in vivo.

Another desire is to achieve a combination of a high click conjugation reaction rate with a dienophile, a high click conjugation yield between a Construct-bearing dienophile and the tetrazine and a high Construct release yield and a high Construct release rate, preferably both in vitro and in vivo.

Previous studies have attempted to address said desires by engineering the diene, rather than the dienophile, to afford higher conjugation yields, or increased release yields/rates, or both.

A previous study ([R. Rossin, S. M. J. van Duijnhoven, W. ten Hoeve, H. M. Janssen, L. H. J. Kleijn, F. J. M. Hoeben, R. M. Versteegen, M. S. Robillard, Bioconj. Chem., 2016, 27, 1697-1706]) has shown that linking a 10 kDa dextran to a 3-methyl-6-(2-pyridyl)-tetrazine or a 3-methyl-6-(methylene)-tetrazine resulted in high click conjugation yields with a TCO in vivo, but to suboptimal drug release yields both in vitro and vivo.

Another publication ([Fan et al., Angew. Chem. Int. Ed., 2016, 55, 14046-14050]) aimed at in vitro reactions, showed that small, asymmetrical tetrazines give a higher conjugation reactivity with TCOs than symmetrical bis-alkyl-tetrazines, but the click-release yields were still not quantitative.

Two other publications [Carlson et al., J. Am. Chem. Soc. 2018, 140, 3603-3612] and [Sarris et al, Chemistry 2018, 24, 18075-18081] showed that bis-alkyl tetrazines containing carboxylate or amine groups can enhance the click-release rate, but these tetrazine remain relatively unreactive in the click-conjugation with TCO.

It is desired that compounds are developed that address one or more of the abovementioned problems and/or desires.

SUMMARY OF THE INVENTION

In one aspect, the present invention pertains to a compound satisfying Formula (19):

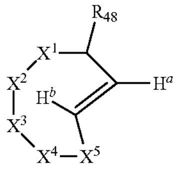

Formula (19), and pharmaceutically acceptable salts thereof, wherein $R_{48}$ is selected from the group consisting of —OH, —OC(O)Cl, —OC(O)O—N-succinimidyl, —OC(O)O-4-nitrophenyl, —OC(O)O-tetrafluorophenyl, —OC(O)O-pentafluorophenyl, —OC(O)—$(S^P)_kC^A$, —OC(S)—$(S^P)_kC^A$, —SC(O)—$(S^P)_kC^A$, —SC(S)—$(S^P)_kC^A$, —O-$(L^C((S^P)_kC^A)_s((S^P)_kC^A)_s((S^P)_i—C^B)_j)_r$—$(S^P)_kC^A$, —S-$(L^C((S^P)_kC^A)_s((S^P)_kC^A)_s((S^P)_i—C^B)_j)_r$—$(S^P)_kC^A$, and —$(S^P)_kC^A$;

r is an integer in range of from 0 to 2; each s is independently 0 or 1; each i is independently an integer in a range of from 0 to 4, preferably 0 or 1; j is an integer in range of from 0 to 4, preferably 0 or 1; each k is independently 0 or 1; $L^C$ is a self-immolative linker and $S^P$ is a spacer; each $C^A$ and $C^B$ are independently selected from the group consisting of organic molecules and inorganic molecules;

wherein at least one of conditions (a)-(c) is met:

(a) at least one of $X^1$, $X^2$, $X^3$, $X^4$, $X^5$, is $CR_{47}Y^{T1}$; and $Y^{T1}$ is positioned cis relative to $H^a$;

(b) $X^3$ is $Y^{T3}$; and (c) two adjacent X moieties selected from $X^1$, $X^2$, $X^3$, $X^4$, $X^5$, are part of a fused ring satisfying one of the Formulae (20a)-(20g):

(20a)

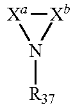

(20b)

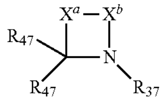

(20c)

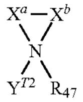

(20d)

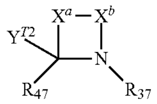

(20e)

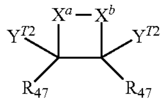

(20f)

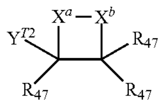

(20g)

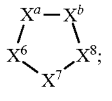

$Y^{T2}$ is positioned syn relative to the 8-membered dienophile ring;

wherein $X^a$ and $X^b$ are part of the 8-membered ring of Formula (19), such that $X^a$—$X^b$ or $X^b$—$X^a$ is $X^1$—$X^2$, $X^2$—$X^3$, $X^3$—$X^4$, or $X^4$—$X^5$;

for Formulae (20a)-(20c), $X^a$ and $X^b$ are $CR_{47}$, preferably CH;

for Formulae (20d)-(20g), $X^a$ and $X^b$ are independently $CR_{47}$ or N, preferably $CR_{47}$, more preferably CH;

$X^6$ and $X^8$ are each independently selected from the group consisting of $Y^{T3}$, $C(R_{47})Y^{T2}$, $C(R_{47})_2$, O, S, C(O), C(S), and $S(O)_2$;

$X^7$ is selected from the group consisting of $Y^{T3}$ and $Z^T$;

when $X^6$ is $Y^{T3}$, then $X^7$ is $Z^T$;

when $X^7$ is $Y^{T3}$, then $X^6$ and $X^8$ are each independently selected from the group consisting of $C(R_{47})Y^{T2}$, $C(R_{47})_2$, O, and S; preferably $C(R_{47})Y^{T2}$ or $C(R_{47})_2$;

wherein the fused ring satisfying Formula (20g) comprises at least one $Y^{T2}$ or $Y^{T3}$ moiety;

for Formulae (20b) and (20f), two $R_{47}$ directly connected to the same carbon may together be $=C-(R_{47})_2$, =S, or =O;

with the proviso that $X^1$—$X^2$, $X^2$—$X^3$, $X^3$—$X^4$, and $X^4$—$X^5$ are not —O—O—, —N—N—, —O—N— or —N—O—;

the direct bonds from $X^a$ and $X^b$ to the remainder of the ring fused to the 8-membered dienophile ring of Formulae (20a)-(20g) are cis relative to one another, and cis relative to $H^a$;

preferably no adjacent pairs of atoms being —O—O— are part of the fused rings of Formulae (20a)-(20g);

$Y^{T1}$ is selected from the group consisting of OH, SH, $N(R_{38})_2$, C(O)OH, C(S)OH, C(O)SH, C(S)SH, O—N$(R_{38})_2$, $SO_4H$, $SO_3H$, $SO_2H$, $PO_4H_2$, $PO_3H$, $PO_2H$, and $C(N)N(R_{38})_2$;

$Y^{T2}$ is selected from the group consisting of OH, SH, and $N(R_{38})_2$;

$Y^{T3}$ is $NR_{38}$ and is not flanked by C(O), C(S), S(O), or $S(O)_2$;

the remaining $X^1$, $X^2$, $X^3$, $X^4$, $X^5$, are independently selected from the group consisting of $C(R_{47})_2$ and O, such that at most two of $X^1$, $X^2$, $X^3$, $X^4$, $X^5$ are O, $NR_{38}$ or N;

wherein, when $R_{48}$ is $-OC(O)-(S^P)_kC^A$, $-OC(S)-(S^P)_kC^A$, $-SC(O)-(S^P)_kC^A$, or $-SC(S)-(S^P)_kC^A$, $S^P$ (when k>0) or $C^A$ (when k=0) is bound to the —OC(O)—, —OC(S)—, —SC(O)—, or —SC(S)— of $R_{48}$ via an atom selected from the group consisting of O, C, S, and N, preferably a secondary or a tertiary N, wherein this atom is part of $S^P$ or $C^A$; preferably $R_{48}$ is $-OC(O)-(S^P)_kC^A$ and $S^P$ or $C^A$ is bound to the —OC(O)— of $R_{48}$ via an N atom;

wherein, when $R_{48}$ is $-O-(L^C((S^P)_kC^A)_s((S^P)_kC^A)_s((S^P)_i-C^B))_r-(S^P)_kC^A$ or $-S-(L^C((S^P)_kC^A)_s((S^P)_kC^A)_s((S^P)_i-C^B))_r-(S^P)_kC^A$ and r is 0, $S^P$ (when k>0) or $C^A$(when k=0) is bound to the —O— or —S— moiety of $R_{48}$ on the allylic position of the trans-cyclooctene ring of Formula (19) via a group selected from the group consisting of —C(O)—, and —C(S)—, wherein this group is part of $S^P$ or $C^A$, wherein, when $R_{48}$ is $-O-(L^C((S^P)_kC^A)_s((S^P)_kC^A)_s((S^P)_i-C^B)_j)_r-(S^P)_kC^A$ or $-S-(L^C((S^P)_kC^A)_s((S^P)_kC^A)_s((S^P)_i-C^B)_j)_r-(S^P)_kC^A$ and r is 1, $L^C$ is bound to the —O— or —S— moiety on the allylic position of the trans-cyclooctene ring of Formula (19) via a group selected from the group consisting of $-C(Y^{C2})Y^{C1}-$, and a carbon atom, preferably an aromatic carbon, wherein this group is part of $L^C$, wherein $Y^{C1}$ is selected from the group consisting of —O—, —S—, and $-NR_{36}-$, wherein $Y^{C2}$ is selected from the group consisting of O and S, wherein, when $R_{48}$ is $-O-(L^C((S^P)_kC^A)_s((S^P)_kC^A)_s((S^P)_i-C^B)_j)_r-(S^P)_kC^A$, or $-S-(L^C((S^P)_kC^A)_s((S^P)_kC^A)_s((S^P)_i-C^B)_j)_r-(S^P)_kC^A$ and r is 1, then $S^P$ (when k>0) or $C^A$ (when k=0) is bound to $L^C$ via a moiety selected from the group consisting of —O—, —S—, and —N—, preferably a secondary or a tertiary N, wherein said moiety is part of $S^P$ or $C^A$, wherein, when $R_{48}$ is $-(S^P)_kC^A$, then $S^P$ (when k>0) or $C^A$ (when k=0) is bound to the allylic position of the trans-cyclooctene of Formula (19) via an —O— or an —S— atom, wherein this atom is part of $S^P$ or $C^A$, wherein $Z^T$ is selected from the group consisting of $C_1$-$C_{12}$ alkylene groups, $C_2$-$C_{12}$ alkenylene groups, $C_7$-$C_{12}$ alkynylene groups, $C_6$ arylene groups, $C_4$-$C_5$ heteroarylene groups, $C_3$-$C_8$ cycloalkylene groups, $C_5$-$C_8$ cycloalkenylene groups, $C_5$-$C_{12}$ alkyl(hetero)arylene groups, $C_5$-$C_{12}$ (hetero)arylalkylene groups, $C_4$-$C_{12}$ alkylcycloalkylene groups, $C_4$-$C_{12}$ cycloalkylalkylene groups, wherein the alkylene groups, alkenylene groups, alkynylene groups, (hetero)arylene groups, cycloalkylene groups, cycloalkenylene groups, alkyl(hetero)arylene groups, (hetero)arylalkylene groups, alkylcycloalkylene groups, cycloalkylalkylene groups, are optionally substituted with a moiety selected from the group consisting of $-(S^P)_i-C^B$ with i independently being an integer in a range of from 0 to 4, preferably i is 0 or 1, —Cl, —F, —Br, —I, $-OR_{37}$, $-N(R_{37})_2$, =O, $=NR_{37}$, $-SR_{37}$, $-SO_3H$, $-PO_3H$, $-PO_4H_2$, $-NO_2$ and $-Si(R_{37})_3$, and optionally contain one or more heteroatoms selected from the group consisting of —O—, —S—, $-NR_{37}-$, —P—, and —Si—, wherein the N, S, and P atoms are optionally oxidized, wherein the N atoms are optionally quaternized;

wherein each $R_{37}$ and $R_{36}$ are independently selected from the group consisting of hydrogen, $-(S^P)_i-C^B$, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ (cyclo)alkyl(hetero)aryl groups, $C_3$-$C_{24}$ (hetero)aryl(cyclo)alkyl, $C_4$-$C_{24}$ (cyclo)alkenyl(hetero)aryl groups, $C_4$-$C_{24}$ (hetero)aryl(cyclo)alkenyl groups, $C_4$-$C_{24}$ (cyclo)alkynyl (hetero)aryl groups, $C_4$-$C_{24}$ (hetero)aryl(cyclo)alkynyl groups, $C_4$-$C_{24}$ alkylcycloalkyl groups, and $C_4$-$C_{24}$ cycloalkylalkyl groups;

wherein i is an integer in a range of from 0 to 4, preferably i is 0 or 1;

wherein the $R_{37}$ and $R_{36}$ groups not being hydrogen are optionally substituted with a moiety selected from the group consisting of —Cl, —F, —Br, —I, —OH, $-NH_2$, $-SO_3H$, $-PO_3H$, $-PO_4H_2$, $-NO_2$, $-CF_3$, =O, =NH, and —SH, and optionally contain one or more heteroatoms selected from the group consisting of O, S, NH, P, and Si, wherein the N, S, and P atoms are optionally oxidized, wherein the N atoms are optionally quaternized, wherein $R_{38}$ is independently selected from the group listed for $R_{37}$ and $R_{36}$, with the proviso that $R_{38}$ is not attached to the remainder of the molecule via C(O), C(S), S(O), or $S(O)_2$;

wherein each $R_{47}$ is independently selected from the group consisting of hydrogen, $-(S^P)_i-C^B$, —F, —Cl, —Br, —I, $-OR_{37}$, $-N(R_{37})_2$, $-SO_3$, $-PO_3^-$, $-NO_2$, $-CF_3$, $-SR_{37}$, $S(=O)_2N(R_{37})_2$, $OC(=O)R_{37}$, $SC(=O)R_{37}$, $OC(=S)R_{37}$, $SC(=S)R_{37}$, $NR_{37}C(=O)-R_{37}$, $NR_{37}C(=S)-R_{37}$, $NR_{37}C(=O)O-R_{37}$, $NR_{37}C(=S)O-R_{37}$, $NR_{37}C(=O)S-R_{37}$, $NR_{37}C(=S)S-R_{37}$, $OC(=O)N(R_{37})_2$, $SC(=O)N(R_{37})_2$, $OC(=S)N(R_{37})_2$, $SC(=S)N(R_{37})_2$, $NR_{37}C(=O)N(R_{37})_2$, $NR_{37}C(=S)N(R_{37})_2$, $C(=O)R_{37}$, $C(=S)R_{37}$, $C(=O)N(R_{37})_2$, $C(=S)N(R_{37})_2$, $C(=O)O-R_{37}$, $C(=O)S-R_{37}$, $C(=S)O-R_{37}$, $C(=S)S-R_{37}$, $S(O)R_{37}$, $-S(O)_2R_{37}$, $NR_{37}S(O)_2R_{37}$, $-ON(R_{37})_2$, $-NR_{37}OR_{37}$, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ (cyclo)alkyl(hetero)aryl groups, $C_3$-$C_{24}$ (hetero)aryl(cyclo)alkyl, $C_4$-$C_{24}$ (cyclo)alkenyl(hetero) aryl groups, $C_4$-$C_{24}$ (hetero)aryl(cyclo)alkenyl groups, $C_4$-$C_{24}$ (cyclo)alkynyl(hetero)aryl groups, $C_4$-$C_{24}$ (hetero)aryl(cyclo)alkynyl groups, $C_4$-$C_{24}$ alkylcycloalkyl groups, and $C_4$-$C_{24}$ cycloalkylalkyl groups;

wherein i independently being an integer in a range of from 0 to 4, preferably i is an integer ranging from 0 to 1, wherein the alkyl groups, alkenyl groups, alkynyl groups, aryl, heteroaryl, cycloalkyl groups, cycloalkenyl groups, cycloalkynyl groups, (cyclo)alkyl(hetero)aryl groups, (hetero)aryl(cyclo)alkyl groups, (cyclo)alkenyl (hetero)aryl groups, (hetero)aryl(cyclo)alkenyl groups, (cyclo)alkynyl(hetero)aryl groups, (hetero)aryl(cyclo) alkynyl groups, alkylcycloalkyl groups, cycloalkylalkyl groups are optionally substituted with a moiety selected from the group consisting of $-Cl$, $-F$, $-Br$, $-I$, $-OR_{37}$, $-N(R_{37})_2$, $-SO_3R_{37}$, $-PO_3(R_{37})_2$, $-PO_4(R_{37})_2$, $-NO_2$, $-CF_3$, $=O$, $=NR_{37}$, and $-SR_{37}$, and optionally contain one or more heteroatoms selected from the group consisting of O, S, $NR_{37}$, P, and Si, wherein the N, S, and P atoms are optionally oxidized, wherein the N atoms are optionally quaternized, wherein two $R_{37}$, $R_{38}$, $R_{47}$ groups are optionally comprised in a ring, wherein two $R_{37}$, $R_{38}$, $R_{47}$ groups are optionally comprised in a ring so as to form a ring fused to the eight-membered trans-ring.

In a further aspect, the invention relates to a combination comprising the compound according to the invention, and a diene, preferably a tetrazine.

In yet another aspect, the invention relates to the compound of the invention, or the combination according to the invention for use as a medicament.

In another aspect still, the invention pertains to the compound of the invention, or the combination according to the invention for use in the treatment of a disease in a subject, preferably a human, wherein the disease is selected from the group consisting of cancer, central nervous system (CNS) diseases, infection, inflammation, cardiovascular diseases In another aspect still, the invention pertains to a non-therapeutic method for releasing a molecule from a compound according to the invention, said non-therapeutic method comprising the step of contacting a compound according to Formula (19) as defined herein with a diene as defined herein.

In another aspect, the invention relates to a non-therapeutic method for imaging a compound according to the invention in a subject, preferably a human, said non-therapeutic method comprising the steps of (a) administering a compound according to Formula (19) as defined herein comprising a label, to the subject;

(b) imaging the compound according to Formula (19) present in the subject; wherein the label is selected from the group consisting of radionuclides, fluorescent dyes, and phosphorescent dyes.

In another aspect, the invention relates to a non-therapeutic use of a compound according to the invention, or a combination according to the invention, for imaging in a subject, preferably a human, wherein the compound, or in case of the combination at least one of the compound according to Formula (19) and the diene, comprises a label selected from the group consisting of radionuclides, fluorescent dyes, and phosphorescent dyes.

In another aspect still, the invention pertains to a non-therapeutic use of a compound according to the invention, or a combination according to the invention, for releasing a molecule, preferably in vitro.

DETAILED DESCRIPTION OF THE INVENTION

Figure 1:
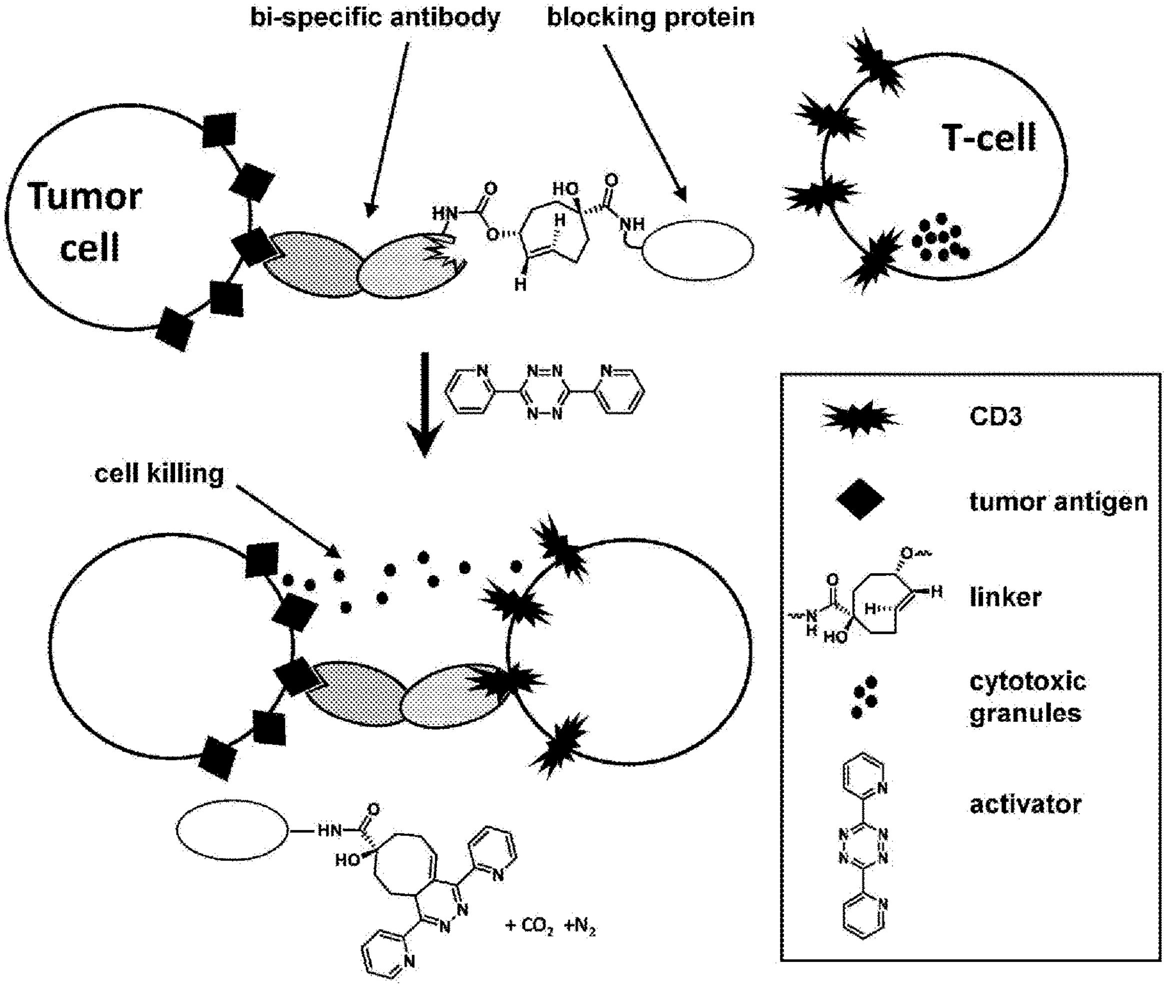
FIG. 1 depicts a preferred embodiment of this invention. In both panels an ADC is administered to a cancer patient, and is allowed to circulate and bind to a target on the cancer cell. After the freely circulating ADC has sufficiently cleared from circulation, for example after 2 days post injection, the Activator, is administered and distributes systemically, allowing the reaction with the Trigger of cancer-bound Prodrug or ADC, releasing the Drug, after which the Drug can penetrate and kill neighbouring cancer cells. Panel A depicts the cleavage of a carbamate-linked Drug and Panel B depicts the cleavage of an ether-linked Drug.

The invention is based on the judicious insight that compounds, combinations, and kits according to the invention better address one or more of the abovementioned desires. This is surprising, for at least the reason that these desires are met by specific features of a dienophile, rather than of a diene where the background art focused on.

In one aspect, the use of compounds, combinations, and kits according to the invention results in a high release yield and/or a fast release.

In another aspect, the use of compounds, combinations, and kits according to the invention results in a fast release.

In another aspect, the use of compounds, combinations, and kits according to the invention results in a fast click-conjugation and a high release yield and/or release rate.

The invention, in a broad sense, is based on the judicious insight that a compound according to Formula (19) as described herein meets one or more of the abovementioned desires and/or resolves one or more of the abovementioned problems.

In another aspect, it is found that a combination of a compound according to Formula (19) as described herein and a diene as defined herein meets one or more of the abovementioned desires and/or resolves one or more of the abovementioned problems.

In yet another aspect, it is found that a kit comprising a combination according to the invention meets one or more of the abovementioned desires and/or resolves one or more of the abovementioned problems.

In a further aspect still, it is found that a combination according to the invention, and a kit according to the invention is useful in the treatment or imaging of patients or animals.

In yet a further aspect, it is found that a compound according to the invention, a combination according to the invention and a kit according to the invention are useful in bioorthogonal reactions in vitro and/or in vivo.

Without wishing to be bound by theory, the inventors believe that the presence of the $Y^{T1}$, $Y^{T2}$ and/or $Y^{T3}$ groups as defined herein in the structures according to Formula (19) results in a higher click release yield and/or click release rate when contacted with a diene, as compared to known TCOs, in particular as compared to the same TCO lacking the said $Y^{T1}$, $Y^{T2}$ and/or $Y^{T3}$ groups. Still without wishing to be bound by theory, the inventors currently believe that this is the result of a destabilizing effect on the dihydropyridazine tautomer intermediates, in particular the 4,5- and/or the 1,4-dihydropyridazine tautomer intermediate that is formed upon conjugation of the TCO to a tetrazine.

Furthermore, it was found that compounds according to Formula (19) as described herein give high click release yields and release rates when being contacted with dienes that give high click conjugation yields and rates.

With reference to an example in Scheme 1A and without wishing to be bound to theory, the inventors believe that upon formation of the 4,5-dihydropyridazine tautomer 3, the $Y^{T1}$ moiety (for example OH, $NH_2$) engages in an hydrogen bond with cis-positioned $H_a$, inducing deprotonation and tautomerization to specifically the 1,4-dihydropyridazine intermediate 4, which then eliminates $C^A$ through pathway A and/or B. Pathway A comprises an 1,4-elimination affording free $C^A$, 5 and subsequently 6. Pathway B comprises a nucleophilic attack of $Y^{T1}$ on the carbon to which $C^A$ is attached via a carbamate linker, resulting in cyclization-mediated release of $C^A$ and formation of 7 and 8. The inventors believe that suitably positioned $Y^{T1}$, $Y^{T2}$, and $Y^{T3}$ moieties result in rapid and high yielding release through one or both of these pathways.

Scheme 1A. Proposed IEDDA pyridazine elimination mechanisms of this invention.

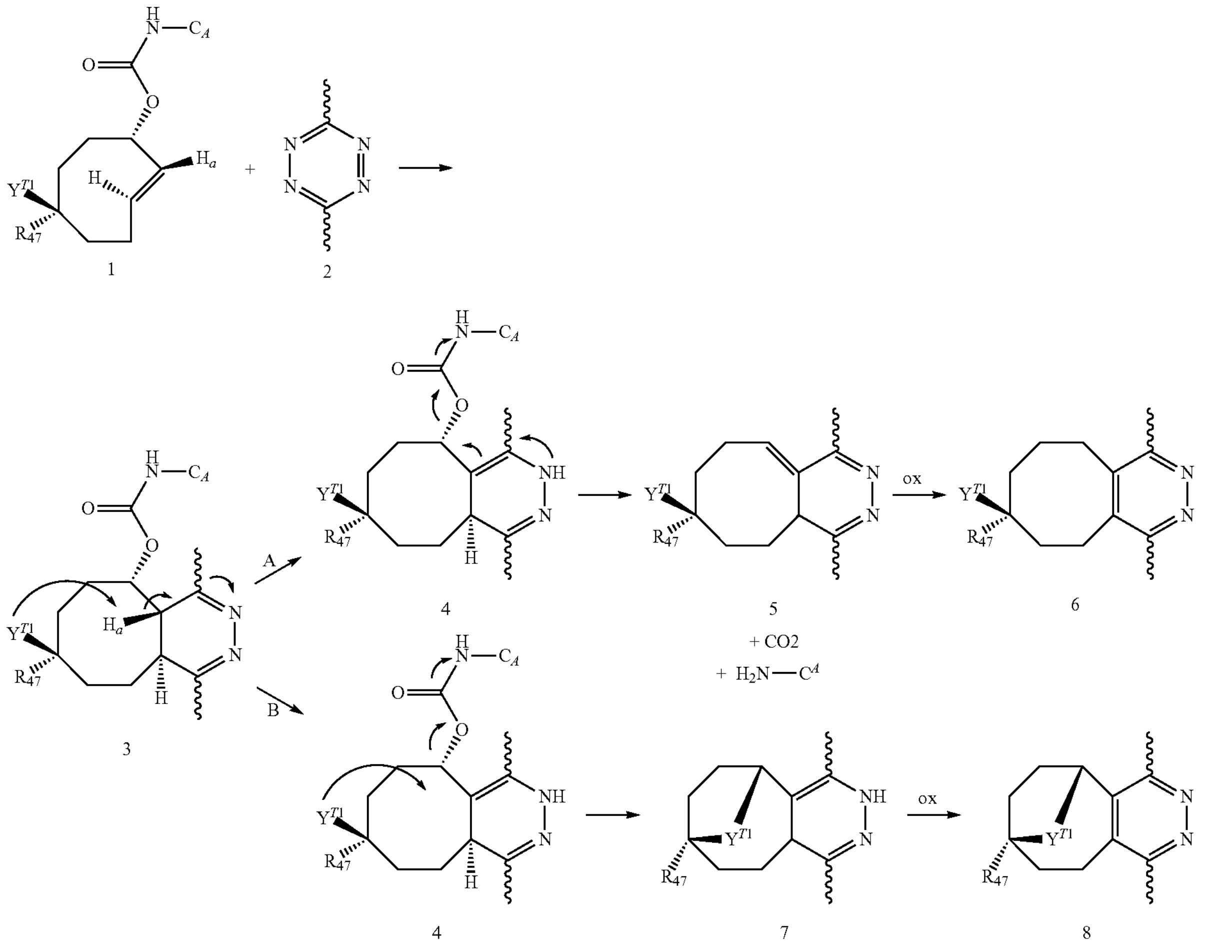

1 2 3 4 5 6 4 7 8

Definitions

The present invention will further be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where an indefinite or definite article is used when referring to a singular noun e.g. "a" or "an", "the", this includes a plural of that noun unless something else is specifically stated.

The verb "to comprise", and its conjugations, as used in this description and in the claims is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

Thus, the scope of the expression "a device comprising means A and B" should not be limited to devices consisting only of components A and B. It means that with respect to the present invention, the only relevant components of the device are A and B.

The compounds disclosed in this description and in the claims may comprise one or more asymmetric centres, and different diastereomers and/or enantiomers may exist of the compounds. The description of any compound in this description and in the claims is meant to include all diastereomers, and mixtures thereof, unless stated otherwise. Thus, it will be understood that if herein a specific stereoisomer is indicated, the compound is limited to this specific stereoisomer. For example, in Formula (19) $Y^{T2}$ is positioned syn relative to the 8-membered dienophile ring. While this includes enantiomers that are still syn, it does not include stereoisomers in which $Y^{T2}$ is positioned anti relative to the 8-membered dienophile ring.

In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer, unless stated otherwise. When the structure of a compound is depicted as a specific diastereomer, it is to be understood that the invention of the present application is not limited to that specific diastereomer, unless stated otherwise.

The compounds may occur in different tautomeric forms. The compounds according to the invention are meant to include all tautomeric forms, unless stated otherwise. When the structure of a compound is depicted as a specific tautomer, it is to be understood that the invention of the present application is not limited to that specific tautomer, unless stated otherwise.

The compounds disclosed in this description and in the claims may further exist as exo and endo diastereomers. Unless stated otherwise, the description of any compound in the description and in the claims is meant to include both the individual exo and the individual endo diastereomers of a compound, as well as mixtures thereof. When the structure of a compound is depicted as a specific endo or exo diastereomer, it is to be understood that the invention of the present application is not limited to that specific endo or exo diastereomer, unless stated otherwise.

The compounds disclosed in this description and in the claims may further exist as anti and syn diastereomers. Unless stated otherwise, the description of any compound in the description and in the claims is meant to include both the individual anti and the individual syn diastereomers of a compound, as well as mixtures thereof. When the structure of a compound is depicted as a specific syn or anti diastereomer, it is to be understood that the invention of the present application is not limited to that specific syn or anti diastereomer, unless stated otherwise.

With respect to Formula (19), wherein $Y^{T2}$ is positioned syn relative to the 8-membered dienophile ring; with "syn" it is meant that $Y^{T2}$ is on the same side of the ring fused to the 8-membered dienophile ring as the 8-membered dienophile ring. Persons skilled in the art will understand that the syn-positioned $Y^{T2}$ is facing towards the 8-membered dienophile as opposed to facing away, and can also be defined as being positioned endo relative to the 8-membered dienophile ring. In particular it is meant that $Y^{T2}$ is facing towards the X moieties that flank $X_a$ and $X_b$, and that are selected from $X^1$, $X^2$, $X^3$, $X^4$, $X^5$. For the sake of clarity, "facing towards" will be understood as "being closer to". Further for the sake of clarity with "positioned syn" it is meant that $Y^{T2}$ is positioned cis relative to the X moieties that flank $X_a$ and $X_b$ and that are selected from $X^1$, $X^2$, $X^3$, $X^4$, $X^5$. Further for the sake of clarity it is meant that $Y^{T2}$ is positioned cis relative to the direct bonds from $X^a$ and $X^b$ to the remainder of the 8-membered dienophile ring.

Unless stated otherwise, the compounds of the invention and/or groups thereof may be protonated or deprotonated. It will be understood that it is possible that a compound may bear multiple charges which may be of opposite sign. For example, in a compound containing an amine and a carboxylic acid, the amine may be protonated while simultaneously the carboxylic acid is deprotonated.

In several formulae, groups or substituents are indicated with reference to letters such as "A", "B", "X", "Y", and various (numbered) "R" groups. In addition, the number of repeating units may be referred to with a letter, e.g. n in $-(CH_2)_n-$. The definitions of these letters are to be read with reference to each formula, i.e. in different formulae these letters, each independently, can have different meanings unless indicated otherwise.

In several chemical formulae and texts below reference is made to "alkyl", "heteroalkyl", "aryl", "heteroaryl", "alkenyl", "alkynyl", "alkylene", "alkenylene", "alkynylene", "arylene", "cycloalkyl", "cycloalkenyl", "cycloakynyl", arenetriyl, and the like. The number of carbon atoms that these groups have, excluding the carbon atoms comprised in any optional substituents as defined below, can be indicated by a designation preceding such terms (e.g. "$C_1$-$C_8$ alkyl" means that said alkyl may have from 1 to 8 carbon atoms). For the avoidance of doubt, a butyl group substituted with a $-OCH_3$ group is designated as a $C_4$ alkyl, because the carbon atom in the substituent is not included in the carbon count.

Unsubstituted alkyl groups have the general formula $C_nH_{2n+1}$ and may be linear or branched. Optionally, the alkyl groups are substituted by one or more substituents further specified in this document. Examples of alkyl groups include methyl, ethyl, propyl, 2-propyl, t-butyl, 1-hexyl, 1-dodecyl, etc. Unless stated otherwise, an alkyl group optionally contains one or more heteroatoms independently selected from the group consisting of O, $NR_5$, S, P, and Si, wherein the N, S, and P atoms are optionally oxidized and the N atoms are optionally quaternized. In preferred embodiments, up to two heteroatoms may be consecutive, such as in for example —$CH_2$—NH—$OCH_3$ and —$CH_2$—O—Si$(CH_3)_3$. In some preferred embodiments the heteroatoms are not directly bound to one another. Examples of heteroalkyls include —$CH_2CH_2$—O—$CH_3$, —$CH_2CH_2$—NH—$CH_3$, —$CH_2CH_2$—S(O)—$CH_3$, —CH═CHO—$CH_3$, —Si$(CH_3)_3$. In preferred embodiments, a $C_1$-$C_4$ alkyl contains at most 2 heteroatoms.

A cycloalkyl group is a cyclic alkyl group. Unsubstituted cycloalkyl groups comprise at least three carbon atoms and have the general formula $C_nH_{2n-1}$. Optionally, the cycloalkyl groups are substituted by one or more substituents further specified in this document. Examples of cycloalkyl groups include cyclopropyl, cyclobutyl, cyclopentyl and cyclohexyl. Unless stated otherwise, a cycloalkyl group optionally contains one or more heteroatoms independently selected from the group consisting of O, $NR_5$, S, P, and Si, wherein the N, S, and P atoms are optionally oxidized and the N atoms are optionally quaternized.

An alkenyl group comprises one or more carbon-carbon double bonds, and may be linear or branched. Unsubstituted alkenyl groups comprising one C—C double bond have the general formula $C_nH_{2n-1}$. Unsubstituted alkenyl groups comprising two C—C double bonds have the general formula $C_nH_{2n-3}$. An alkenyl group may comprise a terminal carbon-carbon double bond and/or an internal carbon-carbon double bond. A terminal alkenyl group is an alkenyl group wherein a carbon-carbon double bond is located at a terminal position of a carbon chain. An alkenyl group may also comprise two or more carbon-carbon double bonds. Examples of an alkenyl group include ethenyl, propenyl, isopropenyl, t-butenyl, 1,3-butadienyl, 1,3-pentadienyl, etc. Unless stated otherwise, an alkenyl group may optionally be substituted with one or more, independently selected, substituents as defined below. Unless stated otherwise, an alkenyl group optionally contains one or more heteroatoms independently selected from the group consisting of O, $NR_5$, S, P, and Si, wherein the N, S, and P atoms are optionally oxidized and the N atoms are optionally quaternized.

An alkynyl group comprises one or more carbon-carbon triple bonds, and may be linear or branched. Unsubstituted alkynyl groups comprising one C—C triple bond have the general formula $C_nH_{2n-3}$. An alkynyl group may comprise a terminal carbon-carbon triple bond and/or an internal carbon-carbon triple bond. A terminal alkynyl group is an alkynyl group wherein a carbon-carbon triple bond is located at a terminal position of a carbon chain. An alkynyl group may also comprise two or more carbon-carbon triple bonds. Unless stated otherwise, an alkynyl group may optionally be substituted with one or more, independently selected, substituents as defined below. Examples of an alkynyl group include ethynyl, propynyl, isopropynyl, t-butynyl, etc. Unless stated otherwise, an alkynyl group optionally contains one or more heteroatoms independently selected from the group consisting of O, $NR_5$, S, P, and Si, wherein the N, S, and P atoms are optionally oxidized and the N atoms are optionally quaternized.

An aryl group refers to an aromatic hydrocarbon ring system that comprises six to twenty-four carbon atoms, more preferably six to twelve carbon atoms, and may include monocyclic and polycyclic structures. When the aryl group is a polycyclic structure, it is preferably a bicyclic structure. Optionally, the aryl group may be substituted by one or more substituents further specified in this document. Examples of aryl groups are phenyl and naphthyl.

Arylalkyl groups and alkylaryl groups comprise at least seven carbon atoms and may include monocyclic and bicyclic structures. Optionally, the arylalkyl groups and alkylaryl may be substituted by one or more substituents further specified in this document. An arylalkyl group is for example benzyl. An alkylaryl group is for example 4-tert-butylphenyl.

Preferably, heteroaryl groups comprise five to sixteen carbon atoms and contain between one to five heteroatoms. Heteroaryl groups comprise at least two carbon atoms (i.e. at least $C_2$) and one or more heteroatoms N, O, P or S. A heteroaryl group may have a monocyclic or a bicyclic structure. Optionally, the heteroaryl group may be substituted by one or more substituents further specified in this document. Examples of suitable heteroaryl groups include pyridinyl, quinolinyl, pyrimidinyl, pyrazinyl, pyrazolyl, imidazolyl, thiazolyl, pyrrolyl, furanyl, triazolyl, benzofuranyl, indolyl, purinyl, benzoxazolyl, thienyl, phospholyl and oxazolyl.

Heteroarylalkyl groups and alkylheteroaryl groups comprise at least three carbon atoms (i.e. at least $C_3$) and may include monocyclic and bicyclic structures. Optionally, the heteroaryl groups may be substituted by one or more substituents further specified in this document.

Where an aryl group is denoted as a (hetero)aryl group, the notation is meant to include an aryl group and a heteroaryl group. Similarly, an alkyl(hetero)aryl group is meant to include an alkylaryl group and an alkylheteroaryl group, and (hetero)arylalkyl is meant to include an arylalkyl group and a heteroarylalkyl group. A $C_2$-$C_{24}$ (hetero)aryl group is thus to be interpreted as including a $C_2$-$C_{24}$ heteroaryl group and a $C_6$-$C_{24}$ aryl group. Similarly, a $C_3$-$C_{24}$ alkyl(hetero)aryl group is meant to include a $C_7$-$C_{24}$ alkylaryl group and a $C_3$-$C_{24}$ alkylheteroaryl group, and a $C_3$-$C_{24}$ (hetero)arylalkyl is meant to include a $C_7$-$C_{24}$ arylalkyl group and a $C_3$-$C_{24}$ heteroarylalkyl group.

A cycloalkenyl group is a cyclic alkenyl group. An unsubstituted cycloalkenyl group comprising one double bond has the general formula $C_nH_{2n-3}$. Optionally, a cycloalkenyl group is substituted by one or more substituents further specified in this document. An example of a cycloalkenyl group is cyclopentenyl. Unless stated otherwise, a cycloalkenyl group optionally contains one or more heteroatoms independently selected from the group consisting of O, $NR_5$, S, P, and Si, wherein the N, S, and P atoms are optionally oxidized and the N atoms are optionally quaternized.

A cycloalkynyl group is a cyclic alkynyl group. An unsubstituted cycloalkynyl group comprising one triple bond has the general formula $C_nH_{2n-5}$. Optionally, a cycloalkynyl group is substituted by one or more substituents further specified in this document. An example of a cycloalkynyl group is cyclooctynyl. Unless stated otherwise, a cycloalkynyl group optionally contains one or more heteroatoms independently selected from the group consisting of O, $NR_5$, S, P, and Si, wherein the N, S, and P atoms are optionally oxidized and the N atoms are optionally quaternized.

When referring to a (hetero)aryl group the notation is meant to include an aryl group and a heteroaryl group. An alkyl(hetero)aryl group refers to an alkylaryl group and an alkylheteroaryl group. A (hetero)arylalkyl group refers to an arylalkyl group and a heteroarylalkyl group. In general, when (hetero) is placed before a group, it refers to both the variant of the group without the prefix hetero- as well as the group with the prefix hetero-.

Herein, the prefix hetero- denotes that the group contains one or more heteroatoms selected from the group consisting of O, N, S, P, and Si. It will be understood that groups with the prefix hetero- by definition contain heteroatoms. Hence, it will be understood that if a group with the prefix hetero- is part of a list of groups that is defined as optionally containing heteroatoms, that for the groups with the prefix hetero- it is not optional to contain heteroatoms, but is the case by definition.

Herein, it will be understood that when the prefix hetero- is used for combinations of groups, the prefix hetero- only refers to the one group before it is directly placed. For example, heteroarylalkyl denotes the combination of a heteroaryl group and an alkyl group, not the combination of a heteroaryl and a heteroalkyl group. As such, it will be understood that when the prefix hetero- is used for a combination of groups that is part of a list of groups that are indicated to optionally contain heteroatoms, it is only optional for the group within the combination without the prefix hetero- to contain a heteroatom, as it is not optional for the group within the combination with the prefix hetero- by definition (see above). For example, if heteroarylalkyl is part of a list of groups indicated to optionally contain heteroatoms, the heteroaryl part is considered to contain heteroatoms by definition, while for the alkyl part it is optional to contain heteroatoms.

Herein, the prefix cyclo- denotes that groups are cyclic. It will be understood that when the prefix cyclo- is used for combinations of groups, the prefix cyclo- only refers to the one group before it is directly placed. For example, cycloalkylalkenylene denotes the combination of a cycloalkylene group (see the definition of the suffix -ene below) and an alkenylene group, not the combination of a cycloalkylene and a cycloalkenylene group.

In general, when (cyclo) is placed before a group, it refers to both the variant of the group without the prefix cyclo- as well as the group with the prefix cyclo-.

Herein, the suffix -ene denotes divalent groups, i.e. that the group is linked to at least two other moieties. An example of an alkylene is propylene ($—CH_2—CH_2—CH_2—$), which is linked to another moiety at both termini. It is understood that if a group with the suffix -ene is substituted at one position with —H, then this group is identical to a group without the suffix. For example, an alkylene substituted with —H is identical to an alkyl group. I.e. propylene, $—CH_2—CH_2—CH_2—$, substituted with —H at one terminus, $—CH_2—CH_2—CH_2—H$, is logically identical to propyl, $—CH_2—CH_2—CH_3$.

Herein, when combinations of groups are listed with the suffix -ene, it refers to a divalent group, i.e. that the group is linked to at least two other moieties, wherein each group of the combination contains one linkage to one of these two moieties. As such, for example alkylarylene is understood as a combination of an arylene group and an alkylene group. An example of an alkylarylene group is -phenyl-$CH_2$—, and an example of an arylalkylene group is —$CH_2$-phenyl-.

Herein, the suffix -triyl denotes trivalent groups, i.e. that the group is linked to at least three other moieties. An example of an arenetriyl is depicted below:

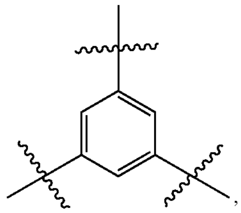 [SMILES: *c1cc(*)cc(*)c1], wherein the wiggly lines denote bonds to different groups of the main compound.

It is understood that if a group with the suffix -triyl is substituted at one position with —H, then this group is identical to a divalent group with the suffix -ene. For example, an arenetriyl substituted with —H is identical to an arylene group. Similarly, it is understood that if a group with the suffix -triyl is substituted at two positions with —H, then this group is identical to a monovalent group. For example, an arenetriyl substituted with two —H is identical to an aryl group.

It is understood that if a group, for example an alkyl group, contains a heteroatom, then this group is identical to a hetero-variant of this group. For example, if an alkyl group contains a heteroatom, this group is identical to a heteroalkyl group. Similarly, if an aryl group contains a heteroatom, this group is identical to a heteroaryl group. It is understood that "contain" and its conjugations mean herein that when a group contains a heteroatom, this heteroatom is part of the backbone of the group. For example, a $C_2$ alkylene containing an N refers to $—NH—CH_2—CH_2—$, $—CH_2—NH—CH_2—$, and $—CH_2—CH_2—NH—$.

Unless indicated otherwise, a group may contain a heteroatom at non-terminal positions or at one or more terminal positions. In this case, "terminal" refers to the terminal position within the group, and not necessarily to the terminal position of the entire compound. For example, if an ethylene group contains a nitrogen atom, this may refer to $—NH—CH_2—CH_2—$, $—CH_2—NH—CH_2—$, and $—CH_2—CH_2—NH—$. For example, if an ethyl group contains a nitrogen atom, this may refer to $—NH—CH_2—CH_3$, $—CH_2—NH—CH_3$, and $—CH_2—CH_2—NH_2$.

Herein, it is understood that cyclic compounds (i.e. aryl, cycloalkyl, cycloalkenyl, etc.) are understood to be monocyclic, polycyclic or branched. It is understood that the number of carbon atoms for cyclic compounds not only refers to the number of carbon atoms in one ring, but that the carbon atoms may be comprised in multiple rings. These rings may be fused to the main ring or substituted onto the main ring. For example, $C_{10}$ aryl optionally containing heteroatoms may refer to inter alia a naphthyl group (fused rings) or to e.g. a bipyridyl group (substituted rings, both containing an N atom).

Unless stated otherwise, (hetero)alkyl groups, (hetero) alkenyl groups, (hetero)alkynyl groups, (hetero)cycloalkyl groups, (hetero)cycloalkenyl groups, (hetero)cycloalkynyl groups, (hetero)alkylcycloalkyl groups, (hetero)alkylcycloalkenyl groups, (hetero)alkylcycloalkynyl groups, (hetero)cycloalkylalkyl groups, (hetero)cycloalkenylalkyl groups, (hetero)cycloalkynylalkyl groups, (hetero)alkenylcycloalkyl groups, (hetero)alkenylcycloalkenyl groups, (hetero)alkenylcycloalkynyl groups, (hetero)cycloalkylalkenyl groups, (hetero)cycloalkenylalkenyl groups, (hetero) cycloalkynylalkenyl groups, (hetero)alkynylcycloalkyl groups, (hetero)alkynylcycloalkenyl groups, (hetero)alkynylcycloalkynyl groups, (hetero)cycloalkylalkynyl groups, (hetero)cycloalkenylalkynyl groups, (hetero)cycloalkynylalkynyl groups, (hetero)aryl groups, (hetero)arylalkyl groups, (hetero)arylalkenyl groups, (hetero)arylalkynyl groups, alkyl(hetero)aryl groups, alkenyl(hetero)aryl groups, alkynyl(hetero)aryl groups, cycloalkyl(hetero)aryl groups, cycloalkenyl(hetero)aryl groups, cycloalkynyl(hetero)aryl groups, (hetero)arylcycloalkyl groups, (hetero)arylcycloalkenyl groups, (hetero)arylcycloalkynyl groups, (hetero)alkylene groups, (hetero)alkenylene groups, (hetero) alkynylene groups, (hetero)cycloalkylene groups, (hetero) cycloalkenylene groups, (hetero)cycloalkynylene groups, (hetero)arylene groups, alkyl(hetero)arylene groups, (hetero)arylalkylene groups, (hetero)arylalkenylene groups, (hetero)arylalkynylene groups, alkenyl(hetero)arylene, alkynyl(hetero)arylene, (hetero)arenetriyl groups, (hetero) cycloalkanetriyl groups, (hetero)cycloalkenetriyl and (hetero)cycloalkynetriyl groups are optionally substituted with one or more substituents independently selected from the group consisting of —Cl, —F, —Br, —I, —OH, $—NH_2$, $—SO_3H$, $—PO_3H$, $—PO_4H_2$, $—NO_2$, $—CF_3$, ═O, $═NR_5$, $—SR_5$, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ alkyl(hetero) aryl groups, $C_3$-$C_{24}$ (hetero)arylalkyl groups, $C_4$-$C_{24}$ (hetero)arylalkenyl groups, $C_4$-$C_{24}$ (hetero)arylalkynyl groups, $C_4$-$C_{24}$ alkenyl(hetero)aryl groups, $C_4$-$C_{24}$ alkynyl(hetero) aryl groups, $C_4$-$C_{24}$ alkylcycloalkyl groups, $C_6$-$C_{24}$ alkylcycloalkenyl groups, $C_{13}$-$C_{24}$ alkylcycloalkynyl groups, $C_4$-$C_{24}$ cycloalkylalkyl groups, $C_6$-$C_{24}$ cycloalkenylalkyl groups, $C_{13}$-$C_{24}$ cycloalkynylalkyl groups, $C_5$-$C_{24}$ alkenylcycloalkyl groups, $C_7$-$C_{24}$ alkenylcycloalkenyl groups, $C_{14}$-$C_{24}$ alkenylcycloalkynyl groups, $C_5$-$C_{24}$ cycloalkylalkenyl groups, $C_7$-$C_{24}$ cycloalkenylalkenyl groups, $C_{14}$-$C_{24}$ cycloalkynylalkenyl groups, $C_5$-$C_{24}$ alkynylcycloalkyl groups, $C_7$-$C_{24}$ alkynylcycloalkenyl groups, $C_{14}$-$C_{24}$ alkynylcycloalkynyl groups, $C_5$-$C_{24}$ cycloalkylalkynyl groups, $C_7$-$C_{24}$ cycloalkenylalkynyl groups, $C_{14}$-$C_{24}$ cycloalkynylalkynyl groups, $C_5$-$C_{24}$ cycloalkyl(hetero)aryl groups, $C_7$-$C_{24}$ cycloalkenyl(hetero)aryl groups, $C_{14}$-$C_{24}$ cycloalkynyl(hetero)aryl groups, $C_5$-$C_{24}$ (hetero)arylcycloalkyl groups, $C_7$-$C_{24}$ (hetero)arylcycloalkenyl groups, and $C_{14}$-$C_{24}$ (hetero)arylcycloalkynyl groups. Unless stated otherwise, the substituents disclosed herein optionally contain one or more heteroatoms selected from the group consisting of O, S, NRs, P, and Si, wherein the N, S, and P atoms are optionally oxidized, wherein the N atoms are optionally quaternized. Preferably, these substituents optionally contain one or more heteroatoms selected from the group consisting of 0, S, and $NR_5$.

In preferred embodiments, the substituents are selected from the group consisting of —Cl, —F, —Br, —I, —OH, $—NH_2$, $—SO_3H$, $—PO_3H$, $—PO_4H_2$, $—NO_2$, $—CF_3$, ═O, $═NR_5$, $—SR_5$, $C_1$-$C_{12}$ alkyl groups, $C_2$-$C_{12}$ alkenyl groups, $C_2$-$C_{12}$ alkynyl groups, $C_6$-$C_{12}$ aryl groups, $C_2$-$C_{12}$ heteroaryl groups, $C_3$-$C_{12}$ cycloalkyl groups, $C_5$-$C_{12}$ cycloalkenyl groups, $C_{12}$ cycloalkynyl groups, $C_3$-$C_{12}$ alkyl(hetero) aryl groups, $C_3$-$C_{12}$ (hetero)arylalkyl groups, $C_4$-$C_{12}$ (hetero)arylalkenyl groups, $C_4$-$C_{12}$ (hetero)arylalkynyl groups, $C_4$-$C_{12}$ alkenyl(hetero)aryl groups, $C_4$-$C_{12}$ alkynyl (hetero)aryl groups, $C_4$-$C_{12}$ alkylcycloalkyl groups, $C_6$-$C_{12}$ alkylcycloalkenyl groups, $C_{13}$-$C_{16}$ alkylcycloalkynyl groups, $C_4$-$C_{12}$ cycloalkylalkyl groups, $C_6$-$C_{12}$ cycloalkenylalkyl groups, $C_{13}$-$C_{16}$ cycloalkynylalkyl groups, $C_5$-$C_{12}$ alkenylcycloalkyl groups, $C_7$-$C_{12}$ alkenylcycloalkenyl groups, $C_{14}$-$C_{16}$ alkenylcycloalkynyl groups, $C_5$-$C_{12}$ cycloalkylalkenyl groups, $C_7$-$C_{12}$ cycloalkenylalkenyl groups, $C_{14}$-$C_{16}$ cycloalkynylalkenyl groups, $C_5$-$C_{12}$ alkynylcycloalkyl groups, $C_7$-$C_{12}$ alkynylcycloalkenyl groups, $C_{14}$-$C_{16}$ alkynylcycloalkynyl groups, $C_5$-$C_{12}$ cycloalkylalkynyl groups, $C_7$-$C_{12}$ cycloalkenylalkynyl groups, $C_{14}$-$C_{16}$ cycloalkynylalkynyl groups, $C_5$-$C_{12}$ cycloalkyl(hetero)aryl groups, $C_7$-$C_{12}$ cycloalkenyl(hetero)aryl groups, $C_{14}$-$C_{16}$ cycloalkynyl(hetero)aryl groups, $C_5$-$C_{12}$ (hetero)arylcycloalkyl groups, $C_7$-$C_{12}$ (hetero)arylcycloalkenyl groups, and $C_{14}$-$C_{16}$ (hetero)arylcycloalkynyl groups.

In preferred embodiments, the substituents are selected from the group consisting of —Cl, —F, —Br, —I, —OH, $—NH_2$, $—SO_3H$, $—PO_3H$, $—PO_4H_2$, $—NO_2$, $—CF_3$, ═O, $═NR_5$, $—SR_5$, $C_1$-$C_7$ alkyl groups, $C_2$-$C_7$ alkenyl groups, $C_2$-$C_7$ alkynyl groups, $C_6$-$C_7$ aryl groups, $C_2$-$C_7$ heteroaryl groups, $C_3$-$C_7$ cycloalkyl groups, $C_5$-$C_7$ cycloalkenyl groups, $C_{12}$ cycloalkynyl groups, $C_3$-$C_7$ alkyl(hetero)aryl groups, $C_3$-$C_7$ (hetero)arylalkyl groups, $C_4$-$C_7$ (hetero)arylalkenyl groups, $C_4$-$C_7$ (hetero)arylalkynyl groups, $C_4$-$C_7$ alkenyl(hetero)aryl groups, $C_4$-$C_7$ alkynyl(hetero)aryl groups, $C_4$-$C_7$ alkylcycloalkyl groups, $C_6$-$C_7$ alkylcycloalkenyl groups, $C_{13}$-$C_{16}$ alkylcycloalkynyl groups, $C_4$-$C_7$ cycloalkylalkyl groups, $C_6$-$C_7$ cycloalkenylalkyl groups, $C_{13}$-$C_{16}$ cycloalkynylalkyl groups, $C_5$-$C_7$ alkenylcycloalkyl groups, $C_7$-$C_7$ alkenylcycloalkenyl groups, $C_{14}$-$C_{16}$ alkenylcycloalkynyl groups, $C_5$-$C_7$ cycloalkylalkenyl groups, $C_7$-$C_8$ cycloalkenylalkenyl groups, $C_{14}$-$C_{16}$ cycloalkynylalkenyl groups, $C_5$-$C_7$ alkynylcycloalkyl groups, $C_7$-$C_8$ alkynylcycloalkenyl groups, $C_{14}$-$C_{16}$ alkynylcycloalkynyl groups, $C_5$-$C_7$ cycloalkylalkynyl groups, $C_7$-$C_8$ cycloalkenylalkynyl groups, $C_{14}$-$C_{16}$ cycloalkynylalkynyl groups, $C_5$-$C_7$ cycloalkyl(hetero)aryl groups, $C_7$-$C_8$ cycloalkenyl (hetero)aryl groups, $C_{14}$-$C_{16}$ cycloalkynyl(hetero)aryl groups, $C_5$-$C_7$ (hetero)arylcycloalkyl groups, $C_7$-$C_8$ (hetero) arylcycloalkenyl groups, and $C_{14}$-$C_{16}$ (hetero)arylcycloalkynyl groups, $C_4$-$C_8$ (hetero)arylalkenyl groups, $C_4$-$C_8$ (hetero)arylalkynyl groups, $C_4$-$C_8$ alkenyl(hetero)aryl groups, $C_4$-$C_8$ alkynyl(hetero)aryl groups, $C_5$-$C_9$ cycloalkyl(hetero) aryl groups, $C_7$-$C_1$ cycloalkenyl(hetero)aryl groups, $C_{14}$-$C_{18}$ cycloalkynyl(hetero)aryl groups, $C_5$-$C_9$ (hetero)arylcycloalkyl groups, $C_7$-$C_{11}$ (hetero)arylcycloalkenyl groups, and $C_{14}$-$C_{18}$ (hetero)arylcycloalkynyl groups.

Unless stated otherwise, any group disclosed herein that is not cyclic is understood to be linear or branched. In particular, hetero)alkyl groups, (hetero)alkenyl groups, (hetero)alkynyl groups, (hetero)alkylene groups, (hetero)alkenylene groups, (hetero)alkynylene groups, and the like are linear or branched, unless stated otherwise.

The general term "sugar" is herein used to indicate a monosaccharide, for example glucose (Glc), galactose (Gal), mannose (Man) and fucose (Fuc). The term "sugar derivative" is herein used to indicate a derivative of a monosaccharide sugar, i.e. a monosaccharide sugar comprising substituents and/or functional groups. Examples of a sugar derivative include amino sugars and sugar acids, e.g. glucosamine ($GlcNH_2$), galactosamine ($GalNH_2$)N-acetylglucosamine (GlcNAc), N-acetylgalactosamine (GalNAc), sialic acid (Sia) which is also referred to as N-acetylneuraminic acid (NeuNAc), and N-acetylmuramic acid (MurNAc), glucuronic acid (GlcA) and iduronic acid (ldoA).

A sugar may be without further substitution, and then it is understood to be a monosaccharide. A sugar may be further substituted with at one or more of its hydroxyl groups, and then it is understood to be a disaccharide or an oligosaccharide. A disaccharide contains two monosaccharide moieties linked together. An oligosaccharide chain may be linear or branched, and may contain from 3 to 10 monosaccharide moieties.

The term "protein" is herein used in its normal scientific meaning. Herein, polypeptides comprising about 10 or more amino acids are considered proteins. A protein may comprise natural, but also unnatural amino acids. The term "protein" herein is understood to comprise antibodies and antibody fragments.

The term "peptide" is herein used in its normal scientific meaning. Herein, peptides are considered to comprise a number of amino acids in a range of from 2 to 9.

The term "peptoids" is herein used in its normal scientific meaning.

An antibody is a protein, typically generated by the immune system, that is capable of recognizing and binding to a specific antigen. While antibodies or immunoglobulins derived from IgG antibodies are particularly well-suited for use in this invention, immunoglobulins from any of the classes or subclasses may be selected, e.g. IgG, IgA, IgM, IgD and IgE. Suitably, the immunoglobulin is of the class IgG including but not limited to IgG subclasses (IgG1, 2, 3 and 4) or class IgM which is able to specifically bind to a specific epitope on an antigen. Antibodies can be intact immunoglobulins derived from natural sources or from recombinant sources and can be immunoreactive portions of intact immunoglobulins. Antibodies may exist in a variety of forms including, for example, polyclonal antibodies, monoclonal antibodies, camelized single domain antibodies, recombinant antibodies, anti-idiotype antibodies, antibody fusions, multispecific antibodies, antibody fragments, such as, Fv, VHH, Fab, $F(ab)_2$, Fab', Fab'-SH, $F(ab')_2$, single chain variable fragment antibodies (scFv), tandem/bis-scFv, Fc, pFc', scFv-Fc, disulfide Fv (dsFv), bispecific antibodies (bc-scFv) such as BiTE antibodies, trispecific antibody derivatives such as tribodies, camelid antibodies, minibodies, nanobodies, resurfaced antibodies, humanized antibodies, fully human antibodies, single domain antibodies (sdAb, also known as Nanobody™), chimeric antibodies, chimeric antibodies comprising at least one human constant region, dual-affinity antibodies such as dual-affinity retargeting proteins (DART™), and multimers and derivatives thereof, such as divalent or multivalent single-chain variable fragments (e.g. di-scFvs, tri-scFvs) including but not limited to minibodies, diabodies, triabodies, tribodies, tetrabodies, and the like, and multivalent antibodies. Reference is made to [Trends in Biotechnology 2015, 33, 2, 65], [Trends Biotechnol. 2012, 30, 575-582], and [Canc. Gen. Prot. 2013 10, 1-18], and [BioDrugs 2014, 28, 331-343], the contents of which are hereby incorporated by reference. "Antibody fragment" refers to at least a portion of the variable region of the immunoglobulin that binds to its target, i.e. the antigen-binding region. Other embodiments use antibody mimetics as Drug or Targeting Agent $T^T$, such as but not limited to Affimers, Anticalins, Avimers, Alphabodies, Affibodies, DARPins, and multimers and derivatives thereof; reference is made to [Trends in Biotechnology 2015, 33, 2, 65], the contents of which is hereby incorporated by reference. For the avoidance of doubt, in the context of this invention the term "antibody" is meant to encompass all of the antibody variations, fragments, derivatives, fusions, analogs and mimetics outlined in this paragraph, unless specified otherwise.

A linker is herein defined as a moiety that connects two or more elements of a compound. For example in a bioconjugate, a biomolecule and a targeting moiety are covalently connected to each other via a linker.

A biomolecule is herein defined as any molecule that can be isolated from nature or any molecule composed of smaller molecular building blocks that are the constituents of macromolecular structures derived from nature, in particular nucleic acids, proteins, glycans and lipids. Examples of a biomolecule include an enzyme, a (non-catalytic) protein, a polypeptide, a peptide, an amino acid, an oligonucleotide, a monosaccharide, an oligosaccharide, a polysaccharide, a glycan, a lipid and a hormone.

As used herein, an organic molecule is defined as a molecule comprising a C—H bond. It will be understood that "organic molecule" as used herein includes biomolecules, such as nucleic acids (oligonucleotides, polynucleotides, DNA, RNA), peptides, proteins (in particular antibodies), carbohydrates (monosaccharides, oligosaccharides, and polysaccharides), aptamers, hormones, toxins, steroids, cytokines, and lipids; small organic molecules as defined herein; polymers (in particular polyethylene glycol); LNA and PNA; amino acids; peptoids; molecules comprising a radionuclide; fluorescent dyes; drugs; resins (in particular polystyrene and agarose); beads; particles (in particular polymersomes, liposomes, and beads); gels; surfaces; organometallic compounds; metal complexes; cells; and combinations thereof.

As used herein, an inorganic molecule is defined as any molecule not being an organic molecule, i.e. not comprising a C—H bond. It will be understood that "inorganic molecule" as used herein includes surfaces (in particular chips, wafers, gold, metal, silica-based surfaces such as glass); particles such as beads (in particular magnetic beads, gold beads), silica-based particles, polymer-based materials, iron oxide particles; carbon nanotubes; allotropes of carbon (in particular fullerenes such as Buckminsterfullerene; graphite, graphene, diamond, Lonsdaleite, Q-carbon, linear acetylenic carbon, amorphous carbon, and carbon nanotubes); drugs (in particular cisplatin); metal complexes; and combinations thereof.

As used herein, "particle" is preferably defined as a microparticle or a nanoparticle.

The term "salt thereof" means a compound formed when an acidic proton, typically a proton of an acid, is replaced by a cation, such as a metal cation or an organic cation and the like. The term "salt thereof" also means a compound formed when an amine is protonated. Where applicable, the salt is a pharmaceutically acceptable salt, although this is not required for salts that are not intended for administration to a patient. For example, in a salt of a compound the compound may be protonated by an inorganic or organic acid to form a cation, with the conjugate base of the inorganic or organic acid as the anionic component of the salt.

The term "pharmaceutically accepted" salt means a salt that is acceptable for administration to a patient, such as a mammal (salts with counter-ions having acceptable mammalian safety for a given dosage regime). Such salts may be derived from pharmaceutically acceptable inorganic or organic bases and from pharmaceutically acceptable inorganic or organic acids.

"Pharmaceutically acceptable salt" refers to pharmaceutically acceptable salts of a compound, which salts are derived from a variety of organic and inorganic counter ions known in the art and include, for example, sodium, potassium, calcium, magnesium, ammonium, tetraalkylammonium, etc., and when the molecule contains a basic functionality, salts of organic or inorganic acids, such as hydrochloride, hydrobromide, formate, tartrate, besylate, mesylate, acetate, maleate, oxalate, etc.

The logarithm of the partition-coefficient, i.e. Log P, is herein used as a measure of the hydrophobicity of a compound. Typically, the Log P is defined as $$\log\left(\frac{[\text{Solute}]_{octanol}^{un\text{-}ionized}}{[\text{Solute}]_{water}^{un\text{-}ionized}}\right)$$

The skilled person is aware of methods to determine the partition-coefficient of compounds without undue experimentation. Alternatively, the skilled person knows that software is available to reliably estimate the Log P value, for example as a function within ChemDraw® software or online available tools.

The unified atomic mass unit or Dalton is herein abbreviated to Da. The skilled person is aware that Dalton is a regular unit for molecular weight and that 1 Da is equivalent to 1 g/mol (grams per mole).

It will be understood that herein, the terms "moiety" and "group" are used interchangeably when referring to a part of a molecule.

It will be understood that when a heteroatom is denoted as —X(R')$_2$—, wherein X is the heteroatom and R' is a certain moiety, then this denotes that two moieties R' are attached to the heteroatom.

It will be understood that when a group is denoted as, for example, —(($R_{51}$)$_2$—$R_{52}$)$_2$— or a similar notation, in which $R_{51}$ and $R_{52}$ are certain moieties, then this denotes that first, it should be written as —$R_{51}$—$R_{51}$—$R_{52}$—$R_{51}$—$R_{51}$—$R_{52}$— before the individual $R_{51}$ and $R_{52}$ moieties are selected, rather than first selecting moieties $R_{51}$ and $R_{52}$ and then writing out the formula.

The Inverse Electron-Demand Diels-Alder Reaction (IEDDA)

The established IEDDA conjugation chemistry generally involves a pair of reactants that comprise, as one reactant (i.e. one Bio-orthogonal Reactive Group), a suitable diene, such as a derivative of tetrazine, e.g. an electron-deficient tetrazine and, as the other reactant (i.e. the other Bio-orthogonal Reactive Group), a suitable dienophile, such as a trans-cyclooctene (TCO). The exceptionally fast reaction of (substituted) tetrazines, in particular electron-deficient tetrazines, with a TCO moiety results in an intermediate that rearranges to a dihydropyridazine Diels-Alder adduct by eliminating $N_2$ as the sole by-product. The initially formed 4,5-dihydropyridazine product may tautomerize to a 1,4- or a 2,5-dihydropyridazine product, especially in aqueous environments. Below a reaction scheme is given for a [4+2] IEDDA reaction between (3,6)-di-(2-pyridyl)-s-tetrazine diene and a trans-cyclooctene dienophile, followed by a retro Diels Alder reaction in which the product and dinitrogen is formed. Because the trans-cyclooctene derivative does not contain electron withdrawing groups as in the classical Diels Alder reaction, this type of Diels Alder reaction is distinguished from the classical one, and frequently referred to as an "inverse-electron-demand Diels Alder (IEDDA) reaction". In the following text the sequence of both reaction steps, i.e. the initial Diels-Alder cyclo-addition (typically an inverse electron-demand Diels Alder cyclo-addition) and the subsequent retro Diels Alder reaction will be referred to in shorthand as the "inverse electron-demand Diels Alder reaction" or "inverse electron-demand Diels Alder conjugation" or "IEDDA". The product of the reaction is then the IEDDA adduct or conjugate. This is illustrated in Scheme 1 below.

Scheme 1: the IEDDA conjugation reaction

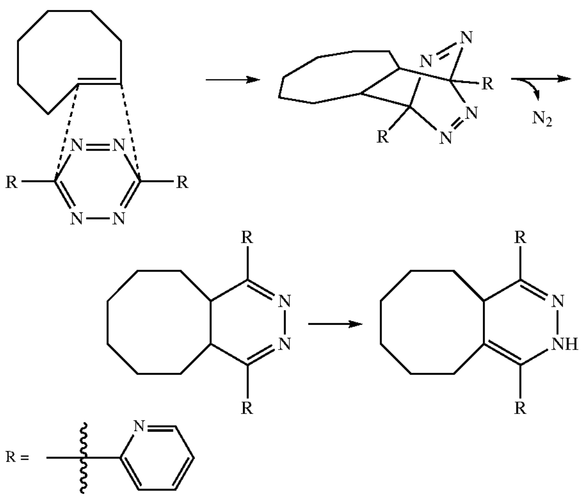

The two reactive species are abiotic and do not undergo fast metabolism or side reactions in vitro or in vivo. They are bio-orthogonal, e.g. they selectively react with each other in physiologic media. Thus, the compounds and the method of the invention can be used in a living organism. Moreover, the reactive groups are relatively small and can be introduced in biological samples or living organisms without significantly altering the size of biomolecules therein. References on the inverse electron demand Diels Alder reaction, and the behavior of the pair of reactive species include: [Thalhammer et al., Tetrahedron Lett., 1990, 31, 47, 6851-6854], [Wijnen et al., J. Org. Chem., 1996, 61, 2001-2005], [Blackman et al., J. Am. Chem. Soc., 2008, 130, 41, 13518-19], Rossin et al., Angew. Chem. Int. Ed. 2010, 49, 3375], [Devaraj et al., Angew. Chem. Int. Ed. 2009, 48, 7013], [Devaraj et al., Angew. Chem. Int. Ed., 2009, 48, 1-5].

The IEDDA Pyridazine Elimination Reaction

Below, the dienophile, a TCO, that is comprised in combinations and kits of the invention may be referred to as a "Trigger". The dienophile is connected at the allylic position to a Construct-A. Moreover, tetrazines that are used in the IEDDA pyridazine elimination reaction may be referred to as "Activators". The term Construct-A in this invention is used to indicate any substance, carrier, biological or chemical group, of which it is desired to have it first in a bound (or masked) state, and being able to provoke release from that state.

The inventors previously demonstrated that the dihydropyridazine product derived from a tetrazine (the Activator) and a TCO containing a carbamate-linked drug (doxorubicin, the Construct-A) at the allylic position is prone to eliminate $CO_2$ and the amine-containing drug, eventually affording aromatic pyridazine.

Without wishing to be bound by theory, the inventors believe that the Activator provokes Construct-A release via a cascade mechanism within the IEDDA adduct, i.e. the dihydropyridazine. The cascade mechanism can be a simple one step reaction, or it can be comprised in multiple steps that involves one or more intermediate structures. These intermediates may be stable for some time or may immediately degrade to the thermodynamic end-product or to the next intermediate structure. In any case, whether it be a simple or a multistep process, the result of the cascade mechanism is that the Construct-A gets released from the IEDDA adduct. Without wishing to be bound by theory, the design of the diene is such that the distribution of electrons within the IEDDA adduct is unfavorable, so that a rearrangement of these electrons must occur. This situation initiates the cascade mechanism, and it therefore induces the release of the Construct-A. Specifically, and without wishing to be bound by theory, the inventors believe that the NH moiety comprised in the various dihydropyridazine tautomers, such as the 1,4-dihydropyridazine tautomer, of the IEDDA adduct can initiate an electron cascade reaction, a concerted or consecutive shift of electrons over several bonds, leading to release of the Construct-A. Occurrence of the cascade reaction in and/or Construct-A release from the Trigger is not efficient or cannot take place prior to the IEDDA reaction, as the Trigger-Construct-A conjugate itself is relatively stable as such. The cascade can only take place after the Activator and the Trigger-Construct conjugate have reacted and have been assembled in the IEDDA adduct.

With reference to Scheme 2 below, and without wishing to be bound by theory, the inventors believe that the pyridazine elimination occurs from the 1,4-dihydropyridazine tautomer 4. Upon formation of the 4,5-dihydropyridazine 3, tautomerization affords intermediates 4 and 7, of which the 2,5-dihydropyridazine 7 cannot eliminate the $C^A$. Instead it can slowly convert into aromatic 8, which also cannot eliminate $C^A$ or it can tautomerize back to intermediate 3. Upon formation of 4 the $C^A$ is eliminated near instantaneously, affording free $C^A$ 8 as an amine, and pyridazine elimination products 5 and 6. This elimination reaction has been shown to work equally well in the cleavage of carbonates, esters and ethers from the TCO trigger [Versteegen et al., Angew. Chem. Int. Ed., 2018, 57, 10494]. The Trigger in Scheme 2 is also optionally bound to a Construct-B ($C^B$), which in this case cannot release from the Trigger. Thereby Construct A can be separated from Construct B by means of the IEDDA pyridazine elimination.

Scheme 2. Proposed IEDDA pyridazine elimination mechanism.

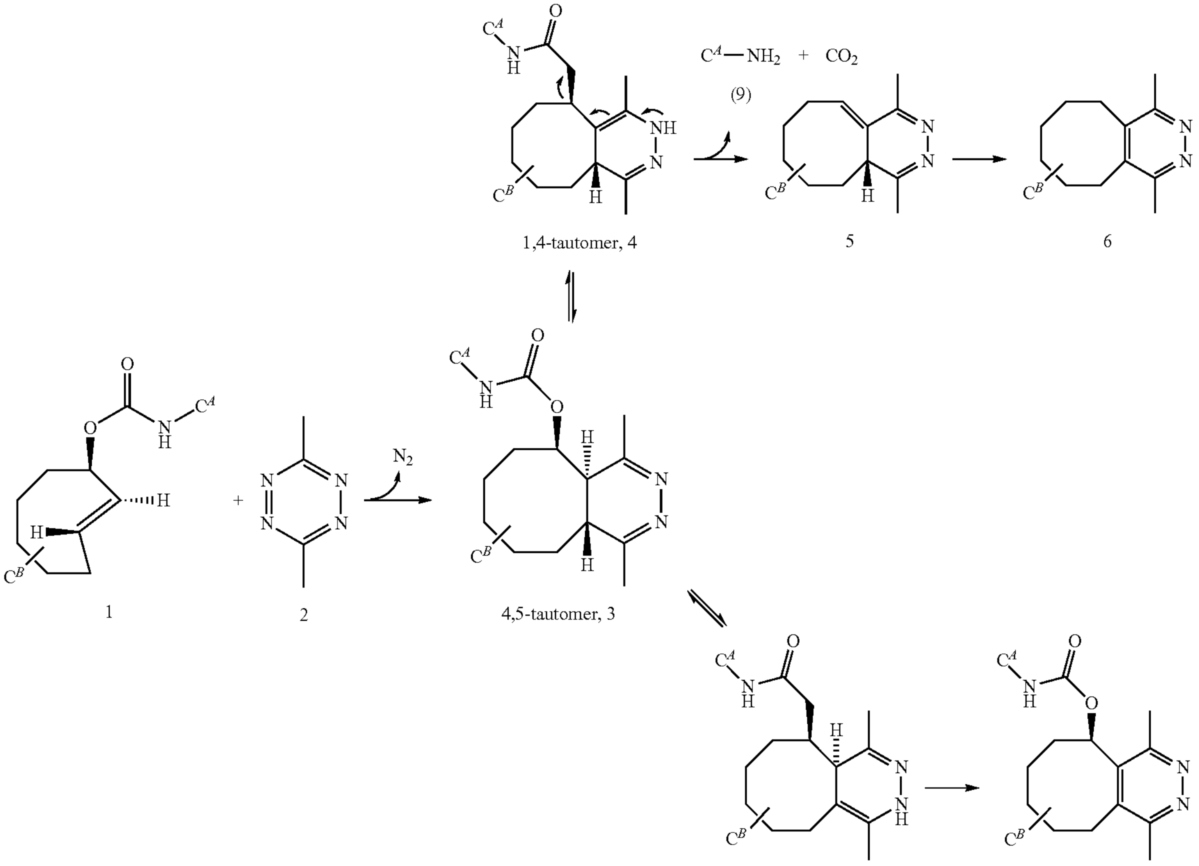

1,4-tautomer, 4 · 5 · 6 · 1 · 2 · 4,5-tautomer, 3 · 2,5-tautomer, 7 · 8

In preferred embodiments, the dienophile trigger moiety used in the present invention comprises a trans-cyclooctene ring. Herein, this eight-membered ring moiety will be defined as a trans-cyclooctene moiety, for the sake of legibility, or abbreviated as "TCO" moiety. It will be understood that the essence resides in the possibility of the eight-membered ring to act as a dienophile and to be released from its conjugated Construct-A upon reaction.

The dienophiles of the invention and tetrazines are capable of reacting in an inverse electron-demand Diels-Alder reaction (IEDDA). IEDDA reaction of the Trigger with the Activator leads to release of the Construct-A through an electron-cascade-based elimination, termed the "pyridazine elimination". When an Activator reacts with a Trigger capable of eliminating Construct-A, the combined process of reaction and Construct-A elimination is termed the "IEDDA pyridazine elimination".

This invention provides a Construct-A-conjugated Trigger that reacts with an Activator, resulting in the cleavage of the Trigger from the Construct-A. In one prominent embodiment this results in the cleavage of Construct-A from Construct-B. In another embodiment the Trigger cleavage results in cleavage of one Construct A from another Construct A, wherein both can release from a self-immolative linker attached to the Trigger. In another embodiment, Trigger cleavage results in the cleavage of one or more Construct-A from one or more Construct-B. Construct-B is the Construct that is bound to the dienophile, and cannot be released from the dienophile, unless it is bound to the allylic position via a spacer or self-immolative linker that also binds Construct-A. In preferred embodiments, the Trigger is used as a reversible covalent bond between two molecular species.

Scheme 3a below is a general scheme of Construct release according to this invention, wherein the Construct being released is termed Construct-A ($C^A$), and wherein another Construct, Construct-B ($C^B$) can optionally be bound to the dienophile, but not via the allylic position, wherein Construct-B cannot be released from the dienophile.

Scheme 3a

General scheme of IEDDA pyridazine elimination reaction for the release of Construct-A according to this invention

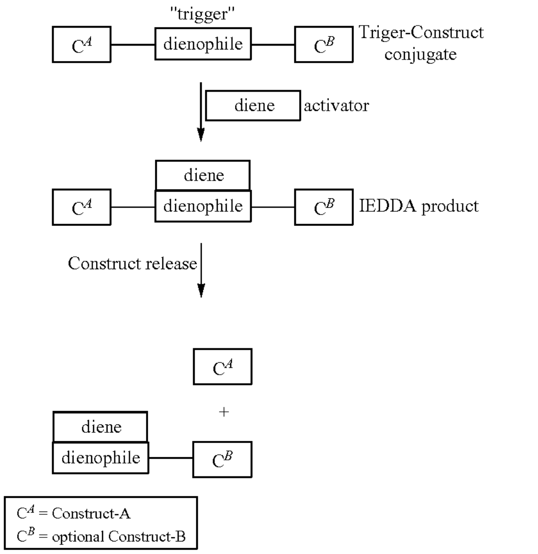

Scheme 3b below is a general scheme of Construct release according to another embodiment of this invention, wherein Construct-B ($C^B$) is bound to the dienophile via a spacer or self-immolative linker that also binds Construct-A and, wherein when the spacer or self-immolative linker is released from the allylic position then Construct-B and Construct A are released from the Trigger and from each other.

Scheme 3b

General scheme of IEDDA pyridazine elimination reaction for the release of Construct-A from Construct-B according to a another embodiment of this invention -continued

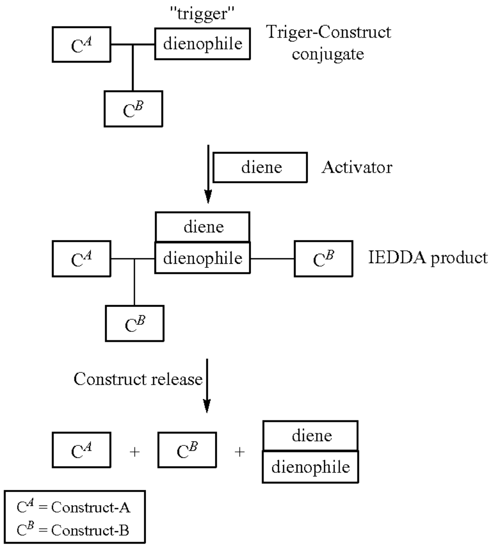

The Construct release occurs through a powerful, abiotic, bio-orthogonal reaction of the dienenophile (Trigger) with the diene (Activator), viz. the aforementioned IEDDA. The masked or bound Construct is a Construct-dienenophile conjugate. Possibly the Construct-A is linked to one or more additional Constructs A linked via a self-immolative linker. It will be understood that in Scheme 3 in the IEDDA adduct as well as in the end product after release, the indicated dienophile group and the indicated diene group are the residues of, respectively, the dienophile and diene groups after these groups have been converted in the IEDDA reaction.

The difference between $C^A$ and $C^B$ is that the bond between $C^B$ and the moiety holding $C^B$ is not broken upon reaction of the Trigger with the diene, whereas the bond between $C^A$ and the moiety holding $C^A$ is broken upon reaction of the Trigger with the diene. A person skilled in the art will understand that the moiety holding $C^A$ and $C^B$ refers to the Trigger, or a self immolative linker $L^C$ bound to the Trigger. For the sake of clarity, when $C^B$ is bound to a $L^C$ that is bound to the Trigger, the $L^C$ holding $C^B$ will release from the Trigger upon reaction with the diene but the $C^B$ will not release from the released $L^C$. Likewise if $C^B$ is bound directly to the Trigger, $C^B$ will not release from the Trigger upon reaction with the diene. A person skilled in the art will understand that when it is required to separate one Construct (1) from another Construct (2), that one of the following requirements have to be met:

1) one $C^A$ is Construct 1 and another $C^A$ is Construct 2
2) Construct 1 is $C^A$ and Construct 2 is $C^B$
3) Construct 1 and 2 are both $C^B$, provided that one $C^B$ is bound directly to the Trigger and the other is bound to a $L^C$, or provided that one $C^B$ moiety is bound to a different $L^C$ moiety than the other $C^B$ moiety.

The invention provides, in one aspect, the use of a tetrazine as an Activator for the release, in a chemical, biological, or physiological environment, of a Construct linked to a TCO. In connection herewith, the invention also pertains to a tetrazine as an Activator for the release, in a chemical, biological, or physiological environment, of a substance linked to a TCO. The fact that the reaction is bio-orthogonal, and that many structural options exist for the reaction pairs, will be clear to the skilled person. E.g., the IEDDA reaction is known in the art of bioconjugation, diagnostics, pretargeted medicine. Reference is made to, e.g., WO 2010/119382, WO 2010/119389, and WO 2010/051530. Whilst the invention presents an entirely different use of the reaction, it will be understood that the various structural possibilities available for the IEDDA reaction pairs as used in e.g. pre-targeting, are also available in the field of the present invention.

Other than is the case with e.g. medicinally active substances, where the in vitro or in vivo action is often changed with minor structural changes, the present invention first and foremost requires the right chemical reactivity combined with sufficient stability for the intended application. Thus, the possible structures extend to those of which the skilled person is familiar with that these are reactive as dienophiles.

Compounds According to Formula (19)

In Formula (19), r is an integer in range of from 0 to 2. In a preferred embodiment, r is 0. In a preferred embodiment, r is 1. In a preferred embodiment, r is 2. In Formula (19), each s is independently 0 or 1. In a preferred embodiment, s is 0. In a preferred embodiment, s is 1. In Formula (19), each i is independently an integer in a range of from 0 to 4, preferably 0 or 1. In Formula (19), j is an integer in range of from 0 to 4, preferably from 0 to 2, more preferably 0 or 1. In Formula (19), each k is independently 0 or 1.

In a preferred embodiment, in Formula (19) only condition (a) is met.

In a preferred embodiment, in Formula (19) only condition (b) is met.

In a preferred embodiment, in Formula (19) only condition (c) is met.

In a preferred embodiment, when in Formula (19) two $R_{37}$, $R_{38}$, $R_{47}$ groups are optionally comprised in a ring so as to form a ring fused to the eight-membered trans-ring, this ring fused to the eight-membered trans-ring is as defined in WO 2012/156919 A1 which is hereby incorporated by reference in its entirety. More preferably the ring fused to the eight-membered trans-ring is as defined in WO 2012/156919 A1 on page 15, line 25 to page 18, line 9.

$Z^T$ $Z^T$ is selected from the group consisting of $C_1$-$C_{12}$ alkylene groups, $C_2$-$C_{12}$ alkenylene groups, $C_7$-$C_{12}$ alkynylene groups, $C_6$ arylene groups, $C_4$-$C_5$ heteroarylene groups, $C_3$-$C_8$ cycloalkylene groups, $C_5$-$C_8$ cycloalkenylene groups, $C_5$-$C_{12}$ alkyl(hetero)arylene groups, $C_5$-$C_{12}$ (hetero)arylalkylene groups, $C_4$-$C_{12}$ alkylcycloalkylene groups, $C_4$-$C_{12}$ cycloalkylalkylene groups, wherein the alkylene groups, alkenylene groups, alkynylene groups, (hetero)arylene groups, cycloalkylene groups, cycloalkenylene groups, alkyl(hetero)arylene groups, (hetero)arylalkylene groups, alkylcycloalkylene groups, cycloalkylalkylene groups, are optionally substituted with a moiety selected from the group consisting of —$(S^P)_i$—$C^B$ with i independently being an integer in a range of from 0 to 4, preferably i is 0 or 1, —Cl, —F, —Br, —I, —$OR_{37}$, —$N(R_{37})_2$, =O, =$NR_{37}$, —$SR_{37}$, —$SO_3H$, —$PO_3H$, —$PO_4H_2$, —$NO_2$ and —$Si(R_{37})_3$, and optionally contain one or more heteroatoms selected from the group consisting of —O—, —S—, —$NR_{37}$—, —P—, and —Si—, wherein the N, S, and P atoms are optionally oxidized, wherein the N atoms are optionally quaternized.

Preferably, $Z^T$ is selected from the group consisting of $C_1$-$C_6$ alkylene groups, $C_2$-$C_6$ alkenylene groups, $C_7$ alkynylene groups, $C_6$ arylene groups, $C_4$-$C_5$ heteroarylene groups, $C_3$-$C_6$ cycloalkylene groups, $C_5$-$C_8$ cycloalkenylene groups, $C_5$-$C_8$ alkyl(hetero)arylene groups, $C_5$-$C_8$ (hetero)arylalkylene groups, $C_4$-$C_8$ alkylcycloalkylene groups, $C_4$-$C_8$ cycloalkylalkylene groups, wherein the alkylene groups, alkenylene groups, alkynylene groups, (hetero)arylene groups, cycloalkylene groups, cycloalkenylene groups, alkyl(hetero)arylene groups, (hetero)arylalkylene groups, alkylcycloalkylene groups, cycloalkylalkylene groups, are optionally substituted with a moiety selected from the group consisting of —$(S^P)_i$—$C^B$ with i independently being an integer in a range of from 0 to 4, preferably i is 0 or 1, —Cl, —F, —Br, —I, —$OR_{37}$, —$N(R_{37})_2$, =O, =$NR_{37}$, —$SR_{37}$, —$SO_3H$, —$PO_3H$, —$PO_4H_2$, —$NO_2$ and —$Si(R_{37})_3$, and optionally contain one or more heteroatoms selected from the group consisting of —O—, —S—, —$NR_{37}$—, —P—, and —Si—, wherein the N, S, and P atoms are optionally oxidized, wherein the N atoms are optionally quaternized.

Preferably, $Z^T$ is selected from the group consisting of $C_1$-$C_3$ alkylene groups, $C_2$-$C_3$ alkenylene groups, $C_3$ alkynylene groups, $C_3$ heteroarylene groups, and $C_3$ cycloalkylene groups, wherein the alkylene groups, alkenylene groups, alkynylene groups, heteroarylene groups, and cycloalkylene groups, are optionally substituted with a moiety selected from the group consisting of —$(S^P)_i$—$C^B$ with i independently being an integer in a range of from 0 to 4, preferably i is 0 or 1, —Cl, —F, —Br, —I, —$OR_{37}$, —$N(R_{37})_2$, =O, =$NR_{37}$, —$SR_{37}$, —$SO_3H$, —$PO_3H$, —$PO_4H_2$, —$NO_2$ and —$Si(R_{37})_3$, and optionally contain one or more heteroatoms selected from the group consisting of —O—, —S—, —$NR_{37}$—, —P—, and —Si—, wherein the N, S, and P atoms are optionally oxidized, wherein the N atoms are optionally quaternized. In preferred embodiments, the $Z^T$ groups are not substituted. In preferred embodiments, the $Z^T$ groups do not contain heteroatoms.

$R_{48}$

Preferably, $R_{48}$ is —OC(O)—$(S^P)_k C^A$, and $S^P$ (when k>0) or $C^A$ (when k=0) is bound to the —OC(O)— of $R_{48}$ via an atom selected from the group consisting of O, C, S, and N, preferably a secondary or a tertiary N, wherein this atom is part of $S^P$ or $C^A$. Preferably, $R_{48}$ is —O-$L^C$-$(S^P)_k C^A$ and $S^P$ (when k>0) or $C^A$(when k=0) is bound to $L^C$ via a moiety selected from the group consisting of —O—, —S—, and —N—, preferably a secondary or a tertiary N, wherein said moiety is part of $S^P$ or $C^A$. It is preferred that $R_{48}$ is axially positioned on the 8-membered dienophile ring. It is preferred that $R_{48}$ is positioned trans relative to $H^a$.

Other Preferred Embodiments

In preferred embodiments, $Y^{T1}$ is OH, $N(R_{38})_2$, C(O)OH, O—$N(R_{38})_2$, SH, more preferably OH, $N(R_{38})_2$, O—N$(R_{38})_2$, more preferably OH, $N(R_{38})_2$, most preferably $Y^{T1}$ is OH. In other preferred embodiments, $Y^{T1}$ is $N(R_{38})_2$, more preferably $NR_{38}H$, most preferably $NH_2$. In preferred embodiments, no $Y^{T2}$ and $Y^{T3}$ are present and $Y^{T1}$ is OH, $N(R_{38})_2$, C(O)OH, O—$N(R_{38})_2$, more preferably OH, $N(R_{38})_2$, most preferably $Y^{T1}$ is OH. In preferred embodiments, $Y^{T2}$ is OH. In preferred embodiments, no $Y^{T1}$ and $Y^{T3}$ are present and $Y^{T2}$ is OH. It is preferred that $X^1$ and $X^5$ are not O.

In preferred embodiments, when a fused ring is present satisfying any of the Formulae (20a)-(20f) that there are no other rings fused to the 8-membered dienophile ring.

In preferred embodiments, $R_{37}$, $R_{38}$, $R_{47}$ groups are not OH, SH, $N(R_{38})_2$, O—$N(R_{38})_2$, C(N)$N(R_{38})_2$. In preferred embodiments, $R_{37}$, $R_{38}$, $R_{47}$ groups are not OH, SH, $N(R_{38})_2$, C(O)OH, C(S)OH, C(O)SH, C(S)SH, O—$N(R_{38})_2$, $SO_4H$, $SO_3H$, $SO_2H$, $PO_4H_2$, $PO_3H$, $PO_2H$, C(N)$N(R_{38})_2$.

In preferred embodiments, the compound of Formula (19) comprises at most three moieties each independently selected from the group consisting of $Y^{T1}$, $Y^{T2}$, $Y^{T3}$, more preferably at most two moieties, even more preferably one moiety.

In preferred embodiments, one of $X^2$, $X^3$, $X^4$ is $CR_{47}Y^{T1}$, most preferably $X^3$ or $X^4$ is $CR_{47}Y^{T1}$. In preferred embodiments, one of $X^2$, $X^3$, $X^4$ is $CR_{47}Y^{T1}$, most preferably $X^3$ or $X^4$ is $CR_{47}Y^{T1}$, and the remaining $X^1$, $X^2$, $X^3$, $X^4$, $X^5$ are $C(R_{47})_2$, preferably $CH_2$. In preferred embodiments, two of $X^2$, $X^3$, $X^4$ are $CR_{47}Y^{T1}$, and the remaining $X^1$, $X^2$, $X^3$, $X^4$, $X^5$ are $C(R_{47})_2$, preferably $CH_2$. In preferred embodiments, $X^3$ is $Y^{T3}$, and the remaining $X^1$, $X^2$, $X^3$, $X^4$, $X^5$ are $C(R_{47})_2$, preferably $CH_2$. In preferred embodiments, $X^2$ and $X^3$ are part of a fused ring satisfying one of the Formulae (20a)-(20g), and the remaining $X^1$, $X^2$, $X^3$, $X^4$, $X^5$ are $C(R_{47})_2$, preferably $CH_2$.

In preferred embodiments, $X^3$ and $X^4$ are part of a fused ring satisfying one of the Formulae (20a)-(20g), and the remaining $X^1$, $X^2$, $X^3$, $X^4$, $X^5$ are $C(R_{47})_2$, preferably $CH_2$.

In preferred embodiments, the fused ring satisfies Formula (20a). In preferred embodiments, the fused ring satisfies Formula (20b). In preferred embodiments, the fused ring satisfies Formula (20c).

For Formula (20g) it is preferred that when $X^6$ and $X^8$ are both $Y^{T3}$ that $X^7$ is not $C_1$ alkylene. For Formula (20g) it is preferred that $X^6$ and $X^8$ are both $Y^{T3}$, preferably $NR_{38}$, and that $X^7$ is $C_2$ alkylene. For Formula (20g) it is preferred that $X^6$ and $X^8$ are both $C(R_{47})_2$, preferably $CH_2$, and $X^7$ is $Y^{T3}$, preferably $NR_{38}$.

In preferred embodiments, $X^a$ and $X^b$ are CH. In preferred embodiments, the fused ring satisfies Formula (20a), and that $X^a$ and $X^b$ are CH.

In a preferred embodiment, at most 4 of $R_{37}$, $R_{38}$, $R_{47}$ comprised in $X^1$, $X^2$, $X^3$, $X^4$, and $X^5$ (i.e. in total for $X^1$—$X^5$, not per moiety X) are not H, preferably at most 3 are not H, more preferably at most 2 are not H, most preferably at most 1 is not H.

It is preferred that when two $R_{37}$, $R_{38}$, $R_{47}$ groups comprised in $X^1$, $X^2$, $X^3$, $X^4$, $X^5$ are comprised in a ring so as to form a ring fused to the eight-membered trans-ring, that these rings fused to the eight-membered trans-ring are $C_3$-$C_7$ cycloalkylene groups and $C_4$-$C_7$ cycloalkenylene groups, optionally substituted and containing heteroatoms as described for $R_{47}$.

In preferred embodiments $C^A$ and/or $C^B$ are bound to the remainder of the molecule via a residue of $R_{32}$ as defined herein, wherein preferably said residue of $R_{32}$ equals or is comprised in a Spacer.

A person skilled in the art will understand that "residue of $R_{32}$" means the conjugation reaction product of $R_{32}$ with another chemical group so as to form a conjugate between $C^A$ and/or $C^B$ with the Trigger, a Spacer, or $L^C$.

In other embodiments, $C^A$ and/or $C^B$ are bound to the remainder of the molecule via $C^{M2}$ as defined herein, wherein preferably $C^{M2}$ equals or is comprised in a Spacer.

In yet other embodiments, $C^A$ and/or $C^B$ are bound to the remainder of the molecule via $C^X$ as defined herein, wherein preferably $C^X$ equals or is comprised in a Spacer.

In preferred embodiments, moiety $C^X$, $C^{M2}$ and the said residue of $R_{32}$ are comprised in $C^A$ and/or $C^B$.

In preferred embodiments, $C^{M2}$ is selected from the group consisting of amine, amide, thioamide, aminooxy, ether, carbamate, thiocarbamate, urea, thiourea, sulfonamide, and sulfoncarbamate.

In preferred embodiments $C^{M2}$ equals $R_{10}$.

In preferred embodiments $C^{M2}$ equals $C^X$. In preferred embodiments, $C^{M2}$ is:

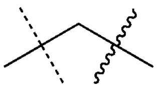 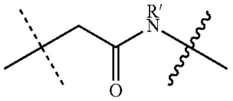

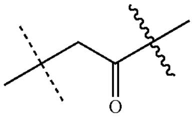 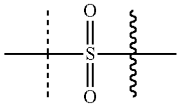

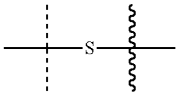 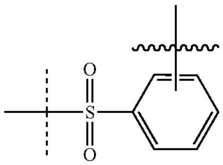

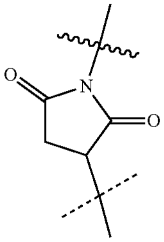 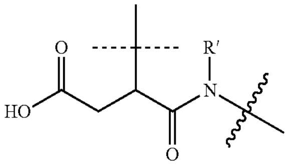

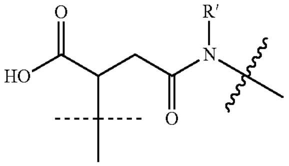

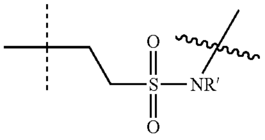 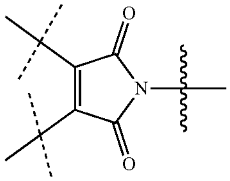

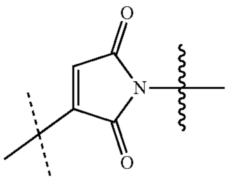 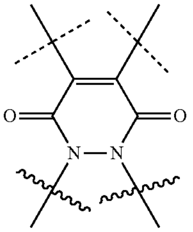

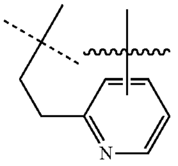 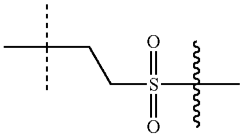

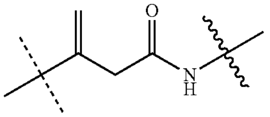

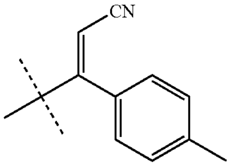 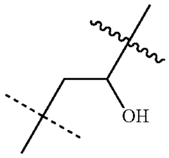

-continued
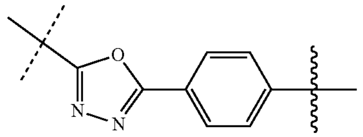
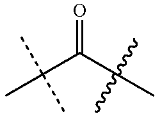
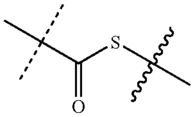
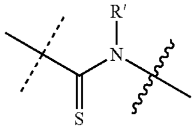
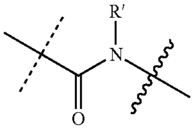
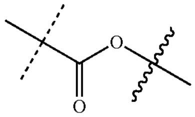
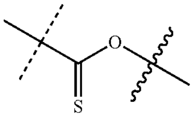
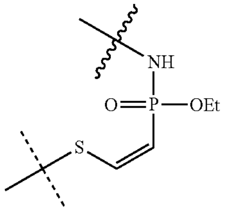
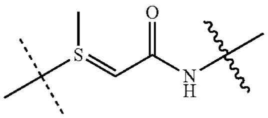
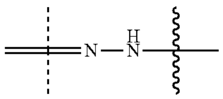
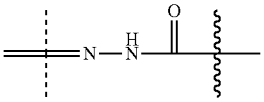
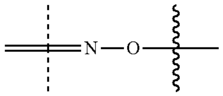
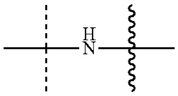
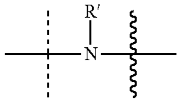
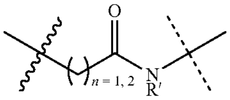
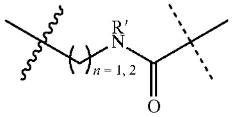
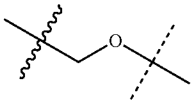
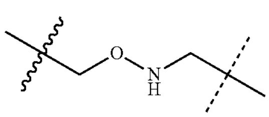
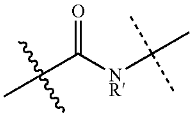
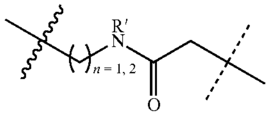
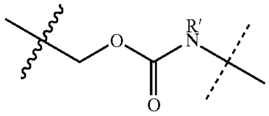
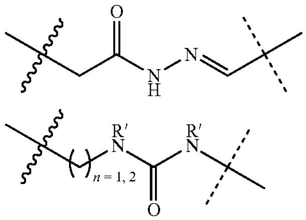
-continued
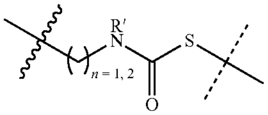
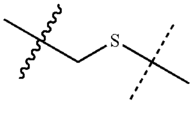
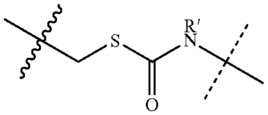
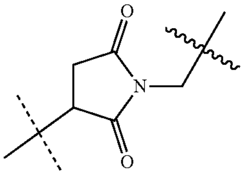
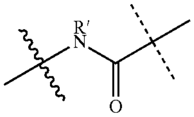
wherein the dashed line denotes a bond to or towards $C^A$ or $C^B$ and the wiggly line denotes a bond to the remaining part of the dienophile. In other embodiments the wiggly line denotes a bond to or towards $C^A$ or $C^B$ and the dashed line denotes a bond to the remaining part of the dienophile.
In preferred embodiments, $C^X$ is:
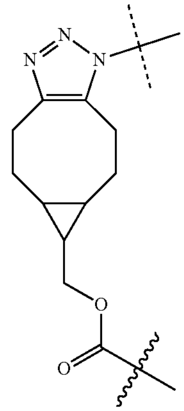
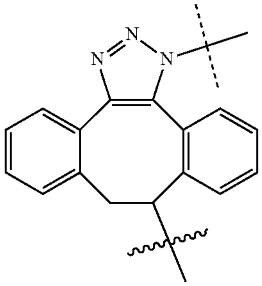
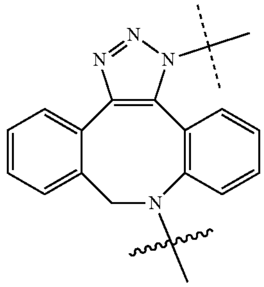
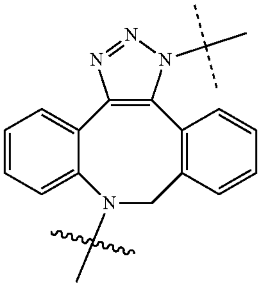
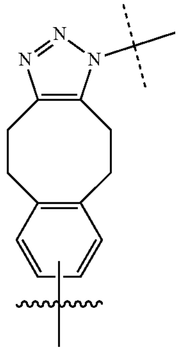
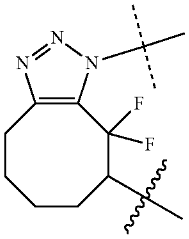

-continued

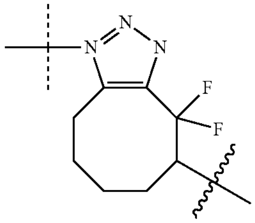
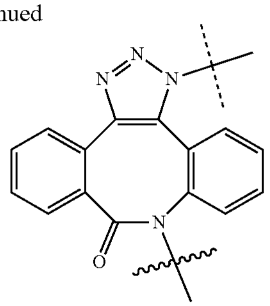
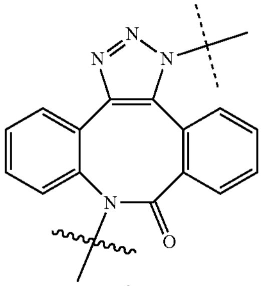
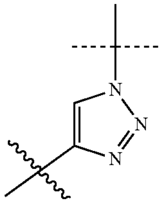
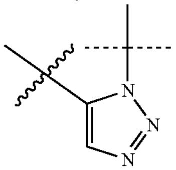
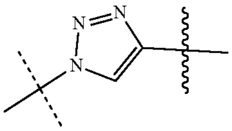
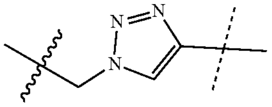
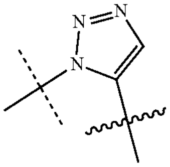
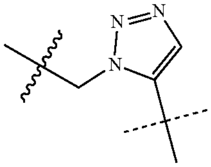
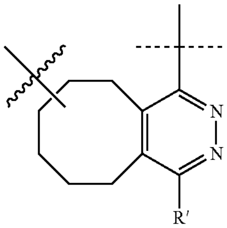
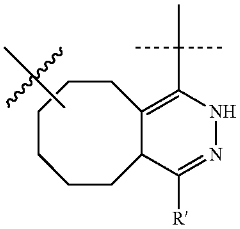

wherein the dashed line denotes a bond to or towards $C^A$ or $C^B$ and the wiggly line denotes a bond to the remaining part of the dienophile. In other embodiments the wiggly line denotes a bond to or towards $C^A$ or $C^B$ and the dashed line denotes a bond to the remaining part of the dienophile.

With reference to above schemes with examples of $C^{M2}$ and $C^X$, in preferred embodiments, when $C^A$ or $C^B$ is a protein, such as an antibody, the dashed line denotes a bond to or towards $C^A$ or $C^B$.

In preferred embodiments, when k or i is 0, $C^A$ and/or $C^B$ is linked to the remaining part of Formula 19 via a moiety selected from the group consisting of —O—, —$C(R^6)_2$—, —$NR^6$—, —C(O)—, and —S—, wherein said moieties are part of $C^A$ and/or $C^B$.

In preferred embodiments, when k or i is at least 1, then $C^A$ and/or $C^B$ is linked to $S^P$ via a moiety selected from the group consisting of —O—, —$C(R^6)_2$—, —$NR^6$—, —C(O)—, and —S—, wherein said moieties are part of $C^A$ and/or $C^B$, and $S^P$ is linked to the remaining part of Formula 19 via a moiety selected from the group consisting of —O—, —$C(R^6)_2$—, —$NR^6$—, —C(O)— and —S—, wherein said moieties are part of $S^P$.

In preferred embodiments, at most three $C^B$ is comprised in the structure of Formula (19), more preferably at most two, most preferably at most one $C^B$ is comprised in the structure of Formula (19).

In a preferred embodiment, $C^A$ and/or $C^B$ before conjugation to the remainder of the compound of Formula (19) comprises at least one moiety selected from the group consisting of —OH, —NHR', —$CO_2H$, —SH, —S—S—, —$SCH_3$—$N_3$, terminal alkynyl, terminal alkenyl, —C(O)R', $C_8$-$C_{12}$ (hetero)cycloalkynyl, $C_3$-$C_4$ cycloalkenyl, nitrone, nitrile oxide, (imino)sydnone, isonitrile, (oxa)norbornene, and tetrazine, said moiety used for conjugation to a moiety comprising the dienophile and $R_{32}$ so as to form the compound satisfying Formula (19), and comprising a $C^{M2}$ or $C^X$ moiety.

In preferred embodiments the $C^A$ and/or $C^B$ is bound to the remainder of the compound of Formula (19) via a $C^{M2}$ selected from the group consisting of amine, amide, thioamide, aminooxy, carbamate, thiocarbamate, urea, thiourea, sulfonamide, and sulfoncarbamate.

In preferred embodiments $C^{M2}$ equals $R_{10}$.

In a preferred embodiment, when $C^A$ or $C^B$ is conjugated via —SH or —S—S—, then $C^{M2}$ is selected from the group consisting of

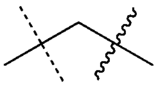
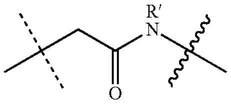
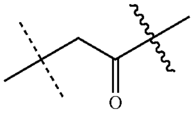
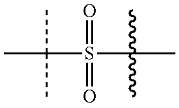
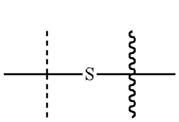
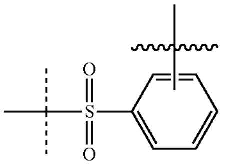
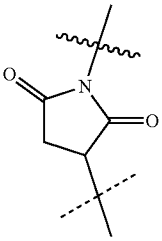
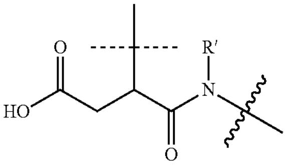
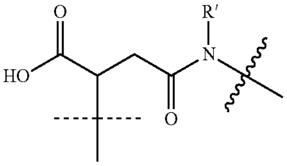

-continued

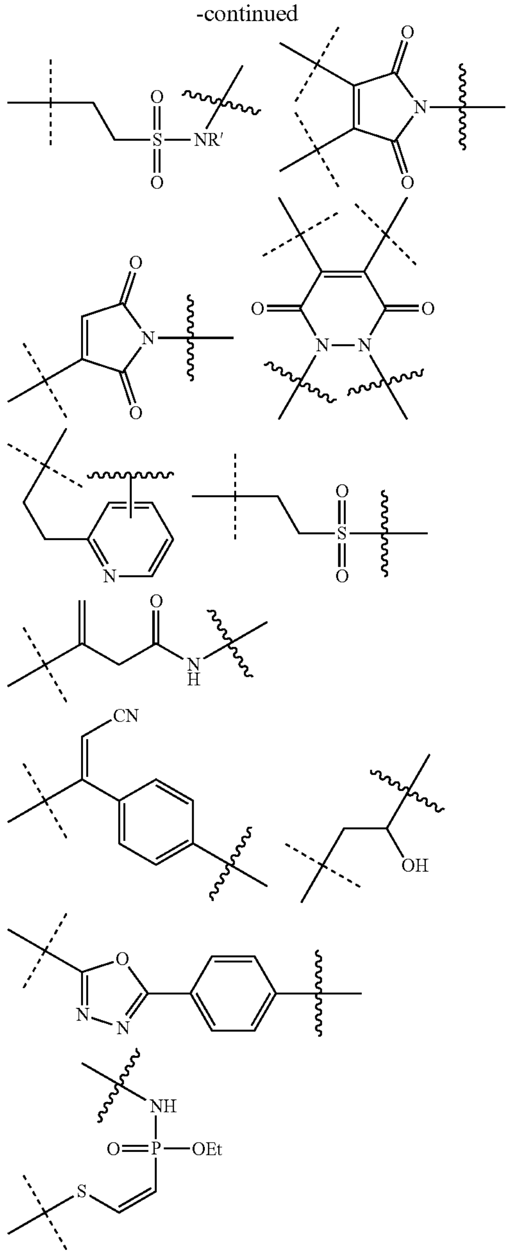

wherein the wiggly line denotes a bond to the remaining part of the molecule, and wherein the dashed line denotes a bond to $C^A$ or $C^B$, In a preferred embodiment, when moiety $C^A$, $C^B$, or the Administration Agent is conjugated via —SMe-, then $C^{M2}$ is:

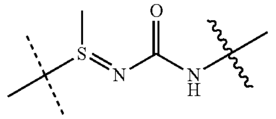

wherein the wiggly line denotes a bond to the remaining part of the molecule, and wherein the dashed line denotes a bond to $C^A$, $C^B$, or the Administration Agent.

In a preferred embodiment, when $C^A$ or $C^B$ is conjugated via —NR'—, then $C^{M2}$ is selected from the group consisting of

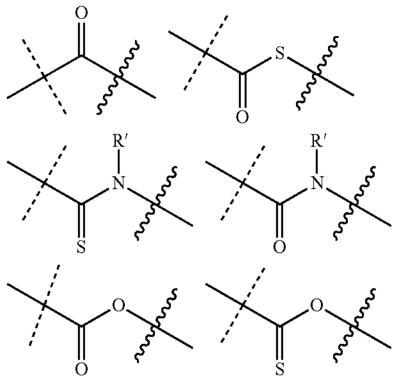

wherein the wiggly line denotes a bond to the remaining part of the molecule, and wherein the dashed line denotes a bond to $C^A$ or $C^B$.

In a preferred embodiment, when $C^A$ or $C^B$ is conjugated via —C-derived from a moiety that was —C(O)R' or —C(O)R'—, then $C^{M2}$ is selected from the group consisting of

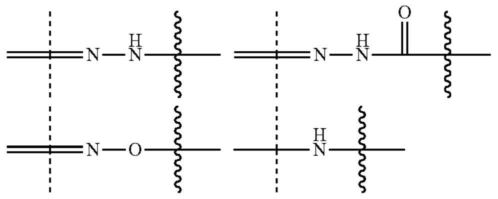

wherein the wiggly line denotes a bond to the remaining part of the molecule, and wherein the dashed line denotes a bond to $C^A$ or $C^B$.

In a preferred embodiment, when $C^A$ or $C^B$ is conjugated via —C(O)-derived from a moiety that was —C(O)OH, then $C^{M2}$ is selected from the group consisting of

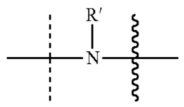

wherein the wiggly line denotes a bond to the remaining part of the molecule, and wherein the dashed line denotes a bond to $C^A$ or $C^B$.

In a preferred embodiment, when $C^A$ or $C^B$ is conjugated via —O—, then $C^{M2}$ is selected from the group consisting of

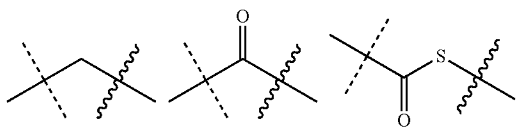

-continued

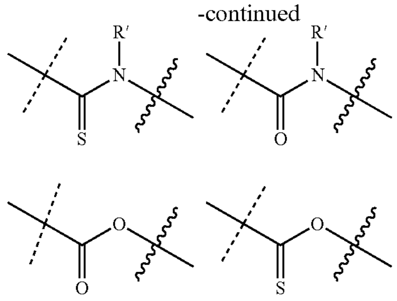

wherein the wiggly line denotes a bond to the remaining part of the molecule, and wherein the dashed line denotes a bond to $C^A$ or $C^B$.

In a preferred embodiment, when $C^A$ or $C^B$ is conjugated via —$N_3$ that was reacted with an $R_{32}$ that comprised an alkyne group, then the resulting $C^X$ comprises a triazole ring, wherein each $C^X$ is independently selected from the group consisting of

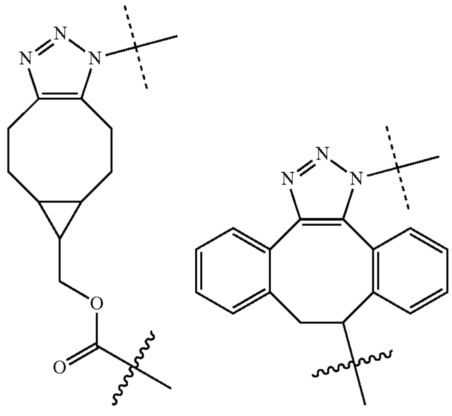

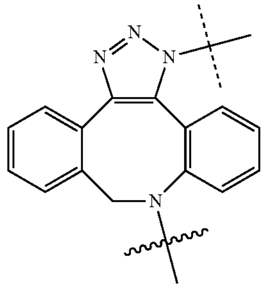

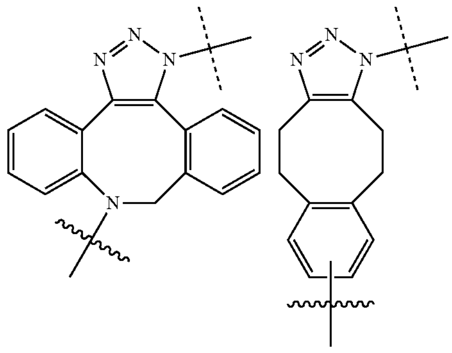

-continued

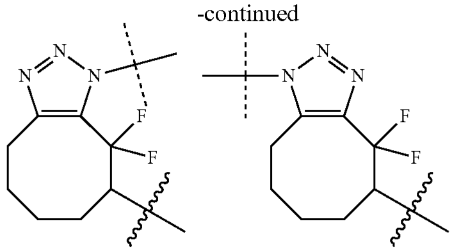

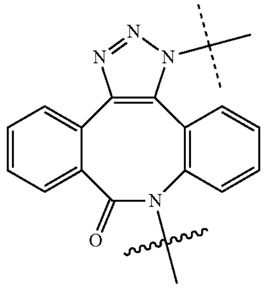

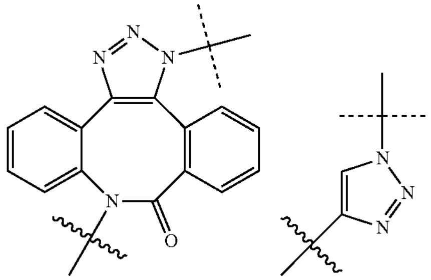

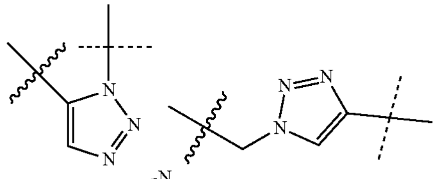

, and

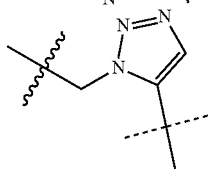

wherein the wiggly line denotes a bond to the remaining part of the molecule, and wherein the dashed line denotes a bond to $C^A$ or $C^B$.

$R^6$

Preferably, each $R^6$ is independently selected from the group consisting of hydrogen, —$(S^P)_i$—$C^B$, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ (cyclo)alkyl(hetero)aryl groups, $C_3$-$C_{24}$ (hetero)aryl(cyclo)alkyl, $C_4$-$C_{24}$ (cyclo)alkenyl(hetero)aryl groups, $C_4$-$C_{24}$ (hetero)aryl(cyclo)alkenyl groups, $C_4$-$C_{24}$ (cyclo)alkynyl(hetero)aryl groups, $C_4$-$C_{24}$ (hetero)aryl(cyclo)alkynyl groups, $C_4$-$C_{24}$ alkylcycloalkyl groups, and $C_4$-$C_{24}$ cycloalkylalkyl groups; wherein i is an integer in a range of from 0 to 4, preferably i is 0 or 1; the $R^6$ groups not being hydrogen are optionally substituted with a moiety selected from the group consisting of —Cl, —F, —Br, —I, —OH, —$NH_2$, —$SO_3H$, —$PO_3H$, —$PO_4H_2$, —$NO_2$, —$CF_3$, =O, =NH, and —SH, and optionally contain one or more heteroatoms selected from the group consisting of O, S, NH, P, and Si, wherein the N, S, and P atoms are optionally oxidized, wherein the N atoms are optionally quaternized.

In preferred embodiments, each $R^6$ is individually selected from the group consisting of hydrogen, $C_1$-$C_8$ alkyl groups, $C_2$-$C_8$ alkenyl groups, $C_2$-$C_8$ alkynyl groups, $C_6$-$C_{12}$ aryl, $C_2$-$C_{12}$ heteroaryl, $C_3$-$C_8$ cycloalkyl groups, $C_5$-$C_8$ cycloalkenyl groups, $C_3$-$C_{12}$ alkyl(hetero)aryl groups, $C_3$-$C_{12}$ (hetero)arylalkyl groups, $C_4$-$C_{12}$ alkylcycloalkyl groups, $C_4$-$C_{12}$ cycloalkylalkyl groups, $C_5$-$C_{12}$ cycloalkyl (hetero)aryl groups and $C_5$-$C_{12}$ (hetero)arylcycloalkyl groups, wherein the $R^6$ groups not being hydrogen are optionally substituted with a moiety selected from the group consisting of —Cl, —F, —Br, —I, —OH, —$NH_2$, —$SO_3H$, —$PO_3H$, —$PO_4H_2$, —$NO_2$, —$CF_3$, =O, =NH, and —SH, and optionally contain one or more heteroatoms selected from the group consisting of O, S, NH, P, and Si, wherein the N, S, and P atoms are optionally oxidized, wherein the N atoms are optionally quaternized.

In preferred embodiments, $R^6$ is selected from the group consisting of hydrogen, $C_1$-$C_4$ alkyl groups, $C_2$-$C_4$ alkenyl groups, $C_2$-$C_4$ alkynyl groups, $C_6$-$C_8$ aryl, $C_2$-$C_8$ heteroaryl, $C_3$-$C_6$ cycloalkyl groups, $C_5$-$C_6$ cycloalkenyl groups, $C_3$-$C_{10}$ alkyl(hetero)aryl groups, $C_3$-$C_{10}$ (hetero)arylalkyl groups, $C_4$-$C_8$ alkylcycloalkyl groups, $C_4$-$C_8$ cycloalkylalkyl groups, $C_5$-$C_{10}$ cycloalkyl(hetero)aryl groups and $C_5$-$C_{10}$ (hetero)arylcycloalkyl groups, wherein the $R^6$ groups not being hydrogen are optionally substituted with a moiety selected from the group consisting of —Cl, —F, —Br, —I, —OH, —$NH_2$, —$SO_3H$, —$PO_3H$, —$PO_4H_2$, —$NO_2$, —$CF_3$, =O, =NH, and —SH, and optionally contain one or more heteroatoms selected from the group consisting of O, S, NH, P, and Si, wherein the N, S, and P atoms are optionally oxidized, wherein the N atoms are optionally quaternized.

In preferred embodiments, $R^6$ is selected from the group consisting of hydrogen, $C_1$-$C_4$ alkyl groups, $C_2$-$C_4$ alkenyl groups, and $C_{4-6}$ (hetero)aryl groups, wherein for $R^6$ the alkyl groups, alkenyl groups, and (hetero)aryl groups are optionally substituted with a moiety selected from the group consisting of —Cl, —F, —Br, —I, —OH, —$NH_2$, =O, —SH, —$SO_3H$, —$PO_3H$, —$PO_4H_2$ and —$NO_2$ and optionally contain at most two heteroatoms selected from the group consisting of —O—, —S—, —NH—, —P—, and —Si—, wherein the N, S, and P atoms are optionally oxidized.

In preferred embodiments, $R^6$ is selected from the group consisting of hydrogen, $C_1$-$C_3$ alkyl groups, $C_2$-$C_3$ alkenyl groups, and $C_{4-6}$ (hetero)aryl groups, wherein for $R^6$ the alkyl groups, alkenyl groups, and (hetero)aryl groups are optionally substituted with a moiety selected from the group consisting of —Cl, —F, —Br, —I, —OH, —$NH_2$, =O, —SH, —$SO_3H$, —$PO_3H$, —$PO_4H_2$ and —$NO_2$ and optionally contain at most two heteroatoms selected from the group consisting of —O—, —S—, —NH—, —P—, and —Si—, wherein the N, S, and P atoms are optionally oxidized.

In preferred embodiments, the $R^6$ groups not being hydrogen are not substituted. In preferred embodiments, the $R^6$ groups not being hydrogen do not contain heteroatoms. In preferred embodiments, the $R^6$ groups are hydrogen.

$R^7$

In preferred embodiments, each $R^7$ is independently selected from the group consisting of hydrogen, —$(S^P)_i$—$C^B$, —F, —Cl, —Br, —I, —$OR_{37}$, —$N(R_{37})_2$, —$SO_3$, —$PO_3^-$, —$NO_2$, —$CF_3$, —$SR_{37}$, $S(=O)_2N(R_{37})_2$, $OC(=O)R_{37}$, $SC(=O)$ $R_{37}$, $OC(=S)R_{37}$, $SC(=S)R_{37}$, $NR_{37}C(=O)$—$R_{37}$, $NR_{37}C(=S)$—$R_{37}$, $NR_{37}C(=O)O$—$R_{37}$, $NR_{37}C(=S)O$—$R_{37}$, $NR_{37}C(=O)S$—$R_{37}$, $NR_{37}C(=S)S$—$R_{37}$, $OC(=O)N(R_{37})_2$, $SC(=O)N(R_{37})_2$, $OC(=S)N(R_{37})_2$, $SC(=S)N(R_{37})_2$, $NR_{37}C(=O)N(R_{37})_2$, $NR_{37}C(=S)N(R_{37})_2$, $C(=O)R_{37}$, $C(=S)R_{37}$, $C(=O)N(R_{37})_2$, $C(=S)N(R_{37})_2$, $C(=O)O$—$R_{37}$, $C(=O)S$—$R_{37}$, $C(=S)O$—$R_{37}$, $C(=S)S$—$R_{37}$, $S(O)R_{37}$, —$S(O)_2R_{37}$, $NR_{37}S(O)_2R_{37}$, —$ON(R_{37})_2$, —$NR_{37}OR_{37}$, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ (cyclo)alkyl(hetero)aryl groups, $C_3$-$C_{24}$ (hetero)aryl(cyclo)alkyl, $C_4$-$C_{24}$ (cyclo)alkenyl(hetero)aryl groups, $C_4$-$C_{24}$ (hetero)aryl(cyclo)alkenyl groups, $C_4$-$C_{24}$ (cyclo)alkynyl(hetero)aryl groups, $C_4$-$C_{24}$ (hetero)aryl(cyclo)alkynyl groups, $C_4$-$C_{24}$ alkylcycloalkyl groups, and $C_4$-$C_{24}$ cycloalkylalkyl groups; wherein i is an integer in a range of from 0 to 4, preferably i is 0 or 1, wherein the alkyl groups, alkenyl groups, alkynyl groups, aryl, heteroaryl, cycloalkyl groups, cycloalkenyl groups, cycloalkynyl groups, (cyclo)alkyl(hetero)aryl groups, (hetero)aryl(cyclo)alkyl groups, (cyclo)alkenyl(hetero)aryl groups, (hetero)aryl(cyclo)alkenyl groups, (cyclo)alkynyl (hetero)aryl groups, (hetero)aryl(cyclo)alkynyl groups, alkylcycloalkyl groups, cycloalkylalkyl groups are optionally substituted with a moiety selected from the group consisting of —Cl, —F, —Br, —I, —$OR_{37}$, —$N(R_{37})_2$, —$SO_3R_{37}$, —$PO_3(R_{37})_2$, —$PO_4(R_{37})_2$, —$NO_2$, —$CF_3$, =O, =$NR_{37}$, and —$SR_{37}$, and optionally contain one or more heteroatoms selected from the group consisting of O, S, $NR_{37}$, P, and Si, wherein the N, S, and P atoms are optionally oxidized, wherein the N atoms are optionally quaternized.

In preferred embodiments, each $R^7$ is independently selected from the group consisting hydrogen, —F, —Cl, —Br, —I, —$OR_{37}$, —$N(R_{37})_2$, —$SO_3$, —$PO_3^-$, —$NO_2$, —$CF_3$, —$SR_{37}$, $S(=O)_2N(R_{37})_2$, $OC(=O)R_{37}$, $SC(=O)R_{37}$, $OC(=S)R_{37}$, $SC(=S)R_{37}$, $NR_{37}C(=O)$—$R_{37}$, $NR_{37}C(=S)$—$R_{37}$, $NR_{37}C(=O)O$—$R_{37}$, $NR_{37}C(=S)O$—$R_{37}$, $NR_{37}C(=O)S$—$R_{37}$, $NR_{37}C(=S)S$—$R_{37}$, $OC(=O)N(R_{37})_2$, $SC(=O)N(R_{37})_2$, $OC(=S)N(R_{37})_2$, $SC(=S)N(R_{37})_2$, $NR_{37}C(=O)N(R_{37})_2$, $NR_{37}C(=S)N(R_{37})_2$, $C(=O)R_{37}$, $C(=S)R_{37}$, $C(=O)N(R_{37})_2$, $C(=S)N(R_{37})_2$, $C(=O)O$—$R_{37}$, $C(=O)S$—$R_{37}$, $C(=S)O$—$R_{37}$, $C(=S)S$—$R_{37}$, $S(O)R_{37}$, —$S(O)_2R_{37}$, $NR_{37}S(O)_2R_{37}$, —$ON(R_{37})_2$, $NR_{37}OR_{37}$, $C_1$-$C_8$ alkyl groups, $C_2$-$C_8$ alkenyl groups, $C_2$-$C_8$ alkynyl groups, $C_6$-$C_{12}$ aryl groups, $C_2$-$C_{12}$ heteroaryl groups, $C_3$-$C_8$ cycloalkyl groups, $C_5$-$C_8$ cycloalkenyl groups, $C_3$-$C_{12}$ alkyl(hetero)aryl groups, $C_3$-$C_{12}$ (hetero) arylalkyl groups, $C_4$-$C_{12}$ alkylcycloalkyl groups, $C_4$-$C_{12}$ cycloalkylalkyl groups, $C_5$-$C_{12}$ cycloalkyl(hetero)aryl groups and $C_5$-$C_{12}$ (hetero)arylcycloalkyl groups, wherein the alkyl groups, alkenyl groups, alkynyl groups, aryl, heteroaryl, cycloalkyl groups, cycloalkenyl groups, alkyl (hetero)aryl groups, (hetero)arylalkyl groups, alkylcycloalkyl groups, cycloalkylalkyl groups, cycloalkyl(hetero)aryl groups and (hetero)arylcycloalkyl groups are optionally substituted with a moiety selected from the group consisting of —Cl, —F, —Br, —I, —$OR_{37}$, —$N(R_{37})_2$, —$SO_3R_{37}$, —$PO_3(R_{37})_2$, —$PO_4(R_{37})_2$, —$NO_2$, —$CF_3$, =O, =$NR_{37}$, and —$SR_{37}$, and optionally contain one or more heteroatoms selected from the group consisting of O, S, $NR_{37}$, P, and Si, wherein the N, S, and P atoms are optionally oxidized, wherein the N atoms are optionally quaternized.

In preferred embodiments, each $R^7$ is independently selected from the group consisting of hydrogen, —F, —Cl, —Br, —I, —$OR_{37}$, —$N(R_{37})_2$, —$SO_3$, —$PO_3^-$, —$NO_2$, —$CF_3$, —$SR_{37}$, $S(=O)_2N(R_{37})_2$, $OC(=O)R_{37}$, $SC(=O)R_{37}$, $OC(=S)R_{37}$, $SC(=S)R_{37}$, $NR_{37}C(=O)—R_{37}$, $NR_{37}C(=S)—R_{37}$, $NR_{37}C(=O)O—R_{37}$, $NR_{37}C(=S)O—R_{37}$, $NR_{37}C(=O)S—R_{37}$, $NR_{37}C(=S)S—R_{37}$, $OC(=O)N(R_{37})_2$, $SC(=O)N(R_{37})_2$, $OC(=S)N(R_{37})_2$, $SC(=S)N(R_{37})_2$, $NR_{37}C(=O)N(R_{37})_2$, $NR_{37}C(=S)N(R_{37})_2$, $C(=O)R_{37}$, $C(=S)R_{37}$, $C(=O)N(R_{37})_2$, $C(=S)N(R_{37})_2$, $C(=O)O—R_{37}$, $C(=O)S—R_{37}$, $C(=S)O—R_{37}$, $C(=S)S—R_{37}$, $S(O)R_{37}$, —$S(O)_2R_{37}$, $NR_{37}S(O)_2R_{37}$, —$ON(R_{37})_2$, —$NR_{37}OR_{37}$, $C_1$-$C_4$ alkyl groups, $C_2$-$C_4$ alkenyl groups, $C_2$-$C_4$ alkynyl groups, $C_6$-$C_8$ aryl groups, $C_2$-$C_8$ heteroaryl groups, $C_3$-$C_6$ cycloalkyl groups, $C_5$-$C_6$ cycloalkenyl groups, $C_3$-$C_{10}$ alkyl(hetero)aryl groups, $C_3$-$C_{10}$ (hetero)arylalkyl groups, $C_4$-$C_{10}$ alkylcycloalkyl groups, $C_4$-$C_{10}$ cycloalkylalkyl groups, $C_5$-$C_{10}$ cycloalkyl(hetero)aryl groups and $C_5$-$C_{10}$ (hetero)arylcycloalkyl groups, wherein the alkyl groups, alkenyl groups, alkynyl groups, aryl, heteroaryl, cycloalkyl groups, cycloalkenyl groups, alkyl (hetero)aryl groups, (hetero)arylalkyl groups, alkylcycloalkyl groups, cycloalkylalkyl groups, cycloalkyl(hetero)aryl groups and (hetero)arylcycloalkyl groups are optionally substituted with a moiety selected from the group consisting of —Cl, —F, —Br, —I, —$OR_{37}$, —$N(R_{37})_2$, —$SO_3R_{37}$, —$PO_3(R_{37})_2$, —$PO_4(R_{37})_2$, —$NO_2$, —$CF_3$, =O, =$NR_{37}$, and —$SR_{37}$, and optionally contain one or more heteroatoms selected from the group consisting of O, S, $NR_{37}$, P, and Si, wherein the N, S, and P atoms are optionally oxidized, wherein the N atoms are optionally quaternized.

In preferred embodiments, each $R^7$ is independently selected from the group consisting of hydrogen and $C_1$-$C_3$ alkyl groups, $C_2$-$C_3$ alkenyl groups, and $C_{4-6}$ (hetero)aryl groups, wherein the alkyl groups, alkenyl groups, and (hetero)aryl groups are optionally substituted with a moiety selected from the group consisting of —Cl, —F, —Br, —I, —OH, —$NH_2$, =O, =NH, —$N(CH_3)_2$, —$S(O)_2CH_3$, and —SH, and are optionally interrupted by at most one heteroatom selected from the group consisting of —O—, —S—, —NH—, —P—, and —Si—, wherein the N, S, and P atoms are optionally oxidized, wherein the N atoms are optionally quaternized.

In preferred embodiments, $R^7$ is preferably selected from the group consisting of hydrogen, methyl, —$CH_2$—$CH_2$—$N(CH_3)_2$, and —$CH_2$—$CH_2$—$S(O)_2$—$CH_3$. In preferred embodiments, the $R^7$ groups not being hydrogen are not substituted. In preferred embodiments, the $R^7$ groups not being hydrogen do not contain heteroatoms. In preferred embodiments, the $R^7$ groups are hydrogen.

$R^8$ and $R^9$

Preferably, $R^8$ and $R^9$ are as defined for $R^7$. In preferred embodiments, at least one or all $R^8$ are —H. In preferred embodiments, at least one or all $R^8$ are —$CH_3$. In preferred embodiments, at least one or all $R^9$ are —H. In preferred embodiments, at least one or all $R^9$ are —$CH_3$.

$R_{32}$ $R_{32}$ is a conjugation moiety, which is chemical group that can be used for binding, conjugation or coupling of a Construct, such as Construct-B, or a Spacer, a Linker $L^C$, the Trigger, or another molecule or construct of interest. The person skilled in the art is aware of the myriad of strategies that are available for the chemoselective or -unselective or enzymatic coupling or conjugation of one molecule or construct to another.

In preferred embodiments, $R_{32}$ is a moiety that allows conjugation to a protein comprising natural and/or non-natural amino acids. Moieties suitable for conjugation are known to the skilled person. Conjugation strategies are for example found in [O. Boutureira, G. J. L. Bernardes, Chem. Rev., 2015, 115, 2174-2195].

In particularly favourable embodiments, $R_{32}$ is selected from the group consisting of N-maleimidyl groups, halogenated N-alkylamido groups, sulfonyloxy N-alkylamido groups, vinyl sulfone groups, (activated) carboxylic acids, benzenesulfonyl halides, ester groups, carbonate groups, sulfonyl halide groups, thiol groups or derivatives thereof, $C_{2-6}$ alkenyl groups, $C_{2-6}$ alkynyl groups, $C_{7-18}$ cycloalkynyl groups, $C_{5-18}$ heterocycloalkynyl groups, bicyclo[6.1.0]non-4-yn-9-yl] groups, $C_{3-12}$ cycloalkenyl groups, azido groups, phosphine groups, nitrile oxide groups, nitrone groups, nitrile imine groups, isonitrile groups, diazo groups, ketone groups, (O-alkyl)hydroxylamino groups, hydrazine groups, halogenated N-maleimidyl groups, aryloxymaleimides, dithiophenolmaleimides, bromo- and dibromopyridazinediones, 2,5-dibromohexanediamide groups, alkynone groups, 3-arylpropiolonitrile groups, 1,1-bis(sulfonylmethyl)-methylcarbonyl groups or elimination derivatives thereof, carbonyl halide groups, allenamide groups, 1,2-quinone groups, isothiocyanate groups, isocyanate groups, aldehyde groups, triazine groups, tetrazine groups, squaric acids, 2-imino-2-methoxyethyl groups, (oxa)norbornene groups, (imino)sydnones, methylsulfonyl phenyloxadiazole groups, aminooxy groups, 2-amino benzamidoxime groups, ethynylphosphonamidates, groups reactive in the Pictet-Spengler ligation and hydrazino-Pictet-Spengler (HIPS) ligation, DNA intercalators and photocrosslinkers.

In preferred embodiments, $R_{32}$ is an N-maleimidyl group connected to the remaining part of the compound according to Formula (19) via the N atom of the N-maleimidyl group.

In other preferred embodiments, $R_{32}$ is selected from the group consisting of, hydroxyl groups, amine groups, halogens, vinyl pyridine groups, disulfide groups, pyridyl disulfide groups, sulfonyloxy groups, mercaptoacetamide groups, anhydride groups, sulfonylated hydroxyacetamido groups, sulfonyl chlorides, thiosemicarbazone, hydrazine carboxylate, and arylhydrazide.

In other embodiments $R_{32}$ is group that can be connected to another group by means of an enzyme, for example sortase or Tubulin tyrosine ligase.

$R_{36}$

In a preferred embodiment, $R_{36}$ is as defined for $R_{37}$.

In Formula (19) $R_{36}$ is preferably selected from the group consisting of hydrogen, $C_1$-$C_8$ alkyl groups, $C_2$-$C_8$ alkenyl groups, and $C_{4-6}$ (hetero)aryl groups, wherein the alkyl groups, alkenyl groups, and (hetero)aryl groups are optionally substituted with a moiety selected from the group consisting of —Cl, —F, —Br, —I, —OH, —$NH_2$, =O, —SH, —$SO_3H$, —$PO_3H$, —$PO_4H_2$ and —$NO_2$ and optionally contain at most two heteroatoms selected from the group consisting of —O—, —S—, —NH—, —P—, and —Si—, wherein the N, S, and P atoms are optionally oxidized.

In preferred embodiments, the $R_{36}$ groups not being hydrogen are not substituted. In preferred embodiments, the $R_{36}$ groups not being hydrogen do not contain heteroatoms.

$R_{37}$

Preferably each $R_{37}$ is independently selected from the group consisting of hydrogen, —$(S^P)_i$—$C^B$, $C_1$-$C_8$ alkyl groups, $C_2$-$C_8$ alkenyl groups, $C_2$-$C_8$ alkynyl groups, $C_6$-$C_{12}$ aryl, $C_2$-$C_{12}$ heteroaryl, $C_3$-$C_8$ cycloalkyl groups, $C_5$-$C_8$ cycloalkenyl groups, $C_3$-$C_{12}$ alkyl(hetero)aryl groups, $C_3$-$C_{12}$ (hetero)arylalkyl groups, $C_4$-$C_{12}$ alkylcycloalkyl groups, $C_4$-$C_{12}$ cycloalkylalkyl groups, $C_5$-$C_{12}$ cycloalkyl (hetero)aryl groups and $C_5$-$C_{12}$ (hetero)arylcycloalkyl groups, wherein i is an integer in the range of from 0 to 4, preferably 1, wherein the $R_{37}$ groups not being hydrogen are optionally substituted with a moiety selected from the group consisting of —Cl, —F, —Br, —I, —OH, —$NH_2$, —$SO_3H$, —$PO_3H$, —$PO_4H_2$, —$NO_2$, —$CF_3$, =O, =NH, and —SH, and optionally contain one or more heteroatoms selected from the group consisting of O, S, NH, P, and Si, wherein the N, S, and P atoms are optionally oxidized, wherein the N atoms are optionally quaternized.

Preferably each $R_{37}$ is independently selected from the group consisting of hydrogen, —$(S^P)_i$—$C^B$, $C_1$-$C_4$ alkyl groups, $C_2$-$C_4$ alkenyl groups, $C_2$-$C_4$ alkynyl groups, $C_6$-$C_5$ aryl, $C_2$-$C_8$ heteroaryl, $C_3$-$C_6$ cycloalkyl groups, $C_5$-$C_6$ cycloalkenyl groups, $C_3$-$C_{10}$ alkyl(hetero)aryl groups, $C_3$-$C_{10}$ (hetero)arylalkyl groups, $C_4$-$C_8$ alkylcycloalkyl groups, $C_4$-$C_8$ cycloalkylalkyl groups, $C_5$-$C_{10}$ cycloalkyl (hetero)aryl groups and $C_5$-$C_{10}$ (hetero)arylcycloalkyl groups, wherein i is an integer in the range of from 0 to 4, preferably 1, wherein the $R_{37}$ groups not being hydrogen are optionally substituted with a moiety selected from the group consisting of —Cl, —F, —Br, —I, —OH, —$NH_2$, —$SO_3H$, —$PO_3H$, —$PO_4H_2$, —$NO_2$, —$CF_3$, =O, =NH, and —SH, and optionally contain one or more heteroatoms selected from the group consisting of O, S, NH, P, and Si, wherein the N, S, and P atoms are optionally oxidized, wherein the N atoms are optionally quaternized.

In preferred embodiments, the $R_{37}$ groups not being hydrogen are not substituted. In preferred embodiments, the $R_{37}$ groups not being hydrogen do not contain heteroatoms.

$R_{47}$

In preferred embodiments, each $R_{47}$ is independently selected from the group consisting of hydrogen, —F, —Cl, —Br, —I, —$OR_{37}$, —$N(R_{37})_2$, —$SO_3$, —$PO_3^-$, —$NO_2$, —$CF_3$, —$SR_{37}$, $S(=O)_2N(R_{37})_2$, $OC(=O)R_{37}$, $SC(=O)R_{37}$, $OC(=S)R_{37}$, $SC(=S)R_{37}$, $NR_{37}C(=O)$—$R_{37}$, $NR_{37}C(=S)$—$R_{37}$, $NR_{37}C(=O)O$—$R_{37}$, $NR_{37}C(=S)O$—$R_{37}$, $NR_{37}C(=O)S$—$R_{37}$, $NR_{37}C(=S)S$—$R_{37}$, $OC(=O)N(R_{37})_2$, $SC(=O)N(R_{37})_2$, $OC(=S)N(R_{37})_2$, $SC(=S)N(R_{37})_2$, $NR_{37}C(=O)N(R_{37})_2$, $NR_{37}C(=S)N(R_{37})_2$, $C(=O)R_{37}$, $C(=S)R_{37}$, $C(=O)N(R_{37})_2$, $C(=S)N(R_{37})_2$, $C(=O)O$—$R_{37}$, $C(=O)S$—$R_{37}$, $C(=S)O$—$R_{37}$, $C(=S)S$—$R_{37}$, $S(O)R_{37}$, —$S(O)_2R_{37}$, $NR_{37}S(O)_2R_{37}$, —$ON(R_{37})_2$, —$NR_{37}OR_{37}$, —$(S^P)_i$—$C^B$, $C_1$-$C_8$ alkyl groups, $C_2$-$C_8$ alkenyl groups, $C_2$-$C_8$ alkynyl groups, $C_6$-$C_{12}$ aryl groups, $C_2$-$C_{12}$ heteroaryl groups, $C_3$-$C_8$ cycloalkyl groups, $C_5$-$C_8$ cycloalkenyl groups, $C_3$-$C_{12}$ alkyl(hetero)aryl groups, $C_3$-$C_{12}$ (hetero)arylalkyl groups, $C_4$-$C_{12}$ alkylcycloalkyl groups, $C_4$-$C_{12}$ cycloalkylalkyl groups, $C_5$-$C_{12}$ cycloalkyl (hetero)aryl groups and $C_5$-$C_{12}$ (hetero)arylcycloalkyl groups, wherein i is an integer in the range of from 0 to 4, preferably 1; wherein the alkyl groups, alkenyl groups, alkynyl groups, aryl, heteroaryl, cycloalkyl groups, cycloalkenyl groups, alkyl(hetero)aryl groups, (hetero)arylalkyl groups, alkylcycloalkyl groups, cycloalkylalkyl groups, cycloalkyl(hetero)aryl groups and (hetero)arylcycloalkyl groups are optionally substituted with a moiety selected from the group consisting of —Cl, —F, —Br, —I, —$OR_{37}$, —$N(R_{37})_2$, —$SO_3R_{37}$, —$PO_3(R_{37})_2$, —$PO_4(R_{37})_2$, —$NO_2$, —$CF_3$, =O, =$NR_{37}$, and —$SR_{37}$, and optionally contain one or more heteroatoms selected from the group consisting of O, S, $NR_{37}$, P, and Si, wherein the N, S, and P atoms are optionally oxidized, wherein the N atoms are optionally quaternized.

In preferred embodiments, each $R_{47}$ is independently selected from the group consisting of hydrogen —F, —Cl, —Br, —I, —$OR_{37}$, —$N(R_{37})_2$, —$SO_3$, —$PO_3^-$, —$NO_2$, —$CF_3$, —$SR_{37}$, $S(=O)_2N(R_{37})_2$, $OC(=O)R_{37}$, $SC(=O)R_{37}$, $OC(=S)R_{37}$, $SC(=S)R_{37}$, $NR_{37}C(=O)$—$R_{37}$, $NR_{37}C(=S)$—$R_{37}$, $NR_{37}C(=O)O$—$R_{37}$, $NR_{37}C(=S)O$—$R_{37}$, $NR_{37}C(=O)S$—$R_{37}$, $NR_{37}C(=S)S$—$R_{37}$, $OC(=O)N(R_{37})_2$, $SC(=O)N(R_{37})_2$, $OC(=S)N(R_{37})_2$, $SC(=S)N(R_{37})_2$, $NR_{37}C(=O)N(R_{37})_2$, $NR_{37}C(=S)N(R_{37})_2$, $C(=O)R_{37}$, $C(=S)R_{37}$, $C(=O)N(R_{37})_2$, $C(=S)N(R_{37})_2$, $C(=O)O$—$R_{37}$, $C(=O)S$—$R_{37}$, $C(=S)O$—$R_{37}$, $C(=S)S$—$R_{37}$, $S(O)R_{37}$, —$S(O)_2R_{37}$, $NR_{37}S(O)_2R_{37}$, —$ON(R_{37})_2$, $NR_{37}OR_{37}$, —$(S^P)_i$—$C^B$, $C_1$-$C_4$ alkyl groups, $C_2$-$C_4$ alkenyl groups, $C_2$-$C_4$ alkynyl groups, $C_6$-$C_8$ aryl groups, $C_2$-$C_8$ heteroaryl groups, $C_3$-$C_6$ cycloalkyl groups, $C_5$-$C_6$ cycloalkenyl groups, $C_3$-$C_{10}$ alkyl(hetero)aryl groups, $C_3$-$C_{10}$ (hetero)arylalkyl groups, $C_4$-$C_{10}$ alkylcycloalkyl groups, $C_4$-$C_{10}$ cycloalkylalkyl groups, $C_5$-$C_{10}$ cycloalkyl(hetero)aryl groups and $C_5$-$C_{10}$ (hetero)arylcycloalkyl groups, wherein i is an integer in the range of from 0 to 4, preferably 1; wherein the alkyl groups, alkenyl groups, alkynyl groups, aryl, heteroaryl, cycloalkyl groups, cycloalkenyl groups, alkyl(hetero)aryl groups, (hetero)arylalkyl groups, alkylcycloalkyl groups, cycloalkylalkyl groups, cycloalkyl(hetero) aryl groups and (hetero)arylcycloalkyl groups are optionally substituted with a moiety selected from the group consisting of —Cl, —F, —Br, —I, —$OR_{37}$, —$N(R_{37})_2$, —$SO_3R_{37}$, —$PO_3(R_{37})_2$, —$PO_4(R_{37})_2$, —$NO_2$, —$CF_3$, =O, =$NR_{37}$, and —$SR_{37}$, and optionally contain one or more heteroatoms selected from the group consisting of O, S, $NR_{37}$, P, and Si, wherein the N, S, and P atoms are optionally oxidized, wherein the N atoms are optionally quaternized.

In a preferred embodiment, $R_{47}$ is a moiety satisfying any one of Formulae (2x) and (2y):

Formula (2x)

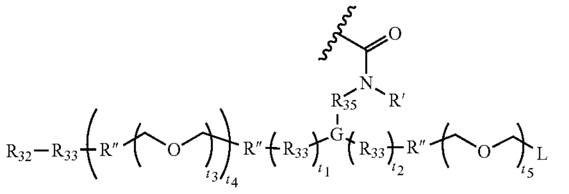

Formula (2y)

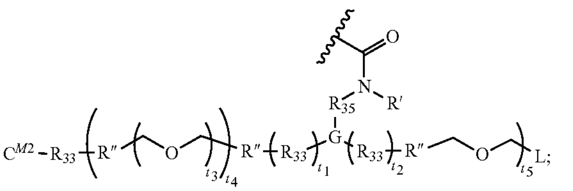

wherein in both Formula (2x) and (2y) the wiggly line denotes a bond to the remainder of the molecule. In Formula (2y), $C^{M2}$ is coupled to a Construct-B ($C^B$), preferably a targeting agent, preferably selected from the group consisting of proteins, antibodies, peptoids and peptides.

In a preferred embodiment, in Formula (19), if $X^3$ is $CR_{47}Y^{T1}$ and $X^1$, $X^2$, $X^4$, and $X^5$ are $CH_2$, then $R_{47}$ in $X^3$ does not satisfy Formula (2x) or (2y).

$R_{33}$

In preferred embodiments, each individual $R_{33}$ is selected from the group consisting of $C_1$-$C_{12}$ alkylene groups, $C_2$-$C_{12}$ alkenylene groups, $C_2$-$C_{12}$ alkynylene groups, $C_6$ arylene groups, $C_4$-$C_5$ heteroarylene groups, $C_3$-$C_8$ cycloalkylene groups, $C_5$-$C_8$ cycloalkenylene groups, $C_5$-$C_{12}$ alkyl(hetero) arylene groups, $C_5$-$C_{12}$ (hetero)arylalkylene groups, $C_4$-$C_{12}$ alkylcycloalkylene groups, $C_4$-$C_{12}$ cycloalkylalkylene groups, wherein the alkylene groups, alkenylene groups, alkynylene groups, (hetero)arylene groups, cycloalkylene groups, cycloalkenylene groups, alkyl(hetero)arylene groups, (hetero)arylalkylene groups, alkylcycloalkylene groups, cycloalkylalkylene groups, are optionally substituted with a moiety selected from the group consisting of —Cl, —F, —Br, —I, —$OR_{37}$, —N(R')$_2$, =O, =NR', —SR', —$SO_3$H, —$PO_3$H, —$PO_4H_2$, —$NO_2$ and —Si(R')$_3$, and optionally contain one or more heteroatoms selected from the group consisting of —O—, —S—, —NR'—, —P—, and —Si—, wherein the N, S, and P atoms are optionally oxidized, wherein the N atoms are optionally quaternized.

In particularly favourable embodiments, each individual $R_{33}$ is selected from the group consisting of $C_1$-$C_6$ alkylene groups, $C_2$-$C_6$ alkenylene groups, and $C_2$-$C_6$ alkynylene groups, more preferably from the group consisting of $C_1$-$C_3$ alkylene groups, $C_2$-$C_3$ alkenylene groups, and $C_2$-$C_3$ alkynylene groups; and wherein preferably the alkylene groups, alkenylene groups, alkynylene groups, cycloalkylene groups, cycloalkenylene groups, and cycloalkynylene groups optionally contain one or more heteroatoms selected from the group consisting of O, S, $NR_5$, P, and Si, wherein the N, S, and P atoms are optionally oxidized, wherein the N atoms are optionally quaternized.

$R_{35}$

In preferred embodiments, each individual $R_{35}$ is selected from the group consisting of $C_1$-$C_8$ alkylene groups, $C_2$-$C_8$ alkenylene groups, $C_2$-$C_8$ alkynylene groups, $C_6$ arylene groups, $C_4$-$C_5$ heteroarylene groups, $C_3$-$C_6$ cycloalkylene groups, $C_5$-$C_8$ cycloalkenylene groups, $C_5$-$C_{12}$ alkyl(hetero)arylene groups, $C_5$-$C_{12}$ (hetero)arylalkylene groups, $C_4$-$C_{12}$ alkylcycloalkylene groups, $C_4$-$C_{12}$ cycloalkylalkylene groups, wherein for the alkylene groups, alkenylene groups, alkynylene groups, (hetero)arylene groups, cycloalkylene groups, cycloalkenylene groups, alkyl(hetero)arylene groups, (hetero)arylalkylene groups, alkylcycloalkylene groups, cycloalkylalkylene groups, are optionally substituted with a moiety selected from the group consisting of —Cl, —F, —Br, —I, —OR', —N(R')$_2$, =O, =NR', —SR', —$SO_3$H, —$PO_3$H, —$PO_4H_2$, —$NO_2$ and —Si(R')$_3$, and optionally contain one or more heteroatoms selected from the group consisting of —O—, —S—, —NR'—, —P—, and —Si—, wherein the N, S, and P atoms are optionally oxidized, wherein the N atoms are optionally quaternized.

In preferred embodiments, each individual $R_{35}$ is selected from the group consisting of $C_1$-$C_4$ alkylene groups, $C_2$-$C_4$ alkenylene groups, $C_2$-$C_4$ alkynylene groups, $C_6$ arylene groups, $C_4$-$C_5$ heteroarylene groups, $C_3$-$C_6$ cycloalkylene groups, wherein the alkylene groups, alkenylene groups, alkynylene groups, (hetero)arylene groups, and cycloalkylene groups, are optionally substituted with a moiety selected from the group consisting of —Cl, —F, —Br, —I, —OR', —N(R')$_2$, =O, =NR', —SR', —$SO_3$H, —$PO_3$H, —$PO_4H_2$, —$NO_2$ and —Si(R')$_3$, and optionally contain one or more heteroatoms selected from the group consisting of —O—, —S—, —NR'—, —P—, and —Si—, wherein the N, S, and P atoms are optionally oxidized, wherein the N atoms are optionally quaternized.

R'

In preferred embodiments, each R' is independently selected from the group consisting of hydrogen, $C_1$-$C_6$ alkylene groups, $C_2$-$C_6$ alkenylene groups, $C_2$-$C_6$ alkynylene groups, $C_6$ arylene, $C_4$-$C_5$ heteroarylene, $C_3$-$C_6$ cycloalkylene groups, $C_5$-$C_8$ cycloalkenylene groups, $C_5$-$C_{12}$ alkyl(hetero)arylene groups, $C_5$-$C_{12}$ (hetero)arylalkylene groups, $C_4$-$C_{12}$ alkylcycloalkylene groups, and $C_4$-$C_{12}$ cycloalkylalkylene groups.

In preferred embodiments, each R' is independently selected from the group consisting of hydrogen, $C_1$-$C_4$ alkylene groups, $C_2$-$C_4$ alkenylene groups, $C_2$-$C_4$ alkynylene groups, $C_6$ arylene, $C_4$-$C_5$ heteroarylene, $C_3$-$C_6$ cycloalkylene groups, $C_5$-$C_8$ cycloalkenylene groups, $C_5$-$C_8$ alkyl(hetero)arylene groups, $C_5$-$C_8$ (hetero)arylalkylene groups, $C_4$-$C_{12}$ alkylcycloalkylene groups, and $C_4$-$C_8$ cycloalkylalkylene groups.

Unless stated otherwise, for R' the alkylene groups, alkenylene groups, alkynylene groups, (hetero)arylene groups, cycloalkylene groups, cycloalkenylene groups, alkyl(hetero)arylene groups, (hetero)arylalkylene groups, alkylcycloalkylene groups, cycloalkylalkylene groups are optionally substituted with a moiety selected from the group consisting of —Cl, —F, —Br, —I, —OH, —$NH_2$, =O, —SH, —$SO_3$H, —$PO_3$H, —$PO_4H_2$, —$NO_2$, and optionally contain one or more heteroatoms selected from the group consisting of —O—, —S—, —NH—, —P—, and —Si, wherein the N, S, and P atoms are optionally oxidized.

In a preferred embodiment, R' is as defined for $R_{37}$.

In a preferred embodiment, in relation to $C^{M2}$, $C^X$, and the conjugation of $C^A$ and $C^B$, R' is as defined for $R_{37}$.

R"

In preferred embodiments, each R" is independently selected from the group consisting of

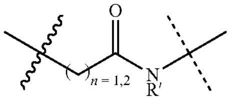
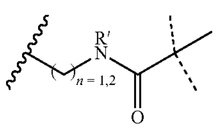
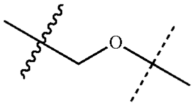
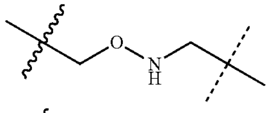
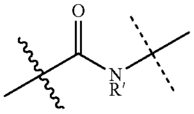
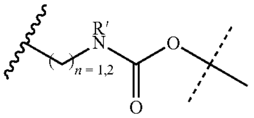
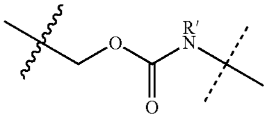
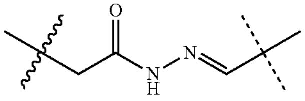
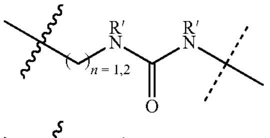
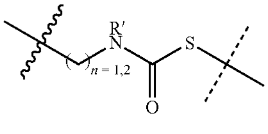
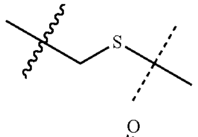
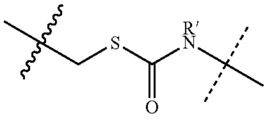
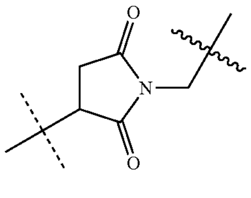

-continued

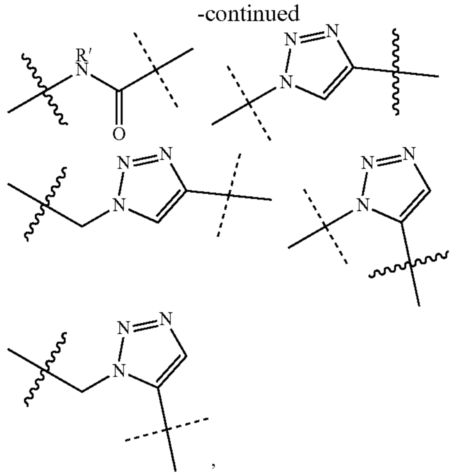

, wherein the wiggly line depicts a bond to an ethylene glycol group or optionally to the $R_{33}$ adjacent to $R_{32}$ when $t_4$ is 0, and the dashed line depicts a bond to $R_{33}$ or G.

In preferred embodiments, R" is —$CH_2$—C(O)NR'— or —$CH_2$—NR', N, $C_5$-$C_6$ arenetriyl, $C_4$-$C_5$ heteroarenetriyl, $C_3$-$C_6$ cycloalkanetriyl, and $C_4$-$C_6$ cycloalkenetriyl, wherein the arenetriyl, heteroarenetriyl, cycloalkanetriyl, and cycloalkenetriyl are optionally further substituted with groups selected from the group consisting of —Cl, —F, —Br, —I, —OR', —$N(R')_2$, —SR', —$SO_3H$, —$PO_3H$, —$PO_4H_2$, —$NO_2$, and —$CF_3$, and optionally contain one or more heteroatoms selected from the group consisting of —O—, —S—, —NR'—, —P—, and —Si—, wherein the N, S, and P atoms are optionally oxidized, wherein the N atoms are optionally quaternized. Preferably, G is CR'.

L

In preferred embodiments, L is selected from the group consisting of —$CH_2$—$OCH_3$, —$CH_2$—OH, —$CH_2$—C(O)OH, —C(O)OH. In preferred embodiments, L is preferably —$CH_2$—$OCH_3$.

$t_1$, $t_2$, $t_3$, $t_4$, $t_5$

In preferred embodiments, $t_1$ is 0. In other embodiments, $t_1$ is 1. In preferred embodiments, $t_2$ is 0. In other embodiments, $t_2$ is 1. In preferred embodiments, $t_3$ is an integer in a range of from 0 to 12. Preferably, $t_3$ is an integer in a range of from 1 to 10, more preferably in a range of from 2 to 8. In particularly favourable embodiments, $t_3$ is 4 and y is 1. In preferred embodiments, $t_4$ is 0. In other embodiments, $t_4$ is 1. In preferred embodiments, $t_5$ is an integer in a range of from 6 to 48, preferably from 15 to 40, more preferably from 17 to 35, even more preferably from 20 to 30, most preferably from 22 to 28. In particularly preferred embodiments, $t_5$ is 23.

Trans-Cyclooctenes

In a preferred embodiment, the dienophile Trigger moiety used in the present invention comprises a trans-cyclooctene ring, and particularly refers to a structure satisfying Formula (19), the ring optionally including one or more hetero-atoms. The skilled person is familiar with the fact that the dienophile activity is not necessarily dependent on the presence of all carbon atoms in the ring, since also heterocyclic monoalkenylene eight-membered rings are known to possess dienophile activity.

Thus, in general, the invention is not limited to strictly trans-cyclooctene. The person skilled in organic chemistry will be aware that other eight-membered ring-based dienophiles exist, which comprise the same endocyclic double bond as the trans-cyclooctene, but which may have one or more heteroatoms elsewhere in the ring. I.e., the invention generally pertains to eight-membered non-aromatic cyclic alkene moieties, preferably a cyclooctene moiety, and more preferably a trans-cyclooctene moiety.

It should be noted that, depending on the choice of nomenclature, the TCO dienophile may also be denoted E-cyclooctene. With reference to the conventional nomenclature, it will be understood that, as a result of substitution on the cyclooctene ring, depending on the location and molecular weight of the substituent, the same cyclooctene isomer may formally become denoted as a Z-isomer. In the present invention, any substituted variants of the invention, whether or not formally "E" or "Z," or "cis" or "trans" isomers, will be considered derivatives of unsubstituted trans-cyclooctene, or unsubstituted E-cyclooctene. The terms "trans-cyclooctene" (TCO) as well as E-cyclooctene are used interchangeably and are maintained for all dienophiles according to the present invention, also in the event that substituents would formally require the opposite nomenclature. I.e., the invention relates to cyclooctene in which carbon atoms 1 and 6 as numbered below in Formula 4b are in the E (entgegen) or trans position.

Formula 4b

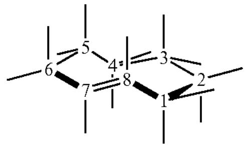

The TCO may consist of multiple isomers, also comprising the equatorial vs. axial positioning of substituents, such as $R_{48}$, on the TCO. In this respect, reference is made to Whitham et al. *J. Chem. Soc.* (C), 1971, 883-896, describing the synthesis and characterization of the equatorial and axial isomers of trans-cyclo-oct-2-en-ol, identified as (1RS,2RS) and (1SR,2RS), respectively. In these isomers the OH substituent is either in the equatorial or axial position. In a preferred embodiment, for TCO structures where the $R_{48}$ can be either in the axial or the equatorial position, the $R_{48}$ is in the axial position.

Trans-cyclooctene or E-cyclooctene derivatives are very suitable as Triggers, especially considering their high reactivity. Optionally, the trans-cyclooctene (TCO) moiety comprises at least two exocyclic bonds fixed in substantially the same plane, and/or it optionally comprises at least one substituent in the axial position, and not the equatorial position. The person skilled in organic chemistry will understand that the term "fixed in substantially the same plane" refers to bonding theory according to which bonds are normally considered to be fixed in the same plane. Typical examples of such fixations in the same plane include double bonds and strained fused rings. E.g., the at least two exocyclic bonds can be the two bonds of a double bond to an oxygen (i.e. C═O). The at least two exocyclic bonds can also be single bonds on two adjacent carbon atoms, provided that these bonds together are part of a fused ring (i.e. fused to the TCO ring) that assumes a substantially flat structure, therewith fixing said two single bonds in substantially one and the same plane. Examples of the latter include strained rings such as cyclopropyl and cyclobutyl. Without wishing to be bound by theory, the inventors believe that the presence of at least two exocyclic bonds in the same plane will result in an at least partial flattening of the TCO ring, which can lead to higher reactivity in the IEDDA reaction. A background reference providing further guidance is WO 2013/153254.

The dienophiles for use in the invention can be synthesized by the skilled person, on the basis of known synthesis routes to cyclooctenes and corresponding hetero atom(s)-containing rings. The skilled person further is aware of the wealth of cyclooctene derivatives that can be synthesized via the ring closing metathesis reaction using Grubbs catalysts. As mentioned above, the TCO possibly includes one or more heteroatoms in the ring. This is as such sufficiently accessible to the skilled person [e.g. WO2016025480]. Reference is made, e.g., to the presence of a thioether in TCO: [Cere et al. J. Org. Chem. 1980, 45, 261]. Also, e.g., an —O—$SiR_2$—O moiety in TCO: [Prevost et al. J. Am. Chem. Soc. 2009, 131, 14182]. References to TCO syntheses wherein the allylic positioned leaving group ($R_{48}$) is an ether, ester, carbonate, carbamate or a thiocarbamate are: [Versteegen et al Angew. Chem. Int. Ed. 2018, 57, 10494], and [Steiger et al Chem Comm 2017, 53, 1378]. Exemplary compounds include the following structures, indicated below with literature references. Where a cyclooctene derivative is depicted as a Z-cyclooctene it is conceived that this can be converted to the E-cyclooctene analog.

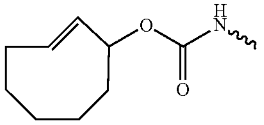

Angew. Chem. Int. Ed. 2013, 52, 14112

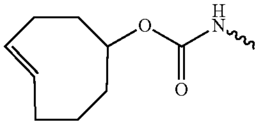

Angew. Chem. Int. Ed. 2010, 49, 3375

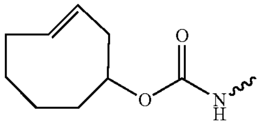

Angew. Chem. Int. Ed. 2014, 53, 2245

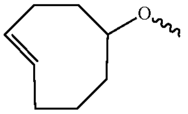

Bioconjug. Chem. 2013, 24, 7, 1210

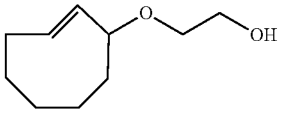

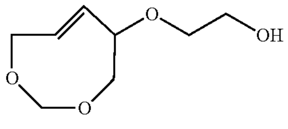

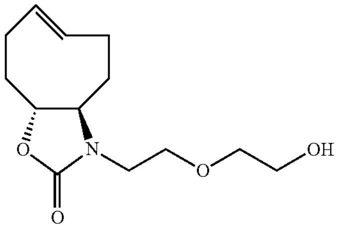

-continued

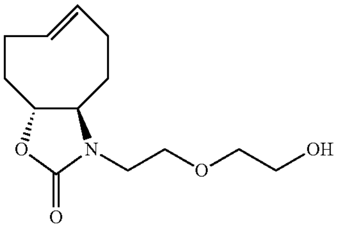

Varga, Thesis, 2014, University of Budapest

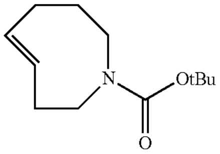

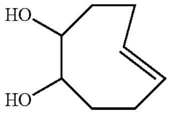

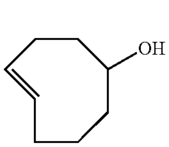

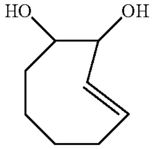

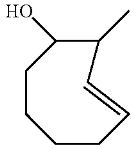

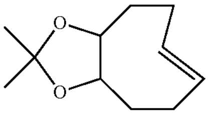

J. Am. Chem. Soc. 2008, 130, 3760

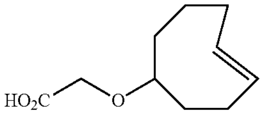

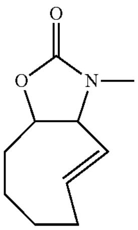

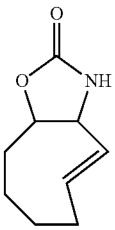

J. Am. Chem. Soc. 2008, 130, 3760

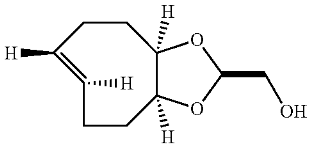

Chem Sci. 2014 Oct 1;5(10):3770

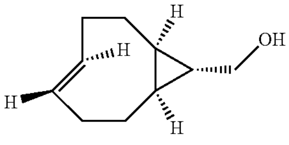

J. Am. Chem. Soc. 2011, 133, 9646

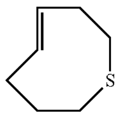

Journal of Organic Chemistry 1980, 45, 261

-continued
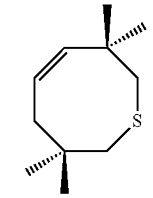
Chem. Ber. 1992, 125, 1431-1437
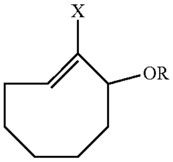
X = Cl, Br
R = H, Me
J. Chem. Soc. Perkin I 1975, 2422
J. Am. Chem. Soc. 1970, 92, 2566
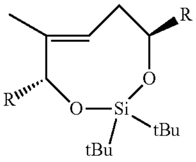
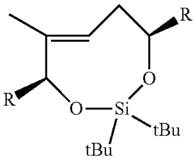
J. Am. Chem. Soc., 2009, 131, 14182
Dalton Trans 2010, 9275
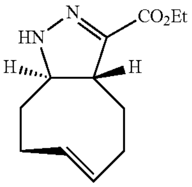
RSC Adv., 2014, 4, 52241
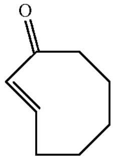
J. Am. Chem. Soc, 1964, 2087
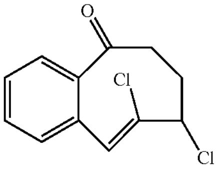
J. Chem. Soc. Chem Comm 1992, 1433
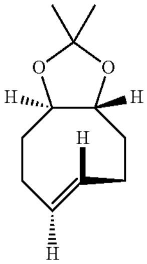
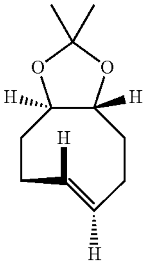
Tetrahedron: Asymmetry 15 (2004) 3123
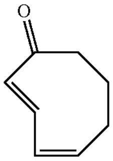
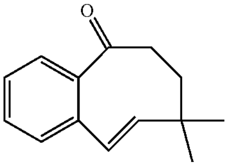
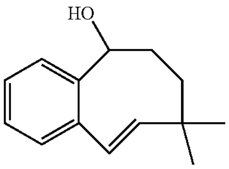
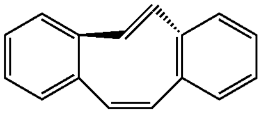
Tetrahedron Lett 1975, 49, 4327
-continued
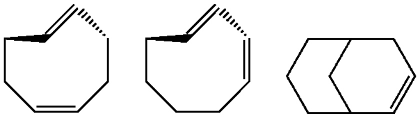
Angew. Chem. Int. Ed. 2008, 47, 2982
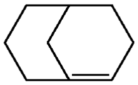
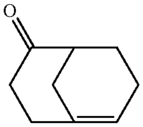
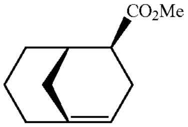
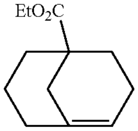
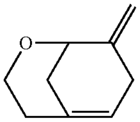
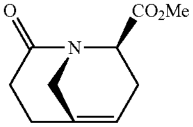
Angew. Chem. Int. Ed. 2001, 40, 820
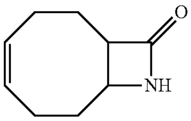
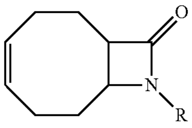
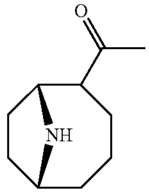
Zuniga, Thesis 2012, University of Salamanca
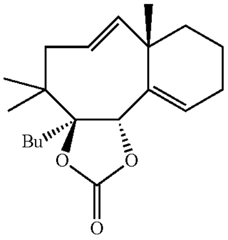
Molecules 2010, 15, 4242-4260
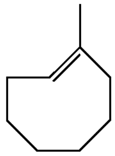
J. Am. Chem. Soc 1992, 114, 3044
 = rest of molecule
Preferred Triggers of this invention include:
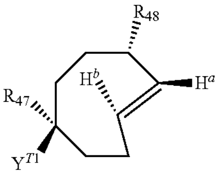
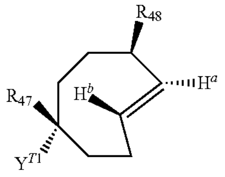
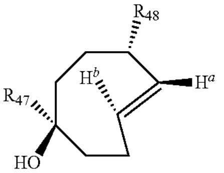
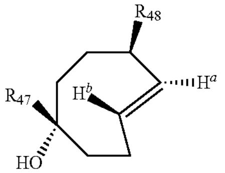

-continued
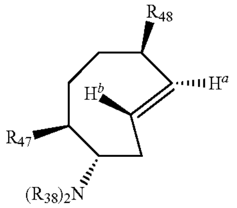
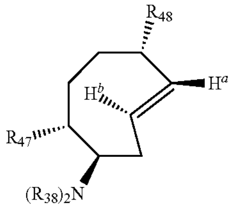
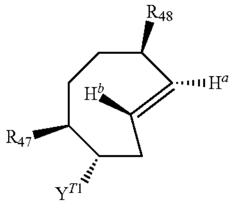
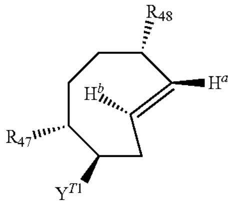
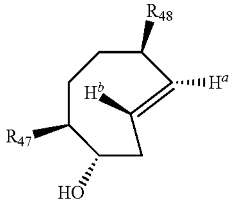
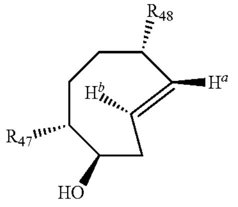
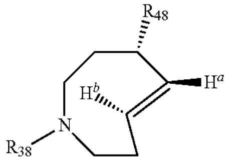
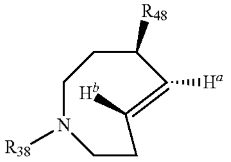
Further preferred Triggers of this invention include:
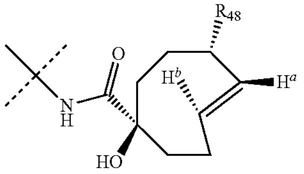
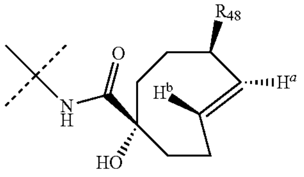
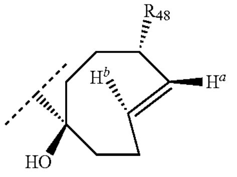
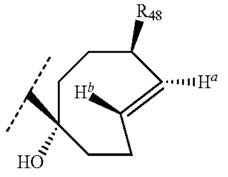
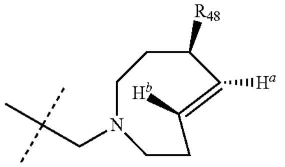
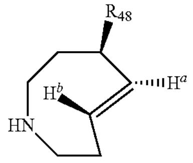
-continued
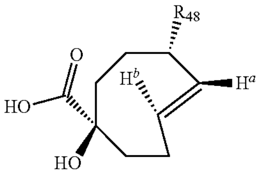
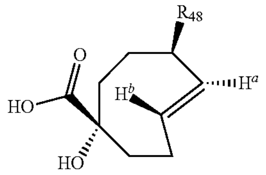
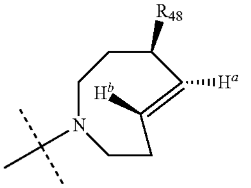
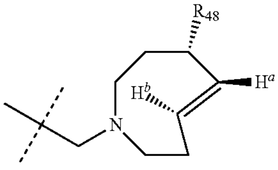
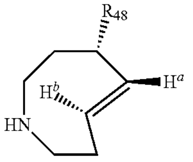
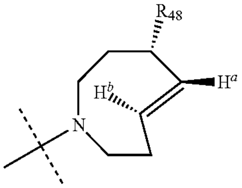
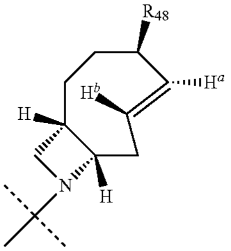
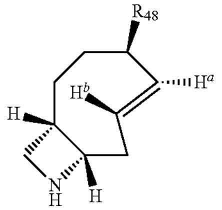
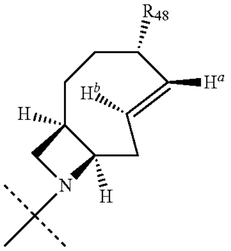
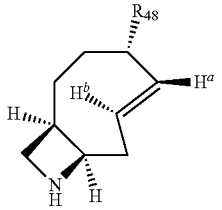
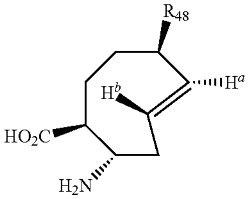
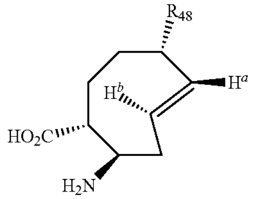
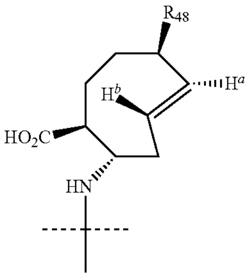
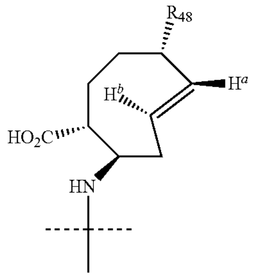
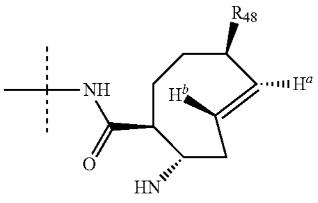

-continued

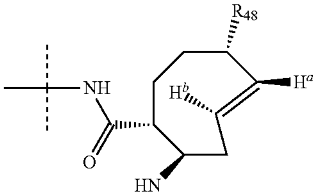

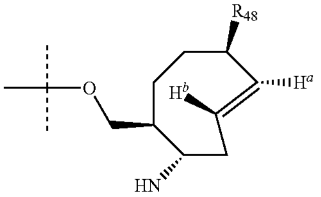

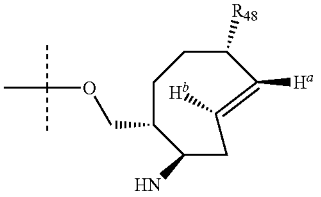

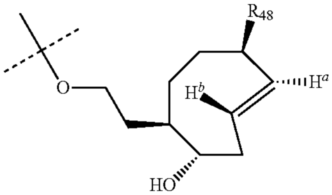

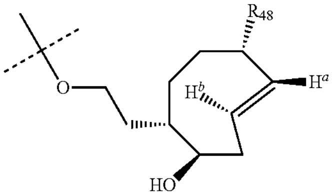

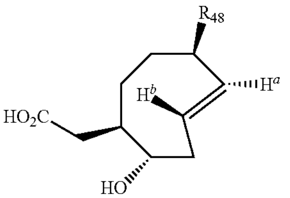

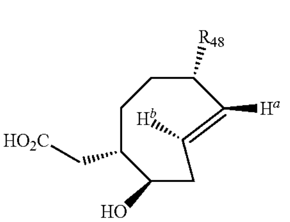

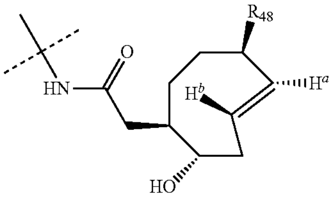

-continued

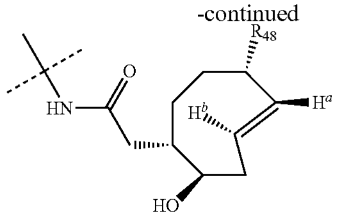

----- = bond to $R_{37}$, $R_{38}$, or $R_{47}$, or bond to remainder of $R_{37}$, $R_{38}$, or $R_{47}$ Construct-A ($C^A$) and Construct-B ($C^B$)

The Constructs A and Constructs B include but are not limited to small molecules, organic molecules, metal coordination compounds, molecules comprising a radionuclide, chelates comprising a radiometal, inorganic molecules, organometallic molecules, biomolecules, polymers, resins, particles (e.g. micro- and nanoparticles), liposomes, micelles, polymersomes, gels, surfaces, cells, biological tissues, and pathogens.

In preferred Prodrug or in vivo embodiments, $C^A$ is selected from the group consisting of Drugs, Targeting Agents, Labels, Administration Agents, and Masking Moieties. Preferably, $C^A$ is a Drug, preferably a Drug as defined herein.

In some preferred Prodrug or in vivo embodiments, $C^B$ is selected from the group consisting of Drugs, Targeting Agents, Labels, Administration Agents, and Masking Moieties. Preferably, $C^B$ is selected from the group consisting of Targeting Agents, and Masking Moieties.

In preferred embodiments, the compounds of Formula (19) comprise at least one Label and at least one Administration Agent, and preferably satisfy at least one of the conditions (i)-(iii):

(i) at least one $C^A$ is a Label, and at least one $C^A$ is an Administration Agent;

(ii) at least one $C^A$ is a Label, and at least one $C^B$ is an Administration Agent;

(iii) at least one $C^A$ is an Administration Agent, and at least one $C^B$ is a Label;

for all conditions (i)-(iii): with the proviso that if $X^1$—$X^5$ contain the Administration Agent and at least one $C^A$ is a Label, $X^1$—$X^5$ do not contain the same Label as the at least one $C^A$; with the proviso that if at least one $C^A$ is a Label and $X^1$—$X^5$ contain the same Label as the at least one $C^A$, $X^1$—$X^5$ do not contain an Administration Agent; with the preference that if at least one $C^B$ comprised in $R_{48}$ is an Administration Agent, then the other $C^B$ comprised in $R_{48}$ are not a Label. In a preferred embodiment, only condition (i) is met. In a preferred embodiment, only condition (ii) is met. In a preferred embodiment, only condition (iii) is met. In a preferred embodiment, both conditions (i) and (ii) are met. In a preferred embodiment, both conditions (i) and (iii) are met. In a preferred embodiment, both conditions (ii) and (iii) are met. In a preferred embodiment, all three conditions (i)-(iii) are met.

In preferred in vitro embodiments $C^A$ and $C^B$ include but are not limited to small molecules, organic molecules (including fluorescent dyes), metal coordination compounds, molecules comprising a radionuclide, chelates comprising a radiometal, inorganic molecules, organometallic molecules, biomolecules, drugs, polymers, resins (e.g. polystyrene, agarose), particles (e.g. beads, magnetic beads, gold, silica-based particles and materials, polymers and polymer-based materials, glass, iron oxide particles, micro- and nanoparticles such as liposomes and polymersomes), gels, surfaces (e.g. glass slides, chips, wafers, gold, metal, silica-based, polymer, plastic, resin), cells, biological tissues, pathogens (viruses, bacteria, fungi, yeast). The Constructs may for example comprise a combination of the aforementioned Constructs. Examples of biomolecules include: carbohydrates, biotin, peptides, peptoids, lipids, proteins, enzymes, oligonucleotides, DNA, RNA, PNA, LNA, aptamers, hormones, toxins, steroids, cytokines, antibodies, antibody fragments (e.g. Fab2, Fab, scFV, diabodies, triabodies, VHH), antibody (fragment) fusions (e.g. bi-specific and trispecific mAb fragments).

In preferred in vitro embodiments $C^A$ and $C^B$ can also be $R_{32}$ or a moiety comprising $R_{32}$, as defined herein, wherein $R_{32}$ can be used to bind to a further $C^A$ and $C^B$. For example, $C^A$ can be $R_{32}$ being a maleimide or photocrosslinker that is bound to the $T^R$ via a Spacer $S^P$. The maleimide or photocrosslinker can be used to further conjugate the $T^R$ to a protein. In this particular embodiment $C^A$ and $C^B$ are a biomolecule-binding moiety.

In preferred embodiments, each $C^A$ and $C^B$ are independently selected from the group consisting of organic molecules, inorganic molecules, organometallic molecules, resins, beads, glass, microparticles, nanoparticles, gels, surfaces, and cells. Preferably, each $C^A$ and $C^B$ are independently selected from the group consisting of organic molecules, and inorganic molecules.

In preferred embodiments, each $C^A$ and $C^B$ are independently selected from the group consisting of small molecules, proteins, carbohydrates, peptides, peptoids, oligosaccharides, molecules comprising a radionuclide, fluorescent dyes, inorganic molecules, organometallic molecules, polymers, lipids, oligonucleotides, DNA, RNA, PNA, LNA, drugs, resins, beads, glass, microparticles, nanoparticles, gels, surfaces, and cells.

Preferably, a small molecule is a small organic molecule. Preferably, a small molecule has a molecular weight of at most 2 kDa, more preferably at most 1 kDa, more preferably at most 750 Da, more preferably at most 500 Da, and most preferably at most 300 Da. Preferably, a small molecule has a molecular weight of at least 15 Da, more preferably at least 50 Da, more preferably at least 75 Da, and most preferably at least 100 Da.

It will be understood that "molecules comprising a radionuclide" include chelators that chelate a radionuclide.

In another preferred embodiment, each $C^A$ and $C^B$ are independently a moiety according to Formula (5) as defined herein.

Construct-Trigger Assemblies

A Construct-Trigger comprises a conjugate of the Construct or Constructs $C^A$ and the Trigger $T^R$. Optionally the Trigger is further linked to Construct or Constructs $C^B$.

The general formula of the Construct-Trigger is shown below in Formula (5a) and (5b). For the avoidance of doubt, as $Y^C$ is part of $L^C$ and $C^A$, $Y^C$ is not separately denoted in Formula (5a) and (5b).

(5a)

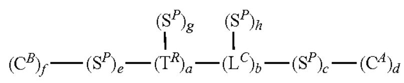

or (5b)

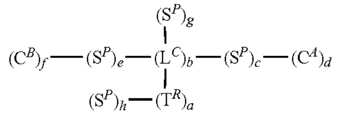

$C^A$ is Construct A, $C^B$ is Construct B, $S^P$ is Spacer; $T^R$ is Trigger, and $L^C$ is Linker. Formula (5a): b, c, e, f, g, h≥0; a, d≥1. Formula (5b): c, e, f, g, h≥0; a, b, d≥1.

In the Trigger-Construct conjugate, the Construct $C^A$ and the Trigger $T^R$—the TCO derivative—can be directly linked to each other. They can also be bound to each other via a self-immolative linker $L^C$, which may consist of multiple (self-immolative, or non immolative) units. With reference to Formula 5a and 5b, when $L^C$ contains a non immolative unit, this unit equals a Spacer $S^P$ and c≥1. It will be understood that the invention encompasses any conceivable manner in which the diene Trigger is attached to the one or more Construct $C^A$. The same holds for the attachment of one or more Construct $C^B$ to the Trigger or the linker L. The same holds for the optional attachment of one or more Spacer $S^P$ to the Trigger or the linker L. Methods of affecting conjugation, e.g. through reactive amino acids such as lysine or cysteine in the case of proteins, are known to the skilled person. Exemplary conjugation methods are outlined in the section on Spacers herein below.

It will be understood that the Construct $C^A$ is linked to the TCO in such a way that the Construct $C^A$ is eventually capable of being released after formation of the IEDDA adduct. Generally, this means that the bond between the Construct $C^A$ and the TCO, or in the event of a self-immolative Linker $L^C$, the bond between the Linker and the TCO and between the Construct $C^A$ and the Linker, should be cleavable. Predominantly, the Construct $C^A$ and the optional Linker is linked via a hetero-atom, preferably via O, N, NH, or S. The cleavable bond is preferably selected from the group consisting of carbamate, thiocarbamate, carbonate, ester, ether, thioether, amide, thioester bonds.

It shall be understood that one $C^B$ can be modified with more than one Trigger. For example, an antibody can be modified with 4 TCO-drug constructs by conjugation to 4 amino acid residues, wherein $C^A$ is drug.

Likewise, it shall be understood that one $C^A$ can be modified with more than one Trigger. For example, a protein drug can be masked by conjugation of 4 amino acid residues to 4 TCO-polyethylene glycol constructs, wherein polyethylene glycol is $C^B$.

Furthermore, it shall be understood that one $C^A$ can be modified with more than one Trigger, wherein at least one Trigger links to a Targeting Agent, being $C^B$, and at least one Trigger links to a Masking Moiety being $C^B$, wherein $C^A$ can be a Drug, preferably a protein.

Spacers $S^P$

It will be understood that when herein, it is stated that "each individual $S^P$ is linked at all ends to the remainder of the structure" this refers to the fact that the spacer $S^P$ connects multiple moieties within a structure, and therefore the spacer has multiple ends by definition. The spacer $S^P$ may be linked to each individual moiety via different or identical moieties that may be each individually selected. Typically, these linking moieties are to be seen to be part of spacer $S^P$ itself. In case the spacer $S^P$ links two moieties within a structure, "all ends" should be interpreted as "both ends". As an example, if the spacer connects a trans-cyclooctene moiety to a Construct A, then "the remainder of the molecule" refers to the trans-cylooctene moiety and Construct A, while the connecting moieties between the spacer and the trans-cyclooctene moiety and Construct A (i.e. at both ends) may be individually selected.

In a preferred embodiment, Spacers $S^P$ may consist of one or multiple Spacer Units $S^U$ arranged linearly and/or branched and may be connected to one or more $C^B$ moieties and/or one or more $L^C$ or $T^R$ moieties. The Spacer may be used to connect $C^B$ to one $T^R$ (Example A below; with reference to Formula 5a and 5b: f, e, a=1) or more $T^R$ (Example B and C below; with reference to Formula 5a and 5b: f, e=1, a≥1), but it can also be used to modulate the properties, e.g. pharmacokinetic properties, of the $C^B$-$T^R$-$C^A$ conjugate (Example D below; with reference to Formula 5a and 5b: one or more of c, e, g, h≥1). Thus a Spacer unit does not necessarily connect two entities together, it may also be bound to only one component, e.g. the $T^R$ or $L^C$. Alternatively, the Spacer may comprise a Spacer Unit linking $C^B$ to $T^R$ and in addition may comprise another Spacer Unit that is only bound to the Spacer and serves to modulate the properties of the conjugate (Example F below; with reference to Formula 5a and 5b: e≥1). The Spacer may also consist of two different types of $S^U$ constructs, e.g. a PEG linked to a peptide, or a PEG linked to an alkylene moiety (Example E below; with reference to Formula 5a and 5b: e≥1). For the sake of clarity, Example B depicts a $S^U$ that is branched by using a multivalent branched $S^U$. Example C depicts a $S^U$ that is branched by using a linear $S^U$ polymer, such as a peptide, whose side chain residues serve as conjugation groups.

A

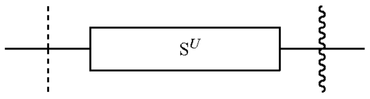

B

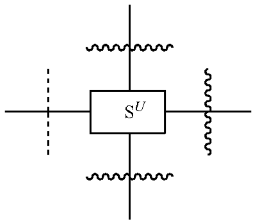

C

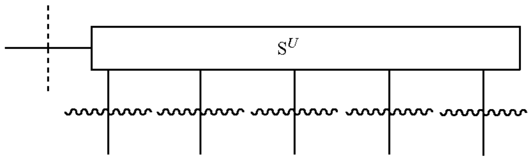

D

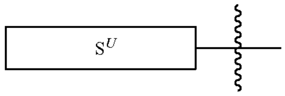

E

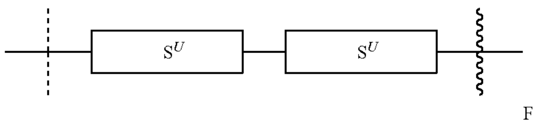

F

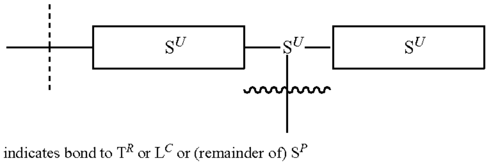

〰 indicates bond to $T^R$ or $L^C$ or (remainder of) $S^P$

----- indicates bond to (remainder of) $C^B$

The Spacer may be bound to the Activator in similar designs such as depicted in above examples A-F.

The Spacer Units include but are not limited to amino acids, nucleosides, nucleotides, and biopolymer fragments, such as oligo- or polypeptides, oligo- or polypeptoids, or oligo- or polylactides, or oligo- or poly-carbohydrates, varying from 2 to 200, particularly 2 to 113, preferably 2 to 50, more preferably 2 to 24 and more preferably 2 to 12 repeating units. Exemplary preferred biopolymer $S^U$ are peptides. Yet other examples are alkyl, alkylene, alkenyl, alkenylene, alkynyl, alkynylene, cycloalkyl, cycloalkylene, cycloalkenyl, cycloalkenylene, cycloalkynyl, cycloalkynylene, aryl, arylene, alkylaryl, alkylarylene, arylalkyl, arylalkylene, arylalkenyl, arylalkenylene, arylalkynyl, arylalkynylene, polyethyleneamino, polyamine, which may be substituted or unsubstituted, linear or branched, may contain further cyclic moieties and/or heteroatoms, preferably O, N, and S, more preferably O; wherein In preferred embodiments these example $S^U$ comprise at most 50 carbon atoms, more preferably at most 25 carbon atoms, more preferably at most 10 carbon atoms. In some preferred embodiments the $S^U$ is independently selected from the group consisting of $(CH_2)_r$, ($C_3$-$C_8$ carbocyclo), O—$(CH_2)_r$, arylene, $(CH_2)_r$-arylene, arylene-$(CH_2)_r$, $(CH_2)_r$—($C_3$-$C_8$ carbocyclo), ($C_3$-$C_8$ carbocyclo)-$(CH_2)_r$, ($C_3$-$C_8$ heterocyclo), $(CH_2)_r$—($C_3$-$C_8$ heterocyclo), ($C_3$-$C_8$ heterocyclo)-$(CH_2)_r$, —$(CH_2)_rC(O)NR_4(CH_2)_r$, $(CH_2CH_2O)_r$, $(CH_2CH_2O)_rCH_2$, $(CH_2)_rC(O)NR_4(CH_2CH_2O)_r$, $(CH_2)_rC(O)NR_4(CH_2CH_2O)_rCH_2$, $(CH_2CH_2O)_rC(O)NR_4(CH_2CH_2O)_r$, $(CH_2CH_2O)_rC(O)NR_4(CH_2CH_2O)_rCH_2$, $(CH_2CH_2O)_rC(O)NR_4CH_2$; wherein r is independently an integer from 1-10, and $R_4$ is as defined herein.

Other examples of Spacer Units $S^U$ are linear or branched polyalkylene glycols such as polyethylene glycol (PEG) or polypropylene glycol (PPG) chains varying from 2 to 200, particularly 2 to 113, preferably 2 to 50, more preferably 2 to 24 and more preferably 2 to 12 repeating units. It is preferred that when polyalkylene glycols such as PEG and PPG polymers are only bound via one end of the polymer chain, that the other end is terminated with —$OCH_3$, —$OCH_2CH_3$, —$OCH_2CH_2CO_2H$.

Other polymeric Spacer Units are polymers and copolymers such as poly-(2-oxazoline), poly(N-(2-hydroxypropyl) methacrylamide) (HPMA), polylactic acid (PLA), polylactic-glycolic acid (PLGA), polyglutamic acid (PG), dextran, polyvinylpyrrolidone (PVP), poly(1-hydroxymethylethylene hydroxymethyl-formal (PHF). Other exemplary polymers are polysaccharides, glycopolysaccharides, glycolipids, polyglycoside, polyacetals, polyketals, polyamides, polyethers, polyesters. Examples of naturally occurring polysaccharides that can be used as $S^U$ are cellulose, amylose, dextran, dextrin, levan, fucoidan, carraginan, inulin, pectin, amylopectin, glycogen, lixenan, agarose, hyaluronan, chondroitinsulfate, dermatansulfate, keratansulfate, alginic acid and heparin. In yet other exemplary embodiments, the polymeric $S^U$ comprises a copolymer of a polyacetal/polyketal and a hydrophilic polymer selected from the group consisting of polyacrylates, polyvinyl polymers, polyesters, polyorthoesters, polyamides, oligopeptides, polypeptides and derivatives thereof. Exemplary preferred polymeric $S^U$ are PEG, HPMA, PLA, PLGA, PVP, PHF, dextran, oligopeptides, and polypeptides.

In some aspects of the invention polymers used in a $S^U$ have a molecular weight ranging from 2 to 200 kDa, from 2 to 100 kDa, from 2 to 80 kDa, from 2 to 60 kDa, from 2 to 40 kDa, from 2 to 20 kDa, from 3 to 15 kDa, from 5 to 10 kDa, from 500 dalton to 5 kDa.

Other exemplary $S^U$ are dendrimers, such as poly(propylene imine) (PPI) dendrimers, PAMAM dendrimers, and glycol based dendrimers.

The $S^U$ of the invention expressly include but are not limited to conjugates prepared with commercially available cross-linker reagents such as BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB, DTME, BMB, BMDB, BMH, BMOE, $BM(PEO)_3$ and $BM(PEO)_4$.

To construct a branching Spacer one may use a $S^U$ based on one or several natural or non-natural amino acids, amino alcohol, aminoaldehyde, or polyamine residues or combinations thereof that collectively provide the required functionality for branching. For example serine has three functional groups, i.e. acid, amino and hydroxyl groups and may be viewed as a combined amino acid an aminoalcohol residue for purpose of acting as a branching $S^U$. Other exemplary amino acids are lysine and tyrosine.

In preferred embodiments, the Spacer consists of one Spacer Unit, therefore in those cases $S^P$ equals $S^U$. In preferred embodiments the Spacer consists of two, three or four Spacer Units.

In some aspects of the $S^P$ has a molecular weight ranging from 2 to 200 kDa, from 2 to 100 kDa, from 2 to 80 kDa, from 2 to 60 kDa, from 2 to 40 kDa, from 2 to 20 kDa, from 3 to 15 kDa, from 5 to 10 kDa, from 500 dalton to 5 kDa. In some aspects of the invention, the $S^P$ has a mass of no more than 5000 daltons, no more than 4000 daltons, no more than 3000 daltons, no more than 2000 daltons, no more than 1000 daltons, no more than 800 daltons, no more than 500 daltons, no more than 300 daltons, no more than 200 daltons. In some aspects the $S^P$ has a mass from 100 daltons, from 200 daltons, from 300 daltons to 5000 daltons. In some aspects of the $S^P$ has a mass from 30, 50, or 100 daltons to 1000 daltons, from about 30, 50, or 100 daltons to 500 daltons.

In preferred embodiments, $S^P$ is a spacer selected from the group consisting of $C_1$-$C_{12}$ alkylene groups, $C_2$-$C_{12}$ alkenylene groups, $C_2$-$C_{12}$ alkynylene groups, $C_6$ arylene groups, $C_4$-$C_5$ heteroarylene groups, $C_3$-$C_8$ cycloalkylene groups, $C_5$-$C_8$ cycloalkenylene groups, $C_5$-$C_{12}$ alkyl(hetero)arylene groups, $C_5$-$C_{12}$ (hetero)arylalkylene groups, $C_4$-$C_{12}$ alkylcycloalkylene groups, $C_4$-$C_{12}$ cycloalkylalkylene groups, wherein for $S^P$ the alkylene groups, alkenylene groups, alkynylene groups, (hetero)arylene groups, cycloalkylene groups, cycloalkenylene groups, alkyl(hetero)arylene groups, (hetero)arylalkylene groups, alkylcycloalkylene groups, cycloalkylalkylene groups, are optionally substituted with a moiety selected from the group consisting of —Cl, —F, —Br, —I, —OR', $—N(R_{37})_2$, =O, $=NR_{37}$, $—SR_{37}$, and $—Si(R_{37})_3$, and optionally contain one or more heteroatoms selected from the group consisting of —O—, —S—, $—NR_{37}—$, —P—, and —Si—, wherein the N, S, and P atoms are optionally oxidized, wherein the N atoms are optionally quaternized.

In preferred embodiments, $S^P$ comprises one or more moiety $C^{M2}$, $C^X$ or a residue of $R_{32}$, as described herein. In preferred embodiments, said $C^{M2}$, $C^X$ or a residue of $R_{32}$ connects the $S^P$ to $C^B$, $C^A$, $L^C$, $T^R$, or another $S^P$.

Linker $L^C$ $L^C$ is an optional self-immolative linker, which may consist of multiple units arranged linearly and/or branched and may release one or more $C^A$ moieties. By way of further clarification, if r is 0 the species $C^A$ directly constitutes the leaving group of the release reaction, and if r>0, the self-immolative linker $L^C$ constitutes the leaving group of the release reaction. The possible $L^C$ structures, their use, position and ways of attachment of linkers $L^C$, constructs $C^A$ and $C^B$, and the $T^R$ are known to the skilled person, see for example [Papot et al., Anticancer Agents Med. Chem., 2008, 8, 618-637]. Nevertheless, preferred but non-limiting examples of self-immolative linkers $L^C$ are benzyl-derivatives, such as those drawn below. There are two main self-immolation mechanisms: electron cascade elimination and cyclization-mediated elimination. The preferred example below on the left functions by means of the cascade mechanism, wherein the bond between the allylic carbon of the Trigger and the —O— or —S— attached to said carbon is cleaved, and an electron pair of $Y^{C1}$, for example an electron pair of $NR^6$, shifts into the benzyl moiety resulting in an electron cascade and the formation of 4-hydroxybenzyl alcohol, $CO_2$ and the liberated $C^A$. The preferred example in the middle functions by means of the cyclization mechanism, wherein cleavage of the bond to the $NR^6$ on the side of the Trigger leads to nucleophilic attack of the amine on the carbonyl, forming a 5-ring 1,3-dimethylimidazolidin-2-one and liberating the $C^A$. The preferred example on the right combines both mechanisms, this linker will degrade not only into $CO_2$ and one unit of 4-hydroxybenzyl alcohol (when $Y^{C1}$ is O), but also into one 1,3-dimethylimidazolidin-2-one unit.

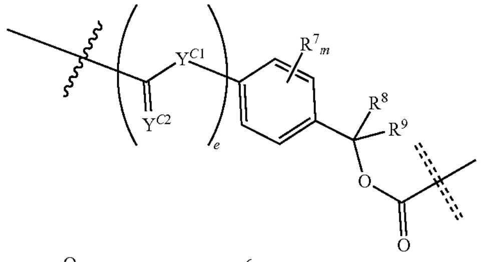

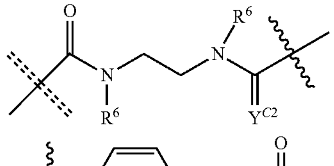

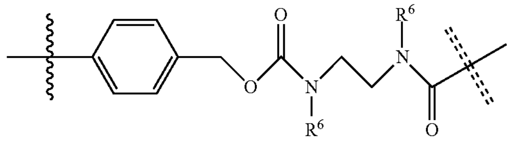

wherein the wiggly line indicates a bond to —O— or —S— on the allylic position of the trans-cyclooctene, and the double dashed line indicates a bond to $C^A$.

By substituting the benzyl groups of aforementioned self-immolative linkers $L^C$, it is possible to tune the rate of release of the construct $C^A$, caused by either steric and/or electronic effects on the cyclization and/or cascade release. Synthetic procedures to prepare such substituted benzyl-derivatives are known to the skilled person (see for example [Greenwald et al, J. Med. Chem., 1999, 42, 3657-3667] and [Thornthwaite et al, Polym. Chem., 2011, 2, 773-790]. Some preferred substituted benzyl-derivatives with different release rates are drawn below.

Self-immolative linkers that undergo cyclization include but are not limited to substituted and unsubstituted aminobutyric acid amide, appropriately substituted bicyclo[2.2.1] and bicyclo[2.2.2] ring system, 2-aminophenylpropionic acid amides, and trimethyl lock-based linkers, see e.g. [Chem. Biol. 1995, 2, 223], [J. Am. Chem. Soc. 1972, 94, 5815], [J. Org. Chem. 1990, 55, 5867], the contents of which are hereby incorporated by reference. Preferably, with an $L^C$ that releases $C^A$ by means of cyclization, the remainder of $C^A$ is bound to $L^C$ via an aromatic oxygen of sulfur. It will be understood that e.g. aromotic oxygen means an oxygen that is directly attached to an aromatic group.

Further preferred examples of $L^C$ can be found in WO2009017394(A1), U.S. Pat. No. 7,375,078, WO2015038426A1, WO2004043493, Angew. Chem. Int. Ed. 2015, 54, 7492-7509, the contents of which are hereby incorporated by reference.

In some aspects of the invention the $L^C$ has a mass of no more than 1000 daltons, no more than 500 daltons, no more than 400 daltons, no more than 300 daltons, or from 10, 50 or 100 to 1000 daltons, from 10, 50, 100 to 400 daltons, from 10, 50, 100 to 300 daltons, from 10, 50, 100 to 200 daltons, e.g., 10-1000 daltons, such as 50-500 daltons, such as 100 to 400 daltons.

A person skilled in the art will know that one $L^C$ may be connected to another $L^C$ that is bound to $C^A$, wherein upon reaction of the Activator with the Trigger $T^R$, $L^C$-$L^C$-$C^A$ is released from the $T^R$, leading to self-immolative release of both $L^C$ moieties and the $C^A$ moiety. With respect to the $L^C$ formulas disclosed herein, the $L^C$ linking the $T^R$ to the other $L^C$ then does not release $C^A$ but an $L^C$ that is bound via $Y^{C1}$ and further links to a $C^A$.

In a preferred embodiment, $L^C$ is selected from the group consisting of linkers according to Group I, Group II, and Group III.

Linkers according to Group I are

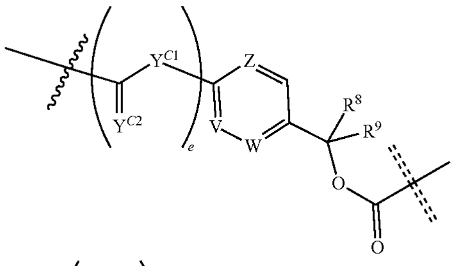

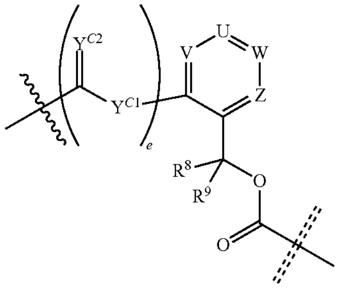

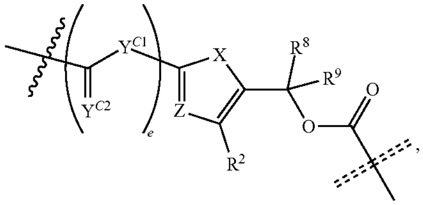

, (wiggly line) indicates bond to —O— on the allylic position of the trans-cyclooctene ring ===== indicated bond to $C^A$ wherein the wiggly line may also indicate a bond to —S— on the allylic position of the trans-cyclooctene, wherein U, V, W, Z are each independently selected from the group consisting of —$CR^7$—, and —N—; wherein e is either 0 or 1; wherein X is selected from the group consisting of —O—, —S— and —$NR^6$—; wherein preferably each $R^8$ and $R^9$ are independently selected from the group consisting of hydrogen, $C_1$-$C_4$ alkyl groups, $C_2$-$C_4$ alkenyl groups, and $C_{4-6}$ (hetero)aryl groups; wherein for $R^8$ and $R^9$ the alkyl groups, alkenyl groups, and (hetero)aryl groups are optionally substituted with a moiety selected from the group consisting of —Cl, —F, —Br, —I, —OH, —$NH_2$, =O, —SH, —$SO_3H$, —$PO_3H$, —$PO_4H_2$ and —$NO_2$ and optionally contain at most two heteroatoms selected from the group consisting of —O—, —S—, —NH—, —P—, and —Si—, wherein the N, S, and P atoms are optionally oxidized; wherein for linkers according to Group I $C^A$ is linked to $L^C$ via a moiety selected from the group consisting of —O—, —N—, —C—, and —S—, preferably from the group consisting of secondary amines and tertiary amines, wherein said moieties are part of $C^A$. Preferably, for linkers of Group I both $R^8$ and $R^9$ are hydrogen.

The linker according to Group II is

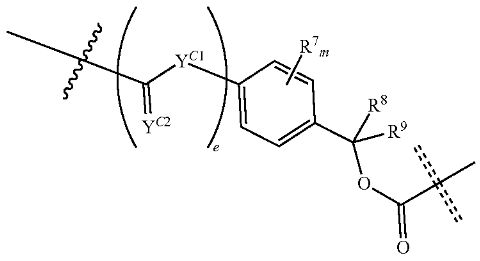

, (wiggly line) indicates bond to —O— on the allylic position of the trans-cyclooctene ring ===== indicated bond to $C^A$ wherein the wiggly line may also indicate a bond to —S— on the allylic position of the trans-cyclooctene, wherein m is an integer between 0 and 2, preferably m is 0; wherein e is either 0 or 1; wherein for linkers according to Group II $C^A$ is linked to $L^C$ via a moiety selected from the group consisting of —O—, —N—, —C—, and —S—, preferably from the group consisting of secondary amines and tertiary amines, wherein said moieties are part of $C^A$. Preferably, for linkers of Group II both $R^8$ and $R^9$ are hydrogen. Preferably, for linkers of Group II $R^7$ is methyl or isopropyl.

Linkers according to Group III are

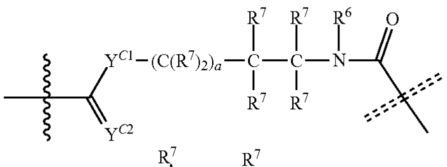

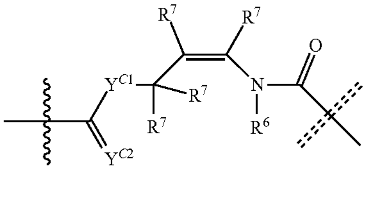

-continued

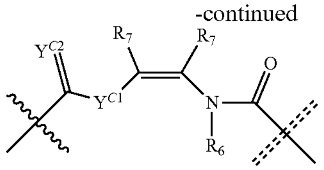

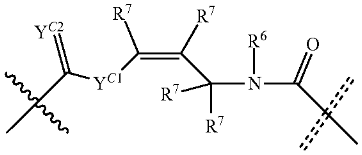

indicates bond to —O— on the allylic position of the trans-cyclooctene ring indicated bond to $C^A$ wherein the wiggly line may also indicate a bond to —S— on the allylic position of the trans-cyclooctene, wherein for linkers according to Group III $C^A$ is linked to $L^C$ via a moiety selected from the group consisting of —O— and —S—, preferably —O— or —S— bound to a $C_{4-6}$ (hetero)aryl group, wherein said moieties are part of $C^A$, wherein preferably each $R^6$ is independently selected from the group consisting of hydrogen, $C_1$-$C_4$ alkyl groups, $C_2$-$C_4$ alkenyl groups, and $C_{4-6}$ (hetero)aryl groups, wherein for $R^6$ the alkyl groups, alkenyl groups, and (hetero)aryl groups are optionally substituted with a moiety selected from the group consisting of —Cl, —F, —Br, —I, —OH, —$NH_2$, =O, —SH, —$SO_3H$, —$PO_3H$, —$PO_4H_2$ and —$NO_2$ and optionally contain at most two heteroatoms selected from the group consisting of —O—, —S—, —NH—, —P—, and —Si—, wherein the N, S, and P atoms are optionally oxidized, wherein preferably each $R^7$ is independently selected from the group consisting of hydrogen and $C_1$-$C_3$ alkyl groups, $C_2$-$C_3$ alkenyl groups, and $C_{4-6}$ (hetero)aryl groups, wherein for $R^7$ the alkyl groups, alkenyl groups, and (hetero)aryl groups are optionally substituted with a moiety selected from the group consisting of —Cl, —F, —Br, —I, —OH, —$NH_2$, =O, =NH, —$N(CH_3)_2$, —$S(O)_2CH_3$, and —SH, and are optionally interrupted by at most one heteroatom selected from the group consisting of —O—, —S—, —NH—, —P—, and —Si—, wherein the N, S, and P atoms are optionally oxidized, wherein the N atoms are optionally quaternized, wherein $R^7$ is preferably selected from the group consisting of hydrogen, methyl, —$CH_2$—$CH_2$—$N(CH_3)_2$, and —$CH_2$—$CH_2$—$S(O)_2$—$CH_3$.

Preferably, for linkers of Group III, $R^6$ is hydrogen. Preferably, for linkers of Group III, $R^6$ is methyl.

$R^6$, $R^7$, $R^8$, $R^9$ comprised in said Group I, II and III, can optionally also be —$(S^P)_i$—$C^B$.

For all linkers according to Group I and Group II $Y^{C1}$ is selected from the group consisting of —O—, —S—, and —$NR^6$—, preferably —$NR^6$—. For all linkers according to Group III, $Y^{C1}$ is —$NR^6$—. For all linkers according to Group I, Group II, and Group III, $Y^{C2}$ is selected from the group consisting of O and S, preferably O.

When two $L^C$ are linked to each other, then the $L^C$ attached to the —O— or —S— at the allylic position of the trans-cyclooctene is selected from the group consisting of linkers according to Group I and Group II, and the $L^C$ between the $L^C$ attached to the —O— or —S— at the allylic position of the trans-cyclooctene and $C^A$ is selected from Group III, and that the wiggly line in the structures of Group III then denotes a bond to the $L^C$ attached to the —O— or —S— at the allylic position of the trans-cyclooctene instead of a bond to the allylic —O— or —S— on the trans-cyclooctene ring, and that the double dashed line in the structures of Groups I and II then denotes a bond to the $L^C$ between the $L^C$ attached to the —O— or —S— at the allylic position of the trans-cyclooctene and the $C^A$ instead of a bond to $C^A$.

In preferred embodiments, $L^C$ is selected from the group consisting of linkers according to Group IV, Group V, Group VI, and Group VII, wherein linkers according to Group IV are

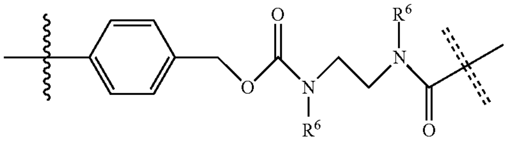

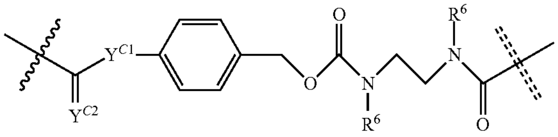

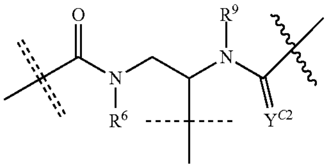

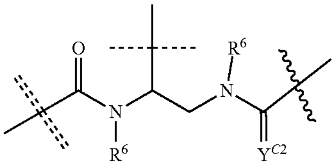

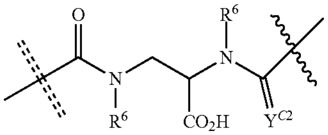

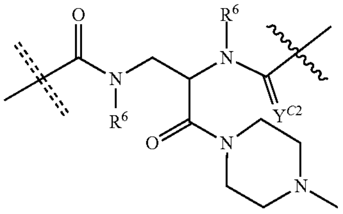

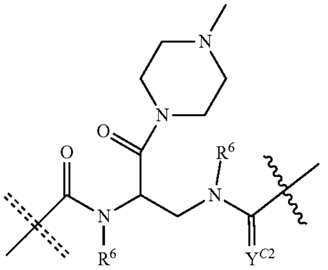

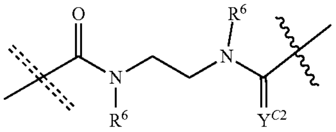

-continued

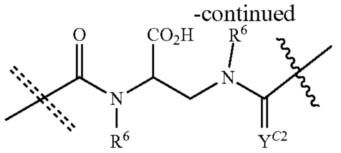

indicates bond to —O— on the allylic position of the trans-cyclooctene indicates optional bond to —$(S^P)_i$—$C^B$ indicates bond to $C^A$ wherein the wiggly line may also indicate a bond to —S— on the allylic position of the trans-cyclooctene, wherein $C^A$ is linked to $L^C$ via a moiety selected from the group consisting of —O— and —S—, preferably from the group consisting of —O—$C_{5-8}$-arylene- and —S—$C_{5-8}$-arylene-, wherein said moieties are part of $C^A$.

Linkers according to Group V are

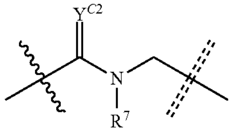

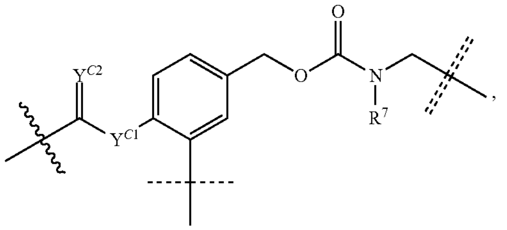

indicates bond to —O— on the allylic position of the trans-cyclooclene indicates optional bond to —$(S^P)_i$—$C^B$ indicates bond to $C^A$ wherein the wiggly line may also indicate a bond to —S— on the allylic position of the trans-cyclooctene, wherein $C^A$ is linked to $L^C$ via a moiety selected from the group consisting of —O— and —S—, wherein said moieties are part of $C^A$. In the first linker of Group V, $R^7$ is preferably —$(CH_2)_2$—$N(CH_3)_2$.

Linkers according to Group VI are

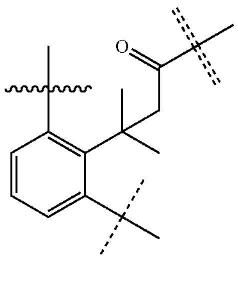

-continued

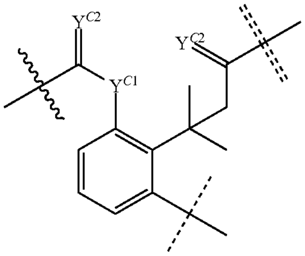

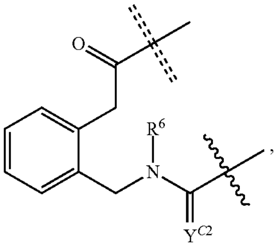

indicates bond to —O— on the allylic position of the trans-cyclooclene indicates optional bond to —$(S^P)_i$—$C^B$ indicates bond to $C^A$ wherein the wiggly line may also indicate a bond to —S— on the allylic position of the trans-cyclooctene, wherein $C^A$ is linked to $L^C$ via a moiety selected from the group consisting of —O—, —N—, and —S—, preferably a secondary or a tertiary amine, wherein said moieties are part of $C^A$.

Linkers according to Group VII are

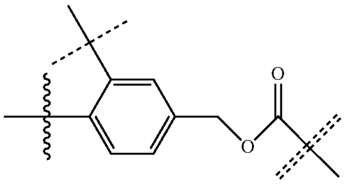

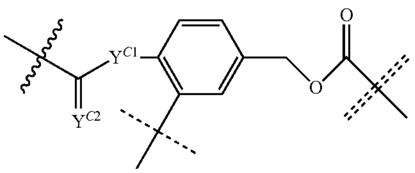

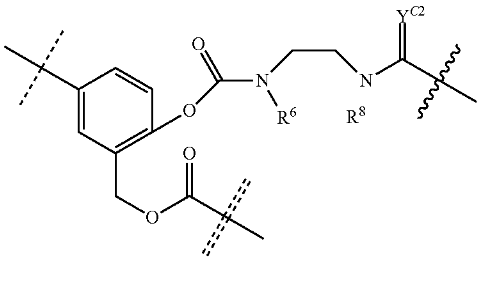

-continued
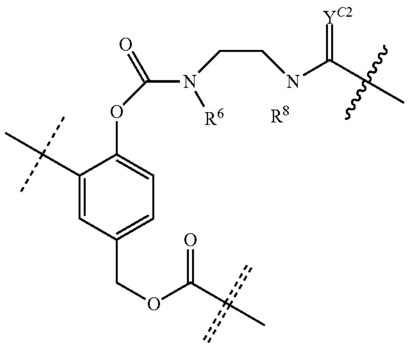
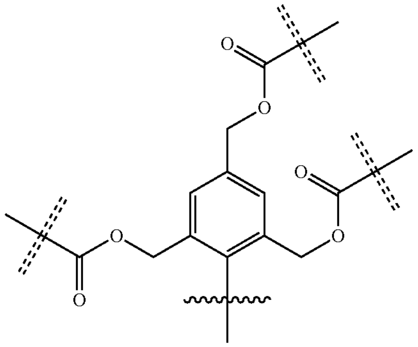
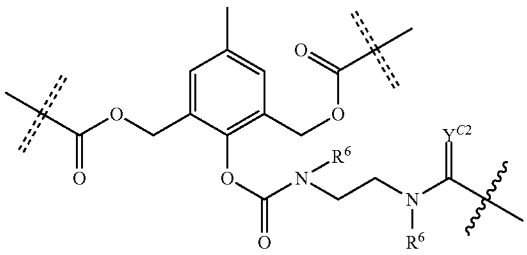
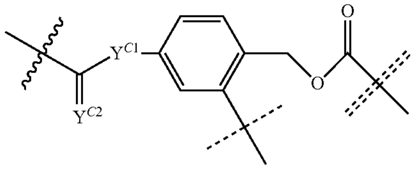
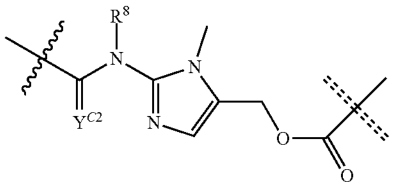
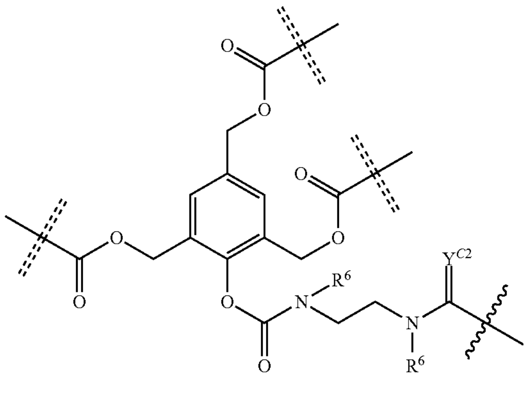
-continued
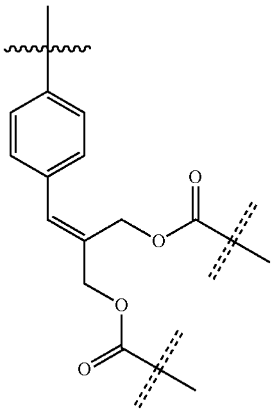
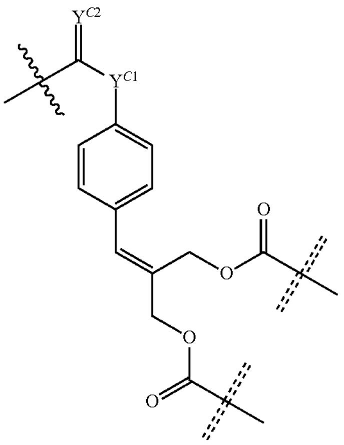
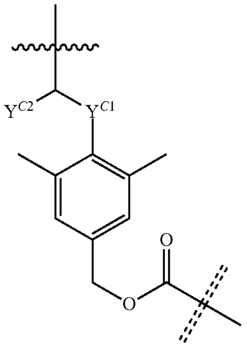
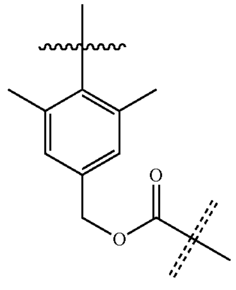
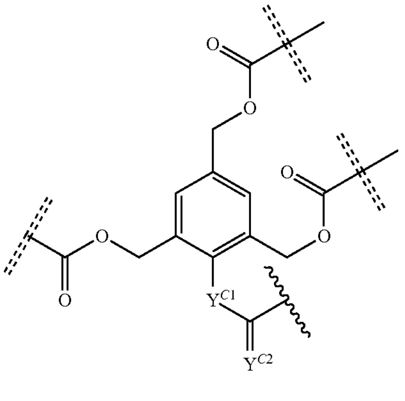

-continued

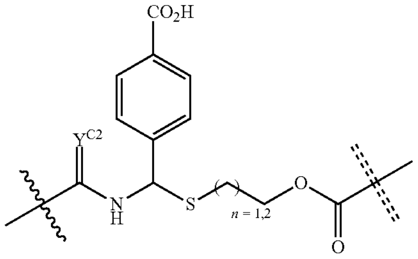

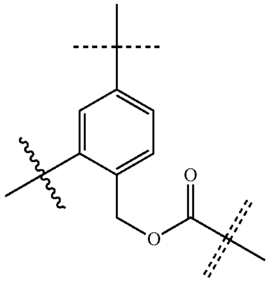

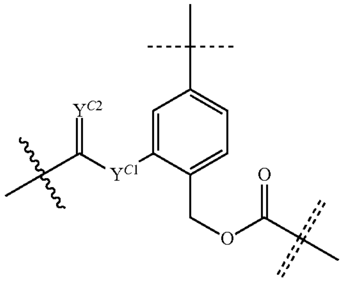

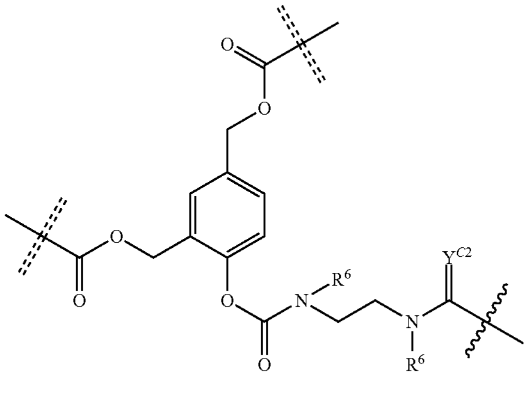

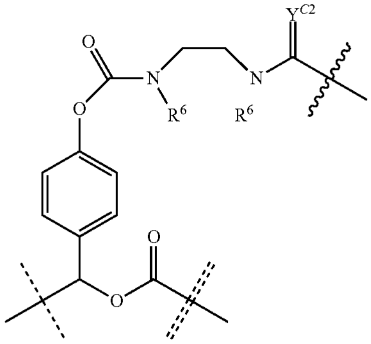

-continued

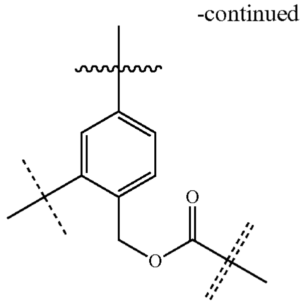

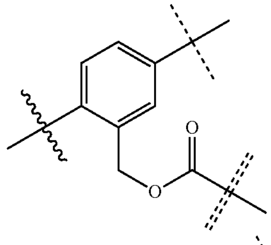

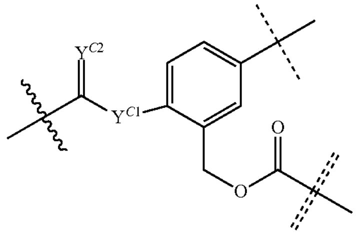

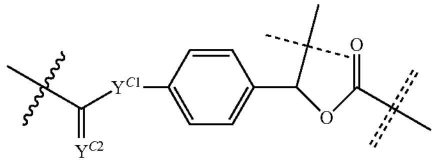

indicates bond to —O— on the allylic position of the trans-cyclooctene

----- indicates optional bond to —$(S^P)_i$-$C^B$

===== indicates bond to $C^A$ wherein the wiggly line may also indicate a bond to —S— on the allylic position of the trans-cyclooctene, wherein $C^A$ is linked to $L^C$ via a moiety selected from the group consisting of —O—, —N—, and —S—, preferably from the group consisting of secondary amines and tertiary amines, wherein said moieties are part of $C^A$, wherein when multiple double dashed lines are shown within one $L^C$, each $C^A$ moiety is independently selected.

For all linkers according to Group IV, Group V, Group VI, and Group VII, $Y^{C1}$ is selected from the group consisting of —O—, —S—, and —$NR^6$—.

For Groups IV-VII preferably $R^6$ and $R^7$ are as defined herein, more preferably as defined for Groups I-III. For Groups I-VII, i is an integer in a range of from 0 to 4, preferably 0 or 1, and wherein j is 0 or 1. Preferably, $R^6$, $R^7$, $R^8$, $R^9$ used in any one of Groups I-VII are not substituted. $R^6$, $R^7$, $R^8$, $R^9$ are as defined herein. Preferably, $R^6$ is hydrogen. Preferably, $R^7$ is hydrogen. Preferably, $R^8$ is hydrogen. Preferably, $R^9$ is hydrogen.

Targeting

The kits of the invention are very suitable for use in targeted imaging, targeted delivery of drugs and therapeutic radiation, and for selective biomolecule or tissue binding in vitro.

A "primary target" as used in the present invention preferably relates to a target for a targeting agent for therapy.

In other embodiments it relates to a target for imaging theranostics, diagnostics, or in vitro studies. For example, a primary target can be any molecule, which is present in an organism, tissue or cell. Targets include cell surface targets, e.g. receptors, glycoproteins; structural proteins, e.g. amyloid plaques; abundant extracellular targets such as stroma targets, tumor microenvironment targets, extracellular matrix targets such as growth factors, and proteases; intracellular targets, e.g. surfaces of Golgi bodies, surfaces of mitochondria, RNA, DNA, enzymes, components of cell signaling pathways; and/or foreign bodies, e.g. pathogens such as viruses, bacteria, fungi, yeast or parts thereof. Examples of primary targets include compounds such as proteins of which the presence or expression level is correlated with a certain tissue or cell type or of which the expression level is up regulated or down-regulated in a certain disorder. According to a particular embodiment of the present invention, the primary target is a protein such as a (internalizing or non-internalizing) receptor.

Furthermore, a preferred primary target is the blood, i.e. to prolong the blood circulation of a compound, and/or to reduce extravasation into other tissues. For example, the blood can be targeted by attaching a polyethylene glycol (PEG) to the compound. This typically increases blood circulation times. For example, by attaching a compound to a 500 nm PLGA particle, the conjugate will not readily extravaste from blood into other tissues (e.g. muscle), except for its rapid uptake and clearance through the liver and spleen. Organs, such as the liver, may also be primary targets. Hexoses can be attached to a compound to specifically target the liver, for example.

A further primary target is the immune system in general. According to the present invention, the primary target can be selected from any suitable targets within the human or animal body or on a pathogen or parasite, e.g. a group comprising cells such as cell membranes and cell walls, receptors such as cell membrane receptors, intracellular structures such as Golgi bodies or mitochondria, enzymes, receptors, DNA, RNA, viruses or viral particles, antibodies, proteins, carbohydrates, monosacharides, polysaccharides, cytokines, hormones, steroids, somatostatin receptor, monoamine oxidase, muscarinic receptors, myocardial sympatic nerve system, leukotriene receptors, e.g. on leukocytes, urokinase plasminogen activator receptor (uPAR), folate receptor, apoptosis marker, (anti-)angiogenesis marker, gastrin receptor, dopaminergic system, serotonergic system, GABAergic system, adrenergic system, cholinergic system, opoid receptors, GPIIb/IIIa receptor and other thrombus related receptors, fibrin, calcitonin receptor, tuftsin receptor, integrin receptor, fibronectin, VEGF/EGF and VEGF/EGF receptors, TAG72, CEA, A33, CD19, CD20, CD22, CD25, CD30, CD33, CD40, CD45, CD56, CD74, CD79, CD105, CD123, CD138, CD163, CD174, CD184, CD227, CD269, CD326, CD340, CD352, MUC1, MUC16, GPNMB, PSMA, Cripto, Tenascin C, Melanocortin-1 receptor, CD44v6, G250, HLA DR, ED-A, ED-B, TMEFF2, EphB2, EphA2, FAP, Mesothelin, GD2, CAIX, 5T4, matrix metalloproteinase (MMP), ADAM-9, P/E/L-selectin receptor, LDL receptor, P-glycoprotein, neurotensin receptors, neuropeptide receptors, substance P receptors, NK receptor, CCK receptors, sigma receptors, interleukin receptors, herpes simplex virus tyrosine kinase, human tyrosine kinase, MSR1, FAP, CXCR, tumor endothelial marker (TEM), cMET, IGFR, FGFR, GPA33, hCG, HER2, HER3, CA19, TAM, LGALS3BP, nectin-4, IFGR, PD1, PDL1, AGS-5, AGS-16, endosialin, ETBR, TM4SF1, BCMA, GPC2, TROP-2, AXL, HLA-DR, B7-H3, MTX3, MTX5, EFNA4, NOTCH, tissue factor (TF), PDGFR, GITR, OX40, RIG, MDA-5, NLRP1, NLRP3, AIM2, IDO, MEK, cGAS, NKG2A.

According to a further particular embodiment of the invention, the primary target and targeting agent are selected so as to result in the specific or increased targeting of a tissue or disease, such as cancer, an inflammation, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme. This can be achieved by selecting primary targets with tissue-, cell- or disease-specific expression. For example, membrane folic acid receptors mediate intracellular accumulation of folate and its analogs, such as methotrexate. Expression is limited in normal tissues, but receptors are overexpressed in various tumor cell types.

In preferred embodiments the Primary Target equals a therapeutic target. It shall be understood that a therapeutic target is the entity that is targeted by the Drug to afford a therapeutic effect.

Targeting Agents $T^T$

A Targeting Agent, $T^T$, binds to a Primary Target. In order to allow specific targeting of the above-listed Primary Targets, the Targeting Agent $T^T$ can comprise compounds including but not limited to antibodies, antibody derivatives, antibody fragments, antibody (fragment) fusions (e.g. bi-specific and tri-specific mAb fragments or derivatives), proteins, peptides, e.g. octreotide and derivatives, VIP, MSH, LHRH, chemotactic peptides, cell penetrating peptide, membrane translocation moiety, bombesin, elastin, peptide mimetics, organic compounds, inorganic compounds, carbohydrates, monosaccharides, oligosaccharides, polysaccharides, oligonucleotides, aptamers, viruses, whole cells, phage, drugs, polymers, liposomes, chemotherapeutic agents, receptor agonists and antagonists, cytokines, hormones, steroids, toxins. Examples of organic compounds envisaged within the context of the present invention are, or are derived from, dyes, compounds targeting CAIX and PSMA, estrogens, e.g. estradiol, androgens, progestins, corticosteroids, methotrexate, folic acid, and cholesterol.

According to a particular embodiment of the present invention, the Primary Target is a receptor and a Targeting Agent is employed, which is capable of specific binding to the Primary Target. Suitable Targeting Agents include but are not limited to, the ligand of such a receptor or a part thereof which still binds to the receptor, e.g. a receptor binding peptide in the case of receptor binding protein ligands. Other examples of Targeting Agents of protein nature include insulin, transferrin, fibrinogen-gamma fragment, thrombospondin, claudin, apolipoprotein E, Affibody molecules such as for example ABY-025, Ankyrin repeat proteins, ankyrin-like repeat proteins, interferons, e.g. alpha, beta, and gamma interferon, interleukins, lymphokines, colony stimulating factors and protein growth factor, such as tumor growth factor, e.g. alpha, beta tumor growth factor, platelet-derived growth factor (PDGF), uPAR targeting protein, apolipoprotein, LDL, annexin V, endostatin, and angiostatin. Alternative examples of targeting agents include DNA, RNA, PNA and LNA which are e.g. complementary to the Primary Target.

Examples of peptides as targeting agents include LHRH receptor targeting peptides, EC-1 peptide, RGD peptides, HER2-targeting peptides, PSMA targeting peptides, somatostatin-targeting peptides, bombesin. Other examples of targeting agents include lipocalins, such as anticalins. One particular embodiment uses Affibodies™ and multimers and derivatives.

In a preferred embodiment $T^T$ is an antibody. In a preferred embodiment the $T^T$ is selected from antibodies and antibody derivatives such as antibody fragments, fragment fusions, proteins, peptides, peptide mimetics, organic molecules, dyes, fluorescent molecules, enzyme substrates.

In a preferred embodiment the $T^T$ being an organic molecule has a molecular weight of less than 2000 Da, more preferably less than 1500 Da, more preferably less than 1000 Da, even more preferably less than 500 Da.

In another preferred embodiment the $T^T$ is selected from antibody fragments, fragment fusions, and other antibody derivatives that do not contain a Fc domain.

In another embodiment the $T^T$ is a polymer and accumulates at the Primary Target by virtue of the EPR effect. Typical polymers used in this embodiment include but are not limited to polyethyleneglycol (PEG), poly(N-(2-hydroxypropyl)methacrylamide) (HPMA), polylactic acid (PLA), polylactic-glycolic acid (PLGA), polyglutamic acid (PG), polyvinylpyrrolidone (PVP), poly(1-hydroxymethylethylene hydroxymethyl-formal (PHF). Other examples are copolymers of a polyacetal/polyketal and a hydrophilic polymer selected from the group consisting of polyacrylates, polyvinyl polymers, polyesters, polyorthoesters, polyamides, oligopeptides, polypeptides and derivatives thereof. Other examples are oligopeptides, polypeptides, glycopolysaccharides, and polysaccharides such as dextran and hyaluronan.

Typically, a suitable polymer is polyethyleneglycol (PEG), preferably with a number of repeating units in a range of from 2 to 4000, and a molecular weight in a range of from 200 Da to 100,000 Da.

In addition reference is made to [G. Pasut, F. M. Veronese, Prog. Polym. Sci. 2007, 32, 933-961].

Other $T^{T'}$ are nanoparticles, microparticles, liposomes, micelles, polymersomes, dendrimers, biomolecules, peptides, peptoids, proteins, carbohydrates, oligonucleotides, oligosaccharides, lipids, liposomes, albumin, albumin-binding moieties, dyes, fluorescent molecules, and enzyme substrates.

In other embodiments, the $T^T$ is selected from amino acids, nucleosides, nucleotides, carbohydrates, and biopolymer fragments, such as oligo- or polypeptides, oligo- or polypeptoids, or oligo- or polylactides, or oligo- or polycarbohydrates, oligonucleotides, varying from 2 to 200, particularly 2 to 113, preferably 2 to 50, more preferably 2 to 24 and more preferably 2 to 12 repeating units.

In some aspects of the invention polymeric $T^T$ moieties have a molecular weight ranging from 2 to 200 kDa, from 2 to 100 kDa, from 2 to 80 kDa, from 2 to 60 kDa, from 2 to 40 kDa, from 2 to 20 kDa, from 3 to 15 kDa, from 5 to 10 kDa, from 500 dalton to 5 kDa.

Other exemplary $T^T$ Moieties are dendrimers, such as poly(propylene imine) (PPI) dendrimers, PAMAM dendrimers, and glycol based dendrimers.

In preferred embodiments the targeting agent $T^T$ localizes or has retention in a particular system, tissue, or organ in the body, for example, blood circulation, lymphatic system, the nervous system, the digestion system, RES system, or organs such as the heart or kidney. For example, microparticles will localize in the liver, large hydrophilic polymers will have retention in circulation. Likewise, use of an albumin binding moiety as $T^T$ will result in prolonged retention in circulation.

In preferred embodiments, $T^T$ is used to modify the pharmacokinetics of the moiety it is attached to. This can include, but is not limited to, delaying the blood clearance of said moiety, affecting the volume of distribution of said moiety (e.g. reducing or increasing the volume of distribution), affecting the metabolism of said moiety, and/or affecting (preferably avoiding) the sticking or uptake of said moiety to non-target tissues. Exemplary $T^T$'s in this regard are polymer, peptide, peptoid, dendrimer, protein, carbohydrate, oligonucleotide, oligosaccharide, lipid, liposome, micelle, nanoparticle, microparticle, albumin, albumin-binding moiety, and small to medium sized organic molecules such as steroids and dyes. Typically, a suitable polymer is polyethyleneglycol (PEG) or polypropyleneglycol (PPG).

According to a further particular embodiment of the invention, the Primary Target and Targeting Agent are selected so as to result in the specific or increased targeting of a tissue or disease, such as cancer, an inflammation, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme. This can be achieved by selecting Primary Targets with tissue-, cell- or disease-specific expression. For example, the CC49 antibody targets TAG72, the expression of which is limited in normal tissues, but receptors are overexpressed in various solid tumor cell types.

In one embodiment the Targeting Agent specifically binds or complexes with a cell surface molecule, such as a cell surface receptor or antigen, for a given cell population. Following specific binding or complexing of the $T^T$ with the receptor, the cell is permissive for uptake of the Prodrug, which then internalizes into the cell. The subsequently administered Activator will then enter the cell and activate the Prodrug, releasing the Drug inside the cell. In another embodiment the Targeting Agent specifically binds or complexes with a cell surface molecule, such as a cell surface receptor or antigen, for a given cell population. Following specific binding or complexing of the $T^T$ with the receptor, the cell is not permissive for uptake of the Prodrug. The subsequently administered Activator will then activate the Prodrug on the outside of the cell, after which the released Drug will enter the cell.

As used herein, a $T^T$ that "specifically binds or complexes with" or "targets" a cell surface molecule, an extracellular matrix target, or another target, preferentially associates with the target via intermolecular forces. For example, the ligand can preferentially associate with the target with a dissociation constant ($K_d$ or $K_D$) of less than about 50 nM, less than about 5 nM, or less than about 500 pM.

In some embodiments the $T^T$ can be a cell penetrating moiety, such as cell penetrating peptide. In a preferred embodiment $T^T$ can be non-functional that becomes functional upon reaction of the Trigger with the Activator. In a particularly preferred embodiment, said non-functional $T^T$ is a portion of a cell penetrating peptide that is bound to another portion of a cell penetrating peptide upon reaction of the Trigger with the Activator. In another preferred embodiment the $T^T$, preferably a cell penetrating peptide is unmasked upon reaction of the Trigger with the Activator.

In other embodiments, the $T^T$ is a polymer, particle, gel, biomolecule or another above listed $T^T$ moiety and is locally injected to create a local depot of Prodrug or Activator, which can subsequently be reacted by with respectively the Activator or the Prodrug.

In another embodiment the targeting agent $T^T$ is a solid material such as but not limited to polymer, metal, ceramic, wherein this solid material is or is comprised in a cartridge, reservoir, depot, wherein preferably said cartridge, reservoir, depot is used for drug release in vivo.

In some embodiments, the targeting agent $T^T$ also acts as a Drug, denoted as $D^D$. In a particularly preferred embodiment, the $T^T$ acts as a Drug $D^D$ by binding the primary target. In other preferred embodiments, the $T^T$ acts as a $D^D$ after the Trigger has been cleaved.

It is preferred that when a $T^T$ is comprised in an embodiment of the invention, it equals $C^B$.

Masking Moieties

In order to avoid the drawbacks of current prodrug activation, such as low release yields and/or slow reactions, as discussed above, the IEDDA pyridazine elimination using the compounds of the invention can be used to provoke release of a Masking Moiety from a masked Drug. In this type of Prodrug, the Masking Moiety is attached to the Drug via a Trigger, and this Trigger is not activated endogenously by e.g. an enzyme or a specific pH, but by a controlled administration of the Activator, i.e. a species that reacts with the Trigger moiety in the Prodrug, to induce release of the Masking Moiety or the Drug from the Trigger (or vice versa, release of the Trigger from the Masking Moiety or Drug, however one may view this release process), resulting in activation of the Drug.

The present invention provides a kit for the administration and activation of a Prodrug, the kit comprising a Masking Moiety, denoted as $M^M$, linked covalently, directly or indirectly, to a Trigger moiety, which in turn is linked covalently, directly or indirectly, to a Drug, denoted as $D^D$, and an Activator for the Trigger moiety, wherein the Trigger moiety comprises a dienophile satisfying Formula (19) and the Activator comprises a tetrazine satisfying any one of Formulae (4), (4a), or (6)-(14).

In another aspect, the invention presents a Prodrug comprising a Masking Moiety, $M^M$, linked, directly or indirectly, to dienophile moiety satisfying above Formula (19).

In yet another aspect, the invention provides a method of modifying a Drug, $D^D$, with one or more Masking Moieties $M^M$ affording a Prodrug that can be activated by an abiotic, bio-orthogonal reaction, the method comprising the steps of providing a Masking Moiety and a Drug and chemically linking the Masking Moiety and a Drug to a dienophile moiety satisfying Formula (19).

In a still further aspect, the invention provides a method of treatment wherein a patient suffering from a disease that can be modulated by a drug, is treated by administering, to said patient, a Prodrug comprising a Trigger moiety linked to a Masking Moiety $M^M$ and a Drug $D^D$, after activation of which by administration of an Activator, satisfying any one of Formulae (4), (4a), or (6)-(14), the Masking Moiety will be released, activating the Drug, wherein the Trigger moiety comprises a dienophile structure satisfying Formula (19).

In a still further aspect, the invention is a compound comprising a dienophile moiety, said moiety comprising a linkage to a Masking Moiety $M^M$, for use in prodrug therapy in an animal or a human being.

In another aspect, the invention is the use of a diene as an Activator for the release, in a physiological environment, of a substance covalently linked to a compound satisfying Formula (19). In connection herewith, the invention also pertains to a diene, for use as an Activator for the release, in a physiological environment, of a substance linked to a compound satisfying Formula (19), and to a method for activating, in a physiological environment, the release of a substance linked to a compound satisfying Formula (19), wherein a tetrazine is used as an Activator.

In another aspect, the invention presents the use of the inverse electron-demand Diels-Alder reaction between a compound satisfying Formula (19) and a dienophile, preferably a trans-cyclooctene, as a chemical tool for the release, in a physiological environment, of a substance administered in a covalently bound form, wherein the substance is bound to a compound satisfying Formula (19).

For the avoidance of doubt, in the context of this invention wherein a $M^M$ is removed from an antibody (i.e. Drug) the terms "activatable antibodies" and "Prodrug" mean the same.

For the avoidance of doubt, in the context of this invention wherein a $M^M$ is removed from a Drug, the Drug itself can optionally bind to one or more Primary Targets without the use of an additional Targeting Agent $T^T$. In this context, the Primary target is preferably the therapeutic target.

In a preferred embodiment, the Drug comprises a Targeting Agent $T^T$ so that the Prodrug can bind a Primary Target. Following activation and $M^M$ removal the Drug then binds another Primary Target, which can be a therapeutic target.

In preferred embodiments, the Drug comprises one or more TT moieties, against one or different Primary Targets.

For the avoidance of doubt, in the context of the use of Masking Moieties, Primary target and therapeutic target are used interchangeably.

For the avoidance of doubt, one Drug construct can be modified by more than one Masking Moieties.

In preferred embodiments the activatable antibodies or Prodrugs of this invention are used in the treatment of cancer. In preferred embodiments the activatable antibodies or Prodrugs of this invention are used in the treatment of an autoimmune disease or inflammatory disease such as rheumatoid arthritis. In preferred embodiments the activatable antibodies or Prodrugs of this invention are used in the treatment of a fibrotic disease such as idiopathic pulmonary fibrosis.

Exemplary classes of Primary Targets for activatable antibodies or Prodrugs of this invention include but are not limited to cell surface receptors and secreted proteins (e.g. growth factors), soluble enzymes, structural proteins (e.g. collagen, fibronectin) and the like. In preferred embodiments the Primary Target is an extracellular target. In preferred embodiments, the Primary Target is an intracellular target.

In another embodiment, the drug is a bi- or trispecific antibody derivative that serves to bind to tumor cells and recruit and activate immune effector cells (e.g. T-cells, NK cells), the immune effector cell binding function of which is masked and inactivated by being linked to a dienophile moiety as described above. The latter, again, serving to enable bio-orthogonal chemically activated drug activation.

When $D^D$ is $C^B$ it is preferred that $D^D$ is not attached to remainder of the Prodrug through its antigen-binding domain. Preferably $D^D$ is $C^A$.

Masking moieties $M^M$ can for example be an antibody, protein, peptide, polymer, polyethylene glycol, polypropylene glycol carbohydrate, aptamers, oligopeptide, oligonucleotide, oligosaccharide, carbohydrate, as well as peptides, peptoids, steroids, organic molecule, or a combination thereof that further shield the bound drug $D^D$ or Prodrug. This shielding can be based on e.g. steric hindrance, but it can also be based on a non covalent interaction with the drug $D^D$. Such Masking Moiety may also be used to affect the in vivo properties (e.g. blood clearance; biodistribution, recognition by the immune system) of the drug $D^D$ or Prodrug.

In preferred embodiments the Masking Moiety is an albumin binding moiety. In preferred embodiments, the Masking Moiety equals a Targeting Agent. In preferred embodiments, the Masking Moiety is bound to a Targeting Agent. In a preferred embodiment the Drug $D^D$, being $C^A$, is modified with multiple $M^M$, being $C^B$, wherein at least one of the bound $M^M$ is $T^T$. In a preferred embodiment, when $C^A$ is $D^D$ then $D^D$ is not bound to $T^R$ via a Spacer $S^P$.

In preferred embodiments the $T^R$ can itself act as a Masking Moiety, provided that $C^A$ is $D^D$. For the sake of clarity, in these embodiments the size of the $T^R$ without the attachment of a $M^M$ is sufficient to shield the Drug $D^D$ from its Primary Target, which, in this context, is preferably the therapeutic target.

The $M^M$ of the modified $D^D$ can reduce the $D^D$'s ability to bind its target allosterically or sterically.

In specific embodiments, the $M^M$ is a peptide and does not comprise more than 50% amino acid sequence similarity to a natural protein-based binding partner of an antibody-based $D^D$.

In preferred embodiments $M^M$ is a peptide between 2 and 40 amino acids in length.

In one embodiment the $M^M$ reduces the ability of the $D^D$ to bind its target such that the dissociation constant of the $D^D$ when coupled to the $M^M$ towards the target is at least 100 times greater than the dissociation constant towards the target of the $D^D$ when not coupled to the $M^M$. In another embodiment, the coupling of the $M^M$ to the $D^D$ reduces the ability of the $D^D$ to bind its target by at least 90%.

In preferred embodiments the $M^M$ in the masked $D^D$ reduces the ability of the $D^D$ to bind the target by at least 50%, by at least 60%, by at least 70%, by at least 75%, by at least 80%, by at least 85%, by at least 90%, by at least 95%, by at least 96%, by at least 97%, by at least 98%, by at least 99%, or by 100%, as compared to the ability of the unmasked $D^D$ to bind the target. The reduction in the ability of a $D^D$ to bind the target can be determined, for example, by using an in vitro displacement assay, such as for example described for antibody $D^D$ in WO2009/025846 and WO2010/081173.

In preferred embodiments the $D^D$ comprised in the masked $D^D$ is an antibody, which expressly includes full-length antibodies, antigen-binding fragments thereof, antibody derivatives antibody analogs, antibody mimics and fusions of antibodies or antibody derivatives.

In certain embodiments the $M^M$ is not a natural binding partner of the antibody. In preferred embodiments, the $M^M$ contains no or substantially no homology to any natural binding partner of the antibody. In preferred embodiments the $M^M$ is no more than 5%, 10%, 15%, 20%, 25%, 30%, 35%, 40%, 45%, 50%, 55%, 60%, 65%, 70%, 75%, or 80% similar to any natural binding partner of the antibody. In preferred embodiments the $M^M$ is no more than 5%, 10%, 15%, 20%, 25%, 30%, 35%, 40%, 45%, 50%, 55%, 60%, 65%, 70%, 75%, or 80% identical to any natural binding partner of the antibody. In preferred embodiments, the $M^M$ is no more than 50% identical to any natural binding partner of the antibody. In preferred embodiments, the $M^M$ is no more than 25% identical to any natural binding partner of the antibody. In preferred embodiments, the $M^M$ is no more than 20% identical to any natural binding partner of the antibody. In preferred embodiments, the $M^M$ is no more than 10% identical to any natural binding partner of the antibody.

In the Prodrug, the $M^M$ and the Trigger $T^R$—the dienophile derivative—can be directly linked to each other. They can also be bound to each other via a spacer $S^P$ or a self-immolative linker $L^C$. It will be understood that the invention encompasses any conceivable manner in which the diene Trigger is attached to the $M^M$. It will be understood that $M^M$ is linked to the dienophile in such a way that the $M^M$ is eventually capable of being released from the $D^D$ after formation of the IEDDA adduct. Generally, this means that the bond between the $D^D$ and the dienophile, or in the event of a self-immolative linker $L^C$ the bond between the $L^C$ and the dienophile and between the $D^D$ and the $L^C$ should be cleavable. Alternatively, this means that the bond between the $M^M$ and the dienophile, or in the event of a self-immolative linker $L^C$ the bond between the $L^C$ and the dienophile and between the $M^M$ and the $L^C$ should be cleavable.

In preferred embodiments, the antibody comprised in the masked antibody is a multi-antigen targeting antibody, comprising at least a first antibody or antigen-binding fragment or mimic thereof that binds a first Primary Target and a second antibody or antigen-binding fragment or mimic thereof that binds a second Primary Target. In preferred embodiments, the antibody comprised in the masked antibody is a multi-antigen targeting antibody, comprising a first antibody or antigen-binding fragment or mimic thereof that binds a first Primary Target, a second antibody or antigen-binding fragment or mimic thereof that binds a second Primary Target, and a third antibody or antigen-binding fragment or mimic thereof that binds a third Primary Target. In preferred embodiments, the multi-antigen targeting antibodies bind two or more different Primary Targets. In preferred embodiments, the multi-antigen targeting antibodies bind two or more different epitopes on the same Primary Target. In preferred embodiments the multi-antigen targeting antibodies bind a combination of two or more different targets and two or more different epitopes on the same Primary Target. In preferred embodiments the masked multi-antigen targeting antibodies comprise one $M^M$ group, or two or more $M^M$ groups. It shall be understood that preferably at least one of the Primary Targets is a therapeutic target.

In preferred embodiments of a multispecific activatable antibody, a scFv can be fused to the carboxyl terminus of the heavy chain of an IgG activatable antibody, to the carboxyl terminus of the light chain of an IgG activatable antibody, or to the carboxyl termini of both light and the heavy chain of an IgG activatable antibody. In preferred embodiments of a multispecific activatable antibody, a scFv can be fused to the amino terminus of the heavy chain of an IgG activatable antibody, to the amino terminus of the light chain of an IgG activatable antibody, or to the amino termini of both light and the heavy chain of an IgG activatable antibody. In preferred embodiments of a multispecific activatable antibody, a scFv can be fused to any combination of one or more carboxyl termini and one or more amino termini of an IgG activatable antibody. Methods of preparing multispecific antibodies are known to the person skilled in the art. In addition reference is made to [Weilde et al., Cancer Genomics & Proteomics 2013, 10, 1-18], [Weidle et al., Seminars in Oncology 2014, 41, 5, 653-660], [Jachimowicz et al., BioDrugs (2014) 28:331-343], the contents of which are hereby incorporated by reference.

In preferred embodiments, a $M^M$ linked to a $T^R$ is attached to and masks an antigen binding domain of the IgG. In preferred embodiments, a $M^M$ linked to a $T^R$ is attached to and masks an antigen binding domain of at least one scFv. In preferred embodiments, a $M^M$ linked to a $T^R$ is attached to and masks an antigen binding domain of the IgG and a $M^M$ linked to a $T^R$ is attached to and masks an antigen binding domain of at least one scFv.

In preferred embodiments, the $M^M$ has a dissociation constant, i.e., dissociation constant at an equilibrium state, $K_d$, for binding to the antibody that is greater than the $K_d$ for binding of the antibody to its Primary Target. In preferred embodiments, the $M^M$ has a $K_d$ for binding to the antibody that is approximately equal to the $K_d$ for binding of the antibody to its Primary Target. In preferred embodiments, the $M^M$ has a $K_d$ for binding to the antibody that is less than the $K_d$ for binding of the antibody to its Primary Target. In preferred embodiments, the $M^M$ has a $K_d$ for binding to the antibody that is no more than 2, 3, 4, 5, 10, 25, 50, 100, 250, 500, or 1,000 fold greater than the $K_d$ for binding of the antibody to its Primary Target. In preferred embodiments, the $M^M$ has a $K_d$ for binding to the antibody that is between 1-5, 2-5, 2-10, 5-10, 5-20, 5-50, 5-100, 10-100, 10-1,000, 20-100, 20-1,000, or 100-1,000 fold greater than the $K_d$ for binding of the antibody to its Primary Target.

In preferred embodiments, the $M^M$ has an affinity for binding to the antibody that is greater than the affinity of binding of the antibody to its Primary Target. In preferred embodiments, the $M^M$ has an affinity for binding to the antibody that is approximately equal to the affinity of binding of the antibody to its Primary Target. In preferred embodiments, the $M^M$ has an affinity for binding to the antibody that is less than the affinity of binding of the antibody to its Primary Target. In preferred embodiments, the $M^M$ has an affinity for binding to the antibody that is 2, 3, 4, 5, 10, 25, 50, 100, 250, 500, or 1,000 fold less than the affinity of binding of the antibody to its Primary Target. In preferred embodiments, the $M^M$ has an affinity of binding to the antibody that is between 1-5, 2-5, 2-10, 5-10, 5-20, 5-50, 5-100, 10-100, 10-1,000, 20-100, 20-1,000, or 100-1,000 fold less than the affinity of binding of the antibody to its Primary Target. In preferred embodiments, the $M^M$ has an affinity of binding to the antibody that is 2 to 20 fold less than the affinity of binding of the antibody to its Primary Target.

In preferred embodiments, a $M^M$ not covalently linked to the antibody and at equimolar concentration to the antibody does not inhibit the binding of the antibody to its Primary Target. In preferred embodiments, the $M^M$ does not interfere of compete with the antibody for binding to the Primary Target when the Prodrug is in a cleaved state.

In preferred embodiments, the antibody has a dissociation constant of about 100 nM or less for binding to its Primary Target. In preferred embodiments, the antibody has a dissociation constant of about 10 nM or less for binding to its Primary Target. In preferred embodiments, the antibody has a dissociation constant of about 1 nM or less for binding to its Primary Target. In preferred embodiments, the coupling of the $M^M$ reduces the ability of the antibody to bind its Primary Target such that the dissociation constant ($K_d$) of the antibody when coupled to the $M^M$ towards its Primary Target is at least 20 times greater than the $K_d$ of the antibody when not coupled to the $M^M$ towards its Primary Target. In preferred embodiments, the coupling of the $M^M$ reduces the ability of the antibody to bind its Primary Target such that the $K_d$ of the antibody when coupled to the $M^M$ towards its Primary Target is at least 40 times greater than the $K_d$ of the antibody when not coupled to the $M^M$ towards its Primary Target. In preferred embodiments, the coupling of the $M^M$ reduces the ability of the antibody to bind its Primary Target such that the $K_d$ of the antibody when coupled to the $M^M$ towards its Primary Target is at least 100 times greater than the $K_d$ of the antibody when not coupled to the $M^M$ towards its Primary Target. In preferred embodiments, the coupling of the $M^M$ reduces the ability of the antibody to bind its Primary Target such that the $K_d$ of the antibody when coupled to the $M^M$ towards its Primary Target is at least 1,000 times greater than the $K_d$ of the antibody when not coupled to the $M^M$ towards its Primary Target. In preferred embodiments, the coupling of the $M^M$ reduces the ability of the antibody to bind its Primary Target such that the $K_d$ of the antibody when coupled to the $M^M$ towards its Primary Target is at least 10,000 times greater than the $K_d$ of the antibody when not coupled to the $M^M$ towards its Primary Target. In preferred embodiments, for example when using a non-binding steric $M^M$ as defined below, the coupling of the $M^M$ reduces the ability of the antibody to bind its Primary Target such that the $K_d$ of the antibody when coupled to the $M^M$ towards its Primary Target is at least 100,000 times greater than the $K_d$ of the antibody when not coupled to the $M^M$ towards its Primary Target. In preferred embodiments, for example when using a non-binding steric $M^M$ as defined below, the coupling of the $M^M$ reduces the ability of the antibody to bind its Primary Target such that the $K_d$ of the antibody when coupled to the $M^M$ towards its Primary Target is at least 1,000,000 times greater than the $K_d$ of the antibody when not coupled to the $M^M$ towards its Primary Target. In preferred embodiments, for example when using a non-binding steric $M^M$ as defined below, the coupling of the $M^M$ reduces the ability of the antibody to bind its Primary Target such that the $K_d$ of the antibody when coupled to the $M^M$ towards its Primary Target is at least 10,000,000 times greater than the $K_d$ of the antibody when not coupled to the $M^M$ towards its Primary Target.

Exemplary drugs that can be used in a Prodrug relevant to this invention using Masking Moieties include but are not limited to: antibodies, antibody derivatives, antibody fragments, proteins, aptamers, oligopeptides, oligonucleotides, oligosaccharides, carbohydrates, as well as peptides, peptoids, steroids, toxins, hormones, viruses, whole cells, phage. In preferred embodiments the drugs are low to medium molecular weight compounds, preferably organic compounds (e.g. about 200 to about 2500 Da, preferably about 300 to about 1750 Da, more preferably about 300 to about 1000 Da).

In one embodiment antibodies are used as the Drug. While antibodies or immunoglobulins derived from IgG antibodies are particularly well-suited for use in this invention, immunoglobulins from any of the classes or subclasses may be selected, e.g. IgG, IgA, IgM, IgD and IgE. Suitably, the immunoglobulins is of the class IgG including but not limited to IgG subclasses (IgG1, 2, 3 and 4) or class IgM which is able to specifically bind to a specific epitope on an antigen. Antibodies can be intact immunoglobulins derived from natural sources or from recombinant sources and can be immunoreactive portions of intact immunoglobulins. Antibodies may exist in a variety of forms including, for example, polyclonal antibodies, monoclonal antibodies, camelized single domain antibodies, recombinant antibodies, anti-idiotype antibodies, multispecific antibodies, antibody fragments, such as Fv, VHH, Fab, $F(ab)_2$, Fab', Fab'-SH, $F(ab')_2$, single chain variable fragment antibodies (scFv), tandem/bis-scFv, Fc, pFc', scFv-Fc, disulfide Fv (dsFv), bispecific antibodies (bc-scFv) such as BiTE antibodies, camelid antibodies, minibodies, nanobodies, resurfaced antibodies, humanized antibodies, fully human antibodies, single domain antibody (sdAb, also known as Nanobody™), chimeric antibodies, chimeric antibodies comprising at least one human constant region, dual-affinity antibodies such as dual-affinity retargeting proteins (DART™), and multimers and derivatives thereof, such as divalent or multivalent single-chain variable fragments (e.g. di-scFvs, tri-scFvs) including but not limited to minibodies, diabodies, triabodies, tribodies, tetrabodies, and the like, and multivalent antibodies. Reference is made to [Trends in Biotechnology 2015, 33, 2, 65], [Trends Biotechnol. 2012, 30, 575-582], and [Canc. Gen. Prot. 2013 10, 1-18], and [BioDrugs 2014, 28, 331-343], the contents of which is hereby incorporated by reference. Other embodiments use antibody mimetics as Drug, such as but not limited to Affimers, Anticalins, Avimers, Alphabodies, Affibodies, DARPins, and multimers and derivatives thereof; reference is made to [Trends in Biotechnology 2015, 33, 2, 65], the contents of which is hereby incorporated by reference. “Antibody fragment” refers to at least a portion of the variable region of the immunoglobulin that binds to its target, i.e. the antigen-binding region. Multimers may be linearly linked or may be branched and may be derived from a single vector or chemically connected, or non-covalently connected. Methods of making above listed constructs are known in the art. For the avoidance of doubt, in the context of this invention the term “antibody” is meant to encompass all of the antibody variations, fragments, derivatives, fusions, analogs and mimetics outlined in this paragraph, unless specified otherwise.

Typical drugs for which the invention is suitable include, but are not limited to: proteins, peptides, oligosaccharides, oligonucleotides, monospecific, bispecific and trispecific antibodies and antibody fragment or protein fusions, preferably bispecific and trispecific. In preferred embodiments the activatable antibody or derivative is formulated as part of a pro-Bispecific T Cell Engager (BITE) molecule.

Other embodiments use immunotoxins, which are a fusion or a conjugate between a toxin and an antibody. Typical toxins comprised in an immunotoxins are cholera toxin, ricin A, gelonin, saporin, bouganin, ricin, abrin, diphtheria toxin, Staphylococcal enterotoxin, *Bacillus* Cyt2Aa1 toxin, *Pseudomonas* exotoxin PE38, *Pseudomonas* exotoxin PE38KDEL, granule-associated serine protease granzyme B, human ribonucleases (RNase), or other pro-apoptotic human proteins. Other exemplary cytotoxic human proteins which may be incorporated into fusion constructs are caspase 3, caspase 6, and BH3-interacting domain death agonist (BID). Current immunotoxins have immunogenicity issues and toxicity issues, especially towards vascular endothelial cells. Masking the targeted toxin by a $M^M$ such as a PEG or peptide and removing the $M^M$ once the masked immunotoxin has bound to its target is expected to greatly reduce the toxicity and immunogenicity problems.

Other embodiments use immunocytokines, which are a fusion or a conjugate between a cytokine and an antibody. Typical cytokines used in cancer therapy include IL-2, IL-7, IL-12, IL-15, IL-21, TNF. A typical cytokine used in autoimmune diseases is the anti-inflammatory IL-10. Masking the targeted cytokine by a $M^M$ such as a PEG or peptide and removing the $M^M$ once the masked immunocytokine has bound to its target is expected to greatly reduce the toxicity problems. Other embodiments use small to medium sized organic drugs.

In preferred embodiments the unmasked Drug is multispecific and binds to two or more same or different Primary Targets. In preferred embodiments the multispecific Drug comprises one or more (masked) antibodies (also referred to as binding moieties) that are designed to engage immune effector cells. In preferred embodiments the masked multispecific Prodrug comprises one or more (masked) antibodies that are designed to engage leukocytes. In preferred embodiments the masked multispecific Prodrug comprises one or more (masked) antibodies that are designed to engage T cells. In preferred embodiments the masked multispecific Prodrug comprises one or more (masked) antibodies that engage a surface antigen on a leukocyte such as on a T cell, natural killer (NK) cell, a myeloid mononuclear cell, a macrophage and/or another immune effector cell. In preferred embodiments the immune effector cell is a leukocyte, a T cell, a NK cell, or a mononuclear cell.

In an exemplary multispecific masked Prodrug the Prodrug comprises an antibody (i.e. Targeting Agent) for a cancer receptor, e.g. TAG72, a antibody for CD3 on T cells, and an antibody for CD28 on T cells, wherein either the antibody for CD3 or for CD28 or both is masked by a $M^M$. Another example is an activatable antibody that comprises an antibody for a cancer receptor, and an antibody for CD3 on T cells, wherein the antibody for CD3 is masked by a $M^M$. Another example is a Prodrug that has an antibody for a cancer receptor, and an antibody for CD28 on T cells, wherein the antibody for CD28 is masked by a $M^M$. Another example is a Prodrug that has an antibody for a cancer receptor, and an antibody for CD16a on NK cells, wherein the antibody for CD16a is masked by a $M^M$. In yet another embodiment the unmasked Drug binds two different immune cells and optionally in addition a tumor cell. Said multispecific antibody derivatives can for example be prepared by fusing or conjugating antibodies, antibody fragments such as Fab, Fabs, scFv, camel antibody heavy chain fragments and proteins.

In some preferred embodiments the $M^M$ reduces the binding of the Drug to Primary Targets, equaling therapeutic targets, selected from CD3, CD28, PD-L1, PD-1, LAG-3, TIGIT, TIM-3, B7H4, Vista, CTLA-4 polysialic acids and corresponding lectins. In other preferred embodiments the $M^M$ masks a T-cell agonist, an NK cell agonist, an DC cell agonist.

In preferred embodiments of an immune effector cell engaging masked multispecific Prodrug such as a T-cell engaging multispecific activatable antibody, at least one antibody comprised in the Prodrug is a Targeting Agent and binds a Primary Target that is typically an antigen present on the surface of a tumor cell or other cell type associated with disease, such as, but not limited to, EGFR, erbB2, EpCAM, PD-L1, B7H3 or CD71 (transferrin receptor), and at least one other antibody comprised in the Prodrug binds Primary Target that is typically a stimulatory or inhibitory antigen present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3 or VISTA. In preferred embodiments it is preferred that the targeted CD3 antigen is CD3ε or CD3 epsilon.

One embodiment of the disclosure is a multispecific activatable antibody that includes an antibody Targeting Agent directed to a tumor target and another agonist antibody, the Drug, directed to a co-stimulatory receptor expressed on the surface of an activated T cell or NK cell, wherein the agonist antibody is masked. Examples of co-stimulatory receptors include but are not limited to CD27, CD137, GITR, HVEM, NKG2D, OX40. In this embodiment, once the Prodrug is tumor-bound and activated it would effectively crosslink and activate the T cell or NK cell expressed co-stimulatory receptors in a tumor dependent manner to enhance the activity of T cell or NK cells that are responding to any tumor antigen via their endogenous T cell or NK cell activating receptors. The activation dependent nature of these T cell or NK cell co-stimulatory receptors would focus the activity of the activated multispecific Prodrug to tumor specific T cells without activating all T cells independent of their antigen specificity.

One embodiment of the disclosure is a multispecific activatable antibody targeted to a disease characterized by T cell overstimulation, such as, but not limited to, an autoimmune disease or inflammatory disease microenvironment. Such a Prodrug includes an antibody, for example a IgG or scFv, directed to a target comprising a surface antigen expressed in a tissue targeted by a T cell in autoimmune or inflammatory disease and an antibody, for example IgG or scFv, directed to an inhibitory receptor expressed on the surface of a T cell or NK cell, wherein the T cell or NK cell inhibitory antibody is masked. Examples of inhibitory receptors include but are not limited to BTLA, CTLA-4, LAG3, PD-1, TIGIT, TIM3, and NK-expressed KIRs. Examples of a tissue antigen targeted by T cells in autoimmune disease include but are not limited to a surface antigen expressed on myelin or nerve cells in multiple sclerosis or a surface antigen expressed on pancreatic islet cells in Type 1 diabetes. In this embodiment, the Prodrug localizes at the tissue under autoimmune attack or inflammation, is activated by the Activator and co-engages the T-cell or NK cell inhibitory receptor to suppress the activity of autoreactive T cells responding to any disease tissue targeted antigens via their endogenous TCR or activating receptors.

Other non-limiting exemplary Primary Targets for the binding moieties comprised in Drugs of this invention are listed in the patent WO2015/013671, the contents of which are hereby incorporated by reference.

In another embodiment, the Drug is a masked vaccine, which can be unmasked at a desired time and/or selected location in the body, for example subcutaneously and/or in the proximity of lymph nodes. In another embodiment, the Drug is a masked antigen, e.g. a masked peptide, which optionally is present in a Major Histocompatibility Complex (MHC) and which can be unmasked at a desired time and/or selected location in the body, for example subcutaneously and/or in the proximity of lymph nodes.

The Prodrug may further comprise another linked drug, which is released upon target binding, either by proteases, pH, thiols, or by catabolism. Examples are provided in the review on Antibody-drug conjugates in [Polakis, *Pharmacol. Rev.* 2016, 68, 3-19]. The invention further contemplates that the Prodrug can induce antibody-dependent cellular toxicity (ADCC) or complement dependent cytotoxicity (CDC) upon unmasking of one or more moieties of the Prodrug. The invention also contemplates that the Prodrug can induce antibody-dependent cellular toxicity (ADCC) or complement dependent cytotoxicity (CDC) independent of unmasking of one or more moieties of the Prodrug.

Some embodiments use as said additional drug antiproliferative/antitumor agents, antibiotics, cytokines, anti-inflammatory agents, anti-viral agents, antihypertensive agents, chemosensitizing, radiosensitizing agents, DNA damaging agents, anti-metabolites, natural products and their analogs. It is preferred that the Drug is a protein or an antibody.

Drugs

Drugs ($D^D$) that can be used in a Prodrug or a Drug that can be deactivated relevant to this invention are pharmaceutically active compounds. In a preferred embodiment the pharmaceutically active compound is selected from the group consisting of cytotoxins, antiproliferative/antitumor agents, antiviral agents, antibiotics, anti-inflammatory agents, chemosensitizing agents, radiosensitizing agents, immunomodulators, immunosuppressants, immunostimulants, anti-angiogenic factors, enzyme inhibitors.

In preferred embodiments these pharmaceutically active compounds are selected from the group consisting of antibodies, antibody derivatives, antibody fragments, proteins, aptamers, oligopeptides, oligonucleotides, oligosaccharides, carbohydrates, as well as peptides, peptoids, steroids, toxins, hormones, cytokines, chemokines.

In preferred embodiments these drugs are low to medium molecular weight compounds, preferably organic compounds (e.g. about 200 to about 2500 Da, preferably about 300 to about 1750 Da, more preferably about 300 to about 1000 Da).

Exemplary cytotoxic drug types for use as conjugates to the TCO and to be released upon IEDDA reaction with the Activator, for example for use in cancer therapy, include but are not limited to DNA damaging agents, DNA crosslinkers, DNA binders, DNA alkylators, DNA intercalators, DNA cleavers, microtubule stabilizing and destabilizing agents, topoisomerases inhibitors, radiation sensitizers, anti-metabolites, natural products and their analogs, peptides, oligonucleotides, enzyme inhibitors such as dihydrofolate reductase inhibitors and thymidylate synthase inhibitors.

Examples include but are not limited to colchinine, vinca alkaloids, anthracyclines (e.g. doxorubicin, epirubicin, idarubicin, daunorubicin), camptothecins, taxanes, taxols, vinblastine, vincristine, vindesine, calicheamycins, tubulysins, tubulysin M, cryptophycins, methotrexate, methopterin, aminopterin, dichloromethotrexate, irinotecans, enediynes, amanitins, deBouganin, dactinomycines, CC1065 and its analogs, duocarmycins, maytansines, maytansinoids, dolastatins, auristatins, pyrrolobenzodiazepines and dimers (PBDs), indolinobenzodiazepines and dimers, pyridinobenzodiazepines and dimers, mitomycins (e.g. mitomycin C, mitomycin A, caminomycin), melphalan, leurosine, leurosideine, actinomycin, tallysomycin, lexitropsins, bleomycins, podophyllotoxins, etoposide, etoposide phosphate, staurosporin, esperamicin, the pteridine family of drugs, SN-38 and its analogs, platinum-based drugs, cytotoxic nucleosides.

Other exemplary drug classes are angiogenesis inhibitors, cell cycle progression inhibitors, P13K/m-TOR/AKT pathway inhibitors, MAPK signaling pathway inhibitors, kinase inhibitors, protein chaperones inhibitors, HDAC inhibitors, PARP inhibitors, Wnt/Hedgehog signaling pathway inhibitors, and RNA polymerase inhibitors.

Examples of auristatins include dolastatin 10, monomethyl auristatin E (MMAE), auristatin F, monomethyl auristatin F (MMAF), auristatin F hydroxypropylamide (AF HPA), auristatin F phenylene diamine (AFP), monomethyl auristatin D (MMAD), auristatin PE, auristatin EB, auristatin EFP, auristatin TP and auristatin AQ. Suitable auristatins are also described in U.S. Publication Nos. 2003/0083263, 2011/0020343, and 2011/0070248; PCT Application Publication Nos. WO09/117531, WO2005/081711, WO04/010957; WO02/088172 and WO01/24763, and U.S. Pat. Nos. 7,498,298; 6,884,869; 6,323,315; 6,239,104; 6,124,431; 6,034,065; 5,780,588; 5,767,237; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,879,278; 4,816,444; and 4,486,414, the disclosures of which are incorporated herein by reference in their entirety.

Exemplary drugs include the dolastatins and analogues thereof including: dolastatin A (U.S. Pat. No. 4,486,414), dolastatin B (U.S. Pat. No. 4,486,414), dolastatin 10 (U.S. Pat. Nos. 4,486,444, 5,410,024, 5,504,191, 5,521,284, 5,530,097, 5,599,902, 5,635,483, 5,663,149, 5,665,860, 5,780,588, 6,034,065, 6,323,315), dolastatin 13 (U.S. Pat. No. 4,986,988), dolastatin 14 (U.S. Pat. No. 5,138,036), dolastatin 15 (U.S. Pat. No. 4,879,278), dolastatin 16 (U.S. Pat. No. 6,239,104), dolastatin 17 (U.S. Pat. No. 6,239,104), and dolastatin 18 (U.S. Pat. No. 6,239,104), each patent incorporated herein by reference in their entirety.

Exemplary maytansines, maytansinoids, such as DM-1 and DM-4, or maytansinoid analogs, including maytansinol and maytansinol analogs, are described in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 6,441,163; 6,716,821 and 7,276,497. Other examples include mertansine and ansamitocin.

Pyrrolobenzodiazepines (PBDs), which expressly include dimers and analogs, include but are not limited to those described in [Denny, Exp. Opin. Ther. Patents, 10(4):459-474 (2000)], [Hartley et al., Expert Opin Investig Drugs. 2011, 20(6):733-44], Antonow et al., Chem Rev. 2011, 111(4), 2815-64]. Exemplary indolinobenzodiazepines are described in literature. Exemplary pyridinobenzodiazepines are described in literature.

Calicheamicins include, e.g. enediynes, esperamicin, and those described in U.S. Pat. Nos. 5,714,586 and 5,739,116.

Examples of duocarmycins and analogs include CC1065, duocarmycin SA, duocarmycin A, duocarmycin B1, duocarmycin B2, duocarmycin C1, duocarmycin C2, duocarmycin D, DU-86, KW-2189, adozelesin, bizelesin, carzelesin, seco-adozelesin, CPI, CBI. Other examples include those described in, for example, U.S. Pat. Nos. 5,070,092; 5,101,092; 5,187,186; 5,475,092; 5,595,499; 5,846,545; 6,534,660; 6,548,530; 6,586,618; 6,660,742; 6,756,397; 7,049,316; 7,553,816; 8,815,226; US20150104407; 61/988,011 filed May 2, 2014 and 62/010,972 filed Jun. 11, 2014; the disclosure of each of which is incorporated herein in its entirety.

Exemplary vinca alkaloids include vincristine, vinblastine, vindesine, and navelbine, and those disclosed in U.S. Publication Nos. 2002/0103136 and 2010/0305149, and in U.S. Pat. No. 7,303,749, the disclosures of which are incorporated herein by reference in their entirety.

Exemplary epothilone compounds include epothilone A, B, C, D, E, and F, and derivatives thereof. Suitable epothilone compounds and derivatives thereof are described, for example, in U.S. Pat. Nos. 6,956,036; 6,989,450; 6,121,029; 6,117,659; 6,096,757; 6,043,372; 5,969,145; and 5,886,026; and WO97/19086; WO98/08849; WO98/22461; WO98/25929; WO98/38192; WO99/01124; WO99/02514; WO99/03848; WO99/07692; WO99/27890; and WO99/28324; the disclosures of which are incorporated herein by reference in their entirety.

Exemplary cryptophycin compounds are described in U.S. Pat. Nos. 6,680,311 and 6,747,021; the disclosures of which are incorporated herein by reference in their entirety. Exemplary platinum compounds include cisplatin, carboplatin, oxaliplatin, iproplatin, ormaplatin, tetraplatin. Exemplary DNA binding or alkylating drugs include CC-1065 and its analogs, anthracyclines, calicheamicins, dactinomycines, mitromycines, pyrrolobenzodiazepines, indolinobenzodiazepines, pyridinobenzodiazepines and the like. Exemplary microtubule stabilizing and destabilizing agents include taxane compounds, such as paclitaxel, docetaxel, tesetaxel, and carbazitaxel; maytansinoids, auristatins and analogs thereof, vinca alkaloid derivatives, epothilones and cryptophycins. Exemplary topoisomerase inhibitors include camptothecin and camptothecin derivatives, camptothecin analogs and non-natural camptothecins, such as, for example, CPT-11, SN-38, topotecan, 9-aminocamptothecin, rubitecan, gimatecan, karenitecin, silatecan, lurtotecan, exatecan, diflometotecan, belotecan, lurtotecan and S39625. Other camptothecin compounds that can be used in the present invention include those described in, for example, J. Med. Chem., 29:2358-2363 (1986); J. Med. Chem., 23:554 (1980); J. Med Chem., 30:1774 (1987). Angiogenesis inhibitors include, but are not limited to, MetAP2 inhibitors, VEGF inhibitors, PIGF inhibitors, VGFR inhibitors, PDGFR inhibitors, MetAP2 inhibitors. Exemplary VGFR and PDGFR inhibitors include sorafenib, sunitinib and vatalanib. Exemplary MetAP2 inhibitors include fumagillol analogs, meaning compounds that include the fumagillin core structure. Exemplary cell cycle progression inhibitors include CDK inhibitors such as, for example, BMS-387032 and PD0332991; Rho-kinase inhibitors such as, for example, AZD7762; aurora kinase inhibitors such as, for example, AZD1152, MLN8054 and MLN8237; PLK inhibitors such as, for example, BI 2536, BI6727, GSK461364, ON-01910; and $KS^P$ inhibitors such as, for example, SB 743921, SB 715992, MK-0731, AZD8477, AZ3146 and ARRY-520. Exemplary P13K/m-TOR/AKT signalling pathway inhibitors include phosphoinositide 3-kinase (P13K) inhibitors, GSK-3 inhibitors, ATM inhibitors, DNA-PK inhibitors and PDK-1 inhibitors. Exemplary P13 kinases are disclosed in U.S. Pat. No. 6,608,053, and include BEZ235, BGT226, BKM120, CAL263, demethoxyviridin, GDC-0941, GSK615, IC87114, LY294002, Palomid 529, perifosine, PF-04691502, PX-866, SAR245408, SAR245409, SF1126, Wortmannin, XL147 and XL765. Exemplary AKT inhibitors include, but are not limited to AT7867. Exemplary MAPK signaling pathway inhibitors include MEK, Ras, JNK, B-Raf and p38 MAPK inhibitors. Exemplary MEK inhibitors are disclosed in U.S. Pat. No. 7,517,944 and include GDC-0973, GSK1120212, MSC1936369B, AS703026, RO5126766 and RO4987655, PD0325901, AZD6244, AZD8330 and GDC-0973. Exemplary B-raf inhibitors include CDC-0879, PLX-4032, and SB590885. Exemplary B p38 MAPK inhibitors include BIRB 796, LY2228820 and SB 202190. Exemplary receptor tyrosine kinases inhibitors include but are not limited to AEE788 (NVP-AEE 788), BIBW2992 (Afatinib), Lapatinib, Erlotinib (Tarceva), Gefitinib (Iressa), AP24534 (Ponatinib), ABT-869 (linifanib), AZD2171, CHR-258 (Dovitinib), Sunitinib (Sutent), Sorafenib (Nexavar), and Vatalinib. Exemplary protein chaperon inhibitors include HSP90 inhibitors. Exemplary inhibitors include 17AAG derivatives, BIIB021, BIIB028, SNX-5422, NVP-AUY-922 and KW-2478. Exemplary HDAC inhibitors include Belinostat (PXD101), CUDC-101, Droxinostat, ITF2357 (Givinostat, Gavinostat), JNJ-26481585, LAQ824 (NVP-LAQ824, Dacinostat), LBH-589 (Panobinostat), MC1568, MGCDO103 (Mocetinostat), MS-275 (Entinostat), PCI-24781, Pyroxamide (NSC 696085), SB939, Trichostatin A and Vorinostat (SAHA). Exemplary PARP inhibitors include iniparib (BSI 201), olaparib (AZD-2281), ABT-888 (Veliparib), AGO14699, CEP9722, MK 4827, KU-0059436 (AZD2281), LT-673, 3-aminobenzamide, A-966492, and AZD2461. Exemplary Wnt/Hedgehog signalling pathway inhibitors include vismodegib, cyclopamine and XAV-939. Exemplary RNA polymerase inhibitors include amatoxins. Exemplary amatoxins include alpha-amanitins, beta amanitins, gamma amanitins, eta amanitins, amanullin, amanullic acid, amanisamide, amanon, and proamanullin. Exemplary immunemodulators are APRIL, cytokines, including IL-2, IL-7, IL-10, IL-12, IL-15, IL-21, TNF, interferon gamma, GMCSF, NDV-GMCSF, and agonists and antagonists of STING, agonists and antagonists of TLRs including TLR1/2, TLR3, TLR4, TLR7/8, TLR9, TLR12, agonists and antagonists of GITR, CD3, CD28, CD40, CD74, CTLA4, OX40, PD1, PDL1, RIG, MDA-5, NLRP1, NLRP3, AIM2, IDO, MEK, cGAS, and CD25, NKG2A. Other exemplary drugs include puromycins, topetecan, rhizoxin, echinomycin, combretastatin, netropsin, estramustine, cemadotin, discodermolide, eleutherobin, mitoxantrone, pyrrolobenzimidazoles (PBI), gamma-interferon, Thialanostatin (A) and analogs, CDK11, immunotoxins, comprising e.g. ricin A, diphtheria toxin, cholera toxin.

In exemplary embodiments of the invention, the drug moiety is a mytomycin compound, a vinca alkaloid compound, taxol or an analogue, an anthracycline compound, a calicheamicin compound, a maytansinoid compound, an auristatin compound, a duocarmycin compound, SN38 or an analogue, a pyrrolobenzodiazepine compound, a indolinobenzodiazepine compound, a pyridinobenzodiazepine compound, a tubulysin compound, a non-natural camptothecin compound, a DNA binding drug, a kinase inhibitor, a MEK inhibitor, a $KS^P$ inhibitor, a P13 kinase inhibitor, a topoisomerase inhibitor, or analogues thereof.

In one preferred embodiment the drug is a non-natural camptothecin compound, vinca alkaloid, kinase inhibitor, (e.g. P13 kinase inhibitor: GDC-0941 and PI-103), MEK inhibitor, $KS^P$ inhibitor, RNA polymerase inhibitor, PARP inhibitor, docetaxel, paclitaxel, doxorubicin, dolastatin, calicheamicins, SN38, pyrrolobenzodiazepines, pyridinobenzodiazepines, indolinobenzodiazepines, DNA binding drugs, maytansinoids DM1 and DM4, auristatin MMAE, CC1065 and its analogs, camptothecin and its analogs, SN-38 and its analogs.

In another preferred embodiment the drug is selected from DNA binding drugs and microtubule agents, including pyrrolobenzodiazepines, indolinobenzodiazepines, pyridinobenzodiazepines, maytansinoids, maytansines, auristatins, tubulysins, duocarmycins, anthracyclines, taxanes. In another preferred embodiment the drug is selected from colchinine, vinca alkaloids, tubulysins, irinotecans, an inhibitory peptide, amanitin and deBouganin.

In another preferred embodiment the drug is a radioactive moiety, said moiety comprising a radioactive isotope for radiation therapy. A radionuclide used for therapy is preferably an isotope selected from the group consisting of $^{24}$Na, $^{32}$P, $^{33}$P, $^{47}$Sc, $^{59}$Fe, $^{67}$Cu, $^{76}$As, $^{77}$As, $^{80}$Br, $^{82}$Br, $^{89}$Sr, $^{90}$Nb, $^{90}$Y, $^{103}$Ru, $^{105}$Rh, $^{109}$Pd, $^{111}$Ag, $^{111}$In, $^{121}$Sn, $^{127}$Te, $^{131}$I, $^{140}$La, $^{141}$Ce, $^{142}$Pr, $^{143}$Pr, $^{144}$Pr, $^{149}$Pm, $^{149}$Tb, $^{151}$Pm, $^{153}$Sm, $^{159}$Gd, $^{161}$Tb, $^{165}$Dy, $^{166}$Dy, $^{166}$Ho, $^{169}$Er, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{212}$Pb, $^{213}$Bi, $^{214}$Bi, $^{223}$Ra, $^{224}$Ra, $^{225}$Ac and $^{227}$Th.

When the radioactive moiety is intended to comprise a metal, such as $^{177}$Lu, such radiometal is preferably provided in the form of a chelate. In such a case the radioactive moiety preferably comprises a structural moiety capable of forming a coordination complex with such a metal. A good example hereof are macrocylic lanthanide(III) chelates derived from 1,4,7,10-tetraazacyclododecane-1,4,7,10-tetraacetic acid ($H_4$dota).

In a preferred embodiment, the moiety is a chelating moiety selected from the group consisting of DTPA (diethylenetriaminepentaacetic acid), DOTA (1,4,7,10-tetraazacyclododecane-N,N',N",N"-tetraacetic acid), NOTA (1,4,7-triazacyclononane-N,N',N"-triacetic acid), TETA (1,4,8,11-tetraazacyclotetradecane-N,N',N",N'-tetraacetic acid), OTTA (N1-(p-isothiocyanatobenzyl)-diethylenetriamine-$N_1$, $N_2$,$N_3$,$N_3$-tetraacetic acid), deferoxamine or DFO (N'-[5-[[4-[[5-(acetylhydroxyamino)pentyl]amino]-1,4-dioxobutyl]hydroxyamino]pentyl]-N-(5-aminopentyl)-N-hydroxybutanediamide), and HYNIC (hydrazinonicotinamide), DOTAM, TACN, sarcophagine, 3,4-HOPO-based chelators.

In other embodiments the radioactive moiety comprises a prostethic group (i.e. a phenol) that is bound by a non-metal radionuclide, such as $^{131}$I.

In another embodiment, a combination of two or more different drugs are used. In preferred embodiments the released Drug is itself a prodrug designed to release a further drug. In preferred embodiments the released Drug is itself a prodrug designed to be coupled to another moiety, (such as another prodrug) to form an active Drug. In preferred embodiments the Drug has increased therapeutic efficacy after reaction of the Trigger with the Activator. In some embodiments the Drug has reduced therapeutic efficacy after reaction of the Trigger with the Activator.

Drugs optionally include a (portion of a) membrane translocation moiety (e.g. adamantine, poly-lysine/arginine, TAT, human lactoferrin) and/or a targeting agent (against e.g. a tumor cell receptor) optionally linked through a stable or labile linker. Exemplary references include: Trends in Biochemical Sciences, 2015, 40, 12, 749; J. Am. Chem. Soc. 2015, 137, 12153-12160; Pharmaceutical Research, 2007, 24, 11, 1977.

It will further be understood that, in addition to one or more targeting agents (or $C^B$) that may be attached to the Trigger or Linker $L^C$ a targeting agent $T^T$ may optionally be attached to a drug, optionally via a spacer $S^P$. In some embodiments, the targeting efficacy of said $T^T$ attached to a drug is increased after reaction of the Trigger with an Activator, wherein preferably the Drug is $C^B$, wherein preferably the Activator comprises a $T^T$, wherein optionally the targeting efficacy of said $T^T$ comprised in the Activator is increased after reaction of the Trigger with an Activator.

Alternatively, it will be further understood that the targeting agent (or $C^B$) may comprise one or more additional drugs which are bound to the targeting agent by other types of linkers, e.g. cleavable by proteases, pH, thiols, or by catabolism.

The invention further contemplates that when a targeting agent is a suitably chosen antibody or antibody derivative that such targeting agent can induce antibody-dependent cellular toxicity (ADCC) or complement dependent cytotoxicity (CDC).

Several drugs may comprise or be replaced by an imageable label to measure drug targeting and release.

It will be understood that chemical modifications may also be made to the desired compound in order to make reactions of that compound more convenient for purposes of preparing conjugates of the invention.

Drugs containing an amine functional group for coupling to the TCO include mitomycin-C, mitomycin-A, daunorubicin, doxorubicin, aminopterin, actinomycin, bleomycin, 9-amino camptothecin, N8-acetyl spermidine, 1-(2 chloroethyl)1,2-dimethanesulfonyl hydrazide, tallysomycin, cytarabine, dolastatins (including auristatins) and derivatives thereof.

Drugs containing a hydroxyl function group for coupling to the TCO include etoposide, camptothecin, taxol, esperamicin, 1,8-dihydroxy-bicyclo[7.3.1]trideca-4-9-diene-2,6-diyne-13-one (U.S. Pat. No. 5,198,560), podophyllotoxin, anguidine, vincristine, vinblastine, morpholine-doxorubicin, n-(5,5-diacetoxy-pentyl)doxorubicin, and derivatives thereof.

Drugs containing a sulfhydryl functional group for coupling to the TCO include esperamicin and 6-mecaptopurine, and derivatives thereof.

It will be understood that the drugs can optionally be attached to the TCO derivative through a self-immolative linker $L^C$, or a combination thereof, and which may consist of multiple (self-immolative, or non immolative) units.

According to a further particular embodiment of the invention, the Prodrug is selected so as to target and or address a disease, such as cancer, an inflammation, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme.

In the Prodrug, the Construct-A and the TCO derivative can be directly linked to each other. They can also be bound to each other via a linker or a self-immolative linker $L^C$. It will be understood that the invention encompasses any conceivable manner in which the dienophile TCO is attached to the Contruct-A. In preferred embodiments Construct-A is a Drug. Methods of affecting conjugation to these drugs, e.g. through reactive amino acids such as lysine or cysteine in the case of proteins, are known to the skilled person.

Label

The compound of Formula (19) preferably comprises a Label that is capable of providing the desired diagnostic, imaging, and/or radiotherapeutic effect.

In a preferred embodiment, the Label is selected from the group consisting of MRI-imageable constructs, moieties comprising a spin label, moieties comprising an optical label, ultrasound-responsive constructs, X-ray-responsive moieties, moieties comprising a radionuclide, fluorescent dyes, luminescent dyes, FRET dyes, paramagnetic ions, superparamagnetic particles, and peptides.

Especially for imaging applications, it is preferred that the Label is a detectable label. A "detectable label" as used herein relates to the part of the compound of Formula (19) which allows detection of the compound of Formula (19) when present in a cell, tissue or organism. One type of detectable label envisaged within the context of the present invention is a contrast providing label. Different types of detectable labels are envisaged within the context of the present invention and are described hereinbelow.

Thus, according to a particular embodiment of the present invention, the compounds, combinations, kits, and methods of the present invention are used in imaging, especially medical imaging. In order to identify the Primary Target and/or to evaluate the biodistribution of the compound of Formula (19), use is made of a detectable Label.

Preferred detectable labels for imaging are contrast-providing moieties used in traditional imaging systems such as MRI-imageable constructs, moieties comprising spin labels, moieties comprising optical labels, ultrasound-responsive constructs, X-ray-responsive moieties, moieties comprising radionuclides, (bio)luminescent and FRET-type dyes.

Furthermore, preferred detectable labels envisaged within the context of the present invention include, and are not necessarily limited to, fluorescent molecules, e.g. autofluorescent molecules, molecules that fluoresce upon contact with a reagent, radioactive moieties or complexes; biotin, e.g., to be detected through binding of biotin by avidin; fluorescent tags, imaging constructs for MRI comprising a paramagnetic metal, imaging reagents, e.g., those described in U.S. Pat. Nos. 4,741,900 and 5,326,856) and the like.

Preferably, the radionuclide comprised in a Label for imaging is an isotope selected from the group consisting of $^{3}H$, $^{11}C$, $^{13}N$, $^{15}O$, $^{18}F$, $^{19}F$, $^{44}Sc$, $^{51}Cr$, $^{52}Fe$, $^{52}Mn$, $^{55}Co$, $^{60}Cu$, $^{61}Cu$, $^{62}Zn$, $^{62}Cu$, $^{63}Zn$, $^{64}Cu$, $^{66}Ga$, $^{67}Ga$, $^{68}Ga$, $^{70}As$, $^{71}As$, $^{72}As$, $^{74}As$, $^{75}Se$, $^{75}Br$, $^{76}Br$, $^{77}Br$, $^{80}Br$, $^{82}Br$, $^{82}Rb$, $^{86}Y$, $^{88}Y$, $^{89}Sr$, $^{89}Zr$, $^{97}Ru$, $^{99m}Tc$, $^{110}In$, $^{111}In$, $^{113}In$, $^{114}In$, $^{117}Sn$, $^{120}I$, $^{122}Xe$, $^{123}I$, $^{124}I$, $^{125}I$, $^{166}Ho$, $^{167}Tm$, $^{169}Yb$, $^{193}Pt$, $^{195}Pt$, $^{201}Tl$, and $^{203}Pb$. More preferably, the radionuclide comprised in a Label for imaging is an isotope selected from the group consisting of $^{18}F$, $^{44}Sc$, $^{64}Cu$, $^{68}Ga$, $^{89}Zr$, $^{99m}Tc$, $^{111}In$, $^{123}I$, $^{124}I$.

Other elements and isotopes, such as being used for therapy may also be applied for imaging in certain applications.

In preferred embodiments, the MRI-imageable moiety is a paramagnetic ion or a superparamagnetic particle. The paramagnetic ion preferably is an element selected from the group consisting of Gd, Fe, Mn, Cr, Co, Ni, Cu, Pr, Nd, Yb, Tb, Dy, Ho, Er, Sm, Eu, Ti, Pa, La, Sc, V, Mo, Ru, Ce, Dy, Tl. The ultrasound responsive moiety can comprise a microbubble, the shell of which consisting of a phospholipid, and/or (biodegradable) polymer, and/or human serum albumin. The microbubble can be filled with fluorinated gasses or liquids.

The X-ray-responsive moieties include but are not limited to iodine, barium, barium sulfate, gastrografin or can comprise a vesicle, liposome or polymer capsule filled with iodine compounds and/or barium sulfate.

Moreover, detectable labels envisaged within the context of the present invention also include peptides or polypeptides that can be detected by antibody binding, e.g., by binding of a detectable labeled antibody or by detection of bound antibody through a sandwich-type assay. In one embodiment the detectable labels comprise small size organic PET and SPECT radioisotopes, such as $^{18}F$, $^{11}C$, $^{123}I$ or $^{124}I$. Due to their small size, organic PET or SPECT radioisotopes are ideally suited for monitoring intracellular events as they do not greatly affect the properties of the Targeting Agent in general and its membrane transport in particular.

In preferred embodiments, especially when the compound of Formula (19) is used in therapeutic applications, the Label is a therapeutic Label, said Label comprising a radioactive isotope for radiation therapy. A radionuclide used for therapy is preferably an isotope selected from the group consisting of $^{24}Na$, $^{32}P$, $^{33}P$, $^{47}Sc$, $^{59}Fe$, $^{67}Cu$, $^{76}As$, $^{77}As$, $^{80}Br$, $^{82}Br$, $^{89}Sr$, $^{90}Nb$, $^{90}Y$, $^{103}Ru$, $^{105}Rh$, $^{109}Pd$, $^{111}Ag$, $^{111}In$, $^{121}Sn$, $^{127}Te$, $^{131}I$, $^{140}La$, $^{141}Ce$, $^{142}Pr$, $^{143}Pr$, $^{144}Pr$, $^{149}Pm$, $^{149}Tb$, $^{151}Pm$, $^{153}Sm$, $^{159}Gd$, $^{161}Tb$, $^{165}Dy$, $^{166}Dy$, $^{166}Ho$, $^{169}Er$, $^{172}Tm$, $^{175}Yb$, $^{177}Lu$, $^{186}Re$, $^{188}Re$, $^{198}Au$, $^{199}Au$, $^{211}At$, $^{211}Bi$, $^{212}Bi$, $^{212}Pb$, $^{213}Bi$, $^{214}Bi$, $^{223}Ra$, $^{224}Ra$, $^{225}Ac$ and $^{227}Th$. More preferably, the radionuclide comprised in a Label for therapy is an isotope selected from the group consisting of $^{90}Y$, $^{111}In$, $^{131}I$, $^{177}Lu$, $^{186}Re$, $^{188}Re$, $^{211}At$, $^{212}Pb$, $^{213}Bi$, $^{225}Ac$, and $^{227}Th$.

When the Label is intended to comprise a metal, such as $^{111}In$ for SPECT imaging, such is preferably provided in the form of a chelate. In such a case the Label preferably comprises a structural moiety capable of forming a coordination complex with such a metal. A good example hereof are macrocylic lanthanide(III) chelates derived from 1,4,7,10-tetraazacyclododecane-1,4,7,10-tetraacetic acid ($H_4$dota).

In preferred embodiments, the Label is selected from the group consisting of $—OR_{37}$, $—N(R_{37})_2$, $—CF_3$, $—SR_{37}$, $S(═O)_2N(R_{37})_2$, $OC(═O)R_{37}$, $SC(═O)R_{37}$, $OC(═S)R_{37}$, $SC(═S)R_{37}$, $NR_{37}C(═O)—R_{37}$, $NR_{37}C(═S)—R_{37}$, $NR_{37}C(═O)O—R_{37}$, $NR_{37}C(═S)O—R_{37}$, $NR_{37}C(═O)S—R_{37}$, $NR_{37}C(═S)S—R_{37}$, $OC(═O)N(R_{37})_2$, $SC(═O)N(R_{37})_2$, $OC(═S)N(R_{37})_2$, $SC(═S)N(R_{37})_2$, $NR_{37}C(═O)N(R_{37})_2$, $NR_{37}C(═S)N(R_{37})_2$, $C(═O)R_{37}$, $C(═S)R_{37}$, $C(═O)N(R_{37})_2$, $C(═S)N(R_{37})_2$, $C(═O)O—R_{37}$, C(═O)

S—$R_{37}$, C(═S)O—$R_{37}$, C(═S)S—$R_{37}$, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ (cyclo)alkyl(hetero)aryl groups, $C_3$-$C_{24}$ (hetero)aryl(cyclo)alkyl, $C_4$-$C_{24}$ (cyclo)alkenyl(hetero)aryl groups, $C_4$-$C_{24}$ (hetero)aryl(cyclo)alkenyl groups, $C_4$-$C_{24}$ (cyclo)alkynyl(hetero)aryl groups, $C_4$-$C_{24}$ (hetero)aryl(cyclo)alkynyl groups, $C_4$-$C_{24}$ alkylcycloalkyl groups, and $C_4$-$C_{24}$ cycloalkylalkyl groups; the $R_{37}$ groups, alkyl groups, alkenyl groups, alkynyl groups, aryl, heteroaryl, cycloalkyl groups, cycloalkenyl groups, cycloalkynyl groups, (cyclo)alkyl(hetero)aryl groups, (hetero)aryl(cyclo)alkyl groups, (cyclo)alkenyl(hetero)aryl groups, (hetero)aryl(cyclo)alkenyl groups, (cyclo)alkynyl(hetero)aryl groups, (hetero)aryl(cyclo)alkynyl groups, alkylcycloalkyl groups, cycloalkylalkyl groups comprise, are substituted with and/or chelating at least one isotope selected from the group consisting of $^{3}$H, $^{11}$C, $^{13}$N, $^{15}$O, $^{18}$F, $^{19}$F, $^{44}$Sc, $^{51}$Cr, $^{52}$Fe, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{67}$Ga, $^{68}$Ga, $^{70}$As, $^{71}$As, $^{72}$As, $^{74}$As, $^{75}$Se, $^{75}$Br, $^{76}$Br, $^{77}$Br, $^{80}$Br, $^{82}$Br, $^{82}$Rb, $^{86}$Y, $^{88}$Y, $^{89}$Sr, $^{89}$Zr, $^{97}$Ru, $^{99m}$Tc, $^{110}$In, $^{111}$In, $^{113}$In, $^{114}$In, $^{117}$Sn, $^{120}$I, $^{122}$Xe, $^{123}$I, $^{124}$I, $^{125}$I, $^{166}$Ho, $^{167}$Tm, $^{169}$Yb, $^{193}$Pt, $^{195}$Pt, $^{201}$Tl, $^{203}$Pb, $^{24}$Na, $^{32}$P, $^{33}$P, $^{47}$Sc, $^{59}$Fe, $^{67}$Cu, $^{76}$As, $^{77}$As, $^{80}$Br, $^{82}$Br, $^{89}$Sr, $^{90}$Nb, $^{90}$Y, $^{103}$Ru, $^{105}$Rh, $^{109}$Pd, $^{111}$Ag, $^{111}$In, $^{121}$Sn, $^{127}$Te, $^{131}$I, $^{140}$La, $^{141}$Ce, $^{142}$Pr, $^{143}$Pr, $^{144}$Pr, $^{149}$Pm, $^{149}$Tb, $^{151}$ Pm, $^{153}$Sm, $^{159}$Gd, $^{161}$Tb, $^{165}$Dy, $^{166}$Dy, $^{166}$Ho, $^{169}$Er, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{212}$Pb, $^{213}$Bi, $^{214}$Bi, $^{223}$Ra, $^{224}$Ra, $^{225}$Ac and $^{227}$Th; and are optionally further substituted with a moiety selected from the group consisting of —Cl, —F, —Br, —I, —$OR_{37}$, —$N(R_{37})_2$, —$SO_3R_{37}$, —$PO_3(R_{37})_2$, —$PO_4(R_{37})_2$, —$NO_2$, —$CF_3$, ═O, ═$NR_{37}$, and —$SR_{37}$, and optionally contain one or more heteroatoms selected from the group consisting of O, S, $NR_{37}$, P, and Si, wherein the N, S, and P atoms are optionally oxidized, wherein the N atoms are optionally quaternized.

In another preferred embodiment, the Label is selected from the group consisting of —$OR_{37}$, —$N(R_{37})_2$, —$CF_3$, —$SR_{37}$, $S(═O)_2N(R_{37})_2$, OC(═O)$R_{37}$, SC(═O)$R_{37}$, OC(═S)$R_{37}$, SC(═S)$R_{37}$, $NR_{37}$C(═O)—$R_{37}$, $NR_{37}$C(═S)—$R_{37}$, $NR_{37}$C(═O)O—$R_{37}$, $NR_{37}$C(═S)O—$R_{37}$, $NR_{37}$C(═O)S—$R_{37}$, $NR_{37}$C(═S)S—$R_{37}$, OC(═O)N$(R_{37})_2$, SC(═O)N$(R_{37})_2$, OC(═S)N$(R_{37})_2$, SC(═S)N$(R_{37})_2$, $NR_{37}$C(═O)N$(R_{37})_2$, $NR_{37}$C(═S)N$(R_{37})_2$, C(═O)$R_{37}$, C(═S)$R_{37}$, C(═O)N$(R_{37})_2$, C(═S)N$(R_{37})_2$, C(═O)O—$R_{37}$, C(═O)S—$R_{37}$, C(═S)O—$R_{37}$, C(═S)S—$R_{37}$, $C_1$-$C_{12}$ alkyl groups, $C_2$-$C_{12}$ alkenyl groups, $C_2$-$C_{12}$ alkynyl groups, $C_6$-$C_{12}$ aryl groups, $C_2$-$C_{12}$ heteroaryl groups, $C_3$-$C_{12}$ cycloalkyl groups, $C_5$-$C_{12}$ cycloalkenyl groups, $C_{12}$-$C_{12}$ cycloalkynyl groups, $C_3$-$C_{12}$ (cyclo)alkyl(hetero)aryl groups, $C_3$-$C_{12}$ (hetero)aryl(cyclo)alkyl, $C_4$-$C_{12}$ (cyclo)alkenyl(hetero)aryl groups, $C_4$-$C_{12}$ (hetero)aryl(cyclo)alkenyl groups, $C_4$-$C_{12}$ (cyclo)alkynyl(hetero)aryl groups, $C_4$-$C_{12}$ (hetero)aryl(cyclo)alkynyl groups, $C_4$-$C_{12}$ alkylcycloalkyl groups, and $C_4$-$C_{12}$ cycloalkylalkyl groups; the $R_{37}$ groups, alkyl groups, alkenyl groups, alkynyl groups, aryl, heteroaryl, cycloalkyl groups, cycloalkenyl groups, cycloalkynyl groups, (cyclo)alkyl(hetero)aryl groups, (hetero)aryl(cyclo)alkyl groups, (cyclo)alkenyl(hetero)aryl groups, (hetero)aryl(cyclo)alkenyl groups, (cyclo)alkynyl(hetero)aryl groups, (hetero)aryl(cyclo)alkynyl groups, alkylcycloalkyl groups, cycloalkylalkyl groups comprise, are substituted with and/or chelating at least one isotope selected from the group consisting of $^{3}$H, $^{11}$C, $^{13}$N, $^{15}$O, $^{18}$F, $^{19}$F, $^{44}$Sc, $^{51}$Cr, $^{52}$Fe, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{67}$Ga, $^{68}$Ga, $^{70}$As, $^{71}$As, $^{72}$As, $^{74}$As, $^{75}$Se, $^{75}$Br, $^{76}$Br, $^{77}$Br, $^{80}$Br, $^{82}$Br, $^{82}$Rb, $^{86}$Y, $^{88}$Y, $^{89}$Sr, $^{89}$Zr, $^{97}$Ru, $^{99m}$Tc, $^{110}$In, $^{111}$In, $^{113}$In, $^{114}$In, $^{117}$Sn, $^{120}$I, $^{122}$Xe, $^{123}$I, $^{124}$I, $^{125}$I, $^{166}$Ho, $^{167}$Tm, $^{169}$Yb, $^{193}$Pt, $^{195}$Pt, $^{201}$Tl, $^{203}$Pb, $^{24}$Na, $^{32}$P, $^{33}$P, $^{47}$Sc, $^{59}$Fe, $^{67}$Cu, $^{76}$As, $^{77}$As, $^{80}$Br, $^{82}$Br, $^{89}$Sr, $^{90}$Nb, $^{90}$Y, $^{103}$Ru, $^{105}$Rh, $^{109}$Pd, $^{111}$Ag, $^{111}$In, $^{121}$Sn, $^{127}$Te, $^{131}$I, $^{140}$La, $^{141}$Ce, $^{142}$Pr, $^{143}$Pr, $^{144}$Pr, $^{149}$Pm, $^{149}$Tb, $^{151}$Pm, $^{153}$Sm, $^{159}$Cd, $^{161}$Tb, $^{165}$Dy, $^{166}$Dy, $^{166}$Ho, $^{169}$Er, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{212}$Pb, $^{213}$Bi, $^{214}$Bi, $^{223}$Ra, $^{224}$Ra, $^{225}$Ac and $^{227}$Th; and are optionally further substituted with a moiety selected from the group consisting of —Cl, —F, —Br, —I, —$OR_{37}$, —$N(R_{37})_2$, —$SO_3R_{37}$, —$PO_3(R_{37})_2$, —$PO_4(R_{37})_2$, —$NO_2$, —$CF_3$, ═O, ═$NR_{37}$, and —$SR_{37}$, and optionally contain one or more heteroatoms selected from the group consisting of O, S, $NR_{37}$, P, and Si, wherein the N, S, and P atoms are optionally oxidized, wherein the N atoms are optionally quaternized.

In preferred embodiments, each Label is independently selected from the group consisting of —$OR_{37}$, —$N(R_{37})_2$, —$CF_3$, —$SR_{37}$, $S(═O)_2N(R_{37})_2$, OC(═O)$R_{37}$, SC(═O)$R_{37}$, OC(═S)$R_{37}$, SC(═S)$R_{37}$, $NR_{37}$C(═O)—$R_{37}$, $NR_{37}$C(═S)—$R_{37}$, $NR_{37}$C(═O)O—$R_{37}$, $NR_{37}$C(═S)O—$R_{37}$, $NR_{37}$C(═O)S—$R_{37}$, $NR_{37}$C(═S)S—$R_{37}$, OC(═O)N$(R_{37})_2$, SC(═O)N$(R_{37})_2$, OC(═S)N$(R_{37})_2$, SC(═S)N$(R_{37})_2$, $NR_{37}$C(═O)N$(R_{37})_2$, $NR_{37}$C(═S)N$(R_{37})_2$, C(═O)$R_{37}$, C(═S)$R_{37}$, C(═O)N$(R_{37})_2$, C(═S)N$(R_{37})_2$, C(═O)O—$R_{37}$, C(═O)S—$R_{37}$, C(═S)O—$R_{37}$, C(═S)S—$R_{37}$, $C_1$-$C_6$ alkyl groups, $C_2$-$C_6$ alkenyl groups, $C_2$-$C_6$ alkynyl groups, $C_6$ aryl groups, $C_2$-$C_6$ heteroaryl groups, $C_3$-$C_6$ cycloalkyl groups, $C_5$-$C_6$ cycloalkenyl groups, $C_8$ cycloalkynyl groups, $C_3$-$C_6$ (cyclo)alkyl(hetero)aryl groups, $C_3$-$C_6$ (hetero)aryl(cyclo)alkyl, $C_4$-$C_6$ (cyclo)alkenyl(hetero)aryl groups, $C_4$-$C_6$ (hetero)aryl(cyclo)alkenyl groups, $C_4$-$C_6$ (cyclo)alkynyl(hetero)aryl groups, $C_4$-$C_6$ (hetero)aryl(cyclo)alkynyl groups, $C_4$-$C_6$ alkylcycloalkyl groups, and $C_4$-$C_6$ cycloalkylalkyl groups; the $R_{37}$ groups, alkyl groups, alkenyl groups, alkynyl groups, aryl, heteroaryl, cycloalkyl groups, cycloalkenyl groups, cycloalkynyl groups, (cyclo)alkyl(hetero)aryl groups, (hetero)aryl(cyclo)alkyl groups, (cyclo)alkenyl(hetero)aryl groups, (hetero)aryl(cyclo)alkenyl groups, (cyclo)alkynyl(hetero)aryl groups, (hetero)aryl(cyclo)alkynyl groups, alkylcycloalkyl groups, cycloalkylalkyl groups comprise, are substituted with and/or chelating at least one isotope selected from the group consisting of $^{3}$H, $^{11}$C, $^{13}$N, $^{15}$O, $^{18}$F, $^{19}$F, $^{44}$Sc, $^{51}$Cr, $^{52}$Fe, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{67}$Ga, $^{68}$Ga, $^{70}$As, $^{71}$As, $^{72}$As, $^{74}$As, $^{75}$Se, $^{75}$Br, $^{76}$Br, $^{77}$Br, $^{80}$Br, $^{82}$Br, $^{82}$Rb, $^{86}$Y, $^{88}$Y, $^{89}$Sr, $^{89}$Zr, $^{97}$Ru, $^{99m}$Tc, $^{110}$In, $^{111}$In, $^{113}$In, $^{114}$In, $^{117}$Sn, $^{120}$I, $^{122}$Xe, $^{123}$I, $^{124}$I, $^{125}$I, $^{166}$Ho, $^{167}$Tm, $^{169}$Yb, $^{193}$Pt, $^{195}$Pt, $^{201}$Tl, $^{203}$Pb, $^{24}$Na, $^{32}$P, $^{33}$P, $^{47}$Sc, $^{59}$Fe, $^{67}$Cu, $^{76}$As, $^{77}$As, $^{80}$Br, $^{82}$Br, $^{89}$Sr, $^{90}$Nb, $^{90}$Y, $^{103}$Ru, $^{105}$Rh, $^{109}$Pd, $^{111}$Ag, $^{111}$In, $^{121}$Sn, $^{127}$Te, $^{131}$I, $^{140}$La, $^{141}$Ce, $^{142}$Pr, $^{143}$Pr, $^{144}$Pr, $^{149}$Pm, $^{149}$Tb, $^{151}$Pm, $^{153}$Sm, $^{159}$Gd, $^{161}$Tb, $^{165}$Dy, $^{166}$Dy, $^{166}$Ho, $^{169}$Er, $^{172}$Tm, $^{175}$Yb, $^{177}$Lu, $^{186}$Re, $^{188}$Re, $^{1}$98Au, $^{199}$Au, $^{211}$At, $^{211}$Bi, $^{212}$Bi, $^{212}$Pb, $^{213}$Bi, $^{214}$Bi, $^{223}$Ra, $^{224}$Ra, $^{225}$Ac and $^{227}$Th; and are optionally further substituted with a moiety selected from the group consisting of —Cl, —F, —Br, —I, —$OR_{37}$, —$N(R_{37})_2$, —$SO_3R_{37}$, —$PO_3(R_{37})_2$, —$PO_4(R_{37})_2$, —$NO_2$, —$CF_3$, ═O, ═$NR_{37}$, and —$SR_{37}$, and optionally contain one or more heteroatoms selected from the group consisting of O, S, $NR_{37}$, P, and Si, wherein the N, S, and P atoms are optionally oxidized, wherein the N atoms are optionally quaternized.

In a preferred embodiment the Label is derived from a prosthetic group. The person skilled in the art will understand that a prosthetic group is a precursor that can be radiolabeled with a radionuclide like $^{131}$I thus forming the Label.

In another preferred embodiment, the Label is selected from the group consisting of $C_1$-$C_{12}$ alkyl groups, $C_2$-$C_{12}$ alkenyl groups, $C_2$-$C_{12}$ alkynyl groups, $C_6$-$C_{12}$ aryl groups, $C_2$-$C_{12}$ heteroaryl groups, $C_3$-$C_{12}$ cycloalkyl groups, $C_5$-$C_{12}$ cycloalkenyl groups, $C_{12}$-$C_{12}$ cycloalkynyl groups, $C_3$-$C_{12}$ (cyclo)alkyl(hetero)aryl groups, $C_3$-$C_{12}$ (hetero)aryl(cyclo) alkyl, $C_4$-$C_{12}$ (cyclo)alkenyl(hetero)aryl groups, $C_4$-$C_{12}$ (hetero)aryl(cyclo)alkenyl groups, $C_4$-$C_{12}$ (cyclo)alkynyl (hetero)aryl groups, $C_4$-$C_{12}$ (hetero)aryl(cyclo)alkynyl groups, $C_4$-$C_{12}$ alkylcycloalkyl groups, and $C_4$-$C_{12}$ cycloalkylalkyl groups; said groups comprise, are substituted with, at least one isotope selected from the group consisting of $^{3}$H, $^{11}$C, $^{13}$N, $^{15}$O, $^{18}$F, $^{19}$F, $^{75}$Br, $^{76}$Br, $^{77}$Br, $^{80}$Br, $^{82}$Br, $^{120}$I, $^{123}$I, $^{124}$I, $^{125}$I, $^{32}$P, $^{33}$P, $^{131}$I, $^{211}$At, and are optionally further substituted with a moiety selected from the group consisting of —Cl, —F, —Br, —I, —$OR_{37}$, —$N(R_{37})_2$, —$SO_3R_{37}$, —$PO_3(R_{37})_2$, —$PO_4(R_{37})_2$, —$NO_2$, —$CF_3$, =O, =$NR_{37}$, and —$SR_{37}$, and optionally contain one or more heteroatoms selected from the group consisting of O, S, $NR_{37}$, P, and Si, wherein the N, S, and P atoms are optionally oxidized, wherein the N atoms are optionally quaternized.

In a preferred embodiment the Label comprises a chelating moiety. In a preferred embodiment, the Label is a chelating moiety selected from the group consisting of conjugates of DTPA (diethylenetriaminepentaacetic acid), DOTA (1,4,7,10-tetraazacyclododecane-N,N',N",N"-tetraacetic acid), DOTAGA anhydride (2,2',2"-(10-(2,6-dioxotetrahydro-2H-pyran-3-yl)-1,4,7,10-tetraazacyclododecane-1,4,7-triyl)triacetic acid), NOTA (1,4,7-triazacyclononane-N,N',N"-triacetic acid), TETA (1,4,8,11-tetraazacyclo tetradecane-N,N',N",N'-tetraacetic acid), OTTA (N1-(p-isothiocyanatobenzyl)-diethylenetriamine-$N_1$,$N_2$,$N_3$,$N_3$-tetra acetic acid), deferoxamine or DFO (N'-[5-[[4-[[5-(acetylhydroxyamino)pentyl]amino]-1,4-dioxobutyl]hydroxyamino] pentyl]-N-(5-aminopentyl)-N-hydroxybutanediamide), and the DFO derivative called DFO*, and HYNIC (hydrazinonicotinamide); and the chelating moiety chelates a metal selected from the group consisting of $^{44}$Sc, $^{51}$Cr, $^{52}$Fe, $^{52}$Mn, $^{55}$Co, $^{60}$Cu, $^{61}$Cu, $^{62}$Zn, $^{62}$Cu, $^{63}$Zn, $^{64}$Cu, $^{66}$Ga, $^{67}$Ga, $^{68}$Ga, $^{70}$As, $^{71}$As, $^{72}$As, $^{74}$As, $^{75}$Se, $^{82}$Rb, $^{86}$Y, $^{88}$Y, $^{89}$Sr, $^{89}$Zr, $^{97}$Ru, $^{99m}$Tc, $^{110}$In, $^{111}$In, $^{113}$In, $^{114}$In, $^{117}$Sn, $^{122}$Xe, $^{166}$Ho, $^{167}$Tm, $^{169}$Yb, $^{193}$Pt, $^{195}$Pt, $^{201}$Tl, $^{203}$Pb, $^{24}$Na, $^{47}$Sc, $^{59}$Fe, $^{67}$Cu, $^{76}$As, $^{77}$As, $^{89}$Sr, $^{90}$Nb, $^{90}$Y, $^{103}$Ru, $^{105}$Rh, $^{109}$Pd, $^{111}$Ag, $^{111}$In, $^{121}$Sn, $^{127}$Te, $^{140}$La, $^{141}$Ce, $^{142}$Pr, $^{143}$Pr, $^{144}$Pr, $^{149}$Pm, $^{149}$Tb, $^{151}$Pm, $^{153}$Sm, $^{159}$Gd, $^{161}$Tb, $^{165}$Dy, $^{166}$Dy, $^{166}$Ho, $^{169}$Er, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{212}$Pb, $^{213}$Bi, $^{214}$Bi, $^{223}$Ra, $^{224}$Ra, $^{225}$Ac and $^{227}$Th.

In a preferred embodiment the metal chelate comprises an acyclic derivative of ethylenediaminotetraacetic acid (EDTA) or diethylenediaminotetraacetic acid (DTPA):

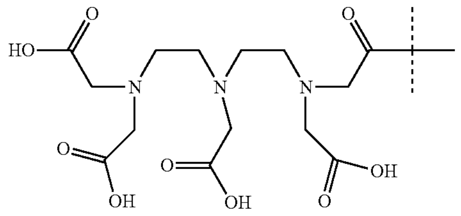

-continued

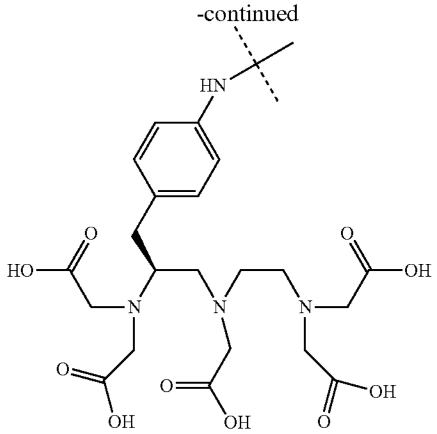

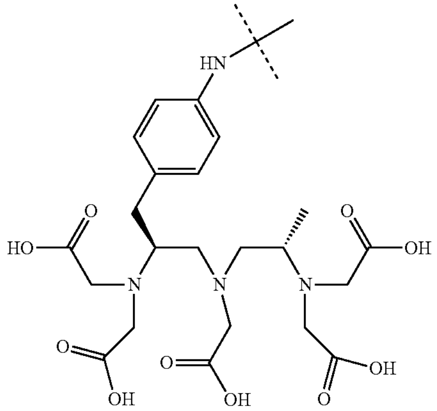

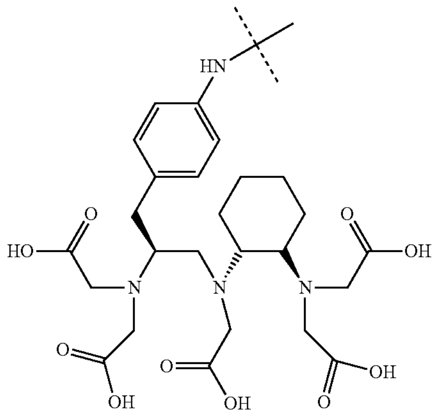

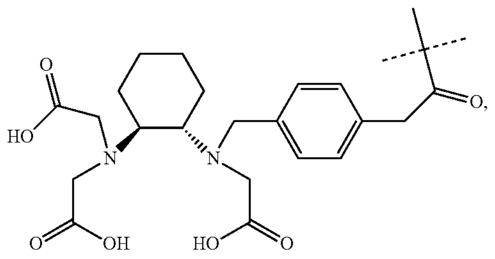

wherein the dashed line denotes a bond to the rest of the molecule.

In another preferred embodiment the metal chelate comprises an acyclic chelator containing carboxy-pyridine groups:

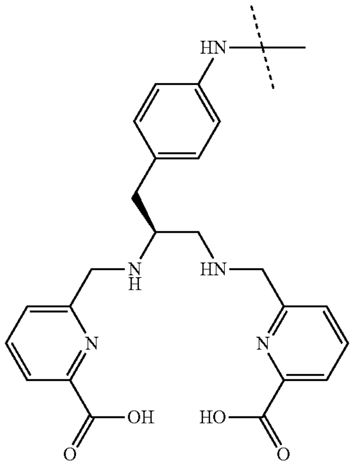
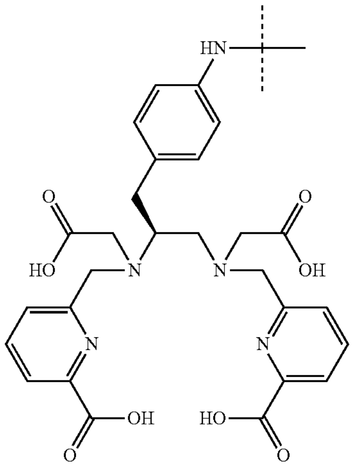
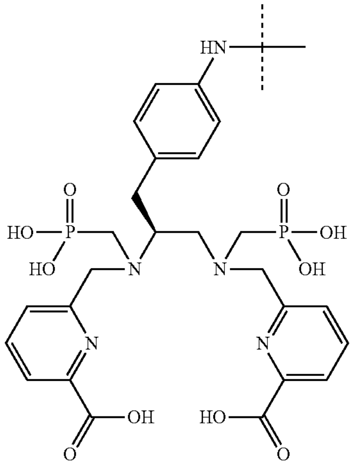
-continued
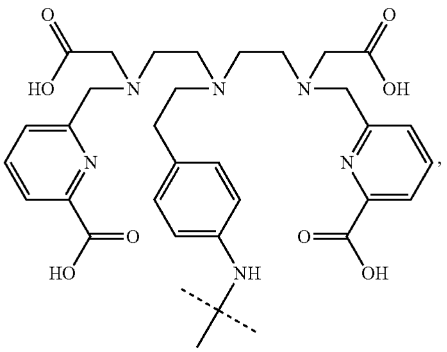
wherein the dashed line denotes a bond to the rest of the molecule.
In another preferred embodiment the metal chelate comprises a cyclic derivative of 1,4,7,10-tetraazadodecane (cyclen):
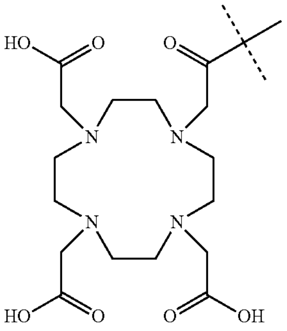
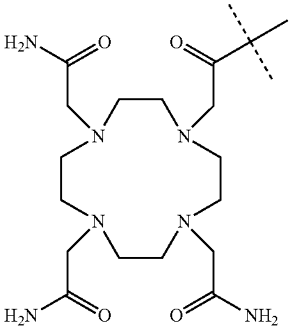
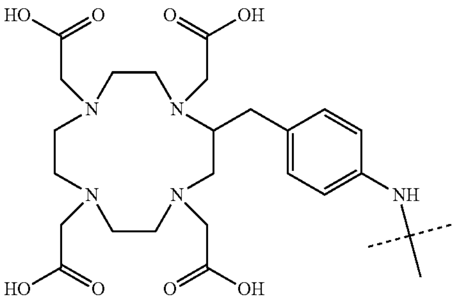

-continued
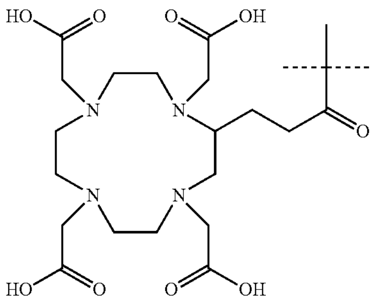
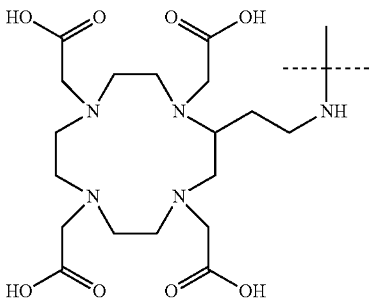
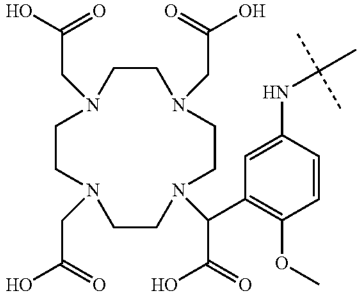
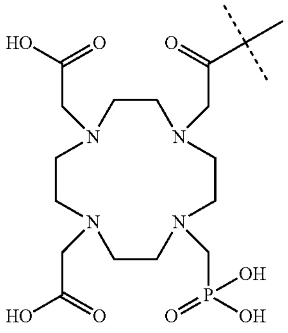
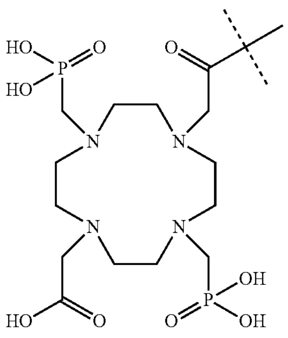
-continued
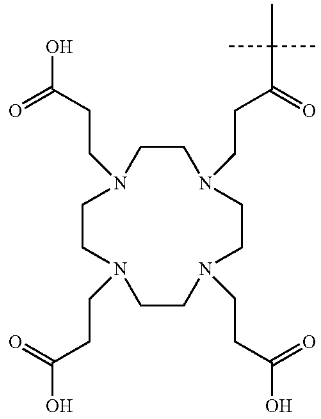
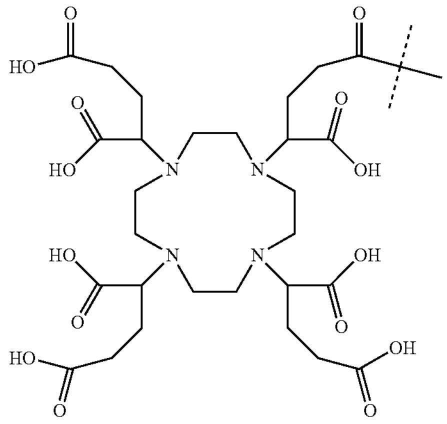
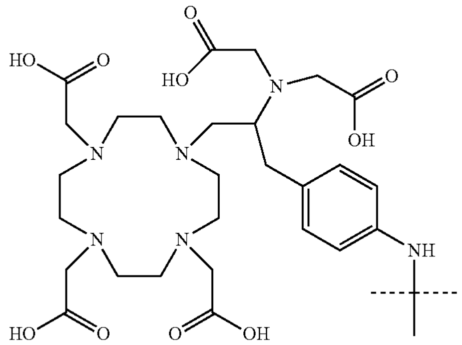
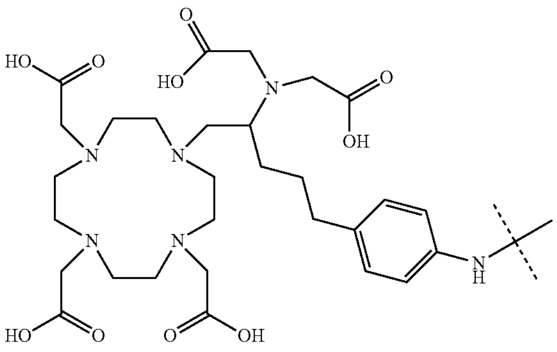

-continued
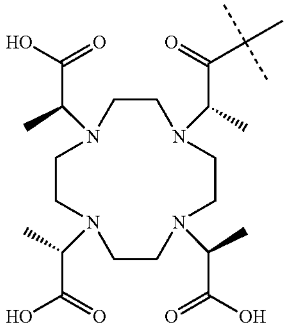
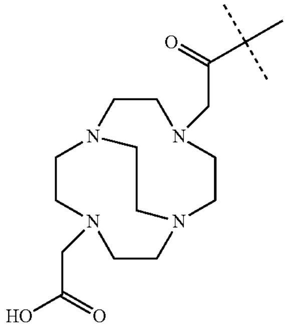
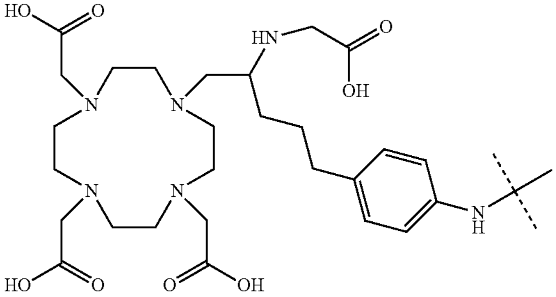
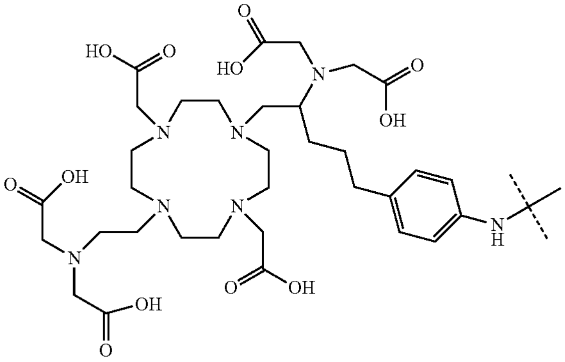
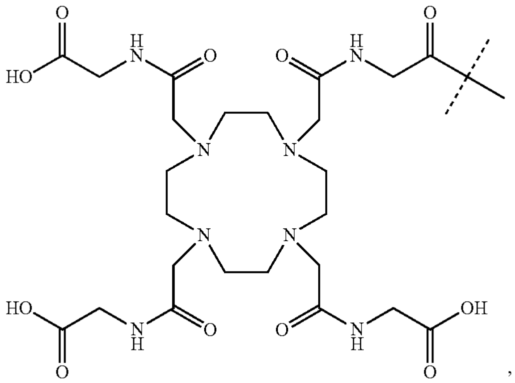
,
wherein the dashed line denotes a bond to the rest of the molecule.
In another preferred embodiment the metal chelate comprises a derivative of 1,4,7-triazacyclononane (TACN):
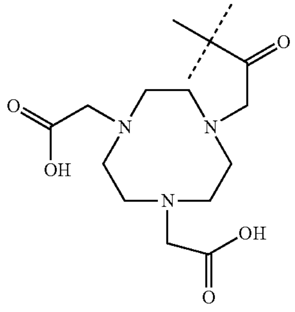
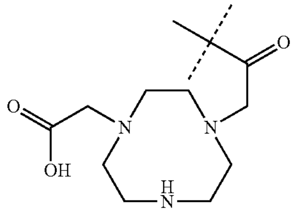
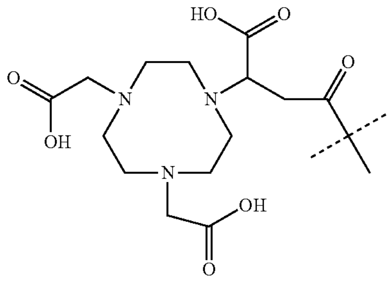
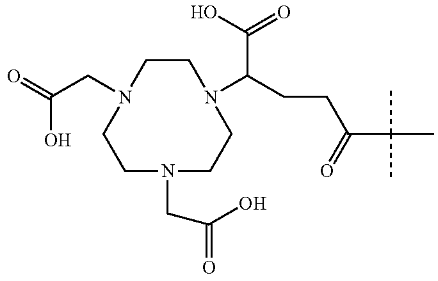
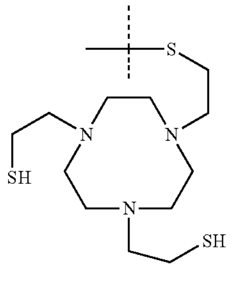

-continued
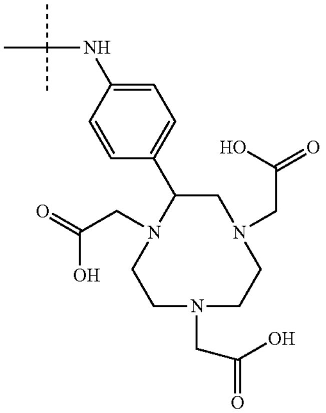
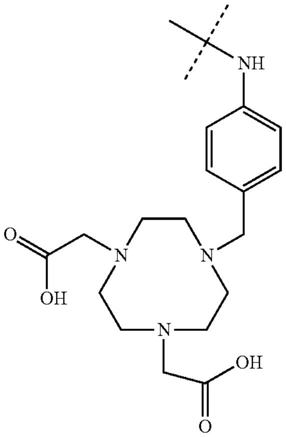
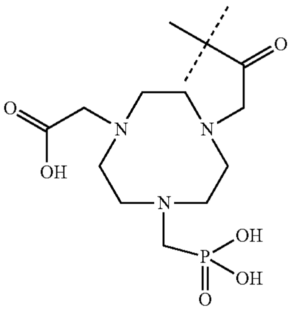
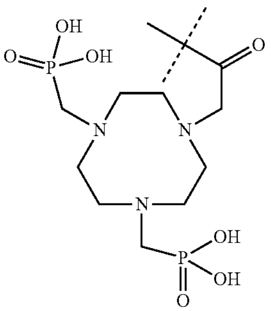
-continued
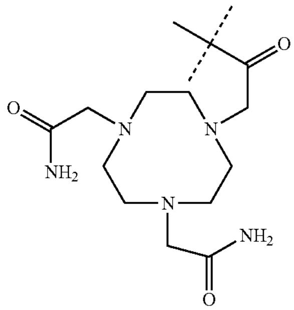
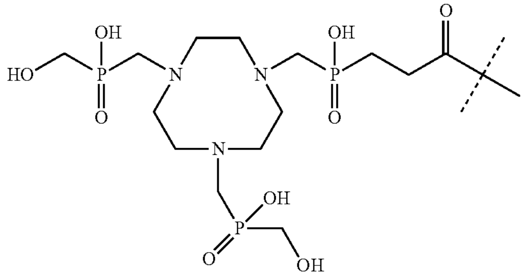
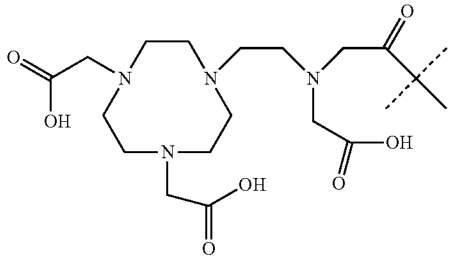
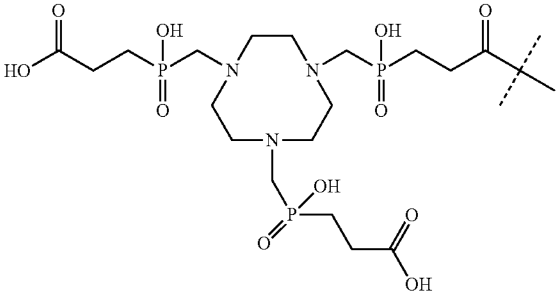
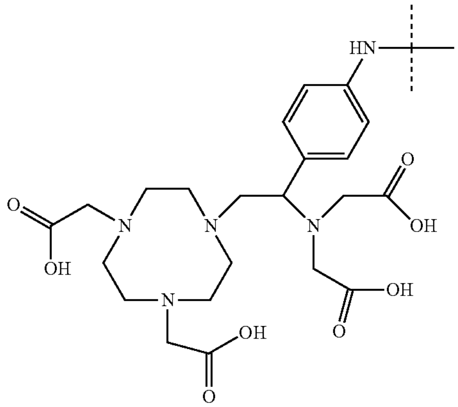

-continued
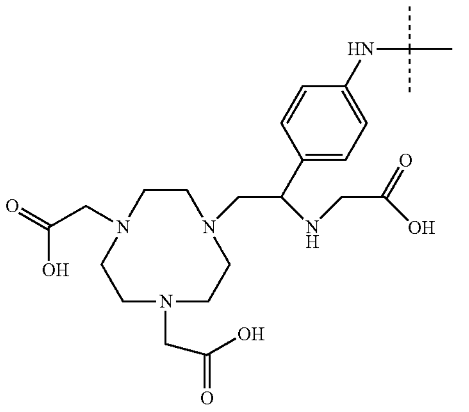
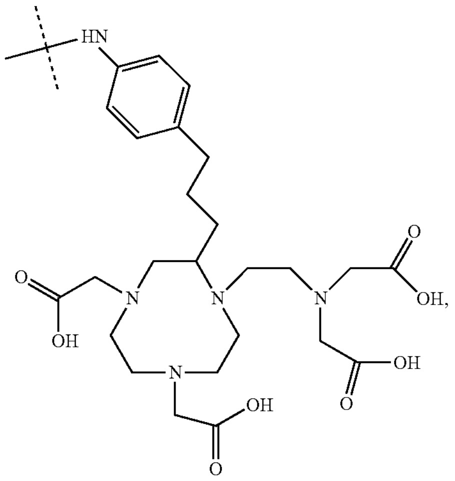
wherein the dashed line denotes a bond to the rest of the molecule.
In yet another preferred embodiment the metal chelate comprises a macrocyclic chelator containing N and O heteroatoms:
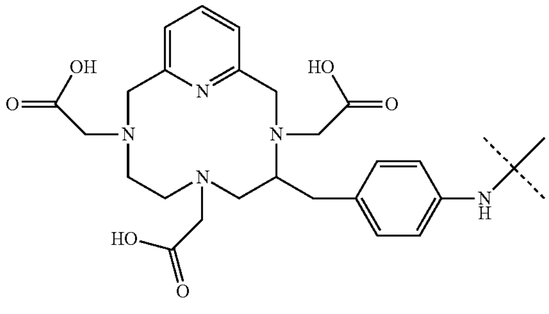
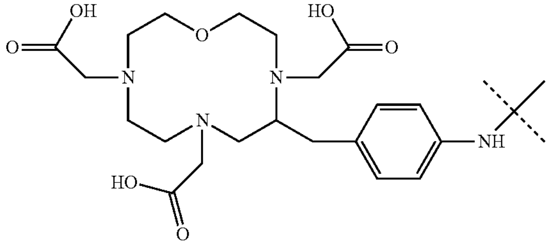
-continued
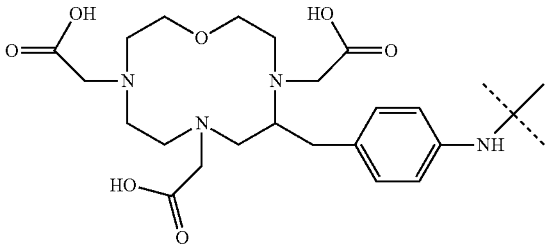
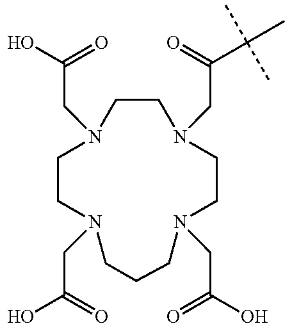
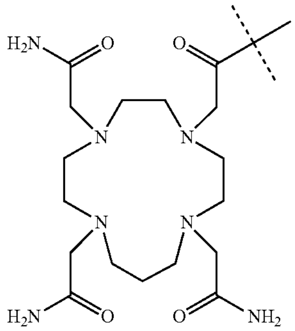
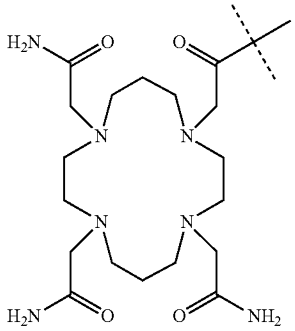
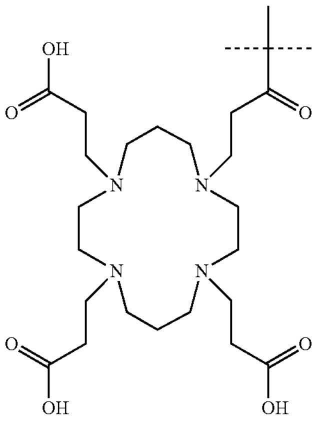

-continued
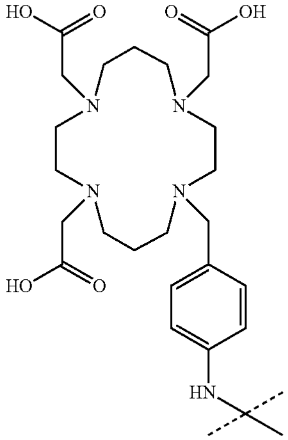
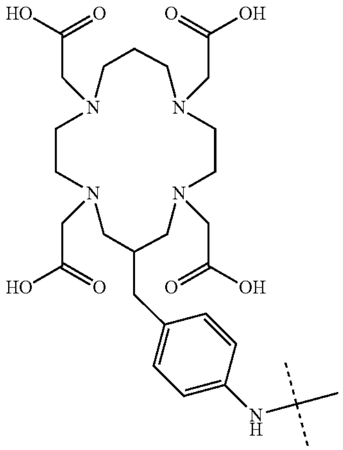
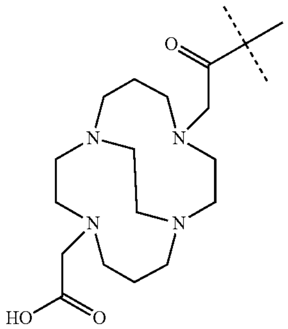
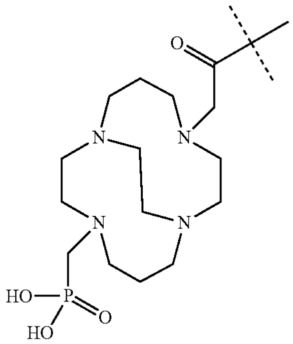
-continued
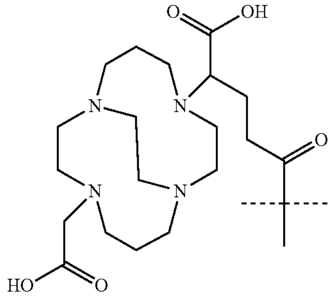
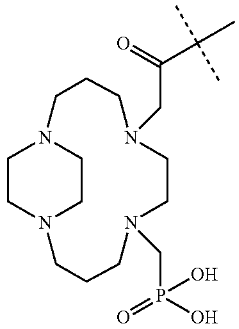
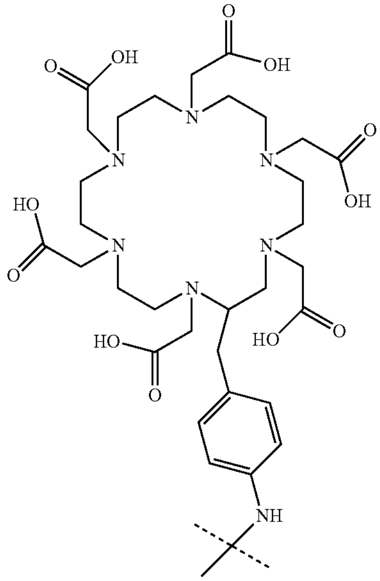
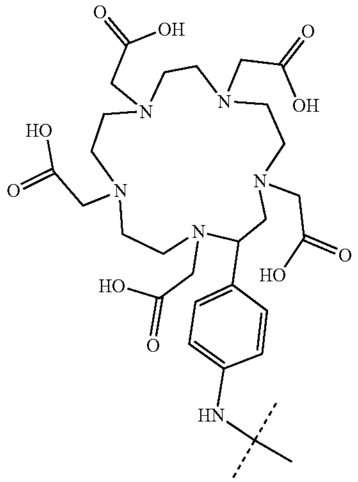

-continued

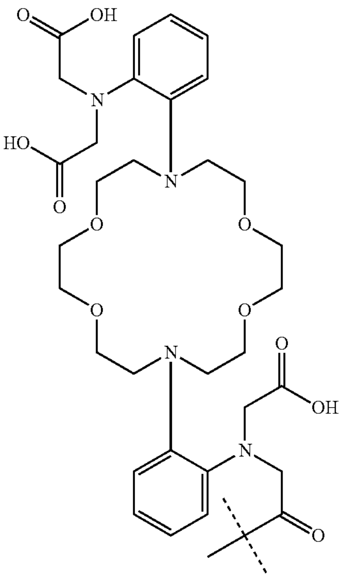

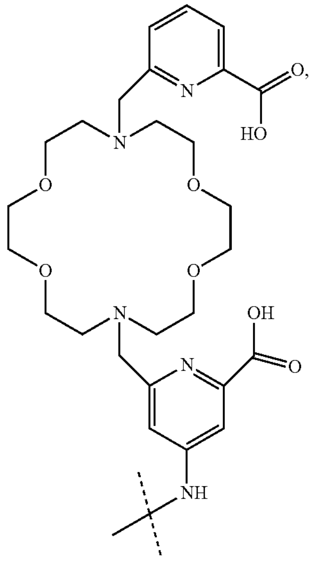

wherein the dashed line denotes a bond to the rest of the molecule.

In another preferred embodiment the metal chelate comprises a derivative of the cryptand agent sarcophagine (Sar):

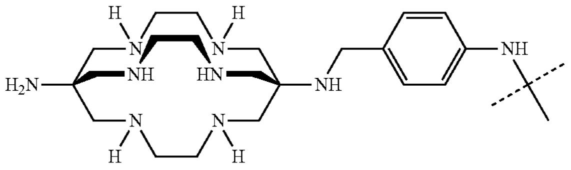

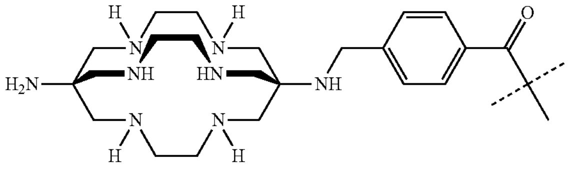

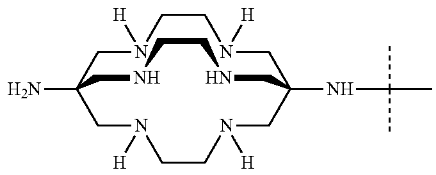

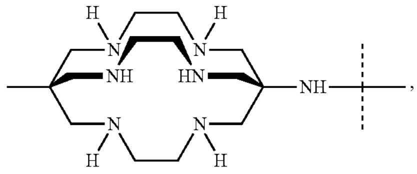

, wherein the dashed line denotes a bond to the rest of the molecule.

In another preferred embodiment the metal chelate comprises a linear or cyclic chelator containing hydroxamate groups:

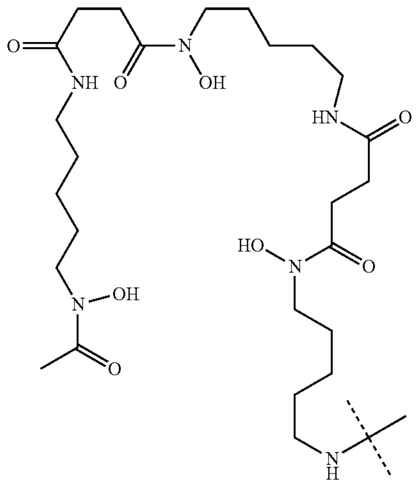

-continued

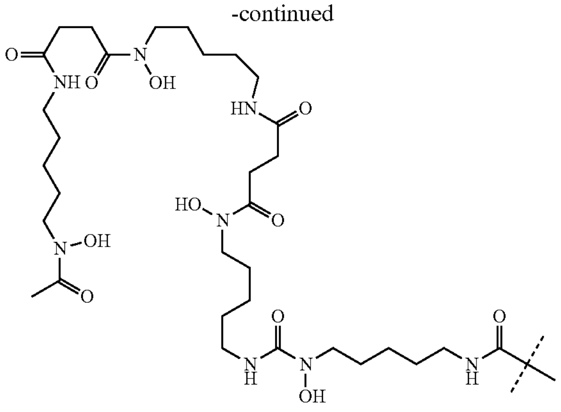

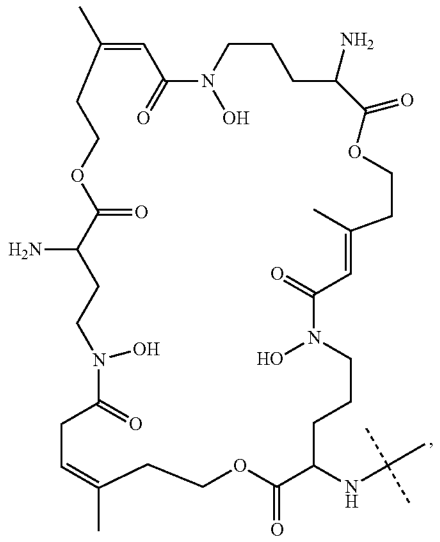

wherein the dashed line denotes a bond to the rest of the molecule.

In yet another preferred embodiment the metal chelate comprises a linear or cyclic chelator containing 3-hydroxy-4-pyridinone (3,4-HOPO) groups and derivatives:

wherein the dashed line denotes a bond to the rest of the molecule.

In another preferred embodiment the metal chelate comprises a linear or cyclic chelator containing N, S and P heteroatoms:

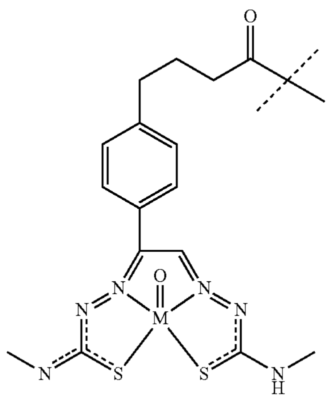

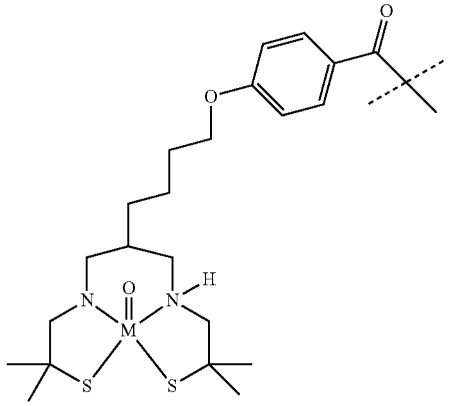

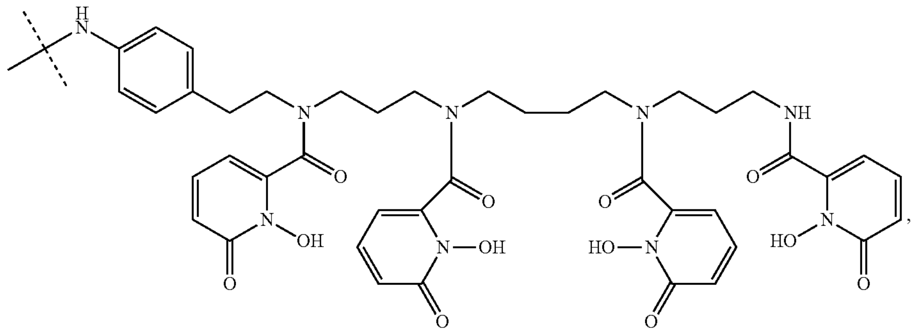

-continued
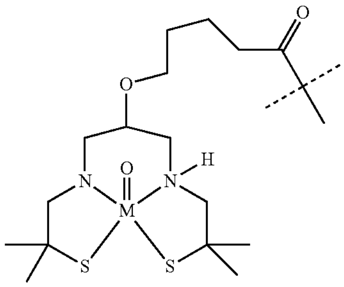
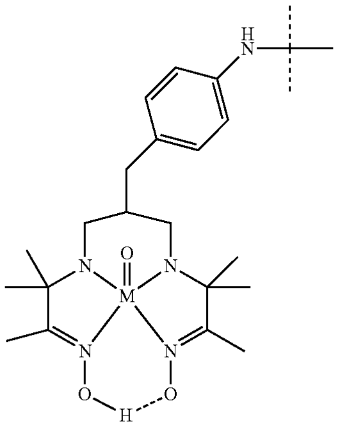
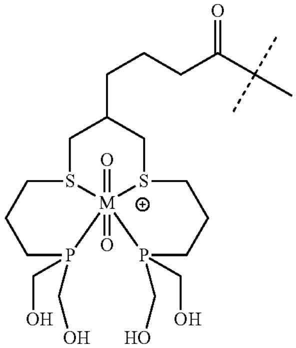
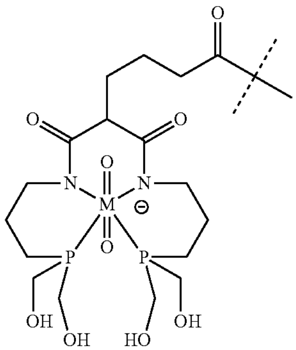
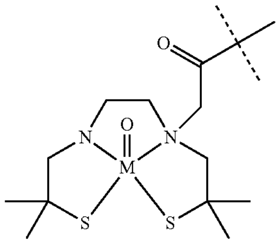
-continued
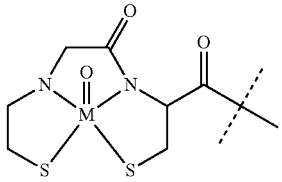
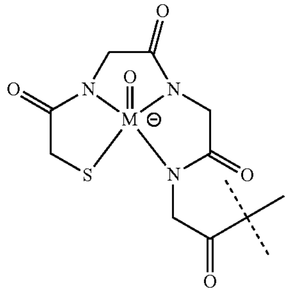
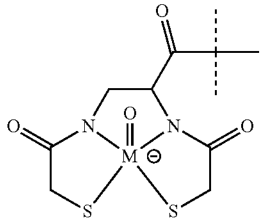
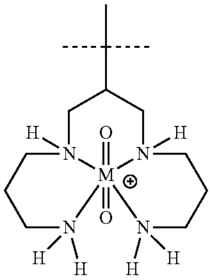
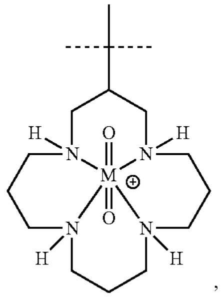
,
wherein the dashed line denotes a bond to the rest of the molecule M denotes a radionuclide selected from the group consisting of $^{99m}$Tc, $^{186}$Re, and $^{188}$Re.
In another preferred embodiment the metal chelate comprises glycine, serine, cysteine, lysine and alanine residues:
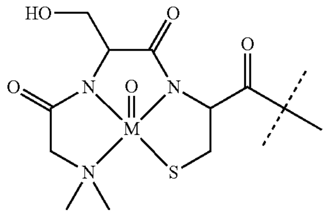
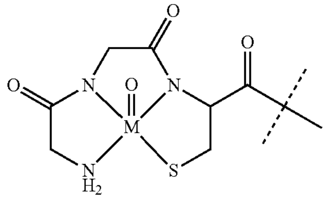

-continued
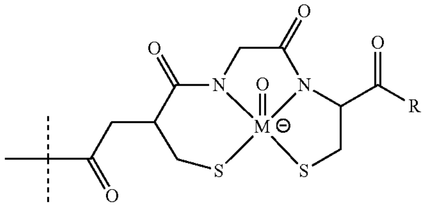
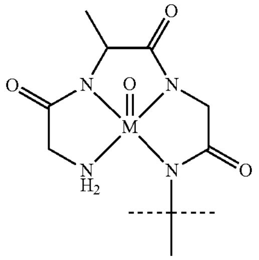
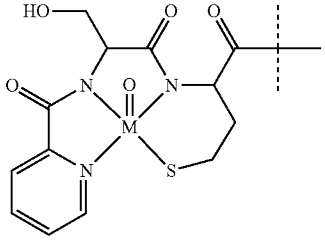
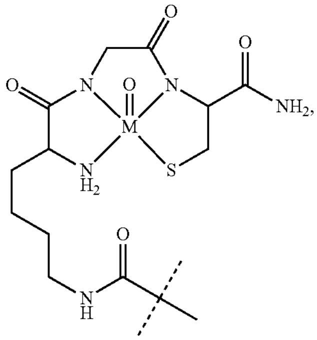
wherein the dashed line denotes a bond to the rest of the molecule M denotes a radionuclide selected from the group consisting of $^{99m}$Tc, $^{186}$Re, and $^{188}$Re.
In another preferred embodiment the metal chelate contains hydrazinonicotinic acid derivatives (HYNIC) and a co-ligand:
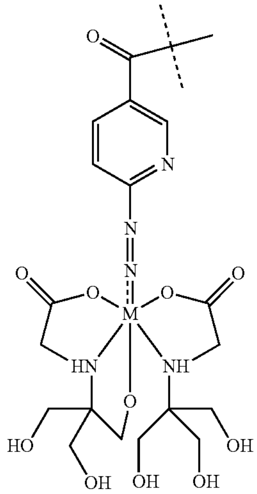
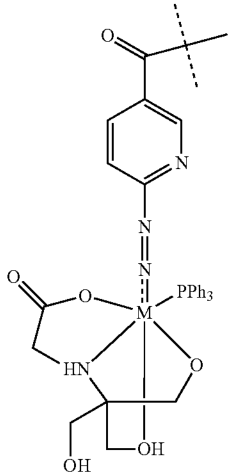
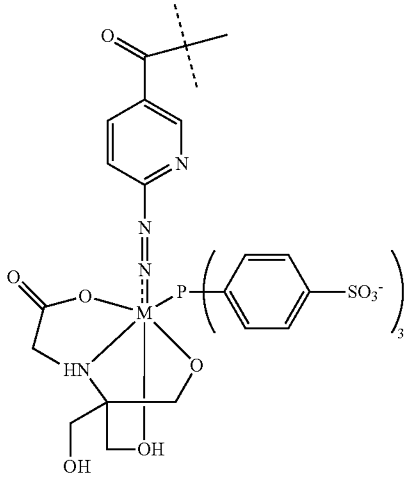

-continued
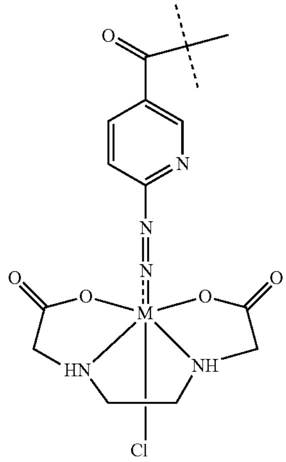
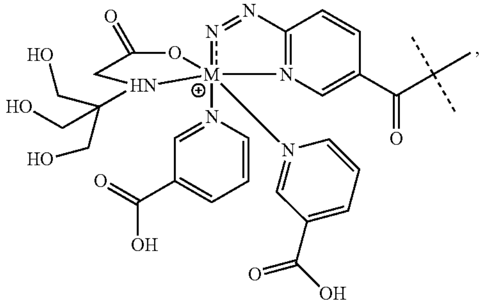
wherein the dashed line denotes a bond to the rest of the molecule M denotes a radionuclide selected from the group consisting of $^{99m}$Tc, $^{186}$Re, and $^{188}$Re.
In another preferred embodiment the chelate comprises carbonyl groups and a chelator containing N, O and S heteroatoms or a cyclopentadienyle:
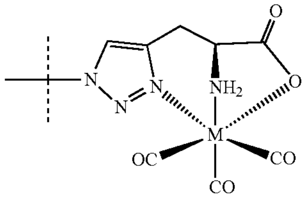
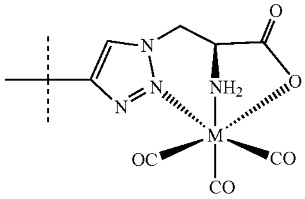
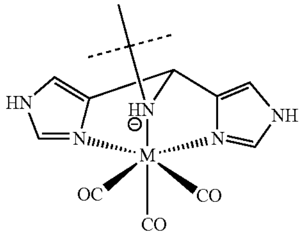
-continued
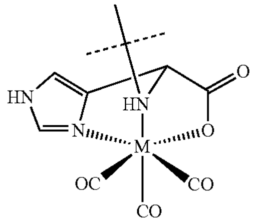
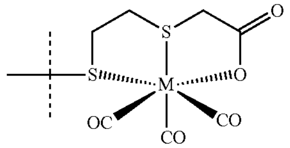
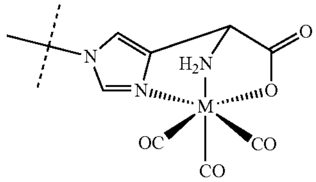
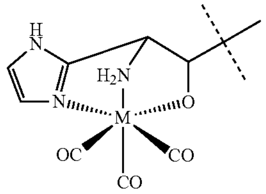
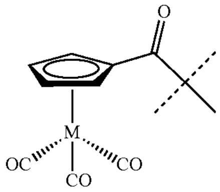
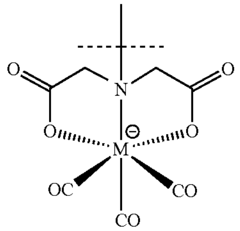
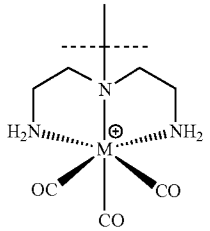
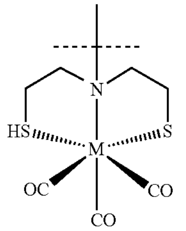
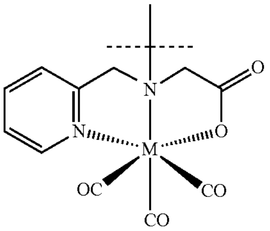
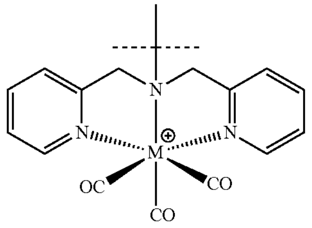
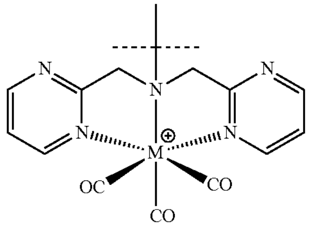

-continued

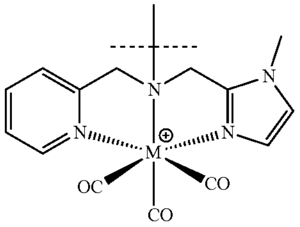

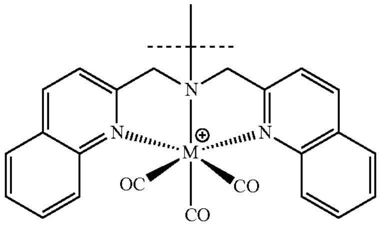

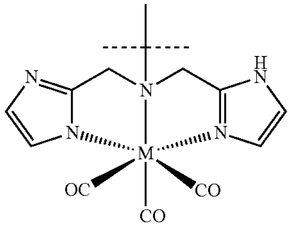

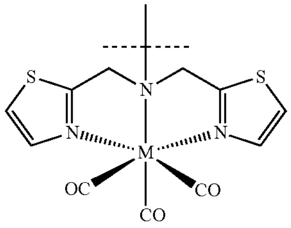

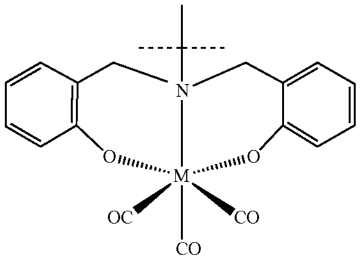

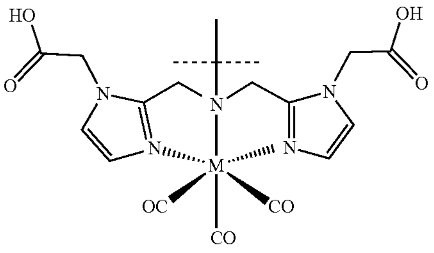

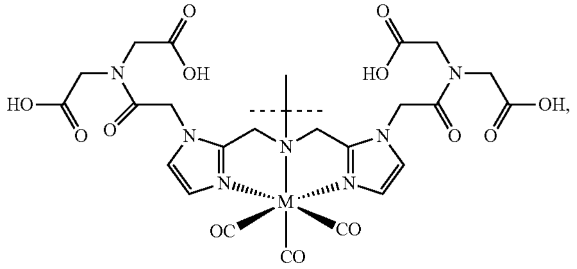

wherein the dashed line denotes a bond to the rest of the molecule M denotes a radionuclide selected from the group consisting of $^{99m}$Tc, $^{186}$Re, and $^{188}$Re.

In some preferred embodiments of the present invention the label contains $^{18}$F and can be produced by the skilled person on the basis of known synthesis routes using known labeled synthons or prosthetic groups. Several non limiting examples of $^{18}$F-containing labels are depicted below:

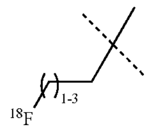

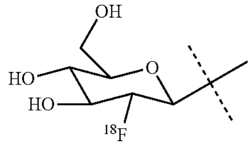

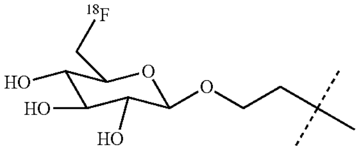

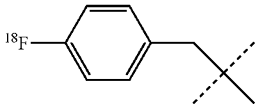

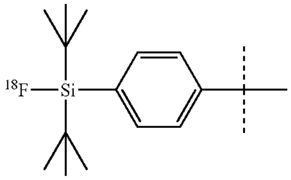

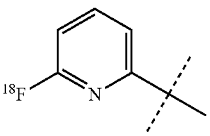

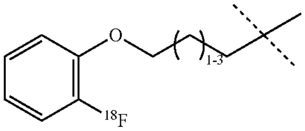

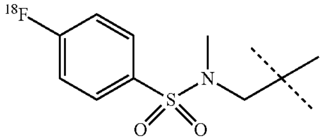

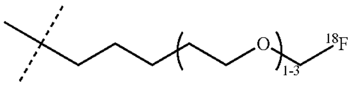

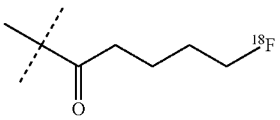

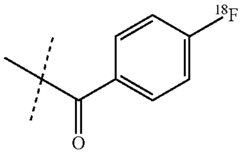

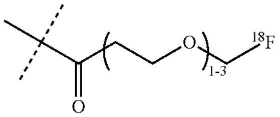

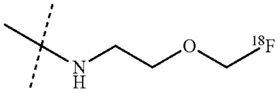

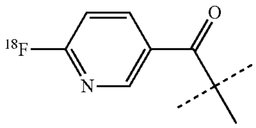

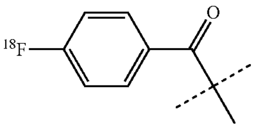

-continued
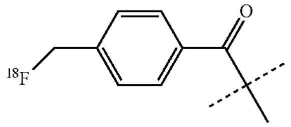
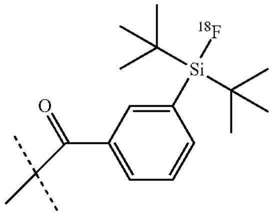
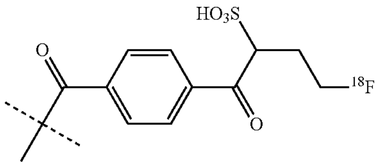
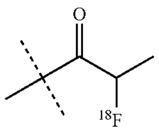
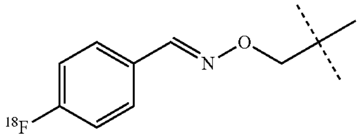
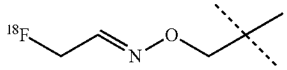
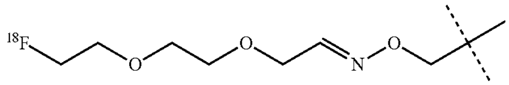
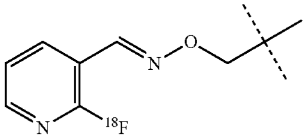
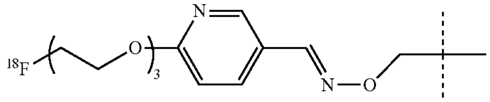
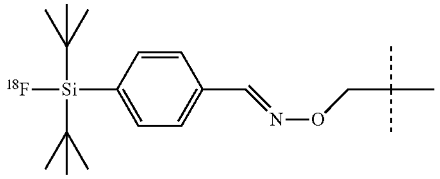
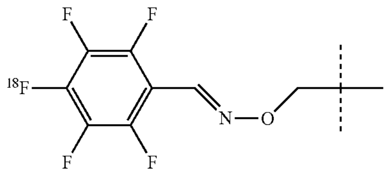
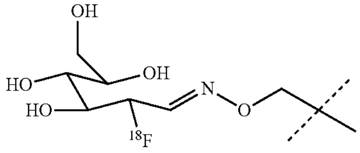
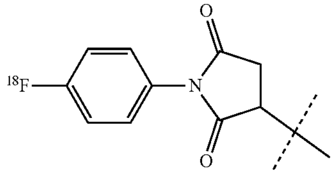
-continued
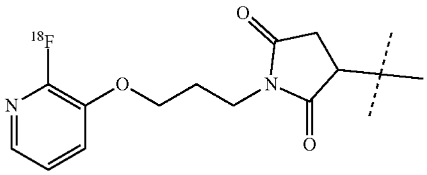
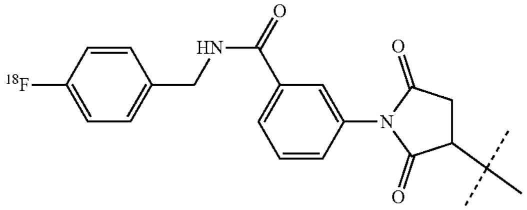
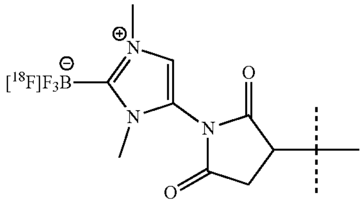
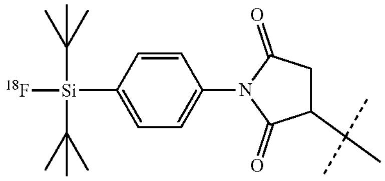
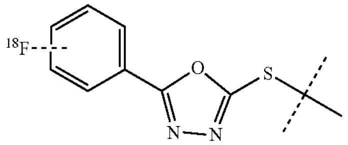
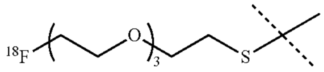
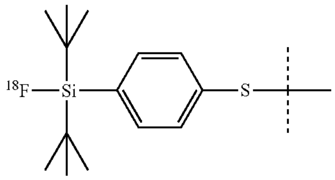
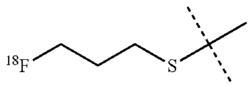
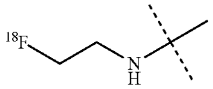
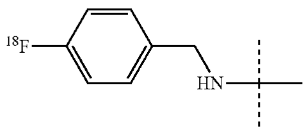
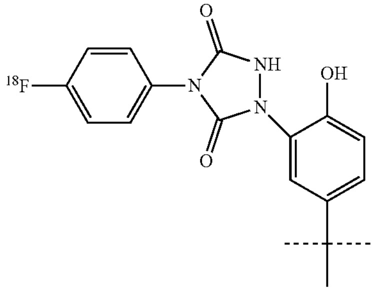

-continued

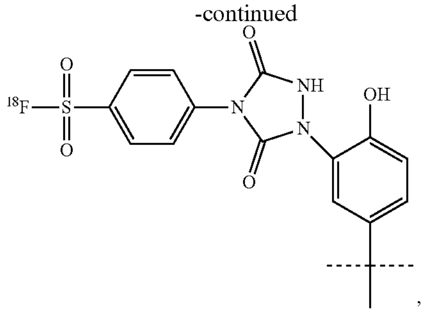

wherein the dashed line denotes a bond to the rest of the molecule.

In preferred embodiments of the present invention the label contains at least one isotope selected from the group consisting of $^{123}I$, $^{124}I$, $^{125}I$, $^{131}I$, and $^{211}At$; and is synthesized by the skilled person on the basis of known synthesis routes using prosthetic groups. Several preferred embodiments of such labels are depicted below:

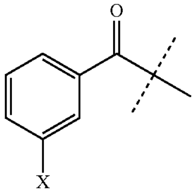
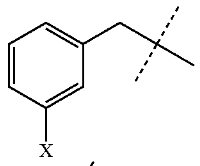
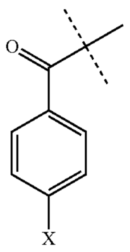
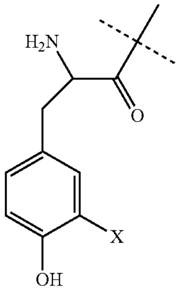
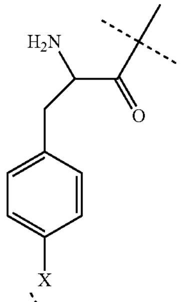
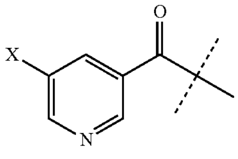
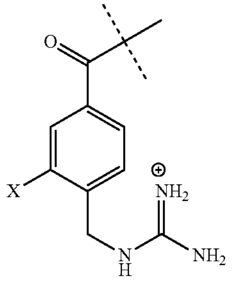
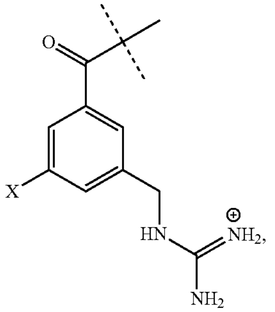

wherein the dashed line denotes a bond to the rest of the molecule and X denotes $^{123}I$, $^{124}I$, $^{125}I$, $^{131}I$ or $^{211}At$.

In yet another preferred embodiment of the present invention the label contains at least one isotope selected from the group consisting of $^{123}I$, $^{124}I$, $^{125}I$, $^{131}I$, and $^{211}At$; and is synthetized by the skilled person on the basis of known synthesis routes using a closo-decaborate(2-) group:

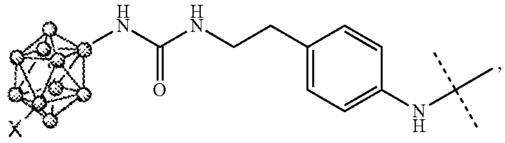

wherein the dashed line denotes a bond to the rest of the molecule and X denotes $^{123}I$, $^{124}I$, $^{125}I$, $^{131}I$ or $^{211}At$.

Administration Agent

The Administration Agent can be any construct of which it is desired to modify it with a Label for imaging or radiotherapy and of which it is desired to remove its imaging or radiotherapy label at a particular time after injection. This particularly is the case in the event of targeted imaging and radiotherapy to a site, such as a tumor, within the body of a subject, notably a human subject. The sole requirement is that it can be provided with a Trigger $T^R$, which is further linker to a Label. The precise linkage of the Trigger to the Administration Agent will depend on the molecular structure of both, but it should be noted that this does not normally present a particular challenge to the person skilled in the art, as many proven conjugation methods and linkage moieties for various biomolecules exist. The linkage can, optionally, be via a spacer such as a polyethylene glycol (PEG) chain.

Typically the Administration Agent can bind to a Primary Target, as defined herein. Said Primary Target can be a target to which a Targeting Agent binds or it can be a therapeutic target upon which a drug has its effect. In a preferred embodiment the Primary Target is a therapeutic target and the Targeting Agent is a drug and binds said Primary Target.

In preferred embodiments, the Administration Agent is a Targeting Agent as defined herein.

Preferably, the Administration Agent is selected from the group consisting of proteins, peptoids and peptides. Most preferably, the Administration Agent is an antibody.

In another preferred embodiment, the Administration Agent is selected from the group consisting of antibodies, antibody-drug conjugates, antibody derivatives, antibody fragments, proteins, polymers, polymer-drug conjugates, drug containing liposomes and polymersomes, nanoparticles, microparticles, aptamers, oligopeptides, oligonucleotides, oligosaccharides, carbohydrates, as well as peptides, peptoids, steroids, toxins, hormones, cytokines, and chemokines.

In other preferred embodiments, the Administration Agent equals a Targeting Agent, and the Targeting Agent is radiolabeled with a therapeutic radioisotope in order to target therapeutic radiation to tissues expressing a Primary Target.

In other preferred embodiments, the Administration Agent equals a Targeting Agent, and the Targeting Agent is radiolabeled with a diagnostic radioisotope in order to image tissues expressing a Primary Target.

In preferred embodiments, the Administration Agent is an antibody, more preferably an antibody that comprises an FcRn binding domain, more preferably an intact IgG antibody.

In other preferred embodiments, the Administration Agent is an antibody that comprises an albumin-binding moiety. In other preferred embodiments, the Administration Agent is a protein that comprises an albumin-binding moiety. In other preferred embodiments the Administration Agent equals a drug. In other preferred embodiments the Administration Agent equals a drug and the drug is labeled using the presented invention for the purpose of imaging in vivo drug distribution.

Drugs that can be used in an Administration Agent relevant to this invention are pharmaceutically active compounds, such as antibodies, antibody-drug conjugates, antibody derivatives, antibody fragments, proteins, biomolecules, polymer-drug conjugates, drug containing liposomes and polymersomes, aptamers, oligopeptides, oligonucleotides, oligosaccharides, carbohydrates, as well as peptides, peptoids, steroids, toxins, hormones, cytokines, and chemokines. Other drugs that can be used are low to medium molecular weight compounds, preferably organic compounds, (e.g. about 200 to about 2500 Da, preferably about 300 to about 1750 Da, more preferably about 300 to about 1000 Da).

In a preferred embodiment the pharmaceutically active compound or drug is selected from the group consisting of cytotoxins, antiproliferative/antitumor agents, antiviral agents, antibiotics, anti-inflammatory agents, chemosensitizing agents, radiosensitizing agents, immunomodulators, immunosuppressants, immunostimulants, anti-angiogenic factors, and enzyme inhibitors.

In other preferred embodiments the drug is designed to act in the central neural system, for example in the context of Alzheimer's disease and Parkinsons' disease, for example antibodies against beta-amyloid and Tau proteins.

Exemplary cytotoxic drug types, for example for use in cancer therapy, include but are not limited to DNA damaging agents, DNA crosslinkers, DNA binders, DNA alkylators, DNA intercalators, DNA cleavers, microtubule stabilizing and destabilizing agents, topoisomerases inhibitors, radiation sensitizers, anti-metabolites, natural products and their analogs, peptides, oligonucleotides, enzyme inhibitors such as dihydrofolate reductase inhibitors and thymidylate synthase inhibitors.

Exemplary immunemodulators are antibodies against PD-L1, PD-1, LAG-3, OX40, TIGIT, TIM-3, B7H4, Vista, CTLA-4, APRIL, cytokines, including IL-2, IL-7, IL-10, IL-12, IL-15, IL-21, TNF, interferon gamma, GMCSF, NDV-GMCSF, and agonists and antagonists of STING, agonists and antagonists of TLRs including TLR1/2, TLR3, TLR4, TLR7/8, TLR9, TLR12, agonists and antagonists of GITR, CD3, CD28, CD40, CD74, CTLA4, OX40, PD1, PDL1, RIG, MDA-5, NLRP1, NLRP3, AIM2, IDO, MEK, cGAS, and CD25, NKG2A.

It will be understood that chemical modifications may also be made to the Administration Agent in order to make reactions of that compound more convenient for purposes of preparing conjugates of the invention.

In a preferred embodiment, the Administration Agent before conjugation to the remainder of the compound of Formula (19) comprises at least one moiety selected from the group consisting of —OH, —NHR', —$CO_2H$, —SH, —S—S—, —$SCH_3$— —$N_3$, terminal alkynyl, terminal alkenyl, —C(O)R', $C_8$-$C_{12}$ (hetero)cycloalkynyl, nitrone, nitrile oxide, (imino)sydnone, isonitrille, and (oxa)norbornene, tetrazine, wherein R' equals $R_{37}$, said moiety used for conjugation to a moiety comprising the dienophile, the Label and $R_{32}$ so as to form the compound satisfying Formula (19), and comprising a $C^{M2}$ or $C^X$ moiety.

In preferred embodiments the Administration Agent is bound to the remainder of the compound of Formula (19) via a $C^{M2}$ selected from the group consisting of amine, amide, thioamide, aminooxy, carbamate, thiocarbamate, urea, thiourea, sulfonamide, and sulfoncarbamate. In preferred embodiments $C^{M2}$ equals $R_{10}$ as defined herein. Preferably, the Administration Agent is coupled as described above in relation to $C^{M2}$ and $C^X$.

Preferably, the Administration Agent, preferably an antibody, is modified with further moieties that equal Formula (19), except that these further moieties do not comprise an Administration Agent (as the first mentioned Administration Agent is already coupled to said moiety). In a preferred embodiment, the Administration Agent, preferably an antibody, is coupled to further moieties as defined in this paragraph at 1 to 8 positions, more preferably from 1 to 6 positions, even more preferably at 1 to 4 positions.

Further Embodiments in Relation to the Compound of Formula (19)

In a preferred embodiment, in the compound of the invention the Administration Agent comprises an antibody, and preferably the Administration Agent is an antibody.

In a preferred embodiment, in the compound of the invention the Label is a radiolabel, preferably a chelating moiety that chelates a radioisotope.

Diene

The combinations according to the invention comprise a compound according to Formula (19) and a diene, preferably a tetrazine. In a preferred embodiment, the combination is in the form of a kit.

The tetrazine compound according to the invention may herein be referred to as "Activator". The tetrazine typically reacts with the other Bio-orthogonal Reactive Group, that is a dienophile (vide supra). The diene of the Activator is selected so as to be capable of reacting with the dienophile of the TCO by undergoing a Diels-Alder cycloaddition followed by a retro Diels-Alder reaction, giving the IEDDA adduct. This intermediate adduct then releases the Construct-A, where this release can be caused by various circumstances or conditions that relate to the specific molecular structure of the IEDDA adduct.

The compound used to release one or more moieties $R_{48}$ from the structure of Formula (19) is herein referred to as Activator.

In a preferred embodiment, the Activator is a tetrazine. Tetrazines are dienes and are highly reactive towards dienophiles, especially the TCO constructs (vide supra). The diene of the Activator is selected so as to be capable of reacting with the dienophile, e.g. the TCO, by undergoing a Diels-Alder cycloaddition followed by a retro Diels-Alder reaction, giving the IEDDA adduct. This intermediate adduct then releases the Construct-A. Synthesis routes to tetrazines in general are readily available to the skilled person, based on standard knowledge in the art. References to tetrazine synthesis routes include for example Lions et al, *J. Org. Chem.*, 1965, 30, 318-319; Horwitz et al, *J. Am. Chem. Soc.*, 1958, 80, 3155-3159; Hapiot et al, *New J. Chem.*, 2004, 28, 387-392, Kaim et al, *Z. Naturforsch.*, 1995, 50b, 123-127; Yang et al., *Angew. Chem.* 2012, 124, 5312-5315; Mao et al., *Angew. Chem. Int. Ed.* 2019, 58, 1106-1109; Qu et al. *Angew. Chem. Int. Ed.* 2018, 57, 12057-12061; Selvaraj et al., *Tetrahedron Lett.* 2014, 55, 4795-4797; Fan et al., *Angew. Chem. Int. Ed.* 2016, 55, 14046-14050.

Preferably, the Activator is a tetrazine satisfying Formula (4) and preferably including pharmaceutically accepted salts thereof:

Formula (4)

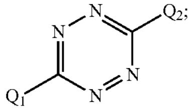

wherein each moiety $Q_1$ and $Q_2$ is independently selected from the group consisting of hydrogen, —F, —Cl, —Br, —I, —$OR_{37}$, —$N(R_{37})_2$, —$SO_3$, —$PO_3$—, —$NO_2$, —$CF_3$, —$SR_{37}$, $S(=O)_2N(R_{37})_2$, $OC(=O)R_{37}$, $SC(=O)R_{37}$, $OC(=S)R_{37}$, $SC(=S)R_{37}$, $NR_{37}C(=O)—R_{37}$, $NR_{37}C(=S)—R_{37}$, $NR_{37}C(=O)O—R_{37}$, $NR_{37}C(=S)O—R_{37}$, $NR_{37}C(=O)S—R_{37}$, $NR_{37}C(=S)S—R_{37}$, $OC(=O)N(R_{37})_2$, $SC(=O)N(R_{37})_2$, $OC(=S)N(R_{37})_2$, $SC(=S)N(R_{37})_2$, $NR_{37}C(=O)N(R_{37})_2$, $NR_{37}C(=S)N(R_{37})_2$, $C(=O)R_{37}$, $C(=S)R_{37}$, $C(=O)N(R_{37})_2$, $C(=S)N(R_{37})_2$, $C(=O)O—R_{37}$, $C(=O)S—R_{37}$, $C(=S)O—R_{37}$, $C(=S)S—R_{37}$, $S(O)R_{37}$, —$S(O)_2R_{37}$, $NR_{37}S(O)_2R_{37}$, —$ON(R_{37})_2$, —$NR_{37}OR_{37}$, alkyl groups, alkenyl groups, alkynyl groups, aryl groups, heteroaryl groups, cycloalkyl groups, cycloalkenyl groups, cycloalkynyl groups, (cyclo)alkyl(hetero)aryl groups, (hetero)aryl(cyclo)alkyl, (cyclo)alkenyl(hetero)aryl groups, (hetero)aryl(cyclo)alkenyl groups, (cyclo)alkynyl (hetero)aryl groups, (hetero)aryl(cyclo)alkynyl groups, alkylcycloalkyl groups, and cycloalkylalkyl groups.

In Formula (4), the $Q_1$ and $Q_2$ groups not being H, —F, —Cl, —Br, —I, —OH, —$NH_2$, —$SO_3$, —$PO_3^-$, —$NO_2$, —$CF_3$, are optionally substituted, preferably with a moiety selected from the group consisting of —Cl, —F, —Br, —I, —$OR_{37}$, —$N(R_{37})_2$, —$SO_3R_{37}$, —$PO_3(R_{37})_2$, —$PO_4(R_{37})_2$, —$NO_2$, —$CF_3$, =O, =$NR_{37}$, and —$SR_{37}$, and optionally contain one or more heteroatoms selected from the group consisting of O, S, $NR_{37}$, P, and Si, wherein the N, S, and P atoms are optionally oxidized, wherein the N atoms are optionally quaternized. Preferably, each individual $Q_1$ and $Q_2$ group comprises at most 4 substituents, more preferably at most 3 substituents, even more preferably at most 2 substituents, and most preferably at most 1 substituent.

In Formula (4), the $Q_1$ and $Q_2$ groups are optionally bound to a polymer, a particle, a peptide, a peptoid, a dendrimer, a protein, an aptamer, a carbohydrate, an oligonucleotide, an oligosaccharide, a lipid, a steroid, a liposome, a Targeting Agent $T^T$, $R^{87}$, an albumin-binding moiety, and a chelating moiety, a moiety comprising a radionuclide, or a Drug $D^D$.

In Formula (4), preferably at least one of moieties $Q_1$ and $Q_2$ is not hydrogen.

In Formula (4), preferably each moiety $Q_1$ and $Q_2$ is independently selected from the group consisting of hydrogen, —F, —Cl, —Br, —I, —$OR_{37}$, —$N(R_{37})_2$, —$SO_3$, —$PO_3^-$, —$NO_2$, —$CF_3$, —$SR_{37}$, $S(=O)_2N(R_{37})_2$, $OC(=O)R_{37}$, $SC(=O)$ $R_{37}$, $OC(=S)R_{37}$, $SC(=S)R_{37}$, $NR_{37}C(=O)—R_{37}$, $NR_{37}C(=S)—R_{37}$, $NR_{37}C(=O)O—R_{37}$, $NR_{37}C(=S)O—R_{37}$, $NR_{37}C(=O)S—R_{37}$, $NR_{37}C(=S)S—R_{37}$, $OC(=O)N(R_{37})_2$, $SC(=O)N(R_{37})_2$, $OC(=S)N(R_{37})_2$, $SC(=S)N(R_{37})_2$, $NR_{37}C(=O)N(R_{37})_2$, $NR_{37}C(=S)N(R_{37})_2$, $C(=O)R_{37}$, $C(=S)R_{37}$, $C(=O)N(R_{37})_2$, $C(=S)N(R_{37})_2$, $C(=O)O—R_{37}$, $C(=O)S—R_{37}$, $C(=S)O—R_{37}$, $C(=S)S—R_{37}$, $S(O)R_{37}$, —$S(O)_2R_{37}$, $NR_{37}S(O)_2R_{37}$, —$ON(R_{37})_2$, —$NR_{37}OR_{37}$, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ (cyclo)alkyl(hetero)aryl groups, $C_3$-$C_{24}$ (hetero)aryl(cyclo)alkyl, $C_4$-$C_{24}$ (cyclo)alkenyl(hetero)aryl groups, $C_4$-$C_{24}$ (hetero)aryl(cyclo)alkenyl groups, $C_4$-$C_{24}$ (cyclo)alkynyl(hetero)aryl groups, $C_4$-$C_{24}$ (hetero)aryl(cyclo)alkynyl groups, $C_4$-$C_{24}$ alkylcycloalkyl groups, and $C_4$-$C_{24}$ cycloalkylalkyl groups.

In preferred embodiments, the $Q_1$ and $Q_2$ groups not being hydrogen are not substituted.

In a preferred embodiment, $Q_1$ and $Q_2$ in Formula (4) are selected from the group of hydrogen, —F, —Cl, —Br, —I, —$OR_{37}$, —$N(R_{37})_2$, —$SO_3$, —$PO_3^-$, —$NO_2$, —$CF_3$, —$SR_{37}$, $S(=O)_2N(R_{37})_2$, $OC(=O)R_{37}$, $SC(=O)$ $R_{37}$, $OC(=S)R_{37}$, $SC(=S)R_{37}$, $NR_{37}C(=O)—R_{37}$, $NR_{37}C(=S)—R_{37}$, $NR_{37}C(=O)O—R_{37}$, $NR_{37}C(=S)O—R_{37}$, $NR_{37}C(=O)S—R_{37}$, $NR_{37}C(=S)S—R_{37}$, $OC(=O)N(R_{37})_2$, $SC(=O)N(R_{37})_2$, $OC(=S)N(R_{37})_2$, $SC(=S)N(R_{37})_2$, $NR_{37}C(=O)N(R_{37})_2$, $NR_{37}C(=S)N(R_{37})_2$, $C(=O)R_{37}$, $C(=S)R_{37}$, $C(=O)N(R_{37})_2$, $C(=S)N(R_{37})_2$, $C(=O)O—R_{37}$, $C(=O)S—R_{37}$, $C(=S)O—R_{37}$, $C(=S)S—R_{37}$, $S(O)R_{37}$, —$S(O)_2R_{37}$, $NR_{37}S(O)_2R_{37}$, —$ON(R_{37})_2$, $NR_{37}OR_{37}$, $C_1$-$C_8$ alkyl groups, $C_2$-$C_8$ alkenyl groups, $C_2$-$C_8$ alkynyl groups, $C_6$-$C_{12}$ aryl groups, $C_2$-$C_{12}$ heteroaryl groups, $C_3$-$C_8$ cycloalkyl groups, $C_5$-$C_8$ cycloalkenyl groups, $C_3$-$C_{12}$ alkyl(hetero)aryl groups, $C_3$-$C_{12}$ (hetero)arylalkyl groups, $C_4$-$C_{12}$ alkylcycloalkyl groups, $C_4$-$C_{12}$ cycloalkylalkyl groups, $C_5$-$C_{12}$ cycloalkyl(hetero)aryl groups and $C_5$-$C_{12}$ (hetero)arylcycloalkyl groups.

In a preferred embodiment, $Q_1$ and $Q_2$ in Formula (4) are selected from the group of hydrogen, —F, —Cl, —Br, —I, —$OR_{37}$, —$N(R_{37})_2$, —$SO_3$, —$PO_3^-$, —$NO_2$, —$CF_3$, —$SR_{37}$, $S(=O)_2N(R_{37})_2$, $OC(=O)R_{37}$, $SC(=O)$ $R_{37}$, $OC(=S)R_{37}$, $SC(=S)R_{37}$, $NR_{37}C(=O)—R_{37}$, $NR_{37}C(=S)—R_{37}$, $NR_{37}C(=O)O—R_{37}$, $NR_{37}C(=S)O—R_{37}$, $NR_{37}C(=O)S—R_{37}$, $NR_{37}C(=S)S—R_{37}$, $OC(=O)N(R_{37})_2$, $SC(=O)N(R_{37})_2$, $OC(=S)N(R_{37})_2$, $SC(=S)N(R_{37})_2$, $NR_{37}C(=O)N(R_{37})_2$, $NR_{37}C(=S)N(R_{37})_2$, $C(=O)R_{37}$, $C(=S)R_{37}$, $C(=O)N(R_{37})_2$, $C(=S)N(R_{37})_2$, $C(=O)O—R_{37}$, $C(=O)S—R_{37}$, $C(=S)O—R_{37}$, $C(=S)S—R_{37}$, $S(O)R_{37}$, —$S(O)_2R_{37}$, $NR_{37}S(O)_2R_{37}$, —$ON(R_{37})_2$, —$NR_{37}OR_{37}$, $C_1$-$C_4$ alkyl groups, $C_2$-$C_4$ alkenyl groups, $C_2$-$C_4$ alkynyl groups, $C_6$-$C_8$ aryl groups, $C_2$-$C_8$ heteroaryl groups, $C_3$-$C_6$ cycloalkyl groups, $C_5$-$C_6$ cycloalkenyl groups, $C_3$-$C_{10}$ alkyl(hetero)aryl groups, $C_3$-$C_{10}$ (hetero)arylalkyl groups, $C_4$-$C_{10}$ alkylcycloalkyl groups, $C_4$-$C_{10}$ cycloalkylalkyl groups, $C_5$-$C_{10}$ cycloalkyl(hetero)aryl groups and $C_5$-$C_{10}$ (hetero)arylcycloalkyl groups.

In a preferred embodiment, $Q_1$ and $Q_2$ in Formula (4) are selected from the group of hydrogen, $C_1$-$C_8$ alkyl, phenyl, 2-pyridyl, 3-pyridyl, 4-pyridyl, 2,6-pyrimidyl, 2,5-pyrimidyl, 3,5-pyrmidyl, and 2,4-pyrimidyl; and $Q_1$ and $Q_2$ not being hydrogen are optionally substituted with a moiety selected from the group consisting of —F, —Cl, —Br, —I, —$OR_{37}$, —$N(R_{37})_2$, —$SO_3$, —$PO_3^-$, —$NO_2$, —$CF_3$, —$SR_{37}$, $S(=O)_2N(R_{37})_2$, $OC(=O)R_{37}$, $SC(=O)$ $R_{37}$, $OC(=S)R_{37}$, $SC(=S)R_{37}$, $NR_{37}C(=O)—R_{37}$, $NR_{37}C(=S)—R_{37}$, $NR_{37}C(=O)O—R_{37}$, $NR_{37}C(=S)O—R_{37}$, $NR_{37}C(=O)S—R_{37}$, $NR_{37}C(=S)S—R_{37}$, $OC(=O)N(R_{37})_2$, $SC(=O)N(R_{37})_2$, $OC(=S)N(R_{37})_2$, $SC(=S)N(R_{37})_2$, $NR_{37}C(=O)N(R_{37})_2$, $NR_{37}C(=S)N(R_{37})_2$, $C(=O)R_{37}$, $C(=S)R_{37}$, $C(=O)N(R_{37})_2$, $C(=S)N(R_{37})_2$, $C(=O)O—R_{37}$, $C(=O)S—R_{37}$, $C(=S)O—R_{37}$, $C(=S)S—R_{37}$, $S(O)R_{37}$, —$S(O)_2R_{37}$, $NR_{37}S(O)_2R_{37}$, —$ON(R_{37})_2$, —$NR_{37}OR_{37}$, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ (cyclo)alkyl(hetero)aryl groups, $C_3$-$C_{24}$ (hetero)aryl(cyclo)alkyl, $C_4$-$C_{24}$ (cyclo)alkenyl(hetero)aryl groups, $C_4$-$C_{24}$ (hetero)aryl(cyclo)alkenyl groups, $C_4$-$C_{24}$ (cyclo)alkynyl(hetero)aryl groups, $C_4$-$C_{24}$ (hetero)aryl(cyclo)alkynyl groups, $C_4$-$C_{24}$ alkylcycloalkyl groups, and $C_4$-$C_{24}$ cycloalkylalkyl groups; preferably with a moiety selected from the group consisting of —F, —Cl, —Br, —I, —$OR_{37}$, —$N(R_{37})_2$, —$SO_3$, —$PO_3^-$, —$NO_2$, —$CF_3$, —$SR_{37}$, $S(=O)_2N(R_{37})_2$, $OC(=O)R_{37}$, $SC(=O)$ $R_{37}$, $OC(=S)R_{37}$, $SC(=S)R_{37}$, $NR_{37}C(=O)$—$R_{37}$, $NR_{37}C(=S)$—$R_{37}$, $NR_{37}C(=O)O$—$R_{37}$, $NR_{37}C(=S)O$—$R_{37}$, $NR_{37}C(=O)S$—$R_{37}$, $NR_{37}C(=S)S$—$R_{37}$, $OC(=O)N(R_{37})_2$, $SC(=O)N(R_{37})_2$, $OC(=S)N(R_{37})_2$, $SC(=S)N(R_{37})_2$, $NR_{37}C(=O)N(R_{37})_2$, $NR_{37}C(=S)N(R_{37})_2$, $C(=O)R_{37}$, $C(=S)R_{37}$, $C(=O)N(R_{37})_2$, $C(=S)N(R_{37})_2$, $C(=O)O$—$R_{37}$, $C(=O)S$—$R_{37}$, $C(=S)O$—$R_{37}$, $C(=S)S$—$R_{37}$, $S(O)R_{37}$, —$S(O)_2R_{37}$, $NR_{37}S(O)_2R_{37}$, —$ON(R_{37})_2$, —$NR_{37}OR_{37}$, $C_1$-$C_8$ alkyl groups, $C_2$-$C_8$ alkenyl groups, $C_2$-$C_8$ alkynyl groups, $C_6$-$C_{12}$ aryl groups, $C_2$-$C_{12}$ heteroaryl groups, $C_3$-$C_8$ cycloalkyl groups, $C_5$-$C_8$ cycloalkenyl groups, $C_3$-$C_{12}$ alkyl(hetero)aryl groups, $C_3$-$C_{12}$ (hetero)arylalkyl groups, $C_4$-$C_{12}$ alkylcycloalkyl groups, $C_4$-$C_{12}$ cycloalkylalkyl groups, $C_5$-$C_{12}$ cycloalkyl(hetero)aryl groups, and $C_5$-$C_{12}$ (hetero)arylcycloalkyl groups; more preferably with a moiety selected from the group consisting of —F, —Cl, —Br, —I, —$OR_{37}$, —$N(R_{37})_2$, —$SO_3$, —$PO_3^-$, —$NO_2$, —$CF_3$, —$SR_{37}$, $S(=O)_2N(R_{37})_2$, $OC(=O)R_{37}$, $SC(=O)$ $R_{37}$, $OC(=S)R_{37}$, $SC(=S)R_{37}$, $NR_{37}C(=O)$—$R_{37}$, $NR_{37}C(=S)$—$R_{37}$, $NR_{37}C(=O)O$—$R_{37}$, $NR_{37}C(=S)O$—$R_{37}$, $NR_{37}C(=O)S$—$R_{37}$, $NR_{37}C(=S)S$—$R_{37}$, $OC(=O)N(R_{37})_2$, $SC(=O)N(R_{37})_2$, $OC(=S)N(R_{37})_2$, $SC(=S)N(R_{37})_2$, $NR_{37}C(=O)N(R_{37})_2$, $NR_{37}C(=S)N(R_{37})_2$, $C(=O)R_{37}$, $C(=S)R_{37}$, $C(=O)N(R_{37})_2$, $C(=S)N(R_{37})_2$, $C(=O)O$—$R_{37}$, $C(=O)S$—$R_{37}$, $C(=S)O$—$R_{37}$, $C(=S)S$—$R_{37}$, $S(O)R_{37}$, —$S(O)_2R_{37}$, $NR_{37}S(O)_2R_{37}$, —$ON(R_{37})_2$, —$NR_{37}OR_{37}$, $C_1$-$C_4$ alkyl groups, $C_2$-$C_4$ alkenyl groups, $C_2$-$C_4$ alkynyl groups, $C_6$-$C_8$ aryl groups, $C_2$-$C_8$ heteroaryl groups, $C_3$-$C_6$ cycloalkyl groups, $C_5$-$C_6$ cycloalkenyl groups, $C_3$-$C_{10}$ alkyl (hetero)aryl groups, $C_3$-$C_{10}$ (hetero)arylalkyl groups, $C_4$-$C_{10}$ alkylcycloalkyl groups, $C_4$-$C_{10}$ cycloalkylalkyl groups, $C_5$-$C_{10}$ cycloalkyl(hetero)aryl groups, and $C_5$-$C_{10}$ (hetero) arylcycloalkyl groups.

In a preferred embodiment, in Formula (4):

(a) $Q_1$ and $Q_2$ are independently selected from the group consisting of 2-pyridyl, 3-pyridyl, and 4-pyridyl;

(b) $Q_1$ is selected from the group consisting of 2,6-pyrimidyl, 2,5-pyrimidyl, 3,5-pyrmidyl, and 2,4-pyrimidyl; and $Q_2$ is (hetero)alkyl; or (c) $Q_1$ is phenyl and $Q_2$ is hydrogen;

(d) $Q_1$ is phenyl and $Q_2$ is phenyl;

(e) $Q_1$ is phenyl and $Q_2$ is $C_1$-$C_8$ alkyl;

(f) $Q_1$ and $Q_2$ are $C_1$-$C_8$ alkyl;

and in (a)-(f) all $Q_1$ and $Q_2$ not being hydrogen are optionally substituted as defined in the previous paragraph.

In preferred embodiments, the Activator can be a multimeric compound, comprising a plurality of dienes as defined herein. These multimeric compounds include but are not limited to biomolecules, proteins, peptides, peptoids, polymers, dendrimers, liposomes, micelles, particles, polymer particles, or other polymeric constructs.

Preferred Tetrazines

Formula (4a)

Preferred tetrazines are in accordance with Formula (4a), and preferably include pharmaceutically accepted salts thereof:

Formula (4a)

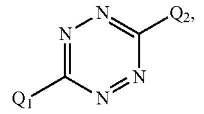

wherein each moiety $Q_1$ and $Q_2$ is independently selected from the group consisting of hydrogen and moieties according to Formula (5):

Formula (5)

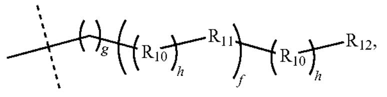

wherein the dashed line indicates a bond to the remainder of the molecule, and wherein $R_{10}$, $R_{11}$, and $R_{12}$ are as defined herein.

In a preferred embodiment, each f in Formula (5) is an integer independently selected from a range of from 0 to 24, preferably in a range of from 1 to 12, more preferably in a range of from 2 to 6, even more preferably from 1 to 3. In a preferred embodiment, f is 1. In other preferred embodiments f is an integer in the range from 12 to 24. In a preferred embodiment, in Formula (5) g is an integer in a range of from 0 to 12, preferably in a range of from 1 to 6, more preferably in a range of from 2 to 4. In a preferred embodiment, in Formula (5) each h is independently 0 or 1. In a preferred embodiment, g is 0, and f is 1. In a preferred embodiment, g is 1, and f is 1.

In case the compound according to the invention comprises more than one moiety satisfying Formula (5), each g, h, and f is independently selected.

In a preferred embodiment, the moiety according to Formula (5) is optionally substituted with another independently selected moiety according to Formula (5). In a preferred embodiment, the moiety according to Formula (5) is not substituted with another independently selected moiety according to Formula (5).

In a preferred embodiment, the moiety according to Formula (5) is $R^{87}$, as defined further below.

In a preferred embodiment, the moiety according to Formula (5) satisfies molecules from Group $R^M$ shown further below.

It is preferred that at least one of moieties $Q_1$ and $Q_2$ in Formula (4a) is not hydrogen.

In preferred embodiments, $Q_1$ in Formula (4a) is selected from the group consisting of $C_6$-$C_{24}$ aryl, and $C_2$-$C_{24}$ heteroaryl, and is optionally further substituted with a moiety according to Formula (5), preferably not more than two, more preferably not more than one moiety according to Formula (5).

In preferred embodiments, $Q_1$ in Formula (4a) is selected from the group consisting of $C_6$-$C_{24}$ aryl, and $C_2$-$C_{24}$ heteroaryl, and is optionally further substituted with a moiety according to Formula (5), preferably not more than two, more preferably not more than one moiety according to Formula (5), and $Q_2$ in Formula (4a) is selected from the group consisting of $C_6$-$C_{24}$ aryl, and $C_2$-$C_{24}$ heteroaryl, and is optionally further substituted with a moiety according to Formula (5), preferably not more than two, more preferably not more than one moiety according to Formula (5).

In preferred embodiments, $Q_1$ in Formula (4a) is selected from the group consisting of $C_6$ aryl, and $C_3$-$C_5$ heteroaryl, and is optionally further substituted with at least one moiety according to Formula (5), preferably not more than two, more preferably not more than one moiety according to Formula (5). Herein, preferred heteroaryls are 2-pyridyl, 3-pyridyl, 4-pyridyl, 2,6-pyrimidyl, 3,5-pyrimidyl, 2,5-pyrimidyl, 2,4-pyrimidyl, 2,4 imidazyl, 2,5 imidazyl, phenyl, 2,3-pyrazyl, 3,4-pyrazyl, oxazol, isoxazol, thiazol, oxazoline, 2-pyrryl, 3-pyrryl, 2-thiophene, and 3-thiophene.

In preferred embodiments, $Q_1$ in Formula (4a) is $C_3$-$C_5$ heteroaryl, and is optionally further substituted with at least one moiety according to Formula (5), preferably not more than two, more preferably not more than one moiety according to Formula (5), and $Q_2$ is $C_3$-$C_5$ heteroaryl, and is optionally further substituted with a moiety according to Formula (5), preferably not more than two, more preferably not more than one moiety according to Formula (5). Herein, preferred heteroaryls are 2-pyridyl, 3-pyridyl, 4-pyridyl, 2,6-pyrimidyl, 3,5-pyrimidyl, 2,5-pyrimidyl, 2,4-pyrimidyl, 2,4 imidazyl, 2,5 imidazyl, phenyl, 2,3-pyrazyl, 3,4-pyrazyl, oxazol, isoxazol, thiazol, oxazoline, 2-pyrryl, 3-pyrryl, 2-thiophene, and 3-thiophene.

In preferred embodiments, $Q_1$ in Formula (4a) is $C_3$-$C_5$ heteroaryl, and is optionally further substituted with at least one moiety according to Formula (5), preferably not more than two, more preferably not more than one moiety according to Formula (5), and $Q_2$ is H.

In preferred embodiments, $Q_1$ in Formula (4a) is a phenyl ring, and is optionally further substituted with at least one moiety according to Formula (5), preferably not more than two, more preferably not more than one moiety according to Formula (5), and $Q_2$ is —H.

In preferred embodiments, $Q_1$ in Formula (4a) is a phenyl ring, and is optionally further substituted with at least one moiety according to Formula (5), preferably not more than two, more preferably not more than one moiety according to Formula (5), and $Q_2$ is a phenyl ring, and is optionally further substituted with at least one moiety according to Formula (5), preferably not more than two, more preferably not more than one moiety according to Formula (5).

In preferred embodiments, $Q_1$ in Formula (4a) is a phenyl ring, and is optionally further substituted with at least one moiety according to Formula (5), preferably not more than two, more preferably not more than one moiety according to Formula (5), and $Q_2$ is selected from the group consisting of $C_6$ aryl, and $C_{3-5}$ heteroaryl, and is optionally further substituted with at least one moiety according to Formula (5), preferably not more than two, more preferably not more than one moiety according to Formula (5).

In preferred embodiments, $Q_1$ in Formula (4a) is $C_1$-$C_{12}$ alkyl, and is optionally further substituted with at least one moiety according to Formula (5), preferably not more than two, more preferably not more than one moiety according to Formula (5), and $Q_2$ selected from the group consisting of $C_6$ aryl, and $C_{3-5}$ heteroaryl, and is optionally further substituted with at least one moiety according to Formula (5), preferably not more than two, more preferably not more than one moiety according to Formula (5).

In preferred embodiments, $Q_1$ in Formula (4a) is $C_1$-$C_{12}$ alkyl, and is optionally further substituted with at least one moiety according to Formula (5), preferably not more than two, more preferably not more than one moiety according to Formula (5), and $Q_2$ in Formula (4a) is $C_1$-$C_{12}$ alkyl, and is optionally further substituted with at least one moiety according to Formula (5), preferably not more than two, more preferably not more than one moiety according to Formula (5).

In preferred embodiments $Q_2$ equals $Q_1$.

$R_{10}$

In preferred embodiments, each $R_{10}$ is independently selected from the group consisting of —O—, —S—, —SS—, —$NR_4$—, —N═N—, —C(O)—, —C(O)$NR_4$—, —OC(O)—, —C(O)O—, —OC(O)O—, —OC(O)$NR_4$—, —$NR_4$C(O)—, —$NR_4$C(O)O—, —$NR_4$C(O)$NR_4$—, —SC(O)—, —C(O)S—, —SC(O)O—, —OC(O)S—, —SC(O)$NR_4$—, —$NR_4$C(O)S—, —S(O)—, —$S(O)_2$—, —$OS(O)_2$—, —$S(O_2)$O—, —$OS(O)_2O$—, —$OS(O)_2NR_4$—, —$NR_4S(O)_2O$—, —C(O)$NR_4S(O)_2NR_4$—, —OC(O)$NR_4S(O)_2NR_4$—, —OS(O)—, —OS(O)O—, —OS(O)$NR_4$—, —$ONR_4$C(O)—, —$ONR_4$C(O)O—, —$ONR_4$C(O)$NR_4$—, —$NR_4$OC(O)—, —$NR_4$OC(O)O—, —$NR_4$OC(O)$NR_4$—, —$ONR_4$C(S)—, —$ONR_4$C(S)O—, —$ONR_4$C(S)$NR_4$—, —$NR_4$OC(S)—, —$NR_4$OC(S)O—, —$NR_4$OC(S)$NR_4$—, —OC(S)—, —C(S)O—, —OC(S)O—, —OC(S)$NR_4$—, —$NR_4$C(S)—, —$NR_4$C(S)O—, —$SS(O)_2$—, —$S(O)_2S$—, —$OS(O_2)S$—, —$SS(O)_2O$—, —$NR_4$OS(O)—, —$NR_4$OS(O)O—, —$NR_4$OS(O)$NR_4$—, —$NR_4OS(O)_2$—, —$NR_4OS(O)_2O$—, —$NR_4OS(O)_2NR_4$—, —$ONR_4$S(O)—, —$ONR_4$S(O)O—, —$ONR_4$S(O)$NR_4$—, —$ONR_4S(O)_2O$—, —$ONR_4S(O)_2NR_4$—, —$ONR_4S(O)_2$—, —$OP(O)(R_4)_2$—, —$S^P(O)(R_4)_2$—, —$NR_4P(O)(R_4)_2$—, and combinations thereof, wherein $R_4$ is defined as described herein. In preferred embodiments, each $R_{10}$ is independently selected from the group consisting of —O—, —S—, —SS—, —$NR_4$—, —N═N—, —C(O)—, —C(O)$NR_4$—, —OC(O)—, —C(O)O—, —OC(O)$NR_4$—, —$NR_4$C(O)—, —$NR_4$C(O)O—, —$NR_4$C(O)$NR_4$—, —SC(O)—, —C(O)S—, —SC(O)O—, —OC(O)S—, —SC(O)$NR_4$—, —$NR_4$C(O)S—, —S(O)—, —$S(O)_2$—, —C(O)$NR_4S(O)_2NR_4$—, —OC(O)$NR_4S(O)_2NR_4$—, —OC(S)—, —C(S)O—, —OC(S)O—, —OC(S)$NR_4$—, —$NR_4$C(S)—, —$NR_4$C(S)O—, —$SS(O)_2$—.

Preferably, each $R_4$ in relation to $R_{10}$ is individually selected from the group consisting of hydrogen and $C_1$-$C_4$ alkyl.

$R_{11}$

In preferred embodiments, each $R_{11}$ is independently selected from the group consisting of $C_1$-$C_{24}$ alkylene groups, $C_2$-$C_{24}$ alkenylene groups, $C_2$-$C_{24}$ alkynylene groups, $C_6$-$C_{24}$ arylene, $C_2$-$C_{24}$ heteroarylene, $C_3$-$C_{24}$ cycloalkylene groups, $C_5$-$C_{24}$ cycloalkenylene groups, and $C_{12}$-$C_{24}$ cycloalkynylene groups, and wherein preferably the alkylene groups, alkenylene groups, alkynylene groups, cycloalkylene groups, cycloalkenylene groups, and cycloalkynylene groups optionally contain one or more heteroatoms selected from the group consisting of O, S, $NR_{36}$, P, and Si, wherein the N, S, and P atoms are optionally oxidized, wherein the N atoms are optionally quaternized.

In preferred embodiments, each Rn is independently selected from the group consisting of $C_1$-$C_{12}$ alkylene groups, $C_2$-$C_{12}$ alkenylene groups, $C_2$-$C_{12}$ alkynylene groups, $C_6$-$C_{12}$ arylene, $C_2$-$C_{12}$ heteroarylene, $C_3$-$C_{12}$ cycloalkylene groups, $C_5$-$C_{12}$ cycloalkenylene groups, and $C_{12}$ cycloalkynylene groups; and wherein preferably the alkylene groups, alkenylene groups, alkynylene groups, cycloalkylene groups, cycloalkenylene groups, and cycloalkynylene groups optionally contain one or more heteroatoms selected from the group consisting of O, S, $NR_{36}$, P, and Si, wherein the N, S, and P atoms are optionally oxidized, wherein the N atoms are optionally quaternized.

In preferred embodiments, each $R_{11}$ is independently selected from the group consisting of $C_1$-$C_6$ alkylene groups, $C_2$-$C_6$ alkenylene groups, $C_2$-$C_6$ alkynylene groups, $C_6$-$C_6$ arylene, $C_2$-$C_6$ heteroarylene, $C_3$-$C_6$ cycloalkylene groups, and $C_5$-$C_6$ cycloalkenylene groups; and wherein preferably the alkylene groups, alkenylene groups, alkynylene groups, cycloalkylene groups, cycloalkenylene groups, and cycloalkynylene groups optionally contain one or more heteroatoms selected from the group consisting of O, S, $NR_{36}$, P, and Si, wherein the N, S, and P atoms are optionally oxidized, wherein the N atoms are optionally quaternized.

In preferred embodiments, the $R_{11}$ groups are optionally further substituted with one or more substituents selected from the group consisting of —Cl, —F, —Br, —I, —OH, —$NH_2$, —$SO_3H$, —$PO_3H$, —$PO_4H_2$, —$NO_2$, —$CF_3$, =O, =$NR_{36}$, —$SR_{36}$, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ alkyl(hetero)aryl groups, $C_3$-$C_{24}$ (hetero)arylalkyl groups, $C_4$-$C_{24}$ (hetero)arylalkenyl groups, $C_4$-$C_{24}$ (hetero)arylalkynyl groups, $C_4$-$C_{24}$ alkenyl(hetero)aryl groups, $C_4$-$C_{24}$ alkynyl(hetero)aryl groups, $C_4$-$C_{24}$ alkylcycloalkyl groups, $C_6$-$C_{24}$ alkylcycloalkenyl groups, $C_{13}$-$C_{24}$ alkylcycloalkynyl groups, $C_4$-$C_{24}$ cycloalkylalkyl groups, $C_6$-$C_{24}$ cycloalkenylalkyl groups, $C_{13}$-$C_{24}$ cycloalkynylalkyl groups, $C_5$-$C_{24}$ alkenylcycloalkyl groups, $C_7$-$C_{24}$ alkenylcycloalkenyl groups, $C_{14}$-$C_{24}$ alkenylcycloalkynyl groups, $C_5$-$C_{24}$ cycloalkylalkenyl groups, $C_7$-$C_{24}$ cycloalkenylalkenyl groups, $C_{14}$-$C_{24}$ cycloalkynylalkenyl groups, $C_5$-$C_{24}$ alkynylcycloalkyl groups, $C_7$-$C_{24}$ alkynylcycloalkenyl groups, $C_{14}$-$C_{24}$ alkynylcycloalkynyl groups, $C_5$-$C_{24}$ cycloalkylalkynyl groups, $C_7$-$C_{24}$ cycloalkenylalkynyl groups, $C_{14}$-$C_{24}$ cycloalkynylalkynyl groups, $C_5$-$C_{24}$ cycloalkyl(hetero)aryl groups, $C_7$-$C_{24}$ cycloalkenyl(hetero)aryl groups, $C_{14}$-$C_{24}$ cycloalkynyl(hetero)aryl groups, $C_5$-$C_{24}$ (hetero)arylcycloalkyl groups, $C_7$-$C_{24}$ (hetero)arylcycloalkenyl groups, and $C_{14}$-$C_{24}$ (hetero)arylcycloalkynyl groups, wherein the substituents optionally contain one or more heteroatoms selected from the group consisting of O, S, $NR_{36}$, P, and Si, wherein the N, S, and P atoms are optionally oxidized, wherein the N atoms are optionally quaternized.

In preferred embodiments, the $R_{11}$ groups are optionally further substituted with one or more substituents selected from the group consisting of —Cl, —F, —Br, —I, —OH, —$NH_2$, —$SO_3H$, —$PO_3H$, —$PO_4H_2$, —$NO_2$, —$CF_3$, =O, =$NR_{36}$, —$SR_{36}$, $C_1$-$C_{12}$ alkyl groups, $C_2$-$C_{12}$ alkenyl groups, $C_2$-$C_{12}$ alkynyl groups, $C_6$-$C_{12}$ aryl groups, $C_2$-$C_{12}$ heteroaryl groups, $C_3$-$C_{12}$ cycloalkyl groups, $C_5$-$C_{12}$ cycloalkenyl groups, $C_{12}$ cycloalkynyl groups, $C_3$-$C_{12}$ alkyl (hetero)aryl groups, $C_3$-$C_{12}$ (hetero)arylalkyl groups, $C_4$-$C_{12}$ (hetero)arylalkenyl groups, $C_4$-$C_{12}$ (hetero)arylalkynyl groups, $C_4$-$C_{12}$ alkenyl(hetero)aryl groups, $C_4$-$C_{12}$ alkynyl (hetero)aryl groups, $C_4$-$C_{12}$ alkylcycloalkyl groups, $C_6$-$C_{12}$ alkylcycloalkenyl groups, $C_{13}$-$C_{18}$ alkylcycloalkynyl groups, $C_4$-$C_{12}$ cycloalkylalkyl groups, $C_6$-$C_{12}$ cycloalkenylalkyl groups, $C_{13}$-$C_{18}$ cycloalkynylalkyl groups, $C_5$-$C_{12}$ alkenylcycloalkyl groups, $C_7$-$C_{12}$ alkenylcycloalkenyl groups, $C_{14}$-$C_{16}$ alkenylcycloalkynyl groups, $C_5$-$C_{12}$ cycloalkylalkenyl groups, $C_7$-$C_{12}$ cycloalkenylalkenyl groups, $C_{14}$-$C_{16}$ cycloalkynylalkenyl groups, $C_5$-$C_{12}$ alkynylcycloalkyl groups, $C_7$-$C_{12}$ alkynylcycloalkenyl groups, $C_{14}$-$C_{16}$ alkynylcycloalkynyl groups, $C_5$-$C_{12}$ cycloalkylalkynyl groups, $C_7$-$C_{12}$ cycloalkenylalkynyl groups, $C_{14}$-$C_{18}$ cycloalkynylalkynyl groups, $C_5$-$C_{12}$ cycloalkyl(hetero)aryl groups, $C_7$-$C_{12}$ cycloalkenyl(hetero)aryl groups, $C_{14}$-$C_{16}$ cycloalkynyl(hetero)aryl groups, $C_5$-$C_{12}$ (hetero)arylcycloalkyl groups, $C_7$-$C_{12}$ (hetero)arylcycloalkenyl groups, and $C_{14}$-$C_{16}$ (hetero)arylcycloalkynyl groups, wherein the substituents optionally contain one or more heteroatoms selected from the group consisting of O, S, $NR_{36}$, P, and Si, wherein the N, S, and P atoms are optionally oxidized, wherein the N atoms are optionally quaternized.

In preferred embodiments, the $R_{11}$ groups are optionally further substituted with one or more substituents selected from the group consisting of —Cl, —F, —Br, —I, —OH, —$NH_2$, —$SO_3H$, —$PO_3H$, —$PO_4H_2$, —$NO_2$, —$CF_3$, =O, =$NR_{36}$, —$SR_{36}$, $C_1$-$C_6$ alkyl groups, $C_2$-$C_6$ alkenyl groups, $C_2$-$C_6$ alkynyl groups, $C_6$ aryl groups, $C_2$-$C_6$ heteroaryl groups, $C_3$-$C_6$ cycloalkyl groups, $C_5$-$C_6$ cycloalkenyl groups, $C_3$-$C_6$ alkyl(hetero)aryl groups, $C_3$-$C_6$ (hetero)arylalkyl groups, $C_4$-$C_6$ (hetero)arylalkenyl groups, $C_4$-$C_6$ (hetero)arylalkynyl groups, $C_4$-$C_6$ alkenyl(hetero)aryl groups, $C_4$-$C_6$ alkynyl(hetero)aryl groups, $C_4$-$C_6$ alkylcycloalkyl groups, $C_6$ alkylcycloalkenyl groups, $C_4$-$C_6$ cycloalkylalkyl groups, $C_6$ cycloalkenylalkyl groups, $C_5$-$C_6$ alkenylcycloalkyl groups, $C_7$ alkenylcycloalkenyl groups, $C_5$-$C_6$ cycloalkylalkenyl groups, $C_7$ cycloalkenylalkenyl groups, $C_5$-$C_6$ alkynylcycloalkyl groups, $C_7$ alkynylcycloalkenyl groups, $C_5$-$C_6$ cycloalkylalkynyl groups, $C_5$-$C_6$ cycloalkyl(hetero) aryl groups, and $C_5$-$C_6$ (hetero)arylcycloalkyl groups, wherein the substituents optionally contain one or more heteroatoms selected from the group consisting of O, S, $NR_{36}$, P, and Si, wherein the N, S, and P atoms are optionally oxidized, wherein the N atoms are optionally quaternized.

In preferred embodiments, the $R_{11}$ groups are optionally further substituted with one or more substituents selected from the group consisting of —Cl, —F, —Br, —I, —OH, —$NH_2$, —$SO_3H$, —$PO_3H$, —$PO_4H_2$, —$NO_2$, —$CF_3$, =O, =$NR_{36}$, —$SR_{36}$, $C_1$-$C_6$ alkyl groups, $C_2$-$C_6$ alkenyl groups, $C_2$-$C_6$ alkynyl groups, $C_6$ aryl groups, $C_2$-$C_6$ heteroaryl groups, $C_3$-$C_6$ cycloalkyl groups, $C_5$-$C_6$ cycloalkenyl groups, $C_3$-$C_7$ alkyl(hetero)aryl groups, $C_3$-$C_7$ (hetero)arylalkyl groups, $C_4$-$C_8$ (hetero)arylalkenyl groups, $C_4$-$C_8$ (hetero)arylalkynyl groups, $C_4$-$C_8$ alkenyl(hetero)aryl groups, $C_4$-$C_8$ alkynyl(hetero)aryl groups, $C_4$-$C_6$ alkylcycloalkyl groups, $C_6$-$C_7$ alkylcycloalkenyl groups, $C_4$-$C_6$ cycloalkylalkyl groups, $C_6$-$C_7$ cycloalkenylalkyl groups, $C_5$-$C_6$ alkenylcycloalkyl groups, $C_7$-$C_8$ alkenylcycloalkenyl groups, $C_5$-$C_6$ cycloalkylalkenyl groups, $C_7$-$C_8$ cycloalkenylalkenyl groups, $C_5$-$C_6$ alkynylcycloalkyl groups, $C_7$-$C_8$ alkynylcycloalkenyl groups, $C_5$-$C_6$ cycloalkylalkynyl groups, $C_5$-$C_9$ cycloalkyl(hetero)aryl groups, and $C_5$-$C_6$ (hetero)arylcycloalkyl groups, wherein the substituents optionally contain one or more heteroatoms selected from the group consisting of O, S, $NR_{36}$, P, and Si, wherein the N, S, and P atoms are optionally oxidized, wherein the N atoms are optionally quaternized.

It is preferred that when f>2, that $R_{11}$ is independently selected from the group consisting of $C_1$-$C_6$ alkylene groups, $C_2$-$C_6$ alkenylene groups, $C_2$-$C_6$ alkynylene groups, $C_6$-$C_6$ arylene, $C_2$-$C_6$ heteroarylene, $C_3$-$C_6$ cycloalkylene groups, and $C_5$-$C_6$ cycloalkenylene groups; and wherein preferably the alkylene groups, alkenylene groups, alkynylene groups, cycloalkylene groups, cycloalkenylene groups, and cycloalkynylene groups optionally contain one or more heteroatoms selected from the group consisting of O, S, $NR_{36}$, P, and Si, wherein the N, S, and P atoms are optionally oxidized, wherein the N atoms are optionally quaternized.

In a preferred embodiment, the $R_{11}$ substituents do not contain heteroatoms. In a preferred embodiment, the $R_1$ groups are not substituted. In another preferred embodiment, the $R_{11}$ groups do not contain heteroatoms.

$R_{12}$ $R_{12}$ is selected from the group consisting of —H, —OH, —$NH_2$, —$N_3$, —Cl, —Br, —F, —I, a polymer, a particle, a peptide, a peptoid, a dendrimer, a protein, a biomolecule, an aptamer, a carbohydrate, an oligonucleotide, an oligosaccharide, a lipid, a steroid, a liposome, a micelle, a Targeting Agent $T^T$, $R^{87}$, a Drug $D^D$, an imaging moiety, an albumin-binding moiety, and a chelating moiety.

Non-limiting examples of chelating moieties for use in $R_{12}$ are DTPA (diethylenetriaminepentaacetic acid), DOTA (1,4,7,10-tetraazacyclododecane-N,N',N",N"-tetraacetic acid), NOTA (1,4,7-triazacyclononane-N,N',N"-triacetic acid), TETA (1,4,8,11-tetraazacyclotetradecane-N,N',N",N'-tetraacetic acid), OTTA (N1-(p-isothiocyanatobenzyl)-diethylenetriamine-$N_1$,$N_2$,$N_3$,$N_3$-tetraacetic acid), deferoxamine or DFO (N'-[5-[[4-[[5-(acetylhydroxyamino)pentyl]amino]-1,4-dioxobutyl]hydroxyamino]pentyl]-N-(5-aminopentyl)-N-hydroxybutanediamide) or HYNIC (hydrazinonicotinamide).

In a preferred embodiment, when $R^{12}$ is a polymer, a particle, a peptide, a peptoid, a dendrimer, a protein, a biomolecule, an oligonucleotide, an oligosaccharide, a lipid, a liposome, a micelle, a Targeting Agent $T^T$, or a $R^{87}$, then f is at most 2, preferably at most 1.

Formulae (6), (7), (8), (9), (10), (11), (12), and (13)

In preferred embodiments of the invention the tetrazine is in accordance with any one of the Formulae (6), (7), (8), (9), (10), (11), (12), or (13):

Formula (6)

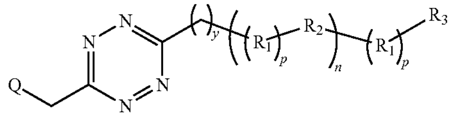

Formula (7)

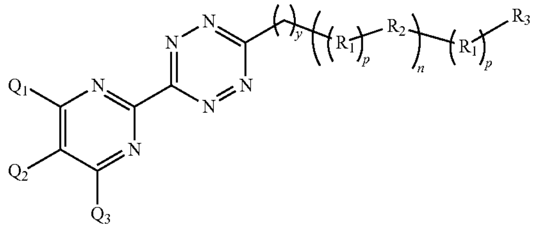

Formula (8)

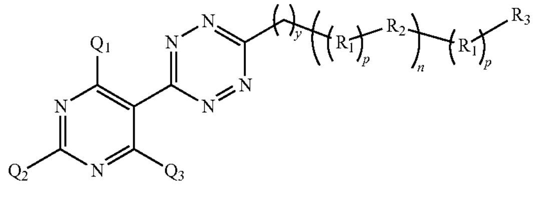

Formula (9)

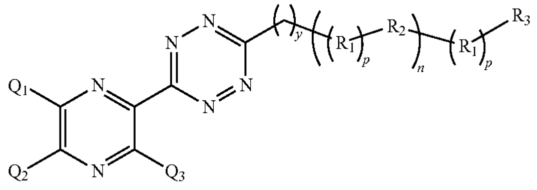

-continued

Formula (10)

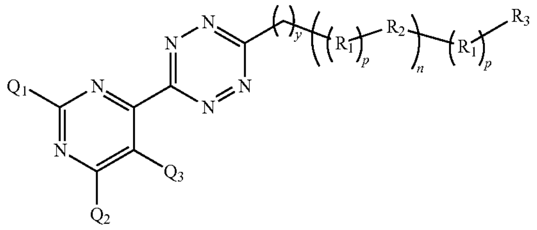

Formula (11)

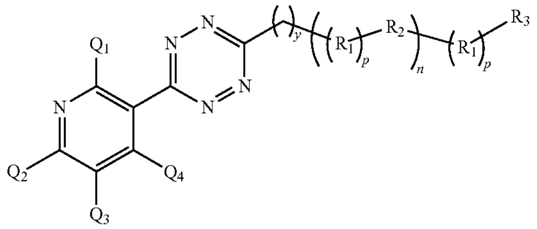

Formula (12)

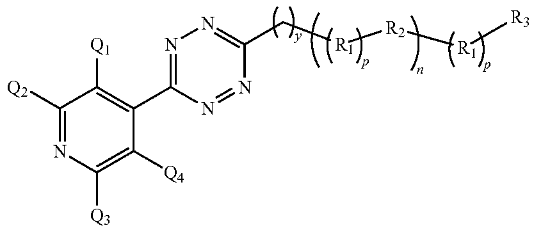

Formula (13)

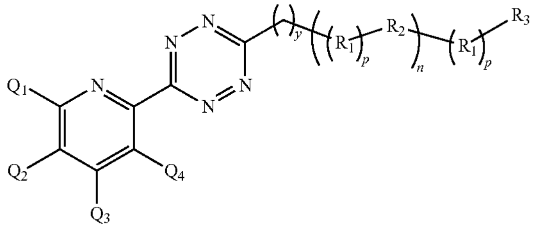

wherein each moiety Q, $Q_1$, $Q_2$, $Q_3$, and $Q_4$ is independently selected from the group consisting of hydrogen and moieties according to Formula (5) as defined herein; and wherein $R_1$, $R_2$, and $R_3$ are as defined herein.

In preferred embodiments, in the tetrazines according to any one of Formulae (6), (7), (8), (9), (10), (11), (12), and (13), at most one moiety selected from the group consisting of Q, $Q_1$, $Q_2$, $Q_3$, and $Q_4$ is hydrogen.

In preferred embodiments, in the tetrazines according to any one of Formulae (7), (8), (9), (10), (11), (12), and (13), at most two moieties selected from the group consisting of Q, $Q_1$, $Q_2$, $Q_3$, and $Q_4$ are hydrogen.

In preferred embodiments, in the tetrazines according to any one of Formulae (7), (8), (9), (10), (11), (12), and (13), at most three moieties selected from the group consisting of Q, $Q_1$, $Q_2$, $Q_3$, and $Q_4$ are hydrogen.

In preferred embodiments, in the tetrazines according to any one of Formulae (7), (8), (9), (10), (11), (12), and (13), all moieties selected from the group consisting of Q, $Q_1$, $Q_2$, $Q_3$, and $Q_4$ are hydrogen.

In preferred embodiments, in the tetrazines according to any one of Formulae (7), (8), (9), (10), (11), (12), and (13), at most one moiety selected from the group consisting of Q, $Q_1$, $Q_2$, $Q_3$, and $Q_4$ is not hydrogen.

In preferred embodiments, in the tetrazines according to any one of Formulae (7), (8), (9), (10), (11), (12), and (13), at most two moieties selected from the group consisting of Q, $Q_1$, $Q_2$, $Q_3$, and $Q_4$ is not hydrogen.

Molecular Weight

Preferably, for all compounds disclosed herein comprising a group Q, $Q_1$, $Q_2$, $Q_3$, $Q_4$ or $—(CH_2)_y—((R_1)_p—R_2)_n—(R_1)_p—R_3$, at least one of these groups has a molecular weight in a range of from 100 Da to 3000 Da. Preferably, at least one of these groups has a molecular weight in a range of from 100 Da to 2000 Da. More preferably, at least one of these groups has a molecular weight in a range of from 100 Da to 1500 Da, even more preferably in a range of from 150 Da to 1500 Da. Even more preferably still, at least one of these groups has a molecular weight in a range of from 150 Da to 1000 Da, most preferably in a range of from 200 Da to 1000 Da.

Preferably, for all compounds disclosed herein comprising a group Q, $Q_1$, $Q_2$, $Q_3$, $Q_4$ or $—(CH_2)_y—((R_1)_p—R_2)_n—(R_1)_p—R_3$, none of these groups has a molecular weight of more than 3000 Da, in particular in the case the Activator needs to efficiently extravasate into tissues.

Group $—(CH_2)_y—((R_1)_p—R_2)_n—(R_1)_p—R_3$

In preferred embodiments, y is an integer in a range of from 1 to 12, preferably from 1 to 10, more preferably from 1 to 8, even more preferably from 2 to 6, most preferably from 2 to 4. In preferred embodiments, y is at least 2, preferably y is at least 3. In preferred embodiments, p is 0 or 1, wherein each p is independently selected. In preferred embodiments, each n is an integer independently selected from a range of from 0 to 24, preferably from 1 to 12, more preferably from 1 to 6, even more preferably from 1 to 3, most preferably n is 0 or 1. In preferred embodiments n is preferably an integer from 12 to 24. In preferred embodiments, n is 1.

In preferred embodiments, the entire group $—((R_1)_p—R_2)_n—(R_1)_p—R_3$ is $R^{87}$. In preferred embodiments, the entire group $—((R_1)_p—R_2)_n—(R_1)_p—R_3$ has a molecular weight in a range of from 100 Da to 3000 Da. Preferably, the entire group $—((R_1)_p—R_2)_n—(R_1)_p—R_3$ has a molecular weight in a range of from 100 Da to 2000 Da. More preferably, the entire group $—((R_1)_p—R_2)_n—(R_1)_p—R_3$ has a molecular weight in a range of from 100 Da to 1500 Da, even more preferably in a range of from 150 Da to 1500 Da. Even more preferably still, the entire group $—((R_1)_p—R_2)_n—(R_1)_p—R_3$ has a molecular weight in a range of from 150 Da to 1000 Da, most preferably in a range of from 200 Da to 1000 Da.

It is preferred that when n>2, that $R_2$ is independently selected from the group consisting of $C_1$-$C_6$ alkylene groups, $C_2$-$C_6$ alkenylene groups, $C_2$-$C_6$ alkynylene groups, $C_6$ arylene, $C_2$-$C_6$ heteroarylene, $C_3$-$C_6$ cycloalkylene groups, and $C_5$-$C_6$ cycloalkenylene groups; and wherein preferably the alkylene groups, alkenylene groups, alkynylene groups, cycloalkylene groups, cycloalkenylene groups, and cycloalkynylene groups optionally contain one or more heteroatoms selected from the group consisting of O, S, $NR_{36}$, P, and Si, wherein the N, S, and P atoms are optionally oxidized, wherein the N atoms are optionally quaternized.

In preferred embodiments, $R^{87}$ or the entire group $—((R_1)_p—R_2)_n—(R_1)_p—R_3$ satisfies molecules from Group $R^M$ shown below:

$R^M$:

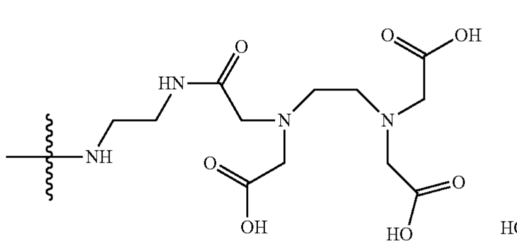

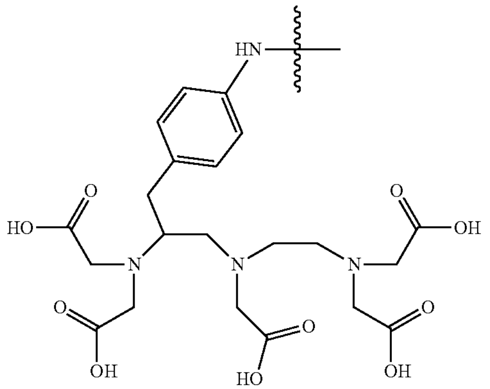

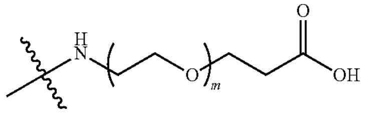

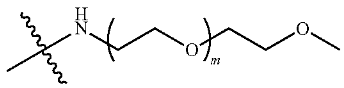

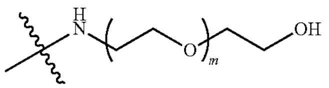

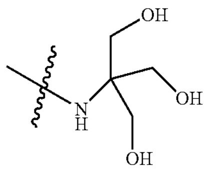

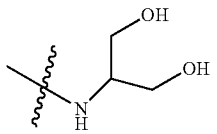

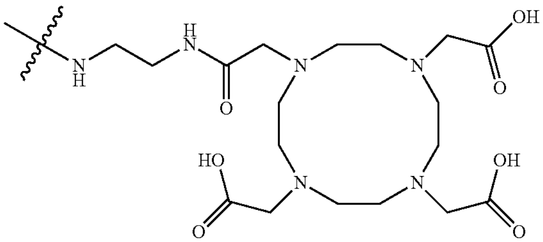

-continued
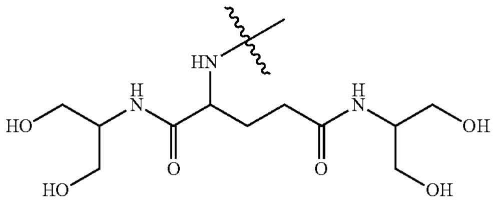
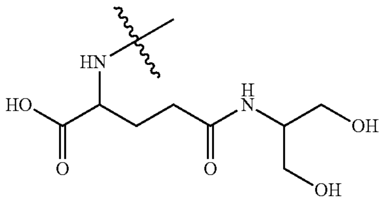
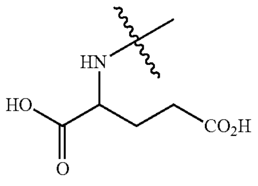
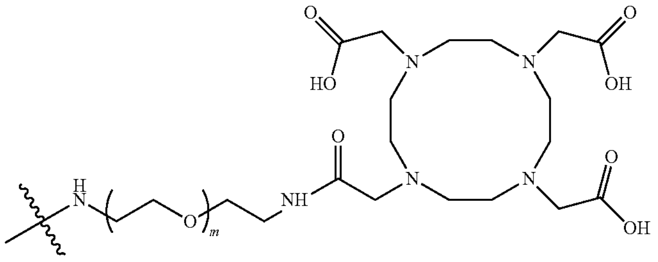
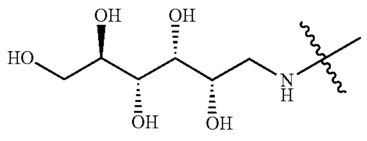
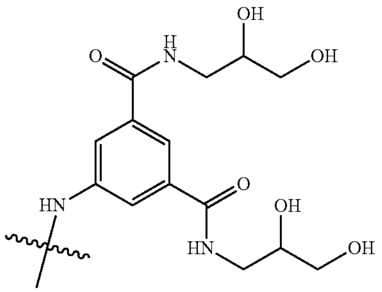
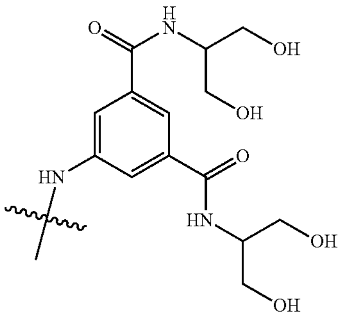
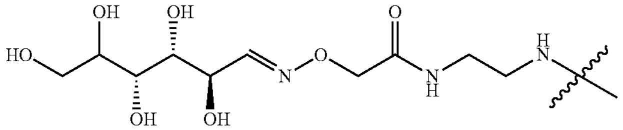
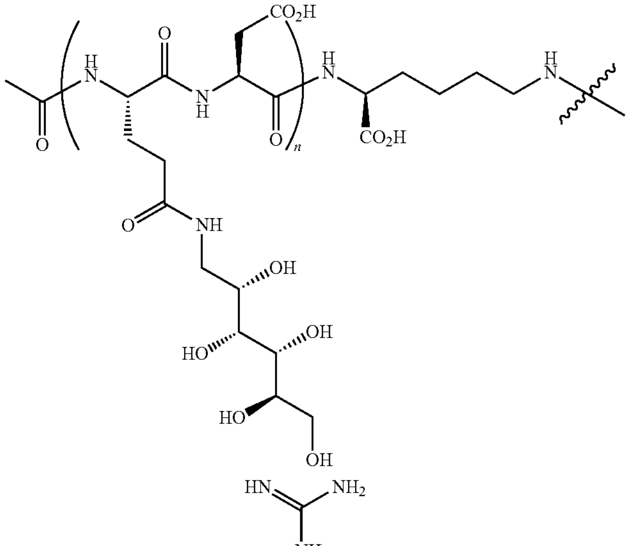
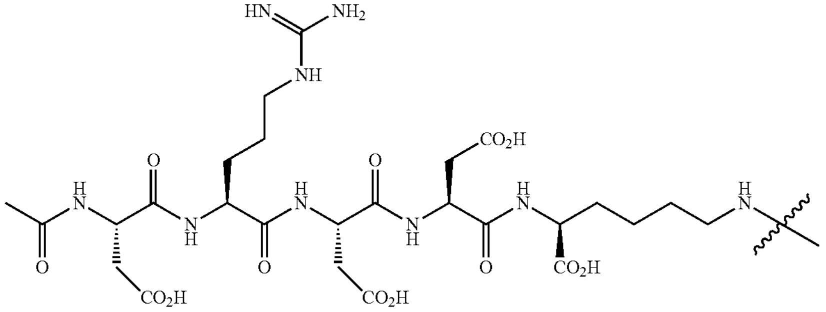

-continued
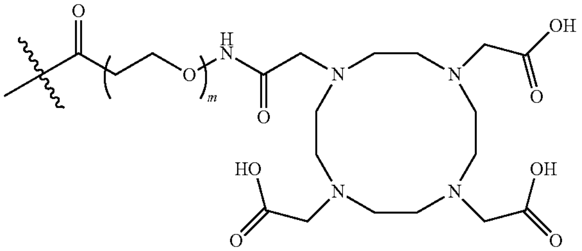
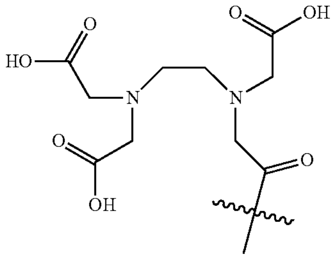
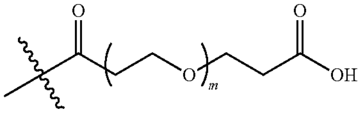
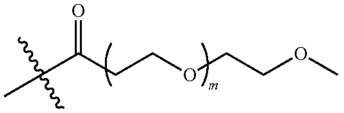
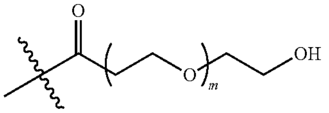
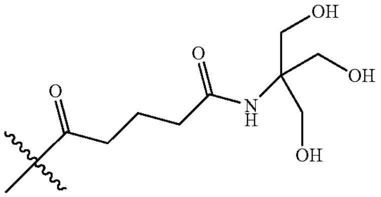
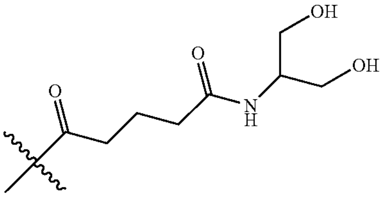
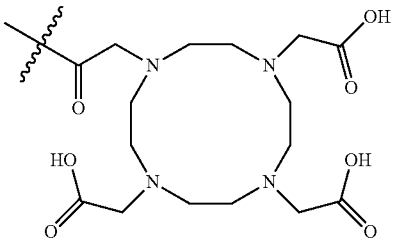
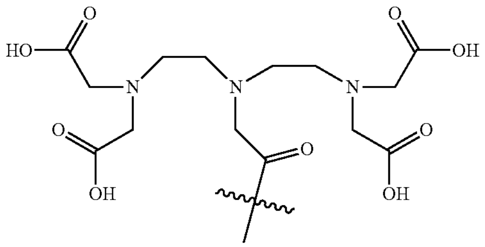
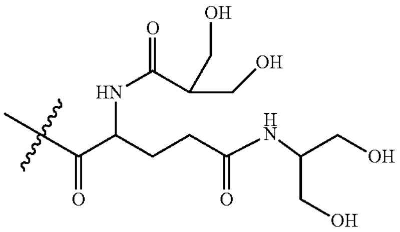
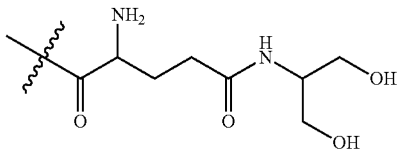
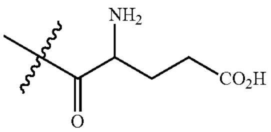
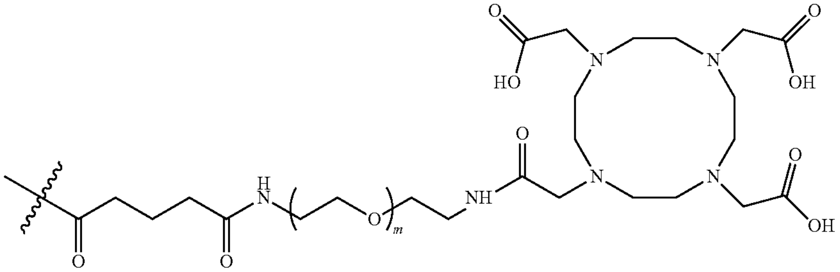
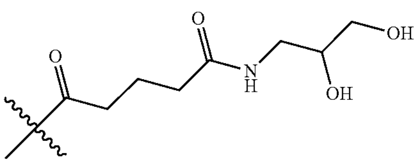
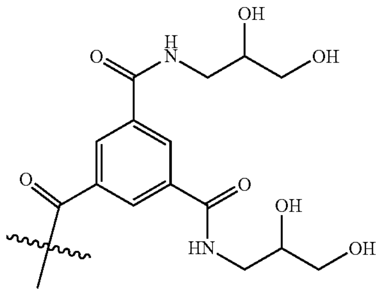
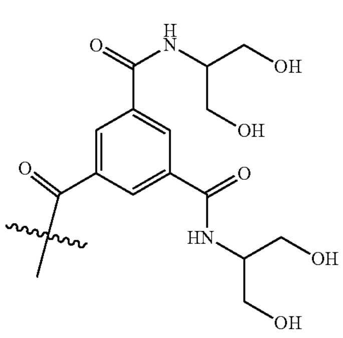

-continued

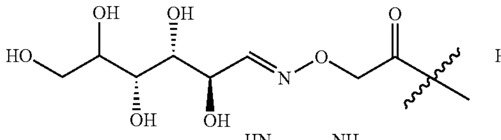

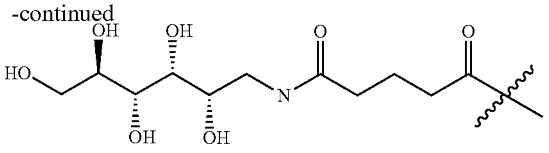

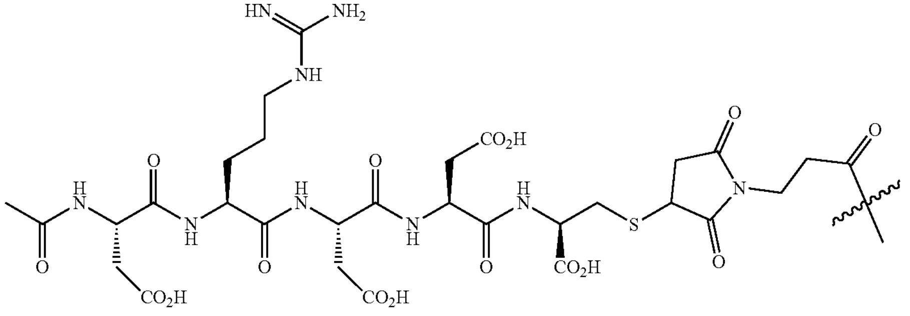

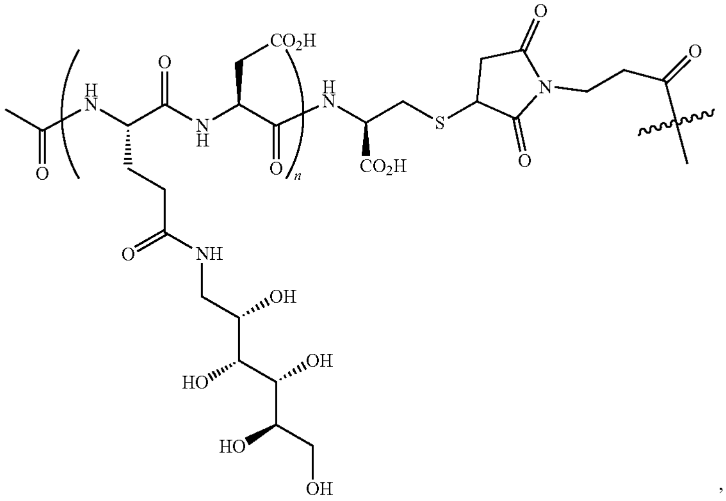

, m = 1-24, pref max 12
n = 1-8, pref max 4 wherein the wiggly line denotes a bond to a tetrazine group as disclosed herein or to a group $R_1$ or $R_2$.

In preferred embodiments, the group —$((R_1)_p$—$R_2)_n$—$(R_1)_p$—$R_3$ satisfies molecules from Group $R^M$, wherein it is understood that when n is more than 1, —$((R_1)_p$—$R_2)_n$—$(R_1)_p$—$R_3$ may be preceded by a group —$((R_1)_p$—$R_2)$— so as to form a group —$((R_1)_p$—$R_2)$—$((R_1)_p$—$R_2)_n$—$(R_1)_p$—$R_3$. It is understood that this follows from the definition of how to write out the repeating units, i.e. —$((R_1)_p$—$R_2)_2$— would first be written as —$(R_1)_p$—$R_2$—$(R_1)_p$—$R_2$— before $R_1$, p, and $R_2$ are independently selected.

$R_1$, $R_2$, $R_3$ $R_1$ is as defined for $R_{10}$. $R_2$ is as defined for $R_{11}$. $R_3$ is as defined for $R_{12}$.

$R_4$

Preferably, each $R_4$ is independently selected from the group consisting of hydrogen, $C_1$-$C_{24}$ alkyl groups, $C_2$-$C_{24}$ alkenyl groups, $C_2$-$C_{24}$ alkynyl groups, $C_6$-$C_{24}$ aryl, $C_2$-$C_{24}$ heteroaryl, $C_3$-$C_{24}$ cycloalkyl groups, $C_5$-$C_{24}$ cycloalkenyl groups, and $C_{12}$-$C_{24}$ cycloalkynyl groups.

In a preferred embodiment, each $R_4$ is independently selected from the group consisting of hydrogen, $C_1$-$C_{12}$ alkyl groups, $C_2$-$C_{12}$ alkenyl groups, $C_2$-$C_{12}$ alkynyl groups, $C_6$-$C_{12}$ aryl, $C_2$-$C_{12}$ heteroaryl, $C_3$-$C_{12}$ cycloalkyl groups, $C_5$-$C_{12}$ cycloalkenyl groups, and $C_{12}$ cycloalkynyl groups.

In a preferred embodiment, each $R_4$ is independently selected from the group consisting of hydrogen, $C_1$-$C_4$ alkyl groups, $C_2$-$C_4$ alkenyl groups, $C_2$-$C_4$ alkynyl groups, $C_6$ aryl, $C_2$-$C_6$ heteroaryl, $C_3$-$C_8$ cycloalkyl groups, $C_5$-$C_8$ cycloalkenyl groups, and $C_8$ cycloalkynyl groups.

Preferably, the $R_4$ groups not being hydrogen, optionally contain one or more heteroatoms selected from the group consisting of O, S, $NR_5$, P, and Si, wherein the N, S, and P atoms are optionally oxidized, wherein the N atoms are optionally quaternized.

Preferably, the $R_4$ groups not being hydrogen, are optionally further substituted with one or more substituents selected from the group consisting of —Cl, —F, —Br, —I, —OH, —$NH_2$, —$SO_3H$, —$PO_3H$, —$PO_4H_2$, —$NO_2$, —$CF_3$, =O, =$NR_5$, —$SR_5$, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ alkyl(hetero)aryl groups, $C_3$-$C_{24}$ (hetero)arylalkyl groups, $C_4$-$C_{24}$ (hetero)arylalkenyl groups, $C_4$-$C_{24}$ (hetero)arylalkynyl groups, $C_4$-$C_{24}$ alkenyl(hetero)aryl groups, $C_4$-$C_{24}$ alkynyl(hetero)aryl groups, $C_4$-$C_{24}$ alkylcycloalkyl groups, $C_6$-$C_{24}$ alkylcycloalkenyl groups, $C_{13}$-$C_{24}$ alkylcycloalkynyl groups, $C_4$-$C_{24}$ cycloalkylalkyl groups, $C_6$-$C_{24}$ cycloalkenylalkyl groups, $C_{13}$-$C_{24}$ cycloalkynylalkyl groups, $C_5$-$C_{24}$ alkenylcycloalkyl groups, $C_7$-$C_{24}$ alkenylcycloalkenyl groups, $C_{14}$-$C_{24}$ alkenylcycloalkynyl groups, $C_5$-$C_{24}$ cycloalkylalkenyl groups, $C_7$-$C_{24}$ cycloalkenylalkenyl groups, $C_{14}$-$C_{24}$ cycloalkynylalkenyl groups, $C_5$-$C_{24}$ alkynylcycloalkyl groups, $C_7$-$C_{24}$ alkynylcycloalkenyl groups, $C_{14}$-$C_{24}$ alkynylcycloalkynyl groups, $C_5$-$C_{24}$ cycloalkylalkynyl groups, $C_7$-$C_{24}$ cycloalkenylalkynyl groups, $C_{14}$-$C_{24}$ cycloalkynylalkynyl groups, $C_5$-$C_{24}$ cycloalkyl(hetero)aryl groups, $C_7$-$C_{24}$ cycloalkenyl(hetero)aryl groups, $C_{14}$-$C_{24}$ cycloalkynyl(hetero)aryl groups, $C_5$-$C_{24}$ (hetero)arylcycloalkyl groups, $C_7$-$C_{24}$ (hetero)arylcycloalkenyl groups, and $C_{14}$-$C_{24}$ (hetero)arylcycloalkynyl groups; wherein the substituents optionally contain one or more heteroatoms selected from the group consisting of O, S, NRs, P, and Si, wherein the N, S, and P atoms are optionally oxidized, wherein the N atoms are optionally quaternized.

Preferably, the $R_4$ groups not being hydrogen, are optionally further substituted with one or more substituents selected from the group consisting of —Cl, —F, —Br, —I, —OH, —$NH_2$, —$SO_3H$, —$PO_3H$, —$PO_4H_2$, —$NO_2$, —$CF_3$, =O, =$NR_5$, —$SR_5$, $C_1$-$C_4$ alkyl groups, $C_2$-$C_4$ alkenyl groups, $C_2$-$C_4$ alkynyl groups, $C_6$ aryl groups, $C_2$-$C_4$ heteroaryl groups, $C_3$-$C_4$ cycloalkyl groups, $C_5$—$C_4$ cycloalkenyl groups, $C_{12}$ cycloalkynyl groups, $C_3$-$C_{12}$ alkyl (hetero)aryl groups, $C_3$-$C_{12}$ (hetero)arylalkyl groups, $C_4$-$C_{12}$ (hetero)arylalkenyl groups, $C_4$-$C_{12}$ (hetero)arylalkynyl groups, $C_4$-$C_{12}$ alkenyl(hetero)aryl groups, $C_4$-$C_{12}$ alkynyl (hetero)aryl groups, $C_4$-$C_{12}$ alkylcycloalkyl groups, $C_6$-$C_{12}$ alkylcycloalkenyl groups, $C_{13}$-$C_{12}$ alkylcycloalkynyl groups, $C_4$-$C_{12}$ cycloalkylalkyl groups, $C_6$-$C_{12}$ cycloalkenylalkyl groups, $C_{13}$ cycloalkynylalkyl groups, $C_5$-$C_{12}$ alkenylcycloalkyl groups, $C_7$-$C_{12}$ alkenylcycloalkenyl groups, $C_{14}$ alkenylcycloalkynyl groups, $C_5$-$C_{12}$ cycloalkylalkenyl groups, $C_7$-$C_{12}$ cycloalkenylalkenyl groups, $C_{14}$ cycloalkynylalkenyl groups, $C_5$-$C_{12}$ alkynylcycloalkyl groups, $C_7$-$C_{12}$ alkynylcycloalkenyl groups, $C_{14}$-$C_{12}$ alkynylcycloalkynyl groups, $C_5$-$C_{12}$ cycloalkylalkynyl groups, $C_7$-$C_{12}$ cycloalkenylalkynyl groups, $C_{14}$ cycloalkynylalkynyl groups, $C_5$-$C_{12}$ cycloalkyl(hetero)aryl groups, $C_7$-$C_{12}$ cycloalkenyl (hetero)aryl groups, $C_{14}$ cycloalkynyl(hetero)aryl groups, $C_5$-$C_{12}$ (hetero)arylcycloalkyl groups, $C_7$-$C_{12}$ (hetero)arylcycloalkenyl groups, and $C_{14}$ (hetero)arylcycloalkynyl groups; wherein the substituents optionally contain one or more heteroatoms selected from the group consisting of O, S, NRs, P, and Si, wherein the N, S, and P atoms are optionally oxidized, wherein the N atoms are optionally quaternized.

In a preferred embodiment, the $R_4$ substituents do not contain heteroatoms. In a preferred embodiment, the $R_4$ groups are not substituted. In another preferred embodiment, the $R_4$ groups do not contain heteroatoms.

$R_5$

Preferably, each $R_5$ is independently selected from the group consisting of hydrogen, $C_1$-$C_8$ alkyl groups, $C_2$-$C_8$ alkenyl groups, $C_2$-$C_8$ alkynyl groups, $C_6$-$C_{12}$ aryl, $C_2$-$C_{12}$ heteroaryl, $C_3$-$C_8$ cycloalkyl groups, $C_5$-$C_8$ cycloalkenyl groups, $C_3$-$C_{12}$ alkyl(hetero)aryl groups, $C_3$-$C_{12}$ (hetero) arylalkyl groups, $C_4$-$C_{12}$ alkylcycloalkyl groups, $C_4$-$C_{12}$ cycloalkylalkyl groups, $C_5$-$C_{12}$ cycloalkyl(hetero)aryl groups and $C_5$-$C_{12}$ (hetero)arylcycloalkyl groups, wherein the $R_5$ groups not being hydrogen are optionally substituted with a moiety selected from the group consisting of —Cl, —F, —Br, —I, —OH, —$NH_2$, —$SO_3H$, —$PO_3H$, —$PO_4H_2$, —$NO_2$, —$CF_3$, =O, =NH, and —SH, and optionally contain one or more heteroatoms selected from the group consisting of O, S, NH, P, and Si, wherein the N, S, and P atoms are optionally oxidized, wherein the N atoms are optionally quaternized.

In a preferred embodiment, the $R_5$ groups are not substituted. In another preferred embodiment, the $R_5$ groups do not contain heteroatoms.

Moieties Q, $Q_1$, $Q_2$, $Q_3$, $Q_4$

In preferred embodiments, g is an integer in a range of from 0 to 12, preferably from 0 to 10, more preferably from 0 to 8, even more preferably from 1 to 6, most preferably from 2 to 4. In other preferred embodiments g is 0. In case more than one moiety selected from the group consisting of Q, $Q_1$, $Q_2$, $Q_3$, and $Q_4$ within one compound satisfies Formula (5), each g is independently selected. In preferred embodiments, h is 0 or 1. In case more than one moiety selected from the group consisting of Q, $Q_1$, $Q_2$, $Q_3$, and $Q_4$ within one compound satisfies Formula (5), each h is independently selected. In preferred embodiments, each f belonging to a moiety Q, $Q_1$, $Q_2$, $Q_3$, or $Q_4$ is an integer independently selected from a range of from 0 to 24, preferably from 1 to 12, more preferably from 1 to 6, even more preferably from 1 to 3, most preferably f is 0 or 1. In preferred embodiments f is preferably an integer from 12 to 24. In other preferred embodiments, f is 1.

In preferred embodiments, the group $—((R_{10})_h—R_{11})_f—(R_{10})_h—R_{12}$ satisfies molecules from Group $R^M$ shown above.

In preferred embodiments, the group $—((R_{10})_h—R_{11})_f—(R_{10})_h—R_{12}$ satisfies molecules from Group $R^M$, wherein it is understood that when f is more than 1, e.g. $—((R_{10})_h—R_{11})_{f-1}—(R_{10})_h—R_{12}$ may be preceded by a group $—(R_{10})_h—R_{11}—$ so as to form a group $—(R_{10})_h—R_{11}—((R_{10})_h—R_{11})_{f-1}—(R_{10})_h—R_{12}$. It is understood that this follows from the definition of how to write out the repeating units, i.e. $—((R_{10})_h—R_{11})_2—$ would first be written as $—(R_{10})_h—R_{11}—(R_{10})_h—R_{11}—$ before $R_{10}$, h, and $R_{11}$ are independently selected.

Formula (14)

In a preferred embodiment, the Activator is a tetrazine satisfying Formula (14):

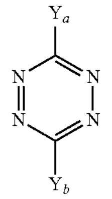

Formula (14), and preferably including pharmaceutically acceptable salts thereof, wherein, $Y_a$ is selected from the group consisting of $Y_1$, $Y_2$, $Y_3$, $Y_4$, $Y_5$, $Y_6$, and $Y_7$:

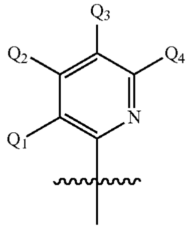

$Y_1$

-continued

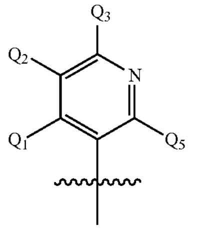

$Y_2$

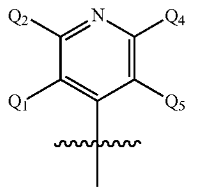

$Y_3$

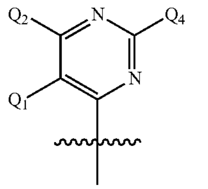

$Y_4$

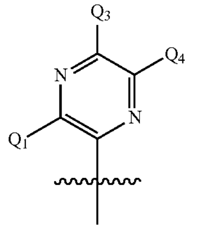

$Y_5$

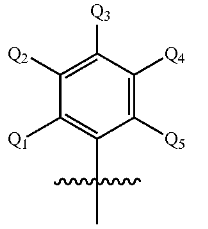

$Y_6$

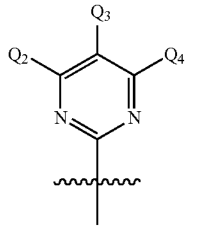

$Y_7$ wherein, $Y_b$ is selected from the group consisting of $Y_1$, $Y_2$, $Y_3$, $Y_4$, $Y_5$, $Y_6$, $Y_7$, hydrogen, $X_{47}$, and —$(S^P)_D$—$R^{87}$; wherein D is 0 or 1; wherein when $Y_a$ is $Y_6$, then Yb is hydrogen, wherein each $Q_1$ and $Q_5$, are individually selected from the group consisting of $X_{45}$, hydrogen, $X_{47}$ and —$(S^P)_D$ —$R^{87}$; wherein each $Q_2$ and $Q_4$, are individually selected from the group consisting of $X_{46}$, hydrogen, $X_{47}$, and —$(S^P)$D-$R^{87}$; wherein each $Q_3$ is individually selected from the group consisting of hydrogen, $X_{47}$, and —$(S^P)$D-$R^{87}$; wherein preferably the compound of Formula (14) comprises at least one $X_{45}$ or $X_{46}$ group, wherein each $X_{45}$ individually is selected from the group consisting of $N(X_{50})_2$, $C(X_{51})_2N(X_{50})_2$, $NX_{50}C(O)X_{51}$, $NX_{50}C(S)X_{51}$, OH, SH, C(O)OH, C(S)OH, C(O)SH, C(S)SH, $NX_{50}C(O)OX_{51}$, $NX_{50}C(S)OX_{51}$, $NX_{50}C(O)SX_{51}$, $NX_{50}C(S)SX_{51}$, $NX_{50}C(O)N(X_{51})_2$, $NX_{50}C(S)N(X_{51})_2$, $NX_{50}SO_2X_{51}$, $NX_{50}SO_3X_{51}$, $NX_{50}OX_{51}$, $SO_3H$, and $PO_3H_2$; wherein each $X_{46}$ individually is selected from the group consisting of $N(X_{50})_2$, $C(X_{51})_2N(X_{50})_2$, $NX_{50}C(O)X_{51}$, $NX_{50}C(S)X_{51}$, OH, SH, C(O)OH, C(S)OH, C(O)SH, C(S)SH, $NX_{50}C(O)OX_{51}$, $NX_{50}C(S)OX_{51}$, $NX_{50}C(O)SX_{51}$, $NX_{50}C(S)SX_{51}$, $NX_{50}C(O)N(X_{51})_2$, $NX_{50}C(S)N(X_{51})_2$, $NX_{50}SO_2X_{51}$, $NX_{50}SO_3X_{51}$, $NX_{50}OX_{51}$, $SO_3H$, and $PO_3H_2$; wherein each $X_{50}$ and $X_{51}$ individually is selected from the group consisting of hydrogen, $X_{48}$, and —$(S^P)$D-$R^{87}$; wherein each $X_{48}$ is preferably independently selected from the group consisting of hydrogen, $C_1$-$C_4$ alkyl groups, $C_2$-$C_4$ alkenyl groups, and $C_{4-6}$ (hetero)aryl groups; wherein for $X_{48}$ the alkyl groups, alkenyl groups, and (hetero)aryl groups are optionally substituted with a moiety selected from the group consisting of —Cl, —F, —Br, —I, —OH, —$NH_2$, =O, —SH, —$SO_3H$, —$PO_3H$, —$PO_4H_2$, and —$NO_2$; and optionally contain at most two heteroatoms selected from the group consisting of —O—, —S—, —NH—, —P—, and —Si—, wherein the N, S, and P atoms are optionally oxidized, wherein each $X_{47}$ is selected from the group consisting of —F, —Cl, —Br, —I, —$OX_{49}$, —$N(X_{49})_2$, —$SO_3$, —$PO_3$—, —$NO_2$, —$CF_3$, —$SX_{49}$, $S(=O)_2N(X_{49})_2$, $OC(=O)X_{49}$, $SC(=O)X_{49}$, $OC(=S)X_{49}$, $SC(=S)X_{49}$, $NX_{49}C(=O)$—$X_{49}$, $NX_{49}C(=S)$—$X_{49}$, $NX_{49}C(=O)O$—$X_{49}$, $NX_{49}C(=S)O$—$X_{49}$, $NX_{49}C(=O)S$—$X_{49}$, $NX_{49}C(=S)S$—$X_{49}$, $OC(=O)N(X_{49})_2$, $SC(=O)N(X_{49})_2$, $OC(=S)N(X_{49})_2$, $SC(=S)N(X_{49})_2$, $NX_{49}C(=O)N(X_{49})_2$, $NX_{49}C(=S)N(X_{49})_2$, $C(=O)X_{49}$, $C(=S)X_{49}$, $C(=O)N(X_{49})_2$, $C(=S)N(X_{49})_2$, $C(=O)O$—$X_{49}$, $C(=O)S$—$X_{49}$, $C(=S)O$—$X_{49}$, $C(=S)S$—$X_{49}$, —$S(O)X_{49}$, —$S(O)_2X_{49}$, $NX_{49}S(O)_2X_{49}$, —$ON(X_{49})_2$, —$NX_{49}OX_{49}$, $C_1$-$C_8$ alkyl groups, $C_2$-$C_8$ alkenyl groups, $C_2$-$C_8$ alkynyl groups, $C_6$-$C_{12}$ aryl, $C_2$-$C_{12}$ heteroaryl, $C_3$-$C_8$ cycloalkyl groups, $C_5$-$C_8$ cycloalkenyl groups, $C_3$-$C_{12}$ alkyl(hetero)aryl groups, $C_3$-$C_{12}$ (hetero)arylalkyl groups, $C_4$-$C_{12}$ alkylcycloalkyl groups, $C_4$-$C_{12}$ cycloalkylalkyl groups, $C_5$-$C_{12}$ cycloalkyl (hetero)aryl groups and $C_5$-$C_{12}$ (hetero)arylcycloalkyl groups, wherein the alkyl groups, alkenyl groups, alkynyl groups, aryl, heteroaryl, cycloalkyl groups, cycloalkenyl groups, alkyl(hetero)aryl groups, (hetero)arylalkyl groups, alkylcycloalkyl groups, cycloalkylalkyl groups, cycloalkyl (hetero)aryl groups and (hetero)arylcycloalkyl groups are optionally substituted with a moiety selected from the group consisting of —Cl, —F, —Br, —I, —$OX_{49}$, —$N(X_{49})_2$, —$SO_3X_{49}$, —$PO_3(X_{49})_2$, —$PO_4(X_{49})_2$, —$NO_2$, —$CF_3$, =O, =$NX_{49}$, and —$SX_{49}$, and optionally contain one or more heteroatoms selected from the group consisting of O, S, $NX_{49}$, P, and Si, wherein the N, S, and P atoms are optionally oxidized, wherein the N atoms are optionally quaternized; wherein $X_{49}$ is selected from the group consisting of hydrogen, $C_1$-$C_8$ alkyl groups, $C_2$-$C_8$ alkenyl groups, $C_2$-$C_8$ alkynyl groups, $C_6$-$C_{12}$ aryl, $C_2$-$C_{12}$ heteroaryl, $C_3$-$C_8$ cycloalkyl groups, $C_5$-$C_8$ cycloalkenyl groups, $C_3$-$C_{12}$ alkyl(hetero)aryl groups, $C_3$-$C_{12}$ (hetero) arylalkyl groups, $C_4$-$C_{12}$ alkylcycloalkyl groups, $C_4$-$C_{12}$ cycloalkylalkyl groups, $C_5$-$C_{12}$ cycloalkyl(hetero)aryl groups and $C_5$-$C_{12}$ (hetero)arylcycloalkyl groups, wherein the $X_{49}$ groups not being hydrogen are optionally substituted with a moiety selected from the group consisting of —Cl, —F, —Br, —I, —OH, —$NH_2$, —$SO_3H$, —$PO_3H$, —$PO_4H_2$, —$NO_2$, —$CF_3$, =O, =NH, and —SH, and optionally contain one or more heteroatoms selected from the group consisting of O, S, NH, P, and Si, wherein the N, S, and P atoms are optionally oxidized, wherein the N atoms are optionally quaternized, wherein preferably at most two, more preferably at most one of $Q_1$, $Q_2$, $Q_3$, $Q_4$, and $Q_5$ are $R^{87}$; wherein the compound according to Formula (14) preferably comprises for each individual $Y_a$ and Yb at most four $R^{87}$ groups, more preferably at most two $R^{87}$ groups, most preferably at most one $R_{87}$; wherein the compound according to Formula (14) preferably comprises at least one $R_{87}$; wherein preferably for each individual $Y_a$ and $Y_b$ at most three, more preferably at most two of $Q_1$, $Q_2$, $Q_3$, $Q_4$, and $Q_5$ are not hydrogen; wherein preferably for each individual $Y_a$ and Yb at most two of $Q_1$, $Q_2$, $Q_3$, $Q_4$, and $Q_5$ are $X_{45}$ or $X_{46}$, wherein preferably for each individual $Y_a$ and $Y_b$ one of $Q_1$, $Q_2$, $Q_4$, and $Q_5$ is $X_{45}$ or $X_{46}$, wherein preferably both $Y_a$ and Yb comprise at least one $X_{45}$ or $X_{46}$, wherein preferably both $Y_a$ and $Y_b$ comprise one $X_{45}$ or $X_{46}$, wherein preferably both $Y_a$ and Yb comprise one $X_{45}$ or $X_{46}$, whereby the $X_{45}$ comprised in $Y_a$ is the same as the $X_{45}$ comprised in $Y_b$, and/or the $X_{46}$ comprised in $Y_a$ is the same as the $X_{46}$ comprised in Yb, wherein preferably $Y_a$ and Yb are both independently selected $Y_1$, or both independently selected $Y_2$, or both independently selected $Y_3$, or both independently selected $Y_4$, or both independently selected $Y_5$; or both independently selected $Y_7$.

In a preferred embodiment, in Formula (14), when $Q_1$ is a $X_{47}$ or —$(S^P)$D-$R^{87}$, then for $Q_1$ the $X_{47}$ and —$(S^P)$D-$R^{87}$ are not a group in accordance with the definition of $X_{45}$. In a preferred embodiment, in Formula (14), when $Q_5$ is a $X_{47}$ or —$(S^P)$D-$R^{87}$, then for $Q_5$ the $X_{47}$ and —$(S^P)$D-$R^{87}$ are not a group in accordance with the definition of $X_{45}$. In a preferred embodiment, in Formula (14), when $Q_2$ is a $X_{47}$ or —$(S^P)$D-$R^{87}$, then for $Q_2$ the $X_{47}$ and —$(S^P)$D-$R^{87}$ are not a group in accordance with the definition of $X_{46}$. In a preferred embodiment, in Formula (14), when $Q_4$ is a $X_{47}$ or —$(S^P)_D$—$R^{87}$, then for $Q_4$ the $X_{47}$ and —$(S^P)$D-$R^{87}$ are not a group in accordance with the definition of $X_{46}$.

In preferred embodiments $Y_a$ equals Yb.

In preferred embodiments $Y_a$ is selected from $Y_1$, $Y_2$, $Y_3$, $Y_4$ or $Y_5$ and $Y_b$ is hydrogen, $X_{47}$ or —$(S^P)_D$—$R^{87}$. In preferred embodiments $Y_a$ is selected from $Y_1$, $Y_2$, $Y_3$, $Y_4$ or $Y_5$ and Yb is hydrogen. In preferred embodiments the compound according to Formula (14) does not comprise —$(S^P)$D-$R^{87}$.

In preferred embodiments, $X_{50}$ is hydrogen.

In preferred embodiments when $X_{45}$ or $X_{46}$ is $N(X_{50})_2$, then one $X_{50}$ is hydrogen and one $X_{50}$ is $X_{48}$ or —$(S^P)$D-$R^{87}$.

In preferred embodiments Formula (14) does not comprise $X_{46}$. In preferred embodiments, both $Q_1$ in Formula (14) are $X_{45}$. In preferred embodiments, both $Q_2$ in Formula (14) are $X_{46}$. In preferred embodiments, both $Q_5$ in Formula (14) are $X_{45}$. In preferred embodiments, both $Q_4$ in Formula (14) are $X_{46}$.

$X_{45}$

In a preferred embodiment, each $X_{45}$ individually is selected from the group consisting of $N(X_{50})_2$, $NX_{50}C(O)X_{51}$, $NX_{50}C(S)X_{51}$, OH, SH, $NX_{50}C(O)OX_{51}$, $NX_{50}C(S)OX_{51}$, $NX_{50}C(O)SX_{51}$, $NX_{50}C(S)SX_{51}$, $NX_{50}C(O)N(X_{51})_2$, $NX_{50}C(S)N(X_{51})_2$, $NX_{50}SO_2X_{51}$, $NX_{50}SO_3X_{51}$, $NX_{50}OX_{51}$.

In a preferred embodiment, each $X_{45}$ individually is selected from the group consisting of $N(X_{50})_2$, $NX_{50}C(O)X_{51}$, $NX_{50}C(S)X_{51}$, OH and SH.

In a preferred embodiment, each $X_{45}$ individually is selected from the group consisting of $NX_{50}C(O)OX_{51}$, $NX_{50}C(S)OX_{51}$, $NX_{50}C(O)SX_{51}$, $NX_{50}C(S)SX_{51}$, $NX_{50}C(O)N(X_{51})_2$, $NX_{50}C(S)N(X_{51})_2$, $NX_{50}SO_2X_{51}$, $NX_{50}SO_3X_{51}$, $NX_{50}OX_{51}$.

In a preferred embodiment, $X_{45}$ is selected from the group consisting of $NHX_{50}$, $C(X_{51})_2NH_2$, $CHX_{51}NH_2$, $CH_2N(X_{50})_2$, $CH_2NHX_{50}$, $NHC(O)X_{51}$, $NHC(S)X_{51}$, OH, and SH.

In a preferred embodiment, $X_{45}$ is $NHX_{50}$. In a preferred embodiment, $X_{45}$ is $C(X_{51})_2NH_2$. In a preferred embodiment, $X_{45}$ is $CHX_{51}NH_2$. In a preferred embodiment, $X_{45}$ is $CH_2N(X_{50})_2$. In a preferred embodiment, $X_{45}$ is $CH_2NHX_{50}$. In a preferred embodiment, $X_{45}$ is $NH_2$. In a preferred embodiment, $X_{45}$ is $CH_2NH_2$. In a preferred embodiment, $X_{45}$ is $NHC(O)X_{51}$. In a preferred embodiment, $X_{45}$ is $NHC(S)X_{51}$. In a preferred embodiment, $X_{45}$ is OH. In a preferred embodiment, $X_{45}$ is SH.

$X_{46}$

In a preferred embodiment, $X_{46}$ is individually selected from the group consisting of $N(X_{50})_2$, $NX_{50}C(O)X_{51}$, $NX_{50}C(O)OX_{51}$, and $NX_{50}C(O)N(X_{51})_2$. In a preferred embodiment, $X_{46}$ is selected from the group consisting of $N(X_{50})_2$, and $NX_{50}C(O)X_{51}$. In a preferred embodiment, $X_{46}$ is selected from the group consisting of $NHX_{50}$ and $NHC(O)X_{51}$. In a preferred embodiment, $X_{46}$ is $NHX_{50}$. In a preferred embodiment, $X_{46}$ is $NH_2$. In a preferred embodiment, $X_{46}$ is $NHC(O)X_{51}$.

$X_{47}$

In a preferred embodiment, each $X_{47}$ is individually selected from the group consisting of F, —OH, —$NH_2$, —$SO_3$—, —$NO_2$, —$CF_3$, —SH, $C_1$-$C_6$ alkyl groups, $C_6$ aryl groups, $C_4$-$C_5$ heteroaryl groups, $C_5$-$C_8$ alkyl(hetero)aryl groups, $C_5$-$C_8$ (hetero)arylalkyl groups, $C_4$-$C_8$ alkylcycloalkyl groups, and $C_4$-$C_8$ cycloalkylalkyl groups. In a more preferred embodiment, each $X_{47}$ is individually selected from the group consisting of F, —$SO_3$—, —$NO_2$, —$CF_3$, $C_1$-$C_6$ alkyl groups, $C_6$ aryl groups, $C_4$-$C_5$ heteroaryl groups, $C_5$-$C_8$ alkyl(hetero)aryl groups, $C_5$-$C_8$ (hetero)arylalkyl groups, $C_4$-$C_8$ alkylcycloalkyl groups, and $C_4$-$C_8$ cycloalkylalkyl groups. In a preferred embodiment, the $X_{47}$ substituents do not contain heteroatoms. In a preferred embodiment, the $X_{47}$ groups are not substituted. In another preferred embodiment, the $X_{47}$ groups do not contain heteroatoms.

$X_{48}$

In a preferred embodiment, each $X_{48}$ is independently selected from the group consisting of hydrogen, $C_1$-$C_4$ alkyl groups, $C_2$-$C_4$ alkenyl groups, and $C_{4-6}$ (hetero)aryl groups. For $X_{48}$ the alkyl groups, alkenyl groups, and (hetero)aryl groups are optionally substituted with a moiety selected from the group consisting of —Cl, —F, —Br, —I, —OH, —$NH_2$, ═O, —SH, —$SO_3H$, —$PO_3H$, —$PO_4H_2$ and —$NO_2$; and optionally contain at most two heteroatoms selected from the group consisting of —O—, —S—, —NH—, —P—, and —Si—, wherein the N, S, and P atoms are optionally oxidized.

In a preferred embodiment, $X_{48}$ is $C_1$-$C_4$ alkyl. In a preferred embodiment, the $X_{48}$ substituents do not contain heteroatoms. In a preferred embodiment, the $X_{48}$ groups are not substituted. In another preferred embodiment, the $X_{48}$ groups do not contain heteroatoms.

$X_{49}$

In preferred embodiments, $X_{49}$ is selected from the group consisting of hydrogen, $C_1$-$C_8$ alkyl groups, $C_2$-$C_8$ alkenyl groups, $C_2$-$C_8$ alkynyl groups, $C_6$-$C_{12}$ aryl, $C_2$-$C_{12}$ heteroaryl, $C_3$-$C_8$ cycloalkyl groups, $C_5$-$C_8$ cycloalkenyl groups, $C_3$-$C_{12}$ alkyl(hetero)aryl groups, $C_3$-$C_{12}$ (hetero)arylalkyl groups, $C_4$-$C_{12}$ alkylcycloalkyl groups, $C_4$-$C_{12}$ cycloalkylalkyl groups, $C_5$-$C_{12}$ cycloalkyl(hetero)aryl groups and $C_5$-$C_{12}$ (hetero)arylcycloalkyl groups, wherein the $X_{49}$ groups not being hydrogen are optionally substituted with a moiety selected from the group consisting of —Cl, —F, —Br, —I, —OH, —$NH_2$, —$SO_3H$, —$PO_3H$, —$PO_4H_2$, —$NO_2$, —$CF_3$, =O, =NH, and —SH, and optionally contain one or more heteroatoms selected from the group consisting of O, S, NH, P, and Si, wherein the N, S, and P atoms are optionally oxidized, wherein the N atoms are optionally quaternized.

In preferred embodiments, $X_{49}$ is selected from the group consisting of hydrogen, $C_1$-$C_4$ alkyl groups, $C_2$-$C_4$ alkenyl groups, $C_2$-$C_4$ alkynyl groups, $C_6$-$C_8$ aryl, $C_2$-$C_8$ heteroaryl, $C_3$-$C_6$ cycloalkyl groups, $C_5$-$C_6$ cycloalkenyl groups, $C_3$-$C_{10}$ alkyl(hetero)aryl groups, $C_3$-$C_{10}$ (hetero)arylalkyl groups, $C_4$-$C_8$ alkylcycloalkyl groups, $C_4$-$C_8$ cycloalkylalkyl groups, $C_5$-$C_{10}$ cycloalkyl(hetero)aryl groups and $C_5$-$C_{10}$ (hetero)arylcycloalkyl groups, wherein the $X_{49}$ groups not being hydrogen are optionally substituted with a moiety selected from the group consisting of —Cl, —F, —Br, —I, —OH, —$NH_2$, —$SO_3H$, —$PO_3H$, —$PO_4H_2$, —$NO_2$, —$CF_3$, =O, =NH, and —SH, and optionally contain one or more heteroatoms selected from the group consisting of O, S, NH, P, and Si, wherein the N, S, and P atoms are optionally oxidized, wherein the N atoms are optionally quaternized.

In a preferred embodiment, the $X_{49}$ substituents do not contain heteroatoms. In a preferred embodiment, the $X_{49}$ groups are not substituted. In another preferred embodiment, the $X_{49}$ groups do not contain heteroatoms.

$X_{50}$

In a preferred embodiment, each $X_{50}$ is individually selected from the group consisting of hydrogen, $X_{48}$, and —$(S^P)_D$—$R^{87}$. In a preferred embodiment, $X_{50}$ is $X_{48}$. In a preferred embodiment, $X_{50}$ is —$(S^P)$D-$R^{87}$. In a preferred embodiment, $X_{50}$ is H.

$X_{51}$

In a preferred embodiment, each $X_{51}$ is individually selected from the group consisting of hydrogen, $X_{48}$, and —$(S^P)_D$—$R^{87}$. In a preferred embodiment, $X_{51}$ is $X_{48}$. In a preferred embodiment, $X_{51}$ is —$(S^P)$D-$R^{87}$. In a preferred embodiment, $X_{51}$ is H.

$Q_1$

In a preferred embodiment, in Formula (14) $Q_1$ is selected from the group consisting of hydrogen, $X_{47}$, and —$(S^P)_D$—$R^{87}$. In a preferred embodiment, $Q_1$ in Formula (14) is hydrogen. In a preferred embodiment, $Q_1$ in Formula (14) is $X_{47}$. In a preferred embodiment, $Q_1$ in Formula (14) is —$(S^P)$D-$R^{87}$, and preferably $Q_2$, $Q_3$, $Q_4$, $Q_5$, $Q_6$, $Q_7$, $Q_8$, $Q_9$, and $Q_{10}$ are $X_{45}$, $X_{46}$, or hydrogen.

$Q_2$

In a preferred embodiment, $Q_2$ in Formula (14) is selected from the group consisting of hydrogen $X_{47}$, and —$(S^P)$D-$R^{87}$. In a preferred embodiment, $Q_2$ in Formula (14) is hydrogen. In a preferred embodiment, $Q_2$ is in Formula (14) $X_{47}$. In a preferred embodiment, $Q_2$ in Formula (14) is —$(S^P)$D-$R^{87}$, and preferably $Q_1$, $Q_3$, $Q_4$, $Q_5$, $Q_6$, $Q_7$, $Q_8$, $Q_9$, and $Q_{10}$ are $X_{45}$, $X_{46}$, or hydrogen.

$Q_3$

In a preferred embodiment, $Q_3$ in Formula (14) is selected from the group consisting of hydrogen $X_{47}$, and —$(S^P)$D-$R^{87}$. In a preferred embodiment, $Q_3$ in Formula (14) is hydrogen. In a preferred embodiment, $Q_3$ in Formula (14) is $X_{47}$. In a preferred embodiment, $Q_3$ in Formula (14) is —$(S^P)$D-$R^{87}$, and preferably $Q_1$, $Q_2$, $Q_4$, $Q_5$, $Q_6$, $Q_7$, $Q_8$, $Q_9$, and $Q_{10}$ are $X_{45}$, $X_{46}$, or hydrogen.

$Q_4$

In a preferred embodiment, $Q_4$ in Formula (14) is selected from the group consisting of hydrogen $X_{47}$, and —$(S^P)$D-$R^{87}$. In a preferred embodiment, $Q_4$ in Formula (14) is hydrogen. In a preferred embodiment, $Q_4$ in Formula (14) is $X_{47}$. In a preferred embodiment, $Q_4$ in Formula (14) is —$(S^P)$D-$R^{87}$, and preferably $Q_1$, $Q_2$, $Q_3$, $Q_5$, $Q_6$, $Q_7$, $Q_8$, $Q_9$ and $Q_{10}$ are $X_{45}$, $X_{46}$, or hydrogen.

$Q_5$

In a preferred embodiment, $Q_5$ in Formula (14) is selected from the group consisting of hydrogen $X_{47}$, and —$(S^P)$D-$R^{87}$. In a preferred embodiment, $Q_5$ in Formula (14) is hydrogen. In a preferred embodiment, $Q_5$ in Formula (14) is $X_{47}$. In a preferred embodiment, $Q_5$ is —$(S^P)$D-$R^{87}$, and preferably $Q_1$, $Q_2$, $Q_3$, $Q_4$, $Q_6$, $Q_7$, $Q_8$, $Q_9$ and $Q_{10}$ are $X_{45}$, $X_{46}$, or hydrogen.

$Q_6$

In a preferred embodiment, $Q_6$ in Formula (14) is selected from the group consisting of hydrogen $X_{47}$, and —$(S^P)$D-$R^{87}$. In a preferred embodiment, $Q_6$ in Formula (14) is hydrogen. In a preferred embodiment, $Q_6$ in Formula (14) is $X_{47}$. In a preferred embodiment, $Q_6$ in Formula (14) is —$(S^P)$D-$R^{87}$, and preferably $Q_1$, $Q_2$, $Q_3$, $Q_4$, $Q_5$, $Q_7$, $Q_8$, $Q_9$ and $Q_{10}$ are $X_{45}$, $X_{46}$, or hydrogen.

$Q_7$

In a preferred embodiment, $Q_7$ in Formula (14) is selected from the group consisting of hydrogen $X_{47}$, and —$(S^P)$D-$R^{87}$. In a preferred embodiment, $Q_7$ in Formula (14) is hydrogen. In a preferred embodiment, $Q_7$ in Formula (14) is $X_{47}$. In a preferred embodiment, $Q_7$ in Formula (14) is —$(S^P)$D-$R^{87}$, and preferably $Q_1$, $Q_2$, $Q_3$, $Q_4$, $Q_5$, $Q_6$, $Q_8$, $Q_9$ and $Q_{10}$ are $X_{45}$, $X_{46}$, or hydrogen.

$Q_8$

In a preferred embodiment, $Q_8$ in Formula (14) is selected from the group consisting of hydrogen $X_{47}$, and —$(S^P)$D-$R^{87}$. In a preferred embodiment, $Q_8$ in Formula (14) is hydrogen. In a preferred embodiment, $Q_8$ in Formula (14) is $X_{47}$. In a preferred embodiment, $Q_8$ in Formula (14) is —$(S^P)$D-$R^{87}$, and preferably $Q_1$, $Q_2$, $Q_3$, $Q_4$, $Q_5$, $Q_6$, $Q_7$, $Q_9$ and $Q_{10}$ are $X_{45}$, $X_{46}$, or hydrogen.

$Q_9$

In a preferred embodiment, $Q_9$ in Formula (14) is selected from the group consisting of hydrogen $X_{47}$, and —$(S^P)$D-$R^{87}$. In a preferred embodiment, $Q_9$ in Formula (14) is hydrogen. In a preferred embodiment, $Q_9$ in Formula (14) is $X_{47}$. In a preferred embodiment, $Q_9$ in Formula (14) is —$(S^P)$D-$R^{87}$, and preferably $Q_1$, $Q_2$, $Q_3$, $Q_4$, $Q_5$, $Q_6$, $Q_7$, $Q_8$ and $Q_{10}$ are $X_{45}$, $X_{46}$, or hydrogen.

$Q_{10}$

In a preferred embodiment, $Q_{10}$ in Formula (14) is selected from the group consisting of hydrogen $X_{47}$, and —$(S^P)_D$—$R^{87}$. In a preferred embodiment, $Q_{10}$ in Formula (14) is hydrogen. In a preferred embodiment, $Q_{10}$ in Formula (14) is $X_{47}$. In a preferred embodiment, $Q_{10}$ in Formula (14) is —$(S^P)$D-$R^{87}$, and preferably $Q_1$, $Q_2$, $Q_3$, $Q_4$, $Q_5$, $Q_6$, $Q_7$, $Q_8$ and $Q_9$ are $X_{45}$, $X_{46}$, or hydrogen.

$R^{87}$

Preferably, $R^{87}$ has a molecular weight of at least 100 Da, more preferably of at least 200 Da, more preferably at least 300 Da, more preferably at least 400 Da, more preferably at least 500 Da, and most preferably at least 1 kDa.

Preferably, $R^{87}$ has a molecular weight of at most 100 kDa, more preferably of at most 75 kDa, more preferably at most 50 kDa, more preferably at most 25 kDa, more preferably at most 10 kDa, and most preferably at most 3 kDa.

Preferably, $R^{87}$ has a molecular weight in a range of from 100 Da to 3000 Da. Preferably, $R^{87}$ has a molecular weight at at least 60 kDa, preferably at least 100 kDa. preferably at least 200 kDa, most preferably at least 500 kDa.

In a preferred embodiment, $R^{87}$ is a polymer, more preferably polyethylene glycol. In another preferred embodiment, $R^{87}$ is a carbohydrate. In another preferred embodiment, $R^{87}$ is a peptide or a protein, more preferably an antibody.

It will be understood that $R^{87}$ in relation to the invention preferably is a moiety that modulates the pharmacokinetics of a compound according to any one of Formulae (4), (4a), and (6)-(14). So, preferably, $R^{87}$ is a pharmacokinetics-modulating moiety ($P^K$ moiety). The functions of $R^{87}$ include, but are not limited to, one or more of delaying clearance of said compound, affecting the volume of distribution of said compound (e.g. reducing or increasing the volume of distribution), affecting the biodistribution of said compound, achieving spatial control over its reaction with the Trigger, affecting (more particularly avoiding) the metabolism of said compound, and/or affecting (more particularly avoiding) the (undesired) sticking or (undesired) uptake of said compound to tissues. The skilled person is well aware of such groups, and how to synthesize these.

In a preferred embodiment $R^{87}$ serves to increase the blood circulation time, increasing reaction time with the Trigger.

In a preferred embodiment $R^{87}$ serves to modulate the pharmacokinetics of a reaction product between a dienophile of this invention and a compound according to any one of Formulae (4), (4a), and (6)-(14).

Without wishing to be bound by theory, it is believed that the function and performance of the tetrazine moiety of the compounds according to any one of Formulae (4), (4a), and (6)-(14) in a bioorthogonal reaction is not significantly affected by the nature of $R^{87}$.

In a preferred embodiment, each $P^K$ Moiety is individually selected from the group consisting of biomolecule, polymer, peptide, peptoid, dendrimer, protein, carbohydrate, oligonucleotide, oligosaccharide, aptamer, steroid, lipid, albumin, albumin-binding moiety, dye moiety, fluorescent moiety, imaging probe, and a Targeting Agent ($T^T$); and wherein $R^{87}$ is optionally bound to the tetrazine via a Spacer ($S^P$). Typically, a suitable polymer as $R^{87}$ is polyethyleneglycol (PEG). Such suitable PEG includes PEG with a number of repeating units in a range of from 2 to 4000, and PEG with a molecular weight in a range of from 200 Da to 100,000 Da.

In a preferred embodiment, $R^{87}$ is a moiety according to Formula (5).

In a preferred embodiment, $R^{87}$ is a moiety according to Formula (5), and is directly linked to the remainder of a compound according to any one of Formulae (4), (4a), and (6)-(14), for example without a spacer $S^P$ between $R^{87}$ and the remainder of the moiety $Y_a$ or Yb of any one of Formulae (4), (4a), and (6)-(14).

In a preferred embodiment, $R^{87}$ is a moiety according to Formula (5), and is directly linked to the remainder of a compound according to any one of Formulae (4), (4a), and (6)-(14), for example without a spacer $S^P$ between $R^{87}$ and the remainder of the moiety $Y_a$ or Yb of any one of Formulae (4), (4a), and (6)-(14), and if attached to an amine functionality of $X_{45}$ or $X_{46}$, z in Formula (5) is not 0.

In a preferred embodiment, $R^{87}$ is linked to the remainder of a compound according to any one of Formulae (4), (4a), and (6)-(14) via a spacer $S^P$ as defined herein.

In a preferred embodiment, $R^{87}$ is linked to the remainder of a compound according to any one of Formulae (4), (4a), and (6)-(14), optionally via a spacer $S^P$ as defined herein and each $R^{87}$ group is individually selected from the group consisting of biomolecule, polymer, peptide, peptoid, dendrimer, protein, carbohydrate, oligonucleotide, oligosaccharide, lipid, micelle, liposomes, polymersome, particle, nanoparticle, microparticle, bead, gel, resin, metal complex, organometallic moiety, albumin, albumin-binding moiety, dye moiety, fluorescent moiety, imaging probe, and a Targeting Agent ($T^T$).

In a preferred embodiment, one or multiple copies of the compound of the invention, i.e. the tetrazine, may be conjugated to $R^{87}$ groups that are gels, resins, polymers.

In a preferred embodiment, one or multiple copies of the compound of the invention may be conjugated to $R^{87}$ that is a Targeting Agent to selectively activate a Prodrug and selected locations in the body.

In a preferred embodiment, one or multiple copies of the compound of the invention may be conjugated to $R^{87}$ that is a membrane translocation moiety (e.g. adamantine, polylysine/arginine, TAT, human lactoferrin) to reach an intracellular Prodrug. Exemplary references regarding such moieties include: Trends in Biochemical Sciences, 2015, 40, 12, 749; J. Am. Chem. Soc. 2015, 137, 12153-12160; Pharmaceutical Research, 2007, 24, 11, 1977.

With respect to application in a cellular environment, such as in vivo, depending on the position of the Trigger-Construct (e.g. inside the cell or outside the cell) the Activator is designed to be able to effectively reach this Trigger-Construct. Therefore, the Activator can for example be tailored by varying its log P value, its reactivity or its charge, and this can optionally be achieved by $R^{87}$.

According to one preferred embodiment, the Activator can be a multimeric compound, comprising a plurality of tetrazines, optionally bound to one $R^{87}$. These multimeric compounds can be but are not limited to biomolecules, peptide, peptoid, protein, oligonucleotide, oligosaccharide, polymersome, bead, gel, polymers, dendrimers, liposomes, micelles, particles, nanoparticles, microparticles, polymer particles, or other polymeric constructs.

In a preferred embodiment, the tetrazine compounds of the invention comprise an imaging moiety instead of $R^{87}$. In other embodiments, $R^{87}$ is or comprises an imaging moiety. In this preferred embodiment the imaging moiety is bound to the remainder of the compounds of the invention in the same way as $R^{87}$. In this embodiment $R^{87}$ equals an imaging moiety. In a preferred embodiment, the compounds of the invention can comprise one or more imaging moieties and one or more $R^{87}$ groups.

In a preferred embodiment, $R^{87}$ is or comprises an imaging moiety. Preferred imaging moieties are radionuclide-chelates complexes, radiolabeled molecules (e.g. with $^{18}F$, $^{124}I$), and fluorescent dyes. In a preferred embodiment, $R^{87}$ is an imaging moiety that comprises at least one $^{18}F$ isotope.

In a preferred embodiment, $R^{87}$ comprises a chelating moiety, preferably a chelating moiety as described herein.

In a preferred embodiment, $R^{87}$ includes but is not limited to amino acids, nucleosides, nucleotides, carbohydrates, and biopolymer fragments, such as oligo- or polypeptides, oligo- or polypeptoids, or oligo- or polylactides, or oligo- or poly-carbohydrates, oligonucleotides, varying from 2 to 200, particularly 2 to 113, preferably 2 to 50, more preferably 2 to 24 and more preferably 2 to 12 repeating units.

In embodiments where it is required that the Activator has an extracellular volume of distribution it is preferred that the Log P of the Activator is at most 2, preferably at most 1, more preferably at most 0, even more preferably at most −1.

In embodiments where it is required that the Activator has an intracellular volume of distribution it is preferred that the Log P of the Activator is at least −1, preferably at least 0, more preferably at least 1, even more preferably at least 2.

In embodiments where it is required that the Activator has an extracellular volume of distribution it is preferred that the Activator has a negative net charge at pH 7.

In embodiments where it is required that the Activator has an intracellular volume of distribution it is preferred that the Activator has a molecular weight of less than 1000 Da, preferably less than 500 Da.

In embodiments where it is required that the Activator has an extracellular volume of distribution it is preferred that the Activator has a molecular weight of more than 500 Da, preferably more than 1 kDa, more preferably more than 2 kDa.

In embodiments where it is required that the Activator has slow or inefficient extravasation from circulation it is preferred that the Activator has a molecular weight of more than 5 kDa, preferably more than 60 Da, more preferably more than 150 Da, even more preferably more than 500 kDa.

In a preferred embodiment, $R^{87}$ is a polymer. This includes linear or branched polyalkylene glycols such as polyethylene glycol (PEG) or polypropylene glycol (PPG) chains varying from 2 to 200, particularly 2 to 113, preferably 2 to 50, more preferably 2 to 24 and more preferably 2 to 12 repeating units. It is preferred that when polyalkylene glycols such as PEG and PPG polymers are only bound via one end of the polymer chain, that the other end is terminated with $-OCH_3$, $-OCH_2CH_3$, $OCH_2CH_2CO_2H$.

Other polymeric $R^{87}$ groups are polymers and copolymers such as poly-(2-oxazoline, poly(N-(2-hydroxypropyl)methacrylamide) (HPMA), polylactic acid (PLA), polylactic-glycolic acid (PLGA), polyglutamic acid (PG), dextran, polyvinylpyrrolidone (PVP), poly(1-hydroxymethylethylene hydroxymethyl-formal (PHF). Other exemplary polymers are polysaccharides, glycopolysaccharides, glycolipids, polyglycoside, polyacetals, polyketals, polyamides, polyethers, polyesters. Examples of naturally occurring polysaccharides that can be used are cellulose, amylose, dextran, dextrin, levan, fucoidan, carraginan, inulin, pectin, amylopectin, glycogen, lixenan, agarose, hyaluronan, chondroitinsulfate, dermatansulfate, keratansulfate, alginic acid and heparin. In yet other exemplary embodiments, the polymer is a copolymer of a polyacetal/polyketal and a hydrophilic polymer selected from the group consisting of polyacrylates, polyvinyl polymers, polyesters, polyorthoesters, polyamides, oligopeptides, polypeptides and derivatives thereof. Exemplary preferred polymeric $R^{87}$ groups are PEG, HPMA, PLA, PLGA, PVP, PHF, dextran, oligopeptides, and polypeptides.

In some aspects of the invention polymeric $R^{87}$ groups have a molecular weight ranging from 2 to 200 kDa, from 2 to 100 kDa, from 2 to 80 kDa, from 2 to 60 kDa, from 2 to 40 kDa, from 2 to 20 kDa, from 3 to 15 kDa, from 5 to 10 kDa, from 500 dalton to 5 kDa.

Other exemplary $R^{87}$ groups are dendrimers, such as poly(propylene imine) (PPI) dendrimers, PAMAM dendrimers, and glycol based dendrimers.

In a preferred embodiment, the tetrazine compounds of the invention comprise a Drug $D^D$ instead of $R^{87}$. In this preferred embodiment the Drug is bound to the remainder of the compounds of the invention in the same way as $R^{87}$. In this embodiment $R^{87}$ equals a Drug. In a preferred embodiment, the compounds of the invention can comprise one or more Drugs and one or more $R^{87}$ groups. In a preferred embodiment, the Drug is a prodrug that becomes a Drug upon reaction of the tetrazine with the Trigger. In a preferred embodiment the Drug is a moiety comprising a therapeutic radionuclide, preferably a radiometal-chelate complex. In other preferred embodiments the moiety comprising a therapeutic radionuclide, is an organic molecule comprising $^{131}I$.

In a preferred embodiment, the tetrazine compounds of the invention comprise an imaging moiety instead of $R^{87}$. In other embodiments, $R^{87}$ is or comprises an imaging moiety. In the context of Prodrug activation in vivo, a tetrazine activator comprising an imaging moiety can be used to activate the Prodrug and at the same to measure the extent of Prodrug activation. In this preferred embodiment the imaging moiety is bound to the remainder of the compounds of the invention in the same way as $R^{87}$. In this embodiment $R^{87}$ equals an imaging moiety. In a preferred embodiment, the compounds of the invention can comprise one or more imaging moieties and one or more $R^{87}$ groups.

Preferred imaging moieties are moieties comprising a diagnostic radionuclide such as radionuclide-chelates complexes, radiolabeled molecules (e.g. with $^{18}F$, $^{124}I$), and fluorescent dyes.

In a preferred embodiment, $R^{87}$ is or comprises an imaging probe that comprises at least one $^{18}F$ isotope.

In a preferred embodiment $R^{87}$ equals Group $R^M$.

In a preferred embodiment $R^{87}$ serves to increase the blood circulation time, increasing reaction time with the Trigger.

In embodiments where it is required that the Activator has an extracellular volume of distribution it is preferred that the Log P of the Activator is at most 2, preferably at most 1, more preferably at most 0, even more preferably at most −1.

In embodiments where it is required that the Activator has an intracellular volume of distribution it is preferred that the Log P of the Activator is at least −1, preferably at least 0, more preferably at least 1, even more preferably at least 2.

In embodiments where it is required that the Activator has an extracellular volume of distribution it is preferred that the Agent has a negative net charge at pH 7.

In embodiments where it is required that the Activator has an intracellular volume of distribution it is preferred that the Agent has a molecular weight of less than 1000 Da, preferably less than 500 Da.

In embodiments where it is required that the Activator has an extracellular volume of distribution it is preferred that the Agent has a molecular weight of more than 500 Da, preferably more than 1 kDa, more preferably more than 2 kDa.

In embodiments where it is required that the Activator has slow or inefficient extravasation from circulation into tissues it is preferred that the Activator has a molecular weight of more than 5 kDa, preferably more than 60 Da, more preferably more than 150 Da, even more preferably more than 500 kDa.

In preferred embodiments wherein the Activator is not cell permeable, $R^{87}$ is a protein or polymer.

In preferred embodiments the $R^{87}$ reduces the extravasation of the Activator from blood into target tissue, by virtue of its large size and/or by the presence of a clearance-directing group. For example, $R^{87}$ being a PLGA microparticle will allow efficient IEDDA reaction with Administration Agent in circulation but will hamper efficient extravasation of the Activator into tumor tissue, and will result in rapid clearance by the liver. Likewise, $R^{87}$ being an albumin protein modified with ca. 10 galactose moieties (i.e. clearance-directing groups) to ensure rapid uptake by the liver, affords efficient IEDDA reaction in blood with no or minimal in minimizing extravasation into tumor tissue. Reference is made to [Rossin et al J. Nucl. Med. 2013, 4, 11, 1989-1995]. Likewise $R^{87}$ can be a small moiety comprising a Clearance-directing group to favor IEDDA reaction in blood vs. in tumor tissue.

Conversely, if whole body extracellular Label cleavage is desired the $R^{87}$ can be a 20 or 40 kDa PEG or albumin or an albumin-binding moiety ensuring prolonged retention in circulation, optionally combined with EPR based targeting of tumor tissue.

In one embodiment the Administration Agent specifically binds or complexes with a cell surface molecule, such as a cell surface receptor or antigen, for a given cell population. Following specific binding or complexing with the receptor, the cell is permissive for uptake of the Administration Agent, which then internalizes into the cell. The subsequently administered Activator will then enter the cell and cleave the Administration Agent, releasing the Label inside the cell. In another embodiment the Administration Agent specifically binds or complexes with a cell surface molecule, such as a cell surface receptor or antigen, for a given cell population. Following specific binding or complexing the receptor, the cell is not permissive for uptake of the Administration Agent. The subsequently administered Activator will then cleave the Administration Agent on the outside of the cell.

In an image cycling embodiment, centered on sequential imaging procedures of the same or different Primary Targets, it is preferred that the Activator acts systemically (i.e. in the whole body). In other image cycling embodiments it is preferred that the Activator comprises a $R^{87}$ that is a $T^T$ and selectively cleaves the Label at the Primary Target being imaged.

Therapeutic Use

In preferred embodiments, the compounds, combinations, and kits are for use as a medicament. Alternatively, the compounds, combinations, and kits are used in a method for treating patients, said method comprising administering the compounds comprised in the compounds, combinations, and kits to a subject.

Prodrug Configuration and Use

A Prodrug is a conjugate of the Drug and the TCO and comprises a Drug that is capable of increased therapeutic action after release of Construct-A from the TCO. Such a Prodrug may optionally have specificity for disease targets.

With reference for Formula 19, each Construct A and each Construct B are independently selected from the group consisting of drugs, targeting agents and masking moieties, provided that at least one Drug is comprised in the structure of Formula (19).

In a preferred embodiment $C^A$ is a Drug $D^D$. In a preferred embodiment, when $C^B$ is a targeting agent or a masking moiety, then $C^A$ is a $D^D$. In a preferred embodiment, when $C^B$ is a $D^D$, then $C^A$ is a masking moiety or a targeting agent. In a preferred embodiment, when $C^A$ is $D^D$ then $D^D$ is not bound to $T^R$ or $L^C$ via a Spacer $S^P$. In a preferred embodiment at most one $C^B$ is comprised in the structure of Formula (19). In preferred embodiments Trigger ($T^R$) cleavage results in the cleavage of one $C^A$ from one $C^B$. In another embodiment the Trigger cleavage results in cleavage of one $C^A$ from another $C^A$ when one $L^C$ is bound to two $C^A$ moieties, wherein one or both $C^A$ can release from the Trigger upon reaction with a diene, and wherein one $C^A$ is a $T^T$ or $M^M$ and the other is the $D^D$. Optionally, one or more $C^B$ can be additionally present and can independently be $T^T/M^M$ or Drug. In preferred embodiments Trigger cleavage results in the cleavage of one $C^A$ from two or more $C^B$. In preferred embodiments Trigger cleavage results in the cleavage of one $C^B$ from two or more $C^A$. In preferred embodiments, the Trigger is bound to only one $C^A$ and one $C^B$. In other preferred embodiments, the Trigger is bound to two $C^A$ moieties and no $C^B$ moieties. In other preferred embodiments, the Trigger is bound to one $C^A$ moiety and no $C^B$ moieties. In other preferred embodiments, the dienophile does not comprise a $C^B$ moiety.

In preferred embodiments wherein a $D^D$ is to be released from a $T^T$ or $M^M$, to ensure efficient cleavage of the $D^D$ from $T^T$ or $M^M$, if there are multiple $C^B$ moieties bound to the Trigger via $X^1$—$X^5$ then all these $C^B$ moieties are collectively either $T^T/M^M$ or $D^D$. If there is one or more $C^B$ bound via $X^1$—$X^5$ and one $C^B$ bound via $L^C$ then the $C^B$ bound via $L^C$ can be selected independently from the $C^B$ moieties bound to $X^1$—$X^5$.

If there are multiple $C^A$ moieties bound to the Trigger, through binding of multiple $C^A$ moieties via one linker $L^C$ (with reference to Formula 19: r is 1 or 2), each $C^A$ can independently be $T^T/M^M$ or Drug.

In a preferred embodiment, $C^B$ is not comprised in $X^5$.

In a preferred embodiment the targeted Prodrug is an Antibody-Drug Conjugate (ADC). Activation of the Prodrug by the IEDDA pyridazine elimination of the TCO with the Activator leads to release of the Drug (FIG. 1). In a preferred embodiment the Drugs comprised in said ADC are low to medium molecular weight compounds, preferably organic compounds (e.g. about 200 to about 2500 Da, preferably about 300 to about 1750 Da, more preferably about 300 to about 1000 Da).

It is desirable to be able to activate targeted Prodrugs such as ADCs selectively and predictably at the target site without being dependent on homogenous penetration and targeting, and on endogenous activation parameters (e.g. pH, enzymes) which may vary en route to and within the target, and from indication to indication and from patient to patient. The use of a biocompatible chemical reaction that does not rely on endogenous activation mechanisms for selective Prodrug activation would represent a powerful new tool in cancer therapy. It would expand the scope to cancer-related receptors and extracellular matrix targets that do not afford efficient internalization of the ADC and therefore cannot be addressed with the current ADC approaches. In addition, extraneous and selective activation of Prodrugs when and where required leads to enhanced control over Prodrug activation, intracellularly and extracellularly. Finally this approach would maximize the bystander effect, allowing more efficient Drug permeation throughout the tumor tissue.

Other areas that would benefit from an effective prodrug approach are protein-based therapies and immunotherapy, for example bispecific T-cell engaging antibody constructs, which act on cancer by binding cancer cells and by engaging the immune system [Trends in Biotechnology 2015, 33, 2, 65]. Antibody constructs containing an active T-cell binding site suffer from peripheral T-cell binding. This not only prevents the conjugate from getting to the tumor but can also lead to cytokine storms and T-cell depletion. Photo-activatable anti-T-cell antibodies, i.e. T-cell directed Prodrugs, in which the anti-T-cell activity is only restored when and where it is required (i.e. after tumor localization via the tumor binding arm), following irradiation with UV light, has been used to overcome these problems [Thompson et al., Biochem. Biophys. Res. Commun. 366 (2008) 526-531]. However, light based activation is limited to regions in the body where light can penetrate, and is not easily amendable to treating systemic disease such as metastatic cancer.

Other proteins that could benefit from a Prodrug approach are immunotoxins and immunocytokines which suffer from respectively immunogenicity and general toxicity.

Hydrophilic polymers (such as polyethylene glycol, peptide and proteins have been used as cleavable masking moieties of various substrates, such as proteins, drugs and liposomes, in order to reduce their systemic activity. However, the used cleavage strategies were biological (pH, thiol, enzyme), as used in the ADC field, with the same drawbacks.

In order to avoid the drawbacks of current prodrug activation, this invention makes use of an abiotic, bio-orthogonal chemical reaction to provoke release of the Drug from the Prodrug, such as an ADC. In this type of ADC, in a preferred embodiment, the Drug is attached to the antibody (or another type of Targeting Agent) via a Trigger, and this Trigger is not activated endogenously by e.g. an enzyme or a specific pH, but by a controlled administration of the Activator, i.e. a species that reacts with the Trigger moiety in the ADC, to induce release of the Drug from the Trigger (or vice versa, release of the Trigger from the Drug, however one may view this release process) (FIG. 1).

Figure 2:
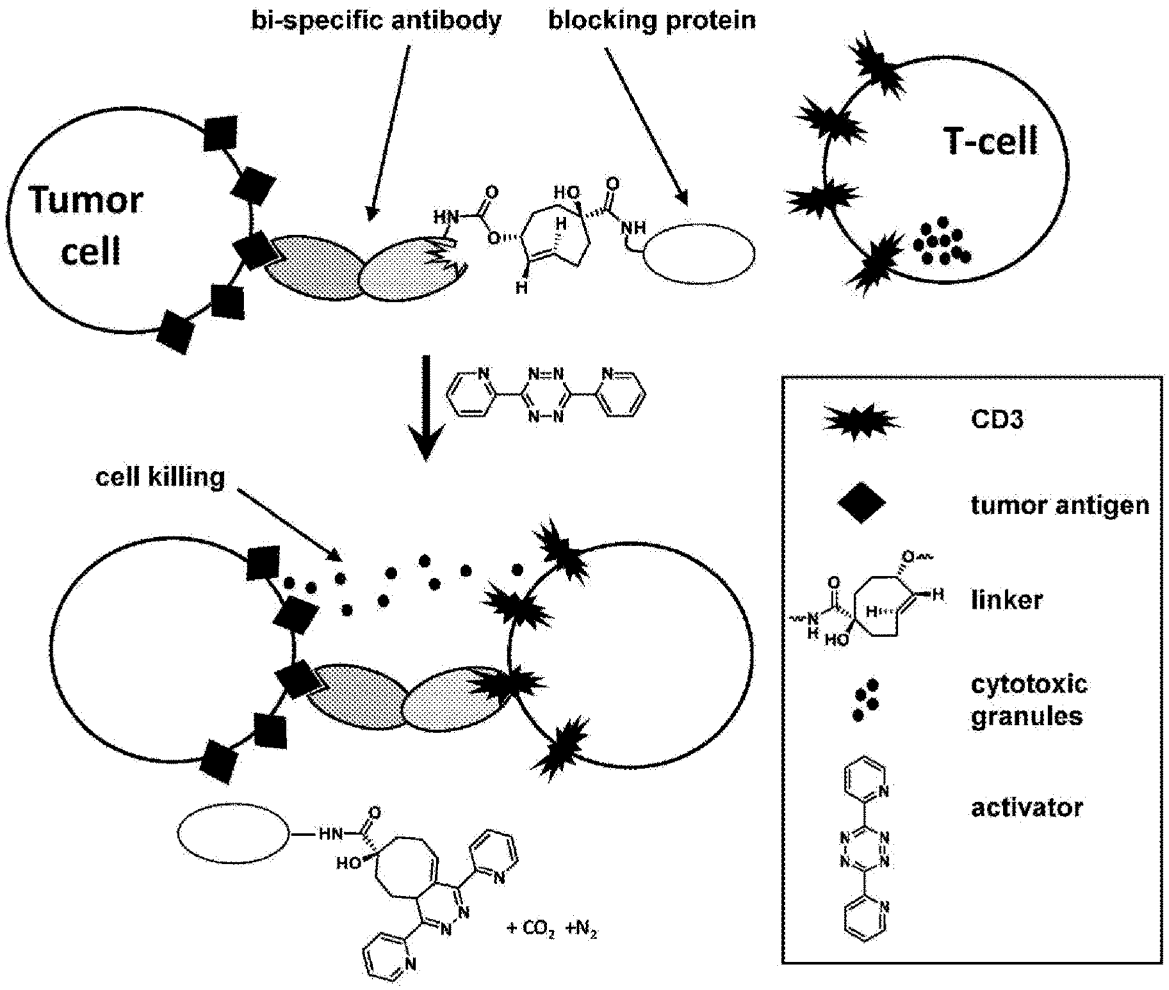
FIG. 2 depicts a preferred embodiment of this invention. An antibody construct comprising a bi-specific (anti-tumor and anti-CD3) antibody and a masking moiety (blocking protein) is administered to a cancer patient, and is allowed to circulate and bind to a target on the cancer cell. After the freely circulating construct has sufficiently cleared from circulation, for example after 2 days post injection, the Activator, is administered and distributes systemically, allowing the reaction with the Trigger of cancer-bound Prodrug, releasing the mask, after which T-cells bind the bi-specific antibody resulting in tumor killing.

In another preferred embodiment, the Prodrug comprises a Drug bound via the trigger to a Masking Moiety. Administration of the Activator, induces release of the Drug from the Masking Moiety, resulting in activation of the Drug. In a particular embodiment, a protein with specificity for a tumor target is fused to a protein with specificity for the CD3 receptor on T-cells, wherein the CD3 binding domain is masked by conjugation of a cysteine near the domain to a Trigger comprising a Masking Moiety. Following tumor binding of the masked bispecific protein, the Activator is administered leading to unmasking of the CD3 domain and the binding to T-cells (FIG. 2).

In a preferred embodiment, the present invention provides a kit for the administration and activation of a Prodrug, the kit comprising a Drug, denoted as $C^A$, linked directly, or indirectly through a linker $L^C$, to a Trigger moiety $T^R$, wherein $T^R$ or $L^C$ is bound to a Construct-B, $C^B$, that is Targeting Agent $T^T$ or a Masking Moiety $M^M$, and an Activator for the Trigger moiety, wherein the Trigger moiety comprises a dienophile and the Activator comprises a diene, the dienophile satisfying Formula (19).

In preferred embodiments, $C^B$ is the Drug and $C^A$ is a targeting agent or a masking moiety.

In yet another aspect, the invention provides a method of modifying a Drug compound into a Prodrug that can be triggered by an abiotic, bio-orthogonal reaction, the method comprising the steps of providing a Drug and chemically linking the Drug to a TCO moiety satisfying Formula (19).

In a still further aspect, the invention provides a method of treatment wherein a patient suffering from a disease that can be modulated by a Drug is treated by administering, to said patient, a Prodrug comprising a Drug, a Trigger moiety and a Targeting agent after activation of which by administration of an Activator the Drug will be released, wherein the Trigger moiety comprises a structure satisfying Formula (19).

In a still further aspect, the invention is a compound comprising a TCO moiety, said moiety comprising a linkage to a Drug, for use in Prodrug therapy in an animal or a human being.

In another aspect, the invention is the use of a tetrazine as an Activator for the release, in a physiological environment, of a substance covalently linked to a compound satisfying Formula (19). In connection herewith, the invention also pertains to a tetrazine for use as an Activator for the release, in a physiological environment, of a substance linked to a compound satisfying Formula (19), and to a method for activating, in a physiological environment, the release of a substance linked to a compound satisfying Formula (19), wherein a tetrazine is used as an Activator.

In preferred embodiments a Prodrug is a conjugate of the Drug and the Trigger and thus comprises a Drug that is preferably capable of increased therapeutic action after its release from the Trigger. In embodiments where the Prodrug is targeted to a Primary Target, as is the case with for example Antibody Drug Conjugates, the Prodrug can comprise a Targeting agent $T^T$, which is bound to either the Trigger or the L.

According to a further particular embodiment of the invention, the Prodrug is selected so as to target and or address a disease, such as cancer, an inflammation, an autoimmune disease, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme.

According to one embodiment, the Prodrug and/or the Activator can be, but are not limited to, multimeric compounds, comprising a plurality of Drugs and/or bioorthogonal reactive moieties. These multimeric compounds can be polymers, dendrimers, liposomes, polymer particles, or other polymeric constructs.

It is preferred that the optional $L^C$ comprised in the Prodrug is self-immolative, affording traceless release of the Drug.

It shall be understood that one $T^T$, being $C^A$ or $C^B$, can be modified with more than one Trigger. For example, an antibody can be modified with four TCO-Drug constructs by conjugation to four amino acid residues, wherein preferably when $C^B$ is the $T^T$ then $C^A$ is a Drug, and wherein when $C^A$ is the $T^T$, then $C^B$ or another $C^A$ is a Drug.

It shall be understood that one $D^D$, being $C^A$ or $C^B$, can be modified with more than one Trigger. For example, an protein drug can be modified with multiple TCO-$M^M$ constructs by conjugation to multiple amino acid residues, wherein preferably when $C^B$ is the $M^M$ then $C^A$ is a Drug, and wherein when $C^A$ is the $M^M$, then $C^B$ or another $C^A$ is a Drug.

Figure 3:
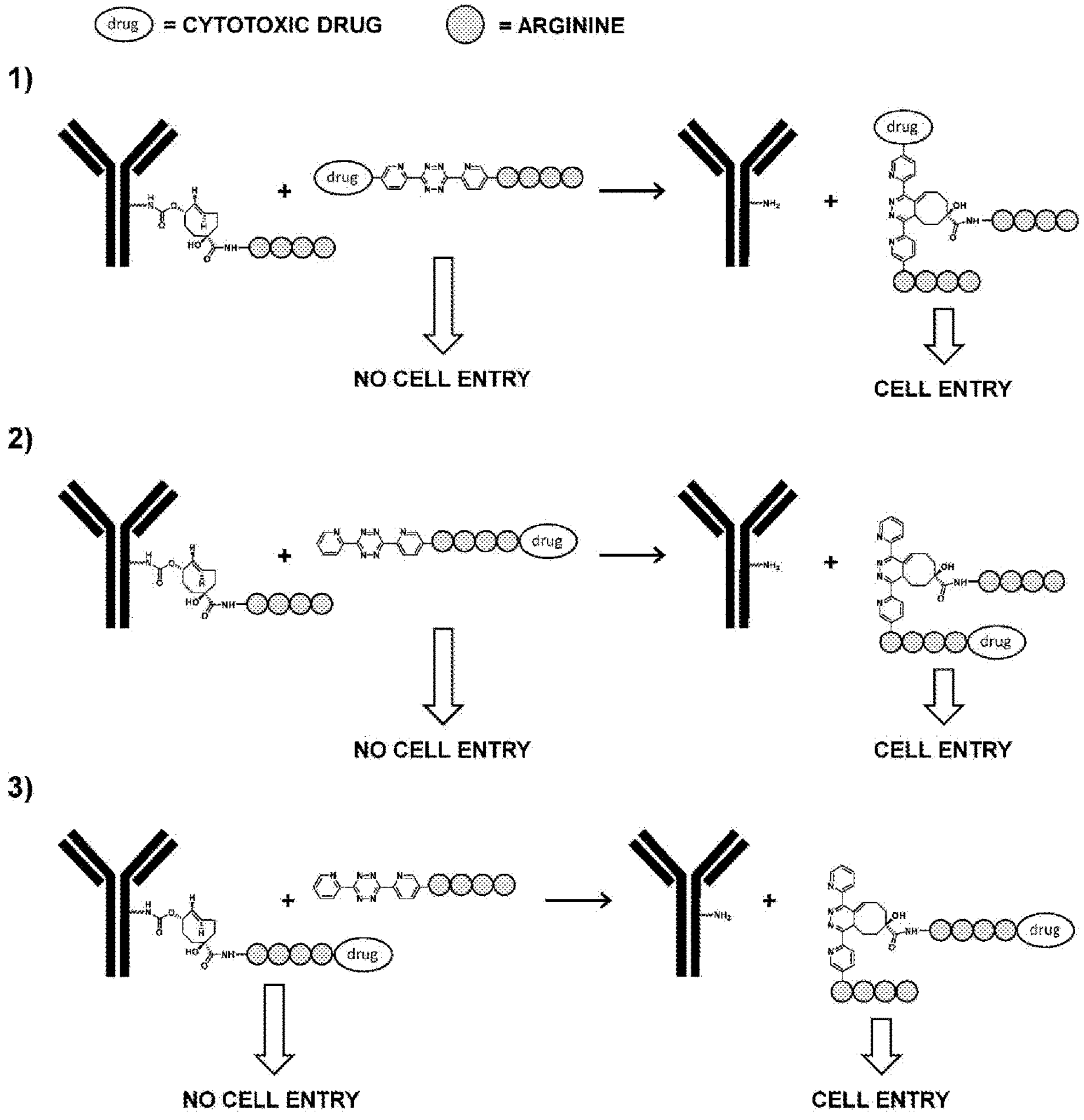
FIG. 3 depicts the in vivo assembly of a functional cell penetration peptide (CPP) at the target site, leading to triggered CPP-induced drug internalization.

In other embodiments the IEDDA pyridazine elimination with the compounds of this invention is used to generate a cell penetrating drug at the target site in vivo. With reference to FIG. 3, in one particular embodiment, a cell penetrating peptide (CPP) containing 8 sequential arginine residues is assembled out of 2 peptides containing 4 arginine residues, which as a tetramer do not exhibit cell penetration [Bode et al., Chem. Sci., 2019, 10, 701]. In FIG. 3 panel 1, a tumor-targeted antibody containing a click-cleavable linker bound to a tetra-arginine moiety (a $T^T$) is reacted with systemically adminstered tetrazine containing a drug and another tetra-arginine moiety (a $T^T$). Reaction leads to formation of a drug linked to 8 arginine residues that can then penetrate surrounding cells. In FIG. 3 panel 2, shows the same concept with the drug bound via a different position. In FIG. 3, panel 3, the tumor-targeted antibody containing a click-cleavable linker bound to a tetra-arginine moiety (a $T^T$), which is further linked to a Drug. This Antibody drug conjugate is reacted with systemically adminstered tetrazine containing another tetra-arginine moiety (a $T^T$). Reaction leads to formation and liberation of a drug linked to 8 arginine residues that can then penetrate surrounding cells.

Figure 4:
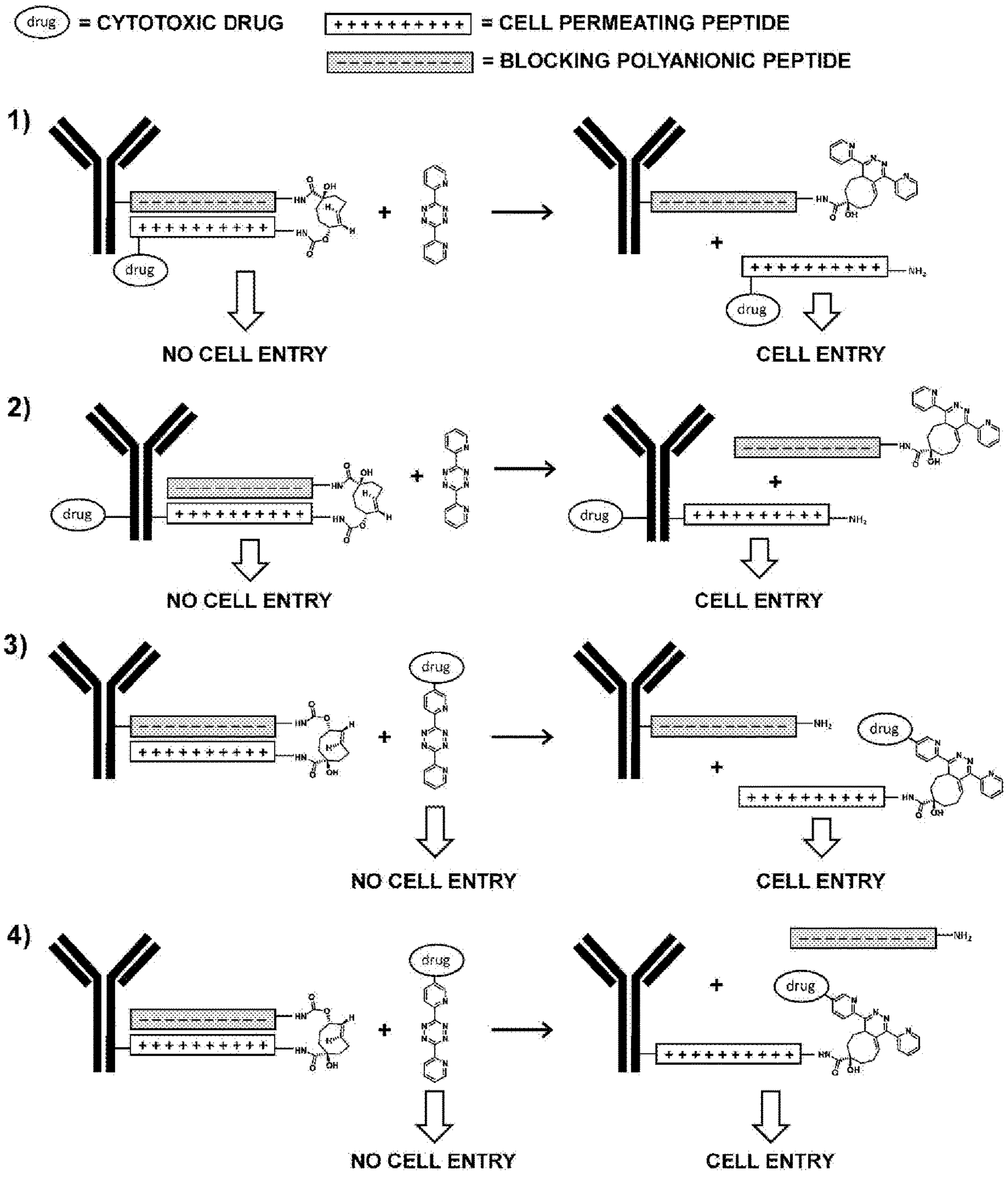
FIG. 4 depicts the in vivo unmasking of a functional cell penetration peptide (CPP) at the target site, leading to triggered CPP-induced drug internalization.
Figure 5:
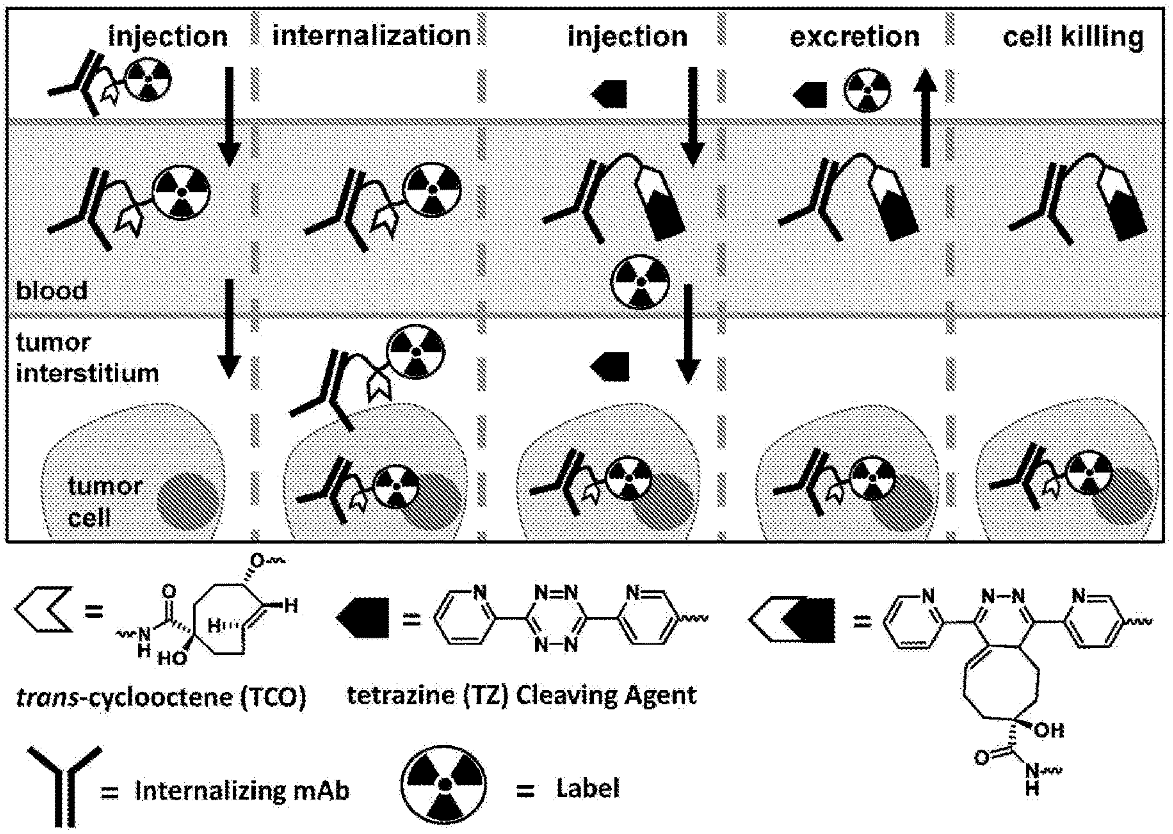
FIG. 5 depicts the use of the invention in radioimmunotherapy. A radiolabelled antibody is administered, allowed to circulate and bind an internalizing cancer receptor, and after sufficient internalization has occurred a Activator is administered that cleaves the radiolabel (e.g. a moiety comprising a radiometal-chelate complex) from the antibody, resulting in rapid renal clearance of the radioactivity from blood and non-target tissues, but not of the tumor cell-internalized radioactivity.

In other embodiments the IEDDA pyridazine elimination with the compounds of this invention is used to unmask a cell penetrating peptide leading to cell penetration of a drug at the target site in vivo. With reference to FIG. 4, in one particular embodiment, a polycationic cell penetrating peptide (CPP) containing 10 sequential arginine residues is masked by a polyanionic polyglutamate peptide containing 10 glutamate residues and which is linked via the TCO linker to the polyarginine linker. Reference is made to [Duijnhoven et al., J Nucl Med 2011, 52, 279]. In FIG. 4, panel 1, the tumor-targeted antibody containing a polyanionic peptide linked to click-cleavable TCO linker which in turn is bound to a poly-arginine peptide which is further linked to a Drug is reacted with systemically administered tetrazine leading to liberation of a drug linked to the polyarginine peptide that can then penetrate surrounding cells. In panel 2, a tumor-bound antibody-drug conjugate (ADC) which in addition is modified with a masked poly-arginine peptide is reacted with systemically administered tetrazine leading to unmasking of poly-arginine peptide and internalization of the ADC. In panel 3, a tumor-bound antibody modified with a masked poly-arginine peptide is reacted with systemically administered tetrazine-drug conjugate leading to unmasking and release of the poly-arginine peptide and its concomitant conjugation to the tetrazine-drug, leading to internalization of said drug. In panel 4, a tumor-bound antibody modified with a masked poly-arginine peptide is reacted with systemically administered tetrazine-drug conjugate leading to unmasking the poly-arginine peptide and the concomitant conjugation to the tetrazine-drug to the antibody, leading to internalization of the in situ formed ADC. In some preferred embodiments the polyanionic and polycationic peptides have a length of 8 amino acids. In some preferred embodiments wherein this invention is used to unmask a cell penetrating peptide leading to cell penetration of a drug at the target site in vivo, the Drug is or comprises a therapeutic radioactive moiety.

In other embodiments the IEDDA pyridazine elimination with the compounds of this invention is used to assemble a Drug in vivo. In an exemplary embodiment, and in a similar approach as with the above used CPP) a Drug being a prodrug is $C^B$ and $T^T$ is $C^A$. After binding to a Primary Target, an Activator that is bound to a Drug being a prodrug is administered and reacts with the Trigger on the Primary Target. This results in the concomitant conjugation of both prodrug moieties to one another, forming an active Drug, and the release of the Drug from the $T^T$.

In other embodiments the Prodrug comprises a Drug bound via $T^R$ to a polymer, a gel, a solid material (e.g. of an implantable drug depot) or a biomolecule reactive moiety such as $R^{32}$, and this Prodrug is directly administered into/near the region of interest (e.g. a tumor), resulting in local immobilization of the Prodrug, which can subsequently be activated by local or systemic administration of the Activator. Conversely, in other embodiments, the Activator is bound to a $R^{87}$ being a polymer, a gel, a solid material (e.g. of an implantable drug depot) or a biomolecule reactive moiety such as $R^{32}$, and is directly administered into/near the region of interest (e.g. a tumor), resulting in local immobilization of the Activator, which can locally activate the subsequently (locally or systemically) adminstered Prodrug (e.g. without a $T^T$). In another embodiment, the Activator, bound to a Targeting Agent, is systemically adminstered and allowed to bind the Primary Target, after which a non-targeted or targeted Prodrug is adminstered systemically and is activated at the Primary Target. In some embodiments the Prodrug consists of two constructs, which are the same or different Drugs $D^D$, and one or both $D^D$ are activated upon cleavage of $T^R$. In some embodiments, the Prodrug comprises two different $D^D$, with one $D^D$ functioning as a targeting agent $T^T$ in addition to being a $D^D$. In a particularly preferred embodiment, one of or both $D^D$ are activated upon cleavage of $T^R$.

In other embodiments, the Activator used to activate a targeted bound Prodrug, e.g. a tumor-bound ADC, comprises a Drug, for example a therapeutic radioactive moiety (e.g. $^{177}$Lu-DOTA chelate complex conjugated to the tetrazine) to augment the therapeutic effect of the released drug. For example, therapeutic radiation (e.g. beta emission) is known to stimulate an anticancer immune response. By releasing an anticancer drug and at the same time activating the immune system a greater anticancer effect can be obtained. In preferred embodiments the released Drug is a cytotoxic molecule, to be combined with therapeutic radiation (low or high dose). In preferred embodiments the released Drug is a radiation sensitizer, to be combined with therapeutic radiation (low or high dose). In other embodiments the released Drug is an immune modulator (e.g. a TLR agonist, or a cytokine) to be combined with therapeutic radiation (low or high dose).

In a preferred embodiment, the Prodrug is a radiosensitizer drug. Then, it is preferred that this Prodrug be combined with a radiolabelled diene. Thus, upon a reaction between the Prodrug and the radiolabelled diene, the radiosensitizer is released, and the radiation from the radiolabelled diene can be augmented.

In another embodiment the Prodrug comprises a $T^T$ bound via the $T^R$ to a Drug, wherein the Drug is or comprises a therapeutic radioactive moiety, and wherein, optionally, release of the radioactive moiety at the target site, e.g. a tumor, may result in deeper and more homogeneous penetration and distribution of the radioactivity than when the radioactive moiety remains bound to $T^T$.

Drug Deactivation

In other embodiments the IEDDA pyridazine elimination with the compounds of this invention is used to deactivate a Drug in vivo. In these embodiments, the compound of Formula (19) may be referred to as a Deactivatable Drug. In these embodiments a Drug is allowed to circulate in vivo and to exert its therapeutic action, and after an optimal interval, the Drug is deactivated by administration of a tetrazine, resulting in cleavage of the Drug and its deactivation, reducing undesired side effects. Exemplary Drugs that can be deactivated in this manner include biomolecules, wherein one (bio)molecule is linked to another (bio)molecule via the Trigger (as $C^A$ or $C^B$) and this (bio)molecule-(bio)molecule conjugate is therapeutically active whereas the cleaved biomolecules are not. Exemplary Drug conjugates are protein-protein, peptide-peptide, protein-peptide, protein-organic molecule, and organic molecule-organic molecule conjugates.

Thus, a compound of Formula (19) may be a conjugate of the Drug and the TCO and that comprises an active drug (e.g. as $C^A$) of which the therapeutic activity is decreased after release of Construct-A from the TCO. In this embodiment, the compound of Formula (19) is therapeutically active, while the compounds obtained after the IEDDA reaction are less therapeutically active, or even do not have a significant therapeutic activity.

In this embodiment, the drug may be coupled to the remainder of the compound of Formula (19) as described herein for other embodiments, in particular regarding Prodrugs.

In a preferred embodiment, the drug deactivation is spatially controlled instead of or in addition to temporally controlled. For example, the Activator can be administered specifically to a location of the body where a systemically administered Drug is not desired to work, e.g. a particular organ, while the Drug remains active in other locations/systemically. Conversely the Activator can be administered systemically to deactivate a Drug in circulation, while maintaining Drug activity in a particular location, e.g. an organ or a site of disease.

In some embodiments the Drug consists of two constructs, which are the same or different Drugs $D^D$, and one or both $D^D$ are deactivated upon cleavage of $T^R$. In a preferred embodiment, administration of a $T^T$-$T^R$-$D^D$ conjugate leads to accumulation and therapeutic activity of the Drug in the target tissue, after which a tetrazine is administered at a desired time and/or location to cleave $D^D$ from $T^T$ resulting in a reduction of the therapeutic or toxic effect at the Primary Target.

Administration of a Prodrug or Deactivatable Drug

When administering the Prodrug or Deactivatable Drug and the Activator to a living system, such as an animal or human, in preferred embodiments the (Pro)drug is administered first, and it will take a certain time period before the Prodrug has reached the Primary Target. This time period may differ from one application to the other and may be minutes, days or weeks. After the time period of choice has elapsed, the Activator is administered, will find and react with the (Pro)drug and will thus (de)activate the (Pro)drug and/or afford Drug release at the Primary Target. In some preferred embodiments, the time interval between the administration of the (Pro)drug and the Activator is between 10 minutes and 4 weeks. In some preferred embodiments, the time interval between the administration of the (Pro)drug and the Activator is between 1 hour and 2 weeks, preferably between 1 and 168 hours, more preferably between 1 and 120 hours, even more preferably between 1 and 96 hours, most preferably between 3 and 72 hours.

The compounds and combinations of the invention can be administered via different routes including but not limited to intravenous or subcutaneous injection, intraperitoneal, local injection, oral administration, rectal administration and inhalation. Formulations suitable for these different types of administrations are known to the skilled person. (Pro)drugs or Activators according to the invention can be administered together with a pharmaceutically acceptable carrier. A suitable pharmaceutical carrier as used herein relates to a carrier suitable for medical or veterinary purposes, not being toxic or otherwise unacceptable. Such carriers are well known in the art and include for example saline, buffered saline, dextrose, water, glycerol, ethanol, and combinations thereof. The formulation should suit the mode of administration.

It will be understood that the chemical entities administered, viz. the (Pro)drug and the Activator, can be in a modified form that does not alter the chemical functionality of said chemical entity, such as salts, hydrates, or solvates thereof.

After administration of the Prodrug, and before the administration of the Activator, it is preferred to remove excess Prodrug by means of a Clearing Agent in cases when Prodrug activation in circulation is undesired and when natural Prodrug clearance is insufficient. A Clearing Agent is an agent, compound, or moiety that is administered to a subject for the purpose of binding to, or complexing with, an administered agent (in this case the Prodrug) of which excess is to be removed from circulation. The Clearing Agent is capable of being directed to removal from circulation. The latter is generally achieved through liver receptor-based mechanisms, although other ways of secretion from circulation exist, as are known to the skilled person. In the invention, the Clearing Agent for removing circulating Prodrug, preferably comprises a dienophile moiety, e.g. as discussed above, capable of reacting to the tetrazine moiety of the Prodrug.

In preferred embodiments the Activator is administered first, followed by the (Pro)drug, wherein the time interval between the administration of the two components ranges from 1 minute to 12 weeks, preferably 1 minute to 2 weeks, preferably from 10 minutes to 3 days.

In preferred embodiments, the (Pro)drug and Activator are administered at the same time. either as two separate administrations or as a co-administration.

In yet another embodiment, the (Pro)drug and Activator are reacted with one another prior to administration and the resulting reaction mixture is then administered, wherein the time interval between start of the reaction and the administration varies from 1 minute to 3 days, preferably 1 minute to 1 day, more preferably from 1 minute to 3 hours.

Cleaving Imaging and Radiotherapy Labels from Biomolecules in Vivo

The compounds, combinations, and kits of the invention can be used to quickly lower the amount of radionuclides in a subject. In particular, the compounds, combinations, and kits of the invention can be used to increase the target-non target ratio of imaging or radiotherapy agents in the clearance process, and more particularly to reach such an increase more rapidly. In this application, the compound of Formula (19) comprises a Label, preferably a molecule comprising a radionuclide, and an Administration Agent, preferably an antibody, that are separable after reaction with a diene. I.e., one of the Label and the Administration Agent is part of $R^{48}$, and the other is bound to any one of $X_1$—$X_5$, or both the Label and Administration Agent are part of $R^{48}$, but are attached to a self-immolative linker.

In preferred embodiments wherein the Primary Target is an internalizing receptor and it is desired to selectively cleave the Label from the Administration Agent in blood and not at the Primary Target, the Activator is preferentially designed to be cell impermeable. In said embodiment, wherein the Label is a chelate then the Activator can be either internalizing or non-internalizing, as the cleaved chelate cannot escape the target cell.

In preferred embodiments, wherein the Primary Target is a non internalizing receptor and it is desired to cleave the Label in blood and not at the Primary Target, the Activator is preferentially designed to extravasate poorly into tissues and rapidly clear, to minimize reaction at the Primary Target while achieving cleavage in blood.

In preferred embodiments the Activator is cell-impermeable, to increase the selective cleavage of a compound of Formula (19) present in non-target sites (e.g. blood).

In preferred embodiments, the properties of the Activator (e.g. level of cell permeability and extravasation) are achieved by a suitably chosen $R^{87}$ group (vide infra).

Preferably, the reaction of the Activator with the Administration Agent present in a tissue of interest in vivo results in at least 20% reduction of radioactivity, more preferably at least 40%, more preferably at least 60%, even more preferably at least 80%.

In one aspect, the invention relates to a compound, a combination, or a kit of the invention for use as a medicament. Alternatively, the kits of the invention are used in a method for treating or imaging patients, said method comprising administering the compounds comprised in the kits of the invention to a subject.

In another aspect, the invention pertains to a compound, a combination, or a kit of the invention for use in the treatment of a disease, preferably cancer, in a subject, preferably a human. Preferably, the treatment is radiotherapy.

The disclosure also pertains to a method of treatment in a subject as defined herein, said method comprising the steps of (a) administering a compound according to Formula (19) as defined herein, to the subject;

(b) administering an Activator as defined herein, to said subject;

Preferably, the method is for treating cancer in said subject.

In another embodiment, step (b) is carried out first, allowing the Activator to accumulate in non-target tissue that needs protecting from the radiation; secondly step (a) is carried out, affording the targeting of the radiation to target tissue, while the Label is cleaved and removed in non-target tissue by the pre-localized Activator. Likewise, the Activator can be locally administered, i.e. directly injected, into tissues that need protecting, as opposed to a systemic i.v. administration.

One prominent application of the invention, is radioimmunotherapy targeted to an internalizing cancer receptor such as HER2. In this approach the HER2-targeting antibody Trastuzumab (Tmab) is modified with, for example three TCO-chelate constructs as shown below. The TCO-chelate construct (NHS-TCO-DOTA) comprises an active ester for lysine conjugation, the TCO linker, and a DOTA chelate for $^{117}$Lu labeling, a therapeutic beta emitter. Following 117Lu-labeling of Tmab and intravenous (i.v.) injection, the $^{117}$Lu-Tmab is allowed to circulate, bind the HER2 target on the breast cancer or ovarian cancer sites, allowed time to internalize (ca 2 days) after which the tetrazine comprising Activator is intravenously injected, which cleaves $^{117}$Lu-DOTA construct from the freely circulating Tmab, resulting in rapid clearance of $^{117}$Lu-DOTA construct via the kidney, and a vast reduction of radiation dose to the bone marrow. Typically the Activator is hydrophilic and as a result non cell permeable and will therefore not cleave the $^{117}$Lu-Tmab inside the target cell. However, even if the Activator is cell permeable and cleaves $^{117}$Lu-Tmab inside the target cell, typically the released $^{117}$Lu-DOTA will remain trapped inside the cell.

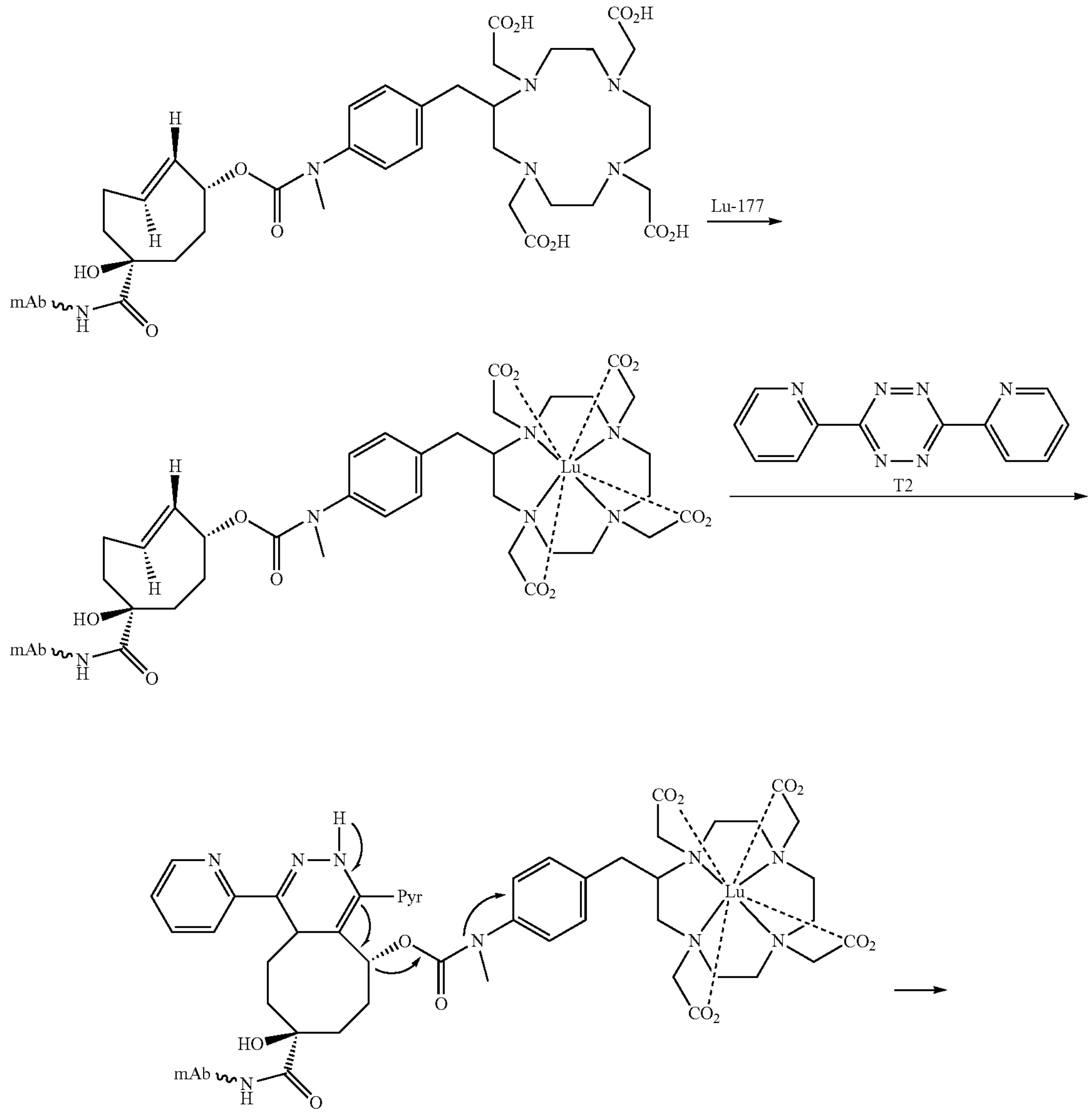

-continued

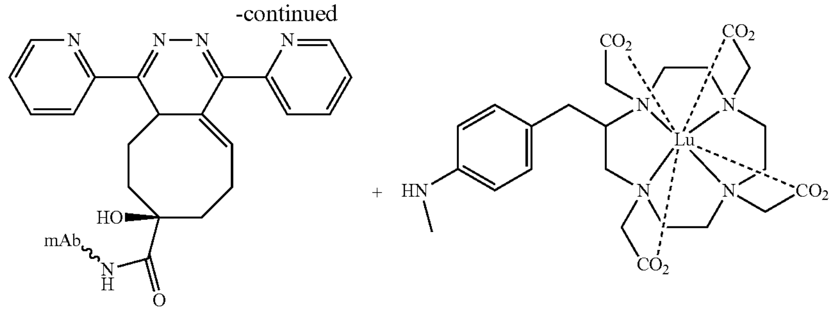

Also non-internalizing cancer receptors can be used as Primary Targets in above examples if the Activator is designed to have a low or slow uptake in the tumor. For example, the Activator can comprise a biodegradable PLGA particle core of ca 500 nm diameter, modified with tetrazine moieties. Such a particle will exhibit rapid clearance from blood by the liver, ensuring that it can only react with TCO containing constructs in circulation, and does not accumulate in the tumor, as previously shown for tetrazine clearing agents Rossin et al., J. Nucl. Med. 2013, 4, 11, 1989-1995; and WO2012085789A1]. For imaging applications, slow accumulation at the target site may be acceptable, in which case the tetrazine can be modified with an albumin binding moiety, or a protein or a polymer such as a PEG, maximizing its retention in circulation, and thereby facilitating its reaction with TCO constructs in circulation.

In one other embodiment of this invention, the administration of the Compound of Formula (19) followed by the Activator allows to tune the blood circulation and excretion pathway of the released Label.

In the context of $^{117}$Lu-Tmab RIT, after cell internalization a Activator comprising, for example, a tetrazine functionalized with a short PEG polymer is injected and binds the TCO Trigger, resulting in the cleavage of the bond between the TCO and the antibody. Subsequently the $^{177}$Lu-DOTA chelate carrying the PEG is released in circulation and due to the PEG it clears via the kidneys.

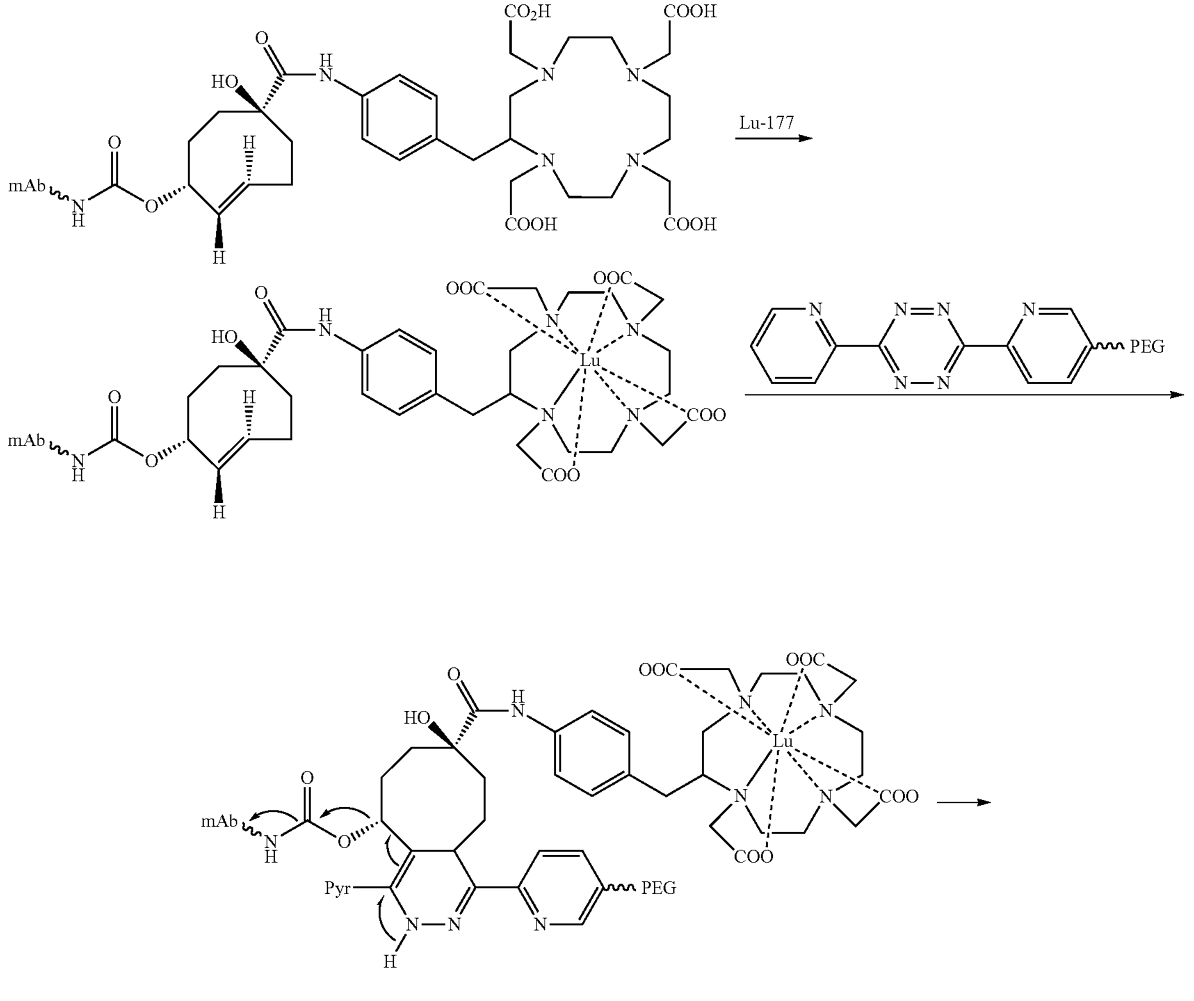

-continued

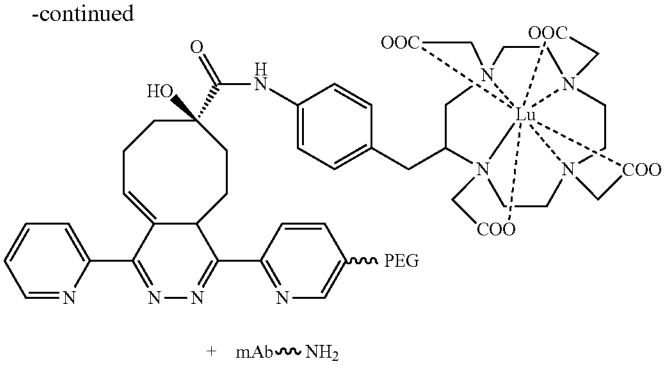

In a similar approach, instead of a linear or branched polymer the Activator carries one or more functional groups that influence the clearance pathway of the released moiety. For instance, an Activator comprising a tetrazine and several galactose groups will produce a released moiety that binds the Ashwell receptor in hepatocytes, therefore resulting in fast hepatobiliary clearance of the label.

In another preferred embodiment of this invention, the targeting agent is a peptide, an antibody fragment or a small molecule carrying an imageable or therapeutic radiometal chelate that accumulates specifically in a tumor or another diseased tissue and internalizes into target cells, but is also non-specifically retained in non-target organs such as, but not restricted to, kidneys, salivary glands and lacrimal glands (as is the case for RGD peptide an PSMA, below). In this approach the Label (e.g. $^{177}Lu$ or $^{225}Ac$ labeled DOTA or $^{89}Zr$ labeled DFO) is linked to the targeting moiety via a TCO trigger. After i.v. injection of the Administration Agent and after such Agent has accumulated in the diseased tissue and internalized into target cells (e.g. 4 to 24 h post-injection), the patient is administered an Activator intravenously. The Activator specifically binds the TCO trigger on the Administration Agent in non-target organs and releases the Label thus inducing radioactivity wash out from these organs via the urine. This reduces the radioactive dose delivered to non-target organs thus increasing the therapeutic index of Administration Agents object of this invention and reducing the chance of toxic side effects for the patient in nuclear imaging procedures.

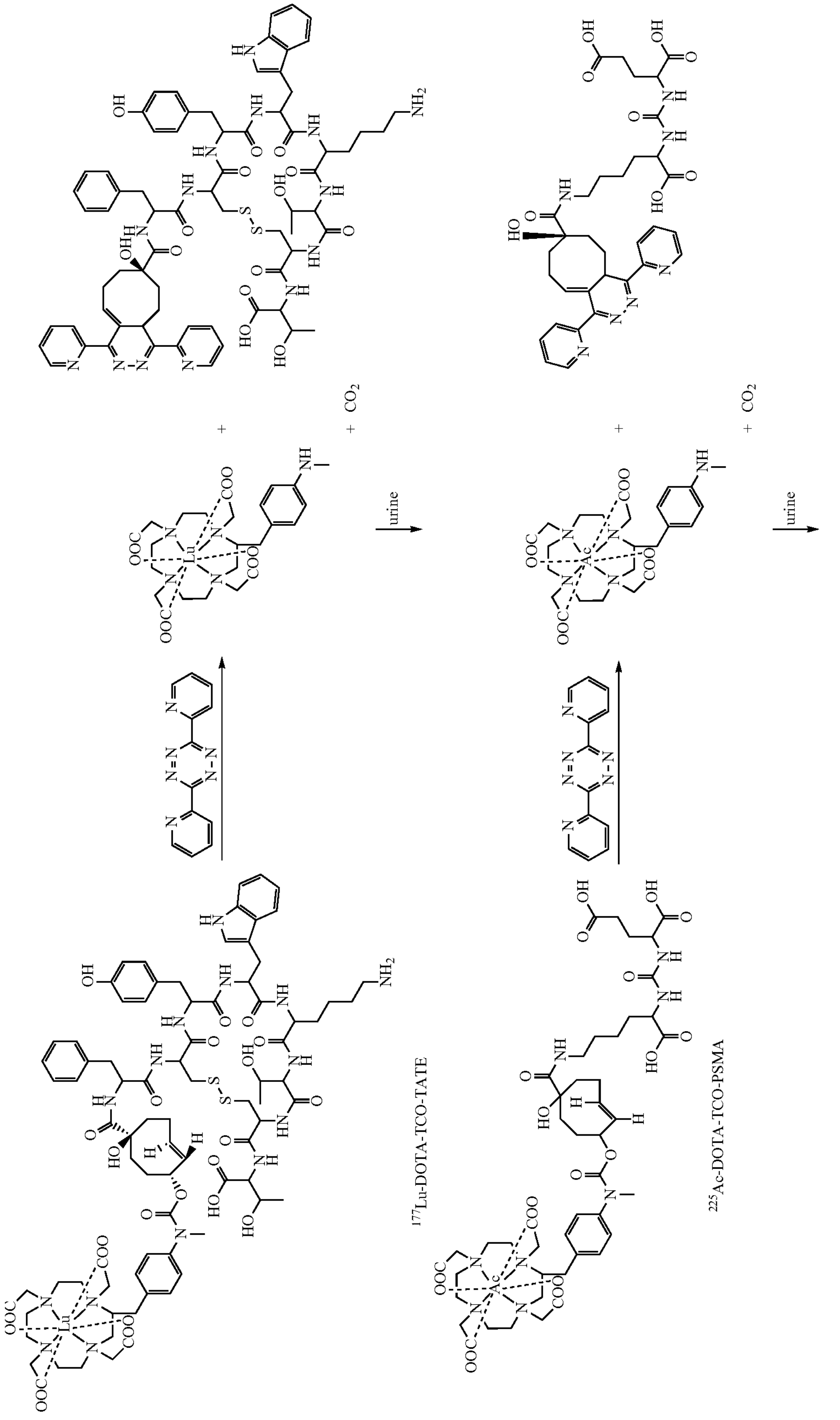
$^{177}$Lu-DOTA-TCO-TATE
$^{225}$Ac-DOTA-TCO-PSMA

In yet another embodiment of this invention the Administration Agent comprises a TCO Trigger conjugated to a Targeting Agent and to an imaging or therapeutic moiety (Label) via a self-immolative linker. The tetrazine reacts with the Trigger resulting in an intermediate that rearranges electronically resulting in the fragmentation of the linker and the detachment of the Label from the Targeting agent. As a result the Label, being a small molecule, rapidly clears from the subject's circulation, preferentially via the kidney.

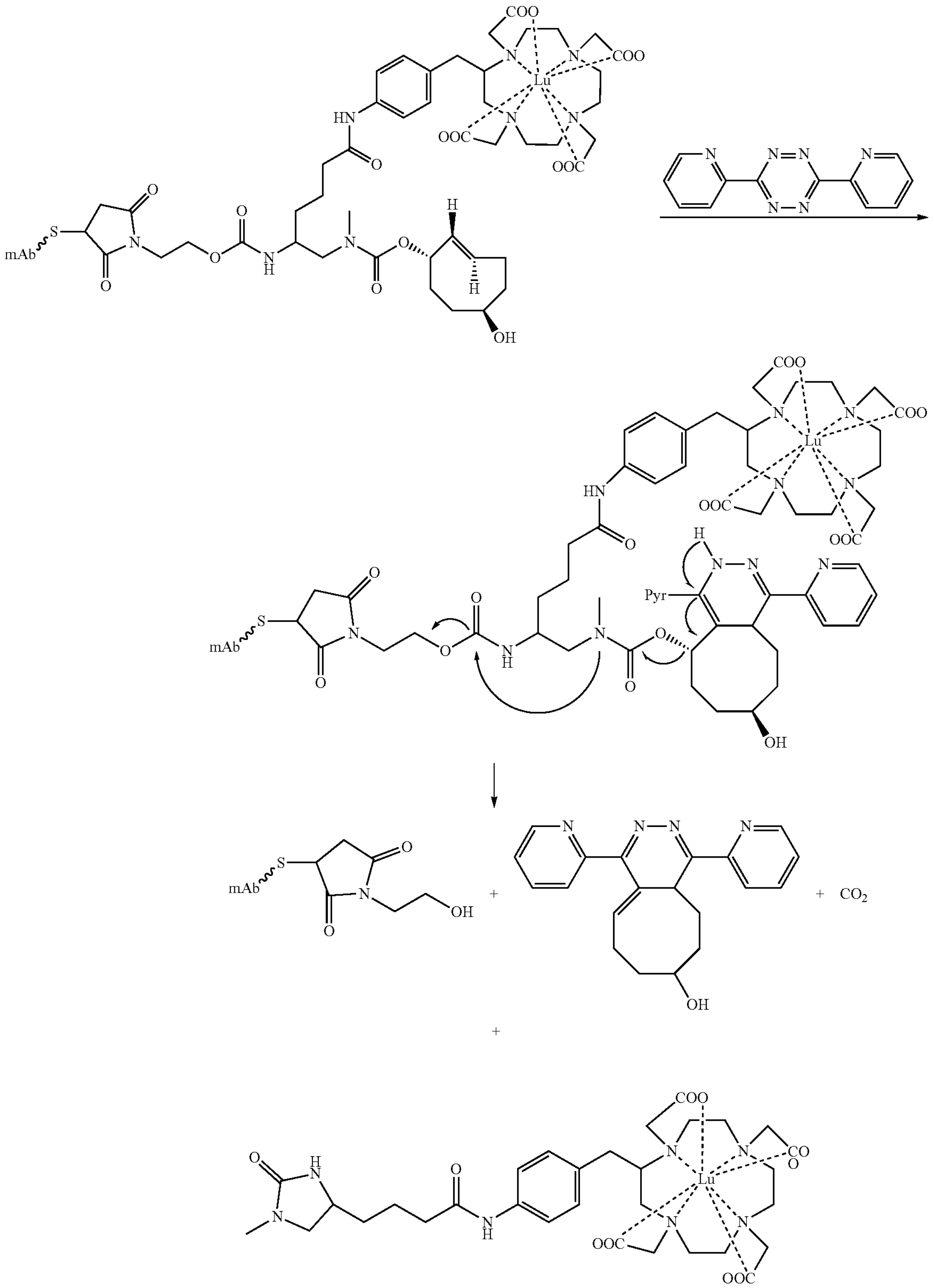

In one other embodiment of this invention the Administration Agent comprises an imageable or therapeutic moiety bound via a TCO Trigger to a Targeting Agent that binds a specific receptor or molecule present both at a disease site and in circulation due to shedding. Non limiting examples of shedding targets are the carcinoembryonic antigen (CEA), the prostate specific antigen (PSA), and the tumor necrosis factor α (TNF-α) receptor. In the presence of target shedding, Administration Agent binding to circulating target is detrimental as it causes loss of image contrast and/or toxic side effects in the subject of the medical intervention. With the approach of this invention, the Administration Agent is injected i.v. in an animal or human subject and binds to its target at the disease site and in circulation. After a suitable time (one or two days) the subject is injected the tetrazine Activator i.v. which reacts specifically with the TCO Trigger on the circulating (bound) Administration Agent. Upon reaction between the tetrazine and the TCO, the imageable or therapeutic moiety is released from the Administration Agent and it clears rapidly from circulation.

In one preferred embodiment, the invention is used to reduce the kidney dose instead of the bone marrow dose. In this embodiment, the Administration Agent being an intact IgG antibody is labeled with $^{225}$Ac and allowed to bind its Primary Target, such as HER2, PSMA. $^{225}$Ac has a chain of daughter isotopes, and upon the $1^{st}$ decay of $^{225}$Ac, the nuclide is separated from the DOTA and the Administration Agent resulting in renal uptake of the free daughter $^{221}$Fr. Timely injection of the Activator results in rapid reaction in blood and elimination of DOTA-$^{225}$Ac via the kidneys and reduced $^{221}$Fr radiation dose to the kidneys.

In another embodiment, the Primary Target is a receptor on a blood cancer cell, i.e. CD33 on AML cells, and the Administration Agent is antiCD33 mAb labeled with DOTA-$^{225}$Ac. After CD33 binding and internalization, the DOTA-$^{225}$Ac Label of the freely circulating mAb in cleaved to reduce the radiation toxicity to kidneys, and also the bone marrow, liver, and spleen.

Furthermore, the disclosure pertains to a diagnostic method comprising the steps of (a) administering a compound according to Formula (19) as defined herein, to a subject, preferably a human;
(b) administering a Activator as defined herein, to said subject;
(c) imaging the compound according to Formula (19) present in the subject to collect data;
(d) comparing said data to standard values;
(e) finding a significant deviation from said standard values during comparison;
(f) attributing the significant deviation to a particular clinical picture, preferably to cancer.

Diagnostic Method

The invention also pertains to a compound of Formula (19) as defined herein, a combination as defined herein, or a kit as defined herein for use in a diagnostic method comprising the steps of (a) administering a compound according to Formula (19) as defined herein, to a subject, preferably a human;
(b) administering a Activator as defined herein, to said subject;
(c) imaging the compound according to Formula (19) present in the subject to collect data;
(d) comparing said data to standard values;
(e) finding a significant deviation from said standard values during comparison;
(f) attributing the significant deviation to a particular clinical picture, preferably to cancer.

Preferably, in the diagnostic method, the compound according to Formula (19) satisfies at least one of the conditions (i), (ii) or (iii) as defined herein.

Non-Therapeutic Method

The invention also pertains to a non-therapeutic method for imaging a compound of Formula (19) as defined herein, in a subject as defined herein, preferably a human, said non-therapeutic method comprising the steps of (a) administering a compound according to Formula (19) as defined herein, to the subject;
(b) administering a Activator as defined herein, to said subject;
(c) imaging the compound according to Formula (19) present in the subject.

Herein, preferably at least one of the compound of Formula (19) and the Activator comprises a label selected from the group consisting of radionuclides, fluorescent dyes, and phosphorescent dyes.

Preferably, in the non-therapeutic method for imaging, the compound according to Formula (19) satisfies at least one of the conditions (i), (ii) or (iii) as defined herein.

In a preferred embodiment, step (a) is carried out first, secondly step (b) is carried out, and then step (c). In that embodiment, preferably step (b) is carried out after waiting a sufficient amount of time after step (a), so that a significant part, preferably at least 10%, more preferably at least 50% of what is maximally achievable, of the of the initial dose of a compound according to Formula (19) has reached the target. Preferably, the Activator and/or its dose are chosen in this embodiment so as to ensure that compound according to Formula (19) that has reached the target is not cleaved in significant amounts, preferably less than 30%, more preferably less than 10%. In such a way, in step (b) the target-to-background ratio of the radionuclide can be optimized before imaging in step (c).

Preferably, in this embodiment a further step (b) is carried out after step (c) so as to quickly reduce the amount of radionuclides in the subject after imaging.

In another embodiment, step (a) is carried out first, secondly step (c) is carried out, and then step (b). In this way, the amount of radionuclides in the subject can be quickly reduced after imaging, to reduce whole body radiation dose and/or optionally to allow for another imaging procedure (image cycling).

In another embodiment, step (b) is carried out first, allowing the Activator to accumulate in non-target tissue that needs protecting from the radiation or that would otherwise obscure imaging of the Primary Target; secondly step (a) is carried out, affording the targeting of the radiation to target tissue, while the Label is cleaved and removed in non-target tissue by the pre-localized Activator; and then step (c) takes place.

Likewise, the Activator can be locally administered, i.e. directly injected, into selected non-target tissues, as opposed to a systemic i.v. administration.

The invention also pertains to non-therapeutic method for imaging a compound according to the invention in a subject, preferably a human, said non-therapeutic method comprising the steps of (a) administering a compound according to Formula (19) as defined herein comprising a label, to the subject;

(b) imaging the compound according to Formula (19) present in the subject; wherein the label is selected from the group consisting of radionuclides, fluorescent dyes, and phosphorescent dyes.

Similar procedures can also be used in the context of radioimmunotherapy.

The invention can be used to improve radioimmunoimaging of HER2 with Trastuzumab (Tmab). In this approach Tmab is modified with for example 2 TCO-DFO chelate constructs, as shown below, wherein the Tmab is conjugated via thiol maleimide chemistry. Following $^{89}$Zr-labeling of Tmab and intravenous (i.v.) injection, the $^{89}$Zr-Tmab is allowed to circulate, bind the HER2 target on the breast cancer or ovarian cancer sites, allowed time to internalize (ca 2 days) after which the tetrazine comprising Activator is i.v. injected, which cleaves the $^{89}$Zr-DFO label from the freely circulating Tmab, resulting in rapid clearance of $^{89}$Zr-DFO construct via the kidney, and a vast improvement tumor-blood ratio in imaging of the target.

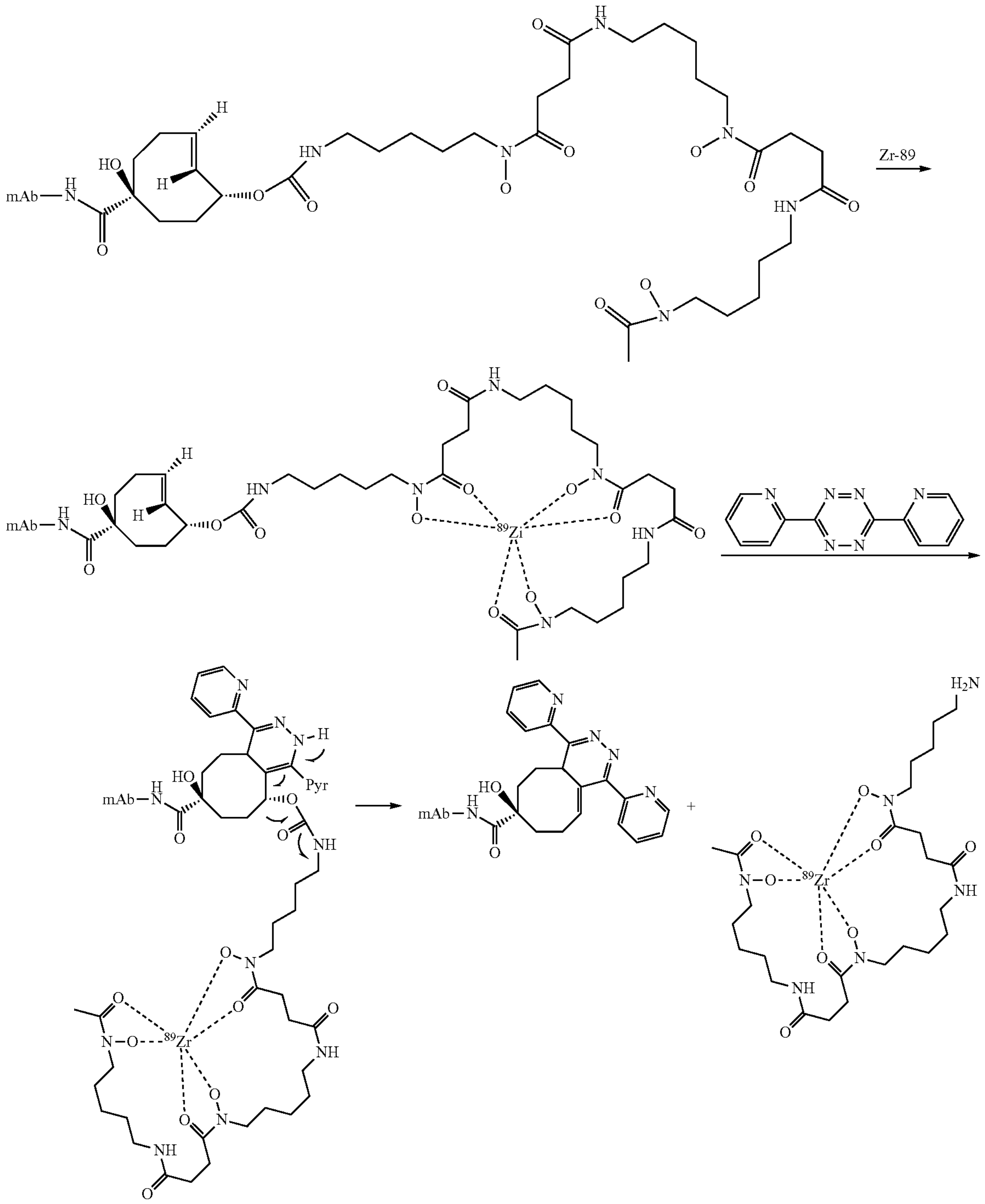

In a similar approach as with the above HER2 imaging example, the invention can be used in companion imaging of antibody drugs that are being developed to cross the blood brain barrier (BBB) to treat, for example, Alzheimer's disease. In such an approach the therapeutic antibody can be modified with an additional domain which binds to the transferrin receptor, resulting in crossing of the BBB. As only a minor amount will cross the BBB and bind to its Primary Target, and as a large amount will still freely circulate in blood, conventional imaging approaches (e.g. by labeling the antibody with $^{89}Zr$) is hampered by very poor target-non-target (T-NT) ratios. Conjugation of the cleavable DFO-TCO-maleimide construct shown above to the anti-Alzheimer antibody, labeling with $^{89}Zr$, i.v. injection, followed by some time for target uptake will allow the cleavage of freely circulating $^{89}Zr$-antibody at desired time points, making the circulating antibody essentially invisible, while retaining the $^{89}Zr$-signal at the target site, boosting T-NT ratios. This approach also allows discriminating between $^{89}Zr$-antibody that has crossed the BBB and the portion that has bound in the brain but has not crossed the BBB, or where the BBB is impaired. In this embodiment, the diene is preferably designed such that it does extravasate, but does not significantly permeate the BBB. In another preferred embodiment, the diene is designed such that it does not extravasate into other tissues.

In yet another embodiment of the present invention the Administration Agent is a macromolecular (e.g. albumin, dextran, micelle, nanoparticle, nanoemulsion or dendrimer based) blood pool contrast agent for magnetic resonance imaging (MRI) or X-ray computed tomography (CT) [H. Kobayashi and M. W. Brechbiel, Adv. Drug Deliv. Rev. 2005, 57, p. 2271-1186 and H. Lusic and M. W. Grinstaff, Chem. Rev. 2013, 113, p. 1641-1666).

Contrast agents carry multiple copies of chelated paramagnetic ions (e.g. $Gd^{3+}$, $Mn^{2+}$, $Dy^{3+}$ and $Tm^{3+}$) for MRI or elements with high atomic number (e.g. iodine) for CT. Because of their high molecular weight, they exhibit a long intra-vascular half-life and allow to acquire high quality angiograms. However, due to the low intrinsic sensitivity of these imaging modalities, high amounts of contrast agents are injected into patients (mM to M concentration needed for MRI and CT, respectively), posing a risk of toxic side effects due to long lasting accumulation of heavy metals and heavy atoms is excretory organs such as the liver.

Non limiting examples of MRI and CT contrast agents object of this invention are shown below. In these Administration Agents the contrast-generating moiety (Label) is linked to a scaffold via the TCO Trigger. Upon contrast agent administration and at the end of image acquisition, i.v. injection of the Activator results in cleavage of the bond between the macromolecular scaffold and the Label. The Label released in blood is then rapidly eliminated via the kidney. The Label released in the liver is recirculated to the blood and eliminated via the kidney or is directly ad rapidly eliminated via the intestine, due to small size.

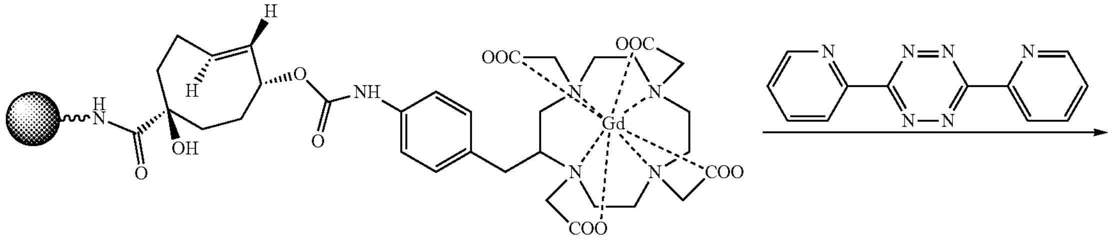

MRI contrast agent

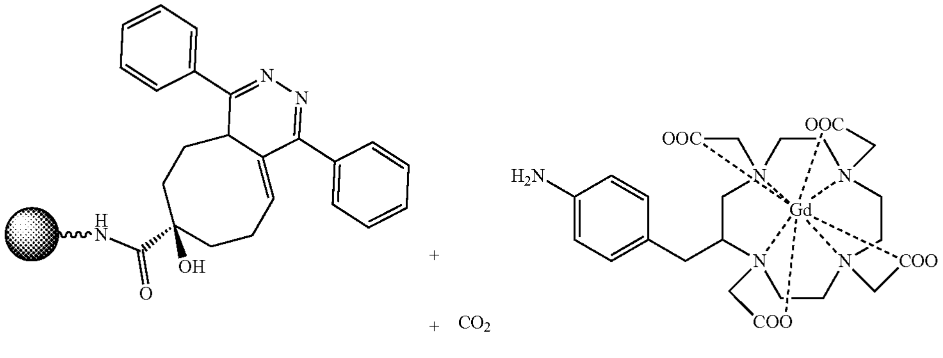

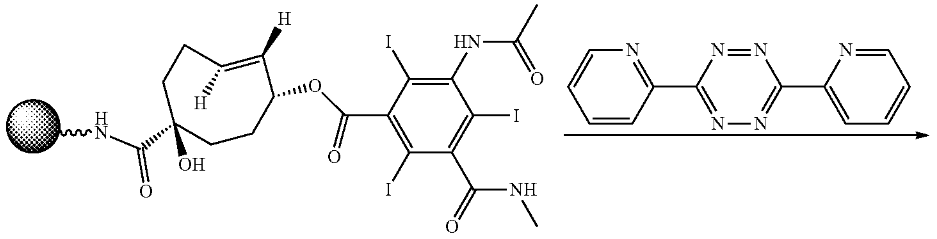

CT contrast agent

-continued

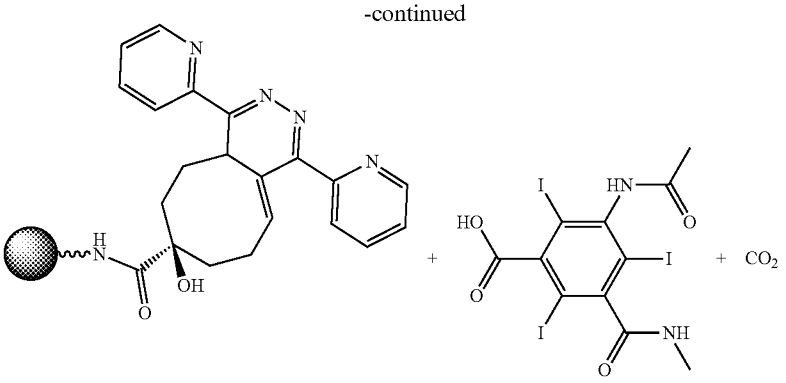

Administration

When administering the compound of Formula (19) and the Activator to a subject, such as an animal or human, in preferred embodiments the compound of Formula (19) is administered first. It will take a certain time period before the the compound of Formula (19) has reached the Primary Target, and optionally internalized in the cell or crossed the blood brain barrier. This time period may differ from one application to the other and may be for example minutes or hours. After the time period of choice has elapsed, the Activator is administered, which reacts with the the compound of Formula (19) to decouple the Administration Agent and the Label preferably in the non-target tissues. In some preferred embodiments, the time interval between the administration of the compound of Formula (19) and the Activator is between 10 minutes and 4 weeks. In some preferred embodiments, the time interval between the administration of the compound of Formula (19) and the Activator is between 1 hour and 2 weeks, preferably between 1 and 168 hours, more preferably between 1 and 120 hours, even more preferably between 1 and 96 hours, most preferably between 3 and 72 hours, more preferably still between 4 and 48 hours, and most preferably between 5 and 24 hours.

The compounds and the combinations of the invention can be administered via different routes including but not limited to intravenous or subcutaneous injection, intraperitoneal, local injection, oral administration, rectal administration and inhalation. Formulations suitable for these different types of administrations are known to the skilled person. Compounds of Formula (19) or Activators according to the invention can be administered together with a pharmaceutically acceptable carrier. A suitable pharmaceutical carrier as used herein relates to a carrier suitable for medical or veterinary purposes, not being toxic or otherwise unacceptable. Such carriers are well known in the art and include for example saline, buffered saline, dextrose, water, glycerol, ethanol, and combinations thereof. The formulation should suit the mode of administration.

It will be understood that the chemical entities administered, viz. the compound of Formula (19) and the Activator, can be in a modified form that does not alter the chemical functionality of said chemical entity, such as salts, hydrates, or solvates thereof.

In preferred embodiments, the Activator, preferably comprising a Targeting Agent, is administered first, and thereafter the compound of Formula (19) is administered. Preferably, in embodiments where the compound of Formula (19) and the Activator are administered approximately simultaneously, they are administered via different routes.

Subject

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., more preferably a human.

Non-Therapeutic Use

The invention also pertains to a use of a compound of Formula (19) as defined herein, a combination as defined herein, or a kit as defined herein, for imaging in a subject, preferably a human. In this use, the compound of Formula (19) preferably comprises a Label and an Administration Agent, and more preferably the compound of Formula (19) satisfies any one of the conditions (i)-(iii) as defined herein.

The invention on-therapeutic use of a compound according to the invention, or a combination according to the invention, for imaging in a subject, preferably a human, wherein the compound, or in case of the combination at least one of the compound according to Formula (19) and the diene, comprises a label selected from the group consisting of radionuclides, fluorescent dyes, and phosphorescent dyes.

In Vitro Applications

The invention provides a tool for the controlled release of a bound substance (bound to any carrier or any other chemical group) for a diverse range of applications, including but not limited to drug delivery, chemical biology, diagnostics, organic, protein, and material chemistry, radiochemistry, capture and release resins, biological and chemical sensors, surface patterning or modification, cell and tissue culture and biomolecule manipulation (e.g. conjugation, crosslinking, trapping, releasing).

Particularly, the release can be in a chemically complex environment, including organic synthesis and material synthesis, biological surroundings, which include the synthesis and handling conditions of biomolecules. This includes the presence of diverse chemical functionalities, organic solvents, aqueous solvents biological media and tissues and cell lysates. The invention preferably relates to in vitro release at ambient temperature.

The invention provides, in one aspect, the use of a tetrazine as an Activator for the release, in a chemical, biological, or physiological environment, of a construct linked to a trans-cyclooctene. The term Construct in this invention is used to indicate any substance, carrier, or chemical group, of which it is desired to have it first in a bound (or masked) state, and being able to provoke release from that state. The Construct may be present in the form of two or more Constructs, linked via a self-immolative linker.

The invention includes in one aspect a Trigger which functions as a protective or masking group for use in organic, peptide, protein, bio-, surface, solid-phase chemistry.

The invention includes in one aspect a Trigger which functions as a cleavable mask or linker for use in organic and bioorganic synthesis, materials science, chemical biology, diagnostics, and medicine. The invention can be used for the manipulation of small molecules, peptides, proteins, oligonucleotides, polymers, glycans, nanoparticles, and on surfaces (e.g., glass slides, gold, resins). Further examples include: compound library synthesis, protein engineering, functional proteomics, activity-based protein profiling, target guided synthesis of enzyme inhibitors, chemical remodeling of cell surfaces, tracking of metabolite analogues, and imaging tagged biomolecules in live cells. Therein, when used as a mask, with reference to formula 5a and 5b: f is preferably 0. Therein, when used as a linker, with reference to formula 5a and 5b: f is preferably 1.

Selective removal of the Trigger via reaction with the Activator unmasks the construct. Exemplary chemical moieties that can be protected and selectively deprotected include, but are not limited to, amines, thiols, hydroxyl, carboxylic acid, aminooxy groups.

Furthermore, the Activator may be conjugated to a resin, especially solid-phase synthesis resins, such as polystyrene, or to a bead. Thus circumventing the need for solution phase purification after the deprotection step. Therein, with reference to any one of Formulae (4), (4a), or (6)-(14), $R^{87}$ is a polymer, resin or a bead.

A

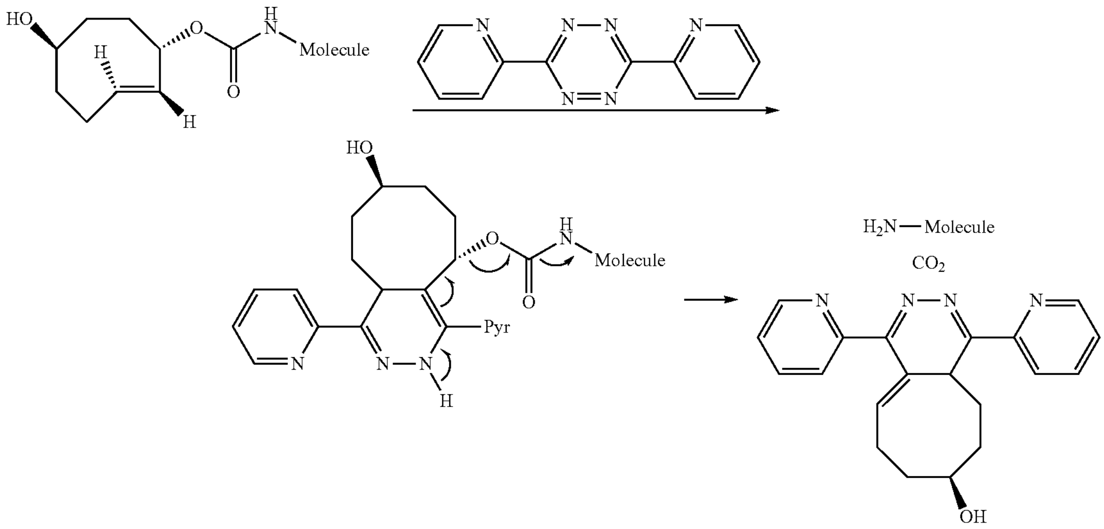

B

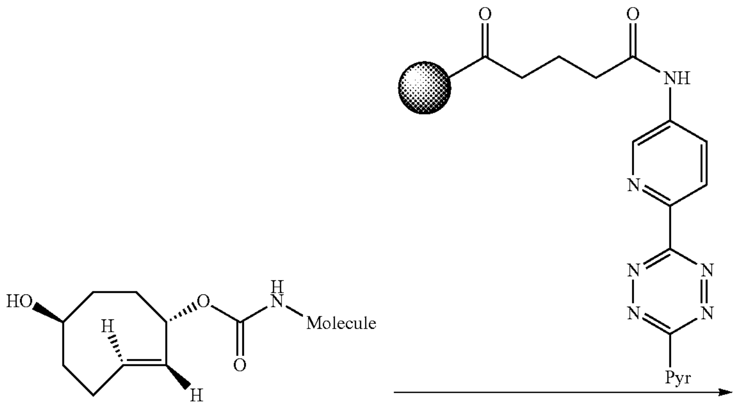

-continued

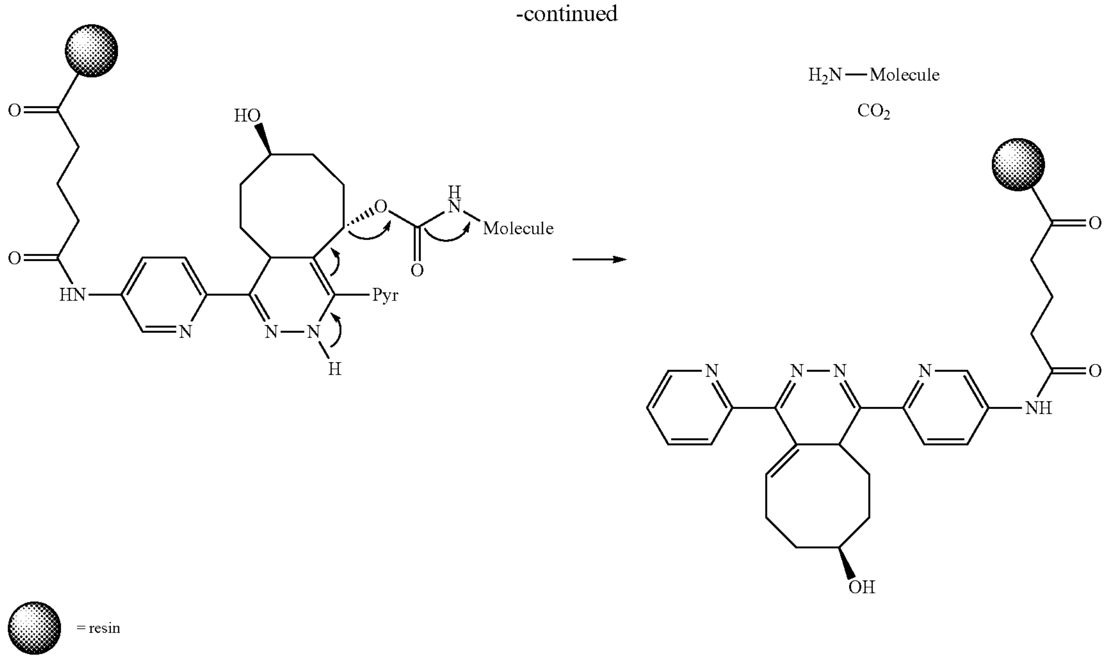

In the case of biomolecules such as proteins the Trigger can be introduced after the protein has been formed or during protein synthesis by means of genetically incorporating a Trigger-modified aminoacid. There have been many studies demonstrating the incorporation of unnatural aminoacids in proteins, including TCO and tetrazine (e.g. Chalker et al. Acc Chem Res, Vol. 44, No. 9, 2011, 730-741). In this way one can for example conduct bioconjugation chemistry elsewhere on the molecule, after which the TCO-masked amino acid can be unveiled and selectively manipulated. This so-called "Tag-and-Modify" approach thus allows for multiple and different post-translational modifications on a single protein and can be extended to controlled assembly and fragmentation of complex materials, proteins, cells, tissues. Examples of masked aminoacid derivatives, which can be used in such as approach are shown below. Compound A is the aminoacid cysteine of which the thiol functionality is masked by TCO. After release of TCO the thiol can be used in conjugation reactions. In addition to achieving selectivity, the ability to mask and unmask a thiol enables stabilization of thiol containing proteins against undesired oxidation and disulfide formation. Compound B is aminoacid lysine conjugated via its e-amine moiety to a TCO. Compound C is the aminoacid lysine conjugated via its e-amine moiety to a TCO-masked aminooxy functionality. After unmasking this aminooxy can be selectively conjugated to aldehyde and ketone derivatives. Compound D is aminoacid serine conjugated via its hydroxyl moiety to TCO. Compound E is aminoacid glutamic acid conjugated via its γ-carboxylate moiety to TCO.

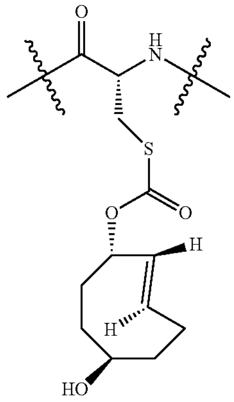

A

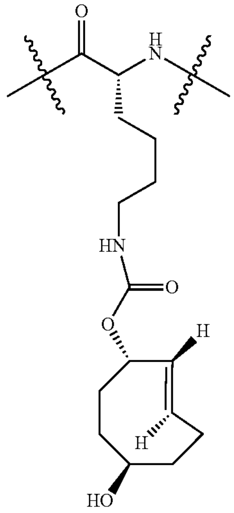

B

-continued

C

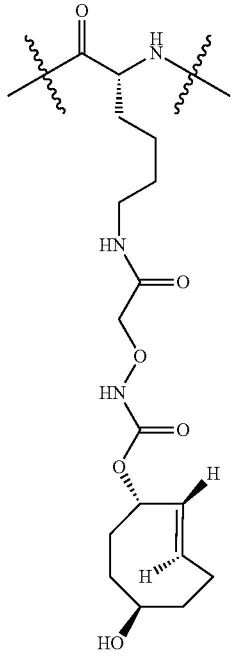

D

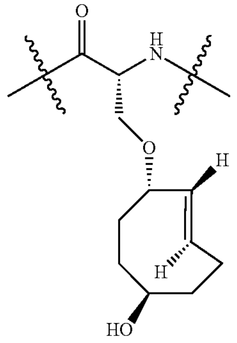

E

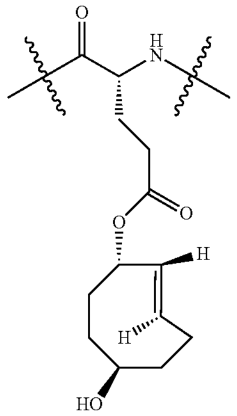

= rest of peptide or protein

In a similar embodiment depicted below the TCO mask is used to stabilize protein formulations in e.g. stock solutions to prevent aggregation and precipitation. For this purpose the TCO is functionalized with $C^B$ being an hydrophilic moiety such as a PEG (or e.g. a carbohydrate moiety), and one or multiple TCO-$C^B$ groups are conjugated to the protein (being $C^A$) via e.g. lysine residues. At the time of use, the protein solution is contacted with the Activator yielding the unmasked parent protein $C^A$. Also here it may be advantageous to use an Activator that is conjugated to solid phase synthesis resins or a bead, thus circumventing the need for solution phase purification after the unmasking step.

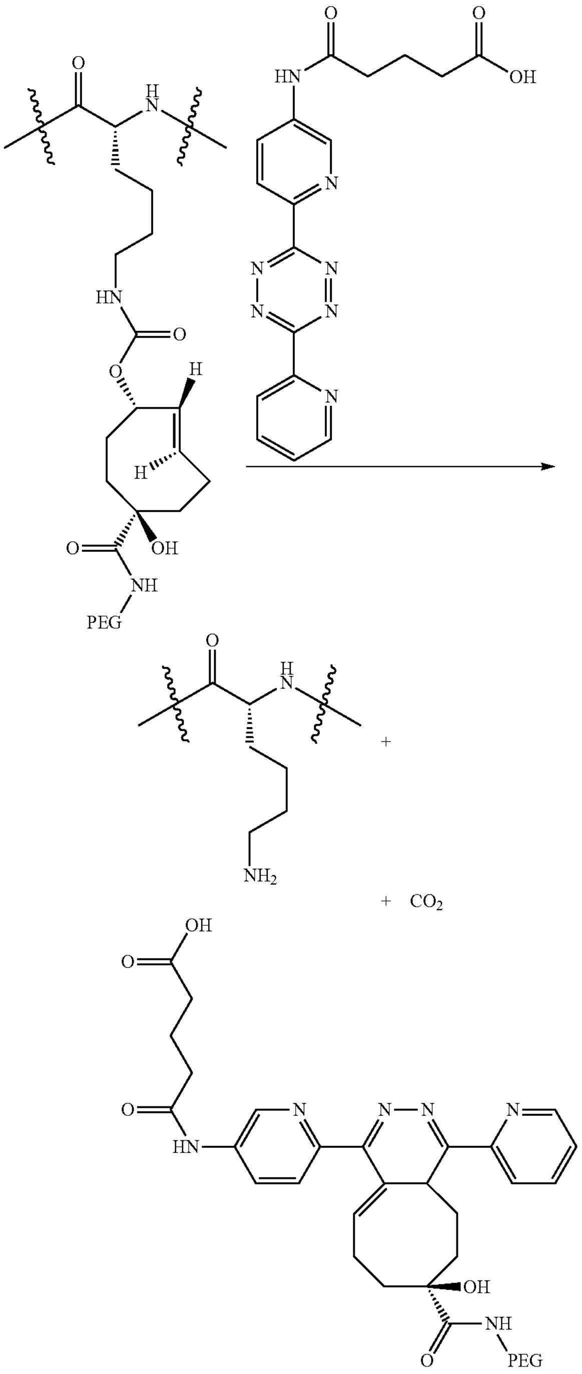

= rest of peptide or protein

In another embodiment the Trigger is used as a chemically cleavable mask in the patterning or etching of surfaces with application in e.g. spatially controlled cell and tissue culture, or for (e.g. protein, DNA) microarray assembly. Selective removal of the mask reveals e.g. free amine or thiol moieties (comprised in $C^A$), which can be used for further modifications, such as the conjugation of cell adhering peptides in the case surfaces for cell culture. For example, the TCO can be used as cleavable linker between a surface or surface-coated gel and cell-interacting moieties, such as integrin binders, for use in cell culture. After cell culture on this surface or in this 3D the cells can be removed from the surface or the surface-coated gel by mild cleavage of the TCO, instead of resorting to harsh trypsinization, or physical force.

A

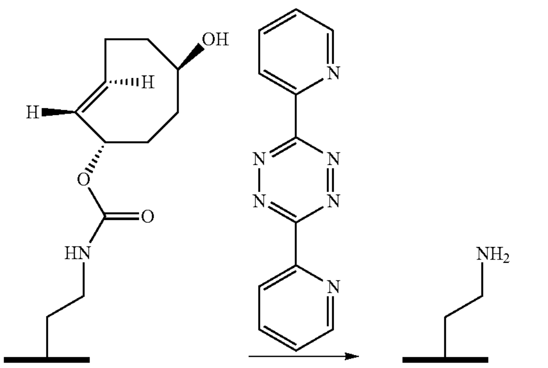

B

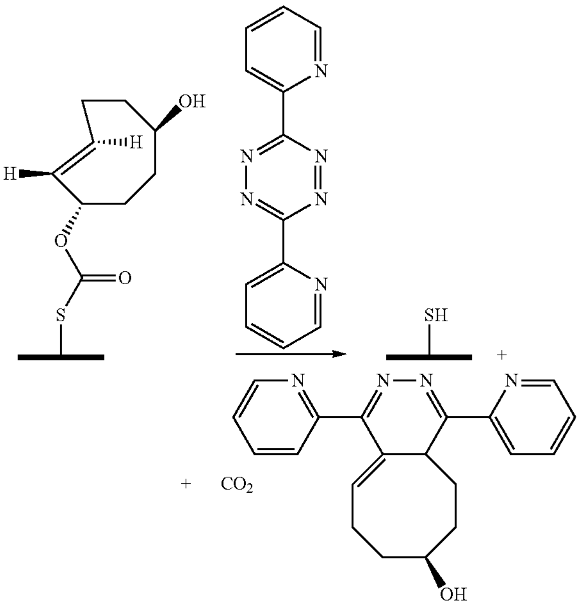

In an alternative embodiment the TCO mask is used to spatially and or temporally control the action of biomolecules in vitro or in vivo. For example, the action of a particular enzyme in an in vitro assay can be controlled by using an enzyme that has been deactivated through conjugation to one or more TCO masks, followed by contacting the enzyme with the Activator followed by release of the TCO mask and, affording the parent, active enzyme ($C^A$). Reference is made to [Li et al. Nat. Chem. Biol., 2014, 10, 1003-1005; Zhang et al. ACS Central Sci. 2016, 2, 5, 325-31]. Another example, useful in chemical biology, is the TCO-protection of certain aminoacid residues in a protein against enzymatic action such as phosphorylation by kinase, allowing spatial and temporal control over the phosphorylation after Activator addition. Alternatively, phospho aminoacids in phosphoproteins can be masked by TCO to be revealed at desired time by use of the Activator, as shown in a similar approach using light activatable masks by Rothman et al (2005) J. Am. Chem. Soc, 127, 847.

In another aspect of the invention the Trigger is used as a cleavable linker in “catch and release” systems, such as those used in chemical biology. Therein, with reference to Formula 5a and 5b: f is preferably 1.

One application of these linkers is in the purification of proteins tagged with a biotinylated Activity Based Probes (ABP). Biotinylated ABPs are often used for enrichment of captured enzymes, for instance, by pull-down with streptavidin-coated beads. The main disadvantages of this approach, however, are that the conditions to liberate the captured proteins from the beads are harsh (boiling of the sample, all or not in the presence of unmodified biotin) and that, beside the target proteins, both endogenously biotinylated proteins and (denatured) streptavidin can end up in the sample. In addition the presence of the biotin complicates MS/MS analysis. Furthermore, in another application, this concept can be used to capture and release whole cells with e.g. antibodies conjugated to e.g. a bead or solid support for example for the purpose of further analysis with FACS, requiring healthy intact cells. Several groups have developed linker systems that can be incorporated in the ABP, or alternatively in a bioorthogonal reagent for two-step ABPP, and that can be cleaved in a chemoselective manner after affinity pull-down. Examples include the disulfide, diazobenzene, and bisaryl hydrazine cleavable linkers (Willems L. I. et al. (2011) Acc. Chem. Res. 44, 718-729). However, these linkers have a limited bioorthogonality. In below scheme several embodiment examples are shown of the use of the Trigger for this application. In addition to the enhanced bioorthogonality this method also offers the opportunity to introduce a new label or affinity tag or to preserve a synthetic handle for further modification, through the binding of the tetrazine activator to the TCO.

Example A1 depicts the capturing of an enzyme by an ABP conjugated to biotin via a TCO linker. The complex is subsequently bound and isolated by streptavidin coated beads, after which the linker is cleaved by the Activator, and the enzyme, comprising the ABP linked to the IEDDA residue is released. In Example A2, the same concept is used with a reversed Trigger, leading to traceless release of the ABP-enzyme complex. Example B depicts an analogous 2 step ABP approach where the enzyme is captured by an ABP functionalized with an azide moiety. The complex is subsequently reacted with a cyclooctyne moiety, which is linked to a biotin via a TCO linker. It has been shown in Weissleder Angewandte Chemie 2011 that the TCO/tetrazine pair can be used orthogonally to and in the presence of the azide-octyn pair. In Example C the cyclooctyne-TCO-biotin probe approach described in B) is used to capture a specific protein, which has metabolically incorporated an azide-modified aminoacid. Example D depicts the capturing of cells using magnetic beads conjugated to antibodies via the Trigger. After binding and isolation using magnetic action, the cells are detached under mild conditions by adding the Activator. Example E depicts an alternative to the general approach in Examples A-D where the TCO combines the function of the biotin tag with the function of releasable linker. In this example, target cells are first bound by TCO-modified antibodies, followed by addition of tetrazine-coated beads. Suitably chosen tetrazine-TCO pairs will give a release with a half life of >2 h and given the required reaction time of <10 minutes thus allow enough time for isolation of the bead-cell complex before the complex releases the cell automatically through release of the linker.

A1
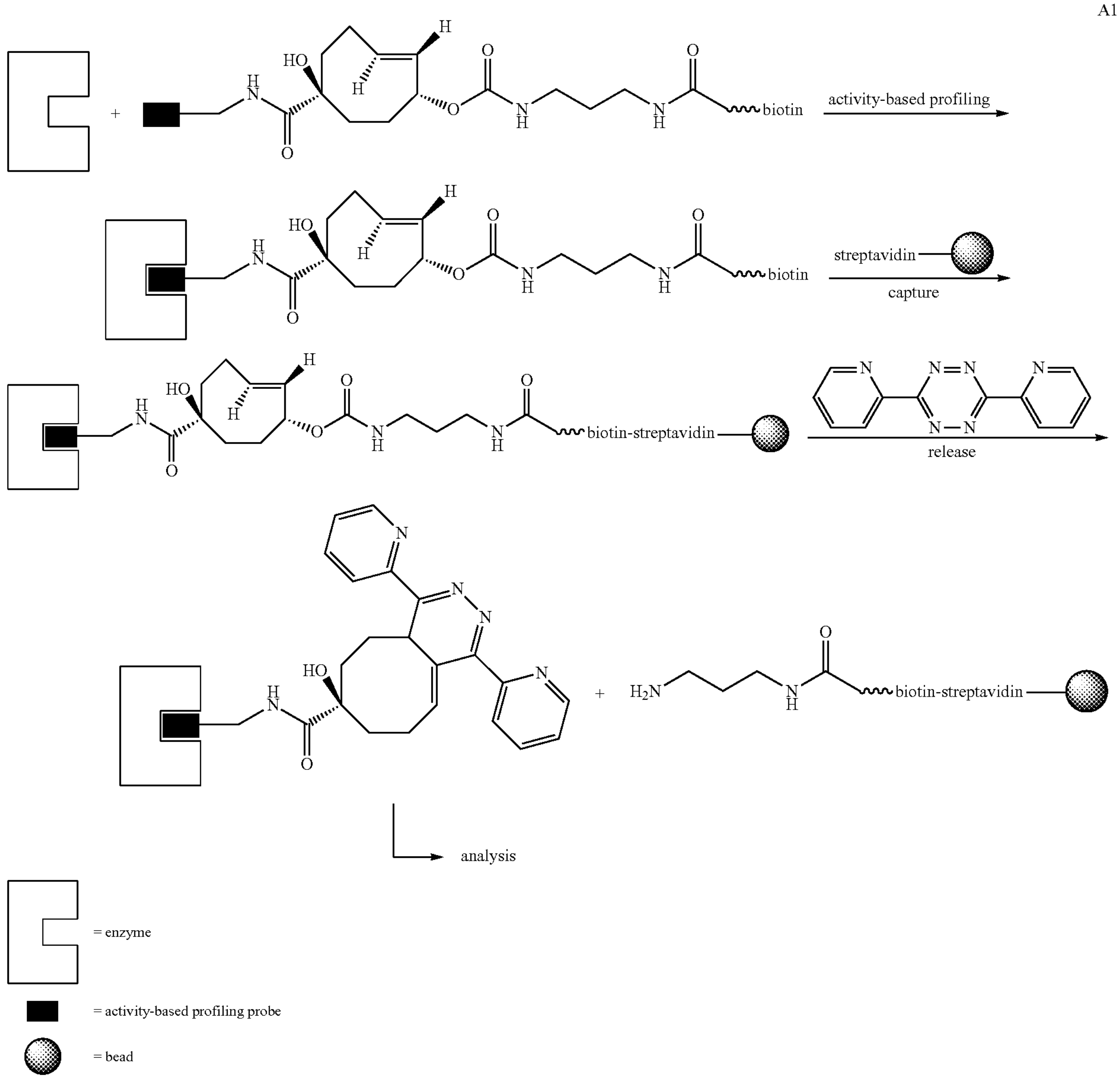
A2
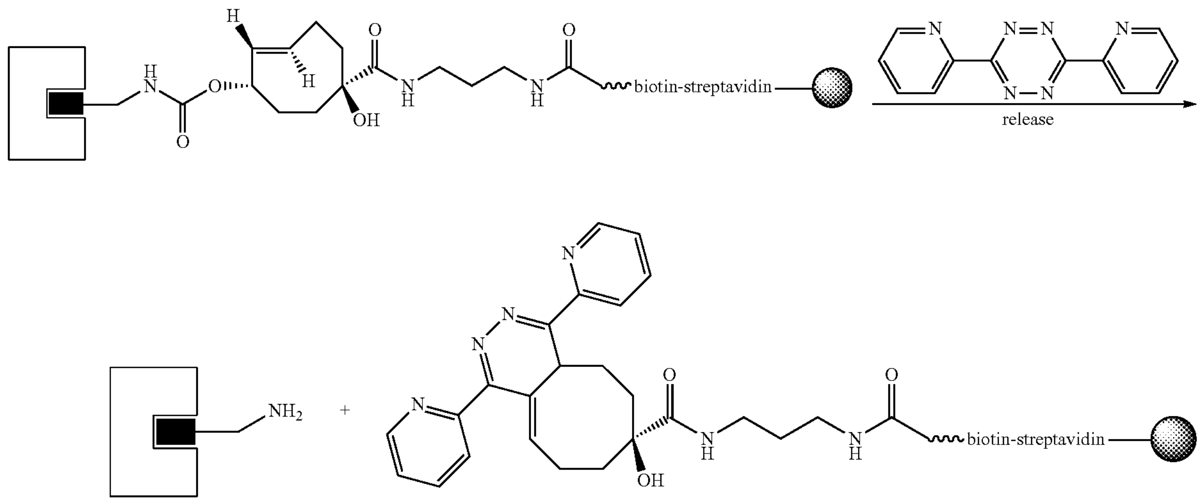

-continued
B
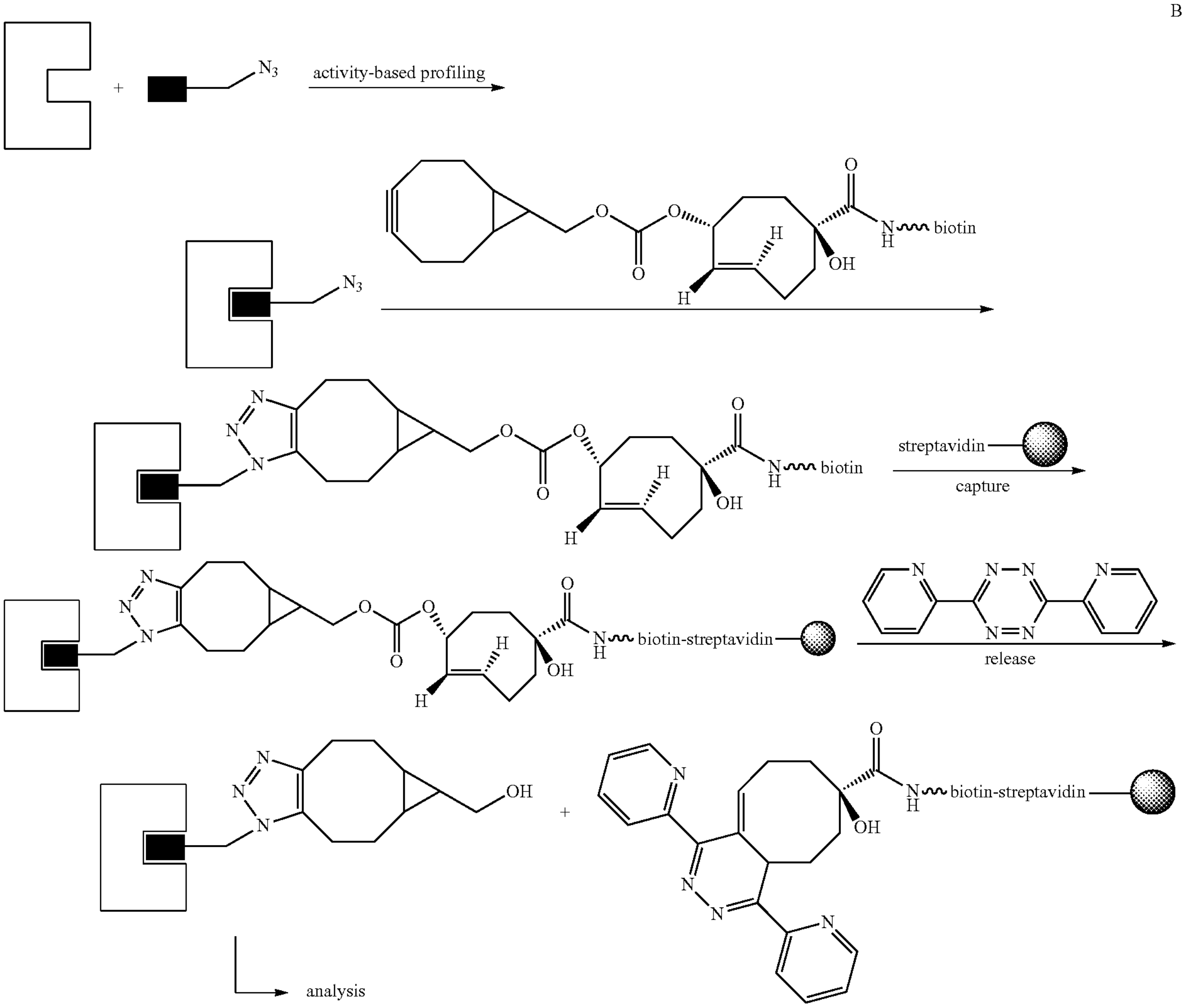
C
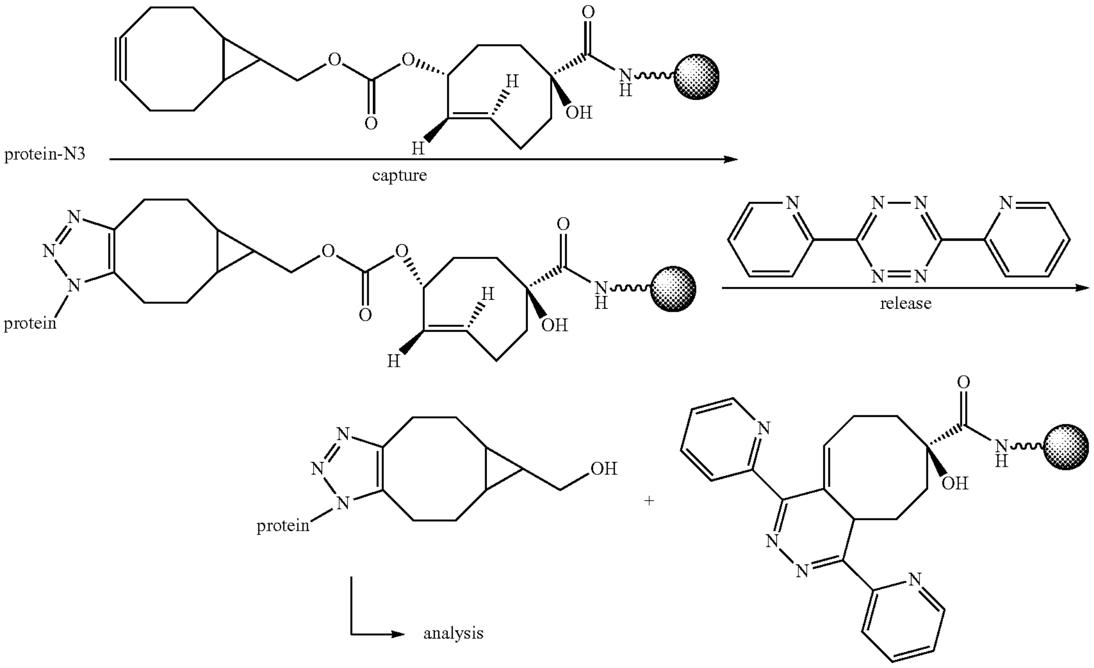

-continued
D
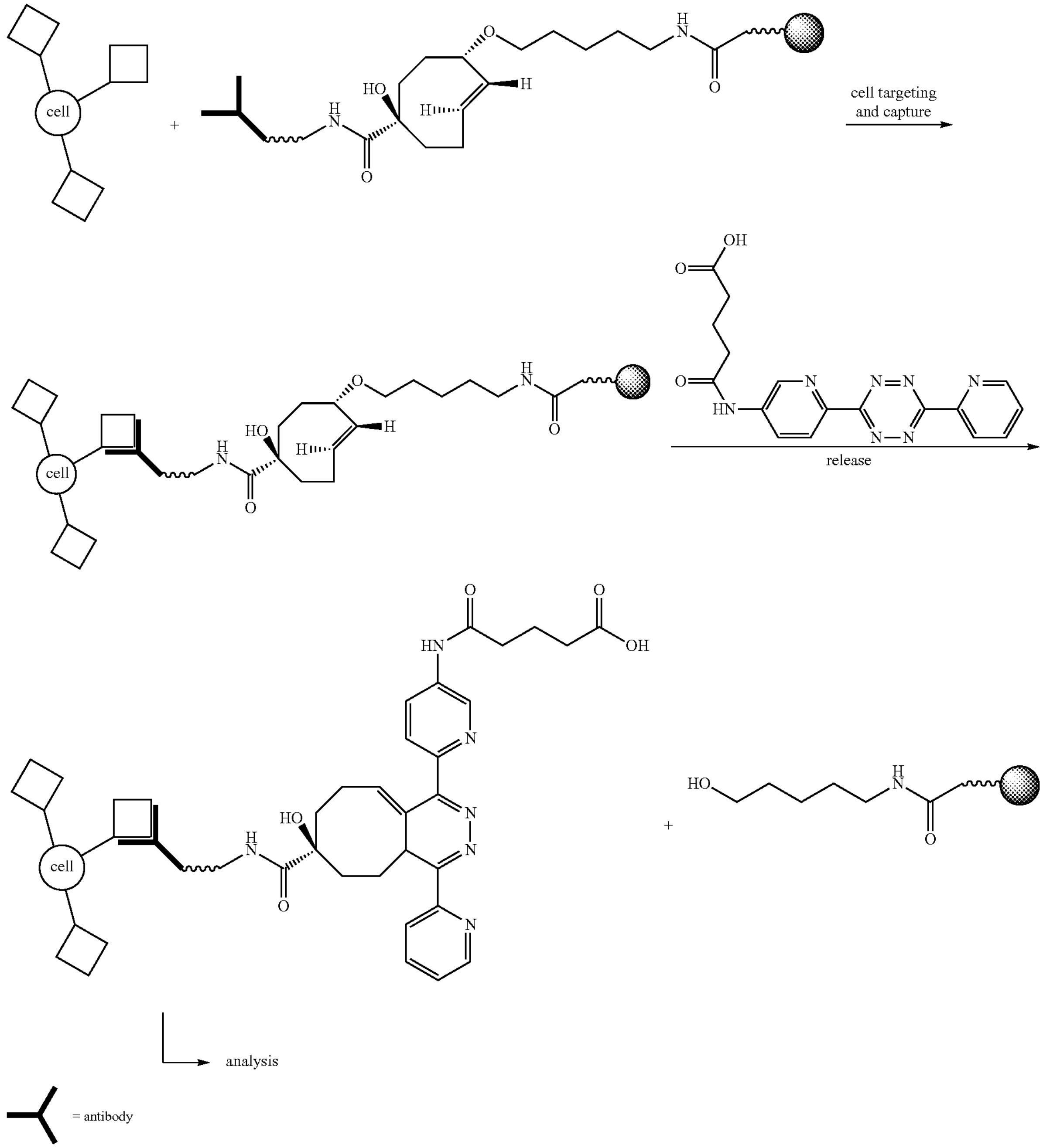
E
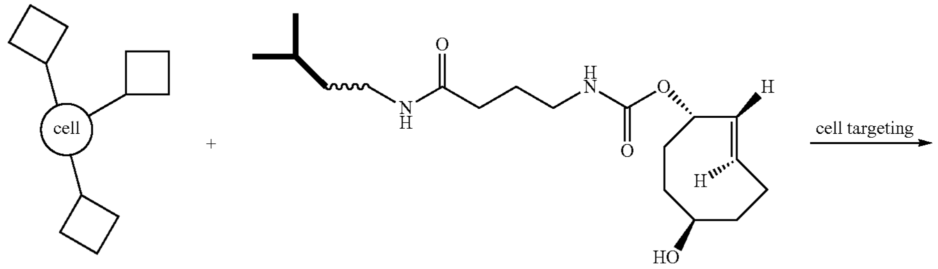

-continued

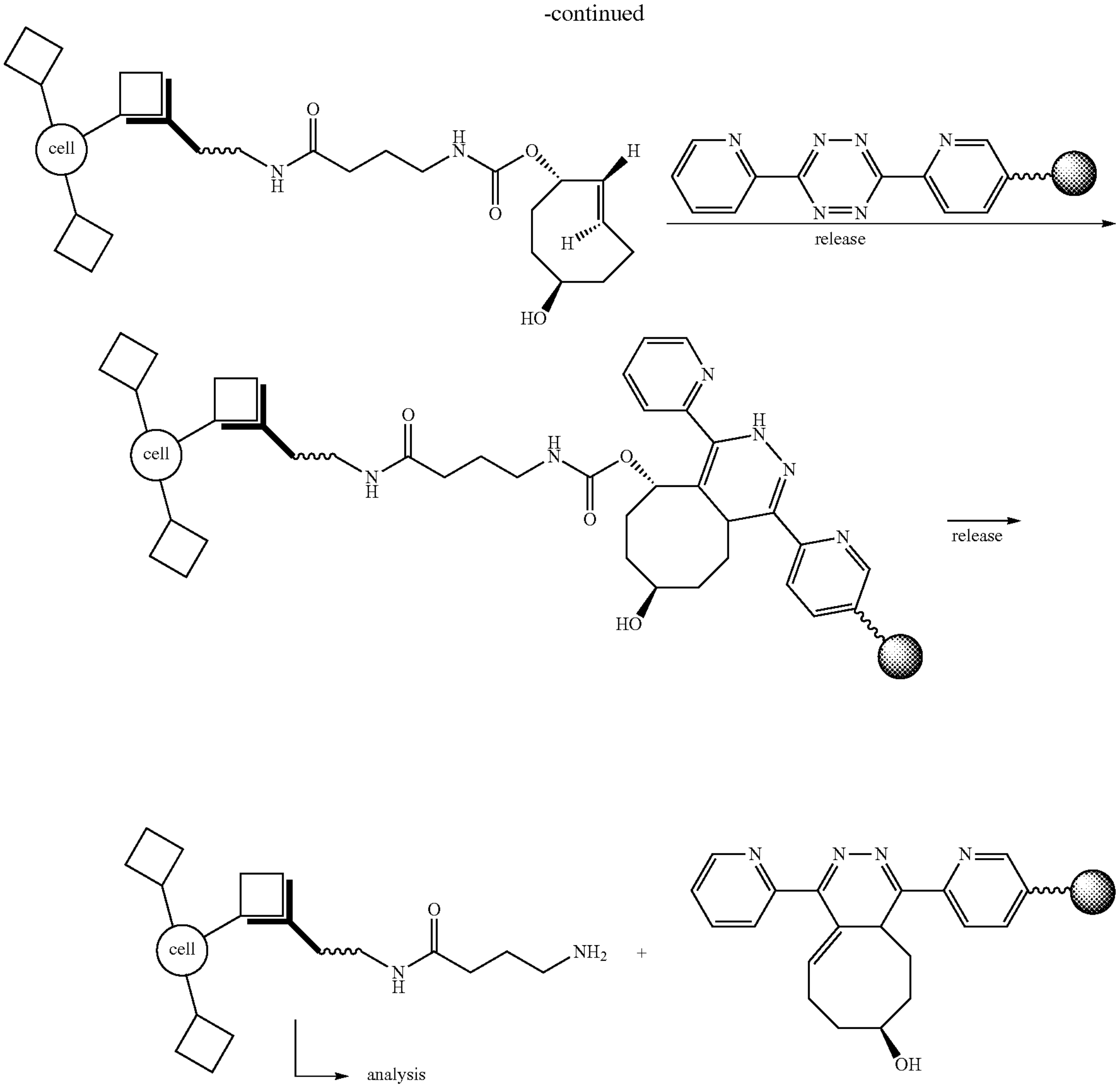

An alternative aspect of the invention comprises the Trigger as a chemoselective cleavable linker between a solid support and a solid support-bound substance. Therein, with reference to formula 5a and 5b: f is preferably 1.

In one embodiment, the Trigger is used as cleavable linker in solid phase synthesis. Solid-phase synthesis methods have been used in organic synthesis over the last decades, first for peptides, then for oligonucleotides, followed by other organic molecules. This development was accompanied by the development of various cleavable linkers for the detachment of molecules from the solid support resin. Examples include linkers that can be cleaved by acids, bases, fluoride ion, or photochemical reactions (Maruta et al. Tetrahedron Letters 47 (2006) 2147-2150; Shabat et al. Chem. Eur. J 2004, 10, 2626). An alternative bioorthogonal approach may expand the scope of compatible functionalities. Here a solid phase synthesis resin, such as polystyrene, is functionalized with TCO Triggers upon which the molecule of interest, for example a peptide, is synthesized. After the synthesis is complete, the Activator is added which reacts with the Trigger releasing the product (e.g. peptide) from the resin-bound Trigger into solution.

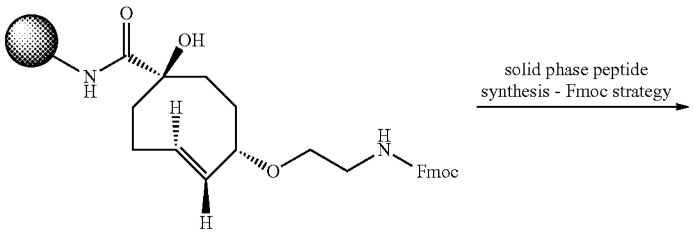

-continued
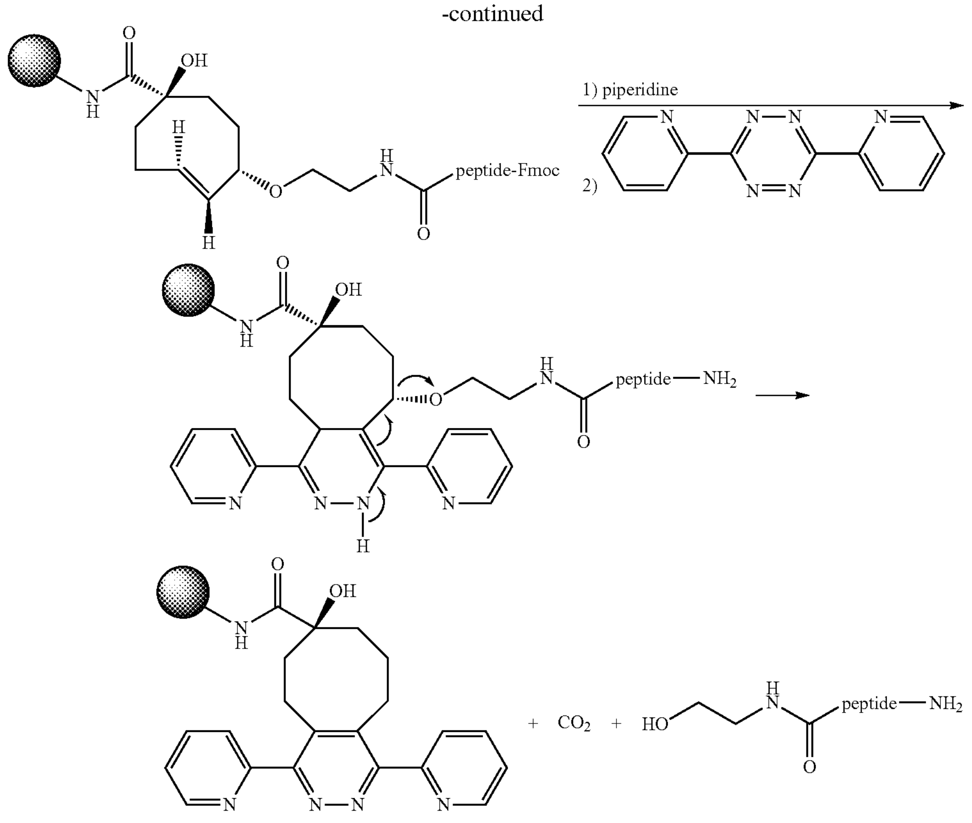
Alternative Solid-Phase Synthesized Compounds:
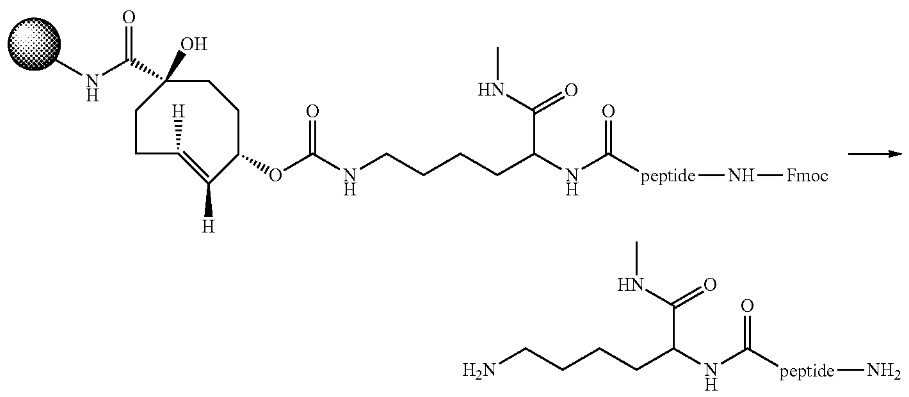
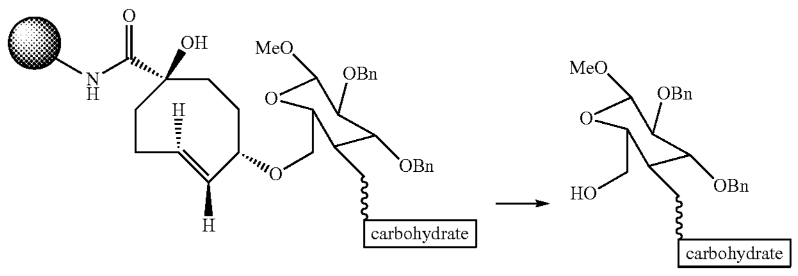

An alternative embodiment, shown directly below, comprises the selective release and activation of a surface-bound chemical reagent in a cartridge or a lab on a chip device.

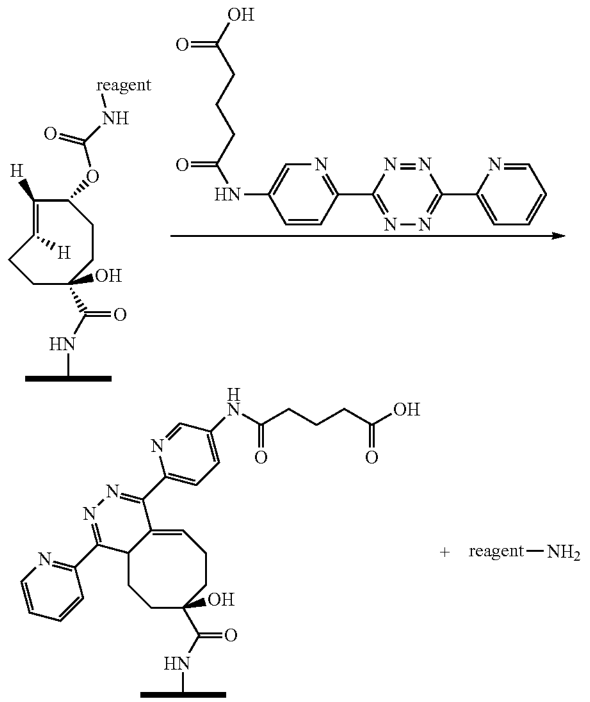

In yet another aspect the Trigger functions as a cleavable linker for reversible biomolecule crosslinking, and/or and immobilization, followed by release. Applications in chemical biology include a) the use of two proteins linked together via TCO, and their studying their action in e.g. a cellular environment before and after TCO cleavage; b) cleavage of a protein-TCO-targeting agent conjugate in cells to release the protein from a particular subcellular domain; c) cleavage of a protein-targeting agent-TCO conjugate in cells to target the protein to a particular subcellular domain (see Lim Acc Chem Res 2011).

In another embodiment, the $C^A$ is a masked antigen, e.g. a masked peptide comprising a peptide linked to a mask via the Trigger, which optionally is present in a Major Histocompatibility Complex (MHC), and which can be unmasked in vitro at a desired time.

In another embodiment, the $C^A$ is DNA or RNA and $C^A$ is linked via the Trigger to a transfection agent (i.e. $C^B$), designed to deliver the DNA or RNA into a cell in vivo or in vitro. Upon transfection, an activator is administered that tracelessly releases the DNA or RNA from the transfection agent.

In one embodiment the Trigger is used as cleavable linker in a biomolecule biotinylation agent for application in biomolecule detection, isolation and purification. Thus, use is made of biomolecule-reactive Trigger-biotin conjugates for the cleavable (reversible) attachment of biotin to peptides, proteins (for example cell surface proteins), glycoproteins, DNA and other biomolecules. The cleavable linker allows mild detachment of the bound biomolecule after affinity purifying biotinylated proteins using immobilized avidin or streptavidin. With reference to the scheme directly below, Probe A is useful for biotinylation of lysine residues in proteins. With R=$SO_3Na$ the agent will remain charged and in the extracellular space and is especially useful for labeling cell membrane proteins. Probe B is an aminooxy-biotin reagent and probe C is a hydrazide-biotin reagent and as such B and C are useful for biotinylating glycoproteins and other molecules that have oxidizable polysaccharides groups. Compounds D-F are a photoactivatable reagent that enables biotinylation of nucleic acids and other molecules that do not have readily available amine or sulfhydryl groups for coupling. When exposed to strong ultraviolet or visible light, the aryl azide group of D-F converts to a reactive nitrene that readily reacts to form covalent bonds with a variety of chemical groups, such as nucleic acids. Compound G enables simple and efficient reversible biotinylation of antibodies, cysteine-containing peptides and other thiol-containing molecules. Compound H is a reagent that enables proteins to be temporarily labeled at sulfhydryl sites for later photo-induced covalent attachment and transfer of biotinylation to an interacting protein, thereby tagging the previously unknown interacting protein(s) for affinity purification, detection, analysis (e.g. mass spectrometry, electrophoresis or sequencing).

A

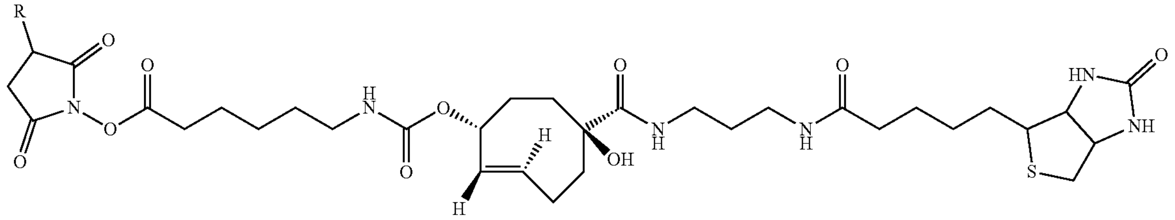

R = H, $SO_3Na$

B

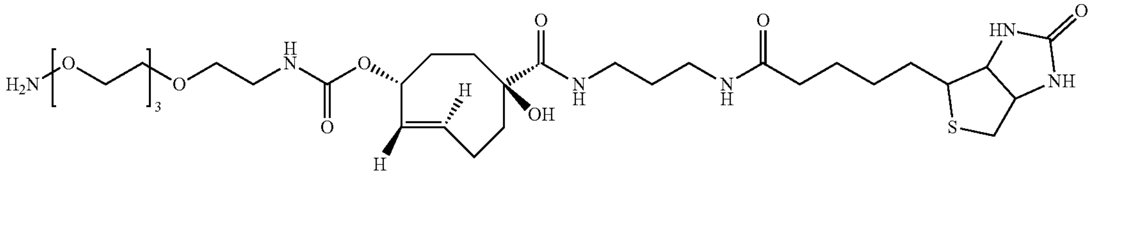

-continued

C

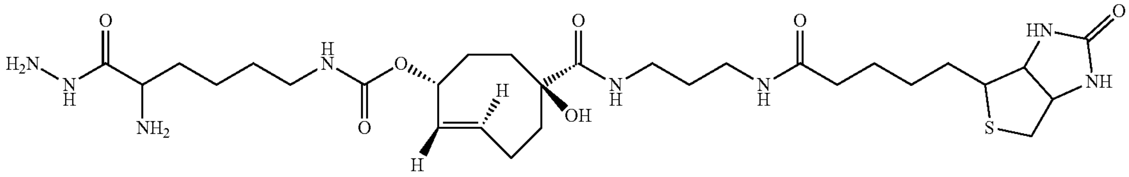

D

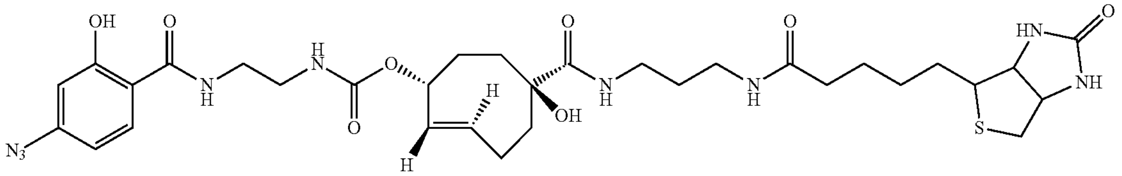

E

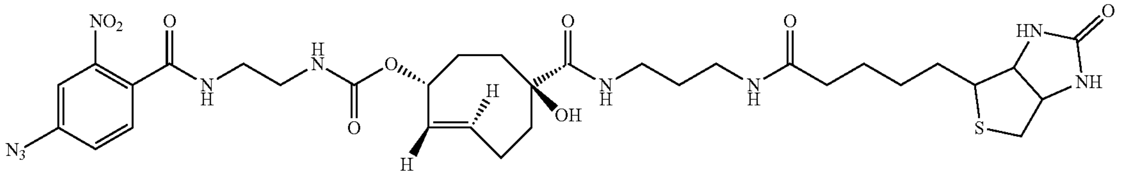

F

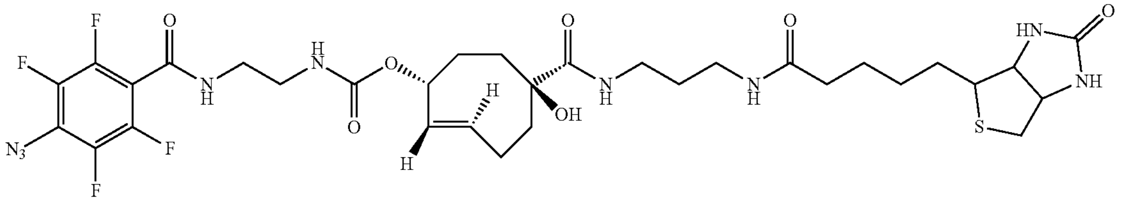

G

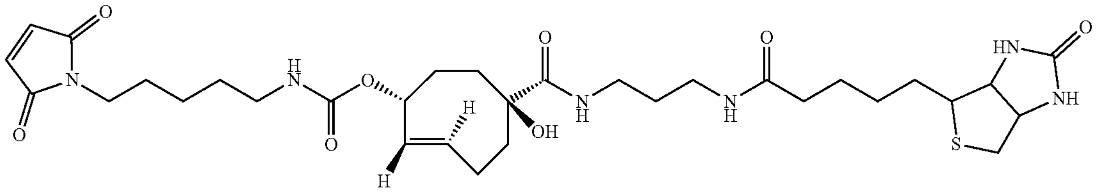

H

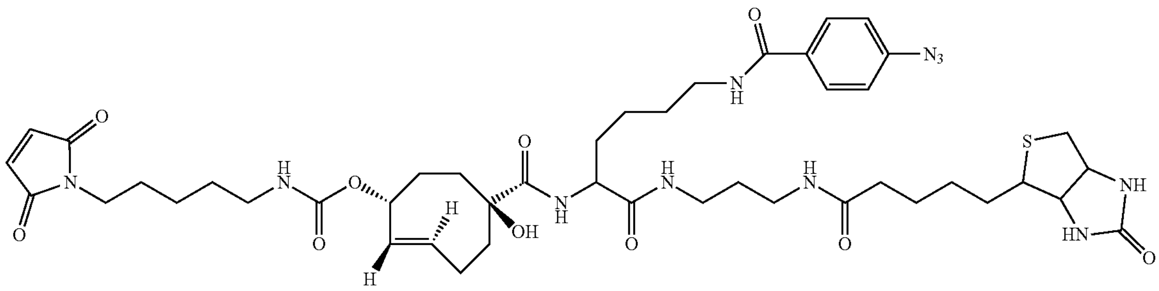

Analogously, the linkers directly below can be used for protein labeling and capture using tetrazine coated beads or resin. The tetrazine moieties will react with the TCO functionalized biomolecule allowing isolation, followed by automatic biomolecule release. Suitably chosen tetrazine-TCO pairs will give a release with a half life of >2 h and given the required reaction time of <10 minutes thus allow enough time for isolation of the complex before the complex releases the biomolecule automatically through release of the linker.

A

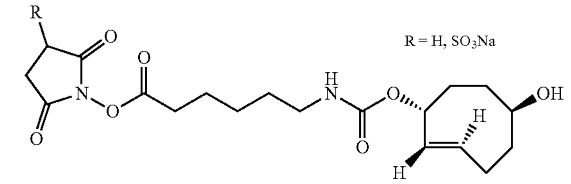

-continued

B

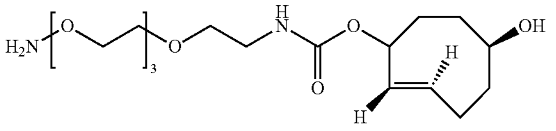

C

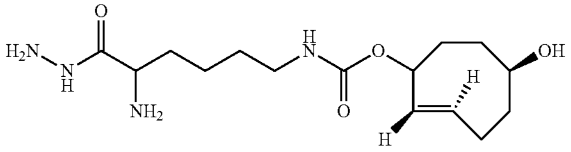

D

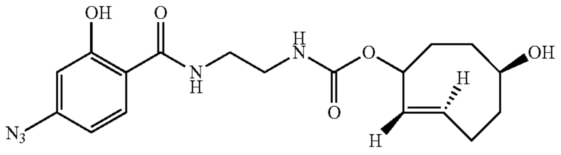

E

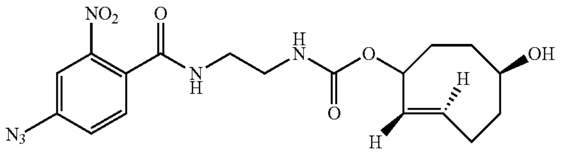

F

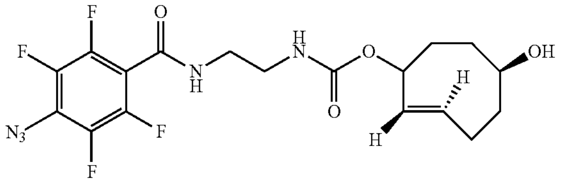

G

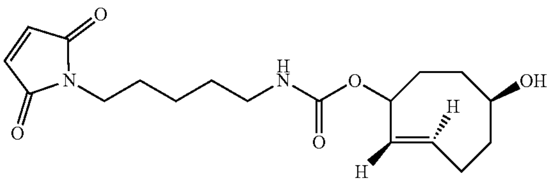

In another embodiment the Trigger is used as cleavable linker in a crosslinker between two biomolecules for e.g. application in biomolecule detection, immobilization, isolation and purification, in particular with respect to biomolecule interactions. Examples include crosslinking of cell surface proteins prior to cell lysis and immunoprecipitation, fixing of protein interactions to allow identification of weak or transient protein interactions, fixing of tissues for immunostaining, 1-step bioconjugations, and immobilization of proteins onto eg amine-coated surfaces. Thus, use is made of biomolecule-reactive bifunctional crosslinkers containing a cleavable Trigger for the cleavable (reversible) attachment of biomolecules such as peptides, glycoproteins, DNA to one another. Such as linker can for example be used in a "shotgun" approach to capture interaction complexes. When using lysine reactive moieties, the reagent will crosslink any and all interacting molecules whose respective lysine residues come within the spacer length of the crosslinker. Subsequently, a particular interaction complex is detected after crosslinking and (usually) cell lysis by immunoprecipitation or by administering a specific antibody or other probe for one of the target molecules in the complex. With reference to the scheme directly below, compound A is an homobifunctional lysine-reactive crosslinker, useful for the crosslinking of for example two proteins. Compound B is a cleavable heterobifunctional amine-reactive photocrosslinker, useful with molecules where no amine residue is available or accessible (even DNA, polysaccharides and other molecules). These heterobifunctional linkers enable "two-step" reactions in which "bait" proteins can be labeled, added to a cell and light-activated to crosslink at the desired time (e.g., upon cell stimulation when the interaction of interested is presumed to occur), followed by isolation and mild cleavage through the Trigger. Compound C is a cleavable homobifunctional thiol reactive crosslinker for covalent but reversible conjugation between e.g. proteins or peptide cysteines. Compound D is a cleavable heterobifunctional thiol and amine reactive crosslinker for covalent but reversible conjugation between e.g. proteins or peptide cysteines and lysines. Compound E is a cleavable modification reagent for aminoacids, allowing a temporary change in protein charge.

A

R = H, $SO_3Na$

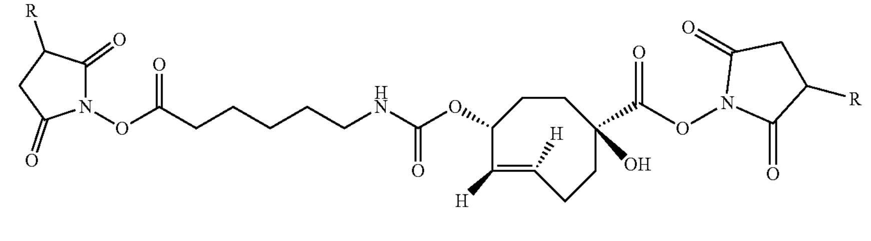

-continued
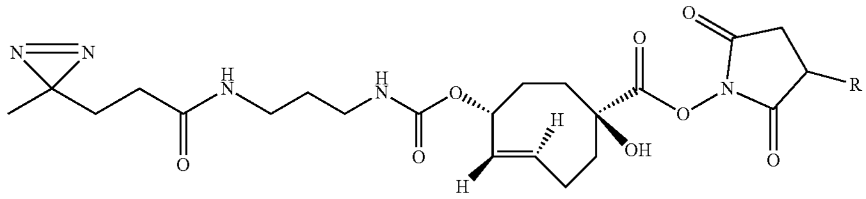
B
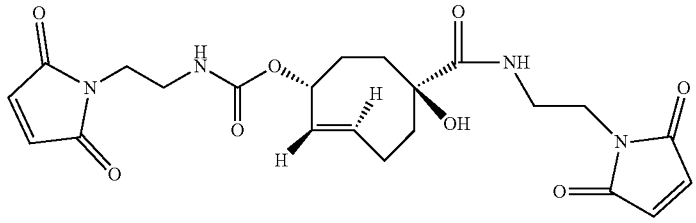
C
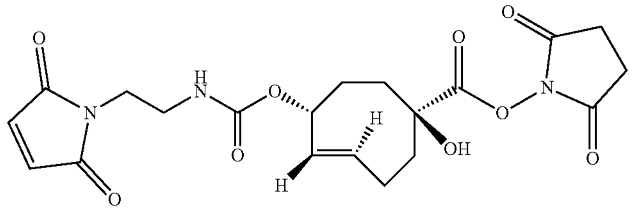
D
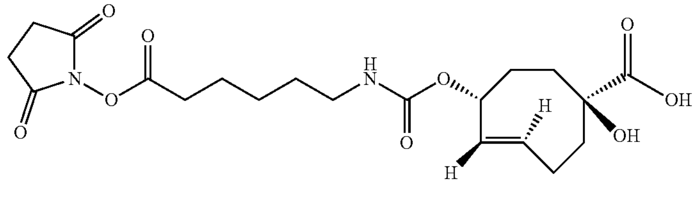
E

In another aspect the Trigger is used as in a radiolabeling kit, as shown in the scheme directly below. Use is made of a bead linked to a $^{18}$F-labeled TCO, and a tetrazine-peptide derivative is added, which reacts with the TCO affording $^{18}$F-TCO-tetrazine-peptide. With reference to formula 5, f is preferably 1. In a different approach, a peptide is bound to the bead via the TCO and a $^{18}$F-tetrazine derivative is added which reacts with the TCO affording a $^{18}$F-tetrazine-TCO-peptide.

A

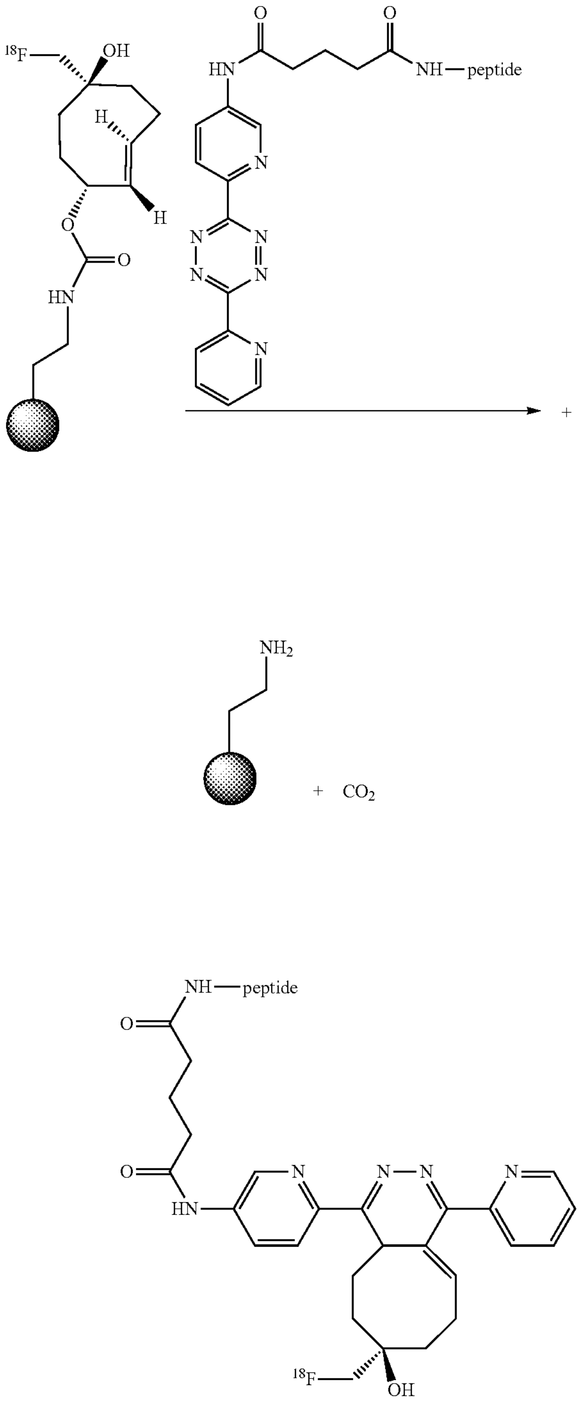

-continued

B

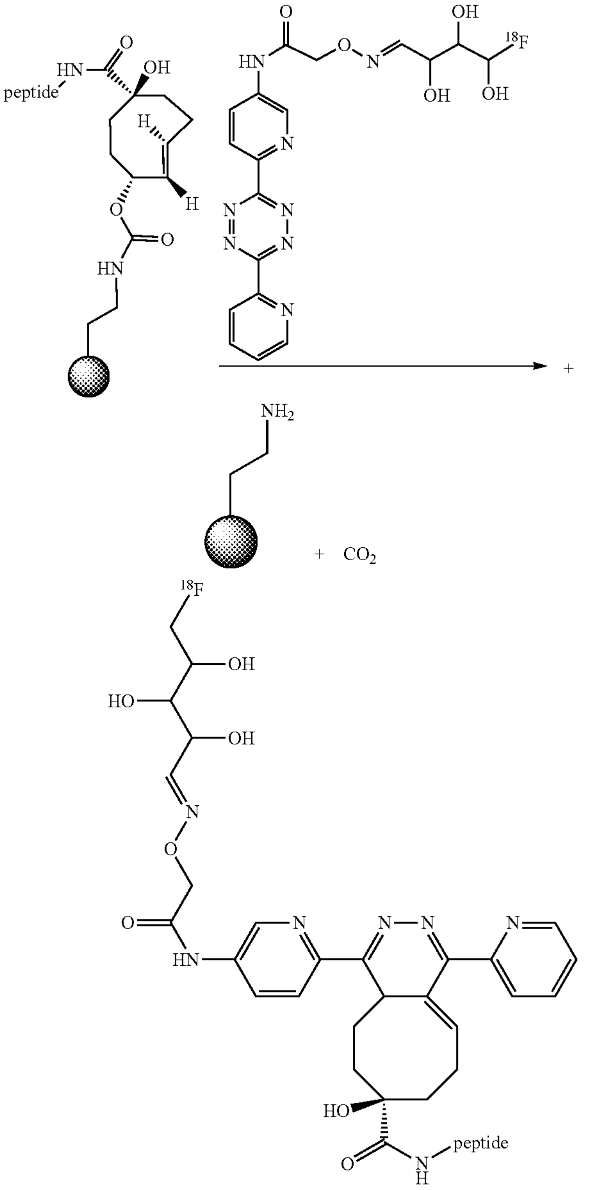

Figure 6:
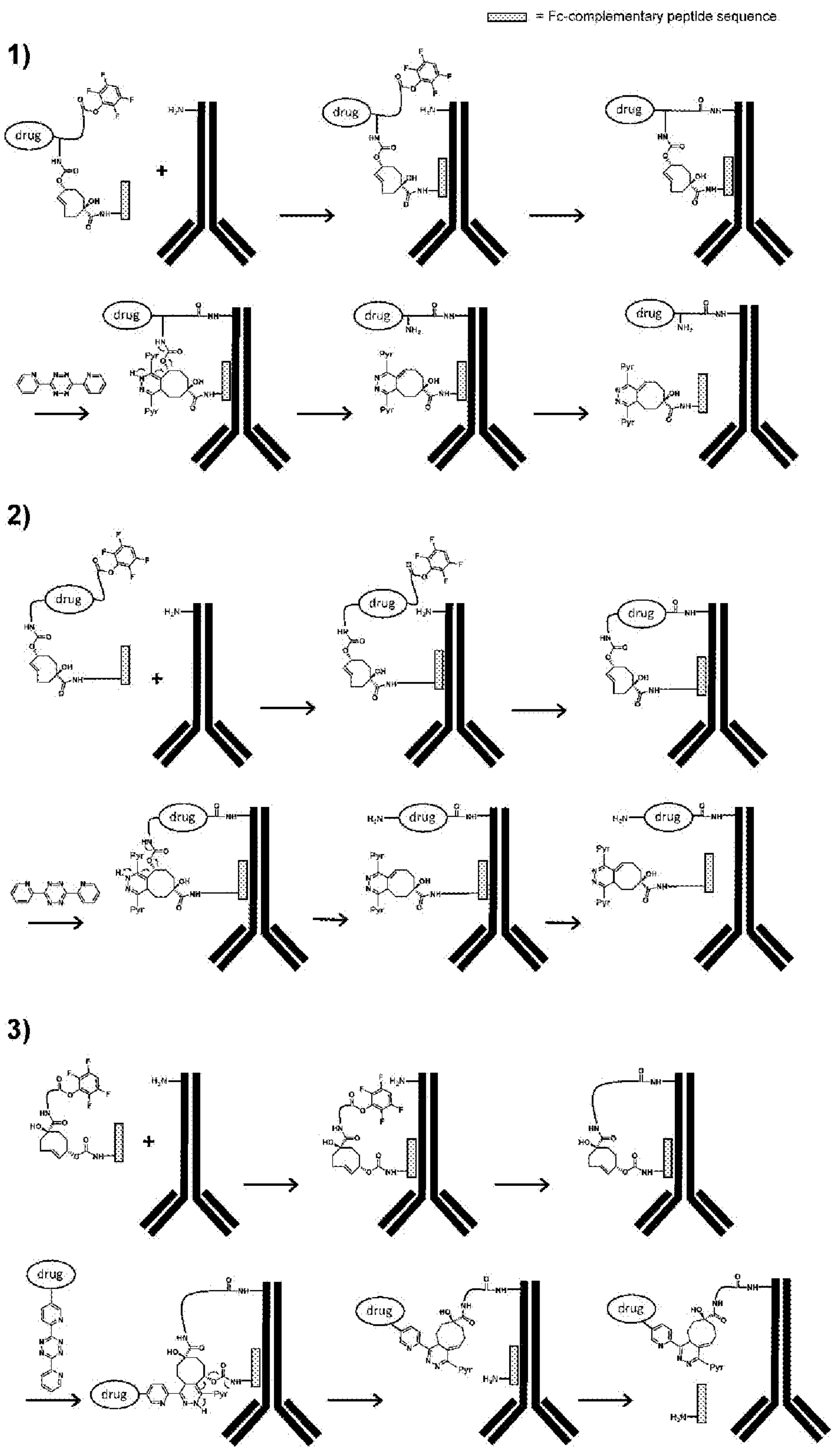
FIG. 6 depicts the use of the compounds of this invention for the site specific antibody conjugation with e.g. a drug, for ADC production.

In another embodiment, the compounds of the invention are used for site specific antibody conjugation. Reference is made to FIG. 6. In panel 1, a peptide that binds to a specific region on the antibody near a specific conjugatable amino acid residue (in this case a lysine), is modified with a click-cleavable TCO linker that further links to a Drug (to be conjugated) and an active ester (e.g. TFP ester) for lysine conjugation. Upon binding of the peptide to the protein the TFP ester will react with the lysine residue due to its proximity. Subsequently, the TCO linker is cleaved by tetrazine, the peptide is washed off the antibody, leading to a site specifically conjugated antibody-drug conjugate. Panel 2 shows the same approach wherein the Drug links the TCO to the active ester. In panel 3, the peptide is modified with a click-cleavable TCO linker that further links to the active ester (e.g. TFP ester) for lysine conjugation. Upon binding of the peptide to the protein and lysine conjugation, a tetrazine-drug conjugate is added which leads to concomitant cleavage of the peptide and conjugation of the drug.

In another aspect the Trigger is used in a diagnostic kit, see directly below. With reference to formula 5, f is preferably 1. Immobilized (e.g. in a 96-well plate) TCO conjugated to one or more quenched fluorophores is contacted with a sample containing an unknown amount of tetrazine moieties. These tetrazines have been previously incorporated in a biomolecule as amino acid residue in a metabolic engineering experiment, or alternatively the sample contains e.g. tetrazine-based pesticide. Reaction of the tetrazine with the TCO effects release and dequenching of the fluorophores, allowing readout via e.g. UV absorption.

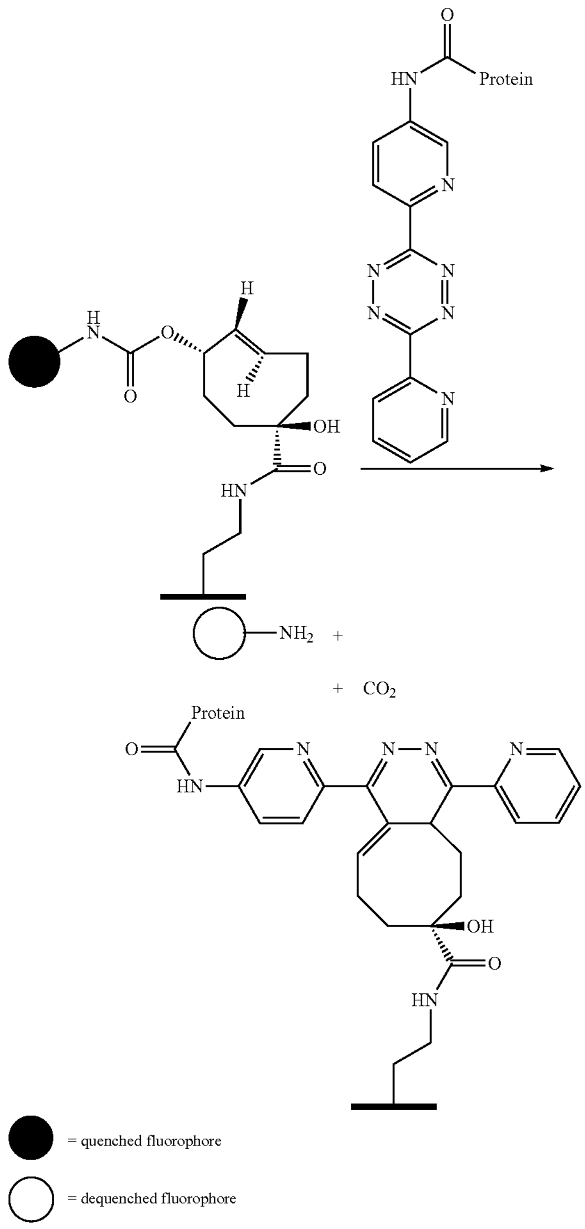

The Constructs A and Constructs B used in in vitro embodiments include but are not limited to small molecules, organic molecules (including fluorescent dyes), metal coordination compounds, molecules comprising a radionuclide, chelates comprising a radiometal, inorganic molecules, organometallic molecules, biomolecules, drugs, polymers, resins (e.g. polystyrene, agarose), particles (e.g. beads, magnetic beads, gold, silica-based particles and materials, polymers and polymer-based materials, glass, iron oxide particles, micro- and nanoparticles (such as liposomes, polymersomes), gels, surfaces (e.g. glass slides, chips, wafers, gold, metal, silica-based, polymer, plastic, resin), cells, biological tissues, pathogens (viruses, bacteria, fungi, yeast). The Constructs may for example comprise a combination of the aforementioned Constructs.

Examples of biomolecules include: carbohydrates, biotin, peptides, peptoids, lipids, proteins, enzymes, oligonucleotides, DNA, RNA, PNA, LNA, aptamers, hormones, toxins, steroids, cytokines, antibodies, antibody fragments (e.g. Fab2, Fab, scFV, diabodies, triabodies, VHH), antibody (fragment) fusions (e.g. bi-specific and trispecific mAb fragments).

Construct A and Construct B can also be $R_{32}$ or a moiety comprising $R_{32}$, as defined herein, wherein $R_{32}$ can be used to bind to a further Construct A or B. For example, Construct A can be $R_{32}$ being a maleimide or photocrosslinker that is bound to the $T^R$ via a Spacer $S^P$. The maleimide or photocrosslinker can be used to further conjugate the $T^R$ to a protein. In this embodiment $C^A$ and $C^B$ are a biomolecule-binding moiety.

In preferred embodiments $C^A$ and $C^B$ are bound to the $T^R$ via a Spacer $S^P$, wherein the $S^P$ is or comprises $C^{M2}$, $C^X$ or a residue of $R_{32}$.

In a preferred embodiment the Construct A is a biomolecule. In another preferred embodiment the $C^A$ is a biomolecule and $C^B$ is selected from the group of polymer, resin, particle, solid support. In another preferred embodiment the $C^B$ is a biomolecule and $C^A$ is selected from the group of polymer, resin, particle, gel, surface. In preferred embodiments of the invention, $C^A$ and/or $C^B$ equals an $R_{32}$ group and this or these groups function as biomolecule binding moieties. Preferred $R_{32}$ groups for use as biomolecule binding moieties include but are not limited to biotin, carboxylic acids and their activated esters such as N-hydroxysuccinimide ester and para-nitrophenyl ester, isocyanate, isothiocyanate, N-maleimide groups, bromoacetamide and iodoacetamides, azido groups, alkynyl groups such as (hetero) cycloalkynyl group and terminal alkynyl groups, aminooxy groups, hydrazinyl groups, and photoreactive groups. In preferred embodiments of the invention, $C^A$ and $C^B$ equal $R_{32}$ and these moieties are bound to different locations on the same biomolecule, resulting in a cycle. In another preferred embodiment the $C^A$ is a $R_{32}$ that is a biomolecule binding moiety, and $C^B$ is a $R_{32}$ that binds to a polymer, resin, particle or a solid support. In another preferred embodiment the $C^B$ is a $R_{32}$ that is a biomolecule binding moiety and $C^A$ is a $R_{32}$ that binds to a polymer, resin, particle or a solid support. In another embodiment, either $C^A$ or $C^B$ is or comprises biotin. In preferred embodiments Trigger cleavage results in the cleavage of one $C^A$ from two or more $C^B$. In preferred embodiments Trigger cleavage results in the cleavage of one $C^B$ from two or more $C^A$. In preferred embodiments, the Trigger is bound to only one $C^A$ and one $C^B$. In other preferred embodiments, the Trigger is bound to two $C^A$ moieties and no $C^B$ moieties. In preferred embodiments wherein a $C^A$ is to be released from the Trigger but not $C^B$, then it is preferred that $C^B$ is not bound via L. In a preferred embodiment, only one surface (being $C^A$ or $C^B$) is bound to the Trigger.

In a preferred embodiment, the Activator may be conjugated to surfaces, gels, resins, especially solid phase synthesis resins, such as polystyrene, Janda gel and the like. In a preferred embodiment, the Activator can comprise a biomolecule, a Drug or a Targeting Agent.

In a preferred embodiment, Activators may optionally comprise a membrane translocation moiety (e.g. adamantine, poly-lysine/arginine, TAT, human lactoferrin). Exemplary references regarding such moieties include: Trends in Biochemical Sciences, 2015, 40, 12, 749; J. Am. Chem. Soc. 2015, 137, 12153-12160; Pharmaceutical Research, 2007, 24, 11, 1977.

In a preferred embodiment, the Activator does not comprise $R^{87}$.

Suitable Spacers $S^P$, for use in a Trigger conjugate of this invention are listed in the section Spacers (vide supra). In preferred embodiments the Spacer has at most 50 carbon atoms, more preferably at most 25 carbon atoms, more preferably at most 10 carbon atoms. Other preferred Spacers are PEG and PPG polymers, and oligopeptoids, preferably ranging from 2 to 50 repeating units, more preferably from 2 to 24 repeating units, more preferably from 2 to 12 repeating units.

EXAMPLES

General Methods

All reagents, chemicals, materials and solvents were obtained from commercial sources and were used as received, including nitrile starting compounds that not have been described. All solvents were of AR quality. [$^{111}$In]Indium and [$^{89}$Zr]zirconium oxalate solutions were purchased from Curium. Zeba desalting spin columns (7 and 40 kDa MW cut-off, 0.5 mL) and Slide-A-Lyzer dialysis cassettes (20 kDa MW cut-off) were purchased from Pierce Protein Research (Thermo Fisher Scientific). Mouse plasma was purchased from Innovative Research. 29-Amino-3,6,9,12,15,18,21,24,27-nonaoxanonacosan-1-ol was purchased from PurePEG. 3,6-Dimethyl-1,2,4,5-tetrazine and (E)-cyclooct-2-en-1-yl (4-nitrophenyl) carbonate were prepared according to literature procedures [Versteegen et al., *Angew. Chem. Int. Ed.* 2013, 52, 14112-14116]. Analytical thin layer chromatography was performed on Kieselgel F-254 precoated silica plates. Column chromatography was carried out on Screening Devices B. V. silica gel (flash: 40-63 μm mesh and normal: 60-200 μm mesh). $^1$H-NMR and $^{13}$C-NMR spectra were recorded on a Bruker Avance III HD (400 MHz for $^1$H-NMR and 100 MHz for $^{13}$C-NMR) spectrometer at 298 K. Chemical shifts are reported in ppm downfield from TMS at rt. Abbreviations used for splitting patterns are s=singlet, d=doublet, dd=double doublet, t=triplet, q=quartet, m=multiplet and br=broad. HPLC-PDA/MS was performed using a Shimadzu $L^C$-10 AD VP series HPLC coupled to a diode array detector (Finnigan Surveyor PDA Plus detector, Thermo Electron Corporation) and an Ion-Trap (LCQ Fleet, Thermo Scientific). HPLC-analyses were performed using a Alltech Alltima HP C18 3μ column using an injection volume of 1-4 μL, a flow rate of 0.2 mL min$^{-1}$ and typically a gradient (5% to 100% in 10 min, held at 100% for a further 3 min) of MeCN in $H_2O$ (both containing 0.1% formic acid) at 298 K.

Size exclusion chromatography (SEC) was performed on an Akta system (GE Healthcare Life Science) equipped with a Superdex200 column. Radio-HPLC was performed on an Agilent 1100 system, equipped with a Gabi radioactive detector (Raytest). The samples were loaded on an Alltima C18 column (4.6×150 mm, 5μ), which was eluted at 1 mL min-1 with a linear gradient of water (A) and acetonitrile (B) containing 0.1% v/v % TFA (4 min at 3% B followed by an increase to 90% B in 15 min). Radio-ITLC was performed on ITLC-SG strips (Varian Inc.) eluted with 200 mM EDTA in saline solution ($^{111}$In) or in 0.1M citrate pH 6.0 ($^{89}$Zr). In these conditions the radiolabeled products remain at the base while unbound radionuclide migrates with an $R_f$ of 0.7-0.9. SDS-PAGE was performed on a Mini-PROTEAN Tetra Cell system using 4-20% precast Mini-PROTEAN TGX gels and Precision Plus Protein All Blue Prestained protein standards (BioRad Laboratories). The radioactivity distribution on ITLC strips and SDS-PAGE gels was monitored with a Typhoon FLA 7000 phosphor imager (GE Healthcare Life Science) using the AIDA software.

Unless stated otherwise, no chiral resolution of synthesized TCO enantiomers is performed in Example 1. When one enantiomer is depicted, the mirror image is present in the synthesized compound as well. E.g. 1.43 is present as both mirror image stereoisomers.

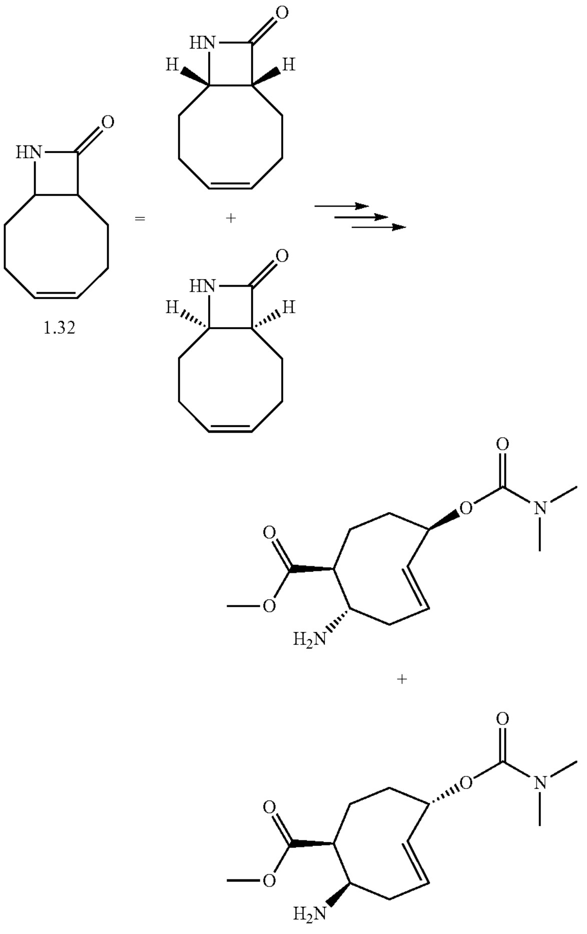

1.32

1.43

Example 1: TCO Synthesis

Compound 1.71 was synthesized as previously described (Carlson et al., *J Am Chem Soc* 2018, 140, 3603-3612)

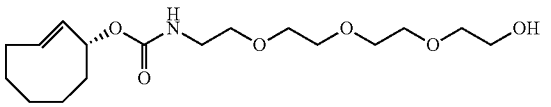

Compound 1.72 was synthesized as 1.15, starting from TCO-2-OH

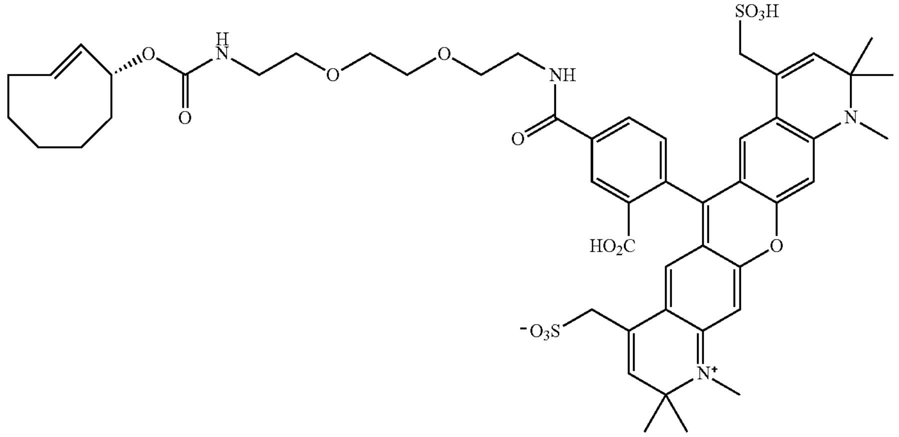

(Z)-5-Bromocyclooct-1-ene (1.1)

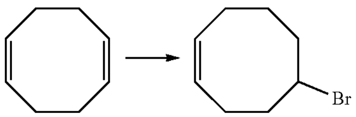 [SMILES: C1=C\CC/C=C\CC/1 ; BrC1CC/C=C\CCC1]

1,5-Cyclooctadiene (450 g, 4.16 mol) was cooled to 0° C. While stirring, HBr (33% in AcOH, 356 mL, 2.08 mol) was added in 1 h. The reaction mixture was then allowed to reach rt and stirred overnight, and poured onto ice water (1 L). $Et_2O$ (600 mL) was added and the aqueous layer was extracted with $Et_2O$ (3×300 mL). The combined organic layer was washed with sat. aq. $NaHCO_3$ (500 mL) and brine (300 mL), dried over $Na_2SO_4$, filtered and the solvent was evaporated. Distillation afforded 1.1 (336 g, 85%). $^1$H-NMR (200 MHz, $CDCl_3$): δ 5.73-5.51 (m, 2H) 4.31 (tdd, J=8.9, 4.7, 1.7 Hz, 1H), 2.56-1.89 (m, 8H), 1.84-1.63 (m, 1H), 1.62-1.42 (m, 1H) ppm.

(Z)-Cyclooct-4-ene-1-carbonitrile (1.2)

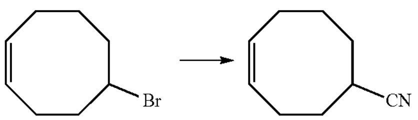 [SMILES: BrC1CC/C=C\CCC1 ; N#CC1CC/C=C\CCC1]

NaCN (95%, 138 g, 2.68 mol) was dissolved in DMSO (anhydrous, 900 mL) and stirred at 100-110° C. Compound 1.1 (422 g, 2.23 mol) dissolved in DMSO (anhydrous, 200 mL) was added in 30 min. After 3 h, the reaction mixture was cooled to rt and poured onto ice water (5 L). The aqueous layer was extracted with $Et_2O$ (4×1600 mL) and the combined organic layer was washed with brine, dried over $Na_2SO_4$, filtered and the solvent was removed in vacuo affording crude product 1.2 (233 g, 77%). $^1$H-NMR (400 MHz, $CDCl_3$): δ 5.76-5.56 (m, 2H), 2.86-2.71 (m, 1H), 2.51-1.72 (m, 8H), 1.65-1.37 (m, 2H) ppm.

(Z)-Cyclooct-4-ene-1-carboxylic acid (1.3)

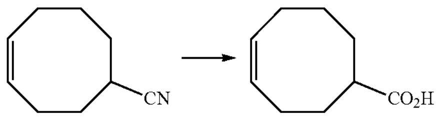 [SMILES: N#CC1CC/C=C\CCC1 ; O=C(O)C1CC/C=C\CCC1]

1.2 (83.0 g, 614 mmol) was suspended in an aqueous solution of KOH (164 g, 2.92 mol, 30% solution) and stirred at 40° C. Then, $H_2O_2$ was added dropwise to the brown reaction mixture leading to formation of a precipitate. After 60 h, the reaction mixture was cooled to rt and then slowly poured onto aqueous $H_3PO_4$ (40%) while cooling with an ice bath. The resulting mixture was stirred at rt for 2.5 h. Due to the formation of a large amount of white precipitate, the reaction mixture was filtered over a glass sinter funnel and washed with $Et_2O$. The filtrate was extracted with $Et_2O$ (6×150 mL), dried over $Na_2SO_4$ and filtered followed by evaporation of the solvent. The resulting brown oil was taken up in DCM (500 mL) and extracted with 2M NaOH (5×200 mL). The aqueous layer was adjusted to pH 1 by addition of 6 M HCl, which led to formation of a white precipitate. The mixture was extracted with DCM (4×200 mL) and the combined organic layer was dried over $Na_2SO_4$, filtered and concentrated affording crude compound 1.3 (59.1 g, 62%). $^1$H-NMR (400 MHz, $CDCl_3$): δ 8.86 (bs, 1H), 5.74-5.60 (m, 2H), 2.54-2.45 (m, 1H), 2.45-2.32 (m, 1H), 2.22-2.02 (m, 4H), 1.98-1.84 (m, 1H), 1.83-1.52 (m, 3H), 1.50-1.34 (m, 1H) ppm.

(Z)-Cyclooct-4-ene-1-carboxylic acid methyl ester (1.4)

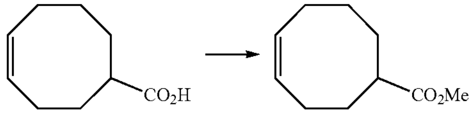 [SMILES: O=C(O)C1CC/C=C\CCC1 ; COC(=O)C1CC/C=C\CCC1]

$SOCl_2$ (7.10 mL, 97.3 mmol) was added dropwise to stirred MeOH (anhydrous, 90 mL) cooled to −10° C. Then, a solution of compound 1.3 in anhydrous MeOH (10 mL) was added dropwise. The reaction mixture was stirred at 0° C. for 30 min and then allowed to reach rt. After 2 h MeOH was removed in vacuo and the resulting residue was taken up in EtOAc and water (150 mL each). The layers were separated and the aqueous layer was extracted with EtOAc (2×70 mL). The combined organic layer was washed with saturated aqueous $NaHCO_3$ (70 mL) and brine (70 mL), dried over $Na_2SO_4$, filtered and the solvent was removed affording compound 1.4 (10.1 g, 93%); $R_f$ (hexanes:EtOAc=3:1)=0.87. $^1$H-NMR (400 MHz, $CDCl_3$): δ 5.78-5.56 (m, 2H), 3.64 (s, 3H), 2.47 (m, 1H), 2.41-2.29 (m, 1H), 2.20-2.06 (m, 3H), 2.05-1.98 (m, 1H), 1.91-1.80 (m, 1H), 1.77-1.51 (m, 3H), 1.45-1.32 (m, 1H) ppm.

(Z)-1-Hydroxycyclooct-4-ene-1-carboxylic acid methyl ester (1.5)

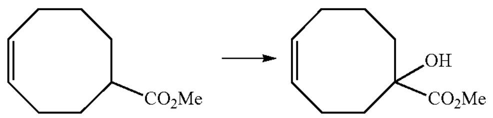 [SMILES: COC(=O)C1CC/C=C\CCC1 ; COC(=O)C1(O)CC/C=C\CCC1]

A 500 mL 3-necked round bottom flask was filled with argon, cooled to 0° C. and THF (anhydrous, 120 mL) and diisopropylamine (4.30 mL, 30.7 mmol) were added and degassed. Subsequently, n-BuLi (2.5 M in hexane, 11.2 mL, 28.1 mmol) was added and the reaction mixture was stirred for 35 min at 0° C. After cooling to −78° C. TMEDA (9.60 mL, 63.9 mmol) was added followed by 1.4 (4.3 g, 25.6 mmol) dissolved in THF (anhydrous, 40 mL). After stirring for 30 min a solution of (1S)-(10-camphorsulfonyl)oxaziridine (6.45 g, 28.1 mmol) in anhydrous THF (100 mL) was added. After 6 h the reaction mixture was quenched with saturated aqueous $NH_4Cl$ solution (100 mL) and water (100 mL), and the mixture was stirred until reaching 10° C. EtOAc (150 mL) was added, layers were separated, and the aqueous layer was extracted with EtOAc (3×200 mL). The combined organic layer was dried over $Na_2SO_4$ and concentrated in vacuo, which led to formation of a white precipitate in a yellow oil. The solvents were evaporated and the mixture of yellow oil and white precipitate was repeatedly filtered and concentrated and finally taken up in EtOAc and purified by column chromatography (gradient: 10% to 90% EtOAc in hexanes within 50 min) affording 1.5 (2.68 g, 57%) as a pale-yellow oil; $^1$H-NMR (400 MHz, $CDCl_3$): δ 5.78 (dt, J=11.1, 6.5 Hz, 1H), 5.62-5.48 (m, 1H), 3.76 (s, 3H), 2.92 (bs, 1H), 2.54-2.34 (m, 2H), 2.22-1.99 (m, 3H), 1.96-1.69 (m, 4H), 1.56-1.38 (m, 1H) ppm; $^{13}$C-NMR (101 MHz, $CD_2Cl_2$): δ 178.7, 131.9, 128.3 (C═C), 77.0, 52.9, 38.2, 32.6, 24.8, 24.3, 23.4 ppm.

(Z)-1-Hydroxycyclooct-4-ene-1-carboxylic acid (1.6)

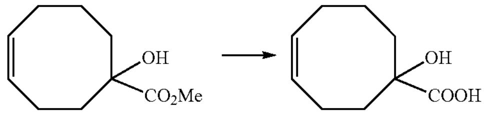 [SMILES: COC(=O)C1(O)CC/C=C\CCC1 ; O=C(O)C1(O)CC/C=C\CCC1]

1.5 (2.60 g, 12.1 mmol) was dissolved in MeOH (65 mL) and the solution was heated to 60° C. After slow addition of an aqueous solution of KOH (3.6 M, 60 mL) the mixture was stirred for 2.5 h. MeOH was removed in vacuo and the remaining aqueous solution was adjusted to pH 2 using 2M HCl and then extracted with DCM (5×80 mL). The combined organic layer was dried over $Na_2SO_4$, filtered and concentrated in vacuo affording crude 1.6 (2.30 g, 96%); $R_f$ (hexanes:EtOAc=3:1)=0.25. $^1$H-NMR (400 MHz, $CDCl_3$): δ 5.83 (dt, J=10.9, 6.6 Hz, 1H), 5.62 (dt, J=10.7, 8.4 Hz), 2.48-2.32 (m, 2H), 2.31-2.09 (m, 3H), 2.05-1.84 (m, 3H), 1.84-1.71 (m, 1H), 1.69-1.45 (m, 1H) ppm; $^{13}$C-NMR (101 MHz, $CDCl_3$): δ 181.9, 131.7, 129.0, 76.8, 37.9, 32.6, 24.8, 24.0, 23.2 ppm.

(Z)-1-Acetoxycyclooct-4-ene-1-carboxylic acid (1.7)

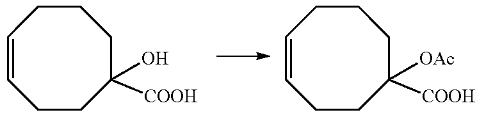 [SMILES: O=C(O)C1(O)CC/C=C\CCC1 ; CC(=O)OC1(C(=O)O)CC/C=C\CCC1]

1.6 (2.70 g, 15.9 mmol) was dissolved in anhydrous pyridine (25 mL) and the solution was cooled to 0° C. Acetic anhydride (12.7 mL, 135 mmol) was slowly added, followed by addition of a spatula tip of DMAP. The reaction mixture was stirred at rt overnight, poured onto ice water (200 mL) and adjusted to pH 2 by addition of 2M HCl. After extraction with DCM (6×100 mL), the combined organic layer was dried over $Na_2SO_4$, filtered and concentrated under high vacuum to afford crude 1.7 (3.37 g, quant.); $R_f$ (hexanes: EtOAc=3:1+1 vol % AcOH)=0.37. $^1$H-NMR (600 MHz, $CDCl_3$): δ 5.76 (dt, J=10.9, 6.4 Hz, 1H), 5.55 (q, J=9.1 Hz, 1H), 2.48-2.36 (m, 2H), 2.34-2.21 (m, 2H), 2.20-2.04 (m, 3H), 2.12 (s, 3H), 2.03-1.94 (m, 1H), 1.59-1.50 (m, 2H) ppm; $^{13}$C-NMR (151 MHz, $CDCl_3$): δ 178.6, 170.1, 131.0, 128.1, 83.3, 35.3, 29.1, 24.4, 23.8, 23.2, 21.0 ppm.

5-Iodo-8-oxo-7-oxabicyclo[4.2.2]decanyl-1-acetate (1.8)

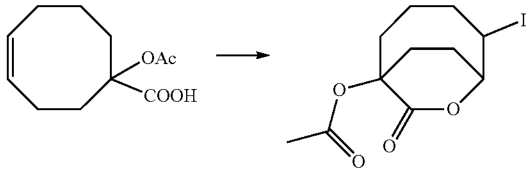 [SMILES: CC(=O)OC1(C(=O)O)CC/C=C\CCC1 ; CC(=O)OC12CCCC(I)C(CC1)OC2=O]

1.7 (3.37 g, 15.9 mmol) was dissolved in anhydrous DCM (40 mL) and a solution of $NaHCO_3$ (4.40 g, 52.4 mmol) in water (40 mL) was added. The reaction mixture was stirred vigorously for 20 min and then cooled to 0° C. A homogenized mixture of KI (7.95 g, 47.6 mmol) and 12 (8.06 g, 31.8 mmol) was added in 6 equal portions in 10 min intervals. After stirring for 10 min at 0° C., the reaction mixture was allowed to reach rt. After 1 h the reaction mixture was poured into an Erlenmeyer flask and, while cooling with an ice bath, sodium metabisulfite was added slowly until the dark color disappeared. (Caution! Excessive formation of foam). Next, the layers were separated and the aqueous layer was extracted with DCM (4×60 mL). The combined organic layer was dried over $Na_2SO_4$, filtered and evaporated in vacuo, affording crude 1.8 (4.33 g, 82%); $^1$H-NMR (200 MHz, $CDCl_3$): δ 5.06-4.96 (m, 1H), 4.68-4.43 (m, 1H), 2.69-2.22 (m, 7H), 2.10 (s, 3H), 2.01-1.74 (m, 2H), 1.71-1.43 (m, 1H) ppm.

(Z)-8-Oxo-7-oxabicyclo[4.2.2]dec-4-enyl-1-acetate (1.9)

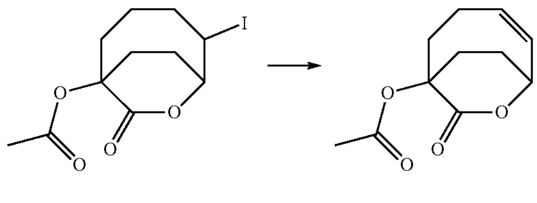 [SMILES: CC(=O)OC12CCCC(I)C(CC1)OC2=O ; CC(=O)OC12CC/C=C\C(CC1)OC2=O]

1.8 (4.67 g, 13.8 mmol) was dissolved in anhydrous toluene (22 mL). DBU (3.57 g, 23.5 mmol) was added and the reaction mixture was stirred at rt overnight. The reaction mixture was heated to reflux for 6 h, which lead to formation of a black precipitate. The mixture was allowed to cool to rt and after addition of water and toluene (400 mL each) the layers were separated and the organic layer was washed with water (2×200 mL). The aqueous layer was extracted with toluene (4×200 mL) and the combined organic layer was dried over $Na_2SO_4$ and filtered. Evaporation of the solvent and column chromatography (gradient: 0-50% EtOAc in hexanes) afforded 1.9 (1.88 g, 65%); $^1$H-NMR (400 MHz, $CDCl_3$): δ 5.93 (ddd, J=12.1, 9.2, 5.0 Hz, 1H), 5.45 (ddd, J=12.0, 4.7, 2.6 Hz, 1H), 5.16 (s, 1H), 2.54-2.33 (m, 3H), 2.24-2.12 (m, 4H), 2.10 (s, 3H), 1.69-1.61 (m, 1H).

(Z)-1,6-Dihydroxycyclooct-4-ene-1-carboxylic acid methyl ester (1.10)

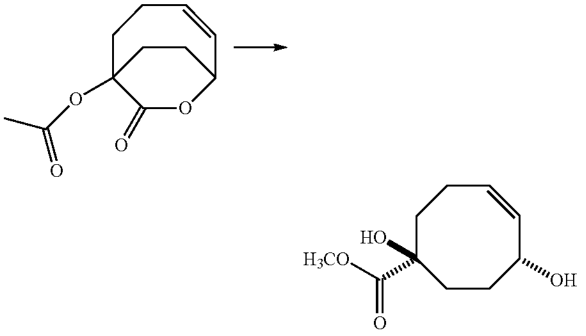

1.9 (1.00 eq., 1.85, 8.00 mmol) was dissolved in anhydrous MeOH (60 mL) and $KHCO_3$ (3.61 g, 36.1 mmol) was added. The resulting reaction mixture was stirred at 30° C. for 50 h, MeOH was removed in vacuo and the residue was taken up in DCM and water (200 mL each). The layers were separated and the aqueous layer was extracted with DCM (5×70 mL), then adjusted to pH 1 by addition of 2M HCl and again extracted with DCM (5×70 mL). The combined organic layer was dried over $Na_2SO_4$, filtered and concentrated in vacuo. The obtained residue was purified by column chromatography (gradient: 15-50% EtOAc in hexanes) to afford both product 1.10 (718 mg, 41%) and the acetylated product (520 mg, 24%); $^1$H-NMR (400 MHz, $CDCl_3$): δ 5.74 (ddt, J=10.8, 7.0, 1.8 Hz, 1H, CH═CH), 5.43 (ddd, J=11.2, 7.0, 2.0 Hz, 1H, CH═CH), 4.97 (dt, J=12.7, 7.2 Hz, 1H), 3.72 (s, 3H), 2.56-2.34 (m, 1H), 2.26-2.11 (m, 1H), 2.09-1.93 (m, 2H), 1.88-1.68 (m, 3H), 1.46-1.31 (m, 1H) ppm; $^{13}$C-NMR (101 MHz, $CD_3OD$): δ 179.0, 134.9, 129.8, 77.3, 68.4, 52.7, 39.0, 33.9, 32.1, 24.1 ppm.

(E)-1,6-Dihydroxycyclooct-4-ene-1-carboxylic acid methyl ester (1.11a, 1.11b; 2 Diastereomers with the Allylic Release-OH Either in Axial or Equatorial Position)

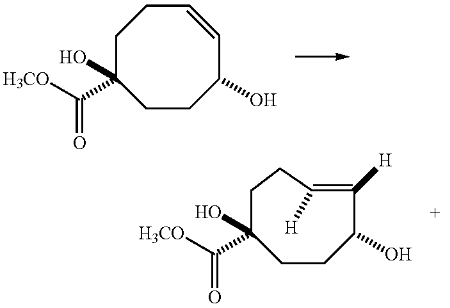

bis-axial diastereomer

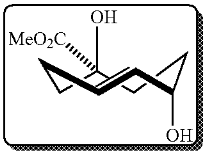

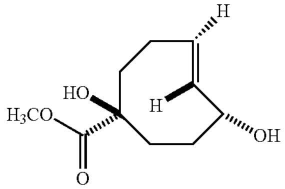

bis-equatorial diastereomer

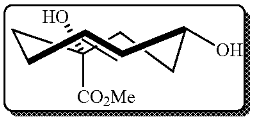

Compound 1.10 (0.58 g, 2.90 mmol) was photoisomerized in the presence of methyl benzoate (0.73 mL, 5.79 mmol) in a flow system (3-necked flask-pump-column-UV-irradiated quartz tube-back to 3-necked flask) using a regenerated Ag(I) tosic silica column (0.57 mmol/g, 11 g, 6.26 mmol) and a degassed mixture of n-hexane and i-PrOH (5:1, 350 mL). After 22 h, the column was washed with MTBE (500 mL). Elution with ammonia (7M solution in MeOH, 350 mL) and evaporation of the solvent afforded a residue that was filtered over a short plug of silica (eluted with ~10% MeOH in MTBE) to separate remaining silver salts. The solvent was evaporated and the two diastereomers of the product were separated and purified by column chromatography (gradient: 2-20% MeOH in DCM) affording the axial isomer 1.11a (169 mg, 30%) and the equatorial isomer 1.11b (110 mg, 18%) as white solids.

Axial Isomer (1.11a)

$^1$H-NMR (400 MHz, MeOD): δ 5.97 (ddd, J=15.2, 11.2, 3.4 Hz, 1H), 5.75 (dd, J=16.5, 2.4 Hz, 1H), 4.41 (dd, J=2.7, 1.3 Hz, 1H), 3.71 (s, 3H), 3.37 (s, 1H), 2.47 (m, 1H), 2.27-2.17 (m, 1H), 2.15-1.91 (m, 4H), 1.80-1.67 (m, 1H), 1.61 (dd, J=15.3, 6.3 Hz, 1H) ppm; $^{13}$C-NMR (101 MHz, MeOD): δ 180.9, 138.5, 127.9, 75.0, 70.3, 52.8, 46.0, 36.4, 31.9, 31.0 ppm.

Equatorial Isomer (1.11b)

$^1$H-NMR (400 MHz, MeOD): δ 5.88 (ddd, J=15.8, 11.2, 4.1 Hz, 1H), 5.43 (dd, J=16.4, 9.3 Hz, 1H), 4.13 (td, J=9.6, 5.2 Hz, 1H), 3.78 (s, 3H), 3.37 (s, 1H), 2.85-2.69 (m, 1H), 2.38-2.28 (m, 1H), 2.22-2.11 (m, 1H), 2.11-2.02 (m, 1H), 2.01-1.84 (m, 2H), 1.78-1.67 (m, 1H), 1.63-1.50 (m, 1H) ppm; $^{13}$C-NMR (101 MHz, MeOD): δ 175.7, 137.1, 132.3, 79.6, 75.0, 52.0, 47.8, 41.5, 39.1, 30.6 ppm.

Methyl(1S,4E,6R)-1-hydroxy-6-{[(4-nitrophenoxy) carbonyl]oxy}-cyclooct-4-ene-1-carboxylate (1.12)

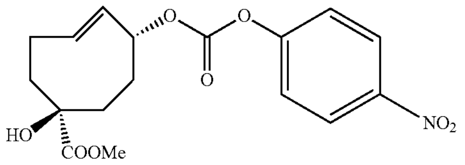

1.11a (axial, 30.0 mg, 0.150 mmol) was dissolved in anh. DCM (2.5 mL) while cooling with an ice bath. DMAP (73.2 mg, 0.599 mmol) and 4-nitrophenyl chloroformate, each dissolved in anh. DCM (1 mL) were added. TLC (hex: EtOAc=3:1) after 1.5 hr confirmed full conversion of the starting material. The reaction mixture was concentrated in vacuo. The obtained residue was taken up in DCM and purified by column chromatography (gradient: 0-5% MTBE in DCM). 1.12 was obtained as a yellow oil (47.7 mg, 87%). $^1$H NMR (400 MHz, $CD^2Cl^2$): δ 8.26 (d, J=9.2 Hz, 2H), 7.39 (d, J=9.1 Hz, 2H), 5.98 (ddd, J=15.5, 11.3, 3.5 Hz, 1H), 5.78 (dd, J=16.6, 2.3 Hz, 1H), 5.31-5.30 (m, 1H), 3.74 (s, 3H), 2.63-2.42 (m, 1H), 2.33-2.19 (m, 2H), 2.12-1.86 (m, 4H), 1.73 (ddd, J=15.9, 6.1, 1.5 Hz, 1H) ppm. $^{13}$C NMR (101 MHz, $CD_2Cl_2$): δ 180.3, 156.3, 152.2, 146.0, 132.5, 130.0, 125.8, 122.5, 78.0, 73.4, 53.7, 45.9, 33.3, 32.1, 30.8 ppm. ESI-MS: calculated for $[M+Na]^+$ 388.10; obs 388.05.

Methyl(1S,4E,6R)-1-hydroxy-6-{[(2-{2-[2-(2-hydroxyethoxy)ethoxy]ethoxy}ethyl)carbamoyl] oxy}cyclooct-4-ene-1-carboxylate (1.13)

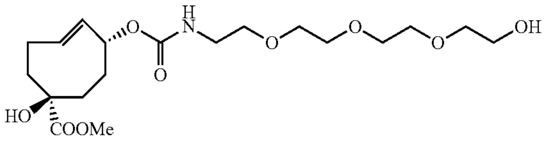

1.12 (35 mg, 0.096 mmol) and $NH_2$—$PEG_4$-OH (22.2 mg, 0.115 mmol) were dissolved in anh. DMF (0.7 mL). DIPEA (61.9 mg, 83 μL, 0.479 mmol) was added and the mixture was stirred for 3 hr at rt. The clear yellow solution was concentrated, acidified with formic acid (15 μL), taken up in water (+0.1% formic acid) and purified by reversed phase chromatography (30 g Biotage SNAP Ultra C18, water/MeCN, gradient elution, 0.1% formic acid) to give 1.13 as a colorless oil (37 mg, 92%). $^1$H NMR (600 MHz, $CD_3OD$) δ 5.89 (ddd, J=15.5, 11.3, 3.5 Hz, 1H), 5.74 (dd, J=16.4, 2.4 Hz, 1H), 5.13 (s, 1H), 3.72 (s, 3H), 3.70-3.66 (m, 8H), 3.66-3.63 (m, 2H), 3.59 (dd, J=5.6, 4.1 Hz, 2H), 3.56 (t, J=5.5 Hz, 2H), 3.31 (t, J=5.5 Hz, 2H), 2.47 (qd, J=11.8, 4.7 Hz, 1H), 2.24-2.12 (m, 2H), 2.11-2.02 (m, 1H), 2.02-1.96 (m, 2H), 1.86 (dd, J=15.1, 6.2 Hz, 1H), 1.70 (dd, J=15.7, 6.1 Hz, 1H) ppm. $^{13}$C NMR (151 MHz, $CD_3OD$) δ 180.7, 158.4, 135.0, 129.2, 74.8, 73.7, 73.6, 71.6, 71.6, 71.4, 71.2, 71.0, 62.2, 52.9, 45.9, 41.6, 34.0, 32.7, 31.0 ppm. ESI-MS: calculated for $[M+Na]^+$ 442.20; observed 442.15.

Methyl(1S,4E,6R)-1-hydroxy-6-{[(4-methyl-2-oxo-2H-chromen-7-yl)carbamoyl]oxy}cyclooct-4-ene-1-carboxylate (1.14)

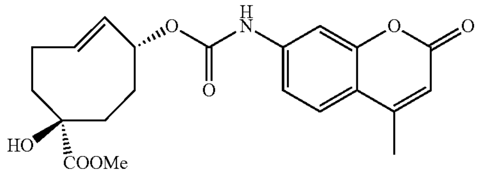

A solution of 1.12 (axial, 25 mg, 0.125 mmol) in anh. DCM and a stock solution of $MoO_2Cl_2$ (0.1 mL, 4.7 mg/mL in anh. DMF) were mixed and added to AMC-isocyanate (27.6 mg, 0.137 mmol) under an atmosphere of Ar and cooling with an ice bath. The reaction mixture was stirred at rt overnight. Subsequently, the mixture was partitioned between water and DCM, and the aq. layer was extracted with DCM (3×9 mL). The combined organic layer was dried over $Na_2SO_4$ and concentrated. The residue was purified by column chromatography (gradient: hex/EtOAc) to obtain 1.14 as a white solid (9 mg, 18%). $^1$H NMR (600 MHz, $CD_2Cl_2$) δ 7.56 (d, J=8.6 Hz, 1H), 7.49 (d, J=2.3 Hz, 1H), 7.37 (dd, J=8.6, 2.2 Hz, 1H), 7.15 (s, 1H), 6.15 (d, J=1.3 Hz, 1H), 5.97-5.89 (m, 1H), 5.79 (dd, J=16.6, 2.4 Hz, 1H), 5.34 (bs, 1H), 3.75 (s, 3H), 3.07 (s, 1H), 2.51 (dtd, J=12.8, 11.6, 4.7 Hz, 1H), 2.40 (s, 3H), 2.26-2.18 (m, 2H), 2.04 (ddd, J=14.1, 12.8, 4.6 Hz, 1H), 1.98-1.90 (m, 3H), 1.70 (dd, J=15.3, 5.5 Hz, 1H) ppm. $^{13}$C NMR (151 MHz, $CD_2Cl_2$) δ 180.40, 161.30, 155.07, 152.97, 152.63, 142.19, 133.71, 129.29, 126.01, 115.98, 114.65, 113.48, 106.01, 73.98, 73.42, 53.55, 45.95, 33.41, 32.20, 30.76, 18.90 ppm. ESI-MS: calc for $[M+H]^+$ 402.15; obs 402.18.

TCO-PEG$_2$-AF594 (1.15)

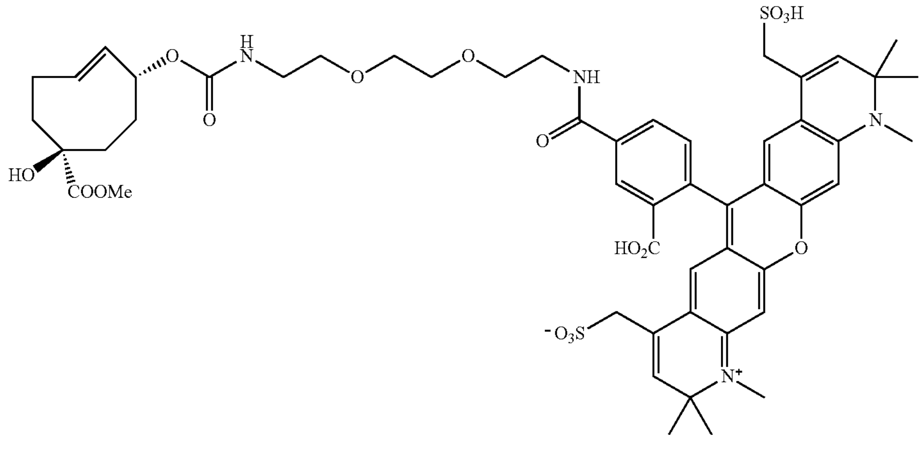

To a solution of 1.12 (2.8 mg. 0.008 mmol) in anh. DMF (0.6 mL) were added AF594-PEG$_2$-amine (5.48 mg, 0.006 mmol) in DMSO (640 μL) and DIPEA (5.6 μL, 0.032 mmol). To accomplish full conversion, another equivalent of 1.12 (2.8 mg, 0.008 mmol) and DIPEA (2 μL) were added and the reaction mixture was stirred at rt overnight. Subsequently, the dark mixture was concentrated, acidified with formic acid (2 μL), taken up in water (+0.1% formic acid) and purified 3 times by prep HPLC (water/MeCN, gradient elution, 0.1% formic acid) to give the desired product 1.15 as a violet oil (2.7 mg, 33%). $^1$H NMR (600 MHz, DMSO-d$_6$) δ 8.99 (t, J=5.6 Hz, 1H), 8.46 (s, 1H), 8.26-8.11 (m, 3H), 7.26 (dt, J=7.5, 3.6 Hz, 1H), 7.20 (t, J=5.8 Hz, 1H), 6.40 (s, 2H), 5.84-5.70 (m, 1H), 5.65-5.53 (m, 3H), 5.13 (s, 1H), 5.03 (s, 1H), 3.62-3.57 (m, 6H), 3.56-3.53 (m, 2H), 3.51-3.45 (m, 2H), 3.43 (t, J=5.9 Hz, 2H), 3.16-3.11 (m, 2H), 3.09 (s, 4H), 2.87 (s, 6H), 2.37-2.28 (m, 1H), 2.07-1.98 (m, 1H), 1.94-1.87 (m, 2H), 1.82 (dd, J=15.7, 12.1 Hz, 1H), 1.73-1.68 (m, 1H), 1.58 (dd, J=15.5, 6.2 Hz, 1H) 1.31 (d, J=4.4 Hz, 12H) ppm. ESI-MS: calculated for $[M+H]^+$ 1079.36; observed 1079.25.

TCO-MMAE (1.16)

To a mixture of MMAE (79 mg, 0.11 mmol) and DIPEA (21 mg, 0.17 mmol) in dry DMSO (0.5 mL) stirred under an Ar atmosphere was added a solution of 1.12 (44 mg, 0.12 mmol) in dry DMSO (0.5 mL). The mixture was stirred at rt for 1 h. Additional DIPEA (21 mg, 0.17 mmol) was added and stirring was continued overnight. As LCMS indicated only poor conversion, HOBt (22 mg, 0.17 mmol) and DIPEA (14 mg, 0.12 mmol) were added and the mixture was allowed to stir for an additional 48 h. Purification was carried out on a C18 column (30 g $C_{18}$—$SiO_2$) followed by reversed phase chromatography (5-90% ACN/$H_2O$ containing 2.5 mM $NH_4OAc$, pH 8.5). Product fractions were concentrated and further purified by prep HPLC. Product 1.16 was obtained as a white solid (44 mg, 42%). $^1$H NMR (600 MHz, DMSO-d$_6$; mixture of diastereomers and rotamers) δ 8.47 (s, 1H), 7.41 (d, J=7.0 Hz, 2H), 7.35 (t, J=7.7 Hz, 1H), 7.31 (t, J=7.7 Hz, 1H), 7.26-7.21 (m, 1H), 5.91-5.75 (m, 2H), 5.27-5.21 (m, 1H), 4.72 (d, J=8.5 Hz, 0.4H), 4.64-4.60 (m, 0.8H), 4.55 (d, J=7.4 Hz, 0.4H), 4.29-4.18 (m, 2.8H), 3.88 (dd, J=9.1, 2.1 Hz, 0.3H), 3.74-3.67 (m, 5H), 3.60-3.54 (m, 0.3H), 3.47-3.40 (m, 1.4H), 3.38-3.36 (m, 6H), 3.24-3.18 (m, 0.5H), 3.17-3.11 (m, 1.4H), 3.07-3.04 (m, 1.4H), 3.03 (s, 1H), 3.02-2.95 (m, 1H), 2.57-2.44 (m, 3.4H), 2.33-1.78 (m, 12H), 1.75-1.68 (m, 1.4H), 1.64-1.55 (m, 1.4H), 1.49-1.39 (m, 1.8H), 1.37-1.25 (m, 3H), 1.20 (dd, J=6.7, 5.1 Hz, 2H), 1.15 (dd, J=13.5, 6.8 Hz, 2H), 1.05-0.86 (m, 20H) ppm. ESI-MS: calculated for $[M+H]^+$ 944.60; observed 944.50.

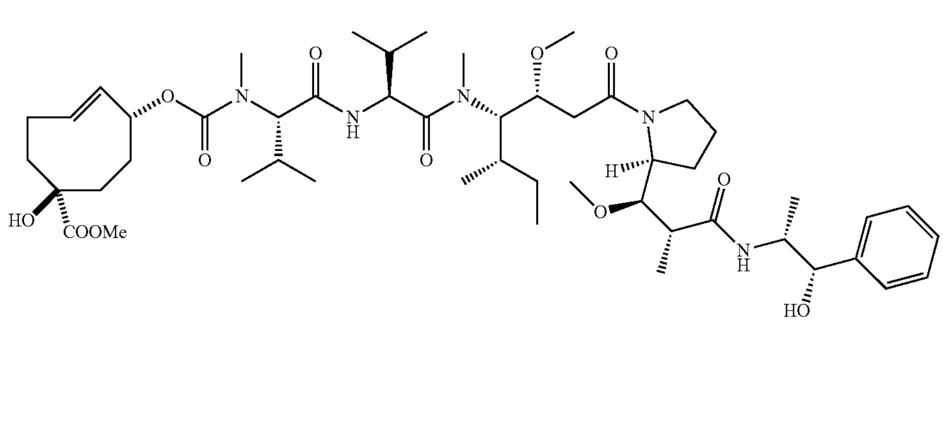

Ethyl 2-hydroxy-2-[4-(methylamino)phenyl]acetate (1.17)

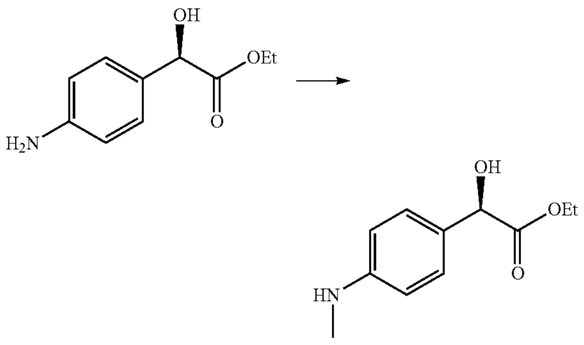

Ethyl 2-(4-aminophenyl)-2-hydroxyacetate (1.5 g, 7.7 mmol) was treated with $K_2CO_3$ (5.3 g, 38.4 mmol) and MeI (0.6 mL, 9.6 mmol) under $N_2$ for 30 min in DMF (10 mL). Water (80 mL) was added followed by extraction with EtOAc (3×80 mL). The combined organics were washed with brine (2×80 mL), dried over $MgSO_4$ and concentrated. Compound 1.17 was isolated after silica gel column chromatography (EtOAc:pentanes, 2:8 to 3:7). Yield: 32% (0.51 g, 2.4 mmol). ESI-MS: m/z calc for $C_{11}H_{15}NO_3$ 209.11; Obs. $[M+H]^+$ 210.08. $^1H$ NMR (400 MHz, $CD_3OD$): δ 7.23 (d, J=8.4 Hz, 2H), 6.60 (d, J=8.6 Hz, 2H), 5.06 (s, 1H), 4.32-4.24 (m, 1H), 4.22-4.14 (m, 1H), 2.85 (s, 3H), 1.25 (t, J=7.14 Hz) ppm.

2-Hydroxy-2-[4-(methylamino)phenyl]acetic acid (1.18)

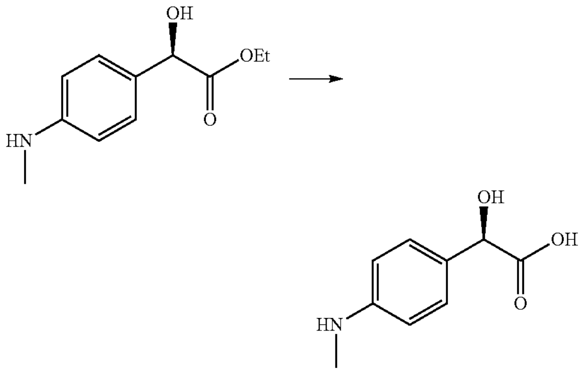

10M NaOH (1 mL, 10 mmol) in water was added to 1.17 (0.48 g, 2.3 mmol) in THF followed by stirring for 2 hr at 40° C. Following acidification, prep HPLC (a water/MeCN gradient with 0.1% TFA) and lyophilization, the TFA salt of 1.18 was isolated in 78% yield (0.52 g, 1.76 mmol). $^1H$ NMR (400 MHz, $CD_3OD$): δ 7.51 (d, J=8.4 Hz, 2H), 7.39 (d, J=8.6 Hz, 2H), 5.24 (s, 1H), 2.96 (s, 3H) ppm. NOESY (400 MHz, $D_2O$) confirmed the location of the methyl group to be at the anilinic amine.

2-Hydroxy-2-{4-[({[(1R,2E,6S)-6-hydroxy-6-(methoxycarbonyl)cyclooct-2-en-1-yl]oxy}carbonyl)(methyl)amino]phenyl}acetic acid (1.19)

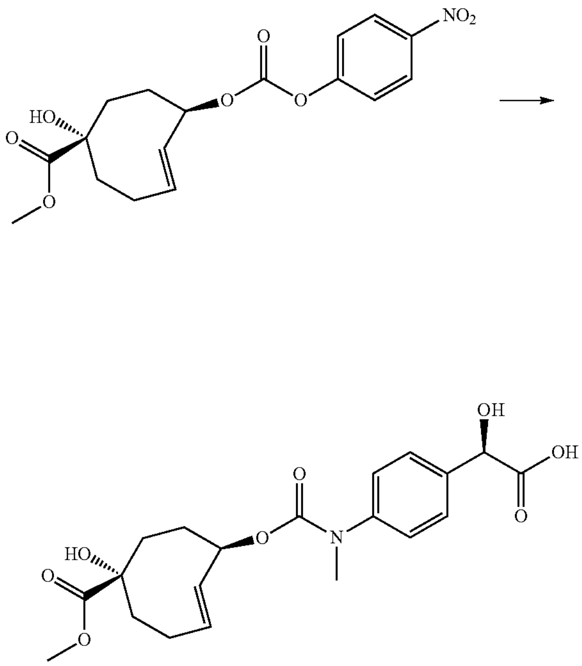

1.12 (33.4 mg, 91.4 μmol) was treated with 1.18 (34.5 mg, 114.1 μmol), HOBt·$H_2O$ (7.1 mg, 47.6 μmol), and DiPEA (99.4 μL, 570.6 μmol) for 16 hr in dry DMF. Following prep HPLC (a $H_2O$/MeCN gradient with 0.1% TFA) and lyophilization, 1.19 was isolated in 21% yield (8 mg, 19.6 mmol). ESI-MS: m/z calc for $C_{20}H_{25}NO_8$ 407.16; Obs. $[M-H]^-$ 406.12.

Methyl (1S,4E,6R)-6-{[(4-{[(2-{2-[2-(2,5-dioxo-2,5-dihydro-1H-pyrrol-1-yl)ethoxy]ethoxy}ethyl)carbamoyl](hydroxy)methyl}phenyl)(methyl)carbamoyl]oxy}-1-hydroxycyclooct-4-ene-1-carboxylate (1.20)

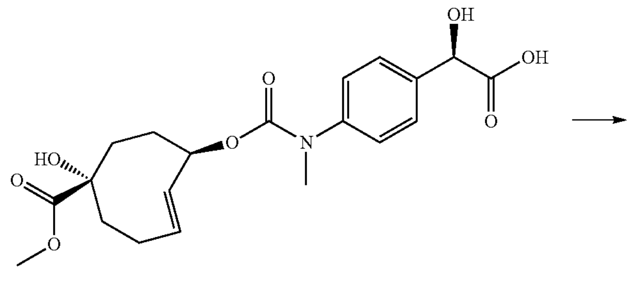

-continued

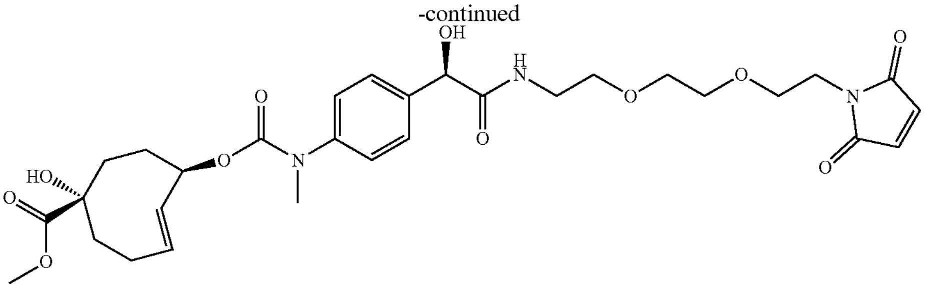

The TFA salt of 1-{2-[2-(2-aminoethoxy)ethoxy]ethyl}-2,5-dihydro-1H-pyrrole-2,5-dione (8.2 mg, 23.9 μmol), PyBOP (12.4 mg, 23.9 μmol), and DiPEA (16 μL, 92 μmol) were added to 1.19 (7.5 mg, 18.4 μmol) in dry MeCN. After stirring for 30 min at rt, the reaction mixture was concentrated and taken up in EtOAc. After washing with aq. HCl, the organics were dried over $Na_2SO_4$ and concentrated to yield 1.20. Yield: 95% (10.8 mg, 17.5 μmol). ESI-MS: m/z calc for $C_{30}H_{39}N_3O_{11}$ 617.26; Obs. $[M+H]^+$ 417.92.

TCO-mandelic-($PEG_2$-Mal)-DFO (1.21)

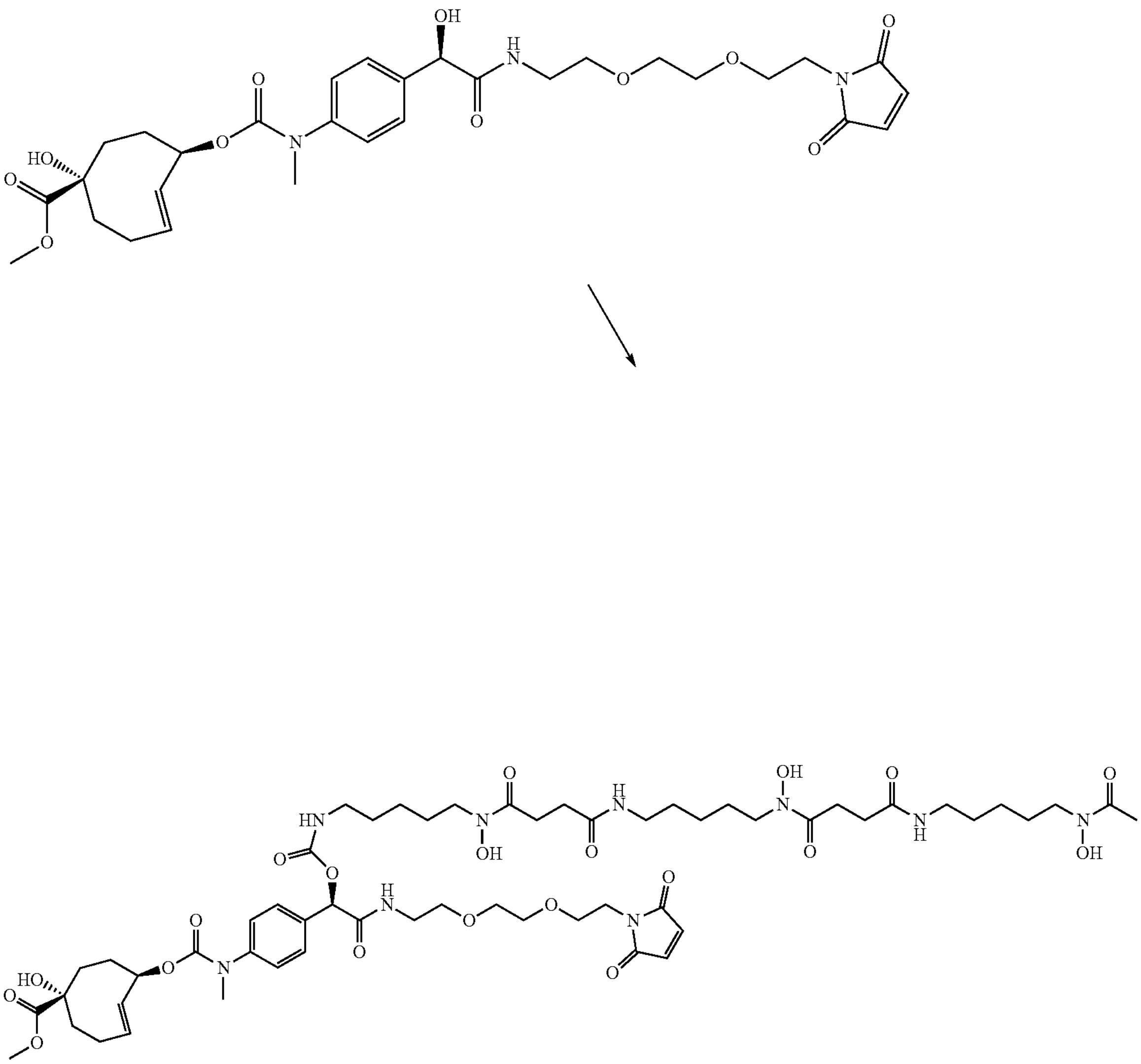

1.20 (6 mg, 9.7 μmol) was treated with DSC (22 mg, 29.2 mol) and DiPEA (10.3 μL, 58.8 μmol) in dry DMSO for 4 days rt. followed by the addition of deferoxamine (31.9 m. 48.5 μmol) and stirring for 1 hour at rt. Following acidification, prep HPLC (a $H_2O$/MeCN gradient with 0.1% TFA) and lyophilization, 1.21 was isolated in 11% yield (1.1 mg, 0.9 μmol) as white powder. ESI-MS: m/z calc for $C_{56}H_{85}N_9O_{20}$ 1203.59; Obs. $[M-H]^-$ 1202.00.

(1S,4E,6R)-1,6-Dihydroxycyclooct-4-ene-1-carboxylic acid (1.22)

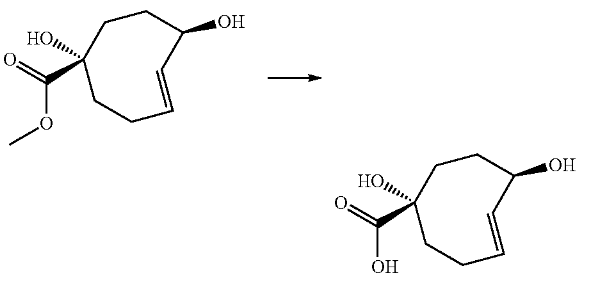

1.11a (15.1 mg, 75 μmol) was dissolved in MeOH (400 NL) and an aq. LiOH solution (200 μL of a 47 mg solution in 2 mL $H_2O$, 0.11 mmol, 1.5 eq LiOH) was added. The solution was stirred at rt in the dark for 20 h. The reaction mixture was transferred to a vial using MeOH (0.5 mL) and $H_2O$ (0.5 mL). DOWEX IR-120H resin beads were added with gentle stirring until the pH turned from basic to slightly acidic. The beads were removed by filtration and the solvents were removed in vacuo. The remaining oil was flushed with MeOH twice and lyophilized from MeCN/water 1:1 (2 mL) yielding 1.22 (14.0 mg, 75 μmol, quant) as a white fluffy solid. $^1$H-NMR (MeOD): δ=5.98 (m, 1H), 5.71 (dd, 1H), 4.39 (s, 1H), 2.43 (m, 1H), 2.22-2.03 (m, 3H), 2.01-1.88 (M, 2H), 1.74-1.58 (m, 2H) ppm.

(1S,4E,6R)-6-({[(2,5-Dioxopyrrolidin-1-yl)oxy]carbonyl}oxy)-1-hydroxycyclooct-4-ene-1-carboxylate (1.23)

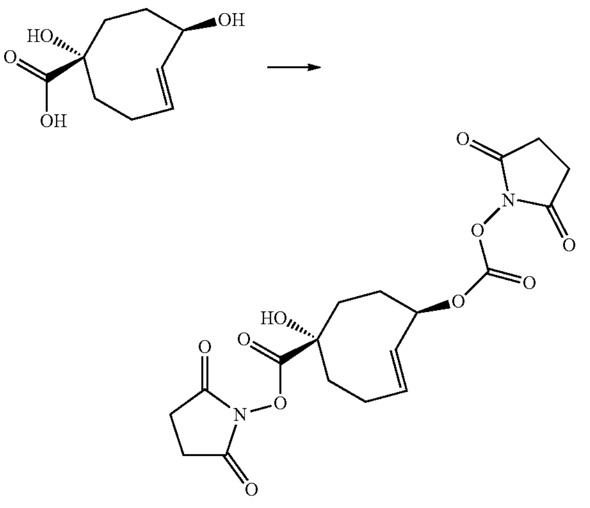

1.22 (5.7 mg, 31 μmol) and DSC (24 mg, 92 μmol, 3 eq) were dissolved in dry MeCN (200 μL, suspension). DiPEA (23 μL, 0.13 mmol) and 4-dimethylaminopyridine (0.6 mg. 5 μmol) were added and the clear mixture was stirred at rt under Ar in the dark for 20 h. The solvent was removed in vacuo and the resulting oil was flushed with $CHCl_3$ twice. Column chromatography (neutralized flash $SiO_2$) using an elution gradient of 2% to 10% acetone in $CH_2Cl_2$ yielded 1.23 (3.5 mg, 8.2 μmol, 27%) as a colorless oil. $^1$H-NMR ($CDCl_3$): δ=6.02 (m, 1H), 5.78 (dd, 1H), 5.34 (s, 1H, CH(O)), 2.86 (s, 4H), 2.84 (s, 4H), 2.58 (m, 1H), (m, 2.41-2.00, 8H).

N-(29-{[(1S,4E,6R)-1,6-Dihydroxycyclooct-4-en-1-yl]formamido}-3,6,9,12,15,18,21,24,27-nonaoxanonacosan-1-yl)-3-(2,5-dioxo-2,5-dihydro-1H-pyrrol-1-yl)propanamide (1.24)

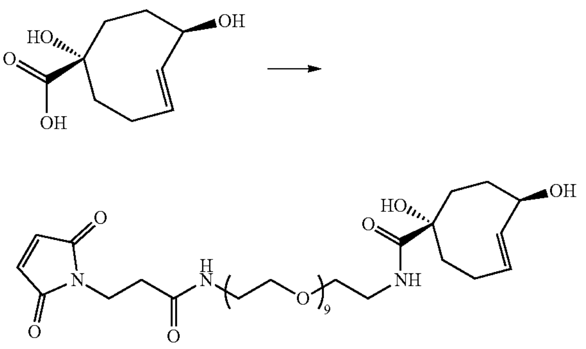

1.22 (6.3 mg, 34 μmol) and N-(29-amino-3,6,9,12,15,18,21,24,27-nonaoxanonacosyl)-3-(2, 5-dioxo-2, 5-dihydro-1H-pyrrol-1-yl)propanamide TFA salt (28 mg, 38 μmol) were dissolved in $CHCl_3$/dry DMF 2:1 (375 μL). DiPEA (23 μL, 0.13 mmol) and PyBOP (20 mg, 37 μmol) were added and the solution was stirred at rt for 1 h. The solvent was removed in vacuo and the resulting oil was flushed with $CHCl_3$ twice. The yellowish oil was redissolved in $CHCl_3$ (50 mL) and the organic layer was washed with 0.1 M HCl (30 mL) and brine (30 mL). The combined aq. layers were back-extracted with $CHCl_3$ once (10 mL). The combined organic layers were dried with $Na_2SO_4$, filtrated and evaporated to dryness. Column chromatography (flash $SiO_2$) using an elution gradient of 4% to 10% MeOH in $CHCl_3$ yielded 1.24 (13 mg, 17 μmol, 50%) as a colorless oil. $^1$H-NMR ($CDCl_3$): δ=6.74 (br t, 1H, NH), 6.71 (s, 2H), 6.59 (br t, 1H), 6.03 (m, 1H), 5.77 (dd, 1H), 4.51 (s, 1H), 3.84 (t, 2H), 3.70-3.58 (m, 36H), 3.54 (q, 2H), 3.42 (m, 2H), 2.52 (t, 2H), 2.48 (m, 1H), 2.26 (m, 1H), 2.16-1.91 (m, 4H), 1.75 (m, 1H), 1.64 (m, 1H), 1.46 (m, 1H) ppm. ESI-MS: m/z Calc. for $C_{36}H_{61}N_3O_{15}$ 775.41; Obs. $[M+H]^+$ 776.33, $[M+Na]^+$ 798.58.

Mal-PEG$_9$-TCO-PEG$_4$-DOTAGA (1.25)

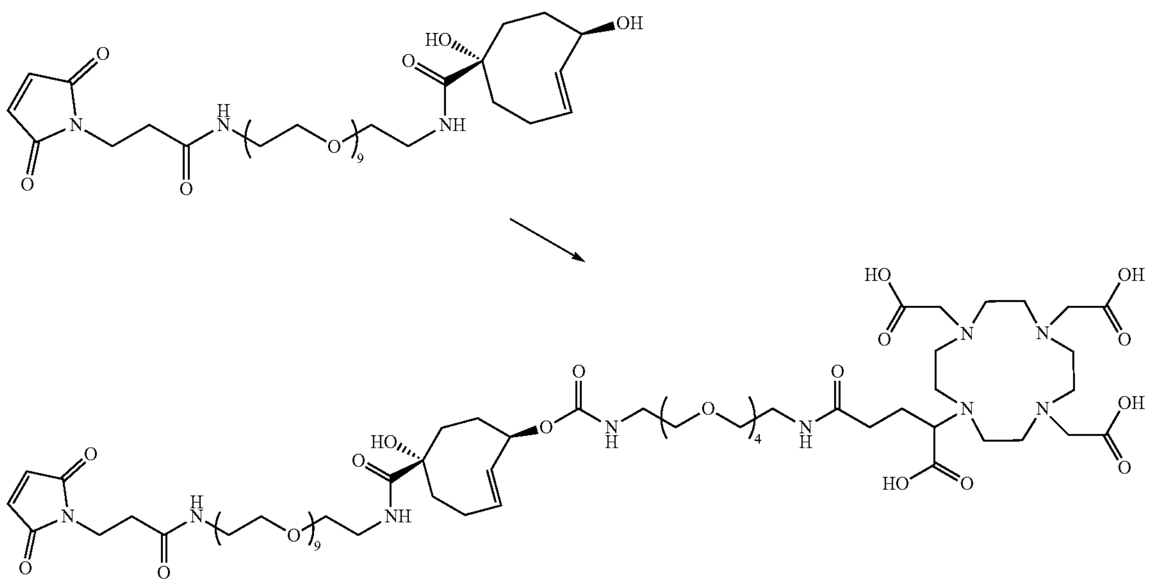

1.24 (4.2 mg, 5.4 μmol) and DSC (3.5 mg, 13 μmol) were dissolved in dry MeCN (100 μL, suspension). DiPEA (5 μL, 28 μmol) was added and the clear mixture was stirred at rt under Ar in the dark for 5 days. The solvent was removed in vacuo and the resulting oil was flushed with $CHCl_3$ twice. The NHS-carbonate intermediate (max. 5.4 μmol) was dissolved in dry DMF (200 μL) and DiPEA (3 μL, 17 μmol) was added. This solution was added to 2,2',2"-(10-(1-amino-19-carboxy-16-oxo-3,6,9,12-tetraoxa-15-azanonadecan-19-yl)-1,4,7,10-tetraazacyclododecane-1,4,7-triyl)triacetic acid HCl (3.9 mg, 5.4 μmol) yielding a suspension. Water (50 μL) was added and the clear mixture was stirred at rt for 3 h. HCOOH (30 μL) was added and the compound was purified using RP-MPLC. Lyophilization yielded 1.25 (1.3 mg, 0.9 μmol, 16%) as an off-white fluffy solid. ESI-MS: m/z Calc. for $C_{66}H_{113}N_9O_{29}$ 1495.76; Obs. $[M+H]^+$ 1496.50, $[M-H]^-$ 1494.67.

I. Mal-PEG$_9$-TCO-doxorubicine (1.26)

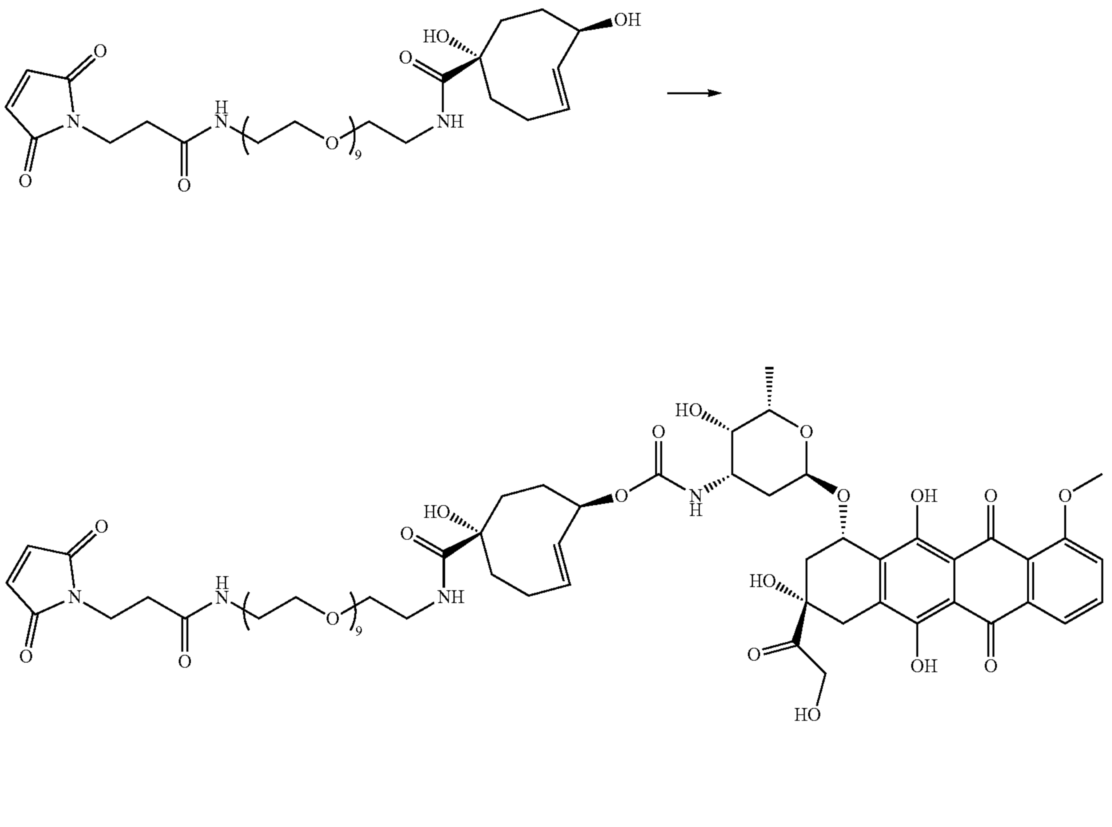

1.24 (4.0 mg, 5.2 μmol) was treated with DSC (2.7 mg, 10.4 μmol) and DiPEA (4.6 μL, 26.0 μmol) in dry DMSO for 16 hr at rt followed by the addition of doxorubicin HCl (12.1 mg, 20.8 μmol) and DiPEA (15 μL, 84.8 μmol) and stirring for 1 hour at rt. Following acidification, prep HPLC (water/MeCN gradient with 0.1% TFA) and lyophilization, 1.26 was isolated in 17% yield (1.1 mg, 0.9 μmol) as white powder. ESI-MS: m/z calc for $C_{64}H_{88}N_4O_{27}$ 1344.56; Obs. $[M+H_2O+Na]^+$ 1385.40.

7-Oxabicyclo[4.2.2]dec-4-en-8-one (1.27)

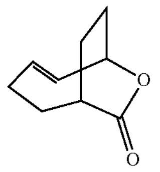 [SMILES: O=C1OC2/C=C/CCC1CC2]

1.3 (5.46 g, 35.4 mmol) was stirred for 1 h with 50 mL DCM, 50 mL water and $NaHCO_3$ (9.13 g, 108.6 mmol). The mixture was cooled on ice and a mixture of KI (7.0 g, 42.2 mmol) and iodine (10.0 g, 39.4 mmol) was added. The mixture was stirred overnight. 50 mL DCM was added, followed by some sodium bisulfite in order to decolorize the mixture. The layers were separated and the upper layer was extracted with DCM. Drying and rotary evaporation yielded 10.17 g of the iodolactone. $^1$H-NMR (300 MHz, $CDCl_3$): δ 5.05 (bs, 1H), 4.61 (m, 1H), 3.02 (m, 1H), 2.7-1.4 (m, 10H) ppm. The iodolactone was heated with DBU (7.5 g, 49.3 mmol) in 50 mL toluene at 85° C. for 6 h, 50 mL toluene was added to the cooled mixture, which was then washed with $H_2O$, the successive $H_2O$ layers being extracted with toluene. Drying and rotary evaporation gave 4.80 g 1.27 (31.5 mmol, 89%). $^1$H-NMR (300 MHz, $CDCl_3$): δ 5.90 (m, 1H), 5.4 (dm, 1H), 5.0 (bs, 1H), 3.0 (t, 1H), 2.5-1.4 (m, 8H) ppm.

Methyl (rel-1R,6S,Z)-6-hydroxycyclooct-4-ene-1-carboxylate (1.28)

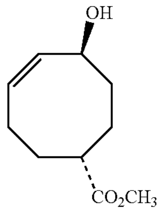 [SMILES: COC(=O)[C@@H]1CC/C=C\[C@@H](O)CC1]

200 mg sodium (8.7 mmol) was dissolved in 30 mL MeOH. This solution was added to 4.58 g of 1.27 (30.0 mmol) in 10 mL MeOH. The solution was stirred for 1 h, followed by concentration. NMR indicated that only the cis isomer (OH vs ester) was present. $^1$H-NMR (300 MHz, $CDCl_3$): δ 5.80 (q, 1H), 5.50 (dd, 1H), 4.70 (m, 1H), 3.68 (s, 3H), 2.45-1.4 (m, 9H) ppm. In order to effect the required epimerization, the residue was stirred for 1 h with 60 mL THF and 5.0 g potassium tert-butoxide, and then rotary evaporated at 60° C. The residue was diluted with 75 mL toluene and 15 mL methanol, the mixture was cooled in ice-water and 5 mL 37% hydrochloric acid was added, followed by 15 mL cold water. The layers were separated and the water layer was extracted with 50 mL toluene. Drying and rotary evaporation yielded a mixture of the two epimeric esters (trans: 4.6 ppm; cis: 4.7 ppm; ratio 1.5/1).

The residue was saponified by heating under reflux for 1 hr with 4.2 g NaOH, 50 mL MeOH and 15 mL water. After removal of MeOH, 100 mL TBME was added, the mixture was cooled and acidified with 37% HCl. The water layer was extracted with 100 mL TBME. Concentration gave the acid as a viscous oil, which was heated under reflux with 50 mL toluene for 1 h to convert the cis-isomer to the starting lacton. The solution was evaporated and the residue was heated in a Kugelrohr at 120° C./0.05 mbar to give a distillate—the starting lactone formed from the cis isomer—and a residue that was the trans-acid (2.05 g, 12.05 mmol), with still 15% cis isomer present.

This residue was heated under reflux for 1 hr with 935 mg potassium hydroxide (14.2 mmol), 1 mL EtOAc was added and reflux was continued for 30 min, followed by concentration resulting in a foam. This was mixed with 25 mL DMF and cooled on ice; 3.2 g iodomethane was added and the mixture was stirred overnight. 75 mL TBME and 50 mL water were added and the organic phase was washed with water. The successive water layers were extracted with toluene. Concentration gave the crude ester, which was chromatographed on silica, using hept and EtOAc, resulting in a mixture of the cis (15%) and trans isomer (OH vs ester) of 1.28. Yield: 1.57 g (8.52 mmol, 28%). $^1$H-NMR (300 MHz, $CDCl_3$): δ 5.65 (m, 1H), 5.55 (m, 1H), 4.60 (m, 1H), 3.67 (s, 3H), 2.55 (m, 1H), 2.4-1.4 (m, 8H) ppm.

Methyl (rel-1R,6S,E)-6-hydroxycyclooct-4-ene-1-carboxylate (1.29a (OH=Axial) and 1.29b (OH=Equatorial))

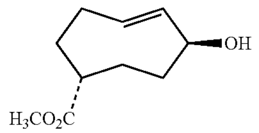

A solution of 1.57 g 1.28 (8.52 mmol), 2.45 g methyl benzoate (18.0 mmol) in hept/EtOAc (4/1) was UV irradiated, with continuous flowing through a 15.2 g 10% silver nitrate on silica column for 18 hr. The column was eluted with 100 mL TBME and with 100 ml TBME/5% MeOH, followed by stirring of the successive fractions and the column material with 30 mL 15% ammonia and TBME. The organic layers were combined (no complete separation of the two isomers in these fractions), dried and concentrated (0.84 g; NMR indicated a ca. 1:1 mixture of the axial TCO and equatorial TCO). Chromatography on silica with hept/EtOAc resulted in the isolation of the 1.29a (axial OH) (120 mg) and 1.29b (equatorial OH) (80 mg), $^1$H-NMR (300 MHz, $CDCl_3$) of 1.29a δ 6.06 (dt, 1H), 5.49 (dd, 1H), 4.47 (bs, 1H), 3.68 (s, 3H), 2.8 (m, 2H), 2.4-1.4 (m, 7H) ppm. $^1$H-NMR (300 MHz, $CDCl_3$) of 1.29b TCO: δ 5.69 (m, 1H), 5.55 (dd, 1H), 4.39 (dt, 1H), 3.64 (s, 3H), 2.47 (m, 1H), 2.3-1.0 (m, 8H) ppm.

Methyl (rel-1R,6S,E)-6-((dimethylcarbamoyl)oxy) cyclooct-4-ene-1-carboxylate (1.30)

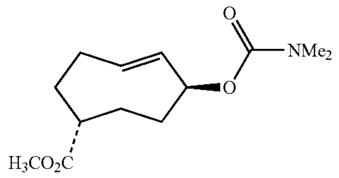

To a cooled solution of 1.29a (120 mg, 0.65 mmol) and 282 mg DMAP (2.31 mmol) in 5 mL DCM was added 274 mg 4-nitrophenylchloroformate (1.36 mmol) followed by stirring cold for 1 h and at rt for 2 days. The crude reaction mixture was purified by silica column (hept/EtOAc/$NEt_3$) yielding the PNP-ester intermediate to which was added 1 mL 2 N dimethylamine in THF. After stirring for 2 days and concentration, 1.30 was isolated after silica column chromatography (EtOAc/hept). Yield: 40 mg. $^1$H-NMR (300 MHz, $CDCl_3$): δ 5.89 (m, 1H), 5.47 (d, 1H), 5.23 (s, 1H), 3.69 (s, 3H), 2.95 (bs, 6H), 2.75 (m, 1H), 2.4-1.4 (m, 8H) ppm.

(rel-1R,6S,E)-6-((Dimethylcarbamoyl)oxy)cyclooct-4-ene-1-carboxylic acid (1.31)

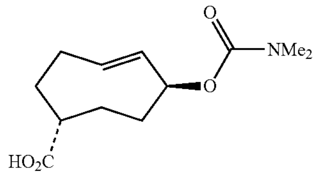

1.30 (40 mg) and LiOH·$H_2O$ (112 mg, 2.67 mmol) was stirred overnight in MeOH/$H_2O$ (10 mL, 1 mL), followed by removal of MeOH and addition of 30 mL TBME. Isolation of the water phase and extraction of the organics with 2×0.5 ml water was followed by mixing of the combined water phases with 30 mL TBME and 670 mg citric acid. Washing of the organic phase with water followed by drying and concentration resulted in 25 mg 1.31. $^1$H-NMR (300 MHz, $CDCl_3$): δ 5.85 (m, 1H), 5.55 (d, 1H), 5.40 (s, 1H), 2.9 (bs, 6H), 2.6 (m, 1H), 2.4-1.3 (m, 8H) ppm.

(Z)-9-Azabicyclo[6.2.0]dec-4-en-10-one (1.32)

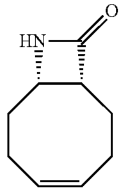 [SMILES: O=C1N[C@H]2CC/C=C\CC[C@@H]12]

To 275 mL cyclooctadiene (2.25 mol), 300 mL DCM and 8.0 g sodium carbonate (75.5 mmol) on ice was added chlorosulfonyl isocyanate (101.9 g, 0.72 mol) over 1 h at 4-6° C. Following 4 days of stirring, the mixture was poured gradually (in 20 min) into a mechanically stirred mixture of 150 g $Na_2HPO_4$ (0.843 mol), 150 g sodium sulfite (1.19 mol) and 1 kg ice/150 mL DCM. The mixture was put in an ice-bath and after stirring rapidly for 15 min, 65.5 g $NaHCO_3$ (0.780 mol) was added in portions over 1 h. After stirring for an hour, water was added. The organic phase was washed with water and the combined water layers were extracted with EtOAc. Drying and concentration of the organic layers gave a residue that, after 4 days of resting, was decanted, treated with hept and filtered to yield 1.32 (20.26 g). $^1$H-NMR (300 MHz, $CDCl_3$): δ 6.0 (bs, 1H), 5.68 (m, 2H), 3.8 (m, 1H), 3.3 (m, 1H), 2.4 (m, 2H), 2.0 (m, 6H) ppm.

Additional crude material was recovered from the decanted liquid and from the combined water layers obtained by repeating the workup steps followed by silica column purification (hept/EtOAc). Combined yield 55.63 g (0.368 mol, 51%).

Methyl (1R,4Z,8S)-8-aminocyclooct-4-ene-1-carboxylate HCl (1.33)

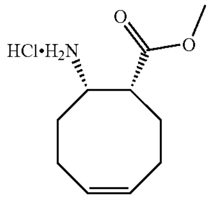

To a cooled solution of 1.32 (55.63 g, 0.368 mol) in 300 mL MeOH was added thionyl chloride (68 mL, 0.937 mol) over 5 hr period. After overnight stirring at rt and concentration, the resulting solidifying oil was stirred for 2 hr with TBME (200 mL). 1.33 was isolated after filtration and washing with TBME. Yield: 54.10 g (0.246 mol, 67%). $^1$H-NMR (300 MHz, $CDCl_3$): δ 5.75-5.58 (m, 2H), 3.79 (s+m, 4H), 3.24 (t, 1H), 2.65 (m, 1H), 2.5-1.7 (m, 7H) ppm.

Methyl (1R,4Z,8S)-8-((tert-butoxycarbonyl)amino) cyclooct-4-ene-1-carboxylate (1.34)

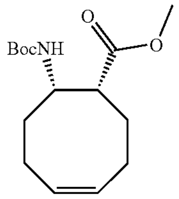 [SMILES: COC(=O)[C@@H]1CC/C=C\CC[C@@H]1NC(=O)OC(C)(C)C]

To 1.33 (17.78 g, 80.9 mmol) and $NEt_3$ (17.3 g, 171.3 mmol) in 25 mL DCM and 100 mL toluene on ice was added Boc-anhydride (20.1 g, 92.2 mmol) over 30 min. After stirring for 3 days at rt, 50 ml water was added and the mixture was stirred for 15 min. The layers were separated and the upper layer was washed with 40 mL water. The successive aq. layers were extracted with 50 mL toluene. Drying and concentrating gave 23.07 g brown oil, (81.4 mmol). $^1$H-NMR (300 MHz, $CDCl_3$): δ 5.8-5.55 (m, 2H), 5.05 (m, 1H), 4.15 (m, 1H), 3.72 (s, 3H), 2.85 (m, 1H), 2.45 (m, 1H), 2.4-1.5 (m, 7H), 1.43 (s, 9H) ppm.

Methyl (rel-1S,8S,Z)-8-((tert-butoxycarbonyl) amino)cyclooct-4-ene-1-carboxylate (1.35)

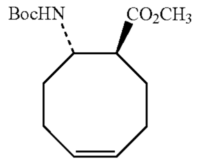 [SMILES: COC(=O)[C@H]1CC/C=C\CC[C@@H]1NC(=O)OC(C)(C)C]

To 1.34 in 75 mL MeOH on ice was slowly added 46 g 25 wt % sodium methoxide in MeOH, followed by stirring overnight and concentration. TBME, ice and water were added to the residue followed by separation and additional washing of the upper layer with $H_2O$. TBME, 15 g citric acid and ice was added to the first water layer. The layers were separated and the upper layer was washed with the second water layer. Drying and rotary evaporation followed by chromatography on silica (hept/EtOAc/$NEt_3$) gave the separated cis and trans isomers (NHBoc vs $CO_2CH_3$). This cis material was treated and purified again to yield a combined yield of 10.64 g trans isomer (37.5 mmol, 46%). $^1$H-NMR (300 MHz, $CDCl_3$): δ 5.7 (m, 2H), 4.63 (m, 1H), 4.0 (m, 1H), 3.66 (s, 3H), 2.75 (m, 1H), 2.5-1.5 (m, 8H), 1.41 (s, 9H) ppm.

(rel-1S,8S,Z)-8-((tert-Butoxycarbonyl)amino)cyclooct-4-ene-1-carboxylic acid (1.36)

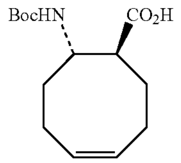

To 1.35 (10.64 g, 37.5 mmol) and 11.0 g potassium carbonate in 50 mL water and was added 50 mL MeOH over a few min and the mixture was stirred at 30° C. over 3 days, then heated at 62° C. for 22 hr to give a clear solution. Most of the MeOH was removed in vacuo and the remaining solution was washed with 2×50 mL toluene. The combined water layers were cooled in ice, 100 mL toluene was added and the mixture was slowly acidified with 11 g citric acid. The layers were separated and the aqueous layer was extracted with toluene. Drying and rotary evaporation gave 10.3 g of the acid. The NMR showed multiple broad signals (at δ 6.6, 5.7, 5.15, 4.9, 4.2, 4.1, 3.9, 2.9, 2.8, 2.7, 2.5-1.4 ppm).

tert-Butyl N-[(1S,2S,4Z,6R)-8-oxo-7-oxabicyclo [4.2.2]dec-4-en-2-yl]carbamate (1.37)

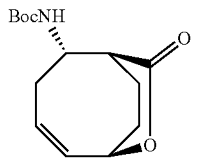

1.36 (31.56, 117.2 mmol) and 36.0 g $NaHCO_3$ (429 mmol) in 200 mL DCM. and 120 ml water was stirred well for 1 h, then cooled on ice. A total amount of 24.97 g KI (150.4 mmol) and 36.00 g iodine (0.142 mol) was added over 90 min and the mixture was stirred for 3 days. After dilution with DCM and $H_2O$, 6.0 g sodium sulfite was added slowly to make the mixture colorless. The organic layer was washed with water. The combined water layers were extracted with DCM. Drying and concentrating gave a residue (40.9 g), which was dissolved in 200 mL toluene. 23.08 g DBU (151.6 mmol) was added, and the mixture was warmed for 18 hr at 70° C. After cooling, toluene and ice were added. The organic layer was washed with water and the successive aq. layers were extracted with toluene. Drying and concentrating gave 1.37 as a viscous oil (18.5 g). $^1$H-NMR (300 MHz, $CDCl_3$): δ 5.83 (m, 1H), 5.62 (m, 1H), 5.10 (m, 1H), 4.76 (broad, 1H), 4.27 (broad, 1H), 3.50 (broad, 1H), 2.73 (broad, 1H), 2.17 (m, 1H), 2.1-1.4 (m, 4H), 1.43 and 1.42 (2s, 9H) ppm.

Methyl (rel-1S,2S,6R,Z)-2-((tert-butoxycarbonyl) amino)-6-hydroxy cyclooct-4-ene-1-carboxylate (1.38)

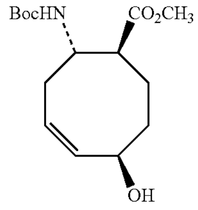 [SMILES: COC(=O)[C@H]1CC[C@@H](O)/C=C\C[C@@H]1NC(=O)OC(C)(C)C]

To cooled 1.37 (9.47 g, 35.42 mmol) in 30 mL THF and 10 mL MeOH was added 110 mg Na (4.8 mmol) in 20 mL MeOH and the solution was stirred overnight (Note: esterification is accompanied by partial epimerization when more than 1 eq. of base is used). The solution was poured into 100 mL water and 100 mL toluene. The layers were separated and the aq. layer was extracted with toluene. The toluene layers were washed with water, dried and concentrated to give 10.3 g of 1.38. $^1$H-NMR (300 MHz, $CDCl_3$): δ 5.7 (m, 1H), 5.55 (m, 1H), 4.6 (m, 2H), 3.65 (s, 3H), 2.55 (m, 2H), 2.3 (m, 1H), 2.1-1.5 (m, 5H), 1.41 (s, 9H) ppm.

Methyl(rel-1S,2S,6R,Z)-6-hydroxy-2-(((2-(trimethylsilyl)ethoxy)-carbonyl)amino)cyclooct-4-ene-1-carboxylate (1.39)

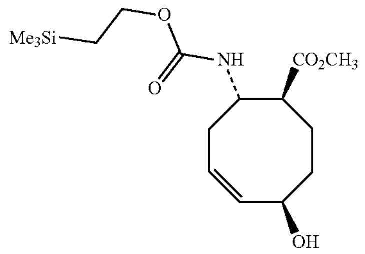 [SMILES: COC(=O)[C@H]1CC[C@@H](O)/C=C\C[C@@H]1NC(=O)OCC[Si](C)(C)C]

To cooled 1.38 (2.25 g, 7.52) in 30 mL DCM was added 6.28 g TFA (55.1 mmol) in 5 mL DCM over 20 min. The solution was stirred for 6 hr, reaching rt after 2 hr, followed by concentration at 25-30° C. (4.40 g). The residue was dissolved in 30 mL DCM, 5.0 g $NEt_3$ was added (49.5 mmol) and the solution was cooled. 2.05 g N-[2-(trimethylsilyl)ethoxycarbonyloxy]succinimide (7.91 mmol) was added and the solution was stirred overnight. The solution was diluted with DCM and washed with water. The successive aq. layers were extracted with DCM. Drying and concentration gave 3.43 g residue, which was chromatographed on silica (hept/EtOAc) Yield: 1.63 g of 1.39 (4.75 mmol, 63%). $^1$H-NMR (300 MHz, $CDCl_3$): δ 5.75 (m, 1H), 5.58 (m, 1H), 4.66 (d, 1H), 4.6 (m, 1H), 4.14 (bt, 2H), 3.65 (s, 3H), 2.55 (m, 2H), 2.3 (m, 1H), 2.1-1.5 (m, 5H), 0.95 (bt, 2H), 0.03 (s, 9H) ppm.

Methyl (1S,2S,4E,6R)-6-hydroxy-2-({[2-(trimethylsilyl)ethoxy]carbonyl}amino)cyclooct-4-ene-1-carboxylate (1.40)

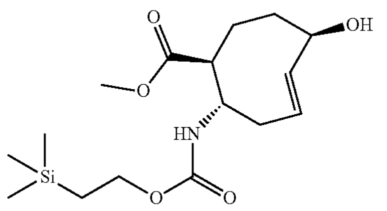

1.39 (1.63 g, 4.75 mmol) and 1.65 g methyl benzoate were irradiated in 4:1 hepts/EtOAc, while flushing the solution continuously through a 10 g column of 10% silver nitrate on silica. After a 23 h irradiation time of, the solution contained no starting compound. The column was eluted with 75 mL TBME, then with 75 ml TBME/5% MeOH. Each eluate was stirred with (the same) 25 mL 15 wt % ammonia. The layers were separated and the organic layer was washed with 15 mL $H_2O$, then dried and concentrated in vacuo. NMR indicated that the material (0.85 g) was the axial-TCO 1.40. $^1$H-NMR (300 MHz, $CDCl_3$): δ 5.86 (m, 1H), 5.52 (d, 1H), 4.68 (bs, 2H), 4.12 (bt, 2H), 3.94 (m, 1H), 3.67 (m) and 3.62 (s) (4H), 2.95 (m, 1H), 2.2 (m, 2H), 1.85 (m, 2H), 1.4 (m, 2H), 0.95 (m, 2H), 0.03 (s, 9H) ppm.

Methyl (1S,2S,4E,6R)-6-{[(4-nitrophenoxy)carbonyl]oxy}-2-({[2-(trimethylsilyl)ethoxy]carbonyl}amino)cyclooct-4-ene-1-carboxylate (1.41)

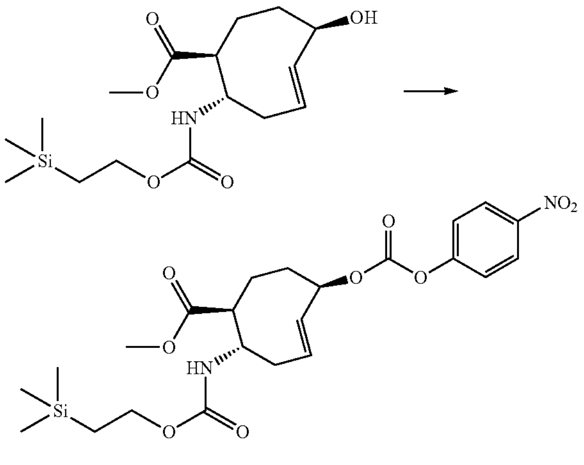

1.40 (140 mg; 0.408 mmol) was dissolved in $CHCl_3$ (10 mL), and DMAP (199 mg; 1.63 mmol) was added. The solution was cooled to 0° C., and 4-nitrophenyl chloroformate (123 mg; 0.612 mmol) was added. The mixture was stirred at 0° C. under Ar for 30 min, and then washed with 0.5M aq. citric acid solution (2×10 mL). The organic layer was isolated, dried over $Na_2SO_4$, filtered, and evaporated to dryness. The crude product was purified by column chromatography on silica gel, using an elution gradient of 5% to 30% EtOAc in n-hept. This yielded 1.41 as a white solid (60 mg). $^1$H-NMR ($CDCl_3$): δ 8.28 (d, J=9.1 Hz, 2H), 7.39 (d, J=9.1 Hz, 2H), 5.86 (ddd, J=15.5, 11.6, 3.7 Hz, 1H), 5.53 (d, J=12.8 Hz, 1H), 5.50 (s, 1H), 4.72 (d, J=10.3 Hz, 1H), 4.13 (t, J=8.4 Hz, 2H), 3.98 (m, 10H), 3.65 (s, 2H), 3.00 (dt, J=11.5, 4.3 Hz, 1H), 2.33-2.11 (br.m, 3H), 2.00 (m, 1H), 1.66 (m, 2H), 0.95 (m, 2H), 0.03 (s, 9H) ppm. $^{13}$C-NMR ($CDCl_3$): δ 13C NMR (101 MHz, CDCl3) δ 175.82, 155.41, 155.30, 151.46, 145.42, 130.42, 127.72, 125.31, 121.72, 77.50, 53.80, 51.90, 36.04, 25.52, 17.71, −1.49 ppm.

Methyl (1S,2S,4E,6R)-6-((dimethylcarbamoyl)oxy)-2-(((2-(trimethyl silyl)ethoxy)carbonyl)amino)cyclooct-4-ene-1-carboxylate (1.42)

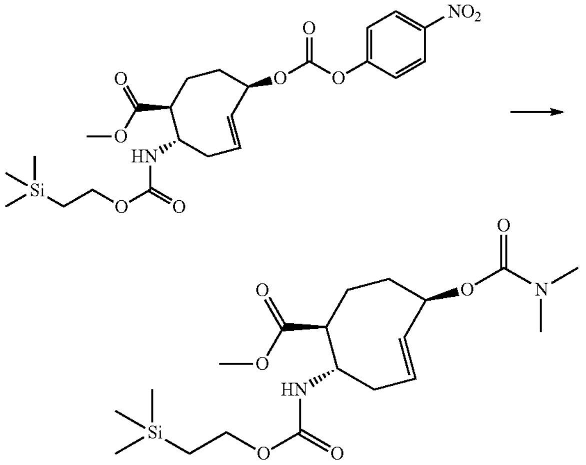

1.41 (30 mg; 0.059 mmol) was dissolved in THF (2 mL). A solution of dimethylamine in THF (0.074 mL 2 M; 0.147 mmol) was added and the mixture was stirred at 20° C. for 30 min. The mixture was evaporated to dryness, dissolved in $CHCl_3$ (15 mL) and washed with subsequently 0.5M citric acid (2×10 mL), and 1M NaOH (2×10 mL). The organic layer was isolated, dried over $Na_2SO_4$, filtered, and evaporated to dryness to yield 1.42 as a colorless oil (29 mg). $^1$H-NMR ($CDCl_3$): δ 5.68 (ddd, J=15.8, 11.4, 3.8 Hz, 1H), 5.50 (dd, J=16.4, 2.5 Hz, 1H), 5.43 (d, J=2.7 Hz, 1H), 4.74 (m, 1H), 4.12 (t, J=8.5 Hz, 2H), 3.96 (m, 1H), 3.63 (s, 2H), 2.93 (t, J=5.5 Hz, 6H), 2.20 (m, 2H), 2.05 (ddd, J=13.7, 5.6, 2.1 Hz, 1H), 1.92 (ddd, J=15.6, 5.6, 2.2 Hz, 1H), 1.57 (m, 2H), 0.95 (m, 2H), 0.06 (s, 9H) ppm. $^{13}$C-NMR ($CDCl_3$): δ 176.12, 155.33, 132.73, 126.04, 125.47, 73.25, 63.13, 58.02, 54.05, 51.74, 42.72, 36.38, 35.81, 30.28, 25.69, 17.67, −1.51 ppm.

Methyl (1S,2S,4E,6R)-2-amino-6-((dimethylcarbamoyl)oxy)cyclooct-4-ene-1-carboxylate (1.43)

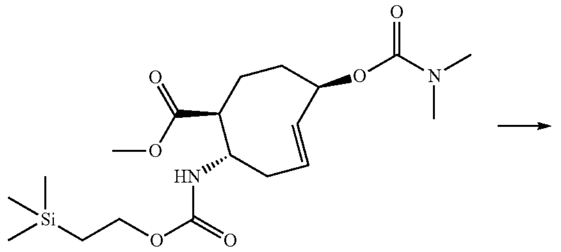

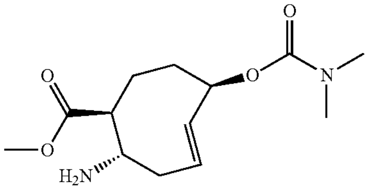

1.42 (7.25 mg; 0.0175 mmol) was dissolved in MeCN (0.5 mL), and KF (4.1 mg; 0.070 mmol) was added, followed by tetrabutylammonium fluoride (0.053 mL of a 1M solution in THF). The mixture was heated to 45° C. for 18 h, and then evaporated to dryness. The crude product was dissolved in $CHCl_3$ (1.5 mL) and washed with 0.1M sodium carbonate (3×1 mL). The organic layer was dried over $Na_2SO_4$, filtered, and evaporated to dryness to yield 1.43 as a mixture of isomers (4 mg, colorless oil). $^1$H-NMR ($CDCl_3$): δ 5.72 (ddd, J=16.0, 11.6, 3.8 Hz, 1H), 5.50 (dd, J=16.4, 2.5 Hz, 1H), 5.42 (d, J=3.0 Hz, 1H), 3.68 (s, 3H), 3.18 (td, J=10.1, 4.7 Hz, 1H), 2.93 (s, 6H), 2.85 (m, 1H), 2.03 (m, 2H), 1.67 (m, 2H), 1.48 (m, 4H) ppm. $^{13}$C-NMR ($CDCl_3$): δ 177.67, 155.44, 132.17, 127.19, 73.46, 59.79, 56.41, 51.60, 44.63, 37.07, 36.40, 35.83, 26.03 ppm.

TCO-doxorubicin (1.44)

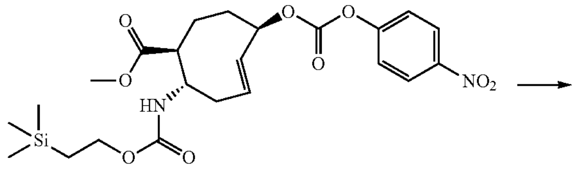

-continued

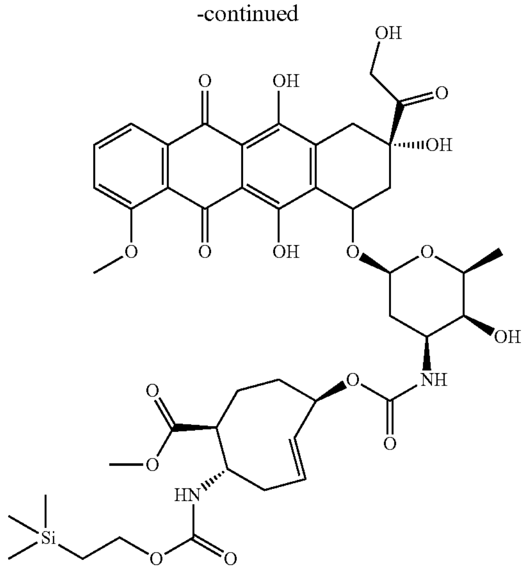

1.41 (11.8 mg, 23.2 μmol) was treated with doxorubicin HCl (25.2 mg, 46.4 μmol) and DiPEA (20.4 μL, 116 μmol) for 18 hr at rt in dry MeCN:DMSO. Following acidification, prep HPLC (a water/MeCN gradient with 0.1% TFA) and lyophilization, 1.44 was isolated in 29% yield (6.2 mg, 6.8 μmol) as white powder. ESI-MS calc. for $C_{44}H_{56}N_2O_{17}Si$ 912.33; Obs. $[M-H]^-$ 911.24, $[M+Na]^+$ 935.24.

TCO-doxorubicin (1.45)

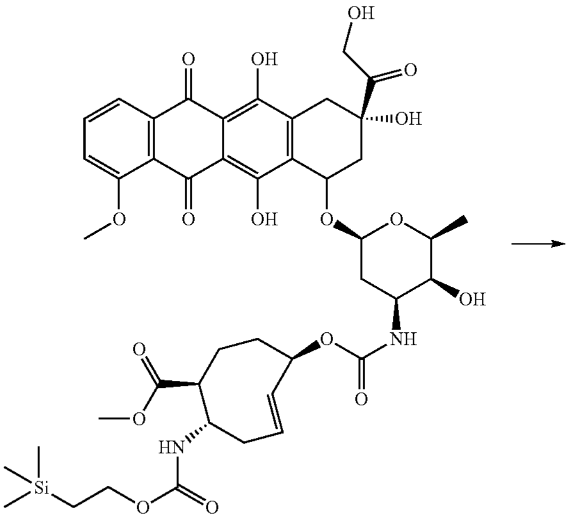

-continued

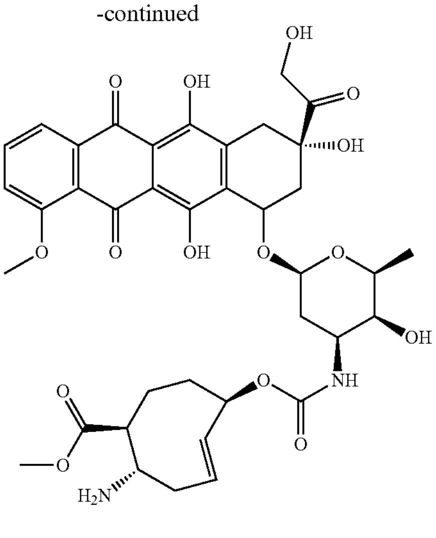

1.44 (2.0 mg, 2.2 μmol) was treated with TBAF (a 1M solution in THF, 17.6 μL) in MeCN at 50° C. for 8 hr followed by concentration. The residue was taken up in $CHCl_3$, washed with sat. $NaHCO_3$ (5×), dried over $Na_2SO_4$, and concentrated. Yield: 82% (1.4 mg, 1.8 μmol). ESI-MS identification of the poorly ionizing 1.45 was performed by reacting with tetrazine 2.20, which resulted in the expected conjugate with mass $C_{27}H_{30}N_6O_5$ 518.23; Obs. $[M+H]^+$ 519.36.

Methyl (rel-1R,2S,6R,Z)-2-((tert-butoxycarbonyl) amino)-6-hydroxycyclooct-4-ene-1-carboxylate (1.46)

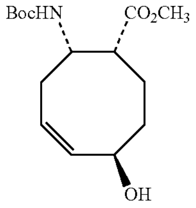 [SMILES: COC(=O)[C@@H]1CC[C@@H](O)/C=C\C[C@@H]1NC(=O)OC(C)(C)C]

To 1.37 (24.9 g) in 50 mL MeOH and 50 mL THF was added 50 mL 5.4 N sodium methoxide in MeOH followed by stirring for 3 days and concentration. To the residue was added 200 mL toluene, 150 g ice and then 45 g citric acid. The aq. layer was extracted with toluene. Drying and rotary evaporation gave partially epimerized ester ('cis'/'trans', orientation of NHBoc vs ester, ca. 60/40 ratio). The material was chromatographed on silica (hept/EtOAc) yielding (8.86 g) of the pure 'cis'-isomer 1.46. 'Trans'-isomer containing fractions were treated and purified as above to generate more cis-product. Total yield 12.82 m. 42.82 mmol. 41%. $^1$H-NMR (300 MHz, $CDCl_3$): δ 5.65 (m, 2H), 4.7 (m, 1H), 4.55 (m, 1H), 4.15 (broad, 1H), 3.66 (s, 3H), 2.95 (m, 1H), 2.4-1.5 (m, 6H), 1.41 (s, 9H) ppm.

tert-Butyl ((rel-1S,5R,8R,Z)-5-hydroxy-8-(hydroxymethyl)cyclooct-3-en-1-yl)carbamate (1.47)

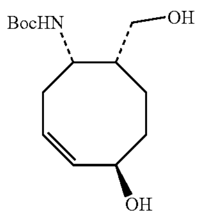 [SMILES: CC(C)(C)OC(=O)N[C@H]1C/C=C\[C@H](O)CC[C@H]1CO]

To 1.46 (1.88 g, 6.28 mmol) in 32 mL THF was added MeOH (1.60 g) followed by cooling at −65° C. and addition of 360 mg lithium borohydride (16.5 mmol). The mixture was stirred for 5 h, whereby rt was reached after 2 h. 5 mL EtOAc was added, the mixture was stirred for 10 min, 20 mL $H_2O$ was added, the mixture was stirred for 10 min. 30 mL water was added and the mixture was extracted with DCM. Drying, filtration and rotary evaporation gave 1.60 g foam (5.90 mmol, 94%), which was used as such in the next step. $^1$H-NMR (300 MHz, $CDCl_3$): δ 5.68 (dd, 1H), 5.50 (m, 1H), 4.46 (m, 1H), 3.97 (m, 1H), 3.30 (dd, 1H), 3.19 (t, 1H), 2.34 (m, 1H), 2.1 (m, 5H), 1.85 (m, 1H), 1.50 (dd) and 1.42 (s) (10H), 1.24 (m, 1H), 0.97 (bd, 1H) ppm.

((rel-1R,2S,6R,Z)-2-((tert-Butoxycarbonyl)amino)-6-hydroxycyclooct-4-en-1-yl)methyl methanesulfonate (1.48)

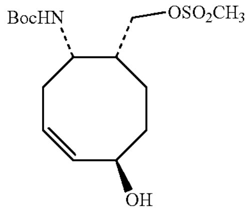

To cooled 1.47 (7.67 g, 28.3 mmol) in 100 mL THF and 8.58 g $NEt_3$ (85.0 mmol) was added 3.50 g methanesulfonyl chloride (30.55 mmol) followed by stirring overnight. 250 mL DCM was added, followed by 100 mL water and the mixture was stirred for 30 min. The layers were separated and the organic layer was washed with $H_2O$. The successive $H_2O$ layers were extracted with DCM. Drying and rotary evaporation gave the crude product without further purification. NMR: 2 singlets at 3.0 and 2.8 ppm in a 2/1 ratio.

(rel-4aR,7R,10aS,Z)-7-Hydroxy-1,4,4a,5,6,7,10,10a-octahydro-2H-cycloocta[d][1,3]oxazin-2-one (1.49)

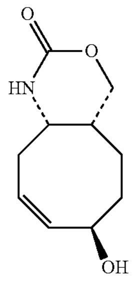

To ice-cooled 1.48 in 15 mL DMF and 40 mL THF was added 1.53 g sodium hydride (60%, 38.3 mmol) in portions. The mixture was stirred over 3 days and 5 mL water was added slowly. The mixture was diluted with hept and the supernatant was purified by silica column (hept to EtOAc/MeOH). Product containing fractions were concentrated and stirred with DCM/MeOH (6/1), filtered, and the solid was washed with DCM. The filtrate was extracted with water, the water layers were washed with DCM and concentrated. The sticky, semi-solid residue was stirred with DCM. Filtration and washing with DCM gave the product (1.10 g) and additional largely pure material from the filtrate (4.9 g). $^{1}$H-NMR (300 MHz, $D_2O$): δ 5.60 (m, 1H), 5.44 (m, 1H), 4.45 (m, 1H), 4.13 (dd, 1H), 4.04 (dd, 1H), 3.57 (m, 1H), 2.2-1.2 (m, 7H) ppm. $^{13}$C-NMR (75 MHz, $D_2O$): δ 138.1, 131.0, 123.7, 74.9, 70.1, 54.3, 37.0, 32.6, 30.5, 22.4 ppm. MS: 198.4 (M+1). Note: this reaction was intended to prepare the Boc-protected azetidine cis-cyclooctene as intermediate to azetidine TCO (see below). The key intermediate Boc-protected azetidine cis-cyclooctene could be prepared but this step required further optimization.

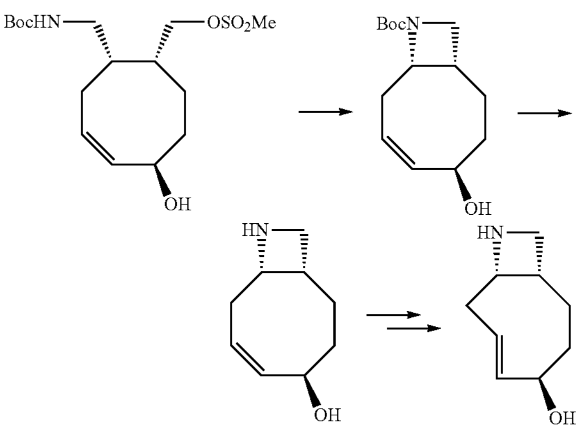

2-(Trimethylsilyl)ethyl ((rel-1S,5R,8R,Z)-5-hydroxy-8-(hydroxy methyl)cyclooct-3-en-1-yl)carbamate (1.50)

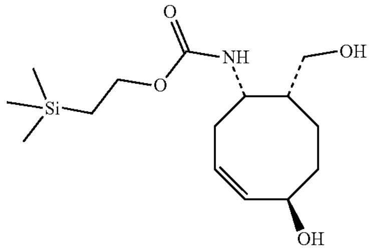 [SMILES: C[Si](C)(C)CCOC(=O)N[C@H]1C/C=C\[C@H](O)CC[C@H]1CO]

1.49 (crude, 4.90 g) and 2.4 g NaOH in 30 mL dioxane and 15 mL water was heated for 30 min at 80° C., then completely evaporated. The residue was chromatographed on silica (DCM/$NEt_3$ with increasing MeOH) and used as such. NMR in $CDCl_3$ showed signals at 5.65 (m, 1H), 5.4 (m, 1H), 4.4 (m, 1H), 3.75 (m, 2H).

The material was mixed with MeOH, isopropanol and toluene to give a solution. This was rotary evaporated at 60° C. to yield a residue, which was stirred with 30 mL MeCN and 2.50 g $NEt_3$, then 3.0 g N-[2-(trimethylsilyl)ethoxycarbonyloxy]succinimide (11.57 mmol) was added, and the mixture was stirred for 3 days. The cloudy solution was concentrated. The residue was mixed with DCM and washed with water. The successive aq. layers were extracted with DCM. Drying and concentration was followed by silica chromatography (EtOAc/hept). Yield: 880 mg of. $^{1}$H-NMR (300 MHz, $CDCl_3$): δ 5.7 (m, 1H), 5.55 (m, 1H), 4.5 (m, 1H), 4.2-4.0 (m, 3H), 3.3 (m, 2H), 2.1 (m, 2H), 1.85 (m, 1H), 1.55 (m, 1H), 1.2 (m, 1H), 1.05-0.8 (m, 5H), 0.04 (s, 9H) ppm. $^{13}$C-NMR (75 MHz, $CDCl_3$): δ 158.0, 139.0, 124.5, 70.9, 64.1, 63.9, 50.1, 41.7, 37.7, 32.2, 21.5, 17.7, −1.5 ppm. MS: 314.5 (M−1).

2-(trimethylsilyl)ethyl N-[(1S,3E,5R,8R)-5-hydroxy-8-(hydroxymethyl)cyclooct-3-en-1-yl]carbamate (1.51)

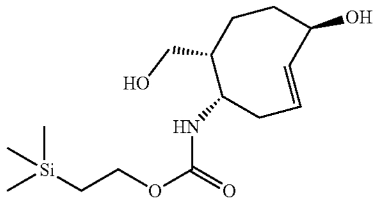

1.50 (800 mg, 2.69 mmol) and 1.00 g methyl benzoate in 4/1 hept/EtOAc was irradiated, the irradiated solution being continuously flushed over a 6.5 g 10% silver nitrate on silica (3.82 mmol) column. After a total irradiation time of 13 hr the column was flushed with 60 mL TBME, 60 mL TBME/5% MeOH, 70 mL TBME/20% MeOH. All fractions, as well as the column material, were stirred successively for 5-10 min with the same 30 mL 15% ammonia. The layers were separated each time, the upper layer was dried and concentrated. 'Cis'-containing fractions were treated again as above to yield a total of 480 mg of the title compound. Complicated NMR, likely due to two TCO-isomers and rotamers. In the 4-6 ppm region the following signals were observed: 6.0-5.3 (m), 4.9 (d), 4.5 (bs), 4.25 (m), 4.15 (m).

(1R,2E,5S,6R)-6-({[(4-Nitrophenoxy)carbonyl]oxy}methyl)-5-({[2-(trimethylsilyl)ethoxy]carbonyl}amino)cyclooct-2-en-1-yl 4-nitrophenyl carbonate (1.52)

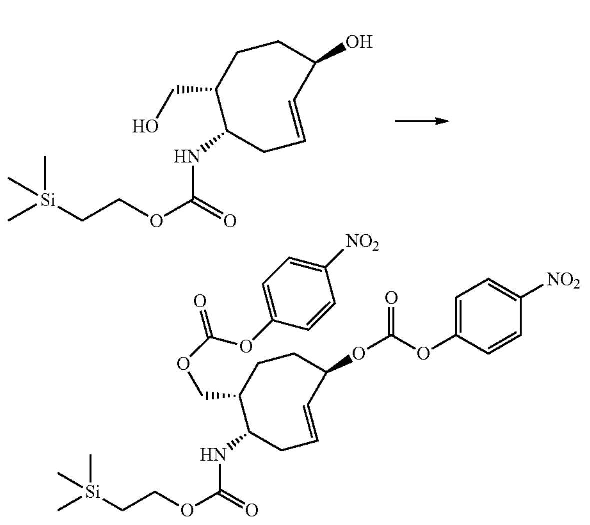

1.51 (424 mg; 1.43 mmol) was dissolved in $CHCl_3$ (20 mL), and DMAP (697 mg; 5.72 mmol) was added. The solution was cooled to 0° C., and 4-nitrophenyl chloroformate (432 mg; 2.15 mmol) was added. The mixture was stirred at 0° C. under an atmosphere of Ar for 30 min, and then washed with 0.5 M aq. citric acid solution (2 times 10 mL), and 1 M aq. NaOH solution (2 times 10 mL). The organic layer was isolated, dried over $Na_2SO_4$, filtered, and evaporated to dryness. The crude product was purified by column chromatography on silica gel, using an elution gradient of 5% to 60% EtOAc in n-hept. This yielded the product as a mixture of isomers as a white solid (252 mg). $^1$H-NMR ($CDCl_3$): δ 8.34-8.24 (m, 4H), 7.40 (td, J=9.3, 8.2, 2.2 Hz, 4H), 6.07-5.75 (m, 2H), 5.57 (dd, J=16.7, 2.5 Hz, 0H), 5.42 (s, 0H), 5.26-5.15 (m, 1H), 5.01-4.93 (m, 1H), 4.55-4.29 (m, 1H), 4.24-4.11 (m, 3H), 4.16-3.94 (m, 1H), 2.73-2.56 (m, 1H), 2.55-2.35 (m, 1H), 2.30-2.13 (m, 1H), 1.89 (t, J=6.0 Hz, 1H), 1.79 (d, J=13.6 Hz, 1H), 1.35-1.18 (m, 3H), 1.03-0.92 (m, 2H), 0.88 (t, J=6.7 Hz, 1H), 0.04 (s, 9H) ppm.

(1R,2E,5S,6R)-6-{[(Dimethylcarbamoyl)oxy]methyl}-5-({[2-(trimethylsilyl)ethoxy]carbonyl}amino)cyclooct-2-en-1-yl N,N-dimethylcarbamate (1.53)

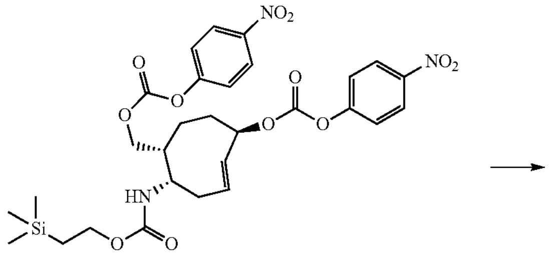

-continued

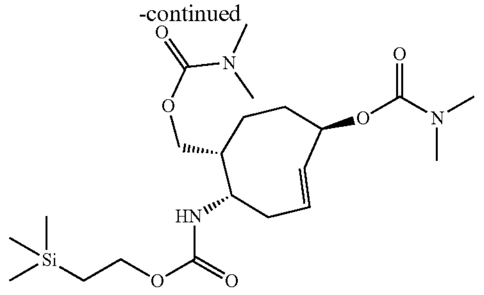

1.52 (115 mg; 0.25 mmol) was dissolved in THF (3 mL). A solution of dimethylamine in THF (0.313 mL 2 M; 0.626 mmol) was added and the mixture was stirred at 20° C. for 30 min. The mixture was evaporated to dryness, dissolved in $CHCCl_3$ (15 mL) and washed with subsequently 0.5 M aq. citric acid solution (2×10 mL), and 1 M aq. NaOH (3 times 20 mL). The organic layer was isolated, dried over $Na_2SO_4$, filtered, and evaporated to dryness to yield the title compound as a mixture of isomers as a colorless oil (90 mg). $^1$H-NMR ($CDCl_3$): δ 5.85 (ddd, J=15.9, 11.9, 3.7 Hz, 1H), 5.68 (dd, J=16.2, 9.6 Hz, 1H), 5.29 (s, 1H), 5.08 (td, J=9.8, 5.8 Hz, 1H), 4.84 (d, J=9.3 Hz, 1H), 4.39 (s, 1H), 4.15 (tt, J=14.4, 7.7 Hz, 4H), 3.94 (dd, J=10.8, 6.9 Hz, 1H), 3.78 (t, J=9.9 Hz, 1H), 2.99-2.86 (m, 20H), 2.56 (d, J=11.0 Hz, 2H), 2.35 (dd, J=12.3, 6.1 Hz, 1H), 2.30-2.14 (m, 1H), 1.96 (dd, J=13.3, 6.7 Hz, 1H), 1.15-0.91 (m, 4H), 0.08 (s, 1H), 0.07 (s, 23H) ppm.

(1S,5R,6S,E)-5-Amino-6-(((dimethylcarbamoyl)oxy)methyl)cyclooct-2-en-1-yl dimethylcarbamate (1.54)

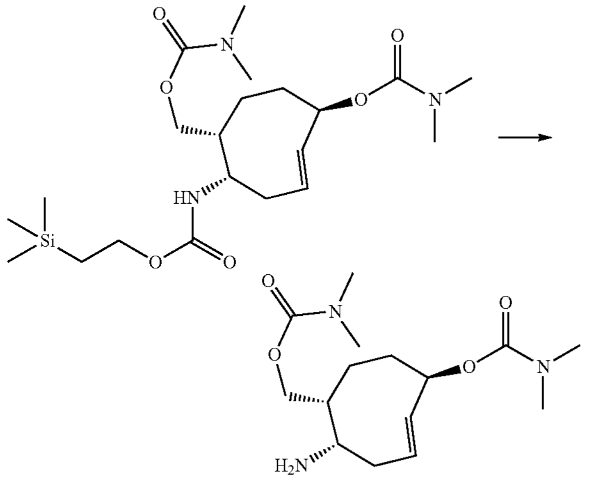

1.53 (22.5 mg; 0.061 mmol) was dissolved in MeCN (1 mL), and potassium fluoride (14.1 mg; 0.24 mmol) was added, followed by tetrabutylammonium fluoride (0.183 mL of a 1 M solution in THF; 0.183 mmol). The mixture was heated to 45° C. for 18 h, and then evaporated to dryness. The crude product was dissolved in $CHCl_3$ (5 mL), and washed with 0.1 M aq. sodium carbonate (3 times 1.5 mL). The organic layer was isolated, dried over $Na_2SO_4$, filtered, and evaporated to dryness to yield the title compound as a mixture of isomers as a colorless oil (12 mg). $^1$H-NMR ($CDCl_3$): δ 6.01 (ddd, J=16.0, 11.8, 3.9 Hz, 1H), 5.64 (dt, J=16.3, 10.0 Hz, 1H), 5.09 (td, J=9.7, 5.7 Hz, 1H), 4.10-3.93 (m, 1H), 3.96-3.85 (m, 1H), 3.53 (s, 1H), 2.91 (d, J=3.7 Hz, 13H), 2.43-2.20 (m, 2H), 2.24-2.00 (m, 1H), 2.03-1.82 (m, 0H), 1.82-1.68 (m, 1H), 1.68-1.49 (m, 1H), 1.42 (dtd, J=18.9, 14.4, 13.4, 5.0 Hz, 2H), 1.24 (d, J=13.3 Hz, 0H), 1.17-1.11 (m, 1H), 1.07-0.87 (m, 1H) ppm.

N-(But-3-en-1-yl)-N-(3,3-diethoxypropyl)-2,2,2-trifluoroacetamide (1.55)

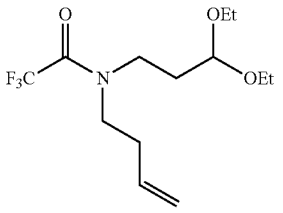 [SMILES: C=CCCN(CCC(OCC)OCC)C(=O)C(F)(F)F]

3,3-diethoxypropan-1-amine (11.1 g, 75.4 mmol), 4-bromo-1-butene (10.8 g, 80.0 mmol) and 24.0 g potassium carbonate (173.9 mmol) in 50 mL DMF was stirred for 45 min at rt, then for 3 hr at 60° C. Following concentration, the residue was diluted with TBME, filtered, and the solid was washed with TBME. 10.05 g DIPEA (77.9 mmol) was added, the solution was cooled and TFA anhydride (16.94 g, 80.66 mmol) was added in 10 min. The solution was stirred for 3 hr at rt, then 12.0 g $NaHCO_3$ was added, followed by 75 g ice. The mixture was stirred for 10 min, and the organic layer was washed with 50 mL water. The successive aq. layers were extracted with 100 mL TBME. Drying and rotary evaporation gave 19.0 g residue, which was chromatographed (hept/EtOAc), to yield 16 g (53.4 mmol, 71% over 2 steps, sufficiently pure for the next step). $^1$H-NMR (300 MHz, $CDCl_3$): δ 5.75 (m, 1H), 5.1 (m, 2H), 4.5 (m, 1H), 3.65 (m, 2H), 3.45 (m, 6H), 2.35 (q, 2H), 1.90 (m, 2H), 1.20 (t, 6H) ppm. $^{19}$F-NMR (282 MHz, $CDCl_3$): δ −69.2, −69.0 ppm.

N-(But-3-en-1-yl)-2,2,2-trifluoro-N-(3-oxopropyl) acetamide (1.56)

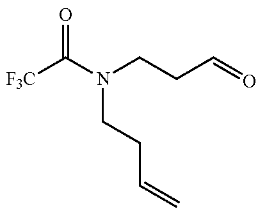

To 1.55 (16.0 g) in 40 mL acetic acid was added 10 mL water and the solution was stirred for 3 days. After removal of some EtOH. It was then stirred for 3 d at 30° C., 5 mL water were added, and the solution was partially evaporated. The remainder was diluted with water, then extracted with toluene. The successive toluene layers were washed with water, then dried and rotary evaporated to give 7.95 g product (35.6 mmol, 47% over 3 steps). $^1$H-NMR (300 MHz, $CDCl_3$): δ 9.64 (2s, 1H), 5.6 (m, 1H), 4.98 (m, 2H), 3.57 (m, 2H), 3.36 (m, 2H), 2.73 (m, 2H), 2.23 (m, 2H) ppm. $^{13}$C-NMR (75 MHz, $CDCl_3$): δ 199.7, 198.8, 157 (m), 133.9, 133.1, 117.9, 117.5, 116.2 (d), 47.7, 47.6, 46.4, 42.9, 41.3, 41.1, 33.0 ppm.

5-(N-(But-3-en-1-yl)-2,2,2-trifluoroacetamido)pent-1-en-3-yl 2,2,2-trifluoroacetate (1.57)

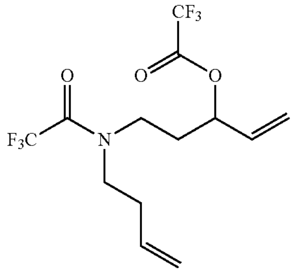 [SMILES: C=CCCN(CCC(C=C)OC(=O)C(F)(F)F)C(=O)C(F)(F)F]

To 1.56 (4.65 g, 20.8 mmol) in 75 mL THF was added 20 mL 1.6 N vinylmagnesium bromide (32 mmol) at −60 to −70° C. over 15 min. The mixture was allowed to warm to 0° C. and then the light-yellow solution was poured into 16 g ammonium chloride in 100 mL water and 100 mL TBME. The layers were separated and the aq. layer was extracted with TBME. Drying and rotary evaporation gave 5.84 g residue. The trifluoroacetyl group appeared to switch partially to the OH (also on standing), therefore it was converted into the bis-TFA compound.

Trifluoroacetic anhydride (4.8 mL, 35 mmol) was added dropwise to a solution of the crude product obtained above in DIPEA (10 mL, 58 mmol) and DCM (100 mL) at 0° C. The mixture was stirred at this temp for 2 h, then rotary evaporated. The residue was purified by column chromatography (EtOAc/het) to give 0.83 g of product 1.57. $^1$H-NMR (300 MHz, $CDCl_3$): δ 5.8 (m), 5.4 (m) and 5.1 (m) (7H), 3.4 (m, 4H), 2.36 (q, 2H), 2.09 (q, 2H) ppm. $^{13}$C-NMR (75 MHz, $CDCl_3$): δ 133.8, 133.0, 132.9, 132.5, 120.3, 120.0, 118.3, 117.8, 77.1, 76.6, 47.4, 47.4, 46.5, 43.4, 43.4, 43.3, 33.1, 32.7, 31.2, 30.8 ppm. $^{19}$F-NMR (282 MHz, $CDCl_3$): δ −75.3, −75.2, −69.3, −69.0 ppm.

(Z)-1-(2,2,2-Trifluoroacetyl)-1,2,3,4,7,8-hexahydroazocin-4-yl 2,2,2-trifluoroacetate (1.58)

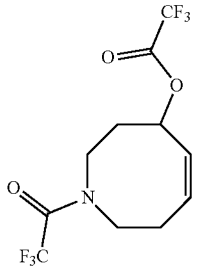 [SMILES: O=C(OC1/C=C\CCN(C(=O)C(F)(F)F)CC1)C(F)(F)F]

A solution of 1.57 (2.3 g, 6.62 mmol) in DCM (700 mL) was degassed and put under $N_2$. Grubbs $2^{nd}$ generation catalyst (282 mg, 0.33 mmol) was added and the mixture was stirred at 45° C. for 18 h and then at rt for 20 h under $N_2$. The solution was rotary evaporated and the residue was purified by column chromatography on silica, using hept/DCM 1/2 to DCM. $^1$H-NMR (300 MHz, $CDCl_3$): δ 5.9 (m, 1H), 5.7 (m, 2H), 3.75 (m, 2H), 3.4 (m, 2H), 2.45 (m, 3H), 2.0 (m, 1H) ppm. $^{19}$F-NMR (282 MHz, $CDCl_3$): δ −75.2, −68.8 ppm.

2-(Trimethylsilyl)ethyl (Z)-4-hydroxy-3,4,7,8-tetrahydroazocine-1(2H)-carboxylate (1.59)

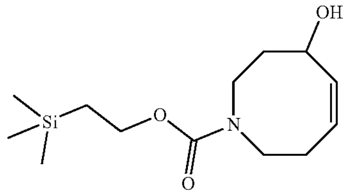 [SMILES: C[Si](C)(C)CCOC(=O)N1CC/C=C\C(O)CC1]

1.58 (1.4 g, 4.39 mmol) was heated under reflux for 2 hr with 550 mg NaOH (13.75 mmol), 5 mL water and 25 mL MeOH. The MeOH was removed by rotary evaporation and 50 mL DCM and $Na_2SO_4$ were added to the residue. Filtration, repetition (2×) and rotary evaporation gave 600 mg of the aminol intermediate (4.72 mmol) as a solidifying oil. $^1$H-NMR (300 MHz, $CDCl_3$): δ 5.65 (m, 2H), 4.67 (m, 1H), 2.93 (2t, 1H), 2.8 (m, 2H), 2.63 (dt, 1H), 2.3 (m, 1H), 2.15 (m, 1H), 1.95 (m, 1H), 1.6 (m, 1H) ppm.

This aminol was dissolved in 20 mL DCM, 1.24 g (12.3 mmol) $NEt_3$ was added, followed by 1.38 g N-[2-(trimethylsilyl)ethoxy carbonyloxy]succinimide (5.32 mmol). The solution was stirred overnight, and concentrated prior to addition of 75 mL toluene and 20 mL water. The layers were separated and the upper layer was washed with water. The successive aq. layers were extracted with toluene. Drying and rotary evaporation yielded a solidifying oil, which was chromatographed on silica (hept/EtOAc). Yield 1.59: 1.11 g (4.09 mmol). $^1$H-NMR (300 MHz, $CDCl_3$, 2 rotational isomers in a ca. 1.5/1 ratio): δ 5.75 (m) and 5.65 (m) (2H), 4.5 (m, 1H), 4.18 (m, 2H), 3.9 (2t) and 3.8 (2t) (1H), 3.5 (m, 1H), 2.9 (m, 2H), 2.6-2.0 (m, 3H), 1.58 (m, 1H), 1.0 (m, 2H), 0.0 (s, 9H) ppm. $^{13}$C-NMR (75 MHz, $CDCl_3$): δ 157, 156, 136.3, 136.1, 127.3, 126.7, 67.5, 67.5, 63.5, 63.4, 49.2, 46.2, 45.4, 36.5, 35.6, 28.2, 27.8, 17.9, 17.8, −1.4, −1.5 ppm.

2-(Trimethylsilyl)ethyl (E)-4-hydroxy-3,4,7,8-tetrahydroazocine-1(2H)-carboxylate (1.60)

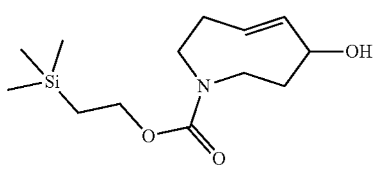 [SMILES: C[Si](C)(C)CCOC(=O)N1CC/C=C/C(O)CC1]

1.59 (1.11 g, 4.09 mmol) and 1.36 g methyl benzoate (10 mmol) in 4/1 hept/EtOAc was irradiated, the irradiated solution being continuously flushed through a column with 8 g 10% silver nitrate (4.70 mmol) on silica for 10 h. The column was flushed with TBME, TBME/5% MeOH and TBME/20% MeOH. All fractions, as well as the column material, were stirred for 10 min with 15 mL 25% ammonia/10 mL water. The layers were separated, the upper layer was dried and concentrated yielding material (total 710 mg) consisting of the product as a mixture of two isomers (predominantly the axial-TCO 1.60, which has a broad singlet at 4.67), and some minor impurities. $^1$H-NMR (300 MHz, $CDCl_3$, positions of relevant signals): δ 5.9 (m), 5.55 (dd), 4.67 (bs), 4.2 (m), 3.6 (m), 2.6 (m), 2.5-2.0 (broad m), 1.9-1.6 (m), 1.3 (m), 1.1-0.8 (m), 0.0 (s) ppm.

2-(Trimethylsilyl)ethyl (S,E)-4-(((4-nitrophenoxy)carbonyl)oxy)-3,4,7,8-tetrahydroazocine-1(2H)-carboxylate (1.61)

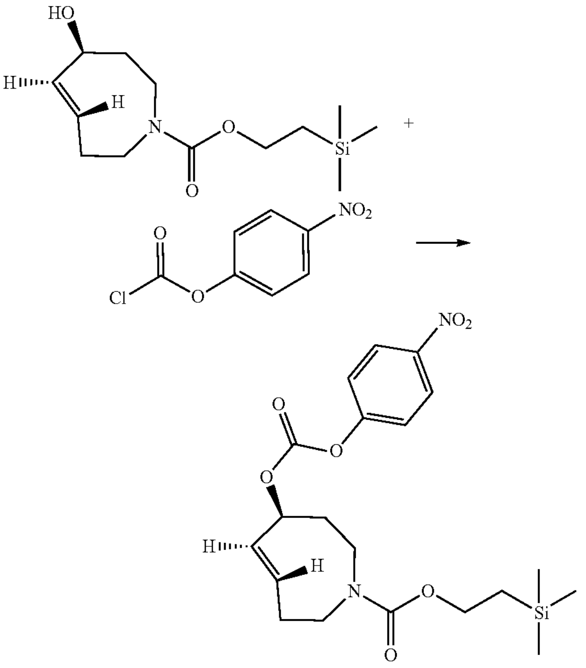

1.60 (115 mg; 0.424 mmol) was dissolved in $CHCl_3$ (10 mL), and DMAP (207 mg; 1.69 mmol) was added. The solution was cooled to 0° C., and 4-nitrophenyl chloroformate (128 mg; 0.636 mmol) was added. The mixture was stirred at 0° C. under an atmosphere of Ar for 1 h, and then washed with 0.5 M aq. citric acid solution (2 times 10 mL). The organic layer was isolated, dried over $Na_2SO_4$, filtered, and evaporated to dryness. The crude product was purified by column chromatography on silica gel, using an elution gradient of 5% to 25% EtOAc in n-hept. This yielded two fractions of different isomers. First the isomer with the carbonate group in axial position (56 mg of a colorless oil), and then the isomer with the carbonate group in equatorial position (36 mg of a colorless oil).

axial 1.61: $^1$H-NMR ($CDCl_3$): δ 8.29 (d, J=9.3 Hz, 2H), 7.41 (d, J=9.3 Hz, 2H), 5.90 (m, 1H), 5.54 (m, 1H), 5.51 (s, 1H), 4.28 (m, 1H), 4.18 (m, 2H), 3.70 (m, 1H), 2.87-2.55 (br.m, 3H), 2.40 (m, 2H), 2.09 (t, J=15.0 Hz, 1H), 1.03 (m, 2H), 0.06 (s, 9H) ppm.

Equatorial 1.61: $^1$H-NMR ($CDCl_3$): δ 8.29 (d, J=9.3 Hz, 2H), 7.40 (d, J=9.3 Hz, 2H), 5.82 (m, 1H), 5.63 (m, 1H), 5.28 (m, 1H), 4.37-4.22 (m, 1H), 4.27-4.12 (m, 2H), 3.85 (m, 1H), 2.67 (m, 2H), 2.55-2.26 (br.m, 4H), 1.05 (m, 2H), 0.06 (s, 9H) ppm.

2-(Trimethylsilyl)ethyl (S,E)-4-((dimethylcarbamoyl)oxy)-3,4,7,8-tetrahydroazocine-1(2H)-carboxylate (1.62)

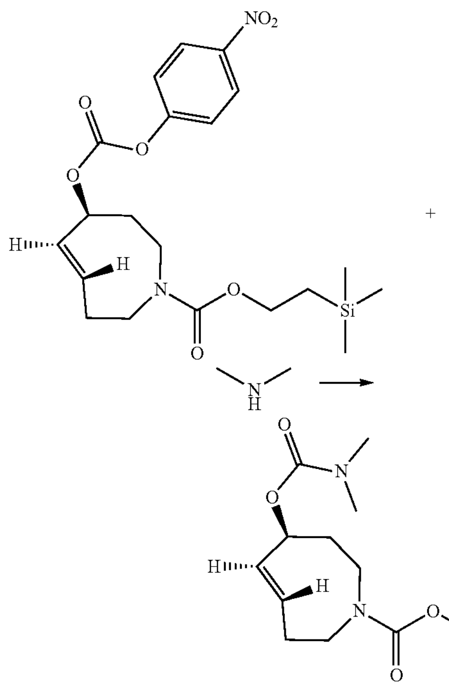

1.61 (35 mg; 0.080 mmol; axial) was dissolved in THF (3 mL). A solution of dimethylamine in THF (0.10 mL 2 M; 0.20 mmol) was added and the mixture was stirred at 20° C. for 30 min. The mixture was evaporated to dryness, dissolved in $CHCl_3$ (10 mL) and washed with subsequently 0.5 M aq. citric acid solution (2 times 5 mL), and 1 M aq. NaOH (2 times 5 mL). The organic layer was isolated, dried over $Na_2SO_4$, filtered, and evaporated to dryness to yield 1.62 as a colorless oil (29 mg). $^{1}H$-NMR ($CDCl_3$): δ 5.70 (m, 1H), 5.52 (dd, J=16.4, 2.0 Hz, 1H), 5.42 (m, 1H), 4.30 (m, 1H), 4.17 (m, 2H), 3.63 (m, 1H), 2.97 (m, 6H), 2.74-2.23 (br.m, 5H), 1.97 (ddd, J=15.8, 13.0, 2.7 Hz, 1H), 1.01 (m, 2H), 0.06 (s, 9H) ppm. $^{13}C$-NMR ($CDCl_3$): δ 156.73, 156.16, 155.48, 155.46, 136.40, 135.69, 127.08, 126.26, 125.00, 122.20, 73.69, 73.55, 63.39, 63.20, 56.57, 55.93, 47.87, 46.77, 39.55, 37.96, 36.40, 36.02, 35.85, 35.57, 30.27, 17.94, 17.90, −1.50, −1.52 ppm.

(S,E)-1,2,3,4,7,8-Hexahydroazocin-4-yl dimethylcarbamate (1.63)

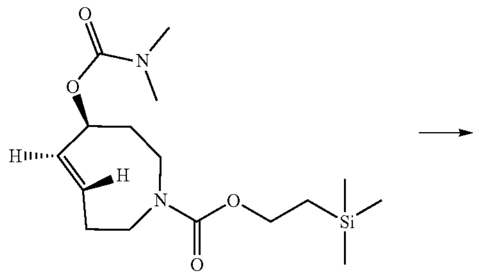

-continued

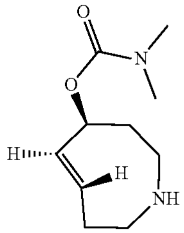

1.62 (7.2 mg; 0.021 mmol, axial) was dissolved in MeCN (0.5 mL), and potassium fluoride (4.8 mg; 0.082 mmol) was added, followed by tetrabutylammonium fluoride (0.062 mL of a 1 M solution in THF; 0.062 mmol). The mixture was heated to 45° C. for 18 h, and then evaporated to dryness. The crude product was dissolved in $CHCl_3$ (1 mL), and washed with 0.1 M aq. sodium carbonate (3×1 mL). The organic layer was isolated, dried over $Na_2SO_4$, filtered, and evaporated to dryness to yield the axial 1.63 as a colorless oil (4 mg). $^{1}H$-NMR ($CDCl_3$): δ 5.79 (m, 1H), 5.63 (m, 1H), 5.46 (m, 1H), 3.24 (m, 1H), 3.03 (m, 1H), 2.59 (m, 1H), 2.41 (m, 1H), 2.22 (m, 1H), 2.02-1.76 (br.m, 3H) ppm. $^{13}C$-NMR ($CDCl_3$): δ 135.90, 127.09, 74.54, 58.90, 55.00, 46.45, 44.48, 38.84, 24.09, 19.76, 13.68 ppm.

TCO-doxorubicin (1.64)

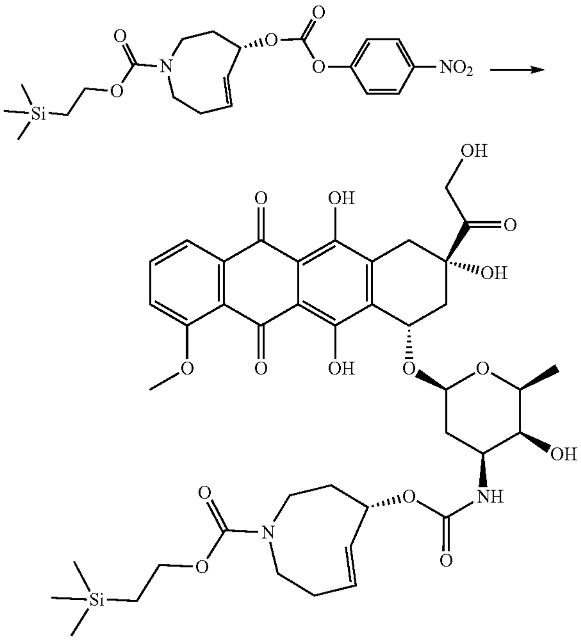

1.61 (6.6 mg, 15 μmol, axial) was treated with doxorubicin HCl (16.3 mg, 30 μmol) and DiPEA (13.2 μL, 75 μmol) for 18 hr at r.t. in dry MeCN:DMSO. Following acidification, prep HPLC (a $H_2O$/MeCN gradient with 0.1% TFA) and lyophilization, 1.64 was isolated in 26% yield (3.3 mg, 3.9 μmol) as white powder. ESI-MS identification of the poorly ionizing 1.64 was performed by reacting with tetrazine 4-({6-[6-(pyridin-2-yl)-1,2,4,5-tetrazin-3-yl]pyridin-3-yl}carbamoyl) butanoic acid, which resulted in the expected 1.64-TZ conjugate with mass [$C_{58}H_{65}N_7O_{18}Si$] 1175.42; Obs. $[M-H]^-$ 1175.08, $[M-2H]^{2-}$ 587.56.

TCO-doxorubicin (1.65)

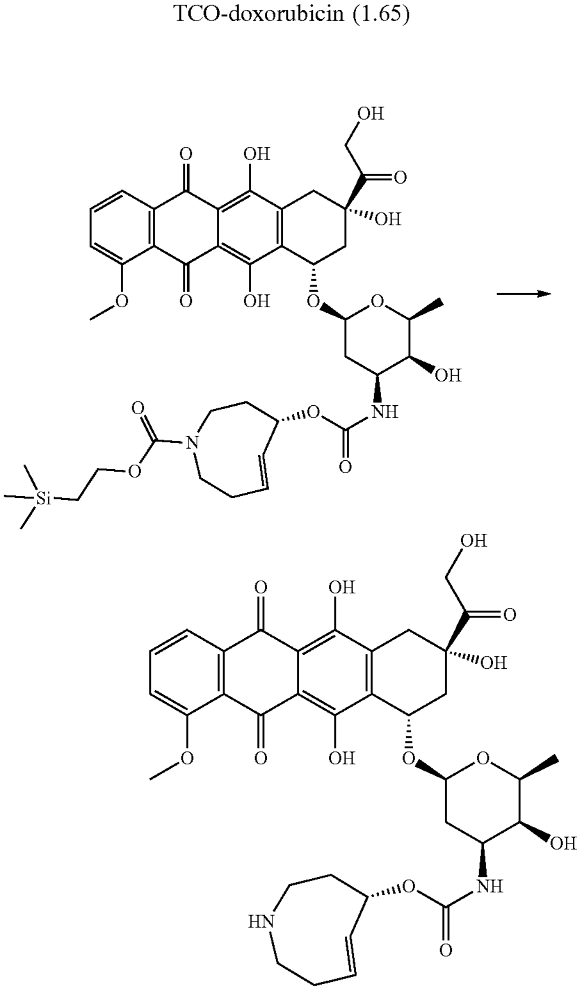

1.64 (3.3 mg, 3.6 μmol) was treated with TBAF (a 1M solution in THF, 31.4 μL, 31.4 μmol) in MeCN at 45° C. for 16 hr followed by concentration. The residue was taken up in $CHCl_3$, washed with sat. $NaHCO_3$ (5x), dried over $Na_2SO_4$, and concentrated. Yield: 83% (2.3 mg, 3.0 μmol). ESI-MS identification of the poorly ionizing 1.65 was performed by reacting with tetrazine 4-({6-[6-(pyridin-2-yl)-1,2,4,5-tetrazin-3-yl]pyridin-3-yl}carbamoyl) butanoic acid, which resulted in the expected 1.65-TZ conjugate with mass $C_{24}H_{26}N_6O_3$ 446.21; Obs. $[M+H]^+$ 447.40 after release of doxorubicin.

Z)-3a,4,5,8,9,9a-Hexahydrocycloocta[b]furan-2(3H)-one (1.66)

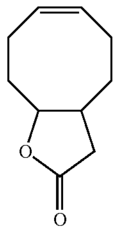 [SMILES: O=C1CC2CC/C=C\CCC2O1]

[Bensel et al., *Chem. Ber.* 1975, 108, 2697] To 26.7 g sodium (1.16 mol) in 400 mL EtOH was added 186.3 g diethyl malonate (1.163 mol) at 50° C. The resulting solution was stirred for 5 min, then crude cyclooctene epoxide was added (79.2 g, 0.782 mol). The mixture was heated under reflux for 4 days resulting in a solid mass. It was cooled, 300 mL water was added, followed by the gradual addition of 90 g potassium hydroxide (1.366 mol). The mixture was heated under reflux for 1 hr, followed by removal of the EtOH. The resulting aq. solution was cooled, washed with 400 mL TBME, and the TBME-layer was extracted with 2×50 ml water. The combined water layers were cooled in ice, 300 mL toluene was added and then 230 mL 37% HCl was added gradually at 15-20° C. The layers were separated and the aq. layer was extracted with 2×300 mL toluene. Drying and rotary evaporation gave 100.5 g solidifying residue.

This solid was heated at 130° C. in a heating mantle, whereby the solid melted. After 1 h, the gas evolution had almost ceased and the residue was distilled in a Kugelrohr at 145-160° C./0.1 mbar to give 53.8 g of the product (0.324 mol, 41%). $^1$H-NMR (300 MHz, $CDCl_3$): δ 5.67 (m, 2H), 4.36 (m, 1H), 2.72 (dd, 1H), 2.6-2.1 (m, 7H), 1.9 (m, 1H), 1.6-1.2 (m, 2H) ppm.

(rel-3aS,6S,9aR,Z)-2-Oxo-2,3,3a,4,5,6,9,9a-octahydrocycloocta[b]furan-6-yl acetate (1.67)

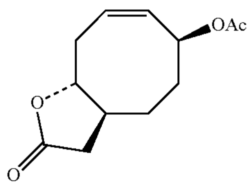 [SMILES: CC(=O)O[C@@H]1/C=C\C[C@H]2OC(=O)C[C@@H]2CC1]

To a solution of 1.66 (4.61 g, 27.73 mmol) in 40 mL acetic acid was added potassium acetate (5.91 g, 60.2 mmol) and the mixture was stirred for 10 min, then cooled in ice water. Phenylselenyl bromide (6.68 g, 28.3 mmol) was added in portions in 30 min to the solution. A light-brown suspension formed. It was stirred over the weekend, then poured into 100 mL toluene. The mixture was washed with 50 and 2×25 mL water. The successive aq. layers were extracted with 50 mL toluene. Drying and rotary evaporation yielded 10.03 g of material, which was dissolved in 50 mL THF, cooled in ice followed by addition of 12 mL 35% hydrogen peroxide over 10 min. The solution was stirred for 4 hr, reaching rt, and was poured into 100 mL toluene and 50 mL water. The layers were separated, the upper layer was washed with 25 mL water and the successive aq. layers were extracted with 50 mL toluene. Drying and rotary evaporation yielded 7.68 g, which was chromatographed on silica (hept/EtOAc). The fractions were a mixture of mainly two isomeric acetoxy-lactones and the purest fraction was concentrated and stirred with hept and some TBME to give pure 1.67 (1.33 g, 5.93 mmol, 21%). $^1$H-NMR (300 MHz, $CDCl_3$): δ 5.84-5.69 (m, 1H), 5.69-5.49 (m, 2H), 3.77 (ddd, J=11.4, 8.5, 2.3 Hz, 1H), 2.73 (ddt, J=13.0, 8.9, 2.2 Hz, 1H), 2.66-2.58 (m, 1H), 2.51 (ddt, J=13.3, 11.7, 4.7 Hz, 1H), 2.40-2.22 (m, 2H), 2.11-1.93 (m, 4H), 1.75 (dd, J=14.6, 6.5 Hz, 1H), 1.59 (dddd, J=12.8, 11.2, 6.0, 1.5 Hz, 1H), 1.53-1.36 (m, 1H) ppm.

(rel-3aS,6S,9aR,E)-2-Oxo-2,3,3a,4,5,6,9,9a-octahydrocycloocta[b]furan-6-yl acetate (1.68)

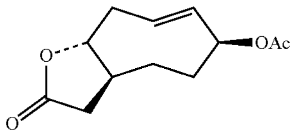

1.67 (1.20 g, 5.35 mmol), mixed with 1.71 g methyl benzoate (12.6 mmol) and 25 mg BHT (0.11 mmol) was irradiated for 31 h, the solution being continuously flushed through a 10.2 g silver nitrate silica column (6 mmol silver nitrate).

The column was eluted with 80 mL TBME and with 100 mL TBME/7% MeOH. These fractions, as well as the silica, were stirred with 7.5 g sodium chloride/25 mL water. The layers were separated and the water layer was extracted with a little TBME. The silica was likewise stirred with the water layer, 10 ml H water $_2$O and 75 mL TBME, then filtered and the solid and the water layer were stirred with 2×50 mL TBME. The fraction obtained from the column material weighed 450 mg and was the nearly pure axial isomer (broad singlet at 5.5 ppm). $^1$H-NMR (300 MHz, $CDCl_3$): δ 5.7-5.5 (m) and 5.50 (bs) (3H), 4.08 (ddd, 1H), 3.15 (m, 1H), 2.66 (dd, 1H), 2.4-2.0 (m) and 2.10 (s) (7H), 1.9 (m, 1H), 1.75-1.4 (m, 2H) ppm.

(rel-3aS,6S,9aR,E)-2-Oxo-2,3,3a,4,5,6,9,9a-octahydrocycloocta[b]furan-6-yl dimethylcarbamate (1.69)

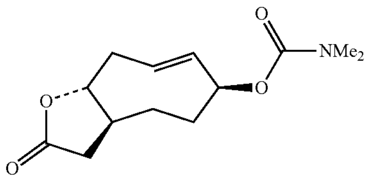

To 1.68 (225 mg) in 10 mL THF was added 2 mL water and 140 mg lithium hydroxide. The mixture was stirred overnight, 10 mL water was added, giving a clear solution. 50 mL TBME was added, followed by 1.0 g citric acid. The layers were separated and the upper layer was washed with 10 mL water. The successive aq. layers were extracted with TBME. Drying and rotary evaporation gave the product. NMR showed relevant signals at 5.8-5.6 (m), 4.73 (bs), 4.08 (ddd), 3.15 (m), 2.64 (dd) ppm.

The intermediate was dissolved in 5 mL THF, then 25 mL toluene was added and the solution was concentrated to give 135 mg residue. This was mixed with 20 mL DCM and 370 mg DMAP was added and the mixture was stirred for 5 min. 460 mg 4-nitrophenylchloroformate was added and the yellow-brown mixture was stirred for 2 h, then cooled in icewater. 4 mL 2 N dimethylamine in THF was added and the solution was stirred for 1 h, reaching rt. Purification by silica column (EtOAc/hept) yielded the product (80 mg). $^1$H-NMR (300 MHz, $CDCl_3$): δ 5.66 (dd, 1H), 5.56 (dd, 1H), 5.47 (bs, 1H), 4.08 (ddd, 1H), 3.18 (m, 1H), 2.94 (s, 6H), 2.67 (dd, 1H), 2.4-2.0 (m) (4H), 1.9 (m, 1H), 1.75-1.4 (m, 2H) ppm.

(rel-1S,5R,6S,E)-5-Hydroxy-6-(2-(methylamino)-2-oxoethyl)cyclooct-2-en-1-yl dimethylcarbamate (1.70)

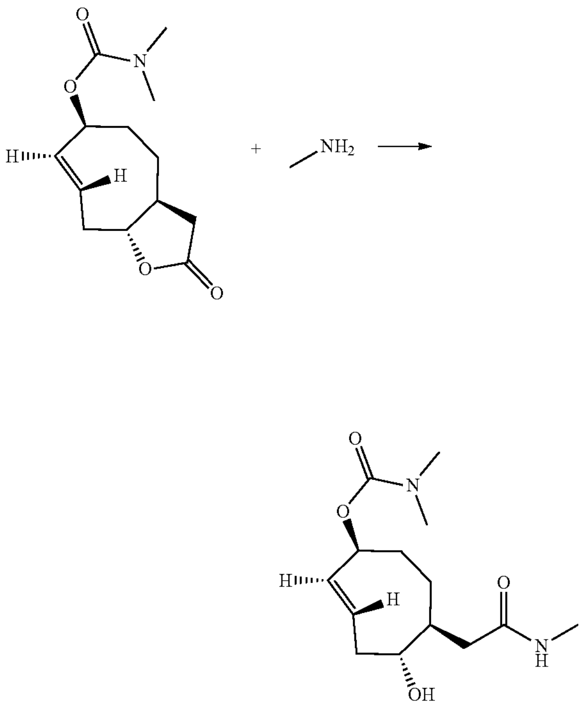

1.69 (80 mg) was stirred overnight with 4 mL 2 N methylamine in THF. The reaction mixture was evaporated to dryness and dried in vacuo to yield the title compound as a yellow oil (88 mg). $^1$H-NMR ($CDCl_3$): δ 5.89 (d, J=5.3 Hz, 1H), 5.66 (dd, J=16.4, 2.3 Hz, 1H), 5.56 (m, 1H), 5.45 (s, 1H), 3.64 (d, J=4.7 Hz, 1H), 3.03 (m, 1H), 2.92 (s, 6H), 2.80 (d, J=4.7 Hz, 3H), 2.58 (m, 1H), 2.33-2.02 (m, 2H), 1.95 (m, 1H). 1.65 (m, 1H), 1.55 (m, 1H), 1.22 (m, 2H) ppm.

Example 2: Tetrazine Synthesis

Tetrazines 2.12 and 2.17 where purchased from commercial sources. Tetrazines 2.9, 2.10, 2.11, 2.13, 2.14, 2.15, 2.16, 2.18, 2.20 were prepared according to literature procedures [Rossin et al., *Angew Chem Int Ed* 2010, 49, 3375-3378; Versteegen et al., *Angew Chem Int Ed* 2013, 52/53, 14112-14116; Fan et al., *Angew Chem Int Ed* 2016, 55, 14046-14050; Carlson et al., *J Am Chem Soc* 2018, 140, 3603-3612; Sarris et al., *Chem Eur J* 2018, 24, 18075-18081] while 2.19 was prepared as reported in WO2010119389(A2) (compound 6, therein).

2.9

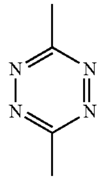

-continued
2.10
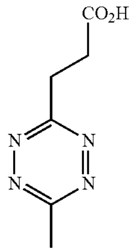
2.11
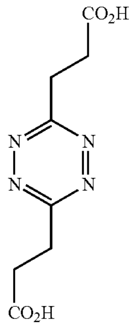
2.12
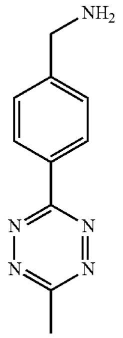
2.13
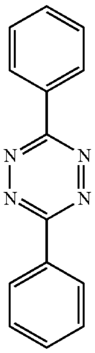
2.14
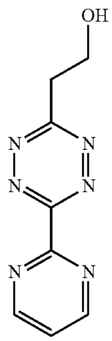
-continued
2.15
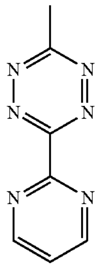
2.16
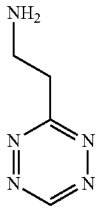
2.17
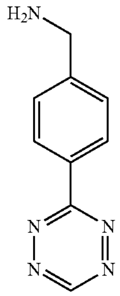
2.18
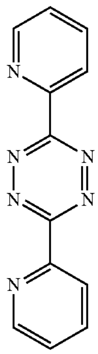

-continued

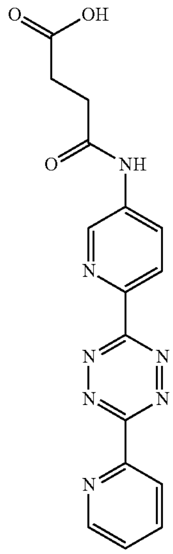

2.19

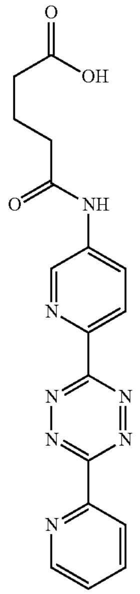

2.20

2,2'-(1,2,4,5-Tetrazine-3,6-diyl)bis(pyridin-3-ol) (2.1)

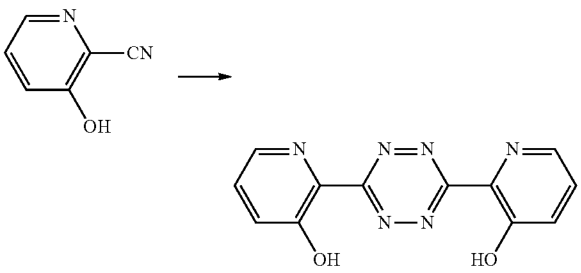

3-Hydroxypicolinonitrile (100 mg, 0.82 mmol) and hydrazine hydrate (280 µL, 4.9 mmol, 6 eq) were stirred at 90° C. for 2 h. Ethanol (4 mL) was added and the suspension was stirred at rt for 5 min. The suspension was filtrated and the solid was washed with ethanol (5x2 mL). Drying of the solid in vacuo yielded pure intermediate [2H]-TZ (59 mg, 0.22 mmol, 54%) as a yellow solid. The [2H]-TZ was suspended in acetic acid (6 mL) and $NaNO_2$ (75 mg, 1.1 mmol) in water (500 µL) was added dropwise. The suspension was stirred at rt for 1 h during which a clear red solution was obtained and, eventually, a red precipitate arose. Chloroform and water (both 40 mL) were added and the layers were separated. The aqueous layer was extracted with chloroform (2x20 mL) and the combined organic layers were dried using $Na_2SO_4$. After filtration, the filtrate was evaporated to dryness yielding pure 2.1 (55 mg, 0.21 mmol, 50% overall) as a red solid. $^1$H-NMR (DMSO-d6): δ=10.74 (br s, 2H, OH), 8.38 (m, 2H, ArH), 7.57 (m, 4H, ArH). $^{13}$C-NMR (DMSO-d6): δ=164.3, 154.3, 141.4, 137.5, 127.5, 125.3. ESI-MS: m/z Calc. for $C_{12}H_8N_6O_2$ 268.07; Obs. $[M+H]^+$ 269.17, $[M+Na]^+$ 291.25.

2,2'-(1,2,4,5-tetrazine-3,6-diyl)bis(pyridin-3-amine) (2.2)

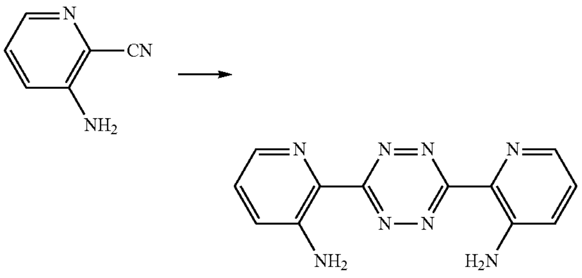

3-Aminopicolinonitrile (125 mg, 1.0 mmol) and hydrazine hydrate (300 µL, 5.0 mmol) were stirred at 100° C. for 20 h. Cold water (2 mL) was added and the suspension was stirred at rt for 5 min. Filtration, washing of the solid with cold water and cold ethanol (both 5x2 mL) and drying in vacuo yielded the intermediate [2H]-TZ (38 mg, 0.14 mmol, 27%) as an orange solid. To the [2H]-TZ and $PhI(OAc)_2$ (75 mg, 0.23 mmol) dichloromethane (1 mL) was added and the suspension was stirred at rt for 3 h. In time a color change occurred from orange to red. The suspension was filtrated, the solid was washed with dichloromethane (5x1 mL) and dried in vacuo yielding pure 2.2 (31 mg, 0.12 mmol, 22% overall) as a red solid. $^1$H-NMR (DMSO-d6): δ=8.13 (dd, 2H, ArH), 7.36 (2dd, 4H, ArH), 6.98 (br s, 4H, $NH_2$) ppm. $^{13}$C-NMR (DMSO-d6): δ=162.8, 146.6, 138.3, 129.5, 126.9, 124.5 ppm. ESI-MS: m/z Calc. for $C_{12}H_{10}N_8$ 266.10; Obs. $[M+H]^+$ 267.08, $[2M+H]^+$532.92, $[2M+Na]^+$ 555.00.

N,N'-(2,2'-(1,2,4,5-Tetrazine-3,6-diyl)bis(pyridine-3,2-diyl))diacetamide (2.3)

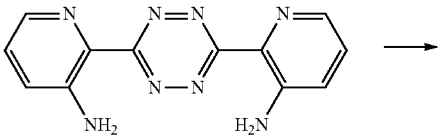

-continued

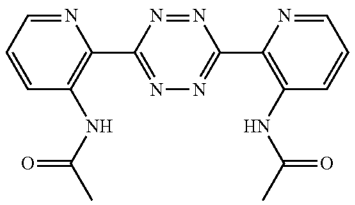

2.3 (12 mg, 45 μmol) was suspended in acetic anhydride (0.5 mL) and the suspension was heated at 50° C. for 3 d. The mixture was precipitated in diethyl ether (6 mL) and the solution was decanted. The solid was washed with diethyl ether (2 mL) and the solution was decanted, after which the wash step was repeated. Next, the solid was triturated with water (2 mL), the mixture was centrifuged at 12.7 krpm for 1 min and the solution was decanted. The solid was subsequently dissolved in methanol (1 mL), after which non-dissolved impurities were removed by filtration. The filtrate was evaporated to dryness and the obtained residue was triturated with water (2 mL). After centrifugation at 12.7 krpm for 1 min and decantation, the solid was dried in vacuo yielding 2.3 (0.75 mg, 2.1 μmol, 5%) as a purple-red solid. ESI-MS: m/z Calc. for $C_{16}H_{14}N_8O_2$ 350.12; Obs. $[M+H]^+$ 351.17, $[2M+Na]^+$ 722.92.

N-(29-Hydroxy-3,6,9,12,15,18,21,24,27-nonaoxanonacosan-1-yl)-N'-{6-[6-(pyridin-2-yl)-1,2,4,5-tetrazin-3-yl]pyridin-3-yl}pentanediamide (2.4)

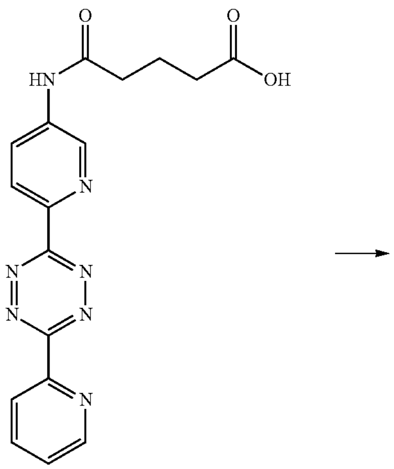

-continued

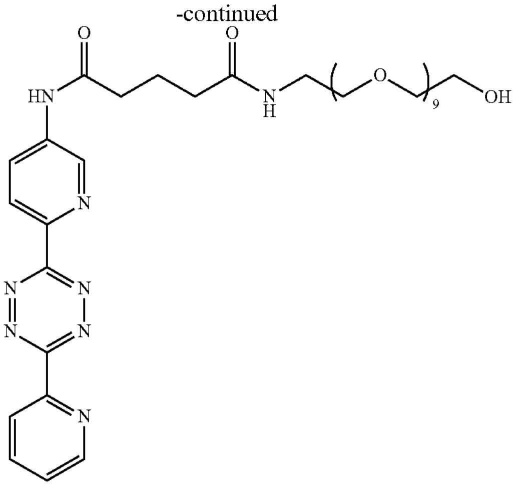

2.20 (39.9 mg, 109.3 μmol) was treated with 29-amino-3,6,9,12,15,18,21,24,27-nonaoxanonacosan-1-ol (50 mg, 109.3 μmol), PyBOP (73.9 mg, 142.09) and DiPEA (76.3 μL, 0.44 mmol) in $CH_2Cl_2$/DMSO for 16 hr. Following removal of $CH_2Cl_2$, prep HPLC (a $H_2O$/MeCN gradient with 0.1% TFA) and lyophilization, 2.4 was isolated in 67% yield (59.0 mg, 73.3 μmol). ESI-MS: m/z calc for $C_{37}H_{56}N_8O_{12}$ 804.40; Obs. $[M+H]^+$ 805.60.

4-(1,2,4,5-Tetrazin-3-yl)phenol (2.5)

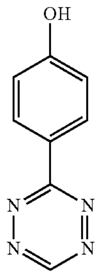

A mixture of methyl 4-hydroxybenziminoester HCl (4.2 g, 22.38 mmol) and formamidine acetate salt (7 g, 67.16 mmol) was treated dropwise with hydrazine monohydrate (18 mL, 371 mmol) at 0° C. under an atmosphere of Ar. After allowing the reaction mixture to warm to rt it was stirred for additional 3 h. The mixture was poured onto ice water (120 mL) and sodium nitrite (24 g, 58 mmol) was added. 2N HCl was added carefully until the evolution of nitrous oxides ceased. The resulting deep purple-red solution was extracted with EtOAc (6×150 mL), and the combined organic layer was dried over $MgSO_4$, filtered and concentrated. The aq. layer was perforated for 3 h with EtOAc and the perforate was dried over $MgSO_4$, filtered and the solvent was evaporated. The combined residues were purified by reversed phase column chromatography (Gradient: 3-70% MeOH in $H_2O$). 2.5 precipitated overnight at 4° C., was filtered and dried in vacuum to yield an orange solid (457 mg, 12%). $^1H$ NMR (400 MHz, $CD_3OD$) δ 10.19 (s, 1H), 8.43 (dt, J=9.0, 1.9 Hz, 2H), 6.98 (dt, J=9.0, 1.9 Hz, 2H) ppm. $^{13}C$ NMR (101 MHz, $CD_3OD$): δ 167.7, 163.8, 158.8, 131.3, 124.4, 117.4 ppm. HR-ESI-MS: calculated for $[M+H]^+$ 175.0614; observed 175.0614.

2-[2-(2-{2-[4-(1,2,4,5-Tetrazin-3-yl)phenoxy] ethoxy}ethoxy) ethoxy]ethan-1-ol (2.6)

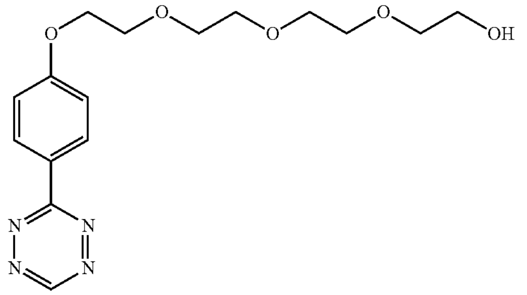 [SMILES: OCCOCCOCCOCCOc1ccc(-c2nncnn2)cc1]

2.5 (40 mg, 0.23 mmol), tetraethylene glycol (892 mg, 4.6 mmol) and $PPh_3$ (120 mg, 0.46 mmol) were mixed with toluene (5 mL). The solvent was removed in vacuo and the vial aired with Ar gas. This procedure was repeated twice. The residue was taken up in 2 mL THF and treated with 730 μL THF and 90.2 μL DIAD. The mixture was stirred at rt for 20 h. The solvent was evaporated and the residue purified by silica gel column chromatography (Gradient: 50-90% EtOAc in hexanes). Further purification was performed by reversed phase chromatography (Gradient: 5-80% MeCN in $H_2O$) to obtain 2.6 (53.1 mg, 66%). $^1H$ NMR (400 MHz, $CDCl_3$) δ 10.05 (s, 1H), 8.49 (d, J=8.0 Hz, 2H), 7.04 (d, J=8.0 Hz, 2H), 4.19 (t, J=4.0 Hz, 2H), 3.85 (t, J=4.0 Hz, 2H), 3.62 (m, 12H) ppm. $^{13}C$ NMR (101 MHz, $CDCl_3$): δ 166.1, 163.0, 157.3, 130.1, 124.1, 115.4, 72.5, 70.9, 70.7, 70.6, 70.3, 69.6, 67.7, 61.7 ppm. ESI-MS: calculated for $[M+H]^+$ 351.17; observed 351.22.

N-(29-Hydroxy-3,6,9,12,15,18,21,24,27-nonaoxanonacosan-1-yl)-N'-{6-[6-(5-{4-[(29-hydroxy-3,6,9,12,15,18,21,24,27-nonaoxa nonacosan-1-yl)carbamoyl]butanamido}pyridin-2-yl)-1,2,4,5-tetrazin-3-yl]pyridin-3-yl}pentanediamide (2.7)

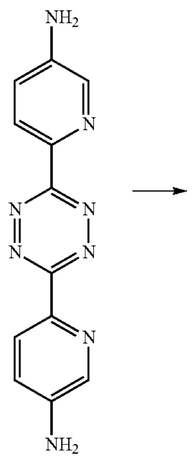

-continued

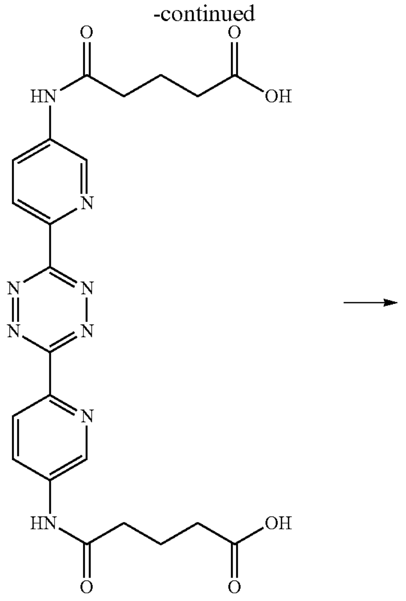

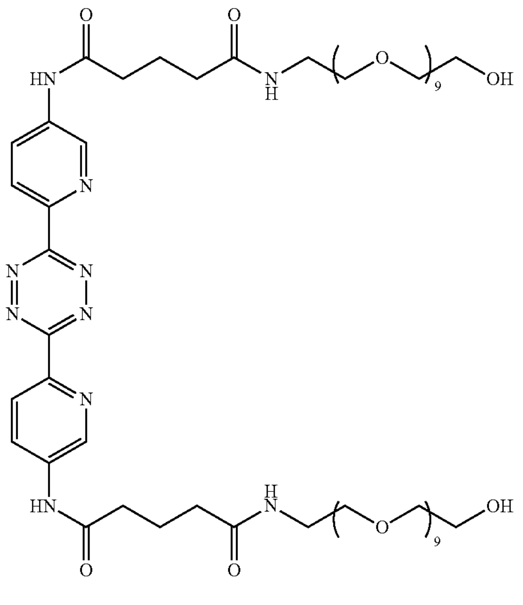

The tetrazine (Asselin, C. M, et al. JACS (1997): 3765-3772) (1 eq) is treated with glutaric anhydride (8 eq.) and DMAP (0.1 eq) in dry THF in a sealed vessel under argon at 70° C. for 18 h. Following concentration, preparative HPLC (a $H_2O$/MeCN gradient with 0.1% TFA) and lyophilization, the intermediate compound is obtained. The intermediate (1 eq) is treated with 29-amino-3,6,9,12,15,18,21,24,27-nonaoxanonacosan-1-ol (3 eq), PyBOP (2.5 eq.) and DiPEA (6 eq) in $CH_2Cl_2$/DMSO for 16 h. Following removal of $CH_2Cl_2$, preparative HPLC (a $H_2O$/MeCN gradient with 0.1% TFA) and lyophilization, the title compound is isolated.

4-({[6-(6-{5-[(4-Carboxybutanamido)methyl]pyridin-2-yl}-1,2,4,5-tetrazin-3-yl)pyridin-3-yl]methyl}carbamoyl)butanoic acid (2.8)

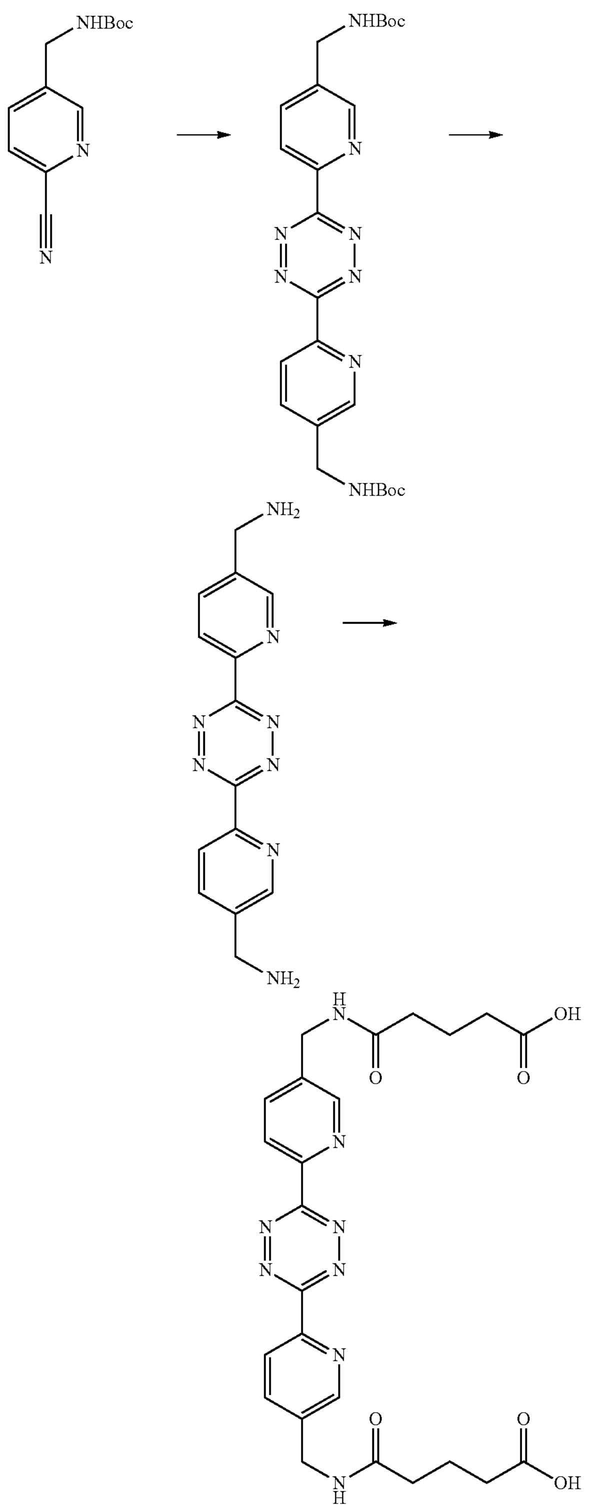

The nitrile, zinc triflate (0.05 eq), and hydrazine monohydrate (2 eq) are heated and stirred in a small amount of EtOH in a sealed vessel for 18 h. The volatiles are removed and the residue is divided between $CHCl_3$ and water and the aqueous layer is extracted with $CHCl_3$ (3×). The organic layer is dried with $Na_2SO_4$, filtered and the volatiles are removed in vacuo. The residue is dissolved in $CH_2Cl_2$ and $PhI(OAc)_2$ (1.5 eq) is added. The mixture is stirred at rt for 2 h. Column chromatography (flash $SiO_2$) using an elution gradient of EtOAc in $CHCl_3$ and, in a second chromatography step (normal $SiO_2$), elution with acetone in heptane yields the Boc-protected tetrazine. The Boc-protected tetrazine is treated with $CHCl_3$/TFA (2/1) for 30 min prior to concentration and co-evaporation with $CHCl_3$. After removal of the excess TFA, the deprotected TZ intermediate is treated with glutaric anhydride (5 eq) and DiPEA (5 eq) in DMSO at rt for 18 h. Following preparative HPLC (a $H_2O$/MeCN gradient with 0.1% TFA) and lyophilization, the title compound is isolated.

Example 3: Reactivity Measurements

Second order rate constants for the reaction of tetrazines activators with 1.13 and 1.71 were determined using a SX20 stopped-flow spectrophotometer from Applied Photophysics. Measurements were performed at 37° C. with 25 μM tetrazine and 50 μM TCO in PBS, in triplicates, monitored at 535 nm. Data was analyzed using GraphPad Prism. Second order rate constants were determined from nonlinear fitting of the absorbance vs. time curves to the second order rate equation. The results in Table 1 demonstrate that the TCO trigger of the invention (1.13) is as reactive as an established TCO trigger (1.71), and shows the same reactivity differences with various tetrazine motifs, due to the difference in electronic and steric properties of the tetrazines. Importantly, 2.17 and 2.18 are very reactive, but afford low release yields with TCO triggers that are not part of this invention (i.e. 1.71) [Versteegen et al., *Angew. Chem. Int. Ed.* 2013, 52, 14112-14116].

TABLE 1

Rate constants ($M^{-1}$ $s^{-1}$) measured for the reaction between model TCO-$C^A$ conjugates and various activators in PBS at 37° C.

| TCO | activator | $k_2$ ($M^{-1}$ $s^{-1}$) |
|---|---|---|
| 1.13 | 2.9 | 70 ± 10 |
| | 2.12 | 260 ± 40 |
| | 2.17 | 8700 ± 1200 |
| | 2.18 | 10400 ± 1100 |
| 1.71 | 2.9 | 80 ± 10 |
| | 2.12 | 280 ± 30 |
| | 2.17 | 10300 ± 1200 |
| | 2.18 | 9300 ± 500 |

Second order rate constant for the reaction between TCO derivatives and tetrazine 2.18 was determined under pseudo-first order conditions in MeCN at 20° C. by UV spectroscopy. A cuvette was filled with MeCN (3 mL) and equilibrated at 20° C. A solution of 2.18 (20 μL, 25 mM in DMSO) was added, followed by a solution of the TCO (5 μL 25 mM in DMSO). The absorption at 540 nm was monitored. The pseudo-first order reaction constant $k_1$' was calculated from the half-life of the decrease of this absorption, and the second order rate constant $k_2$ was estimated from $k_1$' and the initial concentration of tetrazine: $k_2$=$k_1$'/c. The results in Table 2 demonstrate that the highly reactive tetrazine 2.18 shows good reactivity across a wide range of TCO triggers and TCO-$C^A$ conjugates of this invention (the $k_2$ values are lower than Table 1 due to solvent effect).

TABLE 2

| Rate constants ($M^{-1}$ $s^{-1}$) measured for the reaction between model TCO triggers and TCO-$C^4$ conjugates and 2.18 in MeCN at 20° C. | |
|---|---|
| TCO | $k_2$ ($M^{-1}$ $s^{-1}$) |
| 1.19 | 134 |
| 1.40 | 39 |
| 1.43 | 27 |
| 1.51 | 104 |
| 1.54 | 38 |
| 1.60 | 277 |
| 1.62 | 80 |

Example 4: Mechanistic Studies

The model TCO-$C^4$ conjugate 1.13 (400 μM) was reacted with 1.1 eq of activators 2.9 and 2.18 in 100 mL 10 mM citrate-phosphate buffer pH 7.4. The reaction mixtures were incubated at rt for 24 h then 02 was bubbled through the solutions and incubation was continued for 2 days. After incubation, the reaction mixtures were purified by column chromatography and the reaction products were analyzed by 1D and 2D NMR. The results confirmed the formation of two release products from the reaction of 1.13 with 2.9 (release mechanisms A and B combined) while only one release product and the oxidized derivative were found after the reaction of 1.13 with 2.18 (release mechanism B).

TABLE 3

| Products resulting from the reaction of 1.13 with 2.9. | |
|---|---|
| 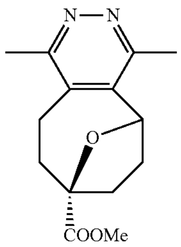 | $^1$H NMR (600 MHz, DMSO-$d_6$) δ 5.47 (dd, J = 9.5, 4.2 Hz, 1H), 3.70 (s, 3H), 2.95 (ddd, J = 16.6, 9.2, 2.9 Hz, 1H), 2.79 (ddd, J = 16.6, 8.9, 2.7 Hz, 1H), 2.65-2.59 (m, 1H), 2.57 (s, 3H), 2.54 (s, 3H), 2.24-2.19 (m, 1H), 2.18-2.11 (m, 2H), 2.05 (ddd, J = 14.7, 9.2, 2.7 Hz, 1H), 1.96-1.89 (m, 1H) ppm; $^{13}$C NMR (151 MHz, DMSO-$d_6$) δ 172.5, 157.7, 154.4, 140.9, 136.4, 85.2, 76.5, 52.2, 35.1, 35.0, 30.4, 24.0, 20.7, 19.8 ppm. |
| 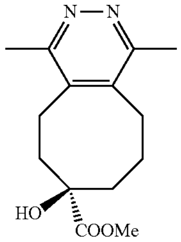 | $^1$H NMR (600 MHz, DMSO-d6) δ 5.45 (bs, 1H), 3.59 (s, 3H), 2.97-2.92 (m, 1H), 2.90 (ddd, J = 14.2, 10.8, 2.6 Hz, 1H), 2.71-2.65 (m, 2H), 2.56 (s, 3H), 2.53 (s, 3H), 2.02-1.93 (m, 2H), 1.80 (ddd, J = 14.1, 11.8, 2.2 Hz, 1H), 1.61-1.51 (m, 2H), 1.14-1.06 (m, 1H) ppm; $^{13}$C NMR (151 MHz, DMSO-$d_6$) δ 176.8, 156.4, 156.4, 139.0, 136.9, 74.9, 51.9, 38.5, 31.7, 25.4, 22.7, 21.8, 20.0, 19.6 ppm. |

TABLE 4

| Products resulting from the reaction of 1.13 with 2.18. | |
|---|---|
| 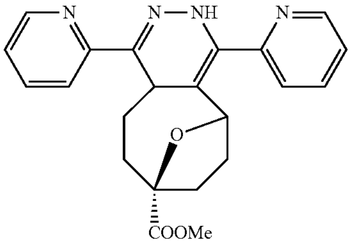 [SMILES: COC(=O)[C@]12CCC(O1)C1=C(c3ccccn3)NN=C(c3ccccn3)C1CC2] | $^1$H NMR (600 MHz, DMSO-$d_6$) δ 9.67 (s, 1H), 8.67 (ddd, J = 4.7, 1.7, 0.9 Hz, 1H), 8.57 (ddd, J = 4.8, 1.7, 0.9 Hz, 1H), 7.96 (dt, J = 8.2, 1.1 Hz, 1H), 7.92 (td, J = 7.7, 1.8 Hz, 1H), 7.78 (td, J = 7.7, 1.9 Hz, 1H), 7.49 (dt, J = 7.9, 1.0 Hz, 1H), 7.44 (ddd, J = 7.6, 4.9, 1.2 Hz, 1H), 7.30 (ddd, J = 7.3, 4.8, 1.2 Hz, 1H), 5.13 (dd, J = 8.6, 2.1 Hz, 1H), 4.15-4.10 (m, 1H), 3.62 (s, 3H), 2.42 (dd, J = 12.9, 4.8 Hz, 1H), 2.26-2.19 (m, 2H), 2.06-1.95 (m, 2H), 1.85 (dddd, J = 12.2, 9.8, 4.8, 2.1 Hz, 1H), 1.76 (dd, J = 13.5, 5.0 Hz, 1H), 1.62 (dddd, J = 13.2, 11.7, 10.2, 6.0 Hz, 1H) ppm; $^{13}$C NMR (151 MHz, DMSO) δ 174.3, 154.8, 152.4, 149.2, 148.6, 141.1, 136.7, 136.0, 132.4, 124.4, 123.4, 122.5, 119.5, 110.4, 83.3, 79.1, 51.6, 39.6, 38.4, 32.9, 28.5, 26.3 ppm. |
| 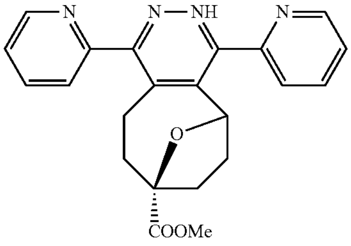 [SMILES: COC(=O)[C@]12CCc3c(-c4ccccn4)nnc(-c4ccccn4)c3C(CC1)O2] | $^1$H NMR (600 MHz, DMSO-$d_6$) δ 8.78-8.74 (m, 1H), 8.75-8.73 (m, 1H), 8.09-8.05 (m, 2H), 8.04-8.02 (m, 1H), 7.89 (dt, J = 7.7, 1.1 Hz, 1H), 7.59-7.54 (m, 2H), 5.61 (dd, J = 9.7, 4.0 Hz, 1H), 3.64 (s, 3H), 3.21 (ddd, J = 16.4, 6.9, 3.1 Hz, 1H), 3.02 (ddd, J = 16.4, 11.3, 3.0 Hz, 1H), 2.68-2.62 (m, 1H), 2.37-2.31 (m, 1H), 2.27 (ddd, J = 12.3, 9.5, 2.5 Hz, 1H), 2.19 (td, J = 12.1, 8.2 Hz, 1H), 2.09 (ddd, J = 14.4, 6.7, 3.1 Hz, 1H), 1.98 (ddd, J = 14.3, 11.4, 3.1 Hz, 1H) ppm; $^{13}$C NMR (151 MHz, DMSO-$d_6$) δ 172.4, 160.1, 156.4, 156.1, 155.4, 148.9, 148.8**, 143.2, 138.6, 137.4, 137.4, 125.0, 125.0, 123.9*, 123.8, 86.9, 77.0, 52.1, 34.1, 33.7, 31.5, 25.5 ppm. (*/**: assignment not possible) |

Example 5: Release Efficiency from TCO-$C^A$ Conjugates 1.15 and 1.72 (as control without an $Y^{T1}$ group) were reacted at a concentration of 25 μM with various tetrazine activators (50 μM) in PBS (DMSO content <1%) at 37° C. Samples were analyzed by HPLC (UV and fluorescence detection; 10-100% MeCN in water with 2.5 mM $NH_4OAc$, pH 8.4) after 48 h to obtain endpoint data for the overall dye release efficiency (Table 5). The results in Table 5 show that the TCO trigger of this invention (1.15) affords consistent (near) quantitative release for the whole tetrazine range, while the control TCO lacking the $Y^{T1}$ group (1.72) only shows high release yields for a minority of tetrazines. Importantly, highly reactive tetrazines that normally give low release yields, now give quantitative release. Compare with [Versteegen et al., *Angew. Chem. Int. Ed.* 2013, 52, 14112-14116, Sarris et al., *Chem Eur J* 2018, 24, 18075-18081].

TABLE 5

Release (%) of fluorescent dye (AF594) upon reaction between TCO triggers and tetrazine activators (n = 2; ±1%)

| | activator | | | | | | | | | | |
|---|---|---|---|---|---|---|---|---|---|---|---|
| TCO | 2.6 | 2.9 | 2.10 | 2.11 | 2.12 | 2.13 | 2.14 | 2.16 | 2.17 | 2.18 | 2.19 |
| 1.15 | 93% | 98% | 99% | 99% | 92% | 99% | 99% | 92% | 96% | 99% | 99% |
| 1.72 | 9% | 79% | 88% | 98% | 26% | 31% | 84% | 43% | 20% | 6% | 4% |

In another experiment, the release of TCO triggers was evaluated with a range of tetrazines. The constructs to be released included the drug doxorubicin, and methylamine as a model $C^A$. TCO-$C^A$ conjugates (10 μL, 25 mM in DMSO) were diluted with MeCN (250 L) and PBS (750 L). Next, a solution of the tetrazine activator (20 μL 25 mM in DMSO) was added, and the release was evaluated by HPLC-MS/PDA. The results in Table 6 show complete $C^A$ release in 5 min from all TCO triggers with all tested activators. Importantly, no release was observed from 1.42 and 1.62 upon reaction with 2.18, which supports Formula (19), wherein an amine being $Y^{T1}$, $Y^{T2}$ or $Y^{T3}$ cannot be bound to a carbonyl.

TABLE 6

Release of various constructs ($C^A$) upon reaction between TCO triggers and tetrazine activators.

| TCO | Tetrazine | Released payload | Time point and release % |
|---|---|---|---|
| 1.19 | 2.1, 2.3, 2.18 | 2-hydroxy-2-[4-(methylamino)phenyl] acetic acid | (For all tested activators) 5 min: 100% |
| 1.43 | 2.1, 2.3, 2.15, 2.17, 2.18 | dimethylamine | (For all tested activators) 5 min: 100% |
| 1.45 | 2.20 | doxorubicin | 10 min: 100% |
| 1.54 | 2.18 | dimethylamine | 5 min: 50% |
| 1.63 | 2.18 | dimethylamine | 5 min: 100% |
| 1.65 | 2.20 | doxorubicin | 10 min: 100% |
| 1.70 | 2.18 | dimethylamine | 5 min: 100% |

Figure 7:
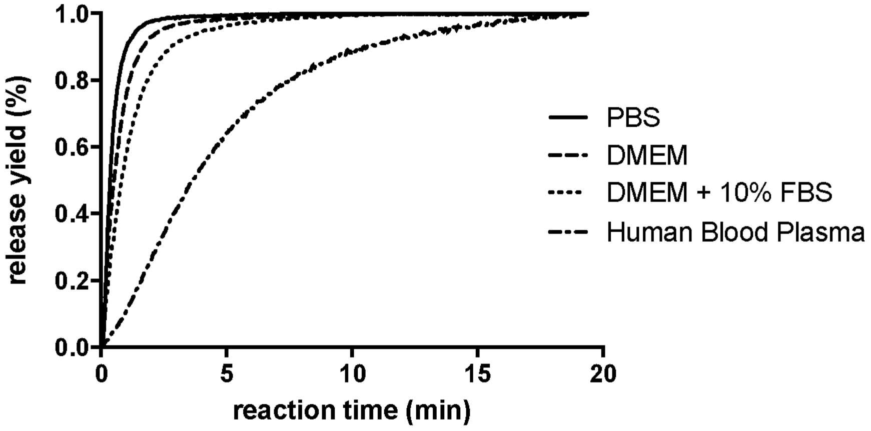
FIG. 7 depicts the results of an in vitro experiment performed with a TCO-construct, containing a quenched fluorophore, and an Activator objects of this invention. The construct and Activator react and release and dequench the fluorophore very rapidly in PBS, cell culture medium and human plasma, producing a detectable increase of fluorescence in solution.

Example 6: Release Kinetics in Various Media 1.14 was reacted in PBS, DMEM buffer, full cell growth medium (DMEM+10% FBS) or human plasma at a concentration of 5 μM with activator 2.18 (7 μM) in a quartz cuvette while magnetic stirring. The increase of fluorescence due to the release of 7-amino-4-methylcoumarin (AMC) was monitored using a Perkin Elmer LS55 fluorescence spectrometer. The results showed very fast AMC release from 1.14 in PBS and medium (neat or containing FBS), reaching 100% in 1-3 min, while in human plasma complete AMC release occurred in approximately 20 min (FIG. 7). In contrast, with TCO triggers not of this invention, 2.18 gives low and slow release [Versteegen et al., *Angew. Chem. Int. Ed.* 2013, 52, 14112-14116, Sarris et al., *Chem Eur J* 2018, 24, 18075-18081].

Example 7: Trigger Stability In Vitro 1.13 was incubated at 37° C. in PBS and human plasma at a concentration of 200 μM. The concentration after 12, 24 and 48 h was determined (n=3) by titration with activator 2.9 and simultaneous absorbance measurements. The results showed high TCO stability in PBS (101±5% intact TCO after 48 h) while very minor TCO deactivation was observed after prolonged 1.13 incubation in plasma (98±7% and 76±9% residual intact TCO after 24 and 48 h incubation, respectively).

Example 8: Cell Viability

HT-1080 cells (human fibrosarcoma) were added with serial dilutions of the TCO-MMAE prodrug 1.16 (100 μM-0.32 nM) in growth medium and 10 μL of a stock solution of activator 2.18 (50 μM in PBS) in a 96-well plate (n=3). After a 2 h incubation at 37° C., the medium was refreshed and the cells were incubated for 94 more hours. After incubation, an MTT assay showed low viability for the cells incubated with 1.16 in the presence of 2.18 (IC50=0.3 nM) with respect to cells incubated with 1.16 alone (IC50=1.3 μM), confirming in vitro MMAE release from the TCO-prodrug upon reaction with the activator.

Example 9: Antibody Conjugation and Radiolabeling

The mAbs CC49, rituximab, cetuximab, and girentuximab were functionalized with 1.25 and 1.26 using 1) partial reduction of the mAb hinge with TCEP (3 eq) in 25 mM borate buffer pH 8.0 (containing 1 mM DTPA) for 2 h at rt, followed by 2) reaction with the maleimide component (ca. 20 eq) overnight at +4° C. (4 mg mAb/mL final concentration). Trastuzumab was conjugated with 1.21 and 1.25 using SATA (4 eq) followed by deprotection with hydroxylamine, according to the protocol provided by the SATA manufacturer (Thermo Fisher Scientific), and incubation with the maleimide component (ca. 20 eq) overnight at +4° C. (4 mg mAb/mL final concentration). After conjugation, the products were purified by dialysis (20 kDa MW cut-off membrane) in chelex-treated PBS (1.21 and 1.26) or 0.25M $NH_4OAc$ buffer pH 5.5 (1.25). After dialysis, all mAb conjugates were characterized by SEC and SDS-PAGE and an average of 2-3 TCO groups were measured per mAb using a tetrazine titration, as previously published [Rossin et al., *Angew Chem Int Ed* 2010, 49, 3375-3378].

The mAbs functionalized with TCO-DOTA derivatives (typically 50-100 μg) were radiolabeled with $^{111}In$ (typically 5-10 MBq) in 0.5M MES buffer pH 5.5 at 37° C. for 1 h in the dark, obtaining 50-70% labeling yields as confirmed by radio-ITLC. The mAbs functionalized with TCO-DFO derivatives (typically 50-100 μg) were radiolabeled with $^{89}Zr$ following established protocols [Vosjan et al., *Nature Protocols* 2010, 5, 739-743], obtaining 80-90% labeling yields as confirmed by radio-ITLC. After a 5 min DTPA challenge, all radiolabeled mAbs were purified using desalting cartridges (Zeba spin columns, 40 kDa MW cut-off) and were then analyzed by SEC and SDS-PAGE, confirming >95% radiochemical purity.

Example 10: Label Release from mAb-Conjugated TCO Triggers Upon Reaction with Various Activators In Vitro mAb conjugate radiolabeled with $^{111}In$ and $^{89}Z$ (ca. 10 μg) was incubated with an excess (ca. 30 eq) of activator or without activator in 100 μL PBS at 37° C. After 15-24 h incubation the mixtures were analyzed by SEC with radioactivity detector and the amount of released Label was quantified. The results in Table 7 show >90% release for all mAb-TCO conjugates with various tetrazine activators, while incubation in PBS without activator shows minimal release (4-5%).

TABLE 7 in vitro Label release from radiolabeled mAb-conjugates after 15-24 h incubation with various activators.

| TCO derivative | mAb | radionuclide | activator | release (%) |
|---|---|---|---|---|
| 1.21 | trastuzumab | $^{89}Zr$ | 2.4 | 97.4 |
| | | | — | 4.7 |
| 1.25 | CC49 | $^{111}Tn$ | 2.4 | 96.6 |
| | | | 2.9 | 92.8 |
| | | | 2.17 | 95.3 |
| | | | — | 5.3 |
| | trastuzumab | | 2.4 | 95.5 |
| | girentuximab | | | 93.7 |
| | rituximab | | | 96.4 |
| | cetuximab | | | 92.1 |

CC49-1.26 (ca. 10 μg) was also incubated with activators 2.4, 2.17 (ca. 30 eq) or without activator in PBS (100 μl) at 37° C. After overnight incubation, the reaction mixtures were analyzed by SEC and the collected fraction were measured in a fluorescence plate reader (excitation: 490 nm; emission: 595 nm). The results showed complete disappearance of the fluorescent signal correlated to the mAb-Dox conjugate (13-15 min Rt) while an intense fluorescent peak appeared at ca. 20 min, consistent with free Dox, when CC49-1.26 was incubated with the activators. On the contrary, when CC49-1.26 was incubated in PBS without an activator, a minimal amount of free Dox (<5%) was detected in solution.

Example 11: Protein-Protein Cleavage for In Vitro and In Vivo Applications

This example features the use of the invention for the cleavage of a protein-protein conjugate in vitro or in vivo. Controlled cleavage of the protein-protein bond may for example be used for the unmasking, i.e. activation, of a protein drug.

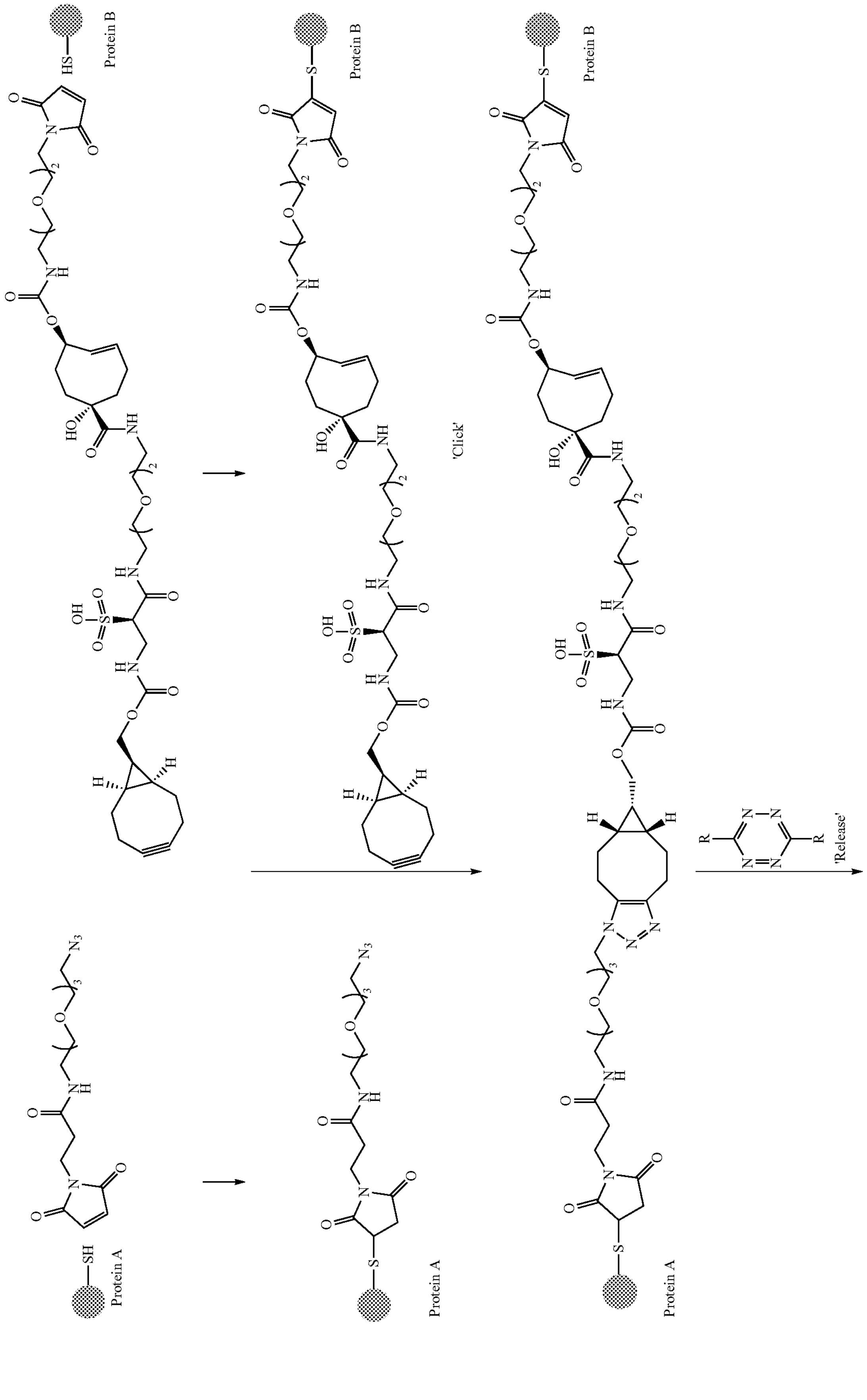
'Click'
'Release'

-continued
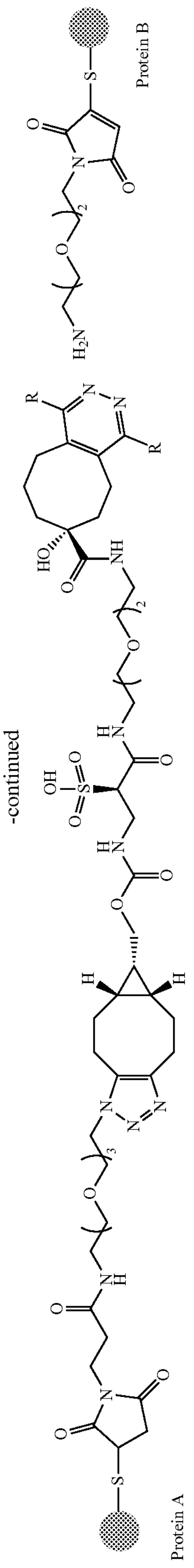

The protein-protein conjugate is prepared via functionalization of one protein with a conjugatable azide (e.g. Mal-PEG-azide). The other protein is conjugated through a cysteine with cleavable linker BCN-TCO-Mal (see below) that enables subsequent click conjugation to the azide functionalized protein, affording a TCO-linked protein-protein conjugate, which can be cleaved on demand by tetrazine activator.

Example 12: Protein-Protein Conjugation and Subsequent Release in Vitro

An anti-TAG72 antibody scFv fragment (MW ca. 25 kDa) was reacted with 5 molar equiv. of bis-NHS TCO linker 1.23 in PBS at pH ca. 9. After overnight incubation at +4° C., SDS-PAGE confirmed the presence in solution of two new protein species with a MW of ca. 50 and 75 kDa, signifying

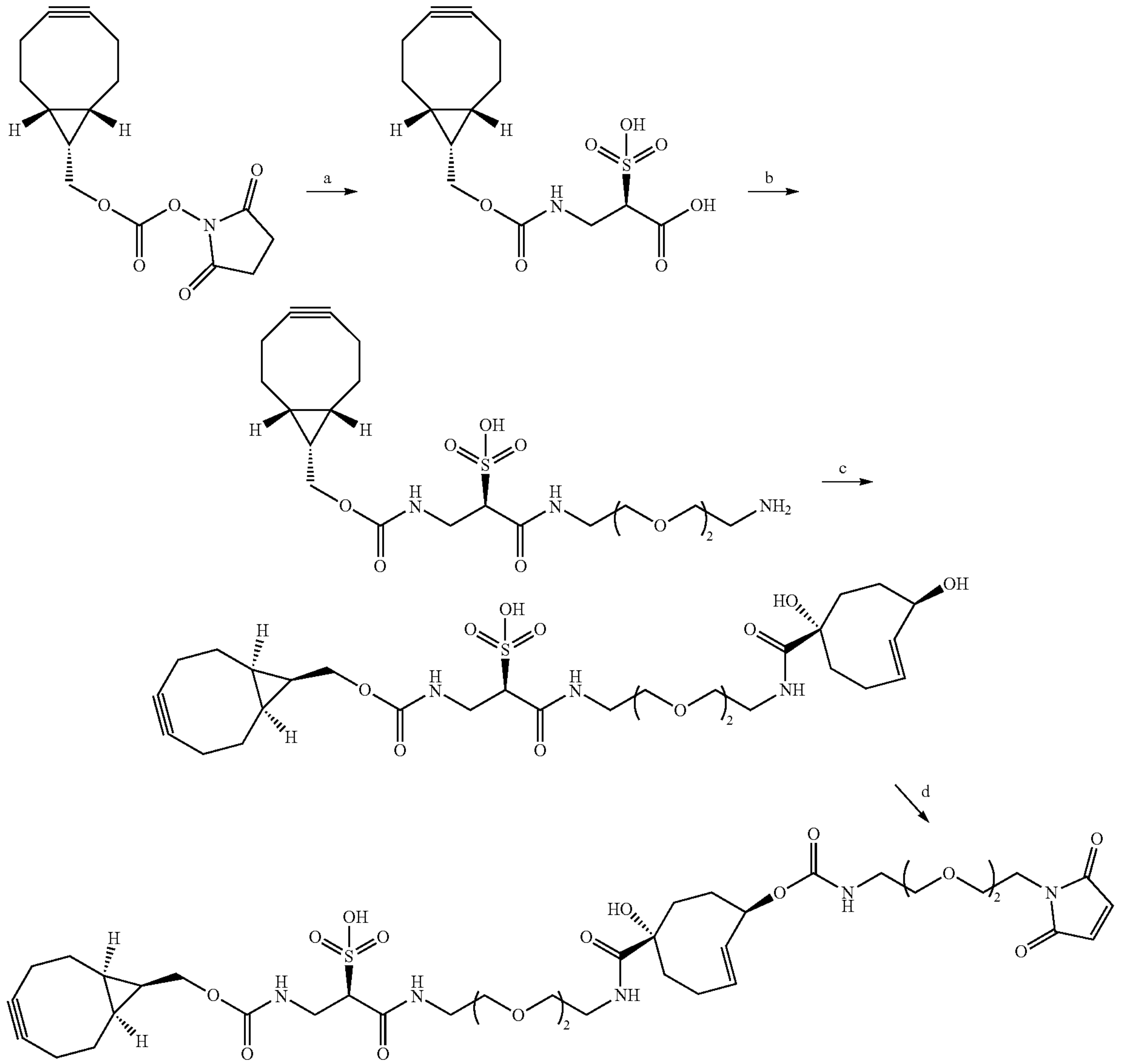

The linker can be prepared from commercially available (1R,8S,9s)-Bicyclo[6.1.0]non-4-yn-9-ylmethyl-N-succinimidyl carbonate (BCN-NHS): a) BCN-NHS is treated with 3-amino-2-sulfopropanoic acid (1.5 eq) in sat. $NaHCO_3$/MeCN for 1 h followed by, prep HPLC (a $H_2O$/MeCN gradient with 0.1% TFA) and lyophilization; b) The acid is treated with PyBOP (1.2 eq) and amino-$PEG_2$-amine (40 eq) in MeCN for 1 h followed by prep HPLC (a $H_2O$/MeCN gradient with 0.1% TFA) and lyophilization; c) analogous to preparation of 1.24. d) Analogous to preparation of 1.25 using the TFA salt of 1-{2-[2-(2-aminoethoxy)ethoxy]ethyl}-2,5-dihydro-1H-pyrrole-2,5-dione.

the formation of a dimeric and a trimeric species conjugated via the TCO. The mixtures were then added with an excess of activator 2.17 (or without activator) and were incubated overnight at 37° C. followed by SDS-PAGE analysis and Coomassie blue staining. showing a strong increase in the 25 kDa band of the original mAb fragment, demonstrating TCO cleavage. On the contrary, the mixture incubated without activator showed the presence of the original 50 and 75 kDa protein bands while the 25 kDa fragment band was almost undetectable.

Example 13: Evaluation of CC49-1.25 Reactivity with Activator 2.4 In Vivo

Two groups of female Balb/C mice (n=4) were i.v. injected $^{111}$In-labeled CC49-1.25 (ca. 0.5 mg/kg, ca. 1 MBq) followed 1 h later by activator 2.4 (ca. 33.5 μmol/kg) or vehicle. Blood samples were withdrawn 5 min before and at various times after activator administration. Twenty-four hours after mAb injection the mice were euthanized, and blood and tissue samples were measured in a gamma-counter. In mice that received the radiolabeled mAb-TCO conjugate followed by vehicle the radioactivity levels in blood showed a ca. 46% decrease in 6 h while a rapid 89% decrease in circulating radioactivity was found in mice that received the activator in the same time window. Twenty-four hours post mAb injection, the $^{111}$In still circulating in blood was 12.3±1.1 vs. 1.3±0.2% ID/g in the group injected with vehicle vs. activator, resulting in a 4.3-times lower AUC in this second group. This enhanced radioactivity clearance demonstrates the efficient reaction between the TCO trigger and the activator in circulation followed by release of the Label, which eliminates rapidly from blood.

Example 14: Evaluation of Trastuzumab-1.21 Reactivity with Tetrazine 2.4 in Tumor Bearing Mice Female Balb/C mice were injected ca 10 million BT-474 breast cancer cells s.c. in the flank. When the tumors became palpable, the mice were injected $^{89}$Zr-trastuzumab-1.21 (ca. 0.5 mg/kg, ca 0.4 MBq; n=3) followed 48 h later by activator 2.4 (ca. 33.5 μmol/kg) or vehicle. The mice were euthanized 72 h post-mAb injection, and blood, tumors and selected non-target tissues were harvested and measured in a gamma counter. In control mice, high tumor uptake (42.3±6.1% ID/g) and sustained $^{89}$Zr-trastuzumab-1.21 circulation in blood (15.9±1.8% ID/g) were observed 72 h post mAb injection. In mice treated with 2.4 lower radioactivity uptake was found in tumors (ca 16% decrease with respect to control group), most likely due to the fraction of residual cell-surface bound trastuzumab. However, significantly lower amounts of radioactivity were also found in blood (1.4±0.6% ID/g) and non-target tissues, therefore resulting in improved tumor-to-organ ratio (Table 8).

TABLE 8

Tumor-to-nontarget tissues ratio calculated in mice pre-treated with $^{89}$Zr-trastuzumab-1.21 followed by activator 2.4 or vehicle 48 h later and euthanized 72 h post-mAb injection.

| | vehicle | 2.4 |
|---|---|---|
| Tumor/Blood | 2.7 | 25.5 |
| Tumor/Liver | 4.1 | 12.5 |
| Tumor/Spleen | 6.5 | 32.4 |
| Tumor/Kidney | 7.7 | 29.2 |
| Tumor/Muscle | 24.6 | 64.9 |

The invention claimed is:

1. A compound satisfying Formula (19):

Formula (19)

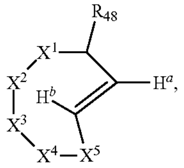

and pharmaceutically acceptable salts thereof, wherein:

$X^1$, $X^2$, $X^4$, and $X^5$, are independently $C(R_{47})_2$ or $CR_{47}Y^{T1}$;

$X^3$ is $C(R_{47})_2$, $CR_{47}Y^{T1}$, or $Y^{T3}$;

wherein at least one of conditions (a)-(b) is met:

(a) at least one of $X^1$, $X^2$, $X^3$, $X^4$, $X^5$, is $CR_{47}Y^{T1}$; $Y^{T1}$ is positioned cis relative to $H^a$; $Y^{T1}$ is selected from the group consisting of OH, SH, and $N(R_{38})_2$; and (b) $X^3$ is $Y^{T3}$; $Y^{T3}$ is $NR_{38}$ and is not flanked by C(O), C(S), S(O), or $S(O)_2$;

$R_{48}$ is selected from the group consisting of $—OC(O)—(S^P)_kC^A$, $—OC(S)—(S^P)_kC^A$, $—SC(O)(S^P)_kC^A$, $—SC(S)—(S^P)_kC^A$, $—O\text{-}(L^C((S^P)_kC^A)_s((S^P)_kC^A)_s((S^P)_i—C^B)_j)_r—(S^P)_kC^A$, $—S\text{-}(L^C((S^P)_kC^A)_s((S^P)_kC^A)_s((S^P)_i—C^B)_j)_r—(S^P)_kC^A$, and $—(S^P)_kC^A$;

r is an integer in range of from 0 to 2;

each s is independently 0 or 1;

each i is independently an integer in a range of from 0 to 4;

j is an integer in range of from 0 to 4;

each k is independently 0 or 1;

$L^C$ is a self-immolative linker and S' is a spacer;

each $C^A$ and $C^B$ are independently selected from the group consisting of organic molecules and inorganic molecules;

wherein, when $R_{48}$ is $—OC(O)—(S^P)_kC^A$, $—OC(S)—(S^P)_kC^A$, $—SC(O)—(S^P)_kC^A$, or $—SC(S)—(S^P)_kC^A$, then $S^P$~, when k>0, or $C^A$, when k=0, is bound to the —OC(O)—, —OC(S)—, —SC(O)—, or —SC(S)— of $R_{48}$ via an atom selected from the group consisting of O, C, S, and N, wherein this atom is part of $S^P$ or $C^A$, wherein, when $R_{48}$ is $—O\text{-}(L^C((S^P)_kC^A)_s((S^P)_kC^A)_s((S^P)_i—C^B)_j)_r—(S^P)_kC^A$ or $—S\text{-}(L^C((S^P)_kC^A)_s((S^P)_kC^A)_s((S^P)_i—C^B)_j)_r—(S^P)_kC^A$ and r is 0, then $S^P$, when k>0, or $C^A$, when k=0, is bound to the —O— or —S— moiety of $R_{48}$ on the allylic position of the trans-cyclooctene ring of Formula (19) via a group selected from the group consisting of —C(O)—, and —C(S)—, wherein this group is part of $S^P$ or $C^A$, wherein, when $R_{48}$ is $—O\text{-}(L^C((S^P)_kC^A)_s((S^P)_kC^A)_s((S^P)_i—C^B)_j)_r—(S^P)_kC^A$ or $—S\text{-}(L^C((S^P)_kC^A)_s((S^P)_kC^A)_s((S^P)_i—C^B)_j)_r—(S^P)_kC^A$ and r is 1, then $L^C$ is bound to the —O— or —S— moiety on the allylic position of the trans-cyclooctene ring of Formula (19) via a group selected from the group consisting of $—C(Y^{C2})Y^{C1}—$, and a carbon atom, wherein this group is part of $L^C$;

wherein $Y^{C1}$ is selected from the group consisting of —O—, —S—, and $—NR_{36}—$, wherein $Y^{C2}$ is selected from the group consisting of O and S, wherein, when $R_{48}$ is $—O\text{-}(L^C((S^P)_kC^A)_s((S^P)_kC^A)_s((S^P)_i—C^B)_j)_r—(S^P)_kC^A$ or $—S\text{-}(L^C((S^P)_kC^A)_s((S^P)_kC^A)_s((S^P)_i—C^B)_j)_r—(S^P)_kC^A$ and r is 1, then $S^P$, when k>0, or $C^A$, when k=0, is bound to $L^C$ via a moiety selected from the group consisting of —O—, —S—, and —N—, wherein said moiety is part of $S^P$ or $C^A$, wherein, when $R_{48}$ is $—(S^P)_kC^A$, then $S^P$, when k>0, or $C^A$, when k=0, is bound to the allylic position of the trans-cyclooctene of Formula (19) via an —O— or an —S— atom, wherein this atom is part of $S^P$ or $C^A$, wherein each $R_{37}$ and $R_{36}$ is independently selected from the group consisting of hydrogen, $—(S^P)_i—C^B$ with i independently being an integer in a range of from 0 to 4, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ (cyclo)alkyl(hetero)aryl groups, $C_3$-$C_{24}$ (hetero)aryl(cyclo)alkyl, $C_4$-$C_{24}$ (cyclo)alkenyl(hetero)aryl groups, $C_4$-$C_{24}$ (hetero)aryl(cyclo)alkenyl groups, $C_4$-$C_{24}$ (cyclo)alkynyl(hetero)aryl groups, $C_4$-$C_{24}$ (hetero)aryl(cyclo)alkynyl groups, $C_4$-$C_{24}$ alkylcycloalkyl groups, and $C_4$-$C_{24}$ cycloalkylalkyl groups;

wherein the $R_{37}$ and $R_{38}$ groups not being hydrogen are optionally substituted with a moiety selected from the group consisting of —Cl, —F, —Br, —I, —OH, $—NH_2$, $—SO_3H$, $—PO_3H$, $—PO_4H_2$, $—NO_2$, $—CF_3$, =O, =NH, and —SH, and optionally contain one or more heteroatoms selected from the group consisting of O, S, NH, P, and Si, wherein the N, S, and P atoms are optionally oxidized, wherein the N atoms are optionally quaternized, wherein $R_{38}$ is independently selected from the group listed for $R_{37}$ and $R_{36}$, with the proviso that $R_{38}$ is not attached to the remainder of the molecule via C(O), C(S), S(O), or $S(O)_2$;

wherein each $R_{47}$ is independently selected from the group consisting of hydrogen, $—(S^P)_i—C^B$, —F, —Cl, —Br, —I, $—OR_{37}$, $—N(R_{37})_2$, $—SO_3$, $—PO_3—$, $—NO_2$, $—CF_3$, $—SR_{37}$, $—S(=O)_2N(R_{37})_2$, $—OC(=O)R_{37}$, $—SC(=O)R_{37}$, $—OC(=S)R_{37}$, $—SC(=S)R_{37}$, $—NR_{37}C(=O)—R_{37}$, $—NR_{37}C(=S)—R_{37}$, $—NR_{37}C(=O)O—R_{37}$, $—NR_{37}C(=S)O—R_{37}$, $—NR_{37}C(=O)S—R_{37}$, $—NR_{37}C(=S)S—R_{37}$, $—OC(=O)N(R_{37})_2$, $—SC(=O)N(R_{37})_2$, $—OC(=S)N(R_{37})_2$, $—SC(=S)N(R_{37})_2$, $—NR_{37}C(=O)N(R_{37})_2$, $—NR_{37}C(=O)N(R_{37})_2$, $—C(=O)R_{37}$, $—C(=S)R_{37}$, $—C(=O)N(R_{37})_2$, $—C(=S)N(R_{37})_2$, $—C(=O)O—R_{37}$, $—C(=O)S—R_{37}$, $—C(=S)O—R_{37}$, $—C(=S)S—R_{37}$, $—S(O)R_{37}$, $—S(O)_2R_{37}$, $—NR_{37}S(O)_2R_{37}$, $—ON(R_{37})_2$, $—NR_{37}OR_{37}$, $C_1$-$C_{24}$ alkyl groups, $C_2$-$C_{24}$ alkenyl groups, $C_2$-$C_{24}$ alkynyl groups, $C_6$-$C_{24}$ aryl groups, $C_2$-$C_{24}$ heteroaryl groups, $C_3$-$C_{24}$ cycloalkyl groups, $C_5$-$C_{24}$ cycloalkenyl groups, $C_{12}$-$C_{24}$ cycloalkynyl groups, $C_3$-$C_{24}$ (cyclo)alkyl(hetero)aryl groups, $C_3$-$C_{24}$ (hetero)aryl(cyclo)alkyl, $C_4$-$C_{24}$ (cyclo)alkenyl(hetero)aryl groups, $C_4$-$C_{24}$ (hetero)aryl(cyclo)alkenyl groups, $C_4$-$C_{24}$ (cyclo)alkynyl(hetero)aryl groups, $C_4$-$C_{24}$ (hetero)aryl(cyclo)alkynyl groups, $C_4$-$C_{24}$ alkylcycloalkyl groups, and $C_4$-$C_{24}$ cycloalkylalkyl groups;

wherein the alkyl groups, alkenyl groups, alkynyl groups, aryl, heteroaryl, cycloalkyl groups, cycloalkenyl groups, cycloalkynyl groups, (cyclo)alkyl(hetero)aryl groups, (hetero)aryl(cyclo)alkyl groups, (cyclo)alkenyl(hetero)aryl groups, (hetero)aryl(cyclo)alkenyl groups, (cyclo)alkynyl(hetero)aryl groups, (hetero)aryl(cyclo)alkynyl groups, alkylcycloalkyl groups, cycloalkylalkyl groups are optionally substituted with a moiety selected from the group consisting of —Cl, —F, —Br, —I, $—OR_{37}$, $—N(R_{37})_2$, $—SO_3R_{37}$, $—PO_3(R_{37})_2$, $—PO_4(R_{37})_2$, $—NO_2$, $—CF_3$, =O, $=NR_{37}$, and $—SR_{37}$, and optionally contain one or more heteroatoms selected from the group consisting of O, S, $NR_{37}$, P, and Si, wherein the N, S, and P atoms are optionally oxidized, wherein the N atoms are optionally quaternized, wherein two $R_{37}$, $R_{38}$, $R_{47}$ groups are optionally comprised in a ring, wherein two $R_{37}$, $R_{38}$, $R_{47}$ groups are optionally comprised in a ring so as to form a ring fused to the eight-membered trans-ring.

2. The compound according to claim 1, wherein at most one of conditions (a) and (b) is met.

3. The compound according to claim 1 selected from the group consisting of

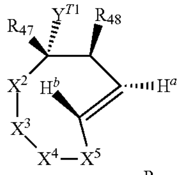
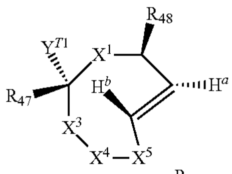
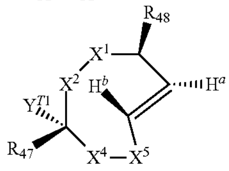
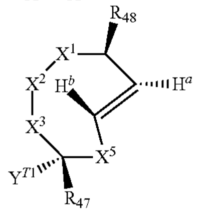
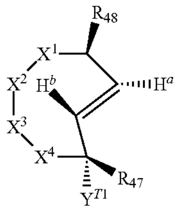
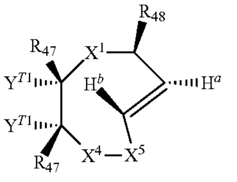
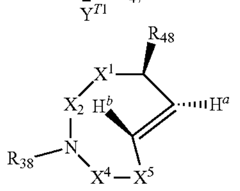

and enantiomers thereof.

4. The compound according to claim 1 selected from the group consisting of

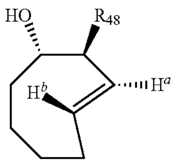
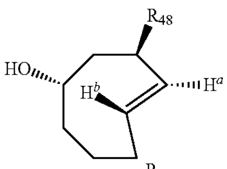
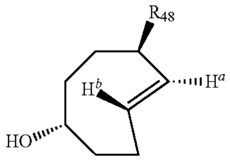
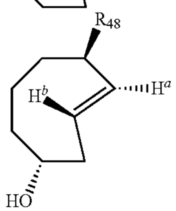

-continued
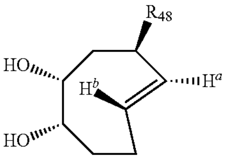
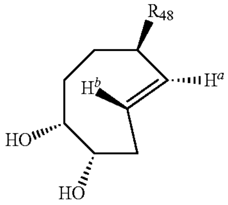
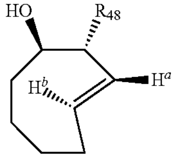
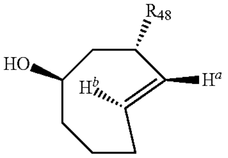
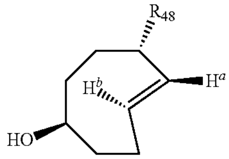
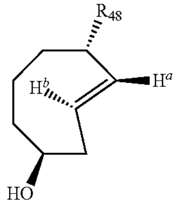
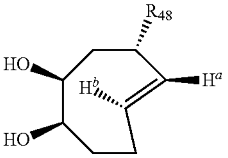
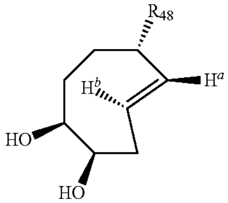
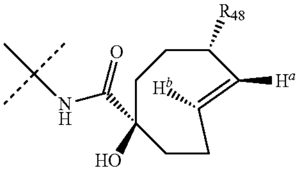
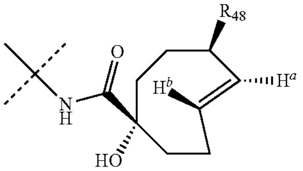
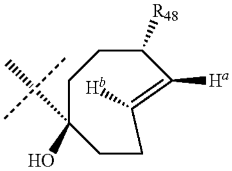
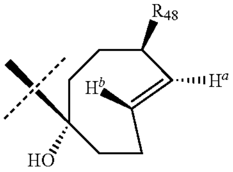
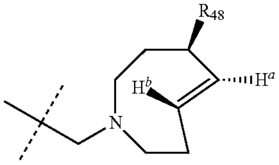
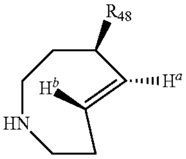
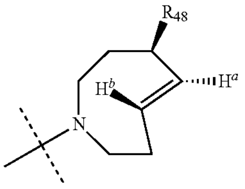
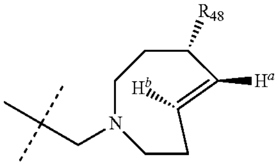
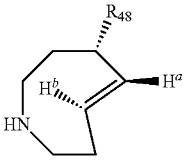
-continued
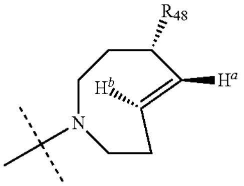
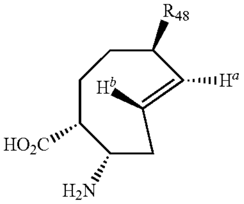
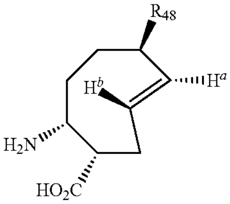
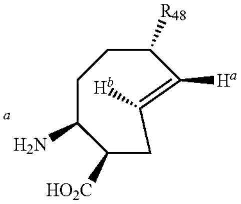
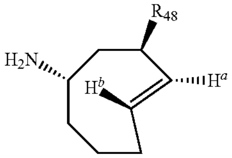
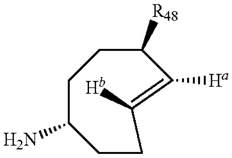
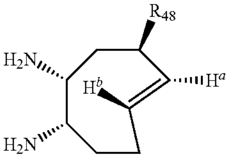
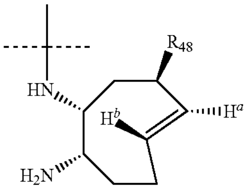
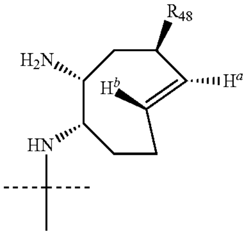
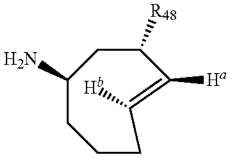
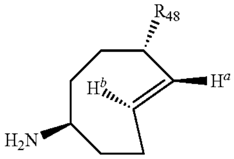
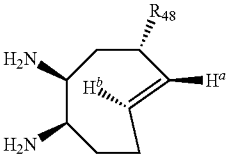
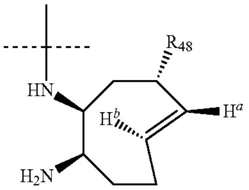
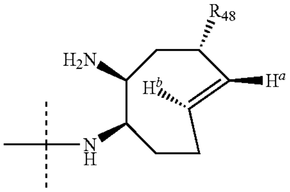
----- = bond to $R_{37}$, $R_{38}$, or $R_{47}$, or bond to remainder of $R_{37}$, $R_{38}$, or $R_{47}$
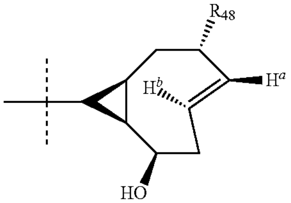

-continued
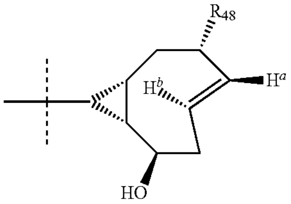
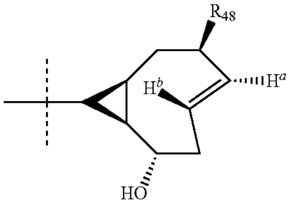
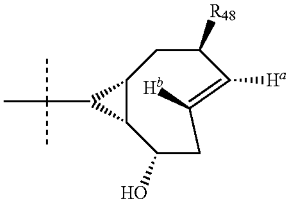
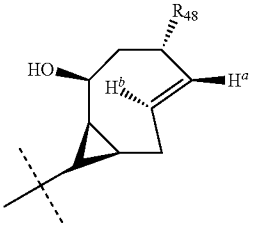
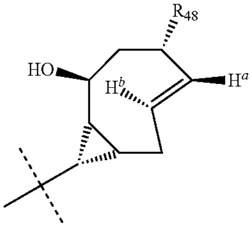
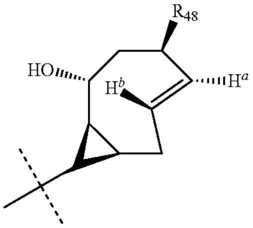
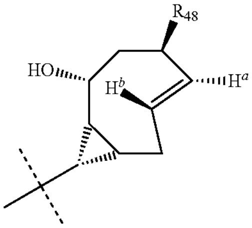
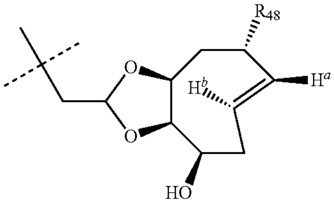
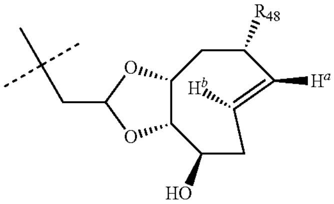
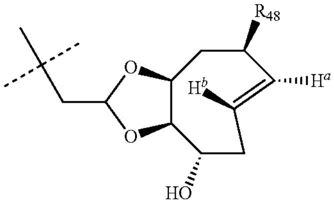
-continued
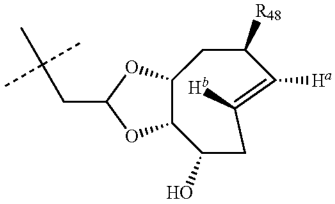
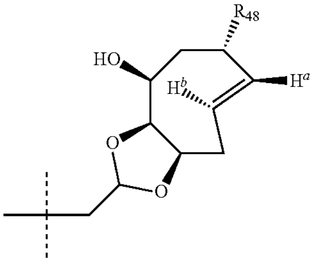
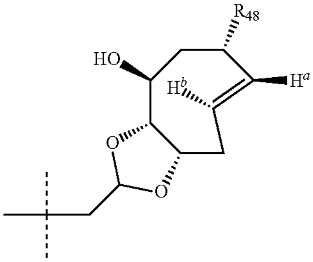
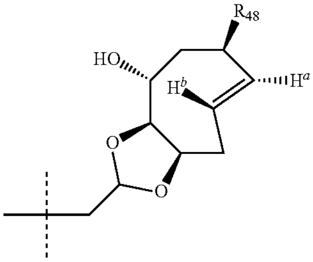
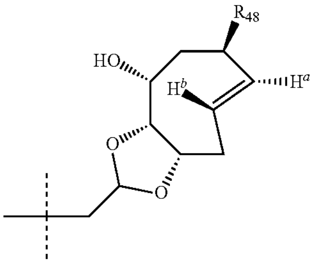
----- = bond to $R_{37}$, $R_{38}$, or $R_{47}$, or bond to remainder of $R_{37}$, $R_{38}$, or $R_{47}$
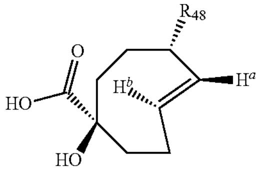
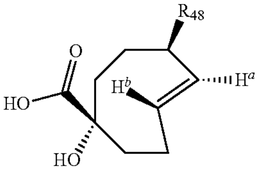
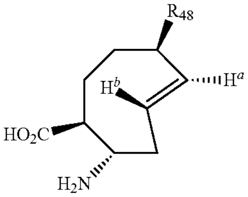
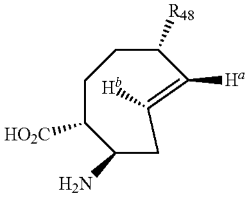

-continued

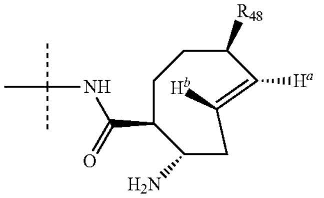

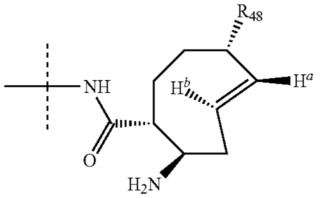

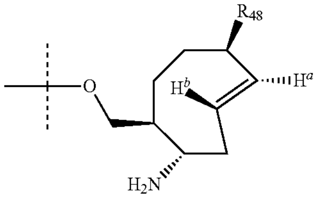

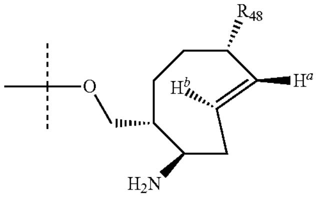

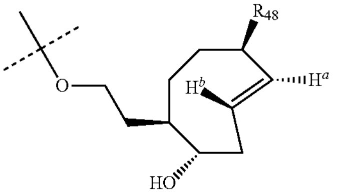

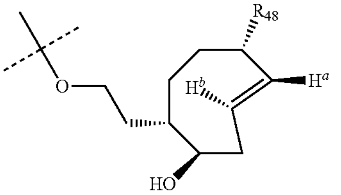

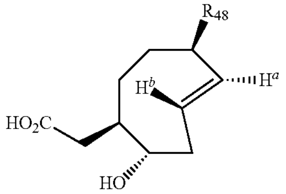

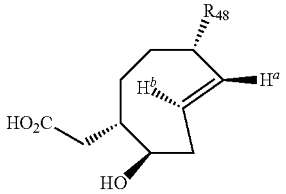

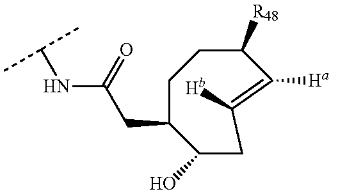

-continued

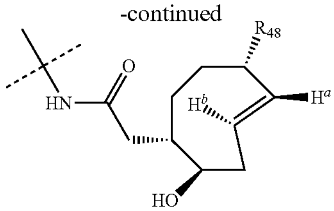

---- = bond to $R_{37}$, $R_{38}$, or $R_{47}$, or bond to remainder of $R_{37}$, $R_{38}$, or $R_{47}$.

5. A combination comprising the compound according to claim 1, and a diene.

6. The combination according to claim 5, wherein the diene is a tetrazine satisfying Formula (4) and pharmaceutically acceptable salts thereof:

Formula (4)

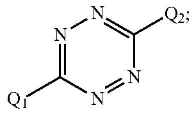

wherein each moiety $Q_1$ and $Q_2$ is independently selected from the group consisting of hydrogen, —F, —Cl, —Br, —I, —$OR_{37}$, —$N(R_{37})_2$, —$SO_3$, —$PO_3$—, —$NO_2$, —$CF_3$, —$SR_{37}$, —$S(=O)_2N(R_{37})_2$, —$OC(=O)R_{37}$, —$SC(=O)R_{37}$, —$OC(=S)R_{37}$, —$SC(=S)R_{37}$, —$NR_{37}C(=O)$—$R_{37}$, —$NR_{37}C(=S)$—$R_{37}$, —$NR_{37}C(=O)O$—$R_{37}$, —$NR_{37}C(=S)O$—$R_{37}$, —$NR_{37}C(=O)S$—$R_{37}$, —$NR_{37}C(=S)S$—$R_{37}$, —$OC(=O)N(R_{37})_2$, —$SC(=O)N(R_{37})_2$, —$OC(=S)N(R_{37})_2$, —$SC(=S)N(R_{37})_2$, —$NR_{37}C(=O)N(R_{37})_2$, —$NR_{37}C(=S)N(R_{37})_2$, —$C(=O)R_{37}$, —$C(=S)R_{37}$, —$C(=O)N(R_{37})_2$, —$C(=S)N(R_{37})_2$, —$C(=O)O$—$R_{37}$, —$C(=O)S$—$R_{37}$, —$C(=S)O$—$R_{37}$, —$C(=S)S$—$R_{37}$, —$S(O)R_{37}$, —$S(O)_2R_{37}$, —$NR_{37}S(O)_2R_{37}$, —$ON(R_{37})_2$, —$NR_{37}OR_{37}$, alkyl groups, alkenyl groups, alkynyl groups, aryl groups, heteroaryl groups, cycloalkyl groups, cycloalkenyl groups, cycloalkynyl groups, (cyclo)alkyl(hetero)aryl groups, (hetero)aryl(cyclo)alkyl, (cyclo)alkenyl(hetero)aryl groups, (hetero)aryl(cyclo)alkenyl groups, (cyclo)alkynyl(hetero)aryl groups, (hetero)aryl(cyclo)alkynyl groups, alkylcycloalkyl groups, and cycloalkylalkyl groups;

wherein the $Q_1$ and $Q_2$ groups not being H, —F, —Cl, —Br, —I, —OH, —$NH_2$, —$SO_3$, —$PO_3$—, —$NO_2$, —$CF_3$, are optionally substituted with a moiety selected from the group consisting of —Cl, —F, —Br, —I, —$OR_{37}$, —$N(R_{37})_2$, —$SO_3R_{37}$, —$PO_3(R_{37})_2$, —$PO_4(R_{37})_2$, —$NO_2$, —$CF_3$, =O, =$NR_{37}$, and —$SR_{37}$, and optionally contain one or more heteroatoms selected from the group consisting of O, S, $NR_{37}$, P, and Si, wherein the N, S, and P atoms are optionally oxidized, wherein the N atoms are optionally quaternized, wherein the $Q_1$ and $Q_2$ groups are optionally bound to —$(S^P)_D$—$R^{87}$;

wherein D is 0 or 1, and each $R^{87}$ is individually selected from the group consisting of a biomolecule, polymer, peptoid, dendrimer, lipid, micelle, liposomes, polymersome, particle, bead, gel, metal complex, organic molecule, organometallic moiety, albumin-binding moiety, radionuclide-comprising moiety, dye moiety, a chelating moiety, and an imaging probe.

7. The combination according to claim 6, wherein $Q_1$ and $Q_2$ are selected from the group consisting of hydrogen, phenyl, 2-pyridyl, 3-pyridyl, 4-pyridyl, 2,6-pyrimidyl, 2,5-pyrimidyl, 3,5-pyrimidyl, and 2,4-pyrimidyl.

8. The combination according to claim 6, wherein in Formula (4):

(a) $Q_1$ and $Q_2$ are selected from the group consisting of 2-pyridyl, 3-pyridyl, and 4-pyridyl; or (b) $Q_1$ is selected from the group consisting of 2,6-pyrimidyl, 2,5-pyrimidyl, 3,5-pyrimidyl, and 2,4-pyrimidyl; and $Q_2$ is (hetero)alkyl; or (c) $Q_1$ is phenyl and $Q_2$ is hydrogen.

9. A non-therapeutic method for releasing a molecule from a compound according to claim 1, said non-therapeutic method comprising the step of contacting a compound according to Formula (19) with a diene.

10. A non-therapeutic method for imaging a compound according to claim 1 in a subject, said non-therapeutic method comprising the steps of (a) administering the compound comprising a label, to the subject; and (b) imaging the compound present in the subject; wherein the label is selected from the group consisting of radionuclides, fluorescent dyes, and phosphorescent dyes.

11. A method for treating cancer, central nervous system (CNS) diseases, infection, inflammation, or cardiovascular diseases in a subject in need thereof, the method comprising administering to the subject an effective amount of the compound according to claim 1.

12. The method according to claim 11 further comprising administering a diene.

13. The combination according to claim 5, wherein the diene is a tetrazine.

14. The combination according to claim 6, wherein at least one of moieties $Q_1$ and $Q_2$ is not hydrogen.

15. The compound according to claim 1, wherein each i and each j are independently 0 or 1.

16. The compound according to claim 1, wherein only condition (a) is met.

17. The compound according to claim 16, wherein group $R_{48}$ is in an axial position.

18. The compound according to claim 17, wherein $X^1$ and $X^5$ are —$C(R_{47})_2$—; and one of $X^2$, $X^3$, and $X^4$ is $CR_{47}Y^{T1}$ and two of $X^2$, $X^3$, and $X^4$ are —$C(R_{47})_2$—.

19. The compound according to claim 18, wherein $Y^{T1}$ is OH.

20. The compound according to claim 19, wherein $C^A$ is a drug and $C^B$ is an antibody or a diabody.

21. The compound according to claim 1, wherein, when $R_{48}$ is —OC(O)—$(S^P)_kC^A$, —OC(S)—$(S^P)_kC^A$, —SC(O)—$(S^P)_kC^A$, or —SC(S)—$(S^P)_kC^A$, then $S^P$, when k>0, or $C^A$, when k=0, is bound to the —OC(O)—, —OC(S)—, —SC(O)—, or —SC(S)— of $R_{48}$ via a secondary or a tertiary N, wherein this group is part of $S^P$ or $C^A$.

22. The compound according to claim 1, wherein, when $R_{48}$ is —O-$(L^C((S^P)_kC^A)_s((S^P)_kC^A)_s((S^P)_i—C^B)_j)_r$—$(S^P)_kC^A$ or —S-$(L^C((S^P)_kC^A)_s((S^P)_kC^A)_s((S^P)_i—C^B)_j)_r$—$(S^P)_kC^A$ and r is 1, then $L^C$ is bound to the —O— or —S— moiety on the allylic position of the trans-cyclooctene ring of Formula (19) via a group selected from the group consisting of —$C(Y^{C2})Y^{C1}$—, and an aromatic carbon, wherein this group is part of $L^C$.

23. The compound according to claim 1, wherein when $R_{48}$ is —O-$(L^C((S^P)_kC^A)_s((S^P)_kC^A)_s((S^P)_i—C^B)_j)_r$—$(S^P)_kC^A$ or —S-$(L^C((S^P)_kC^A)_s((S^P)_kC^A)_s((S^P)_i—C^B)_j)_r$—$(S^P)_kC^A$ and r is 1, then $S^P$, when k>0, or $C^A$, when k=0, is bound to $L^C$ via a moiety selected from a secondary or a tertiary N, wherein said moiety is part of $S^P$ or $C^A$.

24. The compound according to claim 1, wherein at most three moieties $C^B$ are comprised in the structure of Formula (19).

25. The compound according to claim 1, wherein at most one moiety $C^B$ is comprised in the structure of Formula (19).

26. The method according to claim 11, wherein the subject is a human.

27. The non-therapeutic method according to claim 9, wherein the molecule is released in vitro.

28. The method according to claim 10, wherein the subject is a human.

29. The method according to claim 10, further comprising administering a tetrazine activator.

30. The compound according to claim 20, wherein $X^1$ and $X^5$ are —$CH_2$—; and one of $X^2$, $X^3$, and $X^4$ is $CR_{47}Y^{T1}$ and two of $X^2$, $X^3$, and $X^4$ are —$CH_2$—.

* * * * *